US008239136B2

(12) United States Patent
Liew et al.

(10) Patent No.: US 8,239,136 B2
(45) Date of Patent: Aug. 7, 2012

(54) METHOD, COMPUTER SYSTEM AND COMPUTER-READABLE MEDIUM FOR DETERMINING A PROBABILITY OF COLORECTAL CANCER IN A TEST SUBJECT

(75) Inventors: Choong-Chin Liew, Toronto (CA); Mark Han, North York (CA); Thomas Yager, Mississauga (CA); Samuel Chao, Concord (CA); Run Zheng, Richmond Hill (CA); Hongwei Zhang, Toronto (CA)

(73) Assignee: GeneNews Inc., Richmond Hill, Ontario (CA)

( * ) Notice: Subject to any disclaimer, the term of this patent is extended or adjusted under 35 U.S.C. 154(b) by 1386 days.

(21) Appl. No.: 11/585,666

(22) Filed: Oct. 23, 2006

(65) Prior Publication Data

US 2007/0213939 A1 Sep. 13, 2007

Related U.S. Application Data

(60) Provisional application No. 60/729,055, filed on Oct. 21, 2005, provisional application No. 60/758,418, filed on Jan. 12, 2006.

(51) Int. Cl.
*G01N 33/48* (2006.01)
(52) U.S. Cl. ........... 702/19; 702/20; 702/189; 703/2; 703/11; 435/6.1; 435/6.14; 436/63; 436/64
(58) Field of Classification Search .................... None
See application file for complete search history.

(56) References Cited

FOREIGN PATENT DOCUMENTS

| WO | WO 02/44403 A2 | 6/2002 |
|---|---|---|
| WO | WO 2004/079368 A2 | 9/2004 |
| WO | WO/2005/024054 A1 | 3/2005 |
| WO | WO 2005/077065 | 8/2005 |

OTHER PUBLICATIONS

S. Frank, "Identification of Genes Involved in Human Mesothelial Cancer Progression Using a Modified Differential Display Telhnique," *Cancer Letters 123* (1998), pp. 7-14.
W. Shin-Ichi, et al., "Expression of Cytidine Deaminase in Human Solid Tumors and its Regulation by 1 alpha, 25-dihydroxyvitamin D-3," *Biochimica et Biophysica Acta*) 1312:99-104 (1996) (Abstract).
K. Yokoyama, et al., "BANK regulates BCR-induced calcium mobilization by promoting tyrosine phosphorylation of $IP^3$ Receptor," *The EMBO Journal*, 21:83-92 (2002).
PCT International Search Report for PCT/US2006/041600 dated Mar. 9, 2007.
Restriction Requirement in U.S. Appl. No. 12/091,049, dated Mar. 23, 2011 (9 pages).
Fish and Richardson P.C., Response to Restriction Requirement and Preliminary Amendment, dated Mar. 23, 2011, filed Jun. 22, 2011 (17 pages).
Non-final Office Action in U.S. Appl. No. 12/091,049, mailed Aug. 16, 2011, 9 pages.
Fish & Richardson P.C., Amendment in Reply to Office Action in U.S. Appl. No. 12/091,049, mailed Aug. 16, 2011, filed Feb. 15, 2012 (30 pages).

*Primary Examiner* — Carolyn L. Smith
(74) *Attorney, Agent, or Firm* — Fish & Richardson P.C.

(57) ABSTRACT

In one aspect the invention is a method of testing for one or more colorectal pathologies or one or more subtypes of colorectal pathology (in one embodiment colorectal cancer) in a test individual by providing data corresponding to a level of products of selected biomarkers and applying the data to a formula to provide an indication of whether the test individual has one or more colorectal pathologies or one or more subtypes of colorectal pathology. In some aspects the method is computer based and a computer applies the data to the formula. In other aspects a computer system is configured with instructions that cause the processor to provide a user with the indication of whether the test individual has colorectal pathology. Also encompassed are kits for measuring data corresponding to the products of selected biomarkers which in some embodiments include a computer readable medium. Also encompassed are kits and methods of monitoring therapeutic efficacy of treatments for one or more colorectal pathologies.

16 Claims, 6 Drawing Sheets

METHOD, COMPUTER SYSTEM AND COMPUTER-READABLE MEDIUM FOR DETERMINING A PROBABILITY OF COLORECTAL CANCER IN A TEST SUBJECT

PRIORITY CLAIM

This application claims the benefit of priority under 35 U.S.C. §119(e) to U.S. provisional application Ser. No. 60/729,055, filed Oct. 21, 2005, and to U.S. provisional application Ser. No. 60/758,418, filed Jan. 12, 2006, both of which are incorporated herein by reference in their entirety.

MATERIALS ON CD-R

This application includes tabular data in ASCII format text files, presented herewith on a compact disc in duplicate (2 compact discs in total, named "Tables—Copy 1" and "Tables—Copy 2"), and which are hereby incorporated by reference in their entirety. Each compact disc is identical and contains the following files (corresponding to Tables 1 and 11 respectively):

| Table | Size | Created | Text File Name |
| --- | --- | --- | --- |
| 1 | 1,444 KB | Oct. 21, 2005 | Table01.txt |
| 11 | 399 KB | Oct. 21, 2005 | Table11.txt |

TECHNICAL FIELD

The disclosure relates to, apparatus and kits and computer based methods for correlating data corresponding to levels of biomarker products with a disease state in a subject.

BACKGROUND

Colorectal cancer is the second-leading cause of cancer-related deaths in the United States (11). Each year, approximately 150,000 people are diagnosed with colorectal cancer and almost 60,000 people die from the disease. Of those diagnosed, nearly half are expected to die within five years, since most cancers are detected when the cancer is less treatable. For those whose cancer is detected at an earlier stage, the five-year survival rate can be greater than 90%. The American Cancer Society recommends that all Americans age 50 and older be screened regularly for colorectal cancer. Unfortunately, only a fraction of this population is screened for the disease, as currently available screening technologies are considered as either too costly, and/or too invasive or in some cases insufficiently accurate.

Most colorectal cancers begin as small, noncancerous (benign) clumps of cells called polyps. Over time some of these polyps become cancerous. Incidence of polyps increase as individuals get older. It is estimated that 50% of the people over the age of 60 will have at least one polyp.

The significance of identifying one or more colorectal pathologies including polyps is that certain types of polyps are cancerous or indicative of an increased risk to develop cancer. It has been shown that the removal of certain subtypes of polyps reduces the risk of getting colorectal cancer significantly. Therefore, a test to screen for one or more colorectal pathologies including polyps and/or certain subtypes of polyps so as to allow early removal or to prevent unnecessary procedures should markedly reduce the incidence of colorectal cancer (12) and decrease the current costs to the medical system.

Currently utilized screening technologies to identify polyps include 1) a fecal occult blood test (FOBT); 2) a flexible sigmoidoscopy; 3) double contrast barium enema (DCBE); and 4) colonoscopy. Sometimes two or more of these tests are used in combination. The current recommended standards for screening for colorectal cancer in men over the age of 50 and who are considered part of an average risk population include: an FOBT yearly, a sigmoidoscopy every five years, a colonoscopy every ten years and a DCBE every five years. For a high risk population where one or more family members have had colorectal cancer, a colonoscopy is recommended every two years as a follow up to FOBT or sigmoidoscopy.

Each of these tests suffers significant disadvantages. FOBT testing, although a non-invasive procedure, requires significant dietary and other restrictions prior to testing and suffers from a low sensitivity. Sigmoidoscopy and colonoscopy are more sensitive since they involve direct visualization of the lumen, however, sigmoidoscopy only allows partial visualization, and the colonoscopy is known to miss about 12% of advanced adenomas. Both sigmoidoscopy and colonoscopy are highly invasive procedures which cause high levels of discomfort causing many individuals to opt not to undergo these recommended screening procedures. Also sigmoidoscopy and colonoscopy are costly, and may have complications which arise as a result of undergoing the procedure.

Thus, there is a need for an improved test which is minimally invasive so as to permit more widespread testing of the population to indicate the presence of one or more colorectal pathologies, and ensure greater adherence to recommended protocols. To date, despite this need, there have been very few advancements in identifying useful molecular biomarkers to test for colorectal pathology. Recent efforts have focused on DNA based biomarker methods (see for example Shuber et al. U.S. Patent Application Publication No. 2005-0260638A1; or Lofton-Day et al. WO2005/001142).

Identification of biomarkers for use in a non-invasive test for colorectal pathology thus fulfills a longstanding need in the art.

SUMMARY

In contrast to technologies available in the art, the inventions described herein identify biomarkers not previously associated with colorectal pathology whose gene expression levels, measured alone or in combination, and optionally applied to formulas to convert the levels to a measure, give an indication of a likelihood of colorectal pathology.

The present invention discloses novel colorectal pathology-specific biomarkers, such as blood-specific biomarkers, and methods, compositions and kits for use in testing for colorectal pathologies, such as pre-cancerous and cancerous pathologies. This use can be effected in a variety of ways as further described and exemplified herein.

According to one aspect of the present invention there is provided a method of testing for one or more colorectal pathologies in a test subject, the method comprising: (a) providing data representative of a level of one or more products of each of one or more biomarkers in a sample from the test subject; and (b) ascertaining whether the data characterizes either: (i) subjects having the one or more colorectal pathologies, or (ii) subjects not having the one or more colorectal pathologies; thus providing an indication of a probability that the test subject has the one or more colorectal pathologies.

According to another aspect of the present invention there is provided a computer-based method for testing for one or more colorectal pathologies in a test subject, the method comprising: inputting, to a computer, data representing a level of products of each of one or more biomarkers in a sample isolated and/or derived from a test subject, wherein the biomarkers are genes selected from the group consisting of BCNP1, CD163, CDA, MS4A1, BANK1 and MGC20553; and causing the computer to ascertain whether the data characterizes either: (i) subjects having the one or more colorectal pathologies, or (ii) subjects not having the one or more colorectal pathologies, thus providing an indication of a probability that the test subject has the one or more colorectal pathologies.

According to still another aspect of the present invention there is provided a computer-readable medium comprising instructions for ascertaining whether data characterizes either: (i) subjects having one or more colorectal pathologies, or (ii) subjects not having one or more colorectal pathologies, the data representing a level of one or more products of each of one or more biomarkers in a sample isolated and/or derived from a test subject, wherein the biomarkers are genes selected from the group consisting of BCNP1, CD163, CDA, MS4A1, BANK1, and MGC20553, thus providing an indication of a probability that the test subject has the one or more colorectal pathologies.

According to a yet another aspect of the present invention there is provided a computer system for providing an indication of a probability that a test subject has one or more colorectal pathologies, the computer system comprising a processor; and a memory configured with instructions that cause the processor to provide a user with the indication, wherein the instructions comprise ascertaining whether data characterizes either: (i) subjects having one or more colorectal pathologies, or (ii) subjects not having one or more colorectal pathologies, the data representing a level of one or more products of one or more biomarkers in a sample isolated or derived from the test subject, wherein the biomarkers are genes selected from the group consisting of BCNP1, CD163, CDA, MS4A1, BANK1, and MGC20553; thus providing the indication of a probability that the test subject has the one or more colorectal pathologies.

According to further features in preferred embodiments of the invention described below, the products in the sample are RNA.

According to still further features in the described preferred embodiments, the products in the sample are RNA, whereas the data represent a level of cDNA, EST and/or PCR product derived from the RNA.

According to still another aspect of the present invention there is provided a kit comprising packaging and containing one or more primer sets, wherein each set of which is able to generate an amplification product by selective amplification of at least a portion of a polynucleotide complementary to one or more RNA products of a biomarker, wherein the biomarker is a gene selected from the group consisting of: BCNP1, CD163, CDA, MS4A1, BANK1, and MGC20553; and wherein each set of the primer sets is selective for a different biomarker.

According to further features in preferred embodiments of the invention described below, the complementary polynucleotide is selected from the group consisting of total RNA, mRNA, DNA, cDNA and EST.

According to still further features in the described preferred embodiments, the one or more biomarkers are at least two biomarkers.

According to still further features in the described preferred embodiments, each of the probes is capable of selectively hybridizing to either a sense or an antisense strand of the amplification product.

According to still further features in the described preferred embodiments, the kit further comprises two or more components selected from the group consisting of: a thermostable polymerase, a reverse transcriptase, deoxynucleotide triphosphates, nucleotide triphosphates and enzyme buffer.

According to still further features in the described preferred embodiments, the kit further comprises a computer-readable medium encoded with instructions for ascertaining whether data characterizes either: (i) subjects having one or more colorectal pathologies, or (ii) subjects not having one or more colorectal pathologies, the data representing levels of the amplification product in a sample isolated and/or derived from a test subject, thus providing an indication of a probability that the test subject has the one or more colorectal pathologies.

According to still further features in the described preferred embodiments, ascertaining whether the data characterizes either: (i) subjects having the one or more colorectal pathologies, or (ii) subjects not having the one or more colorectal pathologies, comprises applying to the data a formula based on (i) a dataset representing levels of one or more products of each of the biomarkers in each subject of a reference population having the one or more pathologies, and (ii) a dataset representing levels of one or more products of each of the biomarkers in each subject of a reference population not having the one or more pathologies.

According to still further features in the described preferred embodiments, ascertaining whether the data characterizes either: (i) subjects having the one or more colorectal pathologies, or (ii) subjects not having the one or more colorectal pathologies, comprises ascertaining whether the data correlates more closely with (i) a dataset representing levels of one or more products of each of the biomarkers in each subject of a reference population of subjects who have the one or more colorectal pathologies, or (ii) a dataset representing levels of one or more products of each of the biomarkers in each subject of a reference population of subjects who do not have the colorectal pathology.

According to still further features in the described preferred embodiments, the formula has a form: $V = C + \Sigma \beta_i X_i$, wherein V is a value indicating a probability that the test subject has the colorectal pathology, $X_i$ is a level of products of an ith biomarker of the biomarkers in the sample, $\beta_i$ is a coefficient, and C is a constant.

According to still further features in the described preferred embodiments, the formula has a form: $V = C + \Sigma \beta_{ij}(X_i/X_j)$, wherein V is a value indicating a probability that the test subject has the colorectal pathology, $X_i$ is a level of products of an ith biomarker of the biomarkers, and $X_j$ is a level of products of a jth biomarker of the biomarkers in the sample, where the ith biomarker is not the jth biomarker, $\beta_{ij}$ is a coefficient, and C is a constant.

According to still further features in the described preferred embodiments, the formula is derived by a method selected from the group consisting of logistic regression, linear regression, neural networks, and principle component analysis.

According to still further features in the described preferred embodiments, the sample is selected from the group consisting of blood, lymph and lymphoid tissue.

According to still further features in the described preferred embodiments, the sample is selected from the group consisting of a sample of serum-reduced blood, a sample of erythrocyte-reduced blood, a sample of serum-reduced and erythrocyte-reduced blood, a sample of unfractionated cells of lysed blood, and a sample of fractionated blood.

According to a further aspect of the present invention there is provided a composition comprising a collection of two or more isolated polynucleotides, wherein each isolated polynucleotide selectively hybridizes to a biomarker selected from the biomarkers set out in Table 2 and wherein the composition is used to measure the level of expression of at least two of the biomarkers.

According to further features in preferred embodiments of the invention described below, each isolated polynucleotide selectively hybridizes a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); and wherein the composition is used to measure the level of expression of at least two of the biomarkers.

According to yet a further aspect of the present invention there is provided a composition comprising a collection of two or more isolated polynucleotides, wherein each isolated polynucleotide selectively hybridizes to (a) an RNA product of a biomarker selected from the biomarkers set out in Table 2, and/or (b) a polynucleotide sequence complementary to (a), wherein the composition is used to measure the level of RNA expression of at least two of the biomarkers.

According to further features in preferred embodiments of the invention described below, each isolated polynucleotide selectively hybridizes to (a) an RNA product of a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); and/or (b) a polynucleotide sequence complementary to (a), wherein the composition is used to measure the level of RNA expression of at least two of the biomarkers.

According to still a further aspect of the present invention there is provided a composition comprising a collection of two or more isolated polynucleotides, wherein each isolated polynucleotide selectively hybridizes to (a) an RNA sequences set out in Table 3; and/or (b) a polynucleotide sequences complementary to (a).

According to an additional aspect of the present invention there is provided a composition comprising a collection of two or more sets of biomarker specific primers as set out in Table 4 and/or Table 6.

According to yet an additional aspect of the present invention there is provided a composition comprising two or more polynucleotide probes as set out in Table 4.

According to further features in preferred embodiments of the invention described below, the polynucleotides are useful in quantitative RT-PCR (QRT-PCR).

According to still further features in the described preferred embodiments, the isolated polynucleotides comprise single or double stranded RNA.

According to still further features in the described preferred embodiments, the isolated polynucleotides comprise single or double stranded DNA.

According to still an additional aspect of the present invention there is provided a composition comprising a collection of two or more isolated proteins, wherein each isolated protein binds selectively to a protein product of a biomarker selected from the biomarkers set out in Table 2 and wherein the composition is used to measure the level of expression of at least two of the biomarkers.

According to further features in preferred embodiments of the invention described below, each isolated protein binds selectively to a protein product of a biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); and wherein the composition is used to measure the level of expression of at least two of the biomarkers.

According to still further features in the described preferred embodiments, the isolated proteins are selected from the proteins set out in Table 5.

According to still further features in the described preferred embodiments, the isolated proteins are ligands.

According to still further features in the described preferred embodiments, the ligands are antibodies or fragments thereof.

According to still further features in the described preferred embodiments, the antibodies are monoclonal antibodies.

According to yet still an additional aspect of the present invention there is provided a method of diagnosing or detecting one or more colon pathologies in an individual comprising: (a) determining the level of RNA product of one or more biomarker selected from the group consisting of the biomarkers set out in Table 2 in a sample of an individual; and (b) comparing the level of RNA products in the sample with a control, wherein detecting differential expression of the RNA products between the individual and the control is indicative of a one or more colon pathologies in the individual.

According to further features in preferred embodiments of the invention described below, the method of diagnosing or detecting one or more colon pathologies in an individual comprising: (a) determining the level of RNA product of one or more biomarker selected from the group consisting of the biomarkers set out in Table 2 in a sample of an individual; and (b) comparing the level of RNA products in the sample with a control further comprises (a) determining the level of RNA product of one or more biomarker selected from the group consisting of membrane-bound transcription factor protease site 1 (MBTPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); in a sample from an individual; and (b) comparing the level of RNA products in the sample with a control, wherein detecting differential expression of the RNA products between the individual and the control is indicative of a one or more colon pathologies in the individual.

According to still further features in the described preferred embodiments, the sample comprises whole blood.

According to still further features in the described preferred embodiments, the sample comprises a drop of whole blood.

According to still further features in the described preferred embodiments, the sample comprises blood that has been lysed.

According to still further features in the described preferred embodiments, prior to the determining step, the method comprises isolating RNA from the sample.

According to still further features in the described preferred embodiments, the step of determining the level of the RNA products comprises using quantitative RT-PCR (QRT-PCR).

According to still further features in the described preferred embodiments, the QRT-PCR comprises hybridizing primers which hybridize to the one or more RNA products or the complement thereof.

According to still further features in the described preferred embodiments, the primers are 15-25 nucleotides in length.

According to still further features in the described preferred embodiments, the step of determining the level of each of the one or more RNA products comprises hybridizing a first plurality of isolated polynucleotides that correspond to the one or more transcripts, to an array comprising a second plurality of isolated polynucleotides.

According to still further features in the described preferred embodiments, the first plurality of isolated polynucleotides comprises RNA, DNA, cDNA, PCR products or ESTs.

According to still further features in the described preferred embodiments, the array comprises a plurality of isolated polynucleotides comprising RNA, DNA, cDNA, PCR products or ESTs.

According to still further features in the described preferred embodiments, the second plurality of isolated polynucleotides on the array comprises polynucleotides corresponding to one or more of the biomarkers of Table 2.

According to still further features in the described preferred embodiments, the control is derived from an individual that does not have one or more colon pathologies.

According to another aspect of the present invention there is provided a kit for diagnosing or detecting one or more colon pathologies comprising any one of the compositions and instructions for use.

According to yet another aspect of the present invention there is provided a kit for diagnosing or detecting one or more colon pathologies comprising: (a) at least two sets of biomarker specific primers wherein each set of biomarker specific primers produces double stranded DNA complementary to a unique biomarker selected from Table 2; wherein each first primers of the sets contains a sequence which can selectively hybridize to RNA, cDNA or an EST complementary to one of the biomarkers to create an extension product and each the second primers of the sets is capable of selectively hybridizing to the extension product; (b) an enzyme with reverse transcriptase activity; (c) an enzyme with thermostable DNA polymerase activity, and (d) a labeling means; wherein each of the primer sets is used to detect the quantitative expression levels of the biomarker in a test subject.

According to further features in preferred embodiments of the invention described below, the kit for diagnosing or detecting one or more colon pathologies comprising: (a) at least two sets of biomarker specific primers wherein each set of biomarker specific primers produces double stranded DNA complementary to a unique biomarker selected from Table 2; and an enzyme further comprises (a) at least two sets of biomarker specific primers wherein each set of biomarker specific primers produces double stranded DNA complementary to a unique biomarker selected from the group consisting of membrane-bound transcription factor protease site 1 (MB-TPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); wherein each first primers of the sets contains a sequence which can selectively hybridize to RNA, cDNA or an EST complementary to one of the biomarkers to create an extension product and each the second primers of the sets is capable of selectively hybridizing to the extension product; (b) an enzyme with reverse transcriptase activity; (c) an enzyme with thermostable DNA polymerase activity, and (d) a labeling means; wherein each of the primer sets is used to detect the quantitative expression levels of the biomarker in a test subject.

According to still another aspect of the present invention there is provided a method for diagnosing or detecting one or more colon pathologies in an individual comprising: (a) determining the level of protein product of one or more biomarker selected from the group consisting of the biomarkers set out in Table 2 in a sample from an individual; and (b) comparing the level of protein products in the sample with a control, wherein detecting differential expression of the protein products between the individual and the control is indicative of a one or more colon pathologies in the individual.

According to further features in preferred embodiments of the invention described below, the method for diagnosing or detecting one or more colon pathologies in an individual comprising determining the level of protein product of one or more biomarker selected from the group consisting of the biomarkers set out in Table 2 in a sample from an individual further comprises determining the level of protein product of one or more biomarker selected from the group consisting of membrane-bound transcription factor protease site 1 (MB-TPS1); MGC45871; muskelin 1 (MKLN1); nipped-B homolog (NIPBL); acylpeptide hydrolase (APEH); FLJ23091; MGC40157; and protein phosphatase 1 regulatory subunit 2 (PPP1R2); in a sample from an individual; and (b) comparing the level of protein products in the sample with a control, wherein detecting differential expression of the protein products between the individual and the control is indicative of a one or more colon pathologies in the individual.

According to still further features in the described preferred embodiments, the level of protein product is determined using antibodies or fragments thereof.

According to still further features in the described preferred embodiments, the antibodies are selected from the group of antibodies set out in Table 5.

According to still further features in the described preferred embodiments, the antibodies are monoclonal antibodies.

According to a further aspect of the present invention there is provided a composition comprising a collection of two or more isolated polynucleotides, wherein each isolated polynucleotide selectively hybridizes to a biomarker selected from the biomarkers set out in Table 12 and wherein the composition is used to measure the level of expression in blood of at least two of the biomarkers.

According to yet a further aspect of the present invention there is provided a kit for diagnosing or detecting one or more colon pathologies comprising any one of the compositions comprising a collection of two or more isolated proteins and instructions for use.

The present invention successfully addresses the shortcomings of the presently known configurations, in particular by providing an effective and non-invasive method of testing for colorectal pathologies, such as pre-cancerous and cancerous pathologies, via biomarker analysis in surrogate tissues such as blood.

Other features and advantages of the invention will become apparent from the following detailed description. It should be understood, however, that the detailed description and the specific examples while indicating preferred embodiments of the invention are given by way of illustration only, since various changes and modifications within the spirit and scope of the invention will become apparent to those skilled in the art from this detailed description.

BRIEF DESCRIPTION OF THE DRAWINGS

The invention will now be described in relation to the drawings in which.

BRIEF DESCRIPTION OF THE TABLES

Figure 1:
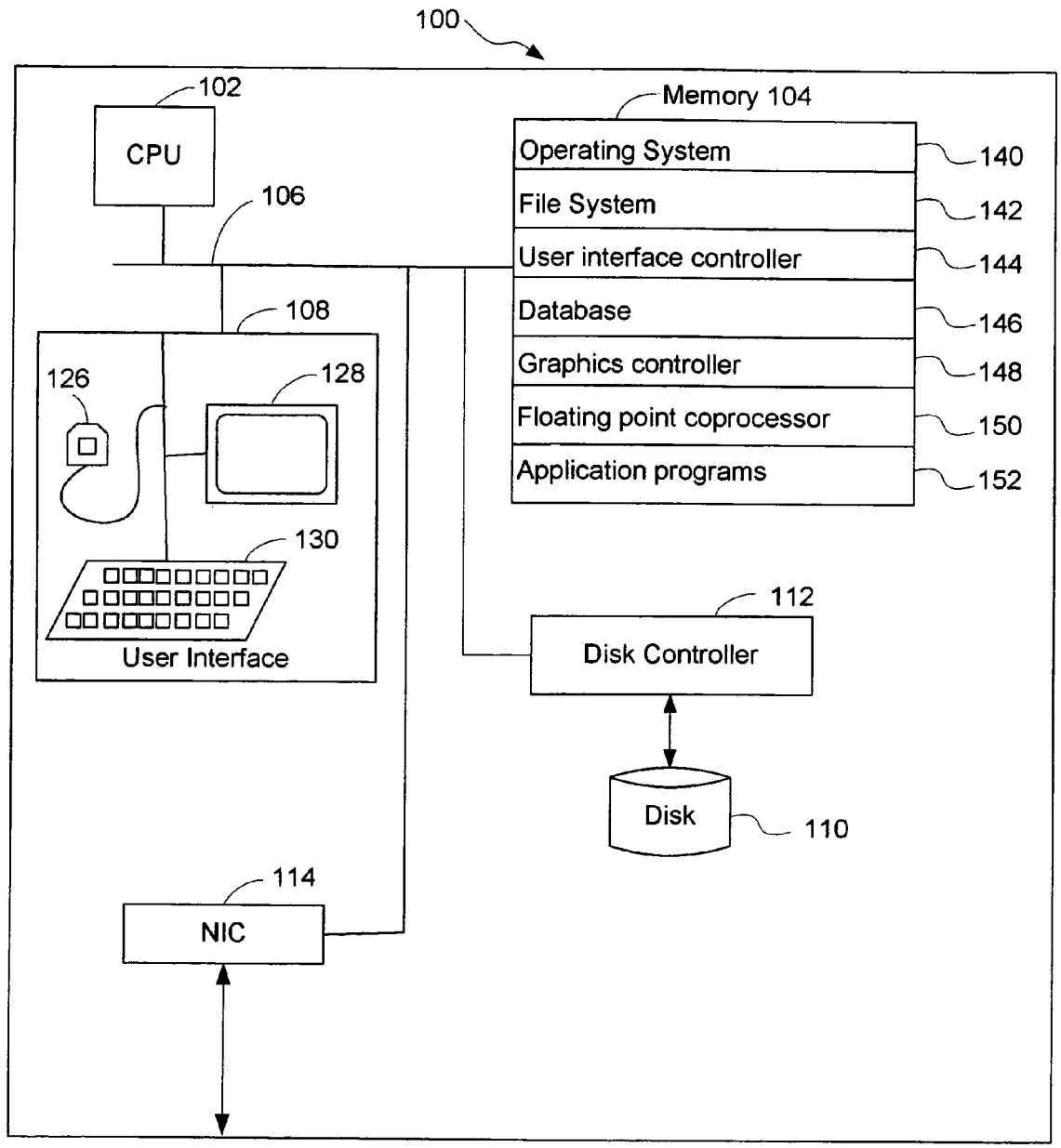
FIG. 1 shows an exemplary computer system for practicing certain of the methods described herein.
Figure 2:
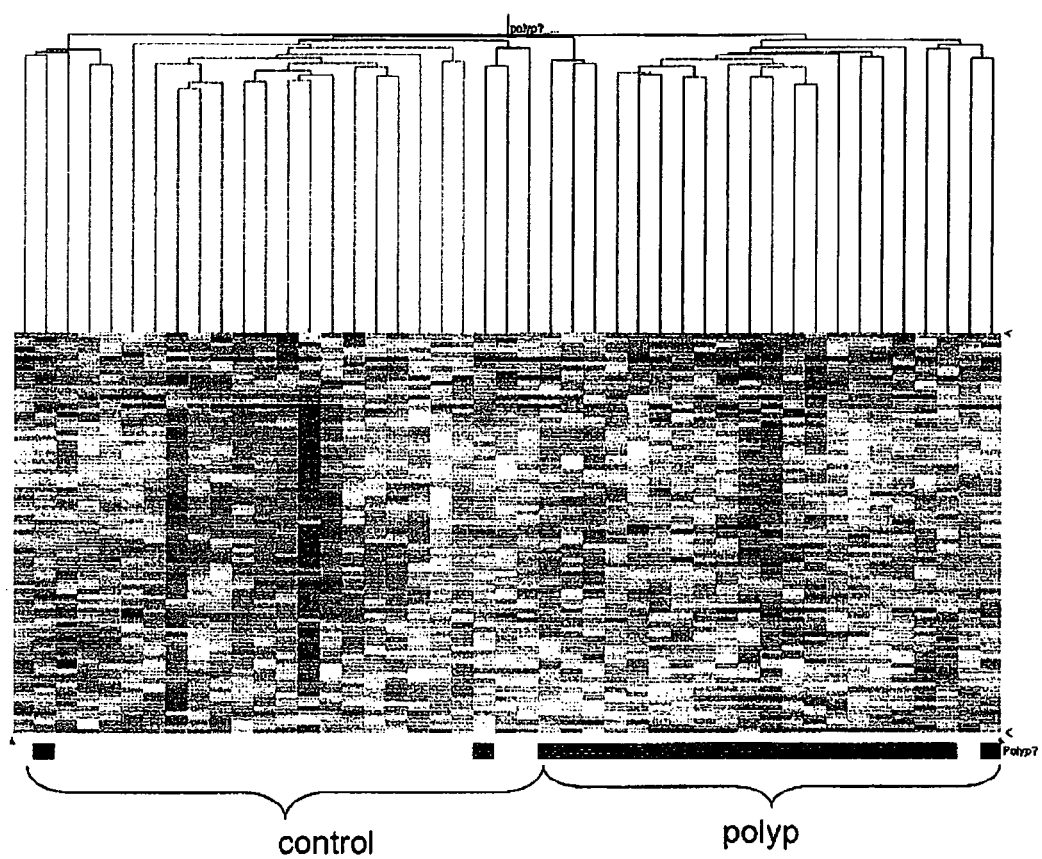
FIG. 2 is a comparison of gene expression profiles obtained from hybridization of RNA isolated from serum-reduced, erythrocyte-reduced blood from 23 controls having no identified colorectal polyps and 22 subjects with colorectal polyps as described in Example 2. Patients with colorectal polyps could have one or more of the subtypes of polyps including Hyperplastic; Tubular Adenoma; Villous Adenoma; Tubulovillous Adenoma; Hyperplasia; High Grade Dysplasia and Colorectal cancer; Gene expression profiles were clustered according to the expression of 86 significantly ($P<0.001$) differentially expressed genes. As noted in grayscale, some of the individuals were misclassified (ie are shown in different grey scale under the appropriate bracket) and are considered outliers. Each column indicates a gene expression profile for a single sample and each row represents the expression level of a single gene in each of the samples. The color of each band within a row indicates the relative level of gene expression (grayscale represents level of expression, from low to high in expression). The resulting gene list from FIG. 2 is shown in Table 1.

Table 1 (provided herewith on CD-R) shows genes identified as differentially expressed in samples from individuals having or not having one or more of any type of colorectal polyps where the polyps can include be one or more of the following subtypes of polyps: Hyperplastic; Tubular Adenoma; Villous Adenoma; Tubulovillous Adenoma; Hyperplasia; High Grade Dysplasia and Cancer. The table provides the Hugo Gene name (second column), symbol and locus link ID; the human RNA and protein accession number; the p value (which represents the statistical significance of the observed differential expression as determined by measuring RNA encoded by the biomarkers noted) and a measure of the fold change as between the average measured level of individuals having one or more types of colorectal pathology and the average measured level of individuals not having colorectal pathology. Column 1 is AffySpotID, column 2 is GeneSymbol, column 3 is GeneID, Column 4 is pvalue, column 5 is the HumanRNA Accession Number, column 6 is the Human Protein Accession Number, column 7 is the Fold Change, and column 8 is the Gene Description.

Table 2 is a selection of genes listed in Table 1. The table provides the gene symbol, locus link ID, and gene description. The table also includes the p value (which represents the statistical significance of the observed differential expression), the Mann-Whitney value (which is another measure to represent the statistical significance of differentiating samples with and without colorectal pathology), the measure of the fold change as between the average measured level of individuals having polyps and the average measured level of individuals not having polyps, and the direction of the differential expression between individuals having colorectal pathology and not having colorectal pathology.

Table 3 provides the human RNA accession number and human protein accession number of various species of the biomarkers identified as differentially expressed in samples from individuals having or not having colorectal polyps. The table provides the gene symbol and a description of the gene.

Table 4 provides a selection of examples of primers and TaqMan® probes useful in the invention for measuring the RNA products of the biomarkers disclosed in Table 2.

Table 5 provides reference to antibodies which are commercially available for protein products of the genes identified in Table 2.

Table 6 shows primer sequences utilized to perform RT-PCR to measure the differential expression of RNA products of the genes (biomarkers) from Table 2 as noted in Example 3 in samples from individuals having or not having one or more polyps. The table also provides the gene symbol and RNA accession number corresponding to the biomarkers tested.

Table 7 provides a summary of the phenotypic information of the patients used as noted in Example 5 to test selected biomarkers for the ability to test for the presence of colorectal polyps. Parameters including the sample size, gender, age and polyp subtype, (as determined by pathology reports), are listed.

Figure 3:
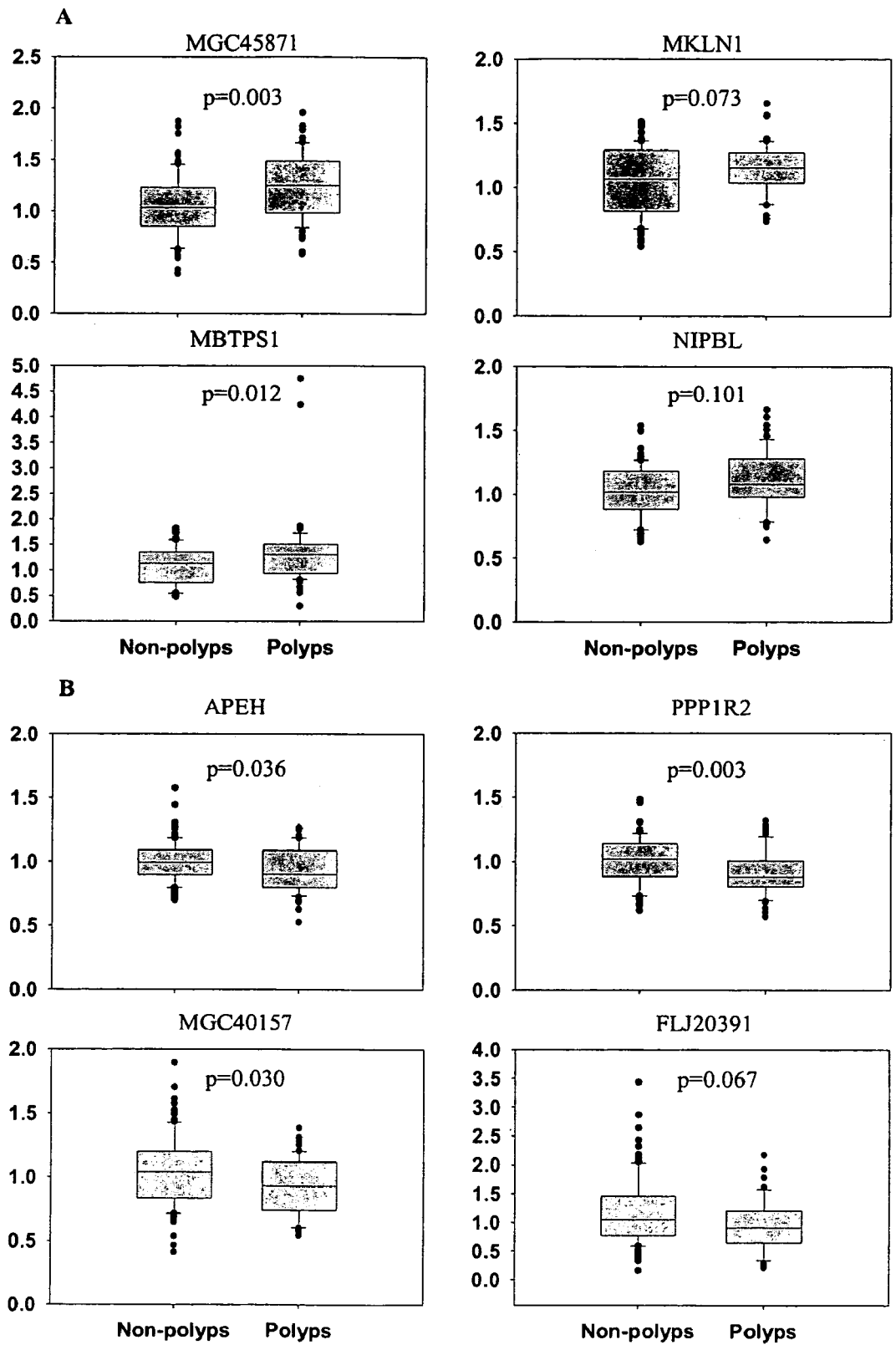
FIG. 3 shows blood mRNA levels as tested by QRT-PCR for four upregulated genes (A) and four downregulated genes (B) selected from the genes demonstrating statistically significant differentially expression using microarray analysis as described in Example 5. QRT-PCR results were tested as between 50 patients diagnosed as having colorectal pathology (ie one or more subtypes of colorectal polyps) (n=50) as compared with 78 control individuals where the control individuals were diagnosed as not having colorectal pathology (n=78). Comparative (Ct) method based fold change was used. Mann-Whitney test was used for statistical analysis between two groups. Results which demonstrated a f value of less than 0.05 were considered statistically significant suggesting that the gene corresponding to the mRNA level tested is differentially expressed as between the two patient populations (patients with colorectal pathology and patients without colorectal pathology). The lines inside the boxes denote the medians. The boxes mark the interval between the $25^{th}$ and $75^{th}$ percentiles. The whiskers denote the interval between the $10^{th}$ and $90^{th}$ percentiles. • indicates data points outside the $10^{th}$ and $90^{th}$ percentiles.

Table 8 lists selected classifiers for use with data corresponding to the eight selected biomarkers MBTPS1, MGC45871, MKLN1, NIPBL APEH, MGC40157, PPP1R2, FLJ23091 which resulted in a ROC area of 0.72 so as to test for the presence of a colorectal polyps as described in Example 5. Results of QRT-PCR of the eight selected genes are shown in FIG. 3.

Table 9 provides the results of the blind test described in Example 5 when applying the formula comprised of classifiers noted in Table 8.

Table 10 is a list of reporter genes and the properties of the reporter gene products which may be used to identify compounds for use in preventing or treating one or more forms of colorectal pathology.

Table 11 (provided herewith on CD-R) shows genes identified as differentially expressed in samples from individuals having "high risk polyps" as compared with individuals not having high risk polyps (ie having low risk polyps or having no pathology at all) using microarray as described in Example 2. The table provides the gene name, gene ID; a representative human RNA accession number, and also provides the p value, the fold change (as between the average of individuals classified as having high risk polyps as compared with the average of individuals having low risk polyps), along with the coefficient of variation for both the high risk polyp individuals and the low risk polyp individuals (the standard deviation of the normalized intensity divided by the mean normalized intensity). Column 1 is AffySpotID, column 2 is Fold Change, column 3 is p value, Column 4 is CV (Coefficient of Variation) (High Risk Polyp), column 5 is CV (Low Risk Polyp), column 6 is Gene ID, column 7 is the HUGO Gene Symbol, column 8 is the Human RNA Accession Number and column 9 is the Gene Description.

Table 12 shows 48 biomarkers tested for differential expression by QRT-PCR in samples from individuals having colorectal cancer and individuals not having colorectal cancer The 48 biomarkers were tested using QRT-PCR. The table provides the gene symbol, locus link ID, and gene description for each biomarker. The table also includes the p value (which represents the statistical significance of the observed differential expression), the measure of the fold change as between the average measured level of individuals having colorectal cancer and the average measured level of individuals not having colorectal cancer and the direction of the differential expression between individuals having colorectal cancer and not having colorectal cancer.

Table 13 provides the human RNA accession number and human protein accession number of various species of the biomarkers identified as differentially expressed in samples from individuals having or not having colorectal cancer in Table 12. The table provides the gene symbol and a description of the gene.

Table 14 provides a selection of examples of primers and TaqMan® probes useful for measuring one or more RNA products of the biomarkers disclosed in Table 12 as described in Examples 6, 7, 8 or 9.

Table 15 provides reference to antibodies which are commercially available to measure protein products of the biomarkers identified in Table 12.

Table 16 shows a selection of primers which have been used for the genes described in Table 12 to quantify one or more RNA products of the biomarkers.

Table 17 shows primers and TaqMan® probes used in Example 11.

DETAILED DESCRIPTION (A) Overview

In one aspect the invention discloses methods of generating formulas/classifiers which can be applied to data corresponding to levels of one or more products of selected biomarker combinations to classify test subjects as having one or more colorectal pathologies or one or more subtypes of colorectal pathologies. Also disclosed are biomarkers whose product levels are useful for testing subjects for one or more colorectal pathologies or one or more subtypes of colorectal pathologies. Also disclosed are computer-readable media comprising instructions for applying a formula to data representing a level of products of biomarkers so as to test subjects for one or more colorectal pathologies. Also disclosed is a computer system which is configured with instructions to provide the user with an indication of the probability of a test subject having one or more colorectal pathologies by applying a formula to biomarker product data.

The present invention provides biomarker product ligands capable of specific hybridization with RNA biomarker products so as to enable quantitation of the biomarker products. The biomarker product ligands may enable quantitation, either directly and/or indirectly in any one of various ways known to the skilled artisan. The biomarker product ligands capable of specifically hybridizing with biomarker RNA products or polynucleotides derived therefrom may have any one of various compositions. For example, specific ligands of biomarker products, such as biomarker RNA products, may be either polynucleotides (e.g. polynucleotides complementary to at least a portion of the RNA products or polynucleotides derived therefrom) or polypeptides (e.g. antibodies or affinity-selected polypeptides specific for at least a portion of the RNA products or polynucleotides derived therefrom). In one embodiment polynucleotide and/or polypeptide ligands are disclosed which are probes capable of specifically and/or selectively hybridizing with so as to quantitate biomarker RNA products and/or polynucleotides products. Such probes include those useful in techniques such as quantitative real-time PCR (QRT-PCR), and may be used, for example, with SYBR®Green, or using TaqMan® or Molecular Beacon techniques. In one embodiment, the polynucleotides useful as nucleic acid probes which can be spotted onto an array to measure levels of biomarker RNA products, or of polynucleotides derived therefrom, which are isolated or derived from test subjects In another embodiment, arrays for use in measuring the expression of the RNA products are contemplated.

In another embodiment, polynucleotide ligands are disclosed which are biomarker specific primer sets capable of specifically amplifying biomarker RNA products and/or polynucleotides corresponding to biomarker RNA products.

Further disclosed are methods of screening of products of the identified biomarkers to screen for therapeutic targets for treating or preventing one or more colorectal pathologies.

Kits of polynucleotides and/or polypeptide ligands which can be used to detect and monitor differential gene expression of the products of the identified biomarkers and biomarker combinations are also provided as are kits which include a computer readable medium to allow an indication of a probability that a test subject has one or more colorectal pathologies. Methods of generating the formulas for testing for one or more colorectal pathologies are also provided.

Further disclosed is the measurement/monitoring of biomarker product levels to screen for therapeutic targets for treating or preventing one or more colorectal pathologies. Methods of generating the formulas for testing a test subject for a one or more colorectal pathologies are also provided.

Also disclosed are methods of testing combinations of biomarkers by generating classifiers. Classifiers are generated by applying one or more mathematical models to data representative of the level of expression of the RNA and/or protein products of the biomarkers across a reference population encompassing subjects who have one or more colorectal pathologies, or one or more subtypes thereof, and subjects who do not have the one or more colorectal pathologies. Classifiers can be used alone or in combination to create a formula which is useful in testing a subject for the probability of having one or more colon pathologies subtypes. Also disclosed are methods of further selecting classifiers on the basis of area under the curve (AUC), sensitivity and/or specificity. One or more selected classifiers can be used to generate a formula and subsequently classifiers can be selected for inclusion into the formulas. Classifiers are generated by measuring levels of one or more RNA products and/or one or more protein products of the biomarkers in a sample and using the data resulting from said measurement for input into the mathematical model. Note that it is not necessary that the same method used to generate the data for creating the formulas is the method used to generate data from the test subject for inclusion within the formula for diagnostic purposes.

Other aspects of the invention are disclosed herein.

(B) Definitions

The practice of the present invention will employ, unless otherwise indicated, techniques of molecular biology, microbiology and recombinant DNA techniques, which are familiar to one of the skill in the art. Such techniques are explained fully in the literature. See, e.g., Sambrook, Fritsch & Maniatis, 1989, Molecular Cloning: A Laboratory Manual, Second Edition; Oligonucleotide Synthesis (M. J. Gait, ed., 1984); Nucleic Acid Hybridization (B. D. Harnes & S. J. Higgins, eds., 1984); A Practical Guide to Molecular Cloning (B. Perbal, 1984); and a series, Methods in Enzymology (Academic Press, Inc.); Short Protocols In Molecular Biology, (Ausubel et al., ed., 1995). All patents, patent applications, and publications mentioned herein, both supra and infra, are hereby incorporated by reference in their entireties.

The following definitions are provided for specific terms which are used in the following written description.

As used herein, the "5' end" refers to the end of an mRNA up to the first 1000 nucleotides or ⅓ of the mRNA (where the full length of the mRNA does not include the poly A tail) starting at the first nucleotide of the mRNA. The "5' region" of a gene refers to a polynucleotide (double-stranded or single-stranded) located within or at the 5' end of a gene, and includes, but is not limited to, the 5' untranslated region, if that is present, and the 5' protein coding region of a gene. The 5' region is not shorter than 8 nucleotides in length and not longer than 1000 nucleotides in length. Other possible lengths of the 5' region include but are not limited to 10, 20, 25, 50, 100, 200, 400, and 500 nucleotides.

As used herein, the "3' end" refers to the end of an mRNA up to the last 1000 nucleotides or ⅓ of the mRNA, where the 3' terminal nucleotide is that terminal nucleotide of the coding or untranslated region that adjoins the poly-A tail, if one is present. That is, the 3' end of an mRNA does not include the poly-A tail, if one is present. The "3' region" of a gene refers to a polynucleotide (double-stranded or single-stranded) located within or at the 3' end of a gene, and includes, but is not limited to, the 3' untranslated region, if that is present, and the 3' protein coding region of a gene. The 3' region is not shorter than 8 nucleotides in length and not longer than 1000 nucleotides in length. Other possible lengths of the 3' region include but are not limited to 10, 20, 25, 50, 100, 200, 400, and 500 nucleotides. As used herein, the "internal coding region" of a gene refers to a polynucleotide (double-stranded or single-stranded) located between the 5' region and the 3' region of a gene as defined herein. The "internal coding region" is not shorter than 8 nucleotides in length and not longer than 1000 nucleotides in length. Other possible lengths of the "internal coding region" include but are not limited to 10, 20, 25, 50, 100, 200, 400, and 500 nucleotides. The 5', 3' and internal regions are non-overlapping and may, but need not be contiguous, and may, but need not, add up to the full length of the corresponding gene.

As used herein, the "amino terminal" region of a polypeptide refers to the polypeptide sequences encoded by polynucleotide sequences (double-stranded or single-stranded) located within or at the 5' end of an mRNA molecule. As used herein, the "amino terminal" region refers to the amino terminal end of a polypeptide up to the first 300 amino acids or ⅓ of the polypeptide, starting at the first amino acid of the polypeptide. The "amino terminal" region of a polypeptide is not shorter than 3 amino acids in length and not longer than 350 amino acids in length. Other possible lengths of the "amino terminal" region of a polypeptide include but are not limited to 5, 10, 20, 25, 50, 100 and 200 amino acids.

As used herein, the "carboxy terminal" region of a polypeptide refers to the polypeptide sequences encoded by polynucleotide sequences (double-stranded or single-stranded) located within or at the 3' end of an mRNA molecule. As used herein, the "carboxy terminal" region refers to the carboxy terminal end of a polypeptide up to 300 amino acids or ⅓ of the polypeptide from the last amino acid of the polypeptide. The "3' end" does not include the polyA tail, if one is present. The "carboxy terminal" region of a polypeptide is not shorter than 3 amino acids in length and not longer than 350 amino acids in length. Other possible lengths of the "carboxy terminal" region of a polypeptide include, but are not limited to, 5, 10, 20, 25, 50, 100 and 200 amino acids.

As used herein, the "internal polypeptide region" of a polypeptide refers to the polypeptide sequences located between the amino terminal region and the carboxy terminal region of a polypeptide, as defined herein. The "internal polypeptide region" of a polypeptide is not shorter than 3 amino acids in length and not longer than 350 amino acids in length. Other possible lengths of the "internal polypeptide region" of a polypeptide include, but are not limited to, 5, 10, 20, 25, 50, 100 and 200 amino acids. The amino terminal, carboxy terminal and internal polypeptide regions of a polypeptide are non-overlapping and may, but need not be contiguous, and may, but need not, add up to the full length of the corresponding polypeptide.

As used herein, the term "amplified", when applied to a nucleic acid sequence, refers to a process whereby one or more copies of a particular nucleic acid sequence is generated from a template nucleic acid, in some embodiments by the method of polymerase chain reaction (Mullis and Faloona, 1987, Methods Enzymol., 155:335). "Polymerase chain reaction" or "PCR" refers to a method for amplifying a specific template nucleic acid sequence. In some embodiments, the PCR reaction involves a repetitive series of temperature cycles and is typically performed in a volume of 50-100 µl. The number of cycles performed in the PCR reaction can include 15, 20, 25, 30, 35, 40, 45, 50, 55 or 60 cycles. The reaction mix comprises dNTPs (each of the four deoxynucleotides dATP, dCTP, dGTP, and dTTP), primers, buffers, DNA polymerase, and nucleic acid template. The PCR reaction can comprise providing a set of polynucleotide primers wherein a first primer contains a sequence complementary to a region in one strand of the nucleic acid template sequence and primes the synthesis of a complementary strand, and a second primer contains a sequence complementary to a region in a second strand of the target nucleic acid sequence and primes the synthesis of a complementary strand, and amplifying the nucleic acid template sequence employing a nucleic acid polymerase as a template-dependent polymerizing agent under conditions which are permissive for PCR cycling steps of (i) annealing of primers required for amplification to a target nucleic acid sequence contained within the template sequence, (ii) extending the primers wherein the nucleic acid polymerase synthesizes a primer extension product. "A set of polynucleotide primers" or "a set of PCR primers" or "a set of primers" can comprise two, three, four or more primers. In some embodiments, nested PCR can occur using a primer set wherein a first subset of primers is utilized to amplify a single product and then a second subset of primers is utilized which hybridize to the product of the first subset of primers to amplify a smaller version of the. In one embodiment, an exo-Pfu DNA polymerase is used to amplify a nucleic acid template in PCR reaction. Other methods of amplification include, but are not limited to, ligase chain reaction (LCR), polynucleotide-specific based amplification (NSBA), or any other method known in the art.

In one aspect an "array" includes a specific set of probes, such as oligonucleotides and/or cDNA's (e.g. ESTs) corresponding in whole or in part, and/or continuously or discontinuously, to regions of expressed genomic DNA; wherein the probes are localized onto a support. In one embodiment, the probes can correspond to the 5' ends or 3' ends of the internal coding regions of a biomarker RNA product of the invention. Of course, mixtures of a 5' end of one gene may be used as a target or a probe in combination with a 3' end of another gene to achieve the same or similar biomarker RNA product level measurements.

As used herein, an "analog" of a reference proteinaceous agent includes any proteinaceous agent that possesses a similar or identical function as the reference proteinaceous agent but does not comprise a similar or identical amino acid sequence as reference proteinaceous agent, and/or possess a similar or identical structure as the reference proteinaceous agent. A proteinaceous agent that has a similar amino acid sequence as a second proteinaceous agent is at least one of the following: (a) a proteinaceous agent having an amino acid sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the amino acid sequence of the second proteinaceous agent; (b) a proteinaceous agent encoded by a nucleotide sequence that hybridizes under stringent conditions to at least a segment of the nucleotide sequence encoding the second proteinaceous agent, where the segment has a length of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least 80 contiguous amino acid residues, at least 90 contiguous amino acid residues, at least 100 contiguous amino acid residues, at least 125 contiguous amino acid residues, or at least 150 contiguous amino acid residues; and (c) a proteinaceous agent encoded by a nucleotide sequence that is at least 30%, at least 35%, at least 40%, at least 45%, at least 50%, at least 55%, at least 60%, at least 65%, at least 70%, at least 75%, at least 80%, at least 85%, at least 90%, at least 95% or at least 99% identical to the nucleotide sequence encoding the second proteinaceous agent. A proteinaceous agent with similar structure to a second proteinaceous agent refers to a proteinaceous agent that has a similar secondary, tertiary or quaternary structure as the second proteinaceous agent. The structure of a proteinaceous agent can be determined by methods known to those skilled in the art, including but not limited to, peptide sequencing, X-ray crystallography, nuclear magnetic resonance, circular dichroism, and crystallographic electron microscopy.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions times 100%). In one embodiment, the two sequences are the same length.

The determination of percent identity between two sequences can also be accomplished using a mathematical algorithm. A preferred, non-limiting example of a mathematical algorithm utilized for the comparison of two sequences is the algorithm of Karlin and Altschul, 1990, Proc. Natl. Acad. Sci. U.S.A. 87:2264-2268, modified as in Karlin and Altschul, 1993, Proc. Natl. Acad. Sci. U.S.A. 90:5873-5877. Such an algorithm is incorporated into the NBLAST and XBLAST programs of Altschul et al., 1990, J. Mol. Biol. 215:403. BLAST nucleotide searches can be performed with the NBLAST nucleotide program parameters set, e.g., for score=100, wordlength=12 to obtain nucleotide sequences homologous to a nucleic acid molecules of the present invention. BLAST protein searches can be performed with the XBLAST program parameters set, e.g., to score—50, wordlength=3 to obtain amino acid sequences homologous to a protein molecule of the present invention. To obtain gapped alignments for comparison purposes, Gapped BLAST can be utilized as described in Altschul et al., 1997, Nucleic Acids Res. 25:3389-3402. Alternatively, PSI-BLAST can be used to perform an iterated search which detects distant relationships between molecules (Id.). When utilizing BLAST, Gapped BLAST, and PSI-Blast programs, the default parameters of the respective programs (e.g., of XBLAST and NBLAST) can be used (see, e.g., the NCBI website). Another preferred, non-limiting example of a mathematical algorithm utilized for the comparison of sequences is the algorithm of Myers and Miller, 1988, CABIOS 4:11-17. Such algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used.

The percent identity between two sequences can be determined using techniques similar to those described above, with or without allowing gaps. In calculating percent identity, typically only exact matches are counted.

As used herein, the term "analog" in the context of a non-proteinaceous molecules refers to a second organic or inorganic molecule which possess a similar or identical function as a first organic or inorganic molecule and is structurally similar to the first organic or inorganic molecule. The term "analog" includes a molecule whose core structure is the same as, or closely resembles that of the first molecule, but which has a chemical or physical modification. The term "analog" includes copolymers of the first molecule that can be linked to other atoms or molecules. A "biologically active analog" and "analog" are used interchangeably herein to cover an organic or inorganic molecule that exhibits substantially the same agonist or antagonist effect of the first organic or inorganic molecule.

A "nucleotide analog", as used herein, refers to a nucleotide in which the pentose sugar and/or one or more of the phosphate esters is replaced with its respective analog. Exemplary phosphate ester analogs include, but are not limited to, alkylphosphonates, methylphosphonates, phosphoramidates, phosphotriesters, phosphorothioates, phosphorodithioates, phosphoroselenoates, phosphorodiselenoates, phosphoroanilothioates, phosphoroanilidates, phosphoroamidates, boronophosphates, etc., including any associated counterions, if present. Also included within the definition of "nucleotide analog" are nucleobase monomers which can be polymerized into polynucleotide analogs in which the DNA/RNA phosphate ester and/or sugar phosphate ester backbone is replaced with a different type of linkage. Further included within "nucleotide analogs" are nucleotides in which the nucleobase moiety is non-conventional, i.e., differs from one of G, A, T, U or C. Generally a non-conventional nucleobase will have the capacity to form hydrogen bonds with at least one nucleobase moiety present on an adjacent counter-directional polynucleotide strand or provide a non-interacting, non-interfering base.

The term "antibody" also encompasses antigen-binding fragments of an antibody. The term "antigen-binding fragment" of an antibody (or simply "antibody portion," or "fragment"), as used herein, refers to one or more fragments of a full-length antibody that retain the ability to specifically bind to a polypeptide encoded by one of the genes of a biomarker of the invention. Examples of binding fragments encompassed within the term "antigen-binding fragment" of an antibody include (i) a Fab fragment, a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) *Nature* 341:544-546), which consists of a VH domain; and (vi) an isolated complementarity determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv); see e.g., Bird et al. (1988) *Science* 242:423-426; and Huston et al. (1988) *Proc. Natl. Acad. Sci. USA* 85:5879-5883). Such single chain antibodies are also intended to be encompassed within the term "antigen-binding fragment" of an antibody. These antibody fragments are obtained using conventional techniques known to those with skill in the art, and the fragments are screened for utility in the same manner as are intact antibodies. The antibody is in some embodiments monospecific, e.g., a monoclonal antibody, or antigen-binding fragment thereof. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition.

As used herein, the terms "attaching" and "spotting" in relation to an array can include a process of depositing or localizing a nucleic acid or proteinaceous agent onto a substrate to form a nucleic acid or protein array. In one embodiment, the substance spotted is attached or localized onto the array via covalent bonds, hydrogen bonds or ionic interactions.

As used herein, the term "biomarker" refers to a gene whose products can be measured and correlated with disease. A biomarker refers to a gene which encodes one or products (e.g. unspliced RNA, mRNA and/or polypeptide) present at measurably different levels in corresponding samples isolated and/or derived from subjects having the pathology and subjects not having the pathology. A biomarker may be a DNA molecule which is transcribed into RNA product. Alternately, the biomarker may be an RNA molecule which is translated into protein product, or reverse-transcribed into DNA product.

As used herein, a "blood nucleic acid sample" or "blood polynucleotide sample", refers to polynucleotides derived from blood and can include polynucleotides isolated and/or derived from whole blood, serum-reduced whole blood, lysed blood (erthyrocyte depleted blood), centrifuged lysed blood (serum-depleted, erythrocyte depleted blood), serum depleted whole blood or peripheral blood leukocytes (PBLs), globin reduced RNA from blood, or any possible fraction of blood as would be understood by a person skilled in the art. A blood polynucleotide sample can refer to RNA, mRNA or a nucleic acid corresponding to mRNA, for example, cDNA or EST derived from RNA isolated from said sample. A blood polynucleotide sample can also include a PCR product derived from RNA, mRNA or cDNA.

As used herein, the term "formula" includes one or more classifiers, or combination of classifiers where the term classifier is used to describe the output of a mathematical model.

As used herein the term "colorectal pathology" comprises any of one or more types or subtypes of pathology of the rectum and/or colon. "Colorectal pathologies" include precancerous polyps, cancerous polyps, polyps at risk of becoming cancerous, and polyps of unknown cancer-related status. As would be understood, in some cases a subject according to embodiments of the invention can have at any one time one or more colorectal pathologies, each of which being of the same or a different type or subtype of polyp. Colorectal pathologies may be classified in any one of various ways, for example as is known in the art. In one embodiment "Polyp" or "colorectal polyp" as would be understood in the art, includes an abnormal growth of cells and/or tissue, and/or a growth of cells and/or tissue that may project into the colon or rectum. A polyp can be further defined according to various factors including the morphology of the polyp; the risk of the polyp developing into a cancerous polyp and the like as would be understood by a person ordinarily skilled in the art. In one embodiment, polyps can be classified into various subtypes including: Hyperplastic; Tubular Adenoma; Villous Adenoma; Tubulovillous Adenoma; Hyperplasia; High Grade Dysplasia; and Cancer. For any one individual and or polyp, one or more polyp subtype description could apply. In another embodiment, (7) colorectal cancer can be subclassified into various categories as well. In yet another embodiment, one or more of the listed subtypes can be grouped together according to any one of various parameters in one category. Alternately, one or more of the listed subtypes can be further subclassified according to any one of various parameters. In yet another embodiment, one or more of the listed subtypes can be grouped together according to any one of various parameters in one category. Alternately, one or more of the listed subtypes can be further subclassified according to any one of various parameters. For example, in one embodiment, Tubular Adenoma polyps can be further classified in accordance with the diameter of the Adenoma polyp. For example Adenoma polyps with a diameter greater than 1 mm, 2 mm, 3 mm, 4 mm, 5 mm, 6 mm, 7 mm, 8 mm, 9 mm, 10 mm, 11 mm, 12 mm, 13 mm, 14 mm or 15 mm are possible. In yet another example, colorectal cancer can be further subclassified in accordance with disease progression as would be understood. For example, colorectal cancer can be subclassified using the Duke or Modified Duke Staging System. The Modified Duke Staging System groups colorectal cancer into four different stages A-D. Stage A indicates the tumor penetrating the mucosa of the colon and/or bowel but no further. Stage B1 indicates the tumor penetrating into, but not through the muscularis propria (the muscular layer) of the colon and/or bowel wall. Stage B2 indicates the tumor has penetrated into and through the muscularis propria of the colon and/or bowel wall. A Stage C1 tumor penetrates into, but not through the muscularis propria of the colon and/or bowel wall; there is pathologic evidence of colorectal cancer in the lymph nodes. Stage C2 tumors penetrates into and through the muscularis propria of the bowel wall; but there is pathologic evidence of colorectal cancer in the lymph nodes. Finally Stage D indicates the tumor has spread beyond the lymph nodes to other organs. In yet another embodiment, colorectal cancer can be subclassified using the TNM staging system. According to the TNM staging system there are four stages, stages I through IV, each reflecting status regarding Tumor, Node, and Metastasis. Tumor is subdivided as follows T1: Tumor invades submucosa, T2: Tumor invades muscularis propria, T3: Tumor invades through the muscularis propria into the subserosa, or into the pericolic or perirectal tissues and T4: Tumor directly invades other organs or structures, and/or perforates. Node is subdivided as follows: N0 indicates no regional lymph node metastasis. N1 indicates metastasis in 1 to 3 regional lymph nodes. N2 indicates metastasis in 4 or more regional lymph nodes. Metastasis is divided as follows: M0 indicates no distant metastasis and M1 indicates distant metastasis present. Thus for Stage I, in accordance with the TNM system, the tumor can either be categorized as T1N0M0 or T2N0M0; the cancer has begun to spread but is still in the inner lining. Stage II is T3N0M0 or T4 N0M0; the cancer has spread to other organs near the colon or rectum but has not yet reached the inner lining. Stage III includes all T's, N1-2 and M0; cancer has spread to lymph nodes but has not been carried to distant parts of the body. Stage IV includes any T, any N and M1; cancer is metastatic and has been carried to other organs, likely the lung or liver.

As used herein, the term "high risk polyps" indicates those subtypes of polyps which are considered at higher risk for developing into cancer or are already cancerous as would be understood by a person skilled in the art, and includes cancer-prone polyps or cancer-disposed polyps and cancerous polyps, whereas a "low risk polyp" includes all other types of polyps. For example, 70 to 90 percent of colorectal cancers arise from adenomatous polyps, and thus are considered high risk polyps. Adenomatous polyps can be further categorized into subtypes including: Tubular adenoma, which has been suggested to have approximately a 4% potential for malignancy; Tubulovillous adenoma, which has been suggested to have approximately a 16% potential for malignancy and Villous adenoma, which has been suggested to have approximately a 21% potential for malignancy. In addition, high grade dysplasia has increased malignant potential. In one embodiment, polyps which are "high risk polyps" are Tubulovillous Adenoma, Villous Adenoma, High Grade Dysplasia and Tubular Adenoma and also includes polyps which are cancerous including those which are cancerous and localized and those which have already led to dissemination in the peripheral blood. In this embodiment, a "low risk polyp" includes any other polyp morphology. In another embodiment, polyps which are "high risk polyps" are Tubulovillous Adenoma, Villous Adenoma, High Grade Dysplasia and Tubular Adenoma and does not include polyps which are already cancerous. The size of the polyp also correlates with the risk for developing into cancer. For example, polyps greater than 10 mm in diameter are considered large polyps and have a greater potential for malignancy. Polyps larger than 2 cm in diameter have a 50 percent chance of becoming malignant. See Zauber (2004) Gastroenterology; 126(5): 1474. In another embodiment "high risk polyps" comprise Tubulovillous Adenoma, Villous Adenoma, High Grade Dysplasia and Tubular Adenoma where the diameter of the Tubular Adenoma polyp is greater than 10 mm and the remaining polyp morphologies are considered "low risk polyps".

As used herein, the terms "compound" and "agent" are used interchangeably.

As used herein, the term "control" or "control sample" can include one or more samples isolated and/or derived from a subject or group of subjects who have been diagnosed as having one or more colorectal pathologies, including having one or more polyps or having one or more subtypes of polyps; not having colorectal pathologies; not having polyps; or not having one or more subtypes of polyps. The term control or control sample can also refer to the compilation of data derived from one or more samples of one or more subjects.

A "coding region" in reference to a DNA refers to DNA which encodes RNA.

A "coding region" in reference to RNA refers to RNA which encodes protein.

As used herein, the term "data" in relation to one or more biomarkers, or the term "biomarker data" generally refers to data reflective of the absolute and/or relative abundance (level) of a product of a biomarker in a sample. As used herein, the term "dataset" in relation to one or more biomarkers refers to a set of data representing levels of each of one or more biomarker products of a panel of biomarkers in a reference population of subjects. A dataset can be used to generate a formula/classifier of the invention. According to one embodiment the dataset need not comprise data for each biomarker product of the panel for each individual of the reference population. For example, the "dataset" when used in the context of a dataset to be applied to a formula can refer to data representing levels of products of each biomarker for each individual in one or more reference populations, but as would be understood can also refer to data representing levels of products of each biomarker for 99%, 95%, 90%, 85%, 80%, 75%, 70% or less of the individuals in each of said one or more reference populations and can still be useful for purposes of applying to a formula.

As used herein, the term "derivative" in the context of proteinaceous agent (e.g., proteins, polypeptides, peptides, and antibodies) refers to a proteinaceous agent that comprises an amino acid sequence which has been altered by the introduction of amino acid residue substitutions, deletions, and/or additions. The term "derivative" as used herein also refers to a proteinaceous agent which has been modified, i.e., by the covalent attachment of any type of molecule to the proteinaceous agent. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative of a proteinaceous agent may be produced by chemical modifications using techniques known to those of skill in the art, including, but not limited to specific chemical cleavage, acetylation, formylation, metabolic synthesis of tunicamycin, etc. Further, a derivative of a proteinaceous agent may contain one or more non-classical amino acids. A derivative of a proteinaceous agent possesses a similar or identical function as the proteinaceous agent from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein the terms "testing", "diagnosis" and "screening", in relation to colorectal pathologies refer to a process of determining a likelihood (probability) of a test subject having one or more colorectal pathologies and includes both traditional medical diagnostic techniques as well as testing methods as encompassed by one or more aspects of the current invention. Traditional medical diagnostic techniques for testing for colorectal pathology includes physical exam and history, medical evaluation, and appropriate laboratory tests which can include FOBT, sigmoidoscopy and colonoscopy. In one embodiment, "diagnosis of colorectal pathology" refers to a determination as between two options: e.g., (i) that an individual has colorectal pathology or one or more subtypes of colorectal pathology, or one or more polyps and (ii) that an individual does not have the colorectal pathology or the one or more polyps or the one or more subtypes of polyps. In another embodiment diagnosis can include an option that it cannot be determined with sufficient degree of certainty as to whether an individual can be characterized as having colorectal pathology or not. In one context, a "sufficient degree of certainty" takes into account any limitations—such as limitations in the technology, equipment or measuring where as a result of the limitations, the result is within a range which suggests that the test is indeterminate. The range which suggests the test is indeterminate will depend upon the specific limitations of the equipment, reagents and technology used. In another context, "sufficient degree of certainty" depends upon the medical requirements for the sensitivity and/or specificity of the test. More particularly the sufficient degree of certainty includes greater than 50% sensitivity and/or specificity, greater than 60% sensitivity and/or specificity, greater than 70% sensitivity and/or specificity, greater than 80% sensitivity and/or specificity, greater than 90% sensitivity and/or specificity and 100% sensitivity and/or specificity.

As used herein, "normal" refers to an individual or group of individuals who do not have colorectal pathology. In some embodiments, the diagnosis of said individual or group of individuals not having colorectal pathology is determined using conventional diagnostic methods. In some embodiments said individual or group of individuals have not been diagnosed with any other disease. "Normal", according to the invention, also refers to samples isolated from normal individuals and includes blood, total RNA or mRNA isolated from normal individuals. A sample taken from a normal individual can include a sample taken from an individual who does not have colorectal pathology at the time the sample is taken.

As used herein, the term "differential expression" refers to a difference in the level of expression of the products of one or more biomarkers. For instance, the term "differential expression" can refer to the difference in the level of RNA of one or more biomarkers between samples from subjects having and subjects not having one or more colorectal pathologies. Differences in biomarker RNA product levels can be determined by directly or indirectly measuring the amount or level of Differentially expressed" can also include different levels of protein encoded by the biomarker of the invention between samples or reference populations. "Differential expression can be determined as the ratio of the levels of one or more biomarker products between reference subjects/populations having or not having one or more colorectal pathologies, wherein the ratio is not equal to 1.0. Differential expression between populations can be determined to be statistically significant as a function of p-value. When using p-value to determine statistical significance, a biomarker, the p-value is preferably less than 0.2. In another embodiment the biomarker is identified as being differentially expressed when the p-value is less than 0.15, 0.1, 0.05, 0.01, 0.005, 0.0001 etc. When determining differential expression on the basis of the ratio, a biomarker product is differentially expressed if the ratio of the level of expression in a first sample as compared with a second sample is greater than or less than 1.0. For example, a ratio of greater than 1.0 for example includes a ratio of greater than 1.1, 1.2, 1.5, 1.7, 2, 3, 4, 10, 20 and the like. A ratio of less than 1.0, for example, includes a ratio of less than 0.9, 0.8, 0.6, 0.4, 0.2, 0.1, 0.05 and the like. In another embodiment of the invention a biomarker product is differentially expressed if the ratio of the mean of the level of expression of a first population as compared with the mean level of expression of the second population is greater than or less than 1.0. For example, a ratio of greater than 1.0 includes a ratio of greater than 1.1, 1.2, 1.5, 1.7, 2, 3, 4, 10, 20 and the like and a ratio less than 1.0, for example includes a ration of less than 0.9, 0.8, 0.6, 0.4, 0.2, 0.1, 0.05 and the like. In another embodiment of the invention a biomarker product is differentially expressed if the ratio of its level of expression in a first sample as compared with the mean of the second population is greater than or less than 1.0 and includes for example, a ratio of greater than 1.1, 1.2, 1.5, 1.7, 2, 3, 4, 10, 20, or a ratio less than 1, for example 0.9, 0.8, 0.6, 0.4, 0.2, 0.1, 0.05.

"Differentially increased expression" or "up regulation" refers to biomarker product levels which are at least 10% or more, for example, 20%, 30%, 40%, or 50%, 60%, 70%, 80%, 90% higher or more, and/or 1.1 fold, 1.2 fold, 1.4 fold, 1.6 fold, 1.8 fold higher or more, than a control.

"Differentially decreased expression" or "down regulation" refers to biomarker product levels which are at least 10% or more, for example, 20%, 30%, 40%, or 50%, 60%, 70%, 80%, 90% lower or less, and/or 0.9 fold, 0.8 fold, 0.6 fold, 0.4 fold, 0.2 fold, 0.1 fold or less lower than a control.

For example, up regulated or down regulated genes include genes having an increased or decreased level, respectively, of expression of product (e.g. mRNA or protein) in blood isolated from individuals characterized as having one or more colorectal pathologies as compared with normal individuals. In another example, up regulated or down regulated genes include genes having an increased or decreased level, respectively, of expression of product (e.g. mRNA or protein) in blood isolated from individuals having one type of colorectal pathology or collection of colorectal pathologies as compared with individuals having a different type of colorectal pathology or collection of colorectal pathologies, respectively.

For example, up regulated genes include genes having an increased level of biomarker products in a test sample as compared with a control sample.

As used herein, the term "differential hybridization" refers to a difference in a quantitative level of hybridization of a nucleic acid or derivative thereof isolated and/or derived from a sample from a first individual or individuals with a trait to a complementary nucleic acid target as compared with the hybridization of a nucleic acid or derivative thereof isolated and/or derived from a second individual or individuals not having said trait to a complementary nucleic acid target. A "differential hybridization" means that the ratio of the level of hybridization of the first sample as compared with the second sample is not equal to 1.0. For example, the ratio of the level of hybridization of the first sample to the target as compared to the second sample is greater than 1.1, 1.2, 1.5, 1.7, 2, 3, 4, 10, 20, or less than 1, for example 0.9, 0.8, 0.6, 0.4, 0.2, 0.1, 0.05. A differential hybridization also exists if the hybridization is detectable in one sample but not another sample.

As used herein, the term "drug efficacy" refers to the effectiveness of a drug. "Drug efficacy" is usually measured by the clinical response of the patient who has been or is being treated with a drug. A drug is considered to have a high degree of efficacy, if it achieves desired clinical results, for example, the alteration of gene expression and the gene expression pattern reflective of one or more colorectal pathologies as described herein. The amount of drug absorbed may be used to predict a patient's response. A general rule is that as the dose of a drug is increased, a greater effect is seen in the patient until a maximum desired effect is reached. If more drug is administered after the maximum point is reached, the side effects will normally increase.

As used herein, the term "effective amount" refers to the amount of a compound which is sufficient to reduce or prevent the progression and/or severity of one or more colorectal pathologies; prevent the development, recurrence of onset of one or more colorectal pathologies; or enhance or improve the prophylactic or therapeutic effect(s) of another therapy.

As used herein, the term "fragment" in the context of a proteinaceous agent refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide or a protein. In a specific embodiment, a fragment of a protein or polypeptide retains at least one function of the protein or polypeptide. In another embodiment, a fragment of a protein or polypeptide retains at least two, three, four, or five functions of the protein or polypeptide. In some embodiments, a fragment of an antibody retains the ability to immunospecifically bind to an antigen.

As used herein, the term "fusion protein" refers to a polypeptide that comprises an amino acid sequence of a first protein or polypeptide or functional fragment, analog or derivative thereof, and an amino acid sequence of a heterologous protein, polypeptide, or peptide (i.e., a second protein or polypeptide or fragment, analog or derivative thereof different than the first protein or fragment, analog or derivative thereof). In one embodiment, a fusion protein comprises a prophylactic or therapeutic agent fused to a heterologous protein, polypeptide or peptide. In accordance with this embodiment, the heterologous protein, polypeptide or peptide may or may not be a different type of prophylactic or therapeutic agent.

As used herein, a "gene" of the invention can include a gene expressed in blood, a gene expressed in blood and in a non-blood tissue, a gene differentially expressed in blood, a gene expressed in a non-blood cell, a gene expressed in a cell which is not of haematopoietic origin, a gene expressed in a specific subtype of cell found in blood including lymphocytes, granulocytes, leukocytes, basophils and the like. A gene can be an immune response gene or a gene not involved in an immune response. In particular an immune response gene is a gene in the major histocompatibility complex that controls a cells response to a foreign antigen. A gene of the invention can also include a gene which is differentially regulated in response to a foreign antigen introduced into peripheral blood.

As used herein, a "gene expression pattern" or "gene expression profile" indicates the pattern of the level of expression of two or more biomarkers of the invention including 2, 3, 4, 5, 6, 7, 8, 9, 10, 11, 12, 13, 14, 15, 16, 17, 18 or more or all of the biomarkers of the invention. A gene expression pattern or gene expression profile can be determined from the measurement of expression levels of the products of the biomarkers of the invention using any known technique. For example techniques to measure expression of the RNA products of the biomarkers of the invention include, PCR based methods (including reverse transcription-PCR, PCR, QRT-PCR) and non PCR based method, as well as microarray analysis. To measure levels of protein products of the biomarkers of the invention, techniques include densitometric western blotting and ELISA analysis.

As used herein, the term "hybridizing to" or "hybridization" refers to the sequence specific non-covalent binding interactions with a complementary nucleic acid, for example interactions between a target nucleic acid sequence and a nucleic acid member on an array.

As used herein, the term "immunoglobulin" refers to a protein consisting of one or more polypeptides substantially encoded by immunoglobulin genes. The recognized human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus. Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

As used herein, the term "in combination" when referring to therapeutic treatments refers to the use of more than one type of therapy (e.g., more than one prophylactic agent and/or therapeutic agent). The use of the term "in combination" does not restrict the order in which therapies (e.g., prophylactic and/or therapeutic agents) are administered to a subject. A first therapy (e.g., a first prophylactic or therapeutic agent) can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second prophylactic or therapeutic agent) to a subject.

As used herein, "indicative of one or more colorectal pathologies" refers to a determination of a probability that a subject has or will have the one or more colorectal pathologies. In one aspect the application of a formula to data corresponding to biomarker products of a test subject can result in determination of the probability of whether the test subject has one or more colorectal pathologies as compared with not having said one or more colorectal pathologies. In another embodiment, an expression pattern can be indicative of one or more colorectal pathologies including one or more polyps or one or more subtypes of polyps if the expression pattern is found significantly more often in patients with said colorectal pathology than in patients without said colorectal pathology (as determined using routine statistical methods setting confidence levels at a minimum of 70%, 75%, 80%, 85%, 90%, 95% and the like). In some embodiments, an expression pattern which is indicative of disease is found in at least 70%, at least 75%, at least 80%, at least 85%, at least 90%, at least 95% or more in patients who have the disease and is found in less than 10%, less than 8%, less than 5%, less than 2.5%, or less than 1% of patients who do not have the disease. "Indicative of colorectal pathology" can also indicates an expression pattern which more properly categorizes with control expression patterns of individuals with the one or more colorectal pathologies as compared with control expression patterns of individuals without the one or more colorectal pathologies using statistical algorithms for class prediction as would be understood by a person skilled in the art and see for example commercially available programs such as those provided by Silicon Genetics (e.g. GeneSpring™).

As used herein, "isolated" or "purified" when used in reference to a nucleic acid means that a naturally occurring sequence has been removed from its normal cellular (e.g., chromosomal) environment or is synthesized in a non-natural environment (e.g., artificially synthesized). Thus, an "isolated" or "purified" sequence may be in a cell-free solution or placed in a different cellular environment. The term "purified" does not imply that the sequence is the only nucleotide present, but that it is essentially free (about 90-95% pure) of non-nucleotide material naturally associated with it, and thus is distinguished from isolated chromosomes.

As used herein, the terms "isolated" and "purified" in the context of a proteinaceous agent (e.g., a peptide, polypeptide, protein or antibody) refer to a proteinaceous agent which is substantially free of cellular material and in some embodiments, substantially free of heterologous proteinaceous agents (i.e., contaminating proteins) from the cell or tissue source from which it is derived, or substantially free of chemical precursors or other chemicals when chemically synthesized. The language "substantially free of cellular material" includes preparations of a proteinaceous agent in which the proteinaceous agent is separated from cellular components of the cells from which it is isolated or recombinantly produced. Thus, a proteinaceous agent that is substantially free of cellular material includes preparations of a proteinaceous agent having less than about 40%, 30%, 20%, 10%, or 5% (by dry weight) of heterologous proteinaceous agent (e.g., protein, polypeptide, peptide, or antibody; also referred to as a "contaminating protein"). When the proteinaceous agent is recombinantly produced, it is also in some embodiments substantially free of culture medium, i.e., culture medium represents less than about 20%, 10%, or 5% of the volume of the protein preparation. When the proteinaceous agent is produced by chemical synthesis, it is in some embodiments substantially free of chemical precursors or other chemicals, i.e., it is separated from chemical precursors or other chemicals which are involved in the synthesis of the proteinaceous agent. Accordingly, such preparations of a proteinaceous agent have less than about 30%, 20%, 10%, 5% (by dry weight) of chemical precursors or compounds other than the proteinaceous agent of interest. In some embodiments, proteinaceous agents disclosed herein are isolated.

As used herein, a sample which is "isolated and/or derived" includes a sample which has been removed it from its natural environment in a subject and also includes samples which are further modified or altered. For example samples can include tissue, lymph, bodily fluid, blood, RNA, protein, mRNA, serum reduced blood, erythrocyte reduced blood, serum reduced and erythrocyte reduced blood, unfractionated cells of a lysed blood, globin reduced mRNA, cDNA, PCR products and the like.

As used herein, the term "level" or "level of expression" when referring to RNA refers to a measurable quantity (either absolute or relative quantity) of a given nucleic acid as determined by hybridization or measurements such as QRT-PCR and includes use of both SYBR® green and TaqMan® technology and which corresponds in direct proportion with the amount of product of the gene in a sample. Level of expression when referring to RNA can also refer to a measurable quantity of a given nucleic acid as determined by PCR wherein the number of cycles of PCR is limited to 10, 15, 20, 25, 30, 35, 40, 45, 50, 55, or 60 cycles. The level of expression when referring to RNA can also refer to a measurable quantity of a given nucleic acid as determined relative to the amount of total RNA, or cDNA used in QRT-PCR wherein the amount of total RNA used is 100 ng; 50 ng, 25 ng; 10 ng; 5 ng; 1.25 ng; 0.05 ng; 0.3 ng; 0.05 ng; 0.09 ng; 0.08 ng; 0.07 ng; 0.06 ng; or 0.05 ng. The level of expression of a nucleic acid can be determined by any methods known in the art. For microarray analysis, the level of expression is measured by hybridization analysis using nucleic acids corresponding to RNA isolated from one or more individuals according to methods well known in the art. The label can either be incorporated into the RNA or used in another manner as would be understood so as to monitor hybridization. The label used can be a luminescent label, an enzymatic label, a radioactive label, a chemical label or a physical label. In some embodiments, target and/or probe nucleic acids are labeled with a fluorescent molecule. Preferred fluorescent labels include, but are not limited to: fluorescein, amino coumarin acetic acid, tetramethylrhodamine isothiocyanate (TRITC), Texas Red, Cyanine 3 (Cy3) and Cyanine 5 (Cy5). The level of expression when referring to RNA can also refer to a measurable quantity of a given nucleic acid as determined relative to the amount of total RNA or cDNA used in microarray hybridizations wherein the amount of total RNA is 10 µg, 5 µg, 2.5 µg; 2 µg; 1 µg; 0.5 µg; 0.1 µg; 0.05 µg; 0.01 µg; 0.005 µg; 0.001 µg and the like.

As used herein, a "ligand" is a molecule that binds to another. "Polynucleotide Ligands" are those that specifically and/or selectively hybridize to products of the biomarkers and/or derivatives thereof. Polynucleotide ligands can specifically and/or selectively hybridize to RNA and/or protein products of the biomarkers, allowing measurement of the levels of the biomarker products. The polynucleotide ligands may be any of various types of molecule, including but not limited to, any of various combinations of oligonucleotides, cDNA, DNA, RNA, PCR products, synthetic DNA, synthetic RNA, and/or modified nucleotides.

A ligand of the invention can also include a "polypeptide ligand" that specifically or selectively binds to the biomarker products, for example, allowing detection or measurement of the level of biomarker products including either RNA products and/or protein products. A polypeptide ligand may include a scaffold peptide, a linear peptide, or a cyclic peptide. In a preferred embodiment, the polypeptide ligand is an antibody. The antibody can be a human antibody, a chimeric antibody, a recombinant antibody, a humanized antibody, a monoclonal antibody, or a polyclonal antibody. The antibody can be an intact immunoglobulin, e.g., an IgA, IgG, IgE, IgD, IgM or subtypes thereof. The antibody can be conjugated to a functional moiety (e.g., a compound which has a biological or chemical function (which may be a second different polypeptide, a therapeutic drug, a cytotoxic agent, a detectable moiety, or a support. A polypeptide ligand e.g. antibody of the invention interacts with a polypeptide, encoded by one of the genes of a biomarker, with high affinity and specificity. For example, the polypeptide ligand binds to a polypeptide, encoded by one of the genes of a biomarker, with an affinity constant of at least $10^7$ $M^{-1}$, preferably, at least $10^8$ $M^{-1}$, $10^9$ $M^{-1}$, or $10^{10}$ $M^{-1}$. The polynucleotide ligands and protein ligands may be used, according to standard art knowledge, to practice techniques such as Western blotting, immunoprecipitation, enzyme-linked immunosorbent assay (ELISA), protein microarray analysis and the like to measure the level of disclosed biomarker protein products.

An "mRNA" means an RNA complementary to a gene; an mRNA includes a protein coding region, and also may include 5' end and 3' untranslated regions (UTR).

As used herein, the term "majority" refers to a number representing more than 50% (e.g., 51%, 60%, or 70%, or 80% or 90% or up to 100%) of the total members of a composition. The term "majority", when referring to an array, it means more than 50% (e.g., 51%, 60%, or 70%, or 80% or 90% or up to 100%) of the total nucleic acid members that are stably associated with the solid substrate of the array.

Treatment of one or more colorectal pathologies or one or more subtypes of colorectal pathology is defined herein to provide medical aid to counteract the disease itself, the symptoms and/or the progression of the disease. Treatments also include removing the one or more colorectal pathologies and include palliative therapy to help relieve symptoms and improve quality of life. Treatments also include reducing or preventing polyp formation, reducing or preventing polyp differentiation or morphology changes, and can also include development, recurrence and onset.

As used herein, "mRNA integrity" refers to the quality of mRNA extracts from either tissue samples or samples. In one embodiment, mRNA extracts with good integrity do not appear to be degraded when examined by methods well known in the art, for example, by RNA agarose gel electrophoresis (e.g., Ausubel et al., John Wiley & Sons, Inc., 1997, Current Protocols in Molecular Biology). Preferably, the mRNA samples have good integrity (e.g., less than 10%, in some embodiments less than 5%, and more in some embodiments less than 1% of the mRNA is degraded) to truly represent the gene expression levels of sample from which they are extracted.

As used herein, "nucleic acid(s)" and "nucleic acid molecule(s)" are interchangeable with the term "polynucleotide(s)" and it generally refers to any polyribonucleotide or poly-deoxyribonucleotide, which may be unmodified RNA or DNA or modified RNA or DNA or any combination thereof. "Nucleic acids" include, without limitation, single- and double-stranded nucleic acids. As used herein, the term "nucleic acid(s)" also includes DNAs or RNAs as described above that contain one or more modified bases. Thus, DNAs or RNAs with backbones modified for stability or for other reasons are "nucleic acids". The term "nucleic acids" as it is used herein embraces such chemically, enzymatically or metabolically modified forms of nucleic acids, as well as the chemical forms of DNA and RNA characteristic of viruses and cells, including for example, simple and complex cells. A "nucleic acid" or "nucleic acid sequence" may also include regions of single- or double-stranded RNA or DNA or any combinations thereof and can include expressed sequence tags (ESTs) according to some embodiments of the invention. An EST is a portion of the expressed sequence of a gene (i.e., the "tag" of a sequence), made by reverse transcribing a region of mRNA so as to make cDNA.

As defined herein, a "nucleic acid array" refers a plurality of nucleic acids (or "nucleic acid members") localized on a support where each of the nucleic acid members is localized to a unique pre-selected region of a support. In one embodiment, a nucleic acid member is attached to the surface of the support and the nucleic acid member is DNA. In another embodiment, the nucleic acid member is either cDNA or and oligonucleotide. In another embodiment, the nucleic acid member localized on the support is cDNA synthesized by polymerase chain reaction (PCR). The term "nucleic acid", as used herein, is interchangeable with the term "polynucleotide". In another preferred embodiment, a "nucleic acid array" refers to a plurality of unique nucleic acids attached to nitrocellulose or other membranes used in Southern and/or Northern blotting techniques.

As used herein "nucleic acid sample for hybridization to an array" is defined as a nucleic acid isolated and/or derived from a sample capable of binding to a nucleic acid bound to an array of complementary sequence through sets of non-covalent bonding interactions including complementary base pairing interactions. The nucleic acid sample for hybridization to an array can either be an isolated nucleic acid sequence corresponding to a gene or portion thereof, total RNA or mRNA isolated from a sample. In one embodiment, the nucleic acid sample for hybridization to an array is a blood nucleic acid sample (including whole blood, lysed blood, serum reduced, erythrocyte reduced blood, or peripheral blood leukocytes (PBLs)). In some embodiments, the nucleic acid sample is single- or double-stranded DNA, RNA, or DNA-RNA hybrids, from human blood and in some embodiments from RNA or mRNA extracts.

As used herein, a "nucleic acid member on an array" or a "nucleic acid member" includes nucleic acid immobilized on an array and capable of binding to a nucleic acid probes or samples of complementary sequence through sets of non-covalent bonding interactions, including complementary base pairing interactions. As used herein, a nucleic acid member or target may include natural (i.e., A, G, C, or T) or modified bases (7-deazaguanosine, inosine, etc.). In addition, the bases in nucleic acids may be joined by a linkage other than a phosphodiester bond, so long as it does not interfere with hybridization (i.e., the nucleic acid target still specifically binds to its complementary sequence under standard stringent or selective hybridization conditions). Thus, nucleic acid members may be peptide nucleic acids in which the constituent bases are joined by peptide bonds rather than phosphodiester linkages. In one embodiment, a conventional nucleic acid array of 'target' sequences bound to the array can be representative of the entire human genome, e.g. Affymetrix chip, and the biomarker or isolated biomarker consisting of or comprising one or more of the genes set out in Table 1, Table 2, or Table 11, or Table 12 or gene probes (e.g. Table 4) is applied to the conventional array. In another embodiment, sequences bound to the array can be the biomarker or isolated biomarker according to the invention and total cellular RNA is applied to the array.

As used herein, the term "oligonucleotide" is defined as a molecule comprised of two or more deoxyribonucleotides and/or ribonucleotides, and preferably more than three. Its exact size will depend upon many factors which, in turn, depend upon the ultimate function and use of the oligonucleotide. The oligonucleotides may be from about 8 to about 1,000 nucleotides long. Although oligonucleotides of 8 to 100 nucleotides are useful in the invention, preferred oligonucleotides range from about 8 to about 15 bases in length, from about 8 to about 20 bases in length, from about 8 to about 25 bases in length, from about 8 to about 30 bases in length, from about 8 to about 40 bases in length or from about 8 to about 50 bases in length.

As used herein, "patient" or "individual" or "subject" refers to a mammal and is in some embodiments human.

As used herein the term "peptide" refers to a polypeptide which is 50 amino acids in length or less.

As used herein, the phrase "pharmaceutically acceptable salt(s)" includes, but is not limited to, salts of acidic or basic groups that may be present in compounds identified using the methods of the present invention. Compounds that are basic in nature are capable of forming a wide variety of salts with various inorganic and organic acids. The acids that can be used to prepare pharmaceutically acceptable acid addition salts of such basic compounds are those that form non-toxic acid addition salts, i.e., salts containing pharmacologically acceptable anions, including but not limited to sulfuric, citric, maleic, acetic, oxalic, hydrochloride, hydrobromide, hydroiodide, nitrate, sulfate, bisulfate, phosphate, acid phosphate, isonicotinate, acetate, lactate, salicylate, citrate, acid citrate, tartrate, oleate, tannate, pantothenate, bitartrate, ascorbate, succinate, maleate, gentisinate, fumarate, gluconate, glucaronate, saccharate, formate, benzoate, glutamate, methanesulfonate, ethanesulfonate, benzenesulfonate, p-toluenesulfonate and pamoate (i.e., 1,1'-methylene-bis-(2-hydroxy-3-naphthoate)) salts. Compounds that include an amino moiety may form pharmaceutically acceptable salts with various amino acids, in addition to the acids mentioned above. Compounds that are acidic in nature are capable of forming base salts with various pharmacologically acceptable cations. Examples of such salts include alkali metal or alkaline earth metal salts and, particularly, calcium, magnesium, sodium lithium, zinc, potassium, and iron salts.

As used herein, "polynucleotide" encompasses single and double stranded polynucleotides, such as double-stranded DNA, single-stranded DNA, double-stranded RNA, single-stranded RNA or DNA-RNA double stranded hybrids, and the like, of more than 8 nucleotides in length. The term "polynucleotide" includes a polymeric form of nucleotides of any length, either ribonucleotides or deoxyribonucleotides, that comprise purine and pyrimidine bases, or other natural, chemically or biochemically modified, non-natural, or derivatized nucleotide bases. The backbone of the polynucleotide can comprise sugars and phosphate groups, as may typically be found in RNA or DNA, or modified or substituted sugar or phosphate groups. A polynucleotide may comprise modified nucleotides, such as methylated nucleotides and nucleotide analogs. The sequence of nucleotides may be interrupted by non-nucleotide components.

As used herein a "polynucleotide ligand that specifically and/or selectively hybridizes to RNA products of the biomarkers" ("biomarker RNA products") and/or to polynucleotides corresponding to biomarker RNA products, allowing measurement of levels of the RNA products are disclosed.

The polynucleotide ligands may be any of various types of molecule, including but not limited to, any of various combinations of oligonucleotides, cDNA, DNA, RNA, PCR products, synthetic DNA, synthetic RNA, and/or modified nucleotides.

As used herein, the term "proteinaceous agent" refers to polypeptides, proteins, peptides, and the like.

As used herein, "polypeptide sequences encoded by or protein products of" refers to the amino acid sequences obtained after translation of the protein coding region of an mRNA transcribed from a gene. As would be understood, one or more mRNA nucleotide sequences for each of the genes (biomarkers) of the invention can be identified using public databases such as the NCBI database found at http://www.ncbi.nlm.nih.gov. For example, representative mRNA species of those biomarkers identified in Table 2 and Table 12 are provided by their Human Genbank Accession number (see Table 3 and Table 13 respectively) and the corresponding polypeptide sequence is identified by a Protein Accession number (see Table 3 and Table 13 respectively). These Genbank Accession numbers provide the sequence of products of the biomarkers. When a protein or fragment of a protein is used to immunize a host animal, numerous regions of the protein may induce the production of antibodies which bind specifically to a given region or three-dimensional structure on the protein; these regions or structures are referred to as epitopes or antigenic determinants. As used herein, "antigenic fragments" refers portions of a polypeptide that contains one or more epitopes. Epitopes can be linear, comprising essentially a linear sequence from the antigen, or conformational, comprising sequences which are genetically separated by other sequences but come together structurally at the binding site for the polypeptide ligand. "Antigenic fragments" may be 5000, 1000, 500, 400, 300, 200, 100, 50 or 25 or 20 or 10 or 5 amino acids in length.

As used herein, the terms "prevent", "preventing" and "prevention" refer to the prevention of the development, recurrence or formation or growth or transformation of colorectal pathology including polyps or subtypes of polyps resulting from the administration of one or more compounds identified in accordance the methods of the invention or the administration of a combination of such a compound and another therapy.

The term, "primer", as used herein refers to an oligonucleotide, whether occurring naturally as in a purified restriction digest or produced synthetically, which is capable of acting as a point of initiation of synthesis when placed under conditions in which synthesis of a primer extension product, which is complementary to a nucleic acid strand, is induced, i.e., in the presence of nucleotides and an inducing agent such as a DNA polymerase and at a suitable temperature and pH. The primer may be either single-stranded or double-stranded and must be sufficiently long to prime the synthesis of the desired extension product in the presence of the inducing agent. The exact length of the primer will depend upon many factors, including temperature, source of primer and the method used and also the specificity or selectivity of the desired priming (ie so as to act as a point of initiation of synthesis which is specific or selective for a given sequence of polynucleotide). For example, for testing applications, depending on the complexity of the target sequence, the oligonucleotide primer typically contains 15-25, but may contain additional nucleotides as well as fewer nucleotides. In addition, in some cases the primer can be selected so as to have a high GC content, can be selected so as to bind to regions which do not contain SNPs, can be selected so as to span an intron/exon junction of RNA and the like. Other factors involved in determining the appropriate length and/or features of a primer are readily known to one of ordinary skill in the art.

The term "biomarker specific set of primers" or "primer sets" as used herein refers to a set of polynucleotide primers wherein one primer primes the synthesis of a sense strand, and the second primer primes the synthesis of an antisense strand so as to produce double stranded DNA complementary to a portion of one or more RNA products of the biomarker of the invention. For example, the primers can include a first primer which is a sequence that can selectively hybridize to RNA, cDNA or EST complementary to a region of the biomarker of the invention to create an extension product and a second primer capable of selectively hybridizing to the extension product, which are used to produce double stranded DNA complementary to a region of the biomarker of the invention or products of the biomarker of the invention. The invention includes primers useful for measuring the level of RNA products of a biomarker. Table 4, Table 6, Table 14, Table 16 and Table 17 provide representative species of primers of the invention. A biomarker specific set of primers can be selected so that they will selectively amplify only portions of a polynucleotide complementary to one or more RNA products of a biomarker and do not amplify portions of polynucleotides complementary to other biomarkers.

As used herein, the term "probe" means oligonucleotides and analogs thereof and refers to a range of chemical species that recognize polynucleotide target sequences through hydrogen bonding interactions with the nucleotide bases of the target sequences. The probe or the target sequences may be single- or double-stranded RNA or single- or double-stranded DNA or a combination of DNA and RNA bases. A probe is at least 8 nucleotides in length and less than the length of a complete gene. A probe may be 10, 20, 30, 50, 75, 100, 150, 200, 250, 400, 500 and up to 2000 nucleotides in length as long as it is less than the full length of the target gene. In some embodiments, probes can be used as target sequences bound on a microarray. In some embodiments, probes can be used for quantitative real-time PCR (QRT-PCR) and include modifications so as to incorporate a fluorophore, a quencher, a minor groove binding reagent or other substances which allow detection of the probe during PCR amplification. The probe can also be modified so as to have both a detectable tag and a quencher molecule, for example Taqman® and Molecular Beacon® probes. The invention includes probes useful for measuring the expression of RNA products of biomarkers of the invention. For example, Table 4, Table 6, and Table 14 and Table 17 provides some representative species of a probe of the invention useful for QRT-PCR.

The oligonucleotides and analogs thereof may be RNA or DNA, or analogs of RNA or DNA, commonly referred to as antisense oligomers or antisense oligonucleotides. Such RNA or DNA analogs comprise but are not limited to 2-'O-alkyl sugar modifications, methylphosphonate, phosphorothiate, phosphorodithioate, formacetal, 3'-thioformacetal, sulfone, sulfamate, and nitroxide backbone modifications, and analogs wherein the base moieties have been modified. In addition, analogs of oligomers may be polymers in which the sugar moiety has been modified or replaced by another suitable moiety, resulting in polymers which include, but are not limited to, morpholino analogs and peptide nucleic acid (PNA) analogs (Egholm, et al. Peptide Nucleic Acids (PNA)—Oligonucleotide Analogues with an Achiral Peptide Backbone, (1992)).

Probes may also be mixtures of any of the oligonucleotide analog types together or in combination with native DNA or RNA and may also include linker species. At the same time, the oligonucleotides and analogs thereof may be used alone or in combination with one or more additional oligonucleotides or analogs thereof.

As used herein, the term "products of the biomarker" or "biomarker products" refers to a species of RNA or a species of protein (wherein a species of RNA or protein can include multiple copies) isolated and/or derived from a sample including a tissue sample, a lymph sample, a lymph tissue sample, or a blood sample, or a fraction of a blood sample which corresponds to the biomarker (i.e., is transcribed from the gene or genetic element or is translated from RNA which is transcribed from the gene or genetic element). See Table 3 and Table 13. The RNA may be pre-mRNA, mRNA, spliced variants of mRNA and the like. The protein may be in its native state or post-translationally processed in any one of various ways.

As used herein, "a plurality of" or "a set of" refers to two or more, for example, 2 or more, 3 or more, 4 or more, 5 or more, 6 or more, 7 or more, 8 or more, 9 or more 10 or more etc.

As used herein, "pre-selected region", "predefined region", or "unique position" refers to a localized area on a substrate which is, was, or is intended to be used for the deposit of a nucleic acid and is otherwise referred to herein in the alternative as a "selected region" or simply a "region." The preselected region may have any convenient shape, e.g., circular, rectangular, elliptical, wedge-shaped, etc. In some embodiments, a pre-selected region is smaller than about 1 cm$^2$, more preferably less than 1 mm$^2$, still more preferably less than 0.5 mm$^2$, and in some embodiments less than 0.1 mm$^2$. A nucleic acid member at a "pre-selected region", "predefined region", or "unique position" is one whose identity (e.g., sequence) can be determined by virtue of its position at the region or unique position.

As used herein, the terms "prophylactic agent" and "prophylactic agents" refer to any compound(s) which can be used to prevent polyp formation, development, recurrence or onset. In certain embodiments, the term "prophylactic agent" refers to a compound identified in the screening assays described herein. In certain other embodiments, the term "prophylactic agent" refers to an agent other than a compound identified in the screening assays described herein which is known to be useful for, or has been or is currently being used to prevent or impede the onset, development and/or progression or transformation of one or more colorectal pathologies including one or more polyps or subtypes of polyps.

As used herein, the phrase "prophylactically effective amount" refers to the amount of a therapy (e.g., a prophylactic agent) which is sufficient to result in the prevention of the development, recurrence or onset or progression or transformation of one or more colorectal pathologies including one or more polyps or subtypes of polyps; the reduction or amelioration of the progression and/or severity of one or more colorectal pathologies including one or more polyps or subtypes of polyps; or the prevention of colorectal pathology including polyps or subtypes of polyps advancing to colorectal cancer.

As used herein, the terms "protein" and "polypeptide" are used interchangeably to refer to a chain of amino acids linked together by peptide bonds. In a specific embodiment, a protein is composed of less than 200, less than 175, less than 150, less than 125, less than 100, less than 50, less than 45, less than 40, less than 35, less than 30, less than 25, less than 20, less than 15, less than 10, or less than 5 amino acids linked together by peptide bonds. In another embodiment, a protein is composed of at least 200, at least 250, at least 300, at least 350, at least 400, at least 450, at least 500 or more amino acids linked together by peptide bonds.

A "protein coding region" refers to the portion of the mRNA encoding a polypeptide.

As used herein the "reference population" or "test population" refers to one or more populations of "control samples" used to develop one or more classifier. In one embodiment a single reference population can be divided into subpopulations. In another embodiment, two or more reference populations can be used. In some instances a classifier can be developed to differentiate between individuals with one or more colorectal pathologies or one or more polyps or one or more subtypes of polyps and individuals without the same colorectal pathology or one or more polyps or one or more subtypes of polyps. In some instances a first reference population would be comprised of individuals with the one or more colorectal pathologies and a second reference population would be comprised of individuals without the one or more colorectal pathologies. The "reference population" or "test population" can be comprised of control samples from a number of individuals diagnosed with one or more colorectal pathologies including one or more polyps or one or more subtypes of polyps and individuals not having the colorectal pathologies or not having the one or more polyps or not having the one or more subtypes of polyps as determined using conventional diagnostic techniques. Note that in some embodiments the population of individuals having one or more colorectal pathologies can be selected to include individuals having a single subtype of polyp or one or more subtypes of polyps. In other embodiments the individuals who do not have one or more colon pathologies can include individuals who have been diagnosed with other disease or diseases. In another embodiment the individuals who do not have one or more colon pathologies can include individuals who have been diagnosed with other cancers. In one embodiment the "reference population" or "test population" is comprised of a roughly equivalent number of "control samples" from each trait subgroup (e.g., in this instance wherein said trait is a determination of status with regards to the presence of colorectal pathology). In another embodiment, each trait subgroup (e.g. having or not having colorectal pathology) of the "reference population" has a similar distribution with regards to other traits e.g., age, sex, drug status, etc.

As used herein, the term "selectively binds" in the context of proteins encompassed by the invention refers to the specific interaction of any two of a peptide, a protein, a polypeptide an antibody, wherein the interaction preferentially occurs as between any two of a peptide, protein, polypeptide and antibody preferentially as compared with any other peptide, protein, polypeptide and antibody. For example, when the two molecules are protein molecules, a structure on the first molecule recognizes and binds to a structure on the second molecule, rather than to other proteins. "Selective binding", "Selective binding", as the term is used herein, means that a molecule binds its specific binding partner with at least 2-fold greater affinity, and preferably at least 10-fold, 20-fold, 50-fold, 100-fold or higher affinity than it binds a non-specific molecule.

As used herein "selective hybridization" can refer to a hybridization which occurs as between a polynucleotide and an RNA or protein product of the biomarker of the invention wherein the hybridization is such that the polynucleotide binds to the RNA products of the biomarker of the invention preferentially to the RNA products of other genes in the genome in question. In a preferred embodiment a polynucleotide which "selectively hybridizes" is one which hybridizes with a selectivity of greater than 70%, greater than 80%, greater than 90% and most preferably on 100% (ie cross hybridization with other RNA species preferably occurs at less than 30%, less than 20%, less than 10%). As would be understood to a person skilled in the art, a polynucleotide which "selectively hybridizes" to the RNA products of a biomarker of the invention can be determined by taking into account the length and composition.

As used herein, "specifically hybridizes", "specific hybridization" can refer to hybridization which occurs when two nucleic acid sequences are substantially complementary (at least about 65% complementary over a stretch of at least 14 to 25 nucleotides, preferably at least about 75% complementary, more preferably at least about 90% complementary). See Kanehisa, M., 1984, Nucleic acids Res., 12:203, incorporated herein by reference. As a result, it is expected that a certain degree of mismatch is tolerated. Such mismatch may be small, such as a mono-, di- or tri-nucleotide. Alternatively, a region of mismatch can encompass loops, which are defined as regions in which there exists a mismatch in an uninterrupted series of four or more nucleotides. Numerous factors influence the efficiency and selectivity of hybridization of two nucleic acids, for example, the hybridization of a nucleic acid member on an array to a target nucleic acid sequence. These factors include nucleic acid member length, nucleotide sequence and/or composition, hybridization temperature, buffer composition and potential for steric hindrance in the region to which the nucleic acid member is required to hybridize. A positive correlation exists between the nucleic acid length and both the efficiency and accuracy with which a nucleic acid will anneal to a target sequence. In particular, longer sequences have a higher melting temperature ($T_M$) than do shorter ones, and are less likely to be repeated within a given target sequence, thereby minimizing non-specific hybridization. Hybridization temperature varies inversely with nucleic acid member annealing efficiency. Similarly the concentration of organic solvents, e.g., formamide, in a hybridization mixture varies inversely with annealing efficiency, while increases in salt concentration in the hybridization mixture facilitate annealing. Under stringent annealing conditions, longer nucleic acids, hybridize more efficiently than do shorter ones, which are sufficient under more permissive conditions.

As used herein, "spotting" or "attaching" refers to a process of depositing a nucleic acid member onto a solid substrate to form a nucleic acid array such that the nucleic acid is stably bound to the solid substrate via covalent bonds, hydrogen bonds or ionic interactions.

As used herein, "stably associated" refers to a nucleic acid that is stably bound to a solid substrate to form an array via covalent bonds, hydrogen bonds or ionic interactions such that the nucleic acid retains its unique pre-selected position relative to all other nucleic acids that are stably associated with an array, or to all other pre-selected regions on the solid substrate under conditions in which an array is typically analyzed (i.e., during one or more steps of hybridization, washes, and/or scanning, etc.).

As used herein, "substrate" or "support" when referring to an array refers to a material capable of supporting or localizing an oligonucleotide or cDNA member. The support may be biological, non-biological, organic, inorganic, or a combination of any of these, existing as particles, strands, precipitates, gels, sheets, tubing, spheres, beads, containers, capillaries, pads, slices, films, plates, slides, chips, etc. Often, the substrate is a silicon or glass surface, (poly)tetrafluoroethylene, (poly)vinylidenedifluoride, polystyrene, polycarbonate, a charged membrane, such as nylon 66 or nitrocellulose, or combinations thereof. In one embodiment, the support is glass. In some embodiments, at least one surface of the substrate will be substantially flat. In some embodiments, the support will contain reactive groups, including, but not limited to, carboxyl, amino, hydroxyl, thiol, and the like. In one embodiment, the support is optically transparent.

As herein used, the term "standard stringent conditions" means hybridization will occur only if there is at least 95% and preferably, at least 97% identity between the sequences, wherein the region of identity comprises at least 10 nucleotides. In one embodiment, the sequences hybridize under stringent conditions following incubation of the sequences overnight at 42° C., followed by stringent washes (0.2×SSC at 65° C.). The degree of stringency of washing can be varied by changing the temperature, pH, ionic strength, divalent cation concentration, volume and duration of the washing. For example, the stringency of hybridization may be varied by conducting the hybridization at varying temperatures below the melting temperatures of the probes. The melting temperature of the probe may be calculated using the following formulas:

For oligonucleotide probes, between 14 and 70 nucleotides in length, the melting temperature (Tm) in degrees Celcius may be calculated using the formula: $Tm=81.5+16.6(\log [Na+])+0.41 \text{(fraction G+C)}-(600/N)$ where N is the length of the oligonucleotide.

For example, the hybridization temperature may be decreased in increments of 5° C. from 68° C. to 42° C. in a hybridization buffer having a Na$^+$ concentration of approximately 1M. Following hybridization, the filter may be washed with 2×SSC, 0.5% SDS at the temperature of hybridization. These conditions are considered to be "moderate stringency" conditions above 50° C. and "low stringency" conditions below 50° C. A specific example of "moderate stringency" hybridization conditions is when the above hybridization is conducted at 55° C. A specific example of "low stringency" hybridization conditions is when the above hybridization is conducted at 45° C.

If the hybridization is carried out in a solution containing formamide, the melting temperature may be calculated using the equation $Tm=81.5+16.6(\log [Na+])+0.41\text{(fraction G+C)}-(0.63\% \text{ formamide})-(600/N)$, where N is the length of the probe.

For example, the hybridization may be carried out in buffers, such as 6×SSC, containing formamide at a temperature of 42° C. In this case, the concentration of formamide in the hybridization buffer may be reduced in 5% increments from 50% to 0% to identify clones having decreasing levels of homology to the probe. Following hybridization, the filter may be washed with 6×SSC, 0.5% SDS at 50° C. These conditions are considered to be "moderate stringency" conditions above 25% formamide and "low stringency" conditions below 25% formamide. A specific example of "moderate stringency" hybridization conditions is when the above hybridization is conducted at 30% formamide. A specific example of "low stringency" hybridization conditions is when the above hybridization is conducted at 10% formamide.

As used herein, the term "significant match", when referring to nucleic acid sequences, means that two nucleic acid sequences exhibit at least 65% identity, at least 70%, at least 75%, at least 80%, at least 85%, and preferably, at least 90% identity, using comparison methods well known in the art (i.e., Altschul, S. F. et al., 1997, *Nucl. Acids Res.*, 25:3389-3402; Schäffer, A. A. et al., 1999, *Bioinformatics* 15: 1000-1011). As used herein, "significant match" encompasses non-contiguous or scattered identical nucleotides so long as the sequences exhibit at least 65%, and preferably, at least 70%, at least 75%, at least 80%, at least 85%, and preferably, at least 90% identity, when maximally aligned using alignment methods routine in the art.

As used herein, the term "synergistic" refers to a combination of a compound identified using one of the methods described herein, and another therapy (e.g., agent), which is more effective than the additive effects of the therapies. In some embodiments, such other therapy has been or is currently being to prevent, treat, or ameliorate one or more colorectal pathologies including one or more polyps or one or more subtypes of polyps. A synergistic effect of a combination of therapies (e.g., prophylactic or therapeutic agents) permits the use of lower dosages of one or more of the therapies and/or less frequent administration of said therapies to an individual with colorectal pathologies including polyps or subtypes of polyps. The ability to utilize lower dosages of a therapy (e.g., a prophylactic or therapeutic agent) and/or to administer said therapy less frequently reduces the toxicity associated with the administration of said agent to an individual without reducing the efficacy of said therapies in the prevention or treatment of colorectal pathology including polyps or subtypes of polyps. In addition, a synergistic effect can result in improved efficacy of therapies (e.g., agents) in the prevention or treatment of colorectal pathology including polyps or subtypes of polyps. Finally, a synergistic effect of a combination of therapies (e.g., prophylactic or therapeutic agents) may avoid or reduce adverse or unwanted side effects associated with the use of either therapy alone.

As used herein, a "therapeutic agent" or "agent" refers to a compound that increases or decreases the expression of a polynucleotide or polypeptide sequences that are differentially expressed in a sample from an individual having one or more colorectal pathologies including polyps or a subtype of polyps. The invention provides for a "therapeutic agent" that 1) prevents the formation of colorectal pathology 2) reduces, delays, or eliminates advancement or transformation of colorectal pathology and/or 3) restores one or more expression profiles of one or more colorectal pathology indicative nucleic acids or polypeptides of a patient to a profile more similar to that of a normal individual when administered to a patient. In addition, the terms "therapeutic agent" and "therapeutic agents" refer to any compound(s) which can be used in the treatment or prevention of colorectal pathology or polyps or a subtype of polyps. In certain embodiments, the term "therapeutic agent" refers to a compound identified in the screening assays described herein. In other embodiments, the term "therapeutic agent" refers to an agent other than a compound identified in the screening assays described herein which is known to be useful for, or has been or is currently being used to treat or prevent colorectal pathology or polyps or subtypes of polyps.

As used herein, the term "therapeutically effective amount" refers to that amount of a therapy (e.g., a therapeutic agent) sufficient to treat one or more colorectal pathologies including polyps or one or more subtypes of polyps; prevent one or more colorectal pathologies including polyps or one or more subtypes of polyps; prevent colorectal pathologies including polyps or one or more subtypes of polyps from transforming and/or advancing to colorectal cancer, cause regression of colorectal pathology, polyps or one or more subtypes of polyps, or to enhance or improve the therapeutic effect(s) of another therapy (e.g., therapeutic agent). In a specific embodiment, a therapeutically effective amount refers to the amount of a therapy (e.g., a therapeutic agent) that modulates gene expression of the products of the biomarkers of the inventions. In some embodiments, a therapeutically effective amount of a therapy (e.g., a therapeutic agent) modulates gene expression of the products of the biomarkers of the invention at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% relative to a control therapeutic agent such as phosphate buffered saline ("PBS").

As used herein, the terms "treat", "treatment" and "treating" refer to the prevention of one or more colorectal pathologies including polyp formation or the formation of one or more subtypes of polyps, development, recurrence onset or transformation of one or more colorectal pathologies and, the reduction or amelioration of the progression and/or severity of one or more colorectal pathologies including polyps or subtypes thereof resulting from the administration of one or more compounds identified in accordance the methods of the invention, or a combination of one or more compounds identified in accordance with the invention and another therapy.

As used herein, a "tissue nucleic acid sample", refers to nucleic acids isolated and/or derived from tissue, for example polyp tissue, colon tissue, rectum tissue, lymphoid tissue, and the like. In some embodiments, a tissue nucleic acid sample is total RNA, mRNA or is a nucleic acid corresponding to RNA, for example, cDNA. A tissue nucleic acid sample can also include a PCR product derived from total RNA, mRNA or cDNA.

(C) Samples for Use in the Invention

Samples for use in the invention include refers to any one of various type of molecules, cells and/or tissues which can be isolated and/or derived from a test subject and/or control subject, and which contains one or more biomarker products. The sample can be isolated and/or derived from any fluid, cell or tissue. The sample can also be one which is isolated and/or derived from any fluid and/or tissue which predominantly comprises blood cells.

The sample which is isolated and/or derived from an individual can be assayed for gene expression products, particularly genes expression products differentially expressed in individuals with or without one or more colorectal pathologies. In one embodiment, the sample is a fluid sample, a lymph sample, a lymph tissue sample or a blood sample. In one embodiment the sample is isolated and/or derived from peripheral blood. Alternately, the sample may be isolated and/or derived from alternate sources, including from any one of various types of lymphoid tissue.

Examples of samples isolated and/or derived from blood include samples of whole blood, serum-reduced whole blood, serum-depleted blood, and serum-depleted and erythrocyte depleted blood.

Unless otherwise indicated herein, samples obtained from any individual may be used in accordance with the methods of the invention. Examples of individuals from which such a sample may be obtained and utilized in accordance with the methods of the invention include, but are not limited to, individuals suspected of having one or more colorectal pathologies, individuals diagnosed as having one or more colorectal pathologies; individuals that have not been diagnosed with having one or more colorectal pathologies; individuals who have been confirmed as not having one or more colorectal pathologies.

In a further embodiment, the individual from whom a sample may be obtained is a test subject wherein it is unknown whether the person has one or more colorectal pathologies or not. In another embodiment, the individual from whom a sample may be obtained is a test subject wherein it is unknown whether the person has one or more colorectal pathologies or not.

Blood

In one aspect of the invention, a sample of blood is obtained from an individual according to methods well known in the art. A sample of blood may be obtained from an individual, for example a subject having one or more colorectal pathologies, suspected of having one or more colorectal pathologies or not having one or more colorectal pathologies. In some embodiments, a drop of blood is collected from a simple pin prick made in the skin of an individual. Blood may be drawn from an individual from any part of the body (e.g., a finger, a hand, a wrist, an arm, a leg, a foot, an ankle, a stomach, and a neck) using techniques known to one of skill in the art, in particular methods of phlebotomy known in the art.

The amount of blood collected will vary depending upon the site of collection, the amount required for a method of the invention, and the comfort of the individual. However, an advantage of one embodiment of the present invention is that the amount of blood required to implement the methods of the present invention can be so small that more invasive procedures are not required to obtain the sample. For example, in some embodiments, all that is required is a drop of blood. This drop of blood can be obtained, for example, from a simple pinprick. In some embodiments, any amount of blood is collected that is sufficient to detect the expression of 1, 2, 3, 4, 5, 6, 7, 8, 9, 10, 11, 12, 13, 14, 15, 16, 17, 18 or all of the genes in Table 1 and Table 2 and Table 11 and Table 12. As such, in some embodiments, the amount of blood that is collected is 1 ml or less, 0.5 ml or less, 0.1 ml or less, or 0.01 ml or less. However, the present invention is not limited to such embodiments. In some embodiments more blood is available and in some embodiments, more blood can be used to effect the methods of the present invention. As such, in various specific embodiments, 0.001 ml, 0.005 ml, 0.01 ml, 0.05 ml, 0.1 ml, 0.15 ml, 0.2 ml, 0.25 ml, 0.5 ml, 0.75 ml, 1 ml, 1.5 ml, 2 ml, 3 ml, 4 ml, 5 ml, 10 ml, 15 ml or more of blood is collected from a subject. In another embodiment, 0.001 ml to 15 ml, 0.01 ml to 10 ml, 0.1 ml to 10 ml, 0.1 ml to 5 ml, 1 to 5 ml of blood is collected from an individual. In a further embodiment, 0.001-100 ml, preferably 0.01-50 ml, more preferably 0.01-25 ml and most preferably 0.01-1 ml of blood is collected from an individual.

In some embodiments of the present invention, blood is stored within a K3/EDTA tube (e.g., from Becton Dickinson). In another embodiment, one can utilize tubes for storing blood which contain stabilizing agents such as disclosed in U.S. Pat. No. 6,617,170 (which is incorporated herein by reference). In another embodiment the PAXgene™ blood RNA system: provided by PreAnalytiX, a Qiagen/BD company, may be used to collect blood. In yet another embodiment, the Tempus™ blood RNA collection tubes, offered by Applied Biosystems may be used. Tempus™ collection tubes provide a closed evacuated plastic tube containing RNA stabilizing reagent for whole blood collection.

The blood collected is in some embodiments utilized immediately or within 1 hour, 2 hours, 3 hours, 4 hours, 5 hours or 6 hours or is optionally stored at temperatures such as 4° C., or at −20° C. prior to use in accordance with the methods of the invention. In some embodiments, a portion of the blood sample is used in accordance with the invention at a first instance of time whereas one or more remaining portions of the blood sample (or fractions thereof) are stored for a period of time for later use. For longer-term storage, storage methods well known in the art, such as storage at cryo temperatures (e.g. below −60° C.) can be used. In some embodiments, in addition to storage of the blood or instead of storage of the blood, plasma, serum, isolated nucleic acid or proteins are stored for a period of time for later use in accordance with methods known in the art.

In one aspect, whole blood is obtained from an individual according to the methods of phlebotomy well known in the art. Whole blood includes blood which can be used as is, and includes blood wherein the serum or plasma has been removed or reduced, and the RNA or mRNA from the remaining blood sample has been isolated in accordance with methods well known in the art (e.g., using, in some embodiments, gentle centrifugation at 300 to 800×g for 5 to 10 minutes). In a specific embodiment, whole blood (i.e., unfractionated blood) obtained from a subject is mixed with lysing buffer (e.g., Lysis Buffer (1 L): 0.6 g EDTA; 1.0 g $KHCO_2$, 8.2 g $NH_4Cl$ adjusted to pH 7.4 (using NaOH)), the sample is centrifuged and the cell pellet retained, and RNA or mRNA extracted in accordance with methods known in the art ("lysed blood") (see for example Sambrook et al.). In one embodiment, it is helpful to use unfractionated whole blood is preferred since it avoids the costly and time-consuming process to separate out the cell types within the blood (Kimoto, 1998, Mol. Gen. Genet 258:233-239; Chelly J et al., 1989, Proc. Nat. Acad. Sci. USA 86:2617-2621; Chelly J et al., 1988, Nature 333:858-860).

In some embodiments of the present invention, whole blood collected from an individual is fractionated (i.e., separated into components) before isolated products of the biomarkers from the sample. In one embodiment, blood is serum depleted (or serum reduced). In another embodiment the blood is plasma depleted (or plasma reduced). In yet other embodiments blood is erythrocyte depleted or reduced. In some embodiments erythrocyte reduction is performed by preferentially lysing the red blood cells. In other embodiments, erythrocyte depletion or reduction is performed by lysing the red blood cells and further fractionating the remaining cells. In yet other embodiments erythrocyte depletion or reduction is performed but the remaining cells are not further fractionated. In other embodiments blood cells are separated from whole blood collected from an individual using other techniques known in the art. For example, blood collected from an individual can be subjected to Ficoll-Hypaque (Pharmacia) gradient centrifugation. Such centrifugation may separate various types of cells from a blood sample. In particular, Ficoll-Hypaque gradient centrifugation is useful to isolate peripheral blood leukocytes (PBLs) which can be used in accordance with the methods of the invention.

By way of example but not limitation, macrophages can be obtained as follows. Mononuclear cells are isolated from peripheral blood of a subject, by syringe removal of blood followed by Ficoll-Hypaque gradient centrifugation. Tissue culture dishes are pre-coated with the subject's own serum or with AB+ human serum and incubated at 37° C. for one hour. Non-adherent cells are removed by pipetting. Cold (4° C.) 1 mM EDTA in phosphate-buffered saline is added to the adherent cells left in the dish and the dishes are left at room temperature for fifteen minutes. The cells are harvested, washed with RPMI buffer and suspended in RPMI buffer. Increased numbers of macrophages can be obtained by incubating at 37° C. with macrophage-colony stimulating factor (M-CSF). Antibodies against macrophage specific surface markers, such as Mac-1, can be labeled by conjugation of an affinity compound to such molecules to facilitate detection and separation of macrophages. Affinity compounds that can be used include but are not limited to biotin, photobiotin, fluorescein isothiocyante (FITC), or phycoerythrin (PE), or other compounds known in the art. Cells retaining labeled antibodies are then separated from cells that do not bind such antibodies by techniques known in the art such as, but not limited to, various cell sorting methods, affinity chromatography, and panning.

Blood cells can be sorted using a using a fluorescence activated cell sorter (FACS). Fluorescence activated cell sorting (FACS) is a known method for separating particles, including cells, based on the fluorescent properties of the particles. See, for example, Kamarch, 1987, Methods Enzymol 151:150-165. Laser excitation of fluorescent moieties in the individual particles results in a small electrical charge allowing electromagnetic separation of positive and negative particles from a mixture. An antibody or ligand used to detect a blood cell antigenic determinant present on the cell surface of particular blood cells is labeled with a fluorochrome, such as FITC or phycoerythrin. The cells are incubated with the fluorescently labeled antibody or ligand for a time period sufficient to allow the labeled antibody or ligand to bind to cells. The cells are processed through the cell sorter, allowing separation of the cells of interest from other cells. FACS sorted particles can be directly deposited into individual wells of microtiter plates to facilitate separation.

Magnetic beads can be also used to separate blood cells in some embodiments of the present invention. For example, blood cells can be sorted using a using a magnetic activated cell sorting (MACS) technique, a method for separating particles based on their ability to bind magnetic beads (0.5-100 m diameter). A variety of useful modifications can be performed on the magnetic microspheres, including covalent addition of an antibody which specifically recognizes a cell-solid phase surface molecule or hapten. A magnetic field is then applied, to physically manipulate the selected beads. In a specific embodiment, antibodies to a blood cell surface marker are coupled to magnetic beads. The beads are then mixed with the blood cell culture to allow binding. Cells are then passed through a magnetic field to separate out cells having the blood cell surface markers of interest. These cells can then be isolated.

In some embodiments, the surface of a culture dish may be coated with antibodies, and used to separate blood cells by a method called panning. Separate dishes can be coated with antibody specific to particular blood cells. Cells can be added first to a dish coated with blood cell specific antibodies of interest. After thorough rinsing, the cells left bound to the dish will be cells that express the blood cell markers of interest. Examples of cell surface antigenic determinants or markers include, but are not limited to, CD2 for T lymphocytes and natural killer cells, CD3 for T lymphocytes, CD11a for leukocytes, CD28 for T lymphocytes, CD19 for B lymphocytes, CD20 for B lymphocytes, CD21 for B lymphocytes, CD22 for B lymphocytes, CD23 for B lymphocytes, CD29 for leukocytes, CD14 for monocytes, CD41 for platelets, CD61 for platelets, CD66 for granulocytes, CD67 for granulocytes and CD68 for monocytes and macrophages.

Whole blood can be separated into cell types such as leukocytes, platelets, erythrocytes, etc. and such cell types can be used in accordance with the methods of the invention. Leukocytes can be further separated into granulocytes and agranulocytes using standard techniques and such cells can be used in accordance with the methods of the invention. Granulocytes can be separated into cell types such as neutrophils, eosinophils, and basophils using standard techniques and such cells can be used in accordance with the methods of the invention. Agranulocytes can be separated into lymphocytes (e.g., T lymphocytes and B lymphocytes) and monocytes using standard techniques and such cells can be used in accordance with the methods of the invention. T lymphocytes can be separated from B lymphocytes and helper T cells separated from cytotoxic T cells using standard techniques and such cells can be used in accordance with the methods of the invention. Separated blood cells (e.g., leukocytes) can be frozen by standard techniques prior to use in the present methods.

(D) RNA Preparation

In one aspect of the invention, RNA is isolated from an individual in order to measure the RNA products of the biomarkers of the invention. RNA is isolated from a sample from individuals diagnosed as having one or more colorectal pathologies including one or more polyps or one or more subtype of polyps, individuals not having one or more colorectal pathologies, not having one or more polyps or not having a subtype of polyps, or test subjects.

In some embodiments, RNA is isolated from blood which is erythrocyte depleted by the following protocol. Lysis Buffer is added to blood sample in a ratio of 3 parts Lysis Buffer to 1 part blood (Lysis Buffer (1 L) 0.6 g EDTA; 1.0 g $KHCO_2$, 8.2 g $NH_4Cl$ adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol® (GIBCO/BRL) in a ratio of approximately 6 ml of TRIzol® for every 10 ml of the original blood sample and vortexed well. Samples are left for 5 minutes at room temperature. RNA is extracted using 1.2 ml of chloroform per 1 ml of TRIzol®. Sample is centrifuged at 12,000×g for 5 minutes at 4° C. and upper layer is collected. To upper layer, isopropanol is added in ratio of 0.5 ml per 1 ml of TRIzol®. Sample is left overnight at −20° C. or for one hour at −20° C. RNA is pelleted in accordance with known methods, RNA pellet air dried, and pellet resuspended in DEPC treated $ddH_2O$. RNA samples can also be stored in 75% ethanol where the samples are stable at room temperature for transportation.

In other aspects, RNA is prepared by first collecting blood into a PAXgene™ collection tube and then subsequently isolating the RNA using the PAXgene™ blood RNA isolated system provided by PreAnalytiX, a Qiagen/BD company. In another embodiment, RNA is prepared by first collecting blood into any known stabilizing solution (e.g. a PAXgene™ collection or a TEMPUS® collection tube and then isolating the RNA using any method known to a person skilled in the art.

In other aspects globin reduced or depleted RNA is prepared. In one embodiment RNA is isolated first and then is subsequently treated to remove globin mRNA using one of any technique known in the art. For example, one can hybridize DNA primers and/or probes specific for globin RNA and utilize RNAse H to selectively degrade globin mRNA. In other embodiments RNA is isolated in a manner which removes the globin RNA during the RNA isolation steps (for example reducing globin RNA by selectively removing globin RNA using globin primers and/or probes attached to paramagnetic particles).

In other aspects of the invention RNA is prepared using one or more known commercial kits for isolating RNA (including isolating total RNA or mRNA and the like) such as oligo dT based purification methods, Qiagen® RNA isolation methods, LeukoLOCKT Total RNA Isolation System, MagMAX-96 Blood Technology from Ambion, Promega® polyA mRNA isolation system and the like.

Purity and integrity of RNA can be assessed by absorbance at 260/280 nm and agarose gel electrophoresis followed by inspection under ultraviolet light. In some embodiments RNA integrity is assessed using more sensitive techniques such as the Agilent 2100 Bioanalyzer 6000 RNA Nano Chip.

(E) Biomarkers of the Invention

In one aspect, the invention provides biomarkers and biomarker combinations wherein the measure of the level of expression of the product or products of said biomarkers is indicative of the presence of one or more colorectal pathologies.

Table 1 is a list of biomarkers of one aspect of the invention. Each biomarker is differentially expressed in samples from individuals having or not having polyps using microarray assays. The table provides the Hugo Gene name, symbol and locus link ID; the RNA and protein accession number; and also includes both the p value (which represents the statistical significance of the observed differential expression) and a measure of the fold change as between the average measured level of individuals having polyps and the average measured level of individuals not having polyps.

Table 2 is a selection of those genes listed in Table 1 and lists the gene symbol and the associated locus link ID for the biomarkers of the invention. The table also provides the fold change and direction of differential gene expression in individuals having polyps as compared to individuals not having polyps. As described, differential expression of the genes between individuals having or not having polyps can be identified using a non-parametic Wilcoxan-Mann-Whitney test or a parametric t test. The results of the tests are also shown in Table 2.

Table 11 shows genes identified as differentially expressed in samples from individuals having "high risk polyps" as compared with individuals not having high risk polyps (ie having low risk polyps or having no pathology at all) using microarray as described in Example 2. The table provides the gene name, gene ID; a representative human RNA accession number, and also provides the p value, the fold change (as between the average of individuals classified as having high risk polyps as compared with the average of individuals having low risk polyps), along with the coefficient of variation for both the high risk polyp individuals and the low risk polyp individuals (the standard deviation of the normalized intensity divided by the mean normalized intensity). Column 1 is AffySpotID, column 2 is Fold Change, column 3 is p value, Column 4 is CV (Coefficient of Variation) (High Risk Polyp), column 5 is CV (Low Risk Polyp)., column 6 is Gene ID, column 7 is the HUGO Gene Symbol, column 8 is the Human RNA Accession Number and column 9 is the Gene Description.

Table 12 shows 48 biomarkers tested for differentially expression by QRT-PCR in samples from individuals having colorectal cancer and individuals not having colorectal cancer The 48 biomarkers were tested using QRT-PCR. The table provides the gene symbol, locus link ID, and gene description for each biomarker. The table also includes the p value (which represents the statistical significance of the observed differential expression), the measure of the fold change as between the average measured level of individuals having colorectal cancer and the average measured level of individuals not having colorectal cancer and the direction of the differential expression between individuals having colorectal cancer and not having colorectal cancer.

Other biomarkers of the invention are described within the specification. The invention thus encompasses the use of those methods known to a person skilled in the art to measure the expression of these biomarkers and combinations of biomarkers for each of the purposes outlined above.

As would be understood by a person skilled in the art, the locus link ID can be used to determine the sequence of all the RNA products and all the protein products of the biomarkers of the invention.

(F) Combinations of Biomarkers

In one embodiment, combinations of biomarkers of the present invention includes any combination of the biomarkers listed in Table 1, Table 2, Table 11, or Table 12. For instance, the number of possible combinations of a subset n of m genes in any of the tables above is described in Feller, *Intro to Probability Theory*, Third Edition, volume 1, 1968, ed. J. Wiley, using the general formula:

$$m!/(n)!(m-n)!$$

For example, where n is 2 and m is 8, the number of combinations of biomarkers is:

$$\frac{8!}{2!(8-2)!} = \frac{8 \times 7 \times 6 \times 5 \times 4 \times 3 \times 2 \times 1}{(2 \times 1)(6 \times 5 \times 4 \times 3 \times 2 \times 1)}$$
$$= 40320/1440 = 28$$

unique two-gene combinations. The measurement of the gene expression of each of these two-gene combinations can independently be used to determine whether a patient has one or more colorectal pathologies. In another specific embodiment in which m is 8 and n is three, there are 8!/3!(8−3)! unique three-gene combinations. Each of these unique three-gene combinations can independently serve as a model for determining whether a patient has one or more colorectal pathologies.

(G) Testing Combinations of Biomarkers by Generating Formulas Resulting from One or More Classifiers The invention further provides a means of testing combinations of biomarkers from Table 1, Table 2, Table 11, or Table 12 or subsets thereof for their ability to test for one or more colorectal pathologies or one or more subtypes of colorectal pathology. Also provided are methods of evaluating the combinations tested for their ability to test an individual for the presence of one or more colorectal pathologies or one or more subtypes of colorectal pathology. In order to test combinations of biomarkers and generate classifiers, a mathematical model of the invention can be used. A mathematical model of the invention can be used to test each selected combination of biomarkers from all combinations of biomarkers or a selected subset thereof.

In some embodiments, it is useful to further select biomarkers to be tested as combinations. in one embodiment, one can select individual biomarkers on the basis of the p value as a measure of the likelihood that the individual biomarker can distinguish as between the two phenotypic trait subgroups. Thus in one embodiment, biomarkers are chosen to test in combination by input into a model wherein the p value of each biomarker is less than 0.2, 0.1, 0.5; less than 0.1, less than 0.05, less than 0.01, less than 0.005, less than 0.001, less than 0.0005, less than 0.0001, less than 0.00005, less than 0.00001, less than 0.000005, less than 0.000001 etc. We have also surprisingly found that even biomarkers which demonstrate a p value of greater than 0.2 (and thus would normally not be considered to be a useful individual biomarker) do significantly increase the ability of a combination of biomarkers in which they are included to distinguish as between two phenotypic trait subgroups. In other embodiments, biomarkers for input into the model to test in combination are chosen on the basis of the fold change of differential expression of the product of the biomarker as between the two phenotypic trait subgroups. Note that in measuring differential fold change in blood, the fold change differences can be quite small, thus in some embodiments, selection of biomarker subsets for input into classifier is based on a differential fold change where the fold change is greater than 1.01, 1.02, 1.03, 1.04, 1.05, 1.06, 1.07, 1.08, 1.09, 1.1, 1.125, 1.15, 1.175, 1, 1.2, 1.225, 1.25, 1.275, 1.30, greater than 1.3, greater than 1.4, greater than 1.5, greater than 1.6, greater than 1.7, greater than 1.8, greater than 1.9, greater than 2.0, greater than 2.1, greater than 2.2, greater than 2.3, greater than 2.4, greater than 2.5, greater than 2.6, greater than 2.7, greater than 2.8, greater than 2.9, greater than 3.0, greater than 3.1, greater than 3.2. greater than 3.3, greater than 3.4 greater than 3.5, greater than 4.0 and the like. In yet other embodiments in order to select subsets of biomarkers to test in combination, one can also take into account the coefficient of variation as a variability of the data representing the level of expression of the product of the biomarker amongst individuals within a phenotypic trait subgroup. In some embodiments, it is helpful to select biomarkers on the basis of a combination of factors including p value, fold change, and coefficient of variation as would be understood by a person skilled in the art. In some embodiments, biomarkers are first selected as outlined above on the basis of the p value resulting from the biomarker data and then a subselection of said biomarkers is chosen on the basis of the differential fold change determined from the biomarker data. In other embodiments, biomarkers are first selected on the basis of differential fold change, and then subselection is made on the basis of p value. In some embodiments, the use of one or more of the selection criteria and subsequent ranking permits the selection of the top 2.5%, 5%, 7.5%, 10%, 12.5%, 15%, 17.5%, 20%, 30%, 40%, 50% or more of the ranked biomarkers for input into the model. In some embodiments, the desired number of selected biomarkers can be 4,000; 3,000; 2,000; 1,000; 900; 800; 700; 600; 500; 400; 300; 200; 190; 180; 170; 160; 150; 140; 130; 120; 110; 100; 90; 80; 70; 60; 50; 40; 30; 20; or 10. In other embodiments, the selection criteria noted above can be set on the basis of the desired number of selected biomarkers for use in the model. As would be understood, one can select therefore all of the individually identified biomarkers or subsets of the individually identified biomarkers and test all possible combinations of the selected biomarkers to identify useful combinations of biomarkers. In another embodiment, one can select a subset of biomarkers and then test all possible combinations of 2 biomarkers from that subset, 3 biomarkers from that subset, 4 biomarkers from that subset, 5 biomarkers from that subset, 6 biomarkers from that subset 7 biomarkers from that subset, 8 biomarkers from that subset 9 biomarkers from that subset or 10 biomarkers from that subset in order to identify useful combinations of biomarkers. A selection criteria to determine the number of selected individual biomarkers to test in combination, and to select the number of possible combinations of biomarkers will depend upon the resources available for obtaining the biomarker data and/or the computer resources available for calculating and evaluating classifiers resulting from the model.

The classifier generated by the mathematical model can be subsequently evaluated by determining the ability of the classifier to correctly call each individual for one of the two phenotypic traits of the population used to generate the classifier (ie having or not having one or more colorectal pathologies). In a preferred embodiment, the individuals of the training population used to derive the model are different from the individuals of the training population used to test the model. As would be understood by a person skilled in the art, this allows one to predict the ability of the combinations as to their ability to properly characterize an individual whose phenotypic trait characterization is unknown.

The data which is input into the mathematical model can be any data which is representative of the expression level of the product of the biomarkers being evaluated. Mathematical models useful in accordance with the invention include those using both supervised or unsupervised learning techniques. In a preferred embodiment of the invention, the mathematical model chosen uses supervised learning in conjunction with a "training population" to evaluate each of the possible combination of biomarkers of the invention. In one embodiment of the invention, the mathematical model used is selected from the following: a regression model, a logistic regression model, a neural network, a clustering model, principal component analysis, nearest neighbour classifier analysis, linear discriminant analysis, quadratic discriminant analysis, a support vector machine, a decision tree, a genetic algorithm, classifier optimization using bagging, classifier optimization using boosting, classifier optimization using the Random Subspace Method, a projection pursuit, genetic programming and weighted voting. In a preferred embodiment, a logistic regression model is used. In another preferred embodiment, a neural network model is used.

The results of applying a mathematical model of the invention to the data will generate one or more classifiers using one or more biomarkers. In some embodiments, multiple classifiers are created which are satisfactory for the given purpose (e.g. all have sufficient AUC and/or sensitivity and/or specificity). In this instance, in some embodiments, a formula is generated which utilizes more than one classifier. For example, a formula can be generated which utilizes classifiers in series (e.g. first obtains results of classifier A, then classifier B e.g. Classifier A differentiates pathology from non pathology; classifier B then determines whether the pathology is colorectal cancer or not colorectal cancer). In another embodiment, a formula can be generated which results from weighting the results of more than one classifier. For example, the results of each classifier can be given a score of 1 and an indication of probability of a test subject having one or more colorectal pathologies is the result of the aggregate score of each of the selected classifiers of a given formula. Other possible combinations and weightings of classifiers would be understood and are encompassed herein.

Classifiers generated can be used to test an unknown or test subject. In one embodiment, the results from equations generated by logistic regression to answer the question does an individual have one or more colorectal pathologies or is an individual "normal". In yet another embodiment of the invention, the answer to the question above may be an answer of non-determinable.

In one embodiment of the invention, each classifier is evaluated for its ability to properly characterize each individual of the training population using those methods known to a person skilled in the art. For example one can evaluate the classifier using cross validation, Leave One out Cross Validation (LOOCV), n-fold cross validation, jackknife analysis using standard statistical methods as disclosed. In another embodiment of the invention, each classifier is evaluated for its ability to properly characterize those individuals of the training population which were not used to generate the classifier.

In one embodiment, the method used to evaluate the classifier for its ability to properly characterize each individual of the training population is a method which evaluates the classifier's sensitivity (TPF, true positive fraction) and 1-specificity (TNF, true negative fraction). In one embodiment, the method used to test the classifier is Receiver Operating Characteristic ("ROC") which provides several parameters to evaluate both the sensitivity and specificity of the result of the equation generated. In one embodiment using the Receiver Operating Characteristic ("ROC") the ROC area (area under the curve) is used to evaluate the equations. A ROC area greater than 0.5, 0.6, 0.7, 0.8, 0.9 is preferred. A perfect ROC area score of 1.0 indicates with both 100% sensitivity and 100% specificity. In some embodiments classifiers are selected on the basis of the score. For example, where the scoring system used is receiver operating characteristic (ROC) curve score determined by an area under the ROC curve, in some embodiments, those classifiers with scores of greater than 0.95, 0.9, 0.85, 0.8, 0.7, 0.65, 0.6, 0.55 0.5 or 0.45 are chosen. In other embodiments, where specificity is important to the use of the classifier, a sensitivity threshold can be set and classifiers ranked on the basis of the specificity chosen. For example classifiers with a cutoff for specificity of greater than 0.95, 0.9, 0.85, 0.8, 0.7, 0.65, 0.6, 0.55 0.5 or 0.45 can be chosen. Similarly, the specificity threshold can be set and classifiers ranked on the basis of sensitivity greater than 0.95, 0.9, 0.85, 0.8, 0.7, 0.65, 0.6, 0.55 0.5 or 0.45 can be chosen. Thus in some embodiments, only the top 10 ranking classifiers, the top 20 ranking classifiers, or the top 100 ranking classifiers are selected.

As would be understood by a person skilled in the art, the utility of the combinations and classifiers determined by a mathematical model will depend upon the phenotypes of the populations used to generate the data for input into the model. Examples of specific embodiments are described more thoroughly herein.

(H) Populations for Input into the Mathematical Models

Populations used for input should be chosen so as to result in statistically significant resulting classifier. In some embodiments, the reference or training population includes between 10 and 30 subjects. In another embodiment the reference population contains between 30-50 subjects. In still other embodiments, the reference population includes two or more populations each containing between 50 and 100, 100 and 500, between 500 and 1000, or more than 1000 subjects. The reference population includes two or more subpopulations. In a preferred embodiment, the phenotypic trait characteristics of the subpopulations are similar but for the diagnosis with respect to the presence of one or more colorectal pathologies, for example the distribution within the subpopulations are similar with regards to the age and sex of the subpopulations. It is also preferred that the subpopulations are of roughly equivalent numbers. It is to be understood that the methods herein do not require using data from every member of a population, but instead may rely on data from a subset of a population in question.

For example, for a reference or test population for input into a mathematical model to identify those biomarkers which are useful in identifying an individual as having any polyps or not having any polyps, the reference population is comprised of individuals having polyps (the first subpopulation), and individuals not having polyps (the second subpopulation). For purposes of characterizing the subpopulations as having or not having polyps, any verified method can be used including digital rectal examination, fecal occult blood testing, rigid sigmoidoscopy, flexible sigmoidoscopy, double-contrast barium enema, colonoscopy, and histological examination. Preferably only those individuals whose diagnoses are certain are utilized as part of the reference population.

In another embodiment, to identify those biomarkers which are useful in identifying an individual as having high risk polyps or not, the reference population is comprised of individuals having high risk polyps (the first subpopulation), and individuals not having high risk polyps (the second subpopulation) where high risk polyps are the following: Tubulovillous Adenoma, Villous Adenoma, Cancer High Grade Dysplasia and Tubular Adenoma where the Tubular Adenoma is greater than 10 mm. For purposes of characterizing the subpopulations as having or not having high risk polyps, any verified method can be used including digital rectal examination, fecal occult blood testing, rigid sigmoidoscopy, flexible sigmoidoscopy, double-contrast barium enema, colonoscopy, and histological examination.

In yet another embodiment, to test biomarkers which are useful in identifying an individual as having early stage of colorectal cancer or not, the reference population can, for example be comprised of individuals having localized colorectal cancer as compared with individuals with other types of colorectal cancer (e.g. late stage).

In another embodiment, to identify those biomarkers which are useful in identifying an individual as having high risk polyps or not, the reference population is comprised of individuals having high risk polyps (the first subpopulation), and individuals not having high risk polyps (the second subpopulation) where high risk polyps are the following: Tubulovillous Adenoma; Villous Adenoma; Cancer; High Grade Dysplasia; and Tubular Adenoma.

(I) Data for Input into the Mathematical Models to Identify Classifiers for Testing for Colorectal Pathology Data for input into the mathematical models is data representative of the level of the products of the biomarkers of the invention. As such the data is the measure of the level of expression of the products of the biomarkers of the invention including either mRNA and/or protein.

In one embodiment of the invention, the RNA products of the biomarkers of the invention which are measured are the population of RNA products including the mRNA, and all of the spliced variants of the mRNA. In another embodiment of the invention the products measured are all of the mRNA products expressed in blood. In yet another embodiment of the invention, the products measured include one or more specific spliced variants of the mRNA which are expressed in blood. In yet another embodiment of the invention, the products measured are the RNA products listed in Table 3 or Table 13.

Protein products of the biomarkers of the invention are also included within the scope of the invention. To practice the invention, measurement of the protein products of the biomarkers of the invention can be used for purposes of testing for one or more colorectal pathologies. More particularly, measurement of those populations of protein products of the biomarkers which are differentially expressed in individuals having or not having any polyps are useful for purposes of testing and are encompassed herein.

In one embodiment of the invention the protein products are those translated from the biomarkers listed in Table 1, Table 2, Table 11, or Table 12. In another embodiment, the protein products are those which are expressed in blood. In yet another embodiment of the invention, the protein products are those corresponding to the proteins listed in Table 3 or Table 13.

In yet another embodiment, data reflective of the level of expression of a combination of protein products and RNA products of the biomarkers are used. As would be understood by a person skilled in the art, other combinations of input data can be utilized to generate classifiers useful in accordance with the invention.

In other embodiments, as would be understood by one of ordinary skill in the art, data reflective of each biomarker in each member of the population is not necessary so long as there are data for sufficient members of each reference population to permit creation of a classifier. For example, data representative of biomarkers in 99%, 95%, 90%, 85%, 80%, or 75% of members of a population may suffice in given circumstances.

(J) Mathematical Models

Formulae for use with the methods described herein may generally have the form:

$$V = C + \Sigma \beta_i f(X_i) + \Sigma \beta_{ij} f(X_i, X_j) + \Sigma \beta_{ijk} f(X_i, X_j, X_k) + \ldots$$

Wherein V is a value indicating the probability that a test subject has one or more colorectal pathologies, $X_i$ is a level of one or more products of an ith biomarker in a sample from the test subject, $\beta_i$ is a coefficient for a term involving only the ith biomarker, $\beta_{ij}$ is a coefficient for a term that is a function of the ith and jth biomarkers, $\beta_{ijk}$ is a coefficient for a term that is a function of the ith, jth and kth biomarkers, and C is a constant. Still other terms may find themselves in this formula, such as terms depending on four or more biomarkers.

By 'indicates' is meant that V might be an actual probability (a number varying between 0 and 1), or V might be a quantity from which a probability can be readily derived.

There are various forms of functions $f(X_i, X_j, \ldots)$ that depend on expression levels of the various biomarkers. For example, the functions may be polynomials in those expression levels, i.e., involve products of the various biomarkers raised to numeric powers. Examples include: $X_i X_j^2$, $X_i X_j X_k$, $(X_i X_j)^{1/2}$, $X_i X_j + X_i X_k$. The functions may additionally or alternatively involve logarithms, exponentials, or still other functions of the expression levels.

In certain embodiments, the $f(X_i, X_j, \ldots)$ depend on ratios of the biomarker expression levels, i.e., $f(X_i, X_j) = X_i / X_j$.

Regression Models

In some embodiments the expression data for some or all of the biomarkers identified in the present invention are used in a regression model, such as but not limited to a logistic regression model or a linear regression model, so as to identify classifiers useful in diagnosing one or more colorectal pathologies. The regression model is used to test various combinations of two or more of the biomarkers identified in Table 1, Table 2, Table 11, or Table 12 to generate classifiers. In the case of regression models, the classifiers which result are in the form of equations which provide a dependent variable Y, which represents the presence or absence of a given phenotype where the data representing the expression of each of the biomarkers in the equation is multiplied by a weighted coefficient as generated by the regression model. The classifiers generated can be used to analyze expression data from a test subject and provide a result indicative of the probability of a test subject having one or more colorectal pathologies. In general, a multiple regression equation of interest can be written $$Y = \alpha + \beta_1 X_1 + \beta_2 X_2 + \ldots + \beta_k X_k + \epsilon$$

where Y, the dependent variable, indicates presence (when Y is positive) or absence (when Y is negative) of the biological feature (e.g., absence or presence of one or more colorectal pathologies) associated with the first subgroup. This model says that the dependent variable Y depends on k explanatory variables (the measured characteristic values for the k select genes (e.g., the biomarkers) from subjects in the first and second subgroups in the reference population), plus an error term that encompasses various unspecified omitted factors. In the above-identified model, the parameter $\beta_1$ gauges the effect of the first explanatory variable $X_1$ on the dependent variable Y (e.g., a weighting factor), holding the other explanatory variables constant. Similarly, $\beta_2$ gives the effect of the explanatory variable $X_2$ on Y, holding the remaining explanatory variables constant.

A logistic regression model is a non-linear transformation of the linear regression. The logistic regression model is often referred to as the "logit" model and can be expressed as $$\ln[p/(1-p)] = \alpha + \beta_1 X_1 + \beta_2 X_2 + \ldots + \beta_k X_k + \epsilon \text{ or}$$

$$[p/(1-p)] = \exp^{\alpha} \exp^{\beta_1 X_1} \exp^{\beta_2 X_2} \times \ldots \times \exp^{\beta_k X_k} \exp^{\epsilon}$$

where,

α and ε are constants ln is the natural logarithm, $\log_e$, where e=2.71828 . . . , p is the probability that the event Y occurs, p(Y=1), p/(1−p) is the "odds ratio", ln[p/(1−p)] is the log odds ratio, or "logit", and all other components of the model are the same as the general linear regression equation described above. It will be appreciated by those of skill in the art that the term for α and ε can be folded into a single constant. Indeed, in preferred embodiments, a single term is used to represent α and ε. The "logistic" distribution is an S-shaped distribution function. The logit distribution constrains the estimated probabilities (p) to lie between 0 and 1.

In some embodiments of the present invention, the logistic regression model is fit by maximum likelihood estimation (MLE). In other words, the coefficents (e.g., α, $\beta_1$, $\beta_2$, . . . ) are determined by maximum likelihood. A likelihood is a conditional probability (e.g., P(Y|X), the probability of Y given X). The likelihood function (L) measures the probability of observing the particular set of dependent variable values ($Y_1$, $Y_2$, . . . , $Y_n$) that occur in the sample data set. It is written as the probability of the product of the dependent variables:

$$L = \text{Prob}(Y_1 * Y_2 *** Y_n)$$

The higher the likelihood function, the higher the probability of observing the Ys in the sample. MLE involves finding the coefficients (α, $\beta_1$, $\beta_2$, . . . ) that makes the log of the likelihood function (LL<0) as large as possible or −2 times the log of the likelihood function (−2LL) as small as possible. In MLE, some initial estimates of the parameters α, $\beta_1$, $\beta_2$, . . . are made. Then the likelihood of the data given these parameter estimates is computed. The parameter estimates are improved the likelihood of the data is recalculated. This process is repeated until the parameter estimates do not change much (for example, a change of less than 0.01 or 0.001 in the probability). Examples of logistic regression and fitting logistic regression models are found in Hastie, *The Elements of Statistical Learning*, Springer, N.Y., 2001, pp. 95-100 which is incorporated herein in its entirety.

Neural Networks

In another embodiment, the expression measured for each of the biomarkers of the present invention can be used to train a neural network. A neural network is a two-stage regression or classification model. A neural network can be binary or non binary. A neural network has a layered structure that includes a layer of input units (and the bias) connected by a layer of weights to a layer of output units. For regression, the layer of output units typically includes just one output unit. However, neural networks can handle multiple quantitative responses in a seamless fashion. As such a neural network can be applied to allow identification of biomarkers which differentiate as between more than two populations (ie more than two phenotypic traits). In one specific example, a neural network can be trained using expression data from the products of the biomarkers in Table 1, Table 2, Table 11, or Table 12 to identify those combinations of biomarkers which are specific for one or more colorectal pathologies. As a result, the trained neural network can be used to directly identify combinations of biomarkers useful to test for one or more colorectal pathologies. In some embodiments, the back-propagation neural network (see, for example Abdi, 1994, "A neural network primer", J. Biol System. 2, 247-283) containing a single hidden layer of ten neurons (ten hidden units) found in EasyNN-Plus version 4.0 g software package (Neural Planner Software Inc.) is used.

Neural networks are described in Duda et al., 2001, *Pattern Classification*, Second Edition, John Wiley & Sons, Inc., New York; and Hastie et al., 2001, *The Elements of Statistical Learning*, Springer-Verlag, New York which is incorporated herein in its entirety.

Singular Value Decomposition (SVD) and Principal Component Analysis (PCA)

Singular value decomposition (SVD) and Principal Component Analysis (PCA) are common techniques for analysis of multivariate data, and we have found that gene expression data is well suited to analysis using SVD/PCA. SVD or equivalently, in this case, PCA, is defined as follows:

Singular value decomposition (SVD) and Principal Component Analysis (PCA) are common techniques for analysis of multivariate data, and we have found gene expression data are well suited to analysis using SVD/PCA. SVD or equivalently, in this case, PCA, is defined as follows:

Let G be an m×n gene expression matrix with rank r, and m≧n, and therefore r≦n where m is a row and n is a column of data of the matrix. In the case of microarray data, gij is the level of one or more products of the ith biomarker in the jth assay. The elements of the ith row of G form the n-dimensional vector bi (where b is a biomarker), which we refer to as the transcriptional response of the ith biomarker. Alternatively, the elements of the jth column of G form the m-dimensional vector aj, which we refer to as the expression profile (or gene expression profile) of the jth assay.

The equation for singular value decomposition of G is the following:

$$G = USV^T$$

where U is an m×n matrix, S is an n×n diagonal matrix, and VT is also an n×n matrix. The columns of U are called the left singular vectors, $\{u_k\}$, and form an orthonormal basis for the assay expression profiles, so that $u_i \cdot u_j = 1$ for i=j, and $u_i \cdot u_j = 0$ otherwise. The rows of $V^T$ contain the elements of the right singular vectors, $\{v_k\}$, and form an orthonormal basis for the gene transcriptional responses. The elements of S are only nonzero on the diagonal, and are called the singular values. Thus, $S = \text{diag}(s_1, \ldots, s_n)$. Furthermore, $s_k > 0$ for $1 \leq k \leq r$, and $s_i = 0$ for $(r+1) \leq k \leq n$. By convention, the ordering of the singular vectors is determined by high-to-low sorting of singular values, with the highest singular value in the upper left index of the S matrix. Note that for a square, symmetric matrix X, singular value decomposition is equivalent to diagonalization, or solution of the eigenvalue problem.

Other Mathematical Models

The pattern classification and statistical techniques described above are merely examples of the types of models that can be used to construct classifiers useful for diagnosing or detecting one or more colorectal pathologies, for example clustering as described on pages 211-256 of Duda and Hart, *Pattern Classification and Scene Analysis*, 1973, John Wiley & Sons, Inc., New York, incorporated herein by reference in its entirety; Principal component analysis, (see for Jolliffe, 1986, *Principal Component* Analysis, Springer, N.Y., incorporated herein by reference); nearest neighbour classifier analysis, (see for example Duda, *Pattern Classification*, Second Edition, 2001, John Wiley & Sons, Inc; and Hastie, 2001, *The Elements of Statistical Learning*, Springer, N.Y.); linear discriminant analysis, (see for example Duda, *Pattern Classification*, Second Edition, 2001, John Wiley & Sons, Inc; and Hastie, 2001, *The Elements of Statistical Learning*, Springer, N.Y.; Venables & Ripley, 1997, *Modern Applied Statistics with s-plus*, Springer, N.Y.); Support Vector Machines (see, for example, Cristianini and Shawe-Taylor, 2000, *An Introduction to Support Vector Machines*, Cambridge University Press, Cambridge, Boser et al., 1992, "A training algorithm for optimal margin classifiers, in *Proceedings of the 5th Annual ACM Workshop on Computational Learning Theory*, ACM Press, Pittsburgh, Pa., pp. 142-152; Vapnik, 1998, *Statistical Learning Theory*, Wiley, New York, incorporated herein by reference.)

Computer Implementation

The methods described herein are preferably performed by a suitably programmed computer. The computer system for use with the methods described herein, as further described herein, is configured to accept and to process data and may be a single-processor or multi-processor computer system. Examples of suitable computer systems include, but are not limited to, any one of various combinations of mainframe computers, minicomputers, personal computers, laptop computers, notebook computers, hand-held computers, personal digital assistants, mobile phones, set-top boxes, microprocessor-based consumer electronics, programmable consumer electronics, and the like. Additionally, the methods of the invention may be practiced on networked computers, CPU-clusters, workstations, and so-called mainframe computers. The computer system may be a locally accessed computer, a remotely accessed computer system (e.g. server), or a combination of both. Depending on the application and purpose, the computer system may have access or be accessible to "the internet" [World Wide Web (WWW)]. It will be appreciated that the computer system may be a stand-alone system or a distributed system comprising multiple devices communicating with each other through a network. Depending on the application and purpose, the computer system may be a static or mobile computer system. One of ordinary skill in the art will possess the necessary knowledge and skills for selecting, obtaining and utilizing a suitable computer system for practicing any aspect of the invention.

It is therefore consistent with the description herein that various methods and formulae are implemented, in the form of computer program instructions, and executed on a computer as also described herein. Suitable programming languages for expressing the program instructions include, but are not limited to, one or more languages selected from the group consisting of: C, C++, an embodiment of FORTRAN such as FORTRAN77 or FORTRAN90, Java, Visual Basic, Perl, Tcl/Tk, JavaScript, and ADA. It is to be understood that various aspects of the methods may be written in different computing languages from one another, where such languages are preferred for particular applications, and the various aspects are caused to communicate with one another by appropriate system-level-tools available on a given computer.

The computer program instructions are stored in a computer memory during execution, and may additionally be stored on any of various forms of computer-readable media known in the art, such as, but not limited to, CD-Rom, CD-R, CD-RW, flash memory, memory cards, memory sticks, DVD-Rom, USB-sticks, optical discs, or high capacity network storage drives. It is thus consistent with ordinary practice of the present invention that the computer program instructions can be delivered to a user on a transferable medium such as a CD-Rom, and also delivered over a computer network, such as by downloading over the Internet through a web-interface.

FIG. 1 shows a schematic of a general-purpose computer system 100 suitable for practicing the methods described herein. The computer system 100, shown as a self-contained unit but not necessarily so limited, comprises at least one data processing unit (CPU) 102, a memory 104, which will typically include both high speed random access memory as well as non-volatile memory (such as one or more magnetic disk drives) but may be simply flash memory, a user interface 108, optionally a disk 110 controlled by a disk controller 112, and at least one optional network or other communication interface card 114 for communicating with other computers as well as other devices. At least the CPU 102, memory 104, user interface 108, disk controller where present, and network interface card, communicate with one another via at least one communication bus 106.

Memory 104 stores procedures and data, typically including: an operating system 140 for providing basic system services; application programs 152 such as user level programs for viewing and manipulating data, evaluating formulae for the purpose of diagnosing a test subject; authoring tools for assisting with the writing of computer programs; a file system 142, a user interface controller 144 for handling communications with a user via user interface 108, and optionally one or more databases 146 for storing microarray data and other information, optionally a graphics controller 148 for controlling display of data, and optionally a floating point coprocessor 150 dedicated to carrying out mathematical operations. The methods of the present invention may also draw upon functions contained in one or more dynamically linked libraries, not shown in FIG. 1, but stored either in Memory 104, or on disk 110, or accessible via network interface connection 114.

User interface 108 may comprise a display 128, a mouse 126, and a keyboard 130. Although shown as separate components in FIG. 1, one or more of these user interface components can be integrated with one another in embodiments such as handheld computers. Display 128 may be a cathode ray tube (CRT), or flat-screen display such as an LCD based on active matrix or TFT embodiments, or may be an electroluminescent display, based on light emitting organic molecules such as conjugated small molecules or polymers. Other embodiments of a user interface not shown in FIG. 1 include, e.g., several buttons on a keypad, a card-reader, a touch-screen with or without a dedicated touching device, a trackpad, a trackball, or a microphone used in conjunction with voice-recognition software, or any combination thereof, or a security-device such as a fingerprint sensor or a retinal scanner that prohibits an unauthorized user from accessing data and programs stored in system 100.

System 100 may also be connected to an output device such as a printer (not shown), either directly through a dedicated printer cable connected to a serial or USB port, or wirelessly, or via a network connection.

The database 146 may instead, optionally, be stored on disk 110 in circumstances where the amount of data in the database is too great to be efficiently stored in memory 104. The database may also instead, or in part, be stored on one or more remote computers that communicate with computer system 100 through network interface connection 114.

The network interface 134 may be a connection to the internet or to a local area network via a cable and modem, or ethernet, firewire, or USB connectivity, or a digital subscriber line. Preferably the computer network connection is wireless, e.g., utilizing CDMA, GSM, or GPRS, or bluetooth, or standards such as 802.11a, 802.11b, or 802.11g.

It would be understood that various embodiments and configurations and distributions of the components of system 10 across different devices and locations are consistent with practice of the methods described herein. For example, a user may use a handheld embodiment that accepts data from a test subject, and transmits that data across a network connection to another device or location wherein the data is analyzed according to a formulae described herein. A result of such an analysis can be stored at the other location and/or additionally transmitted back to the handheld embodiment. In such a configuration, the act of accepting data from a test subject can include the act of a user inputting the information. The network connection can include a web-based interface to a remote site at, for example, a healthcare provider. Alternatively, system 10 can be a device such as a handheld device that accepts data from the test subject, analyzes the data, such as by inputting the data into a formula as further described herein, and generating a result that is displayed to the user. The result can then be, optionally, transmitted back to a remote location via a network interface such as a wireless interface. System 100 may further be configured to permit a user to transmit by e-mail results of an analysis directly to some other party, such as a healthcare provider, or a diagnostic facility, or a patient.

(K) Use of the Biomarkers of the Invention for Testing, Screening or Diagnosing a Test Subject As would be understood by a person skilled in the art, the identification of one or more biomarkers can be used to allow for the testing, screening or diagnosis of one or more colorectal pathologies including polyps or one or more subtypes of polyps within a test subject by measuring the expression of the products of the biomarkers (gene) in the test subject (the "test subject").

In one embodiment, the results from the test subject are compared with the a control wherein the control can be results from one or more individuals having colorectal pathology, having polyps, having one or more subtypes of polyps and/or one or more individuals not having any colorectal pathology, not having any polyps or not having one or more specific subtypes of colorectal polyps.

In another embodiment, one can input data reflective of the expression of the products of the biomarkers of the test subject into a formula of the invention resulting in a determination of whether said test subject has one or more colorectal pathologies. It is not necessary to use the same formula used to test the biomarker combination for its ability to test for colorectal pathologies as to diagnose an individual using the biomarker combination identified. Data representative of the products of the biomarkers of the invention (including RNA and/or Protein) is input into a formula of the invention so as to determine a probability of a test subject having one or more colorectal pathologies. The data can be generated using any technique known to measure the level of expression of either the RNA and protein products of the biomarkers of the invention.

In one embodiment, use of the formula results in a determination of whether the test subject has polyps or does not have polyps. For example, using logistic regression as the model, Y is used as a predictor of polyps, where when $Y>0$ a person is diagnosed as having polyps and where $Y<0$, a person is diagnosed as not having polyps. In yet another embodiment, one can also include a third category of prediction wherein diagnosis is indeterminable. For example, one can determine the standard deviation inherent within the methodology used to measure gene expression of the biomarkers ($\delta$). If $Y<\delta$ but $>0$ or $Y>-\delta$ but $<0$, then the test results are considered indeterminable.

(L) Polynucleotides Used to Measure the Products of the Biomarkers of the Invention Polynucleotides capable of specifically or selectively binding to the RNA products of the biomarkers of the invention are used to measure the level of expression of the biomarkers. For example: oligonucleotides, cDNA, DNA, RNA, PCR products, synthetic DNA, synthetic RNA, or other combinations of naturally occurring or modified nucleotides which specifically and/or selectively hybridize to one or more of the RNA products of the biomarker of the invention are useful in accordance with the invention.

In a preferred embodiment, the oligonucleotides, cDNA, DNA, RNA, PCR products, synthetic DNA, synthetic RNA, or other combinations of naturally occurring or modified nucleotides oligonucleotides which both specifically and selectively hybridize to one or more of the RNA products of the biomarker of the invention are used.

(M) Techniques to Measure the RNA Products of the Biomarkers of the Invention Array Hybridization In one embodiment of the invention, the polynucleotide used to measure the RNA products of the biomarkers of the invention can be used as nucleic acid members localized on a support to comprise an array according to one aspect of the invention. The length of a nucleic acid member can range from 8 to 1000 nucleotides in length and are chosen so as to be specific for the RNA products of the biomarkers of the invention. In one embodiment, these members are selective for the RNA products of the biomarkers of the invention. The nucleic acid members may be single or double stranded, and/or may be oligonucleotides or PCR fragments amplified from cDNA. In some embodiments oligonucleotides are approximately 20-30 nucleotides in length. ESTs are in some embodiments 100 to 600 nucleotides in length. It will be understood to a person skilled in the art that one can utilize portions of the expressed regions of the biomarkers of the invention as a probe on the array. More particularly oligonucleotides complementary to the genes of the invention and or cDNA or ESTs derived from the genes of the invention are useful. For oligonucleotide based arrays, the selection of oligonucleotides corresponding to the gene of interest which are useful as probes is well understood in the art. More particularly it is important to choose regions which will permit hybridization to the target nucleic acids. Factors such as the Tm of the oligonucleotide, the percent GC content, the degree of secondary structure and the length of nucleic acid are important factors. See for example U.S. Pat. No. 6,551,784.

As described, microarrays can be used to identify and select genes differentially expressed in individuals having or not having one or more colorectal pathologies, one or more polyps or one or more subtypes of polyps, and can be used to diagnose or detect polyps or one or more subtypes of polyps using the biomarkers of the invention. Genes identified as differentially expressed using microarrays can be seen in Table 1, and Table 11.

Construction of a Nucleic Acid Array

In the subject methods, an array of nucleic acid members stably associated with the surface of a substantially support is contacted with a sample comprising target nucleic acids under hybridization conditions sufficient to produce a hybridization pattern of complementary nucleic acid members/target complexes in which one or more complementary nucleic acid members at unique positions on the array specifically hybridize to target nucleic acids. The identity of target nucleic acids which hybridize can be determined with reference to location of nucleic acid members on the array.

The nucleic acid members may be produced using established techniques such as polymerase chain reaction (PCR) and reverse transcription (RT). These methods are similar to those currently known in the art (see e.g., *PCR Strategies*, Michael A. Innis (Editor), et al. (1995) and *PCR: Introduction to Biotechniques Series*, C. R. Newton, A. Graham (1997)). Amplified nucleic acids are purified by methods well known in the art (e.g., column purification or alcohol precipitation). A nucleic acid is considered pure when it has been isolated so as to be substantially free of primers and incomplete products produced during the synthesis of the desired nucleic acid. In some embodiments, a purified nucleic acid will also be substantially free of contaminants which may hinder or otherwise mask the specific binding activity of the molecule.

An array, according to one aspect of the invention, comprises a plurality of nucleic acids attached to one surface of a support at a density exceeding 20 different nucleic acids/cm$^2$, wherein each of the nucleic acids is attached to the surface of the support in a non-identical pre-selected region (e.g. a microarray). Each associated sample on the array comprises a nucleic acid composition, of known identity, usually of known sequence, as described in greater detail below. Any conceivable substrate may be employed in the invention.

In one embodiment, the nucleic acid attached to the surface of the support is DNA. In a preferred embodiment, the nucleic acid attached to the surface of the support is cDNA or RNA. In another preferred embodiment, the nucleic acid attached to the surface of the support is cDNA synthesized by polymerase chain reaction (PCR). In some embodiments, a nucleic acid member in the array, according to the invention, is at least 10, 25 or 50 nucleotides in length. In one embodiment, a nucleic acid member is at least 150 nucleotides in length. In some embodiments, a nucleic acid member is less than 1000 nucleotides in length. More preferably, a nucleic acid member is less than 500 nucleotides in length.

In the arrays of the invention, the nucleic acid compositions are stably associated with the surface of a support. In one embodiment, the support may be a flexible or rigid support. By "stably associated" is meant that each nucleic acid member maintains a unique position relative to the support under hybridization and washing conditions. As such, the samples are non-covalently or covalently stably associated with the support surface. Examples of non-covalent association include non-specific adsorption, binding based on electrostatic interactions (e.g., ion pair interactions), hydrophobic interactions, hydrogen bonding interactions, specific binding through a specific binding pair member covalently attached to the support surface, and the like. Examples of covalent binding include covalent bonds formed between the nucleic acids and a functional group present on the surface of the rigid support (e.g., —OH), where the functional group may be naturally occurring or present as a member of an introduced linking group, as described in greater detail below The amount of nucleic acid present in each composition will be sufficient to provide for adequate hybridization and detection of target nucleic acid sequences during the assay in which the array is employed. Generally, the amount of each nucleic acid member stably associated with the support of the array is at least about 0.001 ng, preferably at least about 0.02 ng and more preferably at least about 0.05 ng, where the amount may be as high as 1000 ng or higher, but will usually not exceed about 20 ng. Where the nucleic acid member is "spotted" onto the support in a spot comprising an overall circular dimension, the diameter of the "spot" will generally range from about 10 to 5,000 μm, usually from about 20 to 2,000 μm and more usually from about 100 to 200 μm.

Control nucleic acid members may be present on the array including nucleic acid members comprising oligonucleotides or nucleic acids corresponding to genomic DNA, housekeeping genes, vector sequences, plant nucleic acid sequence, negative and positive control genes, and the like. Control nucleic acid members are calibrating or control genes whose function is not to tell whether a particular "key" gene of interest is expressed, but rather to provide other useful information, such as background or basal level of expression.

Other control nucleic acids are spotted on the array and used as target expression control nucleic acids and mismatch control nucleotides to monitor non-specific binding or cross-hybridization to a nucleic acid in the sample other than the target to which the probe is directed. Mismatch probes thus indicate whether a hybridization is specific or not. For example, if the target is present, the perfectly matched probes should be consistently brighter than the mismatched probes. In addition, if all control mismatches are present, the mismatch probes are used to detect a mutation.

Use of a Microarray

Nucleic acid arrays according to the invention can be used to assay nucleic acids in a sample comprising one or more target nucleic acid sequences (ie such as RNA products of the biomarkers of the invention). The arrays of the subject invention can be used for testing, screening, and/or diagnosis of one or more colorectal pathologies including polyps or one or more subtypes of polyps, or screening for therapeutic targets and the like.

The arrays are also useful in broad scale expression screening for drug discovery and research, such as the effect of a particular active agent on the expression pattern of biomarkers of the invention, where such information is used to reveal drug efficacy and toxicity, environmental monitoring, disease research and the like.

Arrays can be made using at least one, more preferably a combination of these sequences, as a means of diagnosing colon pathology or one or more subtypes of colon pathology.

The choice of a standard sample would be well understood by a person skilled in the art, and would include a sample complementary to RNA isolated from one or more normal individuals, wherein a normal individual is an individual not having polyps.

Preparation of Nucleic Acid Sample for Hybridization to an Array

The samples for hybridization with the arrays according to the invention are in some embodiments derived from total RNA from blood. In another embodiment, targets for the arrays are derived from mRNA from blood.

The nucleic acid sample is capable of binding to a nucleic acid member of complementary sequence through one or more types of chemical bonds, usually through complementary base pairing, usually through hydrogen bond formation.

As used herein, a "nucleic acid derived from an mRNA transcript: or a "nucleic acid corresponding to an mRNA" refers to a nucleic acid for which synthesis of the mRNA transcript or a sub-sequence thereof has ultimately served as a template. Thus, a cDNA reverse transcribed from an mRNA, an RNA transcribed from that cDNA, a DNA amplified from the cDNA, an RNA transcribed from the amplified DNA, etc., are all derived from or correspond to the mRNA transcript and detection of such derived or corresponding products is indicative of or proportional to the presence and/or abundance of the original transcript in a sample. Thus, suitable nucleic acid samples include, but are not limited to, mRNA transcripts of a gene or genes, cDNA reverse transcribed from the mRNA, cRNA transcribed from the cDNA, DNA amplified from a gene or genes, RNA transcribed from amplified DNA, and the like. The nucleic acid samples used herein are in some embodiments derived from blood. Nucleic acids can be single- or double-stranded DNA, RNA, or DNA-RNA hybrids synthesized from human blood using methods known in the art, for example, reverse transcription or PCR.

In the simplest embodiment, such a nucleic acid sample comprises total mRNA or a nucleic acid sample corresponding to mRNA (e.g., cDNA) isolated from blood samples. In another embodiment, total mRNA is isolated from a given sample using, for example, an acid guanidinium-phenol-chloroform extraction method and polyA+ mRNA is isolated by oligo dT column chromatography or by using $(dT)_n$ magnetic beads (see, e.g., Sambrook et al., *Molecular Cloning: A Laboratory Manual* (2nd ed.), Vols. 1-3, Cold Spring Harbor Laboratory, (1989), or Current Protocols in Molecular Biology, F. Ausubel et al., ed. Greene Publishing and Wiley-Interscience, New York (1987). In a preferred embodiment, total RNA is extracted using TRIzol® reagent (GIBCO/BRL, Invitrogen Life Technologies, Cat. No. 15596). Purity and integrity of RNA is assessed by absorbance at 260/280 nm and agarose gel electrophoresis followed by inspection under ultraviolet light.

In some embodiments, it is desirable to amplify the nucleic acid sample prior to hybridization, for example, when only limited amounts of sample can be used (e.g. drop of blood). One of skill in the art will appreciate that whatever amplification method is used, if a quantitative result is desired, care must be taken to use a method that maintains or controls for the relative frequencies of the amplified nucleic acids. Methods of "quantitative" amplification are well known to those of skill in the art. For example, quantitative PCR involves simultaneously co-amplifying a known quantity of a control sequence using the same primers. This provides an internal standard that may be used to calibrate the PCR reaction. The high density array may then include probes specific to the internal standard for quantification of the amplified nucleic acid. Detailed protocols for quantitative PCR are provided in *PCR Protocols, A Guide to Methods and Applications*, Innis et al., Academic Press, Inc. N.Y., (1990).

Other suitable amplification methods include, but are not limited to polymerase chain reaction (PCR) (Innis, et al., *PCR Protocols. A Guide to Methods and Application*. Academic Press, Inc. San Diego, (1990)), ligase chain reaction (LCR) (see Wu and Wallace, 1989, *Genomics,* 4:560; Landegren, et al., 1988, *Science,* 241:1077 and Barringer, et al., 1990, *Gene,* 89:117, transcription amplification (Kwoh, et al., 1989, *Proc. Natl. Acad. Sci. USA,* 86: 1173), and self-sustained sequence replication (Guatelli, et al., 1990, *Proc. Nat. Acad. Sci. USA,* 87: 1874).

In a particularly preferred embodiment, the nucleic acid sample mRNA is reverse transcribed with a reverse transcriptase and a primer consisting of oligo dT and a sequence encoding the phage T7 promoter to provide single-stranded DNA template. The second DNA strand is polymerized using a DNA polymerase. After synthesis of double-stranded cDNA, T7 RNA polymerase is added and RNA is transcribed from the cDNA template. Successive rounds of transcription from each single cDNA template results in amplified RNA. Methods of in vitro transcription are well known to those of skill in the art (see, e.g., Sambrook, supra.) and this particular method is described in detail by Van Gelder, et al., 1990, *Proc. Natl. Acad. Sci. USA,* 87: 1663-1667 who demonstrate that in vitro amplification according to this method preserves the relative frequencies of the various RNA transcripts. Moreover, Eberwine et al. *Proc. Natl. Acad. Sci. USA,* 89: 3010-3014 provide a protocol that uses two rounds of amplification via in vitro transcription to achieve greater than $10^6$ fold amplification of the original starting material thereby permitting expression monitoring even where biological samples are limited.

Labeling of Nucleic Acid Sample or Nucleic Acid Probe

Nucleic acid samples are labelled so as to allow detection of hybridization to an array of the invention. Any analytically detectable marker that is attached to or incorporated into a molecule may be used in the invention. An analytically detectable marker refers to any molecule, moiety or atom which is analytically detected and quantified.

Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like), radiolabels (e.g., $^3$H, $^{125}$I, 35S, $^{14}$C, or $^{32}$P), enzymes (e.g., horse radish peroxidase, alkaline phosphatase and others commonly used in an ELISA), and colorimetric labels such as colloidal gold or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241, the entireties of which are incorporated by reference herein.

Means of detecting such labels are well known to those of skill in the art. Thus, for example, radiolabels may be detected using photographic film or scintillation counters, fluorescent markers may be detected using a photodetector to detect emitted light. Enzymatic labels are typically detected by providing the enzyme with a substrate and detecting the reaction product produced by the action of the enzyme on the substrate, and calorimetric labels are detected by simply visualizing the colored label.

The labels may be incorporated by any of a number of means well known to those of skill in the art. However, in one embodiment, the label is simultaneously incorporated during the amplification step in the preparation of the sample nucleic acids. Thus, for example, polymerase chain reaction (PCR) with labeled primers or labeled nucleotides will provide a labeled amplification product. In a preferred embodiment, transcription amplification, as described above, using a labeled nucleotide (e.g. fluorescein-labeled UTP and/or CTP) incorporates a label into the transcribed nucleic acids.

Alternatively, a label may be added directly to the original nucleic acid sample (e.g., mRNA, polyA mRNA, cDNA, etc.) or to the amplification product after the amplification is completed. Means of attaching labels to nucleic acids are well known to those of skill in the art and include, for example, nick translation or end-labeling (e.g. with a labeled RNA) by kinasing of the nucleic acid and subsequent attachment (ligation) of a nucleic acid linker joining the sample nucleic acid to a label (e.g., a fluorophore).

In another embodiment, the fluorescent modifications are by cyanine dyes e.g. Cy-3/Cy-5 dUTP, Cy-3/Cy-5 dCTP (Amersham Pharmacia) or alexa dyes (Khan, et al., 1998, *Cancer Res.* 58:5009-5013).

In one embodiment, the two Nucleic Acid Sample samples used for comparison are labeled with different fluorescent dyes which produce distinguishable detection signals, for example, nucleic acid samples made from normal intestinal cells are labeled with Cy5 and nucleic acid samples made from intestinal tissue cells are labeled with Cy3. The differently labeled target samples are hybridized to the same microarray simultaneously. In a preferred embodiment, the labeled nucleic acid samples are purified using methods known in the art, e.g., by ethanol purification or column purification.

In another embodiment, the nucleic acid samples will include one or more control molecules which hybridize to control probes on the microarray to normalize signals generated from the microarray. In one embodiment, labeled normalization nucleic acid samples are nucleic acid sequences that are perfectly complementary to control oligonucleotides that are spotted onto the microarray as described above. In another embodiment, labeled normalization nucleic acid samples are nucleic acid sequences that are 99%, 98%, 97%, 96%, 95%, 90%, 85%, 80% or 75% complementary to control oligonucleotides that are spotted onto the microarray as described above. The signals obtained from the normalization controls after hybridization provide a control for variations in hybridization conditions, label intensity, "reading" efficiency and other factors that may cause the signal of a perfect hybridization to vary between arrays. In one embodiment, signals (e.g., fluorescence intensity) read from all other probes in the array are divided by the signal (e.g., fluorescence intensity) from the control probes, thereby normalizing the measurements.

Preferred normalization nucleic acid samples are selected to reflect the average length of the other nucleic acid samples present in the sample, however, they are selected to cover a range of lengths. The normalization control(s) also can be selected to reflect the (average) base composition of the other probes in the array, however, in one embodiment, only one or a few normalization probes are used and they are selected such that they hybridize well (i.e., have no secondary structure and do not self hybridize) and do not match any nucleic acids on the array.

Normalization probes are localized at any position in the array or at multiple positions throughout the array to control for spatial variation in hybridization efficiency. In one embodiment, normalization controls are located at the corners or edges of the array as well as in the middle.

Hybridization Conditions

Nucleic acid hybridization involves providing a nucleic acid sample under conditions where the sample and the complementary nucleic acid member can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids. Under low stringency conditions (e.g., low temperature and/or high salt) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

The invention provides for hybridization conditions comprising the Dig hybridization mix (Boehringer); or formamide-based hybridization solutions, for example as described in Ausubel et al., supra and Sambrook et al. supra.

Methods of optimizing hybridization conditions are well known to those of skill in the art (see, e.g., Laboratory Techniques in *Biochemistry and Molecular Biology*, Vol. 24: *Hybridization With Nucleic acid Probes*, P. Tijssen, ed. Elsevier, N.Y., (1993)).

Following hybridization, non-hybridized labeled or unlabeled nucleic acid is removed from the support surface, conveniently by washing, thereby generating a pattern of hybridized target nucleic acid on the substrate surface. A variety of wash solutions are known to those of skill in the art and may be used. The resultant hybridization patterns of labeled, hybridized oligonucleotides and/or nucleic acids may be visualized or detected in a variety of ways, with the particular manner of detection being chosen based on the particular label of the test nucleic acid, where representative detection means include scintillation counting, autoradiography, fluorescence measurement, calorimetric measurement, light emission measurement and the like.

Image Acquisition and Data Analysis

Following hybridization and any washing step(s) and/or subsequent treatments, as described above, the resultant hybridization pattern is detected. In detecting or visualizing the hybridization pattern, the intensity or signal value of the label will be not only be detected but quantified, by which is meant that the signal from each spot of the hybridization will be measured and compared to a unit value corresponding to the signal emitted by a known number of end labeled target nucleic acids to obtain a count or absolute value of the copy number of each end-labeled target that is hybridized to a particular spot on the array in the hybridization pattern.

Methods for analyzing the data collected from hybridization to arrays are well known in the art. For example, where detection of hybridization involves a fluorescent label, data analysis can include the steps of determining fluorescent intensity as a function of substrate position from the data collected, removing outliers, i.e., data deviating from a predetermined statistical distribution, and calculating the relative binding affinity of the test nucleic acids from the remaining data. The resulting data is displayed as an image with the intensity in each region varying according to the binding affinity between associated oligonucleotides and/or nucleic acids and the test nucleic acids.

The following detection protocol is used for the simultaneous analysis of two samples to be compared, where each sample is labeled with a different fluorescent dye.

Each element of the microarray is scanned for the first fluorescent color. The intensity of the fluorescence at each array element is proportional to the expression level of that gene in the sample. The scanning operation is repeated for the second fluorescent label. The ratio of the two fluorescent intensities provides a highly accurate and quantitative measurement of the relative gene expression level in the two samples.

In a preferred embodiment, fluorescence intensities of immobilized nucleic acid sequences were determined from images taken with a custom confocal microscope equipped with laser excitation sources and interference filters appropriate for the Cy3 and Cy5 fluors. Separate scans were taken for each fluor at a resolution of 225 $\mu m^2$ per pixel and 65,536 gray levels. Image segmentation to identify areas of hybridization, normalization of the intensities between the two fluor images, and calculation of the normalized mean fluorescent values at each target are as described (Khan, et al., 1998, Cancer Res. 58:5009-5013. Chen, et al., 1997, Biomed. Optics 2:364-374). Normalization between the images is used to adjust for the different efficiencies in labeling and detection with the two different fluors. This is achieved by equilibrating to a value of one the signal intensity ratio of a set of internal control genes spotted on the array.

In another preferred embodiment, the array is scanned in the Cy3 and Cy5 channels and stored as separate 16-bit TIFF images. The images are incorporated and analysed using software which includes a gridding process to capture the hybridization intensity data from each spot on the array. The fluorescence intensity and background-subtracted hybridization intensity of each spot is collected and a ratio of measured mean intensities of Cy5 to Cy3 is calculated. A linear regression approach is used for normalization and assumes that a scatter plot of the measured Cy5 versus Cy3 intensities should have a slope of one. The average of the ratios is calculated and used to rescale the data and adjust the slope to one. A ratio of expression not equal to 1 is used as an indication of differential gene expression.

In a particular embodiment, where it is desired to quantify the transcription level (and thereby expression) of one or more nucleic acid sequences in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear and still provide meaningful results. Thus, for example, an assay where a 5 fold difference in concentration of the sample mRNA results in a 3- to 6-fold difference in hybridization intensity is sufficient for most purposes. Where more precise quantification is required, appropriate controls are run to correct for variations introduced in sample preparation and hybridization as described herein. In addition, serial dilutions of "standard" mRNA samples are used to prepare calibration curves according to methods well known to those of skill in the art. Of course, where simple detection of the presence or absence of a transcript is desired, no elaborate control or calibration is required.

For example, if a nucleic acid member on an array is not labeled after hybridization, this indicates that the gene comprising that nucleic acid member is not expressed in either sample. If a nucleic acid member is labeled with a single color, it indicates that a labeled gene was expressed only in one sample. The labeling of a nucleic acid member comprising an array with both colors indicates that the gene was expressed in both samples. Even genes expressed once per cell are detected (1 part in 100,000 sensitivity). A difference in expression intensity in the two samples being compared is indicative of differential expression, the ratio of the intensity in the two samples being not equal to 1.0, greater than 1.1, 1.2, 1.3, 1.4, 1.5, 1.6, 1.7, 1.8, 2.0, 3.0, 4.0 and the like or less than 0.9, 0.8, 0.7, 0.6, 0.5, 0.4, 0.3, 0.2 and the like.

PCR

In one aspect of the invention, the level of the expression of the RNA products of the biomarkers of the invention can be measured by amplifying the RNA products of the biomarkers from a sample by first using reverse transcription (RT). Either in combination, or as a second reaction step, the reverse transcribed product can then be amplified with the polymerase chain reaction (PCR). In accordance with one embodiment of the invention, the PCR can be QRT-PCR as would be understood to a person skilled in the art.

Total RNA, or mRNA from a sample is used as a template and a primer specific to the transcribed portion of a biomarker of the invention is used to initiate reverse transcription. Methods of reverse transcribing RNA into cDNA are well known and described in Sambrook et al., 1989, supra. Primer design can be accomplished utilizing commercially available software (e.g., Primer Designer 1.0, Scientific Software etc.). The product of the reverse transcription is subsequently used as a template for PCR.

PCR provides a method for rapidly amplifying a particular nucleic acid sequence by using multiple cycles of DNA replication catalyzed by a thermostable, DNA-dependent DNA polymerase to amplify the target sequence of interest. PCR requires the presence of a nucleic acid to be amplified, two single-stranded oligonucleotide primers flanking the sequence to be amplified, a DNA polymerase, deoxyribonucleoside triphosphates, a buffer and salts.

The method of PCR is well known in the art. PCR, is performed as described in Mullis and Faloona, 1987, Methods Enzymol., 155: 335, which is incorporated herein by reference. PCR is performed using template DNA (at least 1 fg; more usefully, 1-1000 ng) and at least 25 pmol of oligonucleotide primers. A typical reaction mixture includes: 2 ml of DNA, 25 pmol of oligonucleotide primer, 2.5 ml of 10H PCR buffer 1 (Perkin-Elmer, Foster City, Calif.), 0.4 ml of 1.25 mM dNTP, 0.15 ml (or 2.5 units) of Taq DNA polymerase (Perkin Elmer, Foster City, Calif.) and deionized water to a total volume of 25 ml. Mineral oil is overlaid and the PCR is performed using a programmable thermal cycler.

The length and temperature of each step of a PCR cycle, as well as the number of cycles, are adjusted according to the stringency requirements in effect. Annealing temperature and timing are determined both by the efficiency with which a primer is expected to anneal to a template and the degree of mismatch that is to be tolerated. The ability to optimize the stringency of primer annealing conditions is well within the knowledge of one of moderate skill in the art. An annealing temperature of between 30° C. and 72° C. is used. Initial denaturation of the template molecules normally occurs at between 92° C. and 99° C. for 4 minutes, followed by 20-40 cycles consisting of denaturation (94-99° C. for 15 seconds to 1 minute), annealing (temperature determined as discussed above; 1-2 minutes), and extension (72° C. for 1 minute). The final extension step is generally carried out for 4 minutes at 72° C., and may be followed by an indefinite (0-24 hour) step at 4° C.

QRT-PCR (Quanitative real time RT-PCR), can also be performed to provide a quantitative measure of gene expression levels. Similar to reverse transcription PCR, QRT-PCR reverse transcription and PCR can be performed in two steps, or reverse transcription combined with PCR can be performed concurrently. One of these techniques, for which there are commercially available kits such as Taqman (Perkin Elmer, Foster City, Calif.), is performed with a transcript-specific antisense probe. This probe is specific for the PCR product (e.g. a nucleic acid fragment derived from a gene) and is prepared with a quencher and fluorescent reporter probe complexed to the 5' end of the oligonucleotide. Different fluorescent markers are attached to different reporters, allowing for measurement of two products in one reaction. When Taq DNA polymerase is activated, it cleaves off the fluorescent reporters of the probe bound to the template by virtue of its 5'-to-3' exonuclease activity. In the absence of the quenchers, the reporters now fluoresce. The color change in the reporters is proportional to the amount of each specific product and is measured by a fluorometer; therefore, the amount of each color is measured and the PCR product is quantified. The PCR reactions can be performed in 96 well plates, 384 well plates and the like so that samples derived from many individuals are processed and measured simultaneously. The Taqman system has the additional advantage of not requiring gel electrophoresis and allows for quantification when used with a standard curve.

A second technique useful for detecting PCR products quantitatively without is to use an intercolating dye such as the commercially available QuantiTect SYBR Green PCR (Qiagen, Valencia Calif.). QRT-PCR is performed using SYBR green as a fluorescent label which is incorporated into the PCR product during the PCR stage and produces a flourescense proportional to the amount of PCR product.

Both Taqman and QuantiTect SYBR systems can be used subsequent to reverse transcription of RNA. Reverse transcription can either be performed in the same reaction mixture as the PCR step (one-step protocol) or reverse transcription can be performed first prior to amplification utilizing PCR (two-step protocol).

Additionally, other systems to quantitatively measure mRNA expression products are known including Molecular Beacons® which uses a probe having a fluorescent molecule and a quencher molecule, the probe capable of forming a hairpin structure such that when in the hairpin form, the fluorescence molecule is quenched, and when hybridized the flourescense increases giving a quantitative measurement of gene expression.

Additional techniques to quantitatively measure RNA expression include, but are not limited to, polymerase chain reaction, ligase chain reaction, Qbeta replicase (see, e.g., International Application No. PCT/US87/00880), isothermal amplification method (see, e.g., Walker et al. (1992) PNAS 89:382-396), strand displacement amplification (SDA), repair chain reaction, Asymmetric Quantitative PCR (see, e.g., U.S. Publication No. US20030134307A1) and the multiplex microsphere bead assay described in Fuja et al., 2004, Journal of Biotechnology 108:193-205.

The level of gene expression can be measured by amplifying RNA from a sample using transcription based amplification systems (TAS), including nucleic acid sequence amplification (NASBA) and 3SR. See, e.g., Kwoh et al. (1989) PNAS USA 86:1173; International Publication No. WO 88/10315; and U.S. Pat. No. 6,329,179. In NASBA, the nucleic acids may be prepared for amplification using conventional phenol/chloroform extraction, heat denaturation, treatment with lysis buffer and minispin columns for isolation of DNA and RNA or guanidinium chloride extraction of RNA. These amplification techniques involve annealing a primer that has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by a polymerase such as T7 or SP6. In an isothermal cyclic reaction, the RNA's are reverse transcribed into double stranded DNA, and transcribed once with a polymerase such as T7 or SP6. The resulting products, whether truncated or complete, indicate target specific sequences.

Several techniques may be used to separate amplification products. For example, amplification products may be separated by agarose, agarose-acrylamide or polyacrylamide gel electrophoresis using conventional methods. See Sambrook et al., 1989. Several techniques for detecting PCR products quantitatively without electrophoresis may also be used according to the invention (see for example *PCR Protocols, A Guide to Methods and Applications*, Innis et al., Academic Press, Inc. N.Y., (1990)). For example, chromatographic techniques may be employed to effect separation. There are many kinds of chromatography which may be used in the present invention: adsorption, partition, ion-exchange and molecular sieve, HPLC, and many specialized techniques for using them including column, paper, thin-layer and gas chromatography (Freifelder, Physical Biochemistry Applications to Biochemistry and Molecular Biology, 2nd ed., Wm. Freeman and Co., New York, N.Y., 1982).

Another example of a separation methodology is done by covalently labeling the oligonucleotide primers used in a PCR reaction with various types of small molecule ligands. In one such separation, a different ligand is present on each oligonucleotide. A molecule, perhaps an antibody or avidin if the ligand is biotin, that specifically binds to one of the ligands is used to coat the surface of a plate such as a 96 well ELISA plate. Upon application of the PCR reactions to the surface of such a prepared plate, the PCR products are bound with specificity to the surface. After washing the plate to remove unbound reagents, a solution containing a second molecule that binds to the first ligand is added. This second molecule is linked to some kind of reporter system. The second molecule only binds to the plate if a PCR product has been produced whereby both oligonucleotide primers are incorporated into the final PCR products. The amount of the PCR product is then detected and quantified in a commercial plate reader much as ELISA reactions are detected and quantified. An ELISA-like system such as the one described here has been developed by the Raggio Italgene company under the C-Track trade name.

Amplification products must be visualized in order to confirm amplification of the nucleic acid sequences of interest. One typical visualization method involves staining of a gel with ethidium bromide and visualization under UV light. Alternatively, if the amplification products are integrally labeled with radio- or fluorometrically-labeled nucleotides, the amplification products may then be exposed to x-ray film or visualized under the appropriate stimulating spectra, following separation.

In one embodiment, visualization is achieved indirectly. Following separation of amplification products, a labeled, nucleic acid probe is brought into contact with the amplified nucleic acid sequence of interest. The probe in one embodiment is conjugated to a chromophore but may be radiolabeled. In another embodiment, the probe is conjugated to a binding partner, such as an antibody or biotin, where the other member of the binding pair carries a detectable moiety.

In another embodiment, detection is by Southern blotting and hybridization with a labeled probe. The techniques involved in Southern blotting are well known to those of skill in the art and may be found in many standard books on molecular protocols. See Sambrook et al., 1989, supra. Briefly, amplification products are separated by gel electrophoresis. The gel is then contacted with a membrane, such as nitrocellulose, permitting transfer of the nucleic acid and non-covalent binding. Subsequently, the membrane is incubated with a chromophore-conjugated probe that is capable of hybridizing with a target amplification product. Detection is by exposure of the membrane to x-ray film or ion-emitting detection devices.

One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

One embodiment of the invention includes the primers and probes in Table 4, 6, 16 or 17 can be used for use in measuring the expression of the biomarkers of the invention.

Nuclease Protection Assays

In another embodiment of the invention, Nuclease protection assays (including both ribonuclease protection assays and S1 nuclease assays) can be used to detect and quantitate the RNA products of the biomarkers of the invention. In nuclease protection assays, an antisense probe (labeled with, e.g., radiolabeled or nonisotopic) hybridizes in solution to an RNA sample. Following hybridization, single-stranded, unhybridized probe and RNA are degraded by nucleases. An acrylamide gel is used to separate the remaining protected fragments. Typically, solution hybridization is more efficient than membrane-based hybridization, and it can accommodate up to 100 μg of sample RNA, compared with the 20-30 μg maximum of blot hybridizations.

The ribonuclease protection assay, which is the most common type of nuclease protection assay, requires the use of RNA probes. Oligonucleotides and other single-stranded DNA probes can only be used in assays containing S1 nuclease. The single-stranded, antisense probe must typically be completely homologous to target RNA to prevent cleavage of the probe:target hybrid by nuclease.

Northern Blots

A standard Northern blot assay can also be used to ascertain an RNA transcript size, identify alternatively spliced RNA transcripts, and the relative amounts of RNA products of the biomarker of the invention, in accordance with conventional Northern hybridization techniques known to those persons of ordinary skill in the art. In Northern blots, RNA samples are first separated by size via electrophoresis in an agarose gel under denaturing conditions. The RNA is then transferred to a membrane, crosslinked and hybridized with a labeled probe. Nonisotopic or high specific activity radiolabeled probes can be used including random-primed, nick-translated, or PCR-generated DNA probes, in vitro transcribed RNA probes, and oligonucleotides. Additionally, sequences with only partial homology (e.g., cDNA from a different species or genomic DNA fragments that might contain an exon) may be used as probes. The labeled probe, e.g., a radiolabelled cDNA, either containing the full-length, single stranded DNA or a fragment of that DNA sequence may be at least 20, at least 30, at least 50, or at least 100 consecutive nucleotides in length. The probe can be labeled by any of the many different methods known to those skilled in this art. The labels most commonly employed for these studies are radioactive elements, enzymes, chemicals that fluoresce when exposed to ultraviolet light, and others. A number of fluorescent materials are known and can be utilized as labels. These include, but are not limited to, fluorescein, rhodamine, auramine, Texas Red, AMCA blue and Lucifer Yellow. A particular detecting material is anti-rabbit antibody prepared in goats and conjugated with fluorescein through an isothiocyanate. Proteins can also be labeled with a radioactive element or with an enzyme. The radioactive label can be detected by any of the currently available counting procedures. Non-limiting examples of isotopes include $^{3}H$, $^{14}C$, $^{32}P$, $^{35}S$, $^{36}Cl$, $^{51}Cr$, $^{57}Co$, $^{58}Co$, $^{59}Fe$, $^{90}Y$, $^{125}I$, $^{131}I$, and $^{186}Re$. Enzyme labels are likewise useful, and can be detected by any of the presently utilized colorimetric, spectrophotometric, fluorospectrophotometric, amperometric or gasometric techniques. The enzyme is conjugated to the selected particle by reaction with bridging molecules such as carbodiimides, diisocyanates, glutaraldehyde and the like. Any enzymes known to one of skill in the art can be utilized. Examples of such enzymes include, but are not limited to, peroxidase, beta-D-galactosidase, urease, glucose oxidase plus peroxidase and alkaline phosphatase. U.S. Pat. Nos. 3,654,090, 3,850,752, and 4,016,043 are referred to by way of example for their disclosure of alternate labeling material and methods.

(N) Techniques to Measure the Protein Products of the Biomarkers of the Invention Antibody Based Methodologies Standard techniques can also be utilized for determining the amount of the protein or proteins of interest present in a sample. For example, standard techniques can be employed using, e.g., immunoassays such as, for example, Western blot, immunoprecipitation followed by sodium dodecyl sulfate polyacrylamide gel electrophoresis (SDS-PAGE), immunocytochemistry, and the like to determine the amount of the protein or proteins of interest present in a sample. A preferred agent for detecting a protein of interest is an antibody capable of binding to a protein of interest, in one embodiment an antibody with a detectable label.

For such detection methods, protein from the sample to be analyzed can easily be isolated using techniques which are well known to those of skill in the art. Protein isolation methods can, for example, be such as those described in Harlow and Lane (Harlow, E. and Lane, D., *Antibodies: A Laboratory Manual*, Cold Spring Harbor Laboratory Press, Cold Spring Harbor, N.Y. (1988)).

In some embodiments, methods for the detection of the protein or proteins of interest involve their detection via interaction with a protein-specific antibody. For example, antibodies directed a protein of interest can be utilized as described herein. Antibodies can be generated utilizing standard techniques well known to those of skill in the art. See, e.g., Section 15.13.2 of this application and Section 5.2 of U.S. Publication No. 20040018200 for a more detailed discussion of such antibody generation techniques, which is incorporated herein by reference. Briefly, such antibodies can be polyclonal, or monoclonal. An intact antibody, or an antibody fragment (e.g., Fab or F(ab')$_2$) can, for example, be used. In some embodiments, the antibody is a human or humanized antibody.

Table 5 and Table 15 are tables showing, in one embodiment of the invention, antibodies which are used to detect the proteins of the biomarkers of the invention.

For example, antibodies, or fragments of antibodies, specific for a protein of interest can be used to quantitatively or qualitatively detect the presence of the protein. This can be accomplished, for example, by immunofluorescence techniques. Antibodies (or fragments thereof) can, additionally, be employed histologically, as in immunofluorescence or immunoelectron microscopy, for in situ detection of a protein of interest. In situ detection can be accomplished by removing a histological specimen (e.g., a biopsy specimen) from a patient, and applying thereto a labeled antibody thereto that is directed to a protein. The antibody (or fragment) can be applied by overlaying the labeled antibody (or fragment) onto a biological sample. Through the use of such a procedure, it is possible to determine not only the presence of the protein of interest, but also its distribution, its presence in cells (e.g., intestinal cells and lymphocytes) within the sample. A wide variety of well-known histological methods (such as staining procedures) can be utilized in order to achieve such in situ detection.

Immunoassays for a protein of interest typically comprise incubating a biological sample of a detectably labeled antibody capable of identifying a protein of interest, and detecting the bound antibody by any of a number of techniques well-known in the art. As discussed in more detail, below, the term "labeled" can refer to direct labeling of the antibody via, e.g., coupling (i.e., physically linking) a detectable substance to the antibody, and can also refer to indirect labeling of the antibody by reactivity with another reagent that is directly labeled. Examples of indirect labeling include detection of a primary antibody using a fluorescently labeled secondary antibody.

For example, the biological sample can be brought in contact with and immobilized onto a solid phase support or carrier such as nitrocellulose, or other support which is capable of immobilizing cells, cell particles or soluble proteins. The support can then be washed with suitable buffers followed by treatment with the detectably labeled fingerprint gene-specific antibody. The solid phase support can then be washed with the buffer a second time to remove unbound antibody. The amount of bound label on support can then be detected by conventional means.

By "solid phase support or carrier" in the context of proteinaceous agents is intended any support capable of binding an antigen or an antibody. Well-known supports or carriers include glass, polystyrene, polypropylene, polyethylene, dextran, nylon, amylases, natural and modified celluloses, polyacrylamides, gabbros, and magnetite. The nature of the carrier can be either soluble to some extent or insoluble for the purposes of the present invention. The support material can have virtually any possible structural configuration so long as the coupled molecule is capable of binding to an antigen or antibody. Thus, the support configuration can be spherical, as in a bead, or cylindrical, as in the inside surface of a test tube, or the external surface of a rod. Alternatively, the surface can be flat such as a sheet, test strip, etc. Preferred supports include polystyrene beads. Those skilled in the art will know many other suitable carriers for binding antibody or antigen, or will be able to ascertain the same by use of routine experimentation.

One of the ways in which a specific antibody can be detectably labeled is by linking the same to an enzyme and use in an enzyme immunoassay (EIA) (Voller, A., "The Enzyme Linked Immunosorbent Assay (ELISA)", 1978, Diagnostic Horizons 2:1-7, Microbiological Associates Quarterly Publication, Walkersville, Md.); Voller, A. et al., 1978, J. Clin. Pathol. 31:507-520; Butler, J. E., 1981, Meth. Enzymol. 73:482-523; Maggio, E. (ed.), 1980, *Enzyme Immunoassay*, CRC Press, Boca Raton, Fla.; Ishikawa, E. et al., (eds.), 1981, *Enzyme Immunoassay*, Kgaku Shoin, Tokyo). The enzyme which is bound to the antibody will react with an appropriate substrate, in one embodiment a chromogenic substrate, in such a manner as to produce a chemical moiety which can be detected, for example, by spectrophotometric, fluorimetric or by visual means. Enzymes which can be used to detectably label the antibody include, but are not limited to, malate dehydrogenase, staphylococcal nuclease, delta-5-steroid isomerase, yeast alcohol dehydrogenase, alpha-glycerophosphate, dehydrogenase, triose phosphate isomerase, horseradish peroxidase, alkaline phosphatase, asparaginase, glucose oxidase, beta-galactosidase, ribonuclease, urease, catalase, glucose-6-phosphate dehydrogenase, glucoamylase and acetylcholinesterase. The detection can be accomplished by colorimetric methods which employ a chromogenic substrate for the enzyme. Detection can also be accomplished by visual comparison of the extent of enzymatic reaction of a substrate in comparison with similarly prepared standards.

Detection can also be accomplished using any of a variety of other immunoassays. For example, by radioactively labeling the antibodies or antibody fragments, it is possible to detect a protein of interest through the use of a radioimmunoassay (RIA) (see, for example, Weintraub, B., Principles of Radioimmunoassays, Seventh Training Course on Radioligand Assay Techniques, The Endocrine Society, March, 1986, which is incorporated by reference herein). The radioactive isotope (e.g., $^{125}$I, $^{131}$I, $^{35}$S or $^{3}$H) can be detected by such means as the use of a gamma counter or a scintillation counter or by autoradiography.

It is also possible to label the antibody with a fluorescent compound. When the fluorescently labeled antibody is exposed to light of the proper wavelength, its presence can then be detected due to fluorescence. Among the most commonly used fluorescent labeling compounds are fluorescein isothiocyanate, rhodamine, phycoerythrin, phycocyanin, allophycocyanin, o-phthaldehyde and fluorescamine.

The antibody can also be detectably labeled using fluorescence emitting metals such as $^{152}$Eu, or others of the lanthanide series. These metals can be attached to the antibody using such metal chelating groups as diethylenetriaminepentacetic acid (DTPA) or ethylenediaminetetraacetic acid (EDTA).

The antibody also can be detectably labeled by coupling it to a chemiluminescent compound. The presence of the chemiluminescent-tagged antibody is then determined by detecting the presence of luminescence that arises during the course of a chemical reaction. Examples of particularly useful chemiluminescent labeling compounds are luminol, isoluminol, theromatic acridinium ester, imidazole, acridinium salt and oxalate ester.

Likewise, a bioluminescent compound can be used to label the antibody of the present invention. Bioluminescence is a type of chemiluminescence found in biological systems in, which a catalytic protein increases the efficiency of the chemiluminescent reaction. The presence of a bioluminescent protein is determined by detecting the presence of luminescence. Important bioluminescent compounds for purposes of labeling are luciferin, luciferase and aequorin.

Protein Arrays

Polypeptides which specifically and/or selectively bind to the protein products of the biomarkers of the invention can be immobilized on a protein array. The protein array can be used as a tool, e.g., to test individual samples (such as isolated cells, tissue, lymph, lymph tissue, blood, synovial fluid, sera, biopsies, and the like) for the presence of the polypeptides protein products of the biomarkers of the invention. The protein array can also include antibodies as well as other ligands, e.g., that bind to the polypeptides encoded by the biomarkers of the invention.

Methods of producing polypeptide arrays are described, e.g., in De Wildt et al., 2000, Nature Biotech; 18:989-994; Lueking et al., 1999, Anal. Biochem. 270:103-111; Ge, 2000, Nuc. Acids Res. 28:e3; MacBeath and Schreiber, 2000, Science 289:1760-1763; International Publication Nos. WO 01/40803 and WO 99/51773A1; and U.S. Pat. No. 6,406,921. Polypeptides for the array can be spotted at high speed, e.g., using commercially available robotic apparatus, e.g., from Genetic MicroSystems and Affymetrix (Santa Clara, Calif., USA) or BioRobotics (Cambridge, UK). The array substrate can be, for example, nitrocellulose, plastic, glass, e.g., surface-modified glass. The array can also include a porous matrix, e.g., acrylamide, agarose, or another polymer.

For example, the array can be an array of antibodies, e.g., as described in De Wildt, supra. Cells that produce the polypeptide ligands can be grown on a filter in an arrayed format. Polypeptide production is induced, and the expressed antibodies are immobilized to the filter at the location of the cell. Information about the extent of binding at each address of the array can be stored as a profile, e.g., in a computer database.

In one embodiment the array is an array of protein products of the 1, 2, 3, 4, 5, 6, 7, 8, 9, 10, 11, 12, 13, 14, 15, 16, 17, 18 or all or any combination of the biomarkers of the invention. In one aspect, the invention provides for antibodies that are bound to an array which selectively bind to the protein products of the biomarkers of the invention.

(O) Protein Production

Standard recombinant nucleic acid methods can be used to express a polypeptide or antibody of the invention (e.g., a protein products of a biomarker of the invention). Generally, a nucleic acid sequence encoding the polypeptide is cloned into a nucleic acid expression vector. Of course, if the protein includes multiple polypeptide chains, each chain must be cloned into an expression vector, e.g., the same or different vectors, that are expressed in the same or different cells. If the protein is sufficiently small, i.e., the protein is a peptide of less than 50 amino acids, the protein can be synthesized using automated organic synthetic methods. Polypeptides comprising the 5' region, 3' region or internal coding region of a biomarker of the invention, are expressed from nucleic acid expression vectors containing only those nucleotide sequences corresponding to the 5' region, 3' region or internal coding region of a biomarker of the invention. Methods for producing antibodies directed to protein products of a biomarker of the invention, or polypeptides encoded by the 5' region, 3' region or internal coding regions of a biomarker of the invention.

The expression vector for expressing the polypeptide can include, in addition to the segment encoding the polypeptide or fragment thereof, regulatory sequences, including for example, a promoter, operably linked to the nucleic acid(s) of interest. Large numbers of suitable vectors and promoters are known to those of skill in the art and are commercially available for generating the recombinant constructs of the present invention. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXTI, pSG (Stratagene) pSVK3, pBPV, pMSG, and pSVL (Pharmacia). One preferred class of preferred libraries is the display library, which is described below.

Methods well known to those skilled in the art can be used to construct vectors containing a polynucleotide of the invention and appropriate transcriptional/translational control signals. These methods include in vitro recombinant DNA techniques, synthetic techniques and in vivo recombination/genetic recombination. See, for example, the techniques described in Sambrook & Russell, *Molecular Cloning: A Laboratory Manual*, 3$^{rd}$ Edition, Cold Spring Harbor Laboratory, N.Y. (2001) and Ausubel et al., *Current Protocols in Molecular Biology* (Greene Publishing Associates and Wiley Interscience, N.Y. (1989). Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda P, and trc. Eukaryotic promoters include CMV immediate early, HSV thymidine kinase, early and late SV40, LTRs from retrovirus, mouse metallothionein-I, and various art-known tissue specific promoters. In specific embodiments, the promoter is an inducible promoter. In other embodiments, the promoter is a constitutive promoter. In yet other embodiments, the promoter is a tissue-specific promoter.

Generally, recombinant expression vectors will include origins of replication and selectable markers permitting transformation of the host cell, e.g., the ampicillin resistance gene of *E. coli* and *S. cerevisiae* auxotrophic markers (such as URA3, LEU2, HIS3, and TRP1 genes), and a promoter derived from a highly expressed gene to direct transcription of a downstream structural sequence. Such promoters can be derived from operons encoding glycolytic enzymes such as 3-phosphoglycerate kinase (PGK), a-factor, acid phosphatase, or heat shock proteins, among others. The polynucleotide of the invention is assembled in appropriate phase with translation initiation and termination sequences, and in some embodiments, a leader sequence capable of directing secretion of translated protein into the periplasmic space or extracellular medium. Optionally, a nucleic acid of the invention can encode a fusion protein including an N-terminal identification peptide imparting desired characteristics, e.g., stabilization or simplified purification of expressed recombinant product. Useful expression-vectors for bacteria are constructed by inserting a polynucleotide of the invention together with suitable translation initiation and termination signals, optionally in operable reading phase with a functional promoter. The vector will comprise one or more phenotypic selectable markers and an origin of replication to ensure maintenance of the vector and to, if desirable, provide amplification within the host. Suitable prokaryotic hosts for transformation include *E. coli, Bacillus subtilis, Salmonella typhimurium* and various species within the genera *Pseudomonas, Streptomyces*, and *Staphylococcus*, although others may also be employed as a matter of choice.

As a representative but nonlimiting example, useful expression vectors for bacteria can comprise a selectable marker and bacterial origin of replication derived from commercially available plasmids comprising genetic elements of the well known cloning vector pBR322 (ATCC 37017). Such commercial vectors include, for example, pKK223-3 (Pharmacia Fine Chemicals, Uppsala, Sweden) and pGEM1 (Promega, Madison, Wis., USA).

The present invention provides host cells genetically engineered to contain the polynucleotides of the invention. For example, such host cells may contain nucleic acids of the invention introduced into the host cell using known transformation, transfection or infection methods. The present invention also provides host cells genetically engineered to express the polynucleotides of the invention, wherein such polynucleotides are in operative association with a regulatory sequence heterologous to the host cell which drives expression of the polynucleotides in the cell.

The present invention further provides host cells containing the vectors of the present invention, wherein the nucleic acid has been introduced into the host cell using known transformation, transfection or infection methods. The host cell can be a eukaryotic host cell, such as a mammalian cell, a lower eukaryotic host cell, such as a yeast cell, or the host cell can be a prokaryotic cell, such as a bacterial cell. Introduction of the recombinant construct into the host cell can be effected, for example, by calcium phosphate transfection, DEAE, dextran mediated transfection, or electroporation (Davis, L. et al., *Basic Methods in Molecular Biology* (1986)). Cell-free translation systems can also be employed to produce such proteins using RNAs derived from the DNA constructs of the present invention.

Any host/vector system can be used to express one or more of the proteins products of the biomarkers of the invention including those listed in Table 3 and/or Table 13. Appropriate cloning and expression vectors for use with prokaryotic and eukaryotic hosts are described by Sambrook et al., in *Molecular Cloning: A Laboratory Manual*, Second Edition, Cold Spring Harbor, N.Y. (1989), the disclosure of which is incorporated herein by reference in its entirety. The most preferred host cells are those which do not normally express the particular polypeptide or which expresses the polypeptide at low natural level.

In a specific embodiment, the host cells are engineered to express an endogenous gene comprising the polynucleotides of the invention under the control of inducible regulatory elements, in which case the regulatory sequences of the endogenous gene may be replaced by homologous recombination. As described herein, gene targeting can be used to replace a gene's existing regulatory region with a regulatory sequence isolated from a different gene or a novel regulatory sequence synthesized by genetic engineering methods. Such regulatory sequences may be comprised of promoters, enhancers, scaffold-attachment regions, negative regulatory elements, transcriptional initiation sites, regulatory protein binding sites or combinations of said sequences. Alternatively, sequences which affect the structure or stability of the RNA or protein produced may be replaced, removed, added, or otherwise modified by targeting, including polyadenylation signals. mRNA stability elements, splice sites, leader sequences for enhancing or modifying transport or secretion properties of the protein, or other sequences which alter or improve the function or stability of protein or RNA molecules.

The host of the present invention may also be a yeast or other fungi. In yeast, a number of vectors containing constitutive or inducible promoters may be used. For a review see, Ausubel et al. (eds), *Current Protocols in Molecular Biology*, Vol. 2, Greene Publish. Assoc. & Wiley Interscience, Ch. 13 (1988); Grant et al., 1987, "Expression and Secretion Vectors for Yeast", Methods Enzymol. 153:516-544; Glover, *DNA Cloning*, Vol. II, IRL Press, Wash., D.C., Ch. 3 (1986); Bitter, 1987, "Heterologous Gene Expression in Yeast", Methods Enzymol. 152:673-684; and Strathern et al. (eds), *The Molecular Biology of the Yeast Saccharomyces*, Cold Spring Harbor Press, Vols. I and II (1982).

Potentially suitable yeast strains include *Saccharomyces cerevisiae, Schizosaccharomyces pombe, Kluyveromyces* strains, *Candida*, or any yeast strain capable of expressing heterologous proteins. Potentially suitable bacterial strains include *Escherichia coli*, enterobacteriaceae such as *Serratia marescans*, bacilli such as *Bacillus subtilis, Salmonella typhimurium*, pseudomonads or any bacterial strain capable of expressing heterologous proteins. If the protein is made in yeast or bacteria, it may be necessary to modify the protein produced therein, for example by phosphorylation or glycosylation of the appropriate sites, in order to obtain the functional protein. Such covalent attachments may be accomplished using known chemical or enzymatic methods.

Various mammalian cell culture systems can also be employed to express recombinant protein. Examples of mammalian expression systems include the monkey COS cells such as COS-7 lines of monkey kidney fibroblasts, described by Gluzman, 1981, Cell 23:175 (1981), Chinese Hamster Ovary (CHO) cells, human kidney 293 cells, human epidermal A431 cells, human Colo205 cells, 3T3 cells, CV-1 cells, normal diploid cells, cell strains derived from in vitro culture of primary tissue, primary explants, HeLa cells, mouse L cells, BHK, HL-60, U937, HaK, C127, 3T3, or Jurkat cells, and other cell lines capable of expressing a compatible vector. Mammalian expression vectors will comprise an origin of replication, a suitable promoter and also any necessary ribosome-binding sites, polyadenylation site, splice donor and acceptor sites, transcriptional termination sequences, and 5' flanking nontranscribed sequences.

Microbial cells employed in expression of proteins can be disrupted by any convenient method, including freeze-thaw cycling, sonication, mechanical disruption, or use of cell lysing agents. Recombinant polypeptides produced in bacterial culture are usually isolated by initial extraction from cell pellets, followed by one or more salting-out, aqueous ion exchange or size exclusion chromatography steps. In some embodiments, the template nucleic acid also encodes a polypeptide tag, e.g., penta- or hexa-histidine.

Recombinant proteins can be isolated using an technique well-known in the art. Scopes (*Protein Purification. Principles and Practice*, Springer-Verlag, New York (1994)), for example, provides a number of general methods for purifying recombinant (and non-recombinant) proteins. The methods include, e.g., ion-exchange chromatography, size-exclusion chromatography, affinity chromatography, selective precipitation, dialysis, and hydrophobic interaction chromatography.

(P) Methods for Identifying Compounds for Use in the Prevention, Treatment, or Amelioration of One or More Colorectal Pathologies Methods to Identify Compounds that Modulate the Expression or Activity of a Biomarker The present invention provides methods of identifying compounds that bind to the products of the biomarkers of the invention. The present invention also provides methods for identifying compounds that modulate the expression and/or activity of the products of the biomarkers of the invention. The compounds identified via such methods are useful for the development of one or more animal models to study colorectal pathology including polyps or one or more subtypes of polyps. Further, the compounds identified via such methods are useful as lead compounds in the development of prophylactic and therapeutic compositions for prevention, treatment, and/or amelioration of one or more colorectal pathologies including one or more polyps or one or more subtypes of polyps. Such methods are particularly useful in that the effort and great expense involved in testing potential prophylactics and therapeutics in vivo is efficiently focused on those compounds identified via the in vitro and ex vivo methods described herein.

The present invention provides a method for identifying a compound to be tested for an ability to prevent, treat, or ameliorate one or more colorectal pathologies said method comprising: (a) contacting a cell expressing a protein products of one or more biomarkers of the invention or a fragment thereof, or RNA products of one or more biomarkers of the invention or a fragment thereof with a test compound; and (b) determining the ability of the test compound to bind to the protein products, protein fragment, RNA products, or RNA portion so that if a compound binds to the protein products, protein fragment, RNA products, RNA portions, a compound to be tested for an ability to prevent, treat, or ameliorate one or more colorectal pathologies is identified. The cell, for example, can be a prokaryotic cell, yeast cell, viral cell or a cell of mammalian origin. Determining the ability of the test compound to bind to the protein products, protein fragment, RNA products, or RNA portion can be accomplished, for example, by coupling the test compound with a radioisotope or enzymatic label such that binding of the test compound to the protein products, protein fragment, RNA products, or RNA portion can be determined by detecting the labeled compound in a complex. For example, test compounds can be labeled with $^{125}$I, $^{35}$S, $^{14}$C, or $^{3}$H, either directly or indirectly, and the radioisotope detected by direct counting of radioemmission or by scintillation counting. Alternatively, test compounds can be enzymatically labeled with, for example, horseradish peroxidase, alkaline phosphatase, or luciferase, and the enzymatic label detected by determination of conversion of an appropriate substrate to product. In a specific embodiment, the assay comprises contacting a cell which expresses a protein products of one or more biomarkers of the invention or a fragment thereof, or a RNA products of one or more biomarkers of the invention or a fragment thereof, with a known compound which binds the protein products, protein fragment, RNA products, or RNA portion to form an assay mixture, contacting the assay mixture with a test compound, and determining the ability of the test compound to interact with the protein products, protein fragment, RNA products, or RNA portion, wherein determining the ability of the test compound to interact with the protein products, protein fragment, RNA products, or RNA portion comprises determining the ability of the test compound to preferentially bind to the protein products, protein fragment, RNA products, or RNA portion as compared to the known compound.

Binding of the test compound to the protein products or protein fragment can be determined either directly or indirectly. In a specific embodiment, the assay includes contacting a protein products of one or more biomarkers of the invention or a fragment thereof, or one or more RNA products of one or more biomarkers of the invention or a portion thereof with a known compound which binds the protein products, protein fragment, RNA products, or RNA portion to form an assay mixture, contacting the assay mixture with a test compound, and determining the ability of the test compound to interact with the protein products, protein fragment, RNA products, or RNA portion, wherein determining the ability of the test compound to interact with the protein products, protein fragment, RNA products, or RNA portion comprises determining the ability of the test compound to preferentially bind to the protein products, protein fragment, RNA products, or RNA portion as compared to the known compound. Techniques well known in the art can be used to determine the binding between a test compound and a protein products of a biomarker of the invention or a fragment thereof, or a RNA products of a biomarker of the invention or a portion thereof.

In some embodiments of the above assay methods of the present invention, it may be desirable to immobilize a RNA products of a biomarker of the invention or a portion thereof, or its target molecule to facilitate separation of complexed from uncomplexed forms of the RNA products or RNA portion, the target molecule or both, as well as to accommodate automation of the assay. In more than one embodiment of the above assay methods of the present invention, it may be desirable to immobilize either a protein products of a biomarker of the invention or a fragment thereof, or its target molecule to facilitate separation of complexed from uncomplexed forms of one or both of the proteins, as well as to accommodate automation of the assay. Binding of a test compound to a protein products of a biomarker of the invention or a fragment thereof can be accomplished in any vessel suitable for containing the reactants. Examples of such vessels include microtiter plates, test tubes, and micro-centrifuge tubes. In one embodiment, a fusion protein can be provided which adds a domain that allows one or both of the proteins to be bound to a matrix. For example, glutathione-S-transferase (GST) fusion proteins can be adsorbed onto glutathione sepharose beads (Sigma Chemical; St. Louis, Mo.) or glutathione derivatized microtiter plates, which are then combined with the test compound or the test compound and either the non-adsorbed target protein or a protein products of a biomarker of the invention or a fragment thereof, and the mixture incubated under conditions conducive to complex formation (e.g., at physiological conditions for salt and pH). Following incubation, the beads or microtiter plate wells are washed to remove any unbound components and complex formation is measured either directly or indirectly, for example, as described above. Alternatively, the complexes can be dissociated from the matrix, and the level of binding of a protein products of a biomarker of the invention or a fragment thereof can be determined using standard techniques.

Other techniques for immobilizing proteins on matrices can also be used in the screening assays of the invention. For example, either a protein products of a biomarker of the invention or a fragment thereof, or a target molecule can be immobilized utilizing conjugation of biotin and streptavidin. A biotinylated protein products of a biomarker of the invention or a target molecule can be prepared from biotin-NHS (N-hydroxy-succinimide) using techniques well known in the art (e.g., biotinylation kit, Pierce Chemicals; Rockford, Ill.), and immobilized in the wells of streptavidin-coated 96 well plates (Pierce Chemical). Alternatively, antibodies reactive with a protein products of a biomarker of the invention or a fragment thereof can be derivatized to the wells of the plate, and protein trapped in the wells by antibody conjugation. Methods for detecting such complexes, in addition to those described above for the GST-immobilized complexes, include immunodetection of complexes using antibodies reactive with a protein products of a biomarker of the invention, as well as enzyme-linked assays which rely on detecting an enzymatic activity associated with a protein products of a biomarker of the invention or a fragment thereof, or target molecule.

The interaction or binding of a protein products of a biomarker of the invention or a fragment thereof to a test compound can also be determined using such proteins or protein fragments as "bait proteins" in a two-hybrid assay or three hybrid assay (see, e.g., U.S. Pat. No. 5,283,317; Zervos et al. (1993) Cell 72:223-232; Madura et al. (1993) J. Biol. Chem. 268:12046-12054; Bartel et al. (1993) Bio/Techniques 14:920-924; Iwabuchi et al. (1993) Oncogene 8:1693-1696; and International Publication No. WO 94/10300).

The present invention provides a method for identifying a compound to be tested for an ability to prevent, treat, or ameliorate one or more colorectal pathologies, said method comprising: (a) contacting a cell expressing a protein or RNA products of one or more biomarkers of the invention with a test compound; (b) determining the amount of the protein or RNA products present in (a); and (c) comparing the amount in (a) to that present in a corresponding control cell that has not been contacted with the test compound, so that if the amount of the protein or RNA products is altered relative to the amount in the control, a compound to be tested for an ability to prevent, treat, or ameliorate one or more colorectal pathologies is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control as determined by utilizing an assay described herein (e.g., a microarray or QRT-PCR) or an assay well known to one of skill in the art. In alternate embodiments, such a method comprises determining the amount of the protein or RNA products of at least 2, at least 3, at least 4, at least 5, at least 6, at least 7, at least 8, 1 to 3, 1 to 5, 1-8, all or any combination of the biomarkers of the invention present in the cell and comparing the amounts to those present in the control.

The cells utilized in the cell-based assays described herein can be engineered to express a biomarker of the invention utilizing techniques known in the art. See, e.g., Section III entitled "Recombinant Expression Vectors and Host Cells" of U.S. Pat. No. 6,245,527, which is incorporated herein by reference. Alternatively, cells that endogenously express a biomarker of the invention can be used. For example, intestinal cells may be used.

In a specific embodiment, intestinal cells are isolated from a "normal" individual, or an individual with one or more colorectal pathologies and are incubated in the presence and absence of a test compound for varying amounts of time (i.e., 30 min, 1 hr, 5 hr, 24 hr, 48 hr and 96 hrs). When screening for prophylactic or therapeutic agents, a clone of the full sequence of a biomarker of the invention or functional portion thereof is used to transfect the cells. The transfected cells are cultured for varying amounts of time (i.e., 1, 2, 3, 5, 7, 10, or 14 days) in the presence or absence of test compound. Following incubation, target nucleic acid samples are prepared from the cells and hybridized to a nucleic acid probe corresponding to a nucleic acid sequence which are differentially expressed in individuals with one or more colorectal pathologies. The nucleic acid probe is labeled, for example, with a radioactive label, according to methods well-known in the art and described herein. Hybridization is carried out by northern blot, for example as described in Ausubel et al., supra or Sambrook et al., supra). The differential hybridization, as defined herein, of the target to the samples on the array from normal relative to RNA from samples having one or more colorectal pathologies is indicative of the level of expression of RNA corresponding to a differentially expressed specific nucleic acid sequence. A change in the level of expression of the target sequence as a result of the incubation step in the presence of the test compound, is indicative of a compound that increases or decreases the expression of the corresponding polyp biomarker specific nucleic acid sequence.

The present invention also provides a method for identifying a compound to be tested for an ability to prevent, treat, or ameliorate one or more colorectal pathologies, said method comprises: (a) contacting a cell-free extract (e.g., an intestinal cell extract) with a nucleic acid sequence encoding a protein or RNA products of one or more biomarkers of the invention and a test compound; (b) determining the amount of the protein or RNA product present in (a); and (c) comparing the amount(s) in (a) to that present to a corresponding control that has not been contacted with the test compound, so that if the amount of the protein or RNA product is altered relative to the amount in the control, a compound to be tested for an ability to prevent, treat, or ameliorate one or more colorectal pathologies is identified. In a specific embodiment, the expression level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the expression level in the control sample determined by utilizing an assay described herein (e.g., a microarray or QRT-PCR) or an assay well known to one of skill in the art. In alternate embodiments, such a method comprises determining the amount of a protein or RNA product of at least 2, at least 3, at least 4, at least 5, at least 6, at least 7, at least 8, 1 to 3, 1 to 5, 1-8, all or any combination of the biomarkers of the invention present in the extract and comparing the amounts to those present in the control.

In certain embodiments, the amount of RNA product of a biomarker of the invention is determined, in other embodiments, the amount of protein products of a biomarker of the invention is determined, while in still other embodiments, the amount of RNA and protein products of a biomarker of the invention is determined. Standard methods and compositions for determining the amount of RNA or protein products of a biomarker of the invention can be utilized. Such methods and compositions are described in detail above.

Kits to Identify Compounds that Modulate the Expression or Activity of a Biomarker In specific embodiments, in a screening assay described herein, the amount of protein or RNA product of a biomarker of the invention is determined utilizing kits. Such kits comprise materials and reagents required for measuring the expression of at least 1, at least 2, at least 3, at least 4, at least 5, at least 6, at least 7, at least 8 protein or RNA products of at least 1, at least 2, at least 3, at least 4, at least 5, at least 6, at least 7, at least 8, all or any combination of the biomarkers of the invention. In specific embodiments, the kits may further comprise one or more additional reagents employed in the various methods, such as: (1) reagents for purifying RNA from blood; (2) primers for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization and washing buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA transcript (in some embodiments, mRNA) for use as a control.

In some embodiments, the kits are QRT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In a specific embodiment, kits for measuring a RNA product of a biomarker of the invention comprise materials and reagents that are necessary for measuring the expression of the RNA product. For example, a microarray or QRT-PCR kit may be used and contain only those reagents and materials necessary for measuring the levels of RNA products of at least 1, at least 2, at least 3, at least 4, at least 5, at least 6, at least 7, at least 8, all or any combination of the biomarkers of the invention. Alternatively, in some embodiments, the kits can comprise materials and reagents that are not limited to those required to measure the levels of RNA products of 1, 2, 3, 4, 5, 6, 7, 8 all or any combination of the biomarkers of the invention. For example, a microarray kit may contain reagents and materials necessary for measuring the levels of RNA products 1, 2, 3, 4, 5, 6, 7, 8, all or any combination of the biomarkers of the invention, in addition to reagents and materials necessary for measuring the levels of the RNA products of at least 1, at least 2, at least 3, at least 4, at least 5, at least 6, at least 7, at least 8, or more genes other than the biomarkers of the invention. In a specific embodiment, a microarray or QRT-PCR kit contains reagents and materials necessary for measuring the levels of RNA products of at least 1, at least 2, at least 3, at least 4, at least 5, at least 6, at least 7, at least 8, all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes that are not biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000 or 500-1000 or more genes that are not biomarkers of the invention.

For nucleic acid microarray kits, the kits generally comprise probes attached or localized to a support surface. The probes may be labeled with a detectable label. In a specific embodiment, the probes are specific for the 5' region, the 3' region, the internal coding region, an exon(s), an intron(s), an exon junction(s), or an exon-intron junction(s), of 1, 2, 3, 4, 5, 6, 7, 8, all or any combination of the biomarkers of the invention. The microarray kits may comprise instructions for performing the assay and methods for interpreting and analyzing the data resulting from the performance of the assay. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container.

For QRT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, 8, all or any combination of the biomarkers of the invention. The QRT-PCR kits may also comprise enzymes suitable for reverse transcribing and/or amplifying nucleic acids (e.g., polymerases such as Taq, enzymes such as reverse transcriptase etc.), and deoxynucleotides and buffers needed for the reaction mixture for reverse transcription and amplification. The QRT-PCR kits may also comprise biomarker specific sets of primers specific for 1, 2, 3, 4, 5, 6, 7, 8, all or any combination of the biomarkers of the invention. The QRT-PCR kits may also comprise biomarker specific probes which are specific for the sequences amplified from 1, 2, 3, 4, 5, 6, 7, 8, all or any combination of the biomarkers of the invention using the biomarker specific sets of primers. The probes may or may not be labeled with a detectable label (e.g., a fluorescent label). In some embodiments, when contemplating multiplexing it is helpful if the probes are labeled with a different detectable label (e.g. FAM or HEX) Each component of the QRT-PCR kit is generally in its own suitable container. Thus, these kits generally comprise distinct containers suitable for each individual reagent, enzyme, primer and probe. Further, the QRT-PCR kits may comprise instructions for performing the assay and methods for interpreting and analyzing the data resulting from the performance of the assay.

For antibody based kits, the kit can comprise, for example: (1) a first antibody (which may or may not be attached to a support) which binds to protein of interest (e.g., a protein products of 1, 2, 3, 4, 5, 6, 7, 8, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay.

Reporter gene-based assays may also be conducted to identify a compound to be tested for an ability to prevent, treat, or ameliorate one or more colorectal pathologies. In a specific embodiment, the present invention provides a method for identifying a compound to be tested for an ability to prevent, treat, or ameliorate one or more colorectal pathologies, said method comprising: (a) contacting a compound with a cell expressing a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control cell that has not been contacted with the test compound, so that if the amount of expressed reporter gene is altered relative to the amount in the control cell, a compound to be tested for an ability to prevent, treat, or ameliorate one or more colorectal pathologies is identified. In accordance with this embodiment, the cell may naturally express the biomarker or be engineered to express the biomarker. In another embodiment, the present invention provides a method for identifying a compound to be tested for an ability to prevent, treat, or ameliorate one or more colorectal pathologies, said method comprising: (a) contacting a compound with a cell-free extract and a reporter gene construct comprising a reporter gene operably linked to a regulatory element of a biomarker of the invention (e.g., a promoter/enhancer element); (b) measuring the expression of said reporter gene; and (c) comparing the amount in (a) to that present in a corresponding control that has not been contacted with the test compound, so that if the amount of expressed reporter gene is altered relative to the amount in the control, a compound to be tested for an ability to prevent, treat, or ameliorate one or more colorectal pathologies is identified.

Any reporter gene well-known to one of skill in the art may be used in reporter gene constructs used in accordance with the methods of the invention. Reporter genes refer to a nucleotide sequence encoding a RNA transcript or protein that is readily detectable either by its presence (by, e.g., RT-PCR, Northern blot, Western Blot, ELISA, etc.) or activity. Non-limiting examples of reporter genes are listed in Table 10. Reporter genes may be obtained and the nucleotide sequence of the elements determined by any method well-known to one of skill in the art. The nucleotide sequence of a reporter gene can be obtained, e.g., from the literature or a database such as GenBank. Alternatively, a polynucleotide encoding a reporter gene may be generated from nucleic acid from a suitable source. If a clone containing a nucleic acid encoding a particular reporter gene is not available, but the sequence of the reporter gene is known, a nucleic acid encoding the reporter gene may be chemically synthesized or obtained from a suitable source (e.g., a cDNA library, or a cDNA library generated from, or nucleic acid, preferably poly A+ RNA, isolated from, any tissue or cells expressing the reporter gene) by PCR amplification. Once the nucleotide sequence of a reporter gene is determined, the nucleotide sequence of the reporter gene may be manipulated using methods well-known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate reporter genes having a different amino acid sequence, for example to create amino acid substitutions, deletions, and/or insertions.

In accordance with the invention, cells that naturally or normally express one or more, all or any combination of the biomarkers of the invention can be used in the methods described herein. Alternatively, cells can be engineered to express one or more, all or any combination of the biomarkers of the invention, or a reporter gene using techniques well-known in the art and used in the methods described herein. Examples of such techniques include, but are not to, calcium phosphate precipitation (see, e.g., Graham & Van der E b, 1978, Virol. 52:546), dextran-mediated transfection, calcium phosphate mediated transfection, polybrene mediated transfection, protoplast fusion, electroporation, encapsulation of the nucleic acid in liposomes, and direct microinjection of the nucleic acid into nuclei.

In a specific embodiment, the cells used in the methods described herein are intestinal cells or cell lines, lymphocytes (T or B lymphocytes), monocytes, neutrophils, macrophages, eosinophils, basophils, erythrocytes or platelets. In a preferred embodiment, the cells used in the methods described herein are intestinal cells. In another preferred embodiment, the cells used in the methods described herein are lymphocytes. In another embodiment, the cells used in the methods described herein are immortalized cell lines derived from a source, e.g., a tissue.

Any cell-free extract that permits the translation, and optionally but preferably, the transcription, of a nucleic acid can be used in accordance with the methods described herein. The cell-free extract may be isolated from cells of any species origin. For example, the cell-free translation extract may be isolated from human cells, cultured mouse cells, cultured rat cells, Chinese hamster ovary (CHO) cells, *Xenopus* oocytes, rabbit reticulocytes, wheat germ, or rye embryo (see, e.g., Krieg & Melton, 1984, Nature 308:203 and Dignam et al., 1990 Methods Enzymol. 182:194-203). Alternatively, the cell-free translation extract, e.g., rabbit reticulocyte lysates and wheat germ extract, can be purchased from, e.g., Promega, (Madison, Wis.). In a preferred embodiment, the cell-free extract is an extract isolated from human cells. In a specific embodiment, the human cells are HeLa cells, lymphocytes, or intestinal cells or cell lines.

In addition to the ability to modulate the expression levels of RNA and/or protein products a biomarker of the invention, it may be desirable, at least in certain instances, that compounds modulate the activity of a protein products of a biomarker of the invention. Thus, the present invention provides methods of identifying compounds to be tested for an ability to prevent, treat, or ameliorate one or more colorectal pathologies, comprising methods for identifying compounds that modulate the activity of a protein products of one or more biomarkers of the invention. Such methods can comprise: (a) contacting a cell expressing a protein products of one or more biomarkers of the invention with a test compound; (b) determining the activity level of the protein products; and (c) comparing the activity level to that in a corresponding control cell that has not been contacted with the test compound, so that if the level of activity in (a) is altered relative to the level of activity in the control cell, a compound to be tested for an ability to prevent, treat, or ameliorate one or more colorectal pathologies is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or QRT-PCR) or an assay well known to one of skill in the art. In alternate embodiments, such a method comprises determining the activity level of a protein products of at least 2, at least 3, at least 4, at least 5, at least 6, at least 7, at least 8, at least 9, at least 10, at least 12, at least 15, 1 to 5, 1-10, 5-10, 5-15, or 10-15, or more, or all or any combination of the biomarkers of the invention present in the cell and comparing the activity levels to those present in the control.

The present invention provides methods of identifying compounds to be tested for an ability to prevent, treat, or ameliorate one or more colorectal pathologies, comprising: (a) contacting a cell-free extract with a nucleic acid encoding a protein products of one or more biomarkers of the invention and a test compound; (b) determining the activity level of the protein products; and (c) comparing the activity level to that in a corresponding control that has not been contacted with the test compound, so that if the level of activity in (a) is altered relative to the level of activity in the control, a compound to be tested for an ability to prevent, treat, or ameliorate one or more colorectal pathologies is identified. In a specific embodiment, the activity level(s) is altered by 5%, 10%, 15%, 25%, 30%, 40%, 50%, 5 to 25%, 10 to 30%, at least 1 fold, at least 1.5 fold, at least 2 fold, 4 fold, 5 fold, 10 fold, 25 fold, 1 to 10 fold, or 5 to 25 fold relative to the activity level in the control as determined by utilizing an assay described herein (e.g., a microarray or QRT-PCR) or an assay well known to one of skill in the art. In alternate embodiments, such a method comprises determining the activity level of a protein products of at least 2, at least 3, at least 4, at least 5, at least 6, at least 7, at least 8, 1 to 3, 1 to 5, 1-8 all or any combination of the biomarkers of the invention present in the sample and comparing the activity levels to those present in the control.

Standard techniques can be utilized to determine the level of activity of a protein products of a biomarker of the invention. Activities of protein products of biomarkers of the invention that can be determined using techniques well known in the art.

Method to Utilize the Biological Activity of the Compounds

Upon identification of compounds to be tested for an ability to prevent, treat, or ameliorate one or more colorectal pathologies (for convenience referred to herein as a "lead"

compound), the compounds can be further investigated. For example, the compounds identified via the present methods can be further tested in vivo in accepted animal models of polyp formation. Further, the compounds identified via the methods can be analyzed with respect to their specificity. Techniques for such additional compound investigation are well known to one of skill in the art.

In one embodiment, the effect of a lead compound can be assayed by measuring the cell growth or viability of the target cell. Such assays can be carried out with representative cells of cell types involved in polyp formation (e.g., intestinal cells; cells isolated from different portions of the gastrointestinal system and the like). Alternatively, instead of culturing cells from a patient, a lead compound may be screened using cells of a cell line.

Many assays well-known in the art can be used to assess the survival and/or growth of a patient cell or cell line following exposure to a lead compound; for example, cell proliferation can be assayed by measuring Bromodeoxyuridine (BrdU) incorporation (see, e.g., Hoshino et al., 1986, Int. J. Cancer 38, 369; Campana et al., 1988, J. Immunol. Meth. 107:79) or ($^3$H)-thymidine incorporation (see, e.g., Chen, J., 1996, Oncogene 13:1395-403; Jeoung, J., 1995, J. Biol. Chem. 270:18367-73), by direct cell count, by detecting changes in transcription, translation or activity of known genes such as proto-oncogenes (e.g., fos, myc) or cell cycle markers (Rb, cdc2, cyclin A, D1, D2, D3, E, etc). The levels of such protein and RNA (e.g., mRNA) and activity can be determined by any method well known in the art. For example, protein can be quantitated by known immunological based methods such as Western blotting or immunoprecipitation using commercially available antibodies. mRNA can be quantitated using methods that are well known and routine in the art, for example, using northern analysis, RNase protection, the polymerase chain reaction in connection with the reverse transcription. Cell viability can be assessed by using trypan-blue staining or other cell death or viability markers known in the art. In a specific embodiment, the level of cellular ATP is measured to determined cell viability. Differentiation can be assessed, for example, visually based on changes in morphology.

Animal Models

Compounds can be tested in suitable animal model systems prior to use in humans. Such animal model systems include but are not limited to rats, mice, chicken, cows, monkeys, pigs, dogs, rabbits, etc. Any animal system well-known in the art may be used. In certain embodiments, compounds are tested in a mouse model. Compounds can be administered repeatedly.

Accepted animal models can be utilized to determine the efficacy of the compounds identified via the methods described above for the prevention, treatment, and/or amelioration of one or more colorectal pathologies.

Toxicity

The toxicity and/or efficacy of a compound identified in accordance with the invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). Cells and cell lines that can be used to assess the cytotoxicity of a compound identified in accordance with the invention include, but are not limited to, peripheral blood mononuclear cells (PBMCs), Caco-2 cells, and Huh7 cells. The dose ratio between toxic and therapeutic effects is the therapeutic index and it can be expressed as the ratio $LD_{50}/ED_{50}$. A compound identified in accordance with the invention that exhibits large therapeutic indices is preferred. While a compound identified in accordance with the invention that exhibits toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of a compound identified in accordance with the invention for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the $IC_{50}$ (i.e., the concentration of the compound that achieves a half-maximal inhibition of symptoms) as determined in cell culture. Such information can be used to more accurately determine useful doses in humans. Levels in plasma may be measured, for example, by high performance liquid chromatography.

Design of Congeners or Analogs

The compounds which display the desired biological activity can be used as lead compounds for the development or design of congeners or analogs having useful pharmacological activity. For example, once a lead compound is identified, molecular modeling techniques can be used to design variants of the compound that can be more effective. Examples of molecular modeling systems are the CHARM and QUANTA programs (Polygen Corporation, Waltham, Mass.). CHARM performs the energy minimization and molecular dynamics functions. QUANTA performs the construction, graphic modelling and analysis of molecular structure. QUANTA allows interactive construction, modification, visualization, and analysis of the behavior of molecules with each other.

A number of articles review computer modeling of drugs interactive with specific proteins, such as Rotivinen et al., 1988, Acta Pharmaceutical Fennica 97:159-166; Ripka, 1998, New Scientist 54-57; McKinaly & Rossmann, 1989, Annu. Rev. Pharmacol. Toxiciol. 29:111-122; Perry & Davies, OSAR: Quantitative Structure-Activity Relationships in Drug Design pp. 189-193 (Alan R. Liss, Inc. 1989); Lewis & Dean, 1989, Proc. R. Soc. Lond. 236:125-140 and 141-162; Askew et al., 1989, J. Am. Chem. Soc. 111:1082-1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to any identified region. The analogs and congeners can be tested for binding to the proteins of interest (i.e., the protein products of a biomarker of the invention) using the above-described screens for biologic activity. Alternatively, lead compounds with little or no biologic activity, as ascertained in the screen, can also be used to design analogs and congeners of the compound that have biologic activity.

Compounds

Compounds that can be tested and identified methods described herein can include, but are not limited to, compounds obtained from any commercial source, including Aldrich (1001 West St. Paul Ave., Milwaukee, Wis. 53233), Sigma Chemical (P.O. Box 14508, St. Louis, Mo. 63178), Fluka Chemie AG (Industriestrasse 25, CH-9471 Buchs, Switzerland (Fluka Chemical Corp. 980 South 2nd Street, Ronkonkoma, N.Y. 11779)), Eastman Chemical Company, Fine Chemicals (P.O Box 431, Kingsport, Tenn. 37662), Boehringer Mannheim GmbH (Sandhofer Strasse 116, D-68298 Mannheim), Takasago (4 Volvo Drive, Rockleigh, N.J. 07647), SST Corporation (635 Brighton Road, Clifton, N.J. 07012), Ferro (111 West Irene Road, Zachary, La. 70791), Riedel-deHaen Aktiengesellschaft (P.O. Box D-30918, Seelze, Germany), PPG Industries Inc., Fine Chemicals (One PPG Place, 34th Floor, Pittsburgh, Pa. 15272). Further any kind of natural products may be screened using the methods of the invention, including microbial, fungal, plant or animal extracts.

Compounds from large libraries of synthetic or natural compounds can be screened. Numerous means are currently used for random and directed synthesis of saccharide, peptide, and nucleic acid-based compounds. Synthetic compound libraries are commercially available from a number of companies including Maybridge Chemical Co. (Trevillet, Cornwall, UK), Comgenex (Princeton, N.J.), Brandon Associates (Merrimack, N.H.), and Microsource (New Milford, Conn.). A rare chemical library is available from Aldrich (Milwaukee, Wis.). Combinatorial libraries are available and are prepared. Alternatively, libraries of natural compounds in the form of bacterial, fungal, plant and animal extracts are available from e.g., Pan Laboratories (Bothell, Wash.) or MycoSearch (NC), or are readily producible by methods well known in the art. Additionally, natural and synthetically produced libraries and compounds are readily modified through conventional chemical, physical, and biochemical means.

Furthermore, diversity libraries of test compounds, including small molecule test compounds, may be utilized. Libraries screened using the methods of the present invention can comprise a variety of types of compounds. Examples of libraries that can be screened in accordance with the methods of the invention include, but are not limited to, peptoids; random biooligomers; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; carbohydrate libraries; and small molecule libraries (in some embodiments, small organic molecule libraries). In some embodiments, the compounds in the libraries screened are nucleic acid or peptide molecules. In a non-limiting example, peptide molecules can exist in a phage display library. In other embodiments, the types of compounds include, but are not limited to, peptide analogs including peptides comprising non-naturally occurring amino acids, e.g., D-amino acids, phosphorous analogs of amino acids, such as α-amino phosphoric acids and α-amino phosphoric acids, or amino acids having non-peptide linkages, nucleic acid analogs such as phosphorothioates and PNAs, hormones, antigens, synthetic or naturally occurring drugs, opiates, dopamine, serotonin, catecholamines, thrombin, acetylcholine, prostaglandins, organic molecules, pheromones, adenosine, sucrose, glucose, lactose and galactose. Libraries of polypeptides or proteins can also be used in the assays of the invention.

In a specific embodiment, the combinatorial libraries are small organic molecule libraries including, but not limited to, benzodiazepines, isoprenoids, thiazolidinones, metathiazanones, pyrrolidines, morpholino compounds, and benzodiazepines. In another embodiment, the combinatorial libraries comprise peptoids; random bio-oligomers; benzodiazepines; diversomers such as hydantoins, benzodiazepines and dipeptides; vinylogous polypeptides; nonpeptidal peptidomimetics; oligocarbamates; peptidyl phosphonates; peptide nucleic acid libraries; antibody libraries; or carbohydrate libraries. Combinatorial libraries are themselves commercially available For example, libraries may be commercially obtained from, e.g., Specs and BioSpecs B.V. (Rijswijk, The Netherlands), Chembridge Corporation (San Diego, Calif.), Contract Service Company (Dolgoprudny, Moscow Region, Russia), Comgenex USA Inc. (Princeton, N.J.), Maybridge Chemicals Ltd. (Cornwall PL34 OHW, United Kingdom), Asinex (Moscow, Russia), ComGenex (Princeton, N.J.), Ru, Tripos, Inc. (St. Louis, Mo.), ChemStar, Ltd (Moscow, Russia), 3D Pharmaceuticals (Exton, Pa.), and Martek Biosciences (Columbia, Md.).

In a preferred embodiment, the library is preselected so that the compounds of the library are more amenable for cellular uptake. For example, compounds are selected based on specific parameters such as, but not limited to, size, lipophilicity, hydrophilicity, and hydrogen bonding, which enhance the likelihood of compounds getting into the cells. In another embodiment, the compounds are analyzed by three-dimensional or four-dimensional computer computation programs.

The combinatorial compound library for use in accordance with the methods of the present invention may be synthesized. There is a great interest in synthetic methods directed toward the creation of large collections of small organic compounds, or libraries, which could be screened for pharmacological, biological or other activity. The synthetic methods applied to create vast combinatorial libraries are performed in solution or in the solid phase, i.e., on a support. Solid-phase synthesis makes it easier to conduct multi-step reactions and to drive reactions to completion with high yields because excess reagents can be easily added and washed away after each reaction step. Solid-phase combinatorial synthesis also tends to improve isolation, purification and screening. However, the more traditional solution phase chemistry supports a wider variety of organic reactions than solid-phase chemistry.

Combinatorial compound libraries of the present invention may be synthesized using the apparatus described in U.S. Pat. No. 6,190,619 to Kilcoin et al., which is hereby incorporated by reference in its entirety. U.S. Pat. No. 6,190,619 discloses a synthesis apparatus capable of holding a plurality of reaction vessels for parallel synthesis of multiple discrete compounds or for combinatorial libraries of compounds.

In one embodiment, the combinatorial compound library can be synthesized in solution. The method disclosed in U.S. Pat. No. 6,194,612 to Boger et al., which is hereby incorporated by reference in its entirety, features compounds useful as templates for solution phase synthesis of combinatorial libraries. The template is designed to permit reaction products to be easily purified from unreacted reactants using liquid/liquid or solid/liquid extractions. The compounds produced by combinatorial synthesis using the template will in some embodiments be small organic molecules. Some compounds in the library may mimic the effects of non-peptides or peptides. In contrast to solid phase synthesize of combinatorial compound libraries, liquid phase synthesis does not require the use of specialized protocols for monitoring the individual steps of a multistep solid phase synthesis (Egner et al., 1995, J. Org. Chem. 60:2652; Anderson et al., 1995, J. Org. Chem. 60:2650; Fitch et al., 1994, J. Org. Chem. 59:7955; Look et al., 1994, J. Org. Chem. 49:7588; Metzger et al., 1993, Angew. Chem., Int. Ed. Engl. 32:894; Youngquist et al., 1994, Rapid Commun. Mass Spect. 8:77; Chu et al., 1995, J. Am. Chem. Soc. 117:5419; Brummel et al., 1994, Science 264: 399; and Stevanovic et al., 1993, Bioorg. Med. Chem. Lett. 3:431).

Combinatorial compound libraries useful for the methods of the present invention can be synthesized on supports. In one embodiment, a split synthesis method, a protocol of separating and mixing supports during the synthesis, is used to synthesize a library of compounds on supports (see e.g. Lam et al., 1997, Chem. Rev. 97:41-448; Ohlmeyer et al., 1993, Proc. Natl. Acad. Sci. USA 90:10922-10926 and references cited therein). Each support in the final library has substantially one type of compound attached to its surface. Other methods for synthesizing combinatorial libraries on supports, wherein one product is attached to each support, will be known to those of skill in the art (see, e.g., Nefzi et al., 1997, Chem. Rev. 97:449-472).

In some embodiments of the present invention, compounds can be attached to supports via linkers. Linkers can be integral and part of the support, or they may be nonintegral that are either synthesized on the support or attached thereto after synthesis. Linkers are useful not only for providing points of compound attachment to the support, but also for allowing different groups of molecules to be cleaved from the support under different conditions, depending on the nature of the linker. For example, linkers can be, inter alia, electrophilically cleaved, nucleophilically cleaved, photocleavable, enzymatically cleaved, cleaved by metals, cleaved under reductive conditions or cleaved under oxidative conditions. In a preferred embodiment, the compounds are cleaved from the support prior to high throughput screening of the compounds.

If the library comprises arrays or microarrays of compounds, wherein each compound has an address or identifier, the compound can be deconvoluted, e.g., by cross-referencing the positive sample to original compound list that was applied to the individual test assays.

If the library is a peptide or nucleic acid library, the sequence of the compound can be determined by direct sequencing of the peptide or nucleic acid. Such methods are well known to one of skill in the art.

A number of physico-chemical techniques can be used for the de novo characterization of compounds. Examples of such techniques include, but are not limited to, mass spectrometry, NMR spectroscopy, X-ray crytallography and vibrational spectroscopy.

(Q) Use of Identified Compounds to Prevent, Treat, or Ameliorate One or More Colorectal Pathologies The present invention provides methods of preventing, treating, or ameliorating one or more colorectal pathologies, said methods comprising administering to a subject in need thereof one or more compounds identified in accordance with the methods of the invention. In a preferred embodiment, the individual is human.

In one embodiment, the invention provides a method of preventing, treating, or ameliorating one or more colorectal pathologies, said method comprising administering to an individual in need thereof a dose of a prophylactically or therapeutically effective amount of one or more compounds identified in accordance with the methods of the invention. In a specific embodiment, a compound identified in accordance with the methods of the invention is not administered to prevent, treat, or ameliorate one or more colorectal pathologies, if such compound has been used previously to prevent, treat, or ameliorate one or more colorectal pathologies. In another embodiment, a compound identified in accordance with the methods of the invention is not administered to prevent, treat, or ameliorate one or more colorectal pathologies, if such compound has suggested to be used to prevent, treat, or ameliorate one or more colorectal pathologies. In another embodiment, a compound identified in accordance with the methods of the invention specifically binds to and/or alters the expression and/or activity level of a protein or RNA products of only one biomarker of the invention. In another embodiment, a compound identified in accordance with the methods of the invention is not administered to prevent, treat, or ameliorate one or more colorectal pathologies, if such compound binds to and/or alters the expression and/or activity of a protein or RNA products of 1, 2, 3, 4, 5, 6, 7, 8, 9, 10, 11, 12, 13, 14, 15, 16, 17, 18, or more or all or any combination of the biomarkers of Tables 2 or 6. In yet another embodiment, a compound identified in accordance with the methods of the invention binds to and/or alters the expression and/or activity level of a protein or RNA products of at least 2, at least 3, at least 4, at least 5, at least 10, at least 15, or more biomarkers of the invention.

The invention also provides methods of preventing, treating, or ameliorating one or more colorectal pathologies, said methods comprising administering to a subject in need thereof one or more of the compounds identified utilizing the screening methods described herein, and one or more other therapies (e.g., prophylactic or therapeutic agents and surgery). In a specific embodiment, such therapies are currently being used, have been used or are known to be useful in the prevention, treatment, or amelioration of one or more colorectal pathologies (including, but not limited to the prophylactic or therapeutic agents listed herein). The therapies (e.g., prophylactic or therapeutic agents) of the combination therapies of the invention can be administered sequentially or concurrently. In a specific embodiment, the combination therapies of the invention comprise a compound identified in accordance with the invention and at least one other therapy that has the same mechanism of action as said compound. In another specific embodiment, the combination therapies of the invention comprise a compound identified in accordance with the methods of the invention and at least one other therapy (e.g., prophylactic or therapeutic agent) which has a different mechanism of action than said compound. The combination therapies of the present invention improve the prophylactic or therapeutic effect of a compound of the invention by functioning together with the compound to have an additive or synergistic effect. The combination therapies of the present invention reduce the side effects associated with the therapies (e.g., prophylactic or therapeutic agents).

The prophylactic or therapeutic agents of the combination therapies can be administered to a subject in the same pharmaceutical composition. Alternatively, the prophylactic or therapeutic agents of the combination therapies can be administered concurrently to a subject in separate pharmaceutical compositions. The prophylactic or therapeutic agents may be administered to a subject by the same or different routes of administration.

In specific embodiment, a pharmaceutical composition comprising one or more compounds identified in an assay described herein is administered to an individual, in some embodiments a human, to prevent, treat, or ameliorate one or more colorectal pathologies. In accordance with the invention, the pharmaceutical composition may also comprise one or more prophylactic or therapeutic agents. In some embodiments, such agents are currently being used, have been used or are known to be useful in the prevention, treatment, or amelioration of one or more colorectal pathologies.

(R) Compounds of the Invention

Representative, non-limiting examples of compounds that can be used in accordance with the methods of the invention to prevent, treat, and/or ameliorate one or more colorectal pathologies are described in detail below.

First, such compounds can include, for example, antisense, ribozyme, or triple helix compounds that can downregulate the expression or activity of a protein or RNA products of a biomarker of the invention. Such compounds are described in detail in the subsection below.

Second, such compounds can include, for example, antibody compositions that can modulate the expression of a protein or RNA products of a biomarker of the invention, or the activity of a protein products of a biomarker of the invention. In a specific embodiment, the antibody compositions downregulate the expression a protein or RNA products of a biomarker of the invention, or the activity of a protein products of a biomarker of the invention. Such compounds are described in detail in the subsection below.

Third, such compounds can include, for example, protein products of a biomarker of the invention. The invention encompasses the use of peptides or peptide mimetics selected to mimic a protein products of a biomarker of the invention to prevent, treat, or ameliorate one or more colorectal pathologies. Further, such compounds can include, for example, dominant-negative polypeptides that can modulate the expression a protein or RNA products of a biomarker of the invention, or the activity protein products of a biomarker of the invention.

The methods also encompass the use derivatives, analogs and fragments of protein products of a biomarker of the invention to prevent, treat, or ameliorate one or more colorectal pathologies. In particular, the invention encompasses the use of fragments of protein products of a biomarker of the invention comprising one or more domains of such a protein(s) to prevent, treat, or ameliorate one or more colorectal pathologies. In another specific embodiment, the invention encompasses the use of a protein products of a biomarker of the invention, or an analog, derivative or fragment of such a protein which is expressed as a fusion, or chimeric protein products (comprising the protein, fragment, analog, or derivative joined via a peptide bond to a heterologous protein sequence).

In specific embodiments, an antisense oligonucleotide of at least 1, at least 2, at least 3, at least 4, at least 5, at least 6, at least 7, at least 8, at least 9, at least 10, at least 15, or more of biomarkers of the invention are administered to prevent, treat, or ameliorate one or more colorectal pathologies. In other embodiments, one or more of protein products of a biomarker of the invention or a fragment, analog, or derivative thereof are administered to prevent, treat, or ameliorate one or more colorectal pathologies. In other embodiment, one or more antibodies that specifically bind to protein products of the invention are administered to prevent, treat, or ameliorate one or more colorectal pathologies. In other embodiments, one or more dominant-negative polypeptides are administered to prevent, treat, or ameliorate one or more colorectal pathologies.

Antisense, Ribozyme, Triple-Helix Compositions

Standard techniques can be utilized to produce antisense, triple helix, or ribozyme molecules reactive to one or more of the genes listed in Tables 2 or 6, and transcripts of the genes listed in Tables 2 or 6, for use as part of the methods described herein. First, standard techniques can be utilized for the production of antisense nucleic acid molecules, i.e., molecules which are complementary to a sense nucleic acid encoding a polypeptide of interest, e.g., complementary to the coding strand of a double-stranded cDNA molecule or complementary to an mRNA sequence. Accordingly, an antisense nucleic acid can hydrogen bond to a sense nucleic acid. The antisense nucleic acid can be complementary to an entire coding strand, or to only a portion thereof, e.g., all or part of the protein coding region (or open reading frame). An antisense nucleic acid molecule can be antisense to all or part of a non-coding region of the coding strand of a nucleotide sequence encoding a polypeptide of interest. The non-coding regions ("5' and 3' untranslated regions") are the 5' and 3' sequences that flank the coding region and are not translated into amino acids.

An antisense oligonucleotide can be, for example, about 5, 10, 15, 20, 25, 30, 35, 40, 45 or 50 nucleotides or more in length. An antisense nucleic acid of the invention can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used. Examples of modified nucleotides which can be used to generate the antisense nucleic acid include 5-fluorouracil, 5-bromouracil, 5-chlorouracil, 5-iodouracil, hypoxanthine, xanthine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5'-methoxycarboxymethyluracil, 5-methoxyuracil, 2-methylthio-N6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N-2-carboxypropyl)uracil, (acp3)w, and 2,6-diaminopurine. Alternatively, the antisense nucleic acid can be produced biologically using an expression vector into which a nucleic acid has been subcloned in an antisense orientation (i.e., RNA transcribed from the inserted nucleic acid will be of an antisense orientation to a target nucleic acid of interest).

Antisense nucleic acid molecules administered to a subject or generated in situ such that they hybridize with or bind to cellular mRNA encoding the polypeptide of interest to thereby inhibit expression, e.g., by inhibiting transcription and/or translation. The hybridization can be by conventional nucleotide complementarity to form a stable duplex, or, for example, in the case of an antisense nucleic acid molecule which binds to DNA duplexes, through specific interactions in the major groove of the double helix. An example of a route of administration of antisense nucleic acid molecules of the invention includes direct injection at a tissue, e.g., a joint (e.g., a knee, hip, elbow, and knuckle), site. Alternatively, antisense nucleic acid molecules can be modified to target selected cells and then administered systemically. For example, for systemic administration, antisense molecules can be modified such that they specifically bind to receptors or antigens expressed on a selected cell, e.g., a T cell or intestinal cell, surface, e.g., by linking the antisense nucleic acid molecules to peptides or antibodies which bind to cell surface receptors or antigens. The antisense nucleic acid molecules can also be delivered to cells using vectors, e.g., gene therapy vectors, described below. To achieve sufficient intracellular concentrations of the antisense molecules, vector constructs in which the antisense nucleic acid molecule is placed under the control of a strong pol II or pol III promoter are preferred.

An antisense nucleic acid molecule of interest can be an α-anomeric nucleic acid molecule. An α-anomeric nucleic acid molecule forms specific double-stranded hybrids with complementary RNA in which, contrary to the usual α-units, the strands run parallel to each other (Gaultier et al., 1987, Nucleic Acids Res. 15:6625-6641). The antisense nucleic acid molecule can also comprise a 2'-o-methylribonucleotide (Inoue et al., 1987, Nucleic Acids Res. 15:6131-6148) or a chimeric RNA-DNA analogue (Inoue et al., 1987, FEBS Lett. 215:327-330).

Ribozymes are catalytic RNA molecules with ribonuclease activity that are capable of cleaving a single-stranded nucleic acid, such as an mRNA, to which they have a complementary region, and can also be generated using standard techniques. Thus, ribozymes (e.g., hammerhead ribozymes (described in Haselhoff and Gerlach, 1988, Nature 334:585-591)) can be used to catalytically cleave mRNA transcripts to thereby inhibit translation of the protein encoded by the mRNA. A ribozyme having specificity for a nucleic acid molecule encoding a polypeptide of interest can be designed based upon the nucleotide sequence of a cDNA disclosed herein. For example, a derivative of a Tetrahymena L-19 IVS RNA can be constructed in which the nucleotide sequence of the active site is complementary to the nucleotide sequence to be cleaved in a Cech et al. U.S. Pat. No. 4,987,071; and Cech et al. U.S. Pat. No. 5,116,742. Alternatively, an mRNA encoding a polypeptide of interest can be used to select a catalytic RNA having a specific ribonuclease activity from a pool of RNA molecules. See, e.g., Bartel and Szostak, 1993, Science 261:1411-1418.

Triple helical structures can also be generated using well known techniques. For example, expression of a polypeptide of interest can be inhibited by targeting nucleotide sequences complementary to the regulatory region of the gene encoding the polypeptide (e.g., the promoter and/or enhancer) to form triple helical structures that prevent transcription of the gene in target cells. See generally Helene, 1991, Anticancer Drug Des. 6(6):569-84; Helene, 1992, Ann. N.Y. Acad. Sci. 660:27-36; and Maher, 1992, Bioassays 14(12):807-15.

In various embodiments, nucleic acid compositions can be modified at the base moiety, sugar moiety or phosphate backbone to improve, e.g., the stability, hybridization, or solubility of the molecule. For example, the deoxyribose phosphate backbone of the nucleic acids can be modified to generate peptide nucleic acids (see Hyrup et al., 1996, Bioorganic & Medicinal Chemistry 4(1): 5-23). As used herein, the terms "peptide nucleic acids" or "PNAs" refer to nucleic acid mimics, e.g., DNA mimics, in which the deoxyribose phosphate backbone is replaced by a pseudopeptide backbone and only the four natural nucleobases are retained. The neutral backbone of PNAs has been shown to allow for specific hybridization to DNA and RNA under conditions of low ionic strength. The synthesis of PNA oligomers can be performed using standard solid phase peptide synthesis protocols as described in Hyrup et al., 1996, supra; Perry-O'Keefe et al., 1996, Proc. Natl. Acad. Sci. USA 93: 14670-675.

PNAs can, for example, be modified, e.g., to enhance their stability or cellular uptake, by attaching lipophilic or other helper groups to PNA, by the formation of PNA-DNA chimeras, or by the use of liposomes or other techniques of drug delivery known in the art. For example, PNA-DNA chimeras can be generated which may combine the advantageous properties of PNA and DNA. Such chimeras allow DNA recognition enzymes, e.g., RNAse H and DNA polymerases, to interact with the DNA portion while the PNA portion would provide high binding affinity and specificity. PNA-DNA chimeras can be linked using linkers of appropriate lengths selected in terms of base stacking, number of bonds between the nucleobases, and orientation (Hyrup, 1996, supra). The synthesis of PNA-DNA chimeras can be performed as described in Hyrup, 1996, supra, and Finn et al., 1996, Nucleic Acids Res. 24(17):3357-63. For example, a DNA chain can be synthesized on a support using standard phosphoramidite coupling chemistry and modified nucleoside analogs. Compounds such as 5'-(4-methoxytrityl)amino-5'-deoxy-thymidine phosphoramidite can be used as a link between the PNA and the 5' end of DNA (Mag et al., 1989, Nucleic Acids Res. 17:5973-88). PNA monomers are then coupled in a stepwise manner to produce a chimeric molecule with a 5' PNA segment and a 3' DNA segment (Finn et al., 1996, Nucleic Acids Res. 24(17):3357-63). Alternatively, chimeric molecules can be synthesized with a 5' DNA segment and a 3' PNA segment (Peterser et al., 1975, Bioorganic Med. Chem. Lett. 5:1119-11124).

In other embodiments, the oligonucleotide may include other appended groups such as peptides (e.g., for targeting host cell receptors in vivo), or agents facilitating transport across the cell membrane (see, e.g., Letsinger et al., 1989, Proc. Natl. Acad. Sci. USA 86:6553-6556; Lemaitre et al., 1987, Proc. Natl. Acad. Sci. USA 84:648-652; International Publication No. WO 88/09810) or the blood-brain barrier (see, e.g., International Publication No. WO 89/10134). In addition, oligonucleotides can be modified with hybridization-triggered cleavage agents (see, e.g., Krol et al., 1988, Bio/Techniques 6:958-976) or intercalating agents (see, e.g., Zon, 1988, Pharm. Res. 5:539-549). To this end, the oligonucleotide may be conjugated to another molecule, e.g., a peptide, hybridization triggered cross-linking agent, transport agent, hybridization-triggered cleavage agent, etc.

Antibody Compositions

In one embodiment, antibodies that specifically bind to one or more protein products of one or more biomarkers of the invention are administered to an individual, in some embodiments a human, to prevent, treat, or ameliorate one or more colorectal pathologies. In another embodiment, any combination of antibodies that specifically bind to one or more protein products of one or more biomarkers of the invention are administered to a subject, in some embodiments a human, to prevent, treat, or ameliorate one or more colorectal pathologies. In a specific embodiment, one or more antibodies that specifically bind to one or more protein products of one or more biomarkers of the invention are administered to a subject, in some embodiments a human, in combination with other types of therapies to prevent, treat, or ameliorate one or more colorectal pathologies.

One or more antibodies that specifically bind to one or more protein products of one or more biomarkers of the invention can be administered to a subject, in some embodiments a human, using various delivery systems are known to those of skill in the art. For example, such antibodies can be administered by encapsulation in liposomes, microparticles or microcapsules. See, e.g., U.S. Pat. No. 5,762,904, U.S. Pat. No. 6,004,534, and International Publication No. WO 99/52563. In addition, such antibodies can be administered using recombinant cells capable of expressing the antibodies, or retroviral, other viral vectors or non-viral vectors capable of expressing the antibodies.

Antibodies that specifically bind one or more protein products of one or more biomarkers of the invention can be obtained from any known source. For example, Table 5 provides a list of commercially available antibodies specific for one or more of the protein products of the biomarkers of the invention. Alternatively, antibodies that specifically bind to one or more protein products of one or more biomarkers of the invention can be produced by any method known in the art for the synthesis of antibodies, in particular, by chemical synthesis or in some embodiments, by recombinant expression techniques.

Antibodies include, but are not limited to, polyclonal antibodies, monoclonal antibodies, bispecific antibodies, multi-specific antibodies, human antibodies, humanized antibodies, camelised antibodies, chimeric antibodies, single-chain Fvs (scFv) (see e.g., Bird et al. (1988) Science 242:423-426; and Huston et al. (1988) Proc. Natl. Acad. Sci. USA 85:5879-5883), single chain antibodies, single domain antibodies, Fab fragments, F(ab') fragments, disulfide-linked Fvs (sdFv), and anti-idiotypic (anti-Id) antibodies (including, e.g., anti-Id antibodies to antibodies of the invention), and epitope-binding fragments of any of the above. The term "antibody", as used herein, refers to immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., $IgG_1$, $IgG_2$, $IgG_3$, $IgG_4$, $IgA_1$ and $IgA_2$) or subclass. Examples of immunologically active fragments of immunoglobulin molecules include F(ab) fragments (a monovalent fragment consisting of the VL, VH, CL and CH1 domains) and F(ab')2 fragments (a bivalent fragment comprising two Fab fragments linked by a disulfide bridge at the hinge region) which can be generated by treating the antibody with an enzyme such as pepsin or papain. Immunologically active fragments also include, but are not limited to, Fd fragments (consisting of the VH and CH1 domains), Fv fragments (consisting of the VL and VH domains of a single arm of an antibody), dAb fragments (consisting of a VH domain; Ward et al., (1989) Nature 341:544-546), and isolated complementarity determining regions (CDRs). Antibodies that specifically bind to an antigen can be produced by any method known in the art for the synthesis of antibodies, in particular, by chemical synthesis or in some embodiments, by recombinant expression techniques.

Polyclonal antibodies that specifically bind to an antigen can be produced by various procedures well-known in the art. For example, a human antigen can be administered to various host animals including, but not limited to, rabbits, mice, rats, etc. to induce the production of sera containing polyclonal antibodies specific for the human antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

The term "monospecific antibody" refers to an antibody that displays a single binding specificity and affinity for a particular target, e.g., epitope. This term includes monoclonal antibodies. Monoclonal antibodies can be prepared using a wide variety of techniques known in the art including the use of hybridoma, recombinant, and phage display technologies, or a combination thereof. See, e.g., U.S. Pat. Nos. RE 32,011, 4,902,614, 4,543,439, 4,411,993 and 4,196,265; Kennett et al. (eds.), *Monoclonal Antibodies, Hybridomas: A New Dimension in Biological Analyses*, Plenum Press (1980); and Harlow and Lane (eds.), *Antibodies. A Laboratory Manual*, Cold Spring Harbor Laboratory Press (1988), which are incorporated herein by reference. For example, monoclonal antibodies can be produced using hybridoma techniques including those known in the art and taught, for example, in Harlow et al., *Antibodies: A Laboratory Manual*, (Cold Spring Harbor Laboratory Press, 2nd ed. 1988); Hammerling, et al., in: *Monoclonal Antibodies and T-Cell Hybridomas* 563-681 (Elsevier, N.Y., 1981) (said references incorporated by reference in their entireties). Other techniques that enable the production of antibodies through recombinant techniques (e.g., techniques described by William D. Huse et al., 1989, Science, 246: 1275-1281; L. Sastry et al., 1989, Proc. Natl. Acad. Sci. USA, 86: 5728-5732; and Michelle Alting-Mees et al., Strategies in Molecular Biology, 3: 1-9 (1990) involving a commercial system available from Stratacyte, La Jolla, Calif.) may also be utilized to construct monoclonal antibodies. The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

Methods for producing and screening for specific antibodies using hybridoma technology are routine and well known in the art. Briefly, mice can be immunized with a protein products of a biomarker of the invention, and once an immune response is detected, e.g., antibodies specific for the protein are detected in the mouse serum, the mouse spleen is harvested and splenocytes isolated. The splenocytes are then fused by well known techniques to any suitable myeloma cells, for example cells from cell line SP20 available from the ATCC. Hybridomas are selected and cloned by limited dilution. Additionally, a RIMMS (repetitive immunization multiple sites) technique can be used to immunize an animal (Kilptrack et al., 1997, Hybridoma 16:381-9, incorporated by reference in its entirety). The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating antibodies by culturing a hybridoma cell secreting an antibody of the invention wherein, in some embodiments, the hybridoma is generated by fusing splenocytes isolated from a mouse immunized with a protein products of a biomarker of the invention, with myeloma cells and then screening the hybridomas resulting from the fusion for hybridoma clones that secrete an antibody able to bind to the protein or protein fragment.

Antibody fragments which recognize specific epitopes of a protein products of a biomarker of the invention may be generated by any technique known to those of skill in the art. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain. Further, the antibodies of the present invention can also be generated using various phage display methods known in the art.

In phage display methods, functional antibody domains are displayed on the surface of phage particles which carry the polynucleotide sequences encoding them. In particular, DNA sequences encoding VH and VL domains are amplified from animal cDNA libraries (e.g., human or murine cDNA libraries of affected tissues). The DNA encoding the VH and VL domains are recombined together with an scFv linker by PCR and cloned into a phagemid vector. The vector is electroporated in *E. coli* and the *E. coli* is infected with helper phage. Phage used in these methods are typically filamentous phage including fd and M13 and the VH and VL domains are usually recombinantly fused to either the phage gene III or gene VIII. Phage expressing an antigen binding domain that binds to a particular antigen can be selected or identified with antigen, e.g., using labeled antigen or antigen bound or captured to a solid surface or bead. Examples of phage display methods that can be used to make the antibodies of the present invention include those disclosed in Brinkman et al., 1995, J. Immunol. Methods 182:41-50; Ames et al., 1995, J. Immunol. Methods 184:177-186; Kettleborough et al., 1994, Eur. J. Immunol. 24:952-958; Persic et al., 1997, Gene 187:9-18; Burton et al., 1994, Advances in Immunology 57:191-280; PCT Application No. PCT/GB91/O1 134; International Publication Nos. WO 90/02809, WO 91/10737, WO 92/01047, WO 92/18619, WO 93/1 1236, WO 95/15982, WO 95/20401, and WO97/13844; and U.S. Pat. Nos. 5,698,426, 5,223,409, 5,403,484, 5,580,717, 5,427,908, 5,750,753, 5,821,047, 5,571,698, 5,427,908, 5,516,637, 5,780,225, 5,658,727, 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described below. Techniques to recombinantly produce Fab, Fab' and F(ab')2 fragments can also be employed using methods known in the art such as those disclosed in International Publication No. WO 92/22324; Mullinax et al., 1992, BioTechniques 12(6):864-869; Sawai et al., 1995, AJRI 34:26-34; and Better et al., 1988, Science 240:1041-1043 (said references incorporated by reference in their entireties).

To generate whole antibodies, PCR primers including VH or VL nucleotide sequences, a restriction site, and a flanking sequence to protect the restriction site can be used to amplify the VH or VL sequences in scFv clones. Utilizing cloning techniques known to those of skill in the art, the PCR amplified VH domains can be cloned into vectors expressing a VH constant region, e.g., the human gamma 4 constant region, and the PCR amplified VL domains can be cloned into vectors expressing a VL constant region, e.g., human kappa or lambda constant regions. In some embodiments, the vectors for expressing the VH or VL domains comprise an EF-1a promoter, a secretion signal, a cloning site for the variable domain, constant domains, and a selection marker such as neomycin. The VH and VL domains may also cloned into one vector expressing the necessary constant regions. The heavy chain conversion vectors and light chain conversion vectors are then co-transfected into cell lines to generate stable or transient cell lines that express full-length antibodies, e.g., IgG, using techniques known to those of skill in the art.

For some uses, including in vivo use of antibodies in humans and in vitro detection assays, it may be preferable to use human or chimeric antibodies. Completely human antibodies are particularly desirable for therapeutic treatment of human subjects. Human antibodies can be made by a variety of methods known in the art including phage display methods described above using antibody libraries derived from human immunoglobulin sequences. See also U.S. Pat. Nos. 4,444,887 and 4,716,111; and International Publication Nos. WO 98/46645, WO 98/50433, WO 98/24893, WO98/16654, WO 96/34096, WO 96/33735, and WO 91/10741; each of which is incorporated herein by reference in its entirety.

Antibodies can also be produced by a transgenic animal. In particular, human antibodies can be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered nonfunctional separately or simultaneously with the introduction of human immunoglobulin loci by homologous recombination. In particular, homozygous deletion of the $J_H$ region prevents endogenous antibody production. The modified embryonic stem cells are expanded and microinjected into blastocysts to produce chimeric mice. The chimeric mice are then be bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar (1995, Int. Rev. Immunol. 13:65-93). For a detailed discussion of this technology for producing human antibodies and human monoclonal antibodies and protocols for producing such antibodies, see, e.g., International Publication Nos. WO 98/24893, WO 96/34096, and WO 96/33735; and U.S. Pat. Nos. 5,413,923, 5,625,126, 5,633,425, 5,569,825, 5,661,016, 5,545,806, 5,814,318, and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

U.S. Pat. No. 5,849,992, for example, describes a method of expressing an antibody in the mammary gland of a transgenic mammal. A transgene is constructed that includes a milk-specific promoter and nucleic acids encoding the antibody of interest and a signal sequence for secretion. The milk produced by females of such transgenic mammals includes, secreted-therein, the antibody of interest. The antibody can be purified from the milk, or for some applications, used directly.

A chimeric antibody is a molecule in which different portions of the antibody are derived from different immunoglobulin molecules. Methods for producing chimeric antibodies are known in the art. See e.g., Morrison, 1985, Science 229: 1202; Oi et al., 1986, BioTechniques 4:214; Gillies et al., 1989, J. Immunol. Methods 125:191-202; and U.S. Pat. Nos. 5,807,715, 4,816,567, 4,816,397, and 6,331,415, which are incorporated herein by reference in their entirety.

A humanized antibody is an antibody or its variant or fragment thereof which is capable of binding to a predetermined antigen and which comprises a framework region having substantially the amino acid sequence of a human immunoglobulin and a CDR having substantially the amino acid sequence of a non-human immunoglobulin. A humanized antibody comprises substantially all of at least one, and typically two, variable domains (Fab, Fab', F(ab').sub.2, Fabc, Fv) in which all or substantially all of the CDR regions correspond to those of a non-human immunoglobulin (i.e., donor antibody) and all or substantially all of the framework regions are those of a human immunoglobulin consensus sequence. In some embodiments, a humanized antibody also comprises at least a portion of an immunoglobulin constant region (Fc), typically that of a human immunoglobulin. Ordinarily, the antibody will contain both the light chain as well at least the variable domain of a heavy chain. The antibody also may include the CH1, hinge, CH2, CH3, and CH4 regions of the heavy chain. The humanized antibody can be selected from any class of immunoglobulins, including IgM, IgG, IgD, IgA and IgE, and any isotype, including $IgG_1$, $IgG_2$, $IgG_3$ and $IgG_4$. Usually the constant domain is a complement fixing constant domain where it is desired that the humanized antibody exhibit cytotoxic activity, and the class is typically $IgG_1$. Where such cytotoxic activity is not desirable, the constant domain may be of the $IgG_2$ class. The humanized antibody may comprise sequences from more than one class or isotype, and selecting particular constant domains to optimize desired effector functions is within the ordinary skill in the art. The framework and CDR regions of a humanized antibody need not correspond precisely to the parental sequences, e.g., the donor CDR or the consensus framework may be mutagenized by substitution, insertion or deletion of at least one residue so that the CDR or framework residue at that site does not correspond to either the consensus or the import antibody. Such mutations, however, will not be extensive. Usually, at least 75% of the humanized antibody residues will correspond to those of the parental FR and CDR sequences, more often 90%, and most often greater than 95%. Humanized antibody can be produced using variety of techniques known in the art, including but not limited to, CDR-grafting (European Patent No. EP 239,400; International Publication No. WO 91/09967; and U.S. Pat. Nos. 5,225,539, 5,530,101, and 5,585,089), veneering or resurfacing (European Patent Nos. EP 592,106 and EP 519,596; Padlan, 1991, Molecular Immunology 28(4/5):489-498; Studnicka et al., 1994, Protein Engineering 7(6):805-814; and Roguska et al., 1994, PNAS 91:969-973), chain shuffling (U.S. Pat. No. 5,565,332), and techniques disclosed in, e.g., U.S. Pat. No. 6,407,213, U.S. Pat. No. 5,766,886, WO 9317105, Tan et al., 2002, J. Immunol. 169:1119-25, Caldas et al., 2000, Protein Eng. 13(5): 353-60, Morea et al., 2000, Methods 20(3):267-79, Baca et al., 1997, J. Biol. Chem. 272(16):10678-84, Roguska et al., 1996, Protein Eng. 9(10):895-904, Couto et al., 1995, Cancer Res. 55 (23 Supp):5973s-5977s, Couto et al., 1995, Cancer Res. 55(8):1717-22, Sandhu J S, 1994, Gene 150(2):409-10, and Pedersen et al., 1994, J. Mol. Biol. 235(3):959-73. Often, framework residues in the framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; and Riechmann et al., 1988, Nature 332:323, which are incorporated herein by reference in their entireties.)

Single domain antibodies, for example, antibodies lacking the light chains, can be produced by methods well-known in the art. See Riechmann et al., 1999, J. Immuno. 231:25-38; Nuttall et al., 2000, Curr. Pharm. Biotechnol. 1(3):253-263; Muylderman, 2001, J. Biotechnol. 74(4):277302; U.S. Pat. No. 6,005,079; and International Publication Nos. WO 94/04678, WO 94/25591, and WO 01/44301, each of which is incorporated herein by reference in its entirety.

Further, the antibodies that specifically bind to an antigen can, in turn, be utilized to generate anti-idiotype antibodies that "mimic" an antigen using techniques well known to those skilled in the art. (See, e.g., Greenspan & Bona, 1989, FASEB J. 7(5):437-444; and Nissinoff, 1991, J. Immunol. 147(8): 2429-2438). Such antibodies can be used, alone or in combination with other therapies, in the prevention, treatment, or amelioration of one or more colorectal pathologies.

The invention encompasses polynucleotides comprising a nucleotide sequence encoding an antibody or fragment thereof that specifically binds to an antigen. The invention also encompasses polynucleotides that hybridize under high stringency, intermediate or lower stringency hybridization conditions to polynucleotides that encode an antibody of the invention.

The polynucleotides may be obtained, and the nucleotide sequence of the polynucleotides determined, by any method known in the art. The nucleotide sequences encoding known antibodies can be determined using methods well known in the art, i.e., nucleotide codons known to encode particular amino acids are assembled in such a way to generate a nucleic acid that encodes the antibody. Such a polynucleotide encoding the antibody may be assembled from chemically synthesized oligonucleotides (e.g., as described in Kutmeier et al., 1994, BioTechniques 17:242), which, briefly, involves the synthesis of overlapping oligonucleotides containing portions of the sequence encoding the antibody, fragments, or variants thereof, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library or a cDNA library generated from, or nucleic acid, in some embodiments poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

Once a polynucleotide encoding an antibody molecule, heavy or light chain of an antibody, or fragment thereof (in some embodiments, but not necessarily, containing the heavy or light chain variable domain) of the invention has been obtained, the vector for the production of the antibody molecule may be produced by recombinant DNA technology using techniques well-known in the art.

In one preferred embodiment, monoclonal antibodies are produced in mammalian cells. Preferred mammalian host cells for expressing the clone antibodies or antigen-binding fragments thereof include Chinese Hamster Ovary (CHO cells) (including dhfr-CHO cells, described in Urlaub and Chasin (1980, Proc. Natl. Acad. Sci. USA 77:4216-4220), used with a DHFR selectable marker, e.g., as described in Kaufman and Sharp (1982, Mol. Biol. 159:601-621), lymphocytic cell lines, e.g., NS0 myeloma cells and SP2 cells, COS cells, and a cell from a transgenic animal, e.g., a transgenic mammal. For example, the cell is a mammary epithelial cell.

In addition to the nucleic acid sequence encoding the diversified immunoglobulin domain, the recombinant expression vectors may carry additional sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399, 216, 4,634,665 and 5,179,017). For example, typically the selectable marker gene confers resistance to drugs, such as G418, hygromycin or methotrexate, on a host cell into which the vector has been introduced. Preferred selectable marker genes include the dihydrofolate reductase (DHFR) gene (for use in dhfr⁻ host cells with methotrexate selection/amplification) and the neo gene (for G418 selection).

In an exemplary system for recombinant expression of an antibody, or antigen-binding portion thereof, of the invention, a recombinant expression vector encoding both the antibody heavy chain and the antibody light chain is introduced into dhfr⁻ CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium. Standard molecular biology techniques are used to prepare the recombinant expression vector, transfect the host cells, select for transformants, culture the host cells and recover the antibody from the culture medium. For example, some antibodies can be isolated by affinity chromatography with a Protein A or Protein G.

For antibodies that include an Fc domain, the antibody production system preferably synthesizes antibodies in which the Fc region is glycosylated. For example, the Fc domain of IgG molecules is glycosylated at asparagine 297 in the CH2 domain. This asparagine is the site for modification with biantennary-type oligosaccharides. It has been demonstrated that this glycosylation is required for effector functions mediated by Fcg receptors and complement C1q (Burton and Woof, 1992, Adv. Immunol. 51:1-84; Jefferis et al., 1998, Immunol. Rev. 163:59-76). In a preferred embodiment, the Fc domain is produced in a mammalian expression system that appropriately glycosylates the residue corresponding to asparagine 297. The Fc domain can also include other eukaryotic post-translational modifications.

Once an antibody molecule has been produced by recombinant expression, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. Further, the antibodies or fragments thereof may be fused to heterologous polypeptide sequences known in the art to facilitate purification.

Gene Therapy Techniques

Gene therapy refers to therapy performed by the administration to a subject of an expressed or expressible nucleic acid. Any of the methods for gene therapy available in the art can be used according to the present invention. Exemplary methods are described below.

In specific embodiments, one or more antisense oligonucleotides for one or more biomarkers of the invention are administered to prevent, treat, or ameliorate one or more colorectal pathologies, by way of gene therapy. In other embodiments, one or more nucleic acid molecules comprising nucleotides encoding one or more antibodies that specifically bind to one or more protein products of one or more biomarkers of the invention are administered to prevent, treat, or ameliorate one or more colorectal pathologies, by way of gene therapy. In other embodiments, one or more nucleic acid molecules comprising nucleotides encoding protein products of one or more biomarkers of the invention or analogs, derivatives or fragments thereof, are administered to prevent, treat, or ameliorate one or more colorectal pathologies, by way of gene therapy. In yet other embodiments, one or more nucleic acid molecules comprising nucleotides encoding one or more dominant-negative polypeptides of one or more protein products of one or more biomarker of the invention are administered to prevent, treat, or ameliorate one or more colorectal pathologies, by way of gene therapy.

For general reviews of the methods of gene therapy, see Goldspiel et al., 1993, Clinical Pharmacy 12:488-505; Wu and Wu, 1991, Biotherapy 3:87-95; Tolstoshev, 1993, Ann. Rev. Pharmacol. Toxicol. 32:573-596; Mulligan, 1993, Science 260:926-932; and Morgan and Anderson, 1993, Ann. Rev. Biochem. 62:191-217; May, 1993, TIBTECH 11(5): 155-215). Methods commonly known in the art of recombinant DNA technology which can be used are described in Ausubel et al. (eds.), 1993, Current Protocols in Molecular Biology, John Wiley & Sons, NY; and Kriegler, 1990, Gene Transfer and Expression, A Laboratory Manual, Stockton Press, NY.

In one aspect, a composition of the invention comprises nucleic acid sequences encoding one or more antibodies that specifically bind to one or more protein products of one or more biomarkers of the invention, said nucleic acid sequences being part of expression vectors that express one or more antibodies in a suitable host. In particular, such nucleic acid sequences have promoters operably linked to the antibodies, said promoter being inducible or constitutive, and, optionally, tissue-specific.

In another aspect, a composition of the invention comprises nucleic acid sequences encoding dominant-negative polypeptides of one or protein products of one or more biomarkers of the invention, said nucleic acid sequences being part of expression vectors that express dominant-negative polypeptides in a suitable host. In particular, such nucleic acid sequences have promoters operably linked to the dominant-negative polypeptides, said promoter being inducible or constitutive, and, optionally, tissue-specific. In another particular embodiment, nucleic acid molecules are used in which the dominant-negative coding sequences and any other desired sequences are flanked by regions that promote homologous recombination at a desired site in the genome, thus providing for intrachromosomal expression of the dominant-negative nucleic acids (Koller and Smithies, 1989, Proc. Natl. Acad. Sci. USA 86:8932-8935; Zijlstra et al., 1989, Nature 342: 435-438).

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequence is directly administered in vivo, where it is expressed to produce the encoded product. This can be accomplished by any of numerous methods known in the art, e.g., by constructing it as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, 1987, J. Biol. Chem. 262:4429-4432) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., International Publication Nos. WO 92/06180 dated Apr. 16, 1992 (Wu et al.); WO 92/22635 dated Dec. 23, 1992 (Wilson et al.); WO92/20316 dated Nov. 26, 1992 (Findeis et al.); WO 93/14188 dated Jul. 22, 1993 (Clarke et al.), WO 93/20221 dated Oct. 14, 1993 (Young)). Alternatively, the nucleic acid can be introduced intracellularly and incorporated within host cell DNA for expression, by homologous recombination (Koller and Smithies, 1989, Proc. Natl. Acad. Sci. USA 86:8932-8935; Zijlstra et al., 1989, Nature 342:435-438).

For example, a retroviral vector can be used. These retroviral vectors have been modified to delete retroviral sequences that are not necessary for packaging of the viral genome and integration into host cell DNA. The nucleic acid sequences encoding the antibodies of interest, or proteins of interest or fragments thereof to be used in gene therapy are cloned into one or more vectors, which facilitates delivery of the gene into a patient. More detail about retroviral vectors can be found in Boesen et al., 1994, Biotherapy 6:291-302, which describes the use of a retroviral vector to deliver the mdr1 gene to hematopoietic stem cells in order to make the stem cells more resistant to chemotherapy. Other references illustrating the use of retroviral vectors in gene therapy are: Clowes et al., 1994, J. Clin. Invest. 93:644-651; Kiem et al., 1994, Blood 83:1467-1473; Salmons and Gunzberg, 1993, Human Gene Therapy 4:129-141; and Grossman and Wilson, 1993, Curr. Opin. in Genetics and Devel. 3:110-114.

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, 1993, Current Opinion in Genetics and Development 3:499-503 present a review of adenovirus-based gene therapy. Bout et al., 1994, Human Gene Therapy 5:3-10 demonstrated the use of adenovirus vectors to transfer genes to the respiratory epithelia of rhesus monkeys. Other instances of the use of adenoviruses in gene therapy can be found in Rosenfeld et al., 1991, Science 252:431-434; Rosenfeld et al., 1992, Cell 68:143-155; Mastrangeli et al., 1993, J. Clin. Invest. 91:225-234; PCT Publication WO94/12649; and Wang, et al., 1995, Gene Therapy 2:775-783. In a preferred embodiment, adenovirus vectors are used.

Adeno-associated virus (AAV) has also been proposed for use in gene therapy (Walsh et al., 1993, Proc. Soc. Exp. Biol. Med. 204:289-300; U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, 1993, Meth. Enzymol. 217:599-618; Cohen et al., 1993, Meth. Enzymol. 217:618-644; Cline, 1985, Pharmac. Ther. 29:69-92) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) and/ or intestinal cells are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, intestinal cells, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In one embodiment in which recombinant cells are used in gene therapy, nucleic acid sequences encoding antibodies of interest, or proteins of interest or fragments thereof are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see, e.g., International Publication No. WO 94/08598, dated Apr. 28, 1994; Stemple and Anderson, 1992, Cell 71:973-985; Rheinwald, 1980, Meth. Cell Bio. 21A:229; and Pittelkow and Scott, 1986, Mayo Clinic Proc. 61:771).

Promoters that may be used to control the expression of nucleic acid sequences encoding antibodies of interest, proteins of interest or fragments thereof may be constitutive, inducible or tissue-specific. Non-limiting examples include the SV40 early promoter region (Bernoist and Chambon, 1981, Nature 290:304-310), the promoter contained in the 3' long terminal repeat of Rous sarcoma virus (Yamamoto, et al., 1980, Cell 22:787-797), the herpes thymidine kinase promoter (Wagner et al., 1981, Proc. Natl. Acad. Sci. USA 78:1441-1445), the regulatory sequences of the metallothionein gene (Brinster et al., 1982, Nature 296:39-42); prokaryotic expression vectors such as the β-lactamase promoter (Villa-Kamaroff et al., 1978, Proc. Natl. Acad. Sci. USA 75:3727-3731), or the tac promoter (DeBoer et al., 1983, Proc. Natl. Acad. Sci. USA 80:21-25); see also "Useful proteins from recombinant bacteria" in Scientific American, 1980, 242:74-94; plant expression vectors comprising the nopaline synthetase promoter region (Herrera-Estrella et al., Nature 303:209-213) or the cauliflower mosaic virus 35S RNA promoter (Gardner et al., 1981, Nucl. Acids Res. 9:2871), and the promoter of the photosynthetic enzyme ribulose biphosphate carboxylase (Herrera-Estrella et al., 1984, Nature 310:115-120); promoter elements from yeast or other fungi such as the Gal 4 promoter, the ADC (alcohol dehydrogenase) promoter, PGK (phosphoglycerol kinase) promoter, alkaline phosphatase promoter, and the following animal transcriptional control regions, which exhibit tissue specificity and have been utilized in transgenic animals: elastase I gene control region which is active in pancreatic acinar cells (Swift et al., 1984, Cell 38:639-646; Ornitz et al., 1986, Cold Spring Harbor Symp. Quant. Biol. 50:399-409; MacDonald, 1987, Hepatology 7:425-515); insulin gene control region which is active in pancreatic beta cells (Hanahan, 1985, Nature 315:115-122), immunoglobulin gene control region which is active in lymphoid cells (Grosschedl et al., 1984, Cell 38:647-658; Adames et al., 1985, Nature 318:533-538; Alexander et al., 1987, Mol. Cell. Biol. 7:1436-1444), mouse mammary tumor virus control region which is active in testicular, breast, lymphoid and mast cells (Leder et al., 1986, Cell 45:485-495), albumin gene control region which is active in liver (Pinkert et al., 1987, Genes and Devel. 1:268-276), alpha-fetoprotein gene control region which is active in liver (Krumlauf et al., 1985, Mol. Cell. Biol. 5:1639-1648; Hammer et al., 1987, Science 235:53-58; alpha 1-antitrypsin gene control region which is active in the liver (Kelsey et al., 1987, Genes and Devel. 1:161-171), beta-globin gene control region which is active in myeloid cells (Mogram et al., 1985, Nature 315:338-340; Kollias et al., 1986, Cell 46:89-94; myelin basic protein gene control region which is active in oligodendrocyte cells in the brain (Readhead et al., 1987, Cell 48:703-712); myosin light chain-2 gene control region which is active in skeletal muscle (Sani, 1985, Nature 314:283-286), and gonadotropic releasing hormone gene control region which is active in the hypothalamus (Mason et al., 1986, Science 234:1372-1378).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

(S) Pharmaceutical Compositions

Biologically active compounds identified using the methods of the invention or a pharmaceutically acceptable salt thereof can be administered to a patient, in some embodiments a mammal, including a human, having one or more colorectal pathologies. In a specific embodiment, a compound or pharmaceutically acceptable salt thereof is administered to a patient, in some embodiments a mammal, including a human, having one or more colorectal pathologies. In another embodiment, a compound or a pharmaceutically acceptable salt thereof is administered to a patient, in some embodiments a mammal, including a human, as a preventative measure against one or more colorectal pathologies. In accordance with these embodiments, the patient may be a child, an adult or elderly, wherein a "child" is a subject between the ages of 24 months of age and 18 years of age, an "adult" is a subject 18 years of age or older, and "elderly" is a subject 65 years of age or older.

When administered to a patient, the compound or a pharmaceutically acceptable salt thereof is administered as component of a composition that optionally comprises a pharmaceutically acceptable vehicle. The composition can be administered orally, or by any other convenient route, for example, by infusion or bolus injection, by absorption through epithelial or mucocutaneous linings (e.g., oral mucosa, rectal, and intestinal mucosa, etc.) and may be administered together with another biologically active agent. Administration can be systemic or local. Various delivery systems are known, e.g., encapsulation in liposomes, microparticles, microcapsules, capsules, etc., and can be used to administer the compound and pharmaceutically acceptable salts thereof.

Methods of administration include but are not limited to intradermal, intramuscular, intraperitoneal, intravenous, subcutaneous, intranasal, epidural, oral, sublingual, intranasal, intracerebral, intravaginal, transdermal, rectally, by inhalation, or topically, particularly to the ears, nose, eyes, or skin. The mode of administration is left to the discretion of the practitioner. In most instances, administration will result in the release of the compound or a pharmaceutically acceptable salt thereof into the bloodstream.

In specific embodiments, it may be desirable to administer the compound or a pharmaceutically acceptable salt thereof locally. This may be achieved, for example, and not by way of limitation, by local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as sialastic membranes, or fibers. In a specific embodiment, a compound is administered locally to one or more sections of the gastrointestinal system.

In certain embodiments, it may be desirable to introduce the compound or a pharmaceutically acceptable salt thereof into the gastrointestinal system by any suitable route, including intraventricular, intrathecal and epidural injection. Intraventricular injection may be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compound and pharmaceutically acceptable salts thereof can be formulated as a suppository, with traditional binders and vehicles such as triglycerides.

In another embodiment, the compound and pharmaceutically acceptable salts thereof can be delivered in a vesicle, in particular a liposome (see Langer, 1990, Science 249:1527-1533; Treat et al., in Liposomes in the Therapy of Infectious Disease and Cancer, Lopez-Berestein and Fidler (eds.), Liss, N.Y., pp. 353-365 (1989); Lopez-Berestein, ibid., pp. 317-327; see generally ibid.).

In yet another embodiment, the compound and pharmaceutically acceptable salts thereof can be delivered in a controlled release system (see, e.g., Goodson, in Medical Applications of Controlled Release, supra, vol. 2, pp. 115-138 (1984)). Other controlled-release systems discussed in the review by Langer, 1990, Science 249:1527-1533 may be used. In one embodiment, a pump may be used (see Langer, supra; Sefton, 1987, CRC Crit. Ref. Biomed. Eng. 14:201; Buchwald et al., 1980, Surgery 88:507; Saudek et al., 1989, N. Engl. J. Med. 321:574). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, J. Macromol. Sci. Rev. Macromol. Chem. 23:61; see also Levy et al., 1985, Science 228:190; During et al., 1989, Ann. Neurol. 25:351; Howard et al., 1989, J. Neurosurg. 71:105). In yet another embodiment, a controlled-release system can be placed in proximity of a target RNA of the compound or a pharmaceutically acceptable salt thereof, thus requiring only a fraction of the systemic dose.

The compounds described herein can be incorporated into pharmaceutical compositions suitable for administration. Such compositions typically comprise the active compound and a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

The invention includes methods for preparing pharmaceutical compositions for modulating the expression or activity of a polypeptide or nucleic acid of interest. Such methods comprise formulating a pharmaceutically acceptable carrier with an agent that modulates expression or activity of a polypeptide or nucleic acid of interest. Such compositions can further include additional active agents. Thus, the invention further includes methods for preparing a pharmaceutical composition by formulating a pharmaceutically acceptable carrier with an agent that modulates expression or activity of a polypeptide or nucleic acid of interest and one or more additional active compounds.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Intravenous administration is preferred. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF; Parsippany, N.J.) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a polypeptide or antibody) in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed.

Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from a pressurized container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the individual to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

For antibodies, the preferred dosage is 0.1 mg/kg to 100 mg/kg of body weight (more preferably, 0.1 to 20 mg/kg, 0.1-10 mg/kg). Generally, partially human antibodies and fully human antibodies have a longer half-life within the human body than other antibodies. Accordingly, lower dosages and less frequent administration is often possible. Modifications such as lipidation can be used to stabilize antibodies and to enhance uptake and tissue penetration (e.g., into the gastrointestinal system). A method for lipidation of antibodies is described by Cruikshank et al. (1997, J. Acquired Immune Deficiency Syndromes and Human Retrovirology 14:193).

In a specific embodiment, an effective amount of protein or polypeptide (i.e., an effective dosage) ranges from about 0.001 to 30 mg/kg body weight, preferably about 0.01 to 25 mg/kg body weight, more preferably about 0.1 to 20 mg/kg body weight, and even more preferably about 0.1 to 1.0 mg/kg, 1 to 10 mg/kg, 2 to 9 mg/kg, 3 to 8 mg/kg, 4 to 7 mg/kg, or 5 to 6 mg/kg body weight.

The skilled artisan will appreciate that certain factors may influence the dosage required to effectively treat an individual, including but not limited to the severity of the disease or disorder, previous treatments, the general health and/or age of the individual, and other diseases present. Moreover, treatment of a individual with a therapeutically effective amount of a protein, polypeptide, or antibody can include a single treatment or, preferably, can include a series of treatments.

In addition to those compounds described above, the present invention encompasses the use of small molecules that modulate expression or activity of a nucleic acid or polypeptide of interest. Non-limiting examples of small molecules include peptides, peptidomimetics, amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

It is understood that appropriate doses of small molecule agents depends upon a number of factors within the ken of the ordinarily skilled physician, veterinarian, or researcher. The dose(s) of the small molecule will vary, for example, depending upon the identity, size, and condition of the individual or sample being treated, further depending upon the route by which the composition is to be administered, if applicable, and the effect which the practitioner desires the small molecule to have upon the nucleic acid or polypeptide of the invention. Exemplary doses include milligram or microgram amounts of the small molecule per kilogram of individual or sample weight (e.g., about 1 microgram per kilogram to about 500 milligrams per kilogram, about 100 micrograms per kilogram to about 5 milligrams per kilogram, or about 1 microgram per kilogram to about 50 micrograms per kilogram). It is furthermore understood that appropriate doses of a small molecule depend upon the potency of the small molecule with respect to the expression or activity to be modulated. Such appropriate doses may be determined using the assays described herein. When one or more of these small molecules is to be administered to an individual (e.g., a human) in order to modulate expression or activity of a polypeptide or nucleic acid of the invention, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be modulated.

The pharmaceutical compositions can be included in a container, pack, or dispenser together with instructions for administration.

(T) Kits

The present invention provides kits for measuring the expression of the protein and RNA products of at least 1, at least 2, at least 3, at least 4, at least 5, at least 6, at least 7, at least 8, at least 9, at least 10, at least 12, at least 15, or all or any combination of the biomarkers of the invention. Such kits comprise materials and reagents required for measuring the expression of such protein and RNA products. In specific embodiments, the kits may further comprise one or more additional reagents employed in the various methods, such as: (1) reagents for purifying RNA from blood; (2) biomarker specific primer sets for generating test nucleic acids; (3) dNTPs and/or rNTPs (either premixed or separate), optionally with one or more uniquely labeled dNTPs and/or rNTPs (e.g., biotinylated or Cy3 or Cy5 tagged dNTPs); (4) post synthesis labeling reagents, such as chemically active derivatives of fluorescent dyes; (5) enzymes, such as reverse transcriptases, DNA polymerases, and the like; (6) various buffer mediums, e.g., hybridization, washing and/or enzymatic buffers; (7) labeled probe purification reagents and components, like spin columns, etc.; and (8) protein purification reagents; (9) signal generation and detection reagents, e.g., streptavidin-alkaline phosphatase conjugate, chemifluorescent or chemiluminescent substrate, and the like. In particular embodiments, the kits comprise prelabeled quality controlled protein and or RNA isolated from a sample (e.g., blood) or synthesized for use as a control. In some embodiments kits can include a computer-readable medium which has a formula which uses data representing a level of products of at least one biomarker and generating an indication of the probability that a test subject has one or more colorectal pathologies including one or more polyps or one or more subtypes of polyps. The formula of the computer-readable medium can be generated by using the methods outlined in section (G).

In some embodiments, the kits are PCR kits or Real time PCR kits and/or QRT-PCR kits. In other embodiments, the kits are nucleic acid arrays and protein arrays. Such kits according to the subject invention will at least comprise an array having associated protein or nucleic acid members of the invention and packaging means therefore. Alternatively the protein or nucleic acid members of the invention may be prepackaged onto an array.

In one embodiment, the QRT-PCR kit includes the following: (a) two or more biomarker specific primer sets, each set used to amplify a biomarker within the combination of biomarkers of the invention; (b) buffers and enzymes including a reverse transcripase; (c) one or more thermos table polymerases; and (d) Sybr® Green. In another embodiment, the kit of the invention can include (a) a reference control RNA and/or (b) a spiked control RNA. In another embodiment, the kit also includes a computer readable medium which has a formula which uses data representing a level of products of at least one biomarker and generating an indication of the probability that a test subject has one or more colorectal pathologies including one or more polyps or one or more subtypes of polyps. The formula of the computer-readable medium can be generated by using the methods outlined in section (G).

The invention provides kits that are useful for testing, detecting, screening, diagnosing, monitoring and prognosing one or more colorectal pathologies including one or more polyps or one or more subtypes of polyps. For example, in a particular embodiment of the invention a kit is comprised a forward and reverse primer wherein the forward and reverse primer are designed to quantitate expression of all of the species of mRNA corresponding to a single distinct biomarker, where each of the distinct biomarkers is selected from the group identified in Tables 1, 2, 11, or 12. In certain embodiments, at least one of the primers of a primer set is designed to span an exon junction of a species of mRNA.

The invention includes kits that are useful for testing, detecting, screening, diagnosing, monitoring and prognosing one or more colorectal pathologies including one or more types or subtypes of polyps based upon the expression levels of protein or RNA products of at least 1, at least 2, at least 3, at least 4, at least 5, at least 6, at least 7, at least 8, or all or any combination of the biomarkers of the invention in a sample.

The invention includes kits useful for monitoring the efficacy of one or more therapies that an individual is undergoing based upon the expression of a protein or RNA products of at least 1, at least 2, at least 3, at least 4, at least 5, at least 6, at least 7, at least 8, or all or any combination of the biomarkers of the invention in a sample.

The invention includes kits using for determining whether an individual will be responsive to a therapy based upon the expression of a protein or RNA products of at least 1, at least 2, at least 3, at least 4, at least 5, at least 6, at least 7, at least 8, or all or any combination of the biomarkers of the invention in a sample.

The invention includes kits for measuring the expression of a RNA products of at least 1, at least 2, at least 3, at least 4, at least 5, at least 6, at least 7, at least 8, or all or any combination of the biomarkers of the invention in a sample. In a specific embodiment, such kits comprise materials and reagents that are necessary for measuring the expression of a RNA products of a biomarker of the invention. For example, a microarray or QRT-PCR kit may be produced for detecting one or more colon pathologies including polyps or one or more subtypes of polyps and contain only those reagents and materials necessary for measuring the levels of RNA products of at least 1, at least 2, at least 3, at least 4, at least 5, at least 6, at least 7, at least 8, or all or any combination of the biomarkers of the invention. Alternatively, in some embodiments, the kits can comprise materials and reagents that are not limited to those required to measure the levels of RNA products of 1, 2, 3, 4, 5, 6, 7, 8 or all or any combination of the biomarkers of the invention. For example, a microarray kit may contain reagents and materials necessary for measuring the levels of RNA products not necessarily associated with or indicative of one or more colorectal pathologies, in addition to reagents and materials necessary for measuring the levels of the RNA products of at least 1, at least 2, at least 3, at least 4, at least 5, at least 6, at least 7, at least 8, or all or any combination of the biomarkers of the invention. In a specific embodiment, a microarray or QRT-PCR kit contains reagents and materials necessary for measuring the levels of RNA products of at least 1, at least 2, at least 3, at least 4, at least 5, at least 6, at least 7, at least 8, or all or any combination of the biomarkers of the invention, and 1, 2, 3, 4, 5, 10, 15, 20, 25, 30, 35, 40, 45, 50, 55, 60, 65, 70, 75, 80, 85, 90, 95, 100, 125, 150, 175, 200, 225, 250, 300, 350, 400, 450, or more genes other than the biomarkers of the invention, or 1-10, 1-100, 1-150, 1-200, 1-300, 1-400, 1-500, 1-1000, 25-100, 25-200, 25-300, 25-400, 25-500, 25-1000, 100-150, 100-200, 100-300, 100-400, 100-500, 100-1000, 500-1000 other genes than the biomarkers of the invention.

For nucleic acid microarray kits, the kits generally comprise probes attached or localized to a support surface. The probes may be labeled with a detectable label. In a specific embodiment, the probes are specific for an exon(s), an intron(s), an exon junction(s), or an exon-intron junction(s)), of RNA products of 1, 2, 3, 4, 5, 6, 7, 8, all or any combination of the biomarkers of the invention. The microarray kits may comprise instructions for performing the assay and methods for interpreting and analyzing the data resulting from the performance of the assay. In a specific embodiment, the kits comprise instructions for detecting or diagnosing one or more colorectal pathologies including one or more polyps or one or more subtypes of polyps. The kits may also comprise hybridization reagents and/or reagents necessary for detecting a signal produced when a probe hybridizes to a target nucleic acid sequence. Generally, the materials and reagents for the microarray kits are in one or more containers. Each component of the kit is generally in its own a suitable container. In another embodiment, the kit also includes a computer readable medium which has a formula which uses data representing a level of products of at least one biomarker and generating an indication of the probability that a test subject has one or more colorectal pathologies or a subtype of colorectal pathology including a polyp or one or more subtypes of polyps. The formula of the computer-readable medium can be generated by using the methods outlined in section (G).

For QRT-PCR kits, the kits generally comprise pre-selected primers specific for particular RNA products (e.g., an exon(s), an intron(s), an exon junction(s), and an exon-intron junction(s)) of 1, 2, 3, 4, 5, 6, 7, 8, or all or any combination of the biomarkers of the invention. The QRT-PCR kits may also comprise enzymes suitable for reverse transcribing and/or amplifying nucleic acids (e.g., polymerases such as Taq), and deoxynucleotides and buffers needed for the reaction mixture for reverse transcription and amplification. The QRT-PCR kits may also comprise probes specific for RNA products of 1, 2, 3, 4, 5, 6, 7, 8, or all or any combination of the biomarkers of the invention. The probes may or may not be labeled with a detectable label (e.g., a fluorescent label). Each component of the QRT-PCR kit is generally in its own suitable container. In another embodiment, the kit also includes a computer readable medium which has a formula which uses data representing a level of products of at least one biomarker and generating an indication of the probability that a test subject has one or more colorectal pathologies or a subtype of colorectal pathology including a polyp or one or more subtypes of polyps. The formula of the computer-readable medium can be generated by using the methods outlined in section (G).

Thus, these kits generally comprise distinct containers suitable for each individual reagent, enzyme, primer and probe. Further, the QRT-PCR kits may comprise instructions for performing the assay and methods for interpreting and analyzing the data resulting from the performance of the assay. In a specific embodiment, the kits contain instructions for diagnosing or detecting one or more colorectal pathologies including one or more polyps or one or more subtypes of polyps.

In a specific embodiment, the kit is a QRT-PCR kit. Such a kit may comprise a 96 well plate and reagents and materials necessary for SYBR Green detection. The kit may comprise reagents and materials so that beta-actin can be used to normalize the results. The kit may also comprise controls such as water, phosphate buffered saline, and phage MS2 RNA. Further, the kit may comprise instructions for performing the assay and methods for interpreting and analyzing the date resulting from the performance of the assay. In a specific embodiment, the instructions state that the level of a RNA products of 1, 2, 3, 4, 5, 6, 7, 8, all or any combination of the biomarkers of the invention should be examined at two concentrations that differ by, e.g., 5 fold to 10-fold.

For antibody based kits, the kit can comprise, for example: (1) a first antibody (which may or may not be attached to a support) which binds to protein of interest (e.g., a protein products of 1, 2, 3, 4, 5, 6, 7, 8, all or any combination of the biomarkers of the invention); and, optionally, (2) a second, different antibody which binds to either the protein, or the first antibody and is conjugated to a detectable label (e.g., a fluorescent label, radioactive isotope or enzyme). The antibody-based kits may also comprise beads for conducting an immunoprecipitation. Each component of the antibody-based kits is generally in its own suitable container. Thus, these kits generally comprise distinct containers suitable for each antibody. Further, the antibody-based kits may comprise instructions for performing the assay and methods for interpreting and analyzing the data resulting from the performance of the assay. In a specific embodiment, the kits contain instructions for diagnosing or detecting one or more colorectal pathologies including one or more polyps or one or more subtypes of polyps. In another embodiment, the kit contains instructions for applying the data to a formula in the form of a computer readable medium which contains said instructions. Said computer readable medium can also contain instructions for interpreting the analyzing the data resulting from the performance of the assay.

(U) SNPs

A Single Nucleotide Polymorphism (SNP) is a single nucleotide variation at a specific location in the genome of different individuals. SNPs are found in both coding and non-coding regions of genomic DNA. In spite of the paucity of scorable phenotypes, SNPs are found in large numbers throughout the human genome (Cooper et al., Hum Genet 69:201-205, 1985). SNPs are stable genetic variations frequently found in genes, and contribute to the wide range of phenotypic variations found in organisms. Single nucleotide polymorphisms (SNPs) can be of predictive value in identifying many genetic diseases, as well as phenotypic characteristics. It is known for example that certain SNPs result in disease-causing mutations such as the SNP correlated with heritable breast cancer (Cannon-Albright and Skolnick, Semin. Oncol. 23:1-5, 1996).

A SNP may be identified in the DNA of an organism by a number of methods well known to those of skill in the art, including but not limited to identifying the SNP by DNA sequencing, by amplifying a PCR product and sequencing the PCR product, by Oligonucleotide Ligation Assay (OLA), by Doublecode OLA, by Single Base Extension Assay, by allele specific primer extension, or by mismatch hybridization.

The instant invention offers a more focused and efficient method of screening SNPs to identify those SNPs which are specifically associated with one or more colorectal pathologies by having identified a selection of genes which are differentially expressed in blood from individuals having one or more colorectal pathologies as compared with individuals not having said one or more colorectal pathologies. In one aspect of the invention, a selection of SNPs to be screened are those SNPs found in the genes listed in Tables 2 and 6. In another aspect of the invention, novel SNPs can be identified in the disease-associated biomarkers using those methods listed above.

In particular, this invention focuses on methods for identifying those SNPs which are associated with one or more colorectal pathologies by screening only those SNPs in the biomarkers identified herein. Those SNPs which are identified using the methods disclosed herein will be convenient diagnostic markers.

More specifically a SNP is considered to be a polyp associated SNP, if those individuals having one or more colorectal pathologies have a different polymorphism at the SNP locus than those individuals not having the one or more colorectal pathologies. Further, a particular SNP is considered to be diagnostic for one or more colorectal pathologies if a particular polymorphism of the SNP is found to present at a statistically significant higher frequency in those individuals having one or more colorectal pathologies than in those individuals not having the one or more colorectal pathologies. Indices of statistical significance include $p<0.05$, $p<0.001$, $p<0.01$, and $p<0.10$. This invention includes methods of determining the diagnostic value of SNPs with respect to diagnosing or detecting one or more colorectal pathologies.

As would be understood, a preferred sample is blood, but these methods encompass any samples from which DNA can be obtained including epithelial cells, buccal cells, hair, saliva, tissue cells and the like. There are a variety of available methods for obtaining and storing tissue and/or blood samples. These alternatives allow tissue and blood samples to be stored and transported in a form suitable for the recovery of genomic DNA from the samples for genotype analysis. DNA samples can be collected and stored on a variety of solid mediums, including Whatmann paper, Guthrie cards, tubes, swabs, filter paper, slides, or other containers. When whole blood is collected on filter paper, for example, it can be dried and stored at room temperature.

The blood sample may be any one of various types of blood samples, including, for example, a sample of serum-depleted blood, a sample of erythrocyte-depleted blood, a sample of serum-depleted and erythrocyte-depleted blood, a sample of lysed blood, a blood sample which has not been fractionated into cell types and a sample of unfractionated cells of a lysed blood sample. Examples of blood samples are described in Example 1 of the Examples section below.

In another aspect of the invention, polyp associated SNPs can be identified from RNA transcripts of the polyp biomarker genes, listed in Tables 2 and 6, instead of from genomic DNA. In one embodiment, RNA is isolated from a sample such as blood, from individuals with and without the given disease or disorder, and transcripts encoded by these polyp biomarker genes are reversed transcribed into cDNA. The cDNA is amplified and analyzed to determine the presence of SNPs in the polyp biomarker genes. A polyp associated SNP, can be identified by then comparing the distribution of each of the SNPs identified in the polyp associated biomarker gene(s) differentially expressed in those individuals having one or more colorectal pathologies and individuals who do not have one or more colorectal pathologies. In a further variation of this embodiment, instead analyzing cDNA for the presence of SNPs, the RNA transcripts of the disease specific biomarker genes, or their amplified products, are analyzed for the presence of SNPs.

Analysis of genomic DNA comprising the polyp biomarker genes has the potential to identify SNPs in the coding region as well as in regulatory regions, the latter which may contribute to the change in expression levels of the gene. Analysis of cDNA encoded SNPs has the potential to identify only SNPs in the coding region of the polyp biomarker genes, which may be instrumental in deciphering protein based mechanisms of polyp formation. Methods of analyzing cDNA encoded SNPs can be carried out by analyzing the cDNA generated in the reverse transcription PCR reactions described herein that are used to identify the level of the biomarker in samples from patients and non patients.

A polyp associated SNP may be identified in the DNA of the polyp biomarker genes by a number of methods well known to those of skill in the art (see for example U.S. Pat. Nos. 6,221,592 and 5,679,524), including but not limited to identifying the SNP by PCR or DNA amplification, Oligonucleotide Ligation Assay (OLA) (Landegren et al., Science 241:1077, 1988), Doublecode OLA, mismatch hybridization, mass spectrometry, Single Base Extension Assay, (U.S. Pat. No. 6,638,722), RFLP detection based on allele-specific restriction-endonuclease cleavage (Kan and Dozy, Lancet ii: 910-912, 1978), hybridization with allele-specific oligonucleotide probes (Wallace et al., Nucl Acids Res 6:3543-3557, 1978), including immobilized oligonucleotides (Saiki et al., Proc Natl Acad Sci USA 86:6230-6234, 1989) or oligonucleotide arrays (Maskos and Southern, Nucl Acids Res 21:2269-2270, 1993), allele-specific PCR (Newton et al., Nucl Acids Res 17:2503-16, 1989), mismatch-repair detection (MRD) (Faham and Cox, Genome Res 5:474-482, 1995), binding of MutS protein (Wagner et al., Nucl Acids Res 23:3944-3948, 1995), single-strand-conformation-polymorphism detection (Orita et al., Genomics 5:874-879, 1983), RNAase cleavage at mismatched base-pairs (Myers et al., Science 230:1242, 1985), chemical (Cotton et al., Proc Natl Acad Sci USA 85:4397-4401, 1988) or enzymatic (Youil et al., Proc Natl Acad Sci USA 92:87-91, 1995) cleavage of heteroduplex DNA, methods based on allele specific primer extension (Syvanen et al., Genomics 8:684-692, 1990), genetic bit analysis (GBA) (Nikiforov et al., Nuci Acids Res 22:4167-4175, 1994), and radioactive and/or fluorescent DNA sequencing using standard procedures well known in the art.

The instant methods of screening a subset of SNPs to identify polyp associated SNPs in polyp biomarker genes also encompass non-PCR methods of DNA. These methods include ligase chain reaction ("LCR"), disclosed in European Patent Application No. 320,308, Qbeta Replicase, described in PCT Patent Application No. PCT/US87/00880, isothermal amplification methods, Walker et al. (Nucleic Acids Res 20(7):1691-6, 1992), Strand Displacement Amplification (SDA) described in U.S. Pat. Nos. 5,712,124, 5,648,211 and 5,455,166, Cyclic Probe Reaction, Transcription-Based Amplification, including nucleic acid sequence based amplification (NASBA) and 3SR, Kwoh et al., Proc Natl Acad Sci USA, 86:1173-77, 1989; PCT Patent Application WO 88/10315 et al., 1989, other amplification methods, as described in British Patent Application No. GB 2,202,328, and in PCT Patent Application No. PCT/US89/01025, Davey et al., European Patent Application No. 329,822, Miller et al., PCT Patent Application WO 89/06700, "race and "one-sided PCR TM." described in Frohman, In: PCR Protocols: A Guide To Methods And Applications, Academic Press, N.Y., 1990, methods based on ligation of two (or more) oligonucleotides in the presence of nucleic acid having the sequence of the resulting "di-oligonucleotide, described in Wu et al., Genomics 4:560-569, 1989.

While it is generally contemplated that the polymerase employed will be thermostable, non-thermostable polymerases may also be employed in the context of the present disclosure. Exemplary polymerases and nucleic acid modifying enzymes that may be used in the context of the disclosure include the thermostable DNA Polymerases of OmniBase Sequencing Enzyme, Pfu DNA Polymerase, Taq DNA Polymerase, Taq DNA Polymerase, Sequencing Grade, TaqBead Hot Start Polymerase, AmpliTaq Gold, Vent DNA Polymerase, Tub DNA Polymerase, TaqPlus DNA Polymerase, Tfl DNA Polymerase, Tli DNA Polymerase, Tth DNA Polymerase; the DNA Polymerases of DNA Polymerase I, Klenow Fragment, Exonuclease Minus, DNA Polymerase I, DNA Polymerase I Large (Klenow) Fragment, Terminal Deoxynucleotidyl Transferase, T7 DNA Polymerase, T4 DNA Polymerase; the Reverse transcriptases of AMV Reverse Transcriptase and M-MLV Reverse Transcriptase; T4 DNA ligase and T4 polynucleotide kinase.

Recognition moieties incorporated into primers, incorporated into the amplified product during amplification, or attached to probes are useful in the identification of the amplified molecules. A number of different labels may be used for this purpose such as, for example: fluorophores, chromophores, radio-isotopes, enzymatic tags, antibodies, chemiluminescence, electroluminescence, affinity labels, etc. One of skill in the art will recognize that these and other fluorophores not mentioned herein can also be used with success in this disclosure. Examples of affinity labels include but are not limited to the following: an antibody, an antibody fragment, a receptor protein, a hormone, biotin, DNP, or any polypeptide/protein molecule that binds to an affinity label and may be used for separation of the amplified gene. Examples of enzyme tags include enzymes such as urease, alkaline phosphatase, or peroxidase. Additionally, colorimetric indicator substrates can be employed to provide a detection means visible to the human eye or spectrophotometrically, to identify specific hybridization with complementary nucleic acid-containing samples. All these examples are generally known in the art and the skilled artisan will recognize that the present disclosure is not limited to the examples described above. The following fluorophores are specifically contemplated to be useful in the present disclosure: Alexa 350, Alexa 430, AMCA, BODIPY 630/650, BODIPY 650/665, BODIPY-FL, BODIPY-R6G, BODIPY-TMR, BODIPY-TRX, Cascade Blue, Cy2, Cy3, Cy5, 6-FAM, Fluorescein, HEX, 6-JOE, Oregon Green 488, Oregon Green 500, Oregon Green 514, Pacific Blue, REG, Rhodamine Green, Rhodamine Red, ROX, TAMRA, TET, Tetramethylrhodamine, and Texas Red.

In the context of the present disclosure, it is specifically contemplated that the DNA amplification products of the disclosed methods may be analyzed using DNA chips or microarrays in order to detect SNPs. The amplified DNA products may then be passed over a DNA chip or microarray encompassing oligonucleotide or polynucleotide probes. The ability or inability of the amplified DNA to hybridize to the microarray or DNA chip will facilitate the characterization of the SNPs present in the biomarker genes encoding the transcripts present in the sample.

The following non-limiting examples are illustrative of the present invention:

EXAMPLES

Example 1

RNA Isolation from Unfractionated Whole Blood (a) Centrifuged Lysed Blood (Serum Reduced, Erythrocyte Reduced Blood Sample)

Ten ml of peripheral whole blood was collected in EDTA Vacutainer tubes (Becton Dickinson, Franklin Lakes, N.J.) and stored on ice until processing (within 6 hours). Upon centrifugation, blood samples separated into plasma (including the buffy coat) and red blood cell layers. The plasma was removed and a hypotonic buffer (1.6 mM EDTA, 10 mM KHCO3, 153 mM NH4Cl, pH 7.4) was added to lyse the red blood cells at a 3:1 volume ratio. The mixture was centrifuged to yield a cell pellet, which was dissolved and homogenized into 1.0 ml of TRIzol® Reagent (Invitrogen Corp., Carlsbad, Calif.) and 0.2 ml of chloroform according to the manufacture's instructions. After centrifugation, isopropanol was added to the aqueous phase at a 1:1 ratio and allowed to precipitate at −20° C. Subsequent centrifugation yielded an RNA pellet that was resuspended in water for experimental use. RNA quality was assessed on Agilent 2100 Bioanalyzer RNA 6000 Nano Chips as specified by the manufacturer, and RNA quantity was determined by absorbance at 260 nm in a Beckman-Coulter DU640 Spectrophotometer.

(b) Lysed Blood 10 ml whole blood is obtained in a Vacutainer or any smaller volume container desired. Lysis Buffer is added directly to the blood sample (where the blood sample does not have the serum removed) in a ratio of 3 parts Lysis Buffer to 1 part blood (Lysis Buffer (1 L) 0.6 g EDTA; 1.0 g KHCO2, 8.2 g NH4Cl adjusted to pH 7.4 (using NaOH)). Sample is mixed and placed on ice for 5-10 minutes until transparent. Lysed sample is centrifuged at 1000 rpm for 10 minutes at 4° C., and supernatant is aspirated. Pellet is resuspended in 5 ml Lysis Buffer, and centrifuged again at 1000 rpm for 10 minutes at 4° C. Pelleted cells are homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

(c) From Serum Reduced Whole Blood 10 ml whole blood is obtained in a Vacutainer and spun at 2,000 rpm (800 g) for 5 min at 4° C. and the plasma layer removed. The remaining blood sample is homogenized using TRIzol (GIBCO/BRL) in a ratio of approximately 6 ml of TRIzol for every 10 ml of the original blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

d) From Whole Blood 10 ml whole blood is obtained in a Vacutainer and the sample is homogenized using TRIzol (GIBCO/BRL) in a ratio of approximately 6 ml of TRIzol for every 10 ml of the blood sample and vortexed well. Samples are left for 5 minutes at room temperature. RNA is extracted using 1.2 ml of chloroform per 1 ml of TRIzol. Sample is centrifuged at 12,000×g for 5 minutes at 4° C. and upper layer is collected. To upper layer, isopropanol is added in ratio of 0.5 ml per 1 ml of TRIzol. Sample is left overnight at −20° C. or for one hour at −20° C. RNA is pelleted in accordance with known methods, RNA pellet air dried, and pellet resuspended in DEPC treated ddH$_2$O. RNA samples can also be stored in 75% ethanol where the samples are stable at room temperature for transportation.

(e) From Whole Blood Using PAXgene™

2.5 ml whole blood is collected into PAXgene™ Blood RNA Tubes and processed in accordance with the instructions of the PAXgene™ Blood RNA Kit protocol. In brief after storing the blood in the PAXgene™ tube for at least 2 hours, the blood sample is centriguted and the supernatant discarded. To the remaining sample, 360 µl of the supplied Buffer BR1 is added and the sample is pipetted into the spin column and centrifuged an then washed with numerous wash steps and finally eluted and stored.

(f) From Whole Blood Using PAXgene™ and Subsequent Globin Reduction

RNA isolated from PAXGene™ as noted in (d) above is subsequently treated to selectively remove globin mRNA as is described in Affymetrix® technical note entitled "Globin Reduction Protocol". Oligonucleotides specific for the alpha 1, alpha 2 and beta globin species are incubated with an oligonucleotide hybridization buffer and RNAse H used to specifically target degradation of the globin mRNA and the cRNA clean up column from Affymetrix used to remove the globin mRNA.

Example 2

Target Nucleic Acid Preparation and Hybridization (a) Genes which are Differentially Expressed with the Presence of One or More Colorectal Pathologies Total RNA (5 µg) was labeled and hybridized onto Affymetrix U133Plus 2.0 GeneChips (Affymetrix; Santa Clara, Calif.) along with other similarly prepared samples from individuals having or not having polyps and hybridized according to the manufacturer's instructions. Briefly, the five µg total RNA was used for cDNA synthesis with GeneChip T7-Oligo (dT) primer provided in the promoter primer kit (Affymetrix, P/N 900375). cDNA was cleaned up with cDNA Cleanup Spin Column and then subjected to synthesis of Biotin-Labeled cRNA with Enzo® BioArray™ High Yield™ RNA Transcript Labeling Kit. The labeled cRNA was further purified using the IVT cTNA Cleanup Spin Column and quantified using spectrophotometer with absorbance at 260 nm. 20 µg cRNA was then added into the hybridization cocktail and the cocktail was applied to the probe array cartridge. After approximately 16 hours hybridization, the array washed with Affymetrix fluidics station 400. The array was then scanned with Affymetrix® GeneChip® Scanner.

Hybridization signals were scaled in the Affymetrix GCOS software (version 1.1.1), using a scaling factor determined by adjusting the global trimmed mean signal intensity value to 500 for each array, and imported into GeneSpring version 7.2 (Silicon Genetics; Redwood City, Calif.). Signal intensities were then centered to the $50^{th}$ percentile of each chip, and for each individual gene, to the median intensity of the whole sample set. Only genes called present or marginal by the GCOS software in at least 80% of each group of samples were used for further analysis. Differentially expressed genes were identified using 1) the non-parametric Wilcoxon-Mann-Whitney non-parametric test (P<0.05), 2) parametric t test (P<0.05), and/or the 3) unsupervised analysis method (14). In the un-supervised analysis, the signal-intensity filtered genes were used to select genes with at least 2-fold change (up or down) in expression level, away from the mean, in at least 15% of the samples. Hierarchical cluster analysis was performed on each comparison to assess correlation analysis using Spearman correlation among samples for each identified gene set as the similarity measure with average centroid linkage in GeneSpring v6.0. Results from numerous experiments were analyzed and a compiled list of results provided in Table 1.

(b) Genes which are Differentially Expressed with the Presence of High Risk Polyps Total RNA was isolated from centrifuged lysed blood (ie serum reduced, erythrocyte reduced blood) as described in Example 1 from patients diagnosed with having high risk polyps. 1 µg of Oligo-dT primers were annealed to 10 µg of total RNA for each individual tested in a total volume of 10 µl, by heating to 70° C. for 10 min, and cooled on ice. Individuals were diagnosed as having one or more of the high risk polyp subtypes (colorectal pathology during a colonoscopy identified the polyp identified as one or more of the following types: Tubulovillous Adenoma; Villous Adenoma; Cancer; High Grade Dysplasia; and Tubular Adenoma wherein the diameter of the Tubular Adenoma is greater than 10 mm). Procedures were otherwise carried out as described in Example 2(a) above.

Results from numerous experiments were analyzed and a compiled list of results provided in Table 11.

Example 3

Quantitative Real Time PCR (QRT-PCR)

QRT-PCR was performed on a selection of the genes in Table 1 which are disclosed in Table 2. QRT-PCR was done using either the SYBR® Green Kit from Qiagen (Product Number 204143) and/or using Applied Biosystems PCR reagent kits (Cat 4334973). Amplicons were detected in real time using a Prism 7500 instrument (Applied Biosystems).

Reverse transcription was first performed using the High-Capacity cDNA Archive Kit from Applied Biosystems (Product number 4322171) and following the protocol utilized therein.

More specifically purified RNA as described previously herein was incubated with reverse transcriptase buffer, dNTPs, random primers and reverse transcriptase and incubated for 25° C. for 10 minutes and subsequently for 37° C. for two hours and the resulting mixture utilized as the starting product for quantitative PCR.

cDNA resulting from reverse transcription was incubated with the QuantiTect SYBR® Green PCR Master Mix as provided and no adjustments were made for magnesium concentration. Uracil-N-Glycosylase was not added. 5 µM of both forward primer and reverse primer specific to the genes of the invention were added and the reaction was incubated and monitored in accordance with the standard protocol utilizing the ABI PRISM 7700/ABI GeneAmp 5700/iCycler/ DNA Engine Opticon. Primers utilized are shown in Table 6. Other examples of primers which can be used are disclosed in Table 4. Forward and reverse primers for the candidate biomarkers were designed using "PrimerQuest". A tool which is available from Integrated DNA Technologies, Coralville, Iowa. Table 6 lists the primer sets for eight of the genes of Table 2, namely, MBTPS1 (membrane-bound transcription factor protease site 1), MGC45871, MKLN1 (muskelin 1), NIPBL (Nipped-B homolog (*Drosophila*)), APEH (acylpeptide hydrolase), FLJ23091, MGC40157, and PPP1R2 (protein phosphatase 1, regulatory (inhibitor) subunit 2). Serial dilution measurements for the target genes and a housekeeping gene (beta-actin, ACTB) were assayed, to ensure that the values were within linear range and the amplification efficiency was approximately equal for the target and ACTB. ACTB was selected as a housekeeping gene because no statistical significant differences were observed between control and disease group in this study (data not shown). The melting temperature [Tm] in thermal dissociation, and examination on agarose gels provided confirmation of specific PCR amplification and the lack of primer-dimer formation in each reaction well.

For individual target gene analysis, changes in Ct value between each gene and the ACTB house-keeping was calculated as ΔCt=Ct (target gene)–Ct (house-keeping gene).

Example 4

TaqMan® QRT PCR can also be performed using the QuantiTect™ Probe RT-PCR system from Qiagen (Product Number 204343) in conjunction with a TaqMan® dual labelled probe and primers corresponding to the gene of interest. The TaqMan® probe and primers can be ordered from Applied Biosystems Assays-On-Demand™.

The dual labelled probe contains both a fluorophore and a quencher molecule. The proximity of the fluorescent reporter with the quencher prevents the reporter from fluorescing, but during the PCR extension step, the 5'-3' exonuclease activity of the Taq DNA polymerase releases the fluorophore which allows it to fluoresce. As such, the amount of fluorescence correlates with the amount of PCR product generated. Examples of TaqMan® probes which can be utilized with the genes disclosed in Table 2 are shown in Table 6 and/or 4.

Example 5

Identification of Combinations of Biomarkers Using Logistic Regression

A selection of eight genes from Table 2 were chosen as follows: MBTPS1, MGC45871, MKLN1, NIPBL APEH, MGC40157, PPP1R2, FLJ23091. Combinations of pairs of the selected eight genes were tested to determine the ability of each combination of pairs to screen for one or more colorectal pathologies. Blood samples were drawn into lavender-top BD Vacutainer tube prior to anaesthesia and prior to any surgery. RNA from whole blood was prepared by first removing the serum and subsequently treating the remaining sample with hypotonic Lysis Buffer (Lysis Buffer (1 L) 0.6 g EDTA; 11.0 g $KHCO_2$, 8.2 g $NH_4Cl$ adjusted to pH 7.4 (using NaOH)) in a ratio of 3 parts Lysis Buffer to 1 part blood so as to preferentially lyse the red blood cells. The samples were centrifuged and RNA extracted from the unfractionated cells of the sample.

Real-time quantitative PCR was conducted on 68 patients diagnosed as having colorectal pathology (ie one or more subtypes of polyps) (n=68) and 110 control individuals where the control individuals were diagnosed as not having one or more colorectal pathologies (n=110). QRT-PCR was performed using a two step procedure whereby cDNA was first prepared before performing PCR using ABI reagents. In this example, a matrix containing the ΔCt of "ratios" of the eight biomarkers was used to create a reference training data set (AJ36h). The ratios used to generate the matrix of ΔCts was further constrained by requiring each ratio to be comprised of one upregulated gene and a second downregulated gene where the ΔCt was generated by subtracting the Ct of the downregulated gene from the Ct of the upregulated gene. MBTPS1, MGC45871, MKLN1, NIPBL were identified as upregulated genes (ie when comparing polyps vs non polyp individuals) (FIG. 3). APEH, MGC40157, PPP1R2, FLJ23091 were identified as down regulated genes (FIG. 3). The advantages of gene-pair ratio method include a) reducing inter-individual variability, b) permitting analysis of individual samples without references so as to ensure technical differences between plates are minimized, c) can use any reliable method (microarray, real-time PCR, etc), d) independent of the platform utilized for data acquisition, e) no housekeeping gene required (relatively independent of the input of sample amount), f) translating the strengths of microarray expression profiling into simple clinical tests, g) highly precise in disease discrimination.

A reference (training) data set (AJ36h) was constructed containing ΔCt values for each possible ratio as described and constrained as noted above for the above eight genes assayed against a total of 178 subjects including 110 subject without pathology (Female/male:55/54 with one missing information, age average 57 year ranging 23 to 83 years of age) and 68 subjects with diagnosed colorectal pathology (Female/male: 22/45 with one missing information, age average 57 ranging from 38 to 82 years). The types of pathology identified include 21 (31%) tubular adenomas, 18 (27%) hyperplastic and 7 (10%) high risk pathology (villous morphology) and 22 (32%) other minor polyp (see Table 7).

Logistic regression (15-18) was used to analyze the dependence of the binary variable Y (0=control (has no pathology), 1=disease (has pathology) on all possible combinations of the ΔCt values from the reference data training set AJ36h. If P=probability that a patient sample is diagnosed as "diseased", then a function X=Logit(p) can be defined as follows:

$$X=\text{Logit}(P)=\ln(P/(1-P))=b_0+b_1\Delta Ct_1+b_2\Delta Ct_2+\ldots+b_n\Delta Ct_n \quad (\text{Eq 1})$$

If X≧threshold then Y=1 (diagnosis="diseased"), and if X<threshold then Y=0 (diagnosis="control"). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of each combination of ratios wherein all combinations of ratios as described above were tested (19-21). Each combinations of ratios resulted in an equation in the form of Equation 1. The top 10 best equations that gave an ROC=0.72 were used in a formula where each equation was given equal ranking to perform the subsequent blind test prediction.

Cross Validation

Cross-validation was performed on dataset AJ36h (the 178-sample training set) using WEKA (www.cs.waikato.ac.nz/~ml/weka/index.html) (22). Two different cross-validation schemes were used. The WEKA MetaAnalysis function was used to construct 100 bootstrap replicates of dataset AJ36h. Each of the new datasets was analyzed with the SimpleLogistic classifier. Each of the resultant 100 logistic equations was then analyzed by 10-fold cross-validation. The results for all equations were averaged ("bootstrap aggregating").

Prospective (Blind) Test

A blind set of 80 clinical samples were tested. The test set consisted of 40 controls and 40 subjects with one or more colorectal pathologies (having one or more polyps of any type). None of the test subjects used in the blind test were used to generate a classifier for each possible combination of the ratio of biomarkers "ratios" where each ratio is selected as a combination of an upregulated gene (when comparing colorectal pathology to no colorectal pathology) and a down regulated gene (when comparing colorectal pathology to no colorectal pathology). MBTPS1, MGC45871, MKLN1, NIPBL were identified as upregulated genes (ie when comparing polyps vs non polyp individuals (FIG. 3). APEH, MGC40157, PPP1R2, FLJ23091 were identified as down regulated genes (FIG. 3).

Medical information on subjects in this blind set, including age, gender, and pathologist's report, is summarized in Table 7. Samples were run on a single 96-well plate for QRT-PCR with each of the eight genes measured in triplicate.

The measured values for each blind sample were evaluated using the following algorithm, which consists of an initial calculation, a binary logic gate, and a "committee machine" vote. Initial Calculation: The logit function $X_i$ is computed for each of the equations (I=1 to N) that gave ROC Area=0.72 against the reference data set AJ36h. Logic Gate: If $X_i$<threshold of j (where j stands for an equation number), then the blind sample is given score $S_i=-1$ for Eqn #j. If $X_i \geq$ threshold of j, then it is given score $S_i=+1$ for Eqn #j. Vote by Committee Machine (23): A vote is taken over the scores from the 10 logit equations used for diagnosis. By definition, Vote=$\Sigma S_i$. If Vote$\leq 0$ then the sample is called "no pathology", while if Vote>0 then the sample is called "diseased or with pathology".

Figure 4:
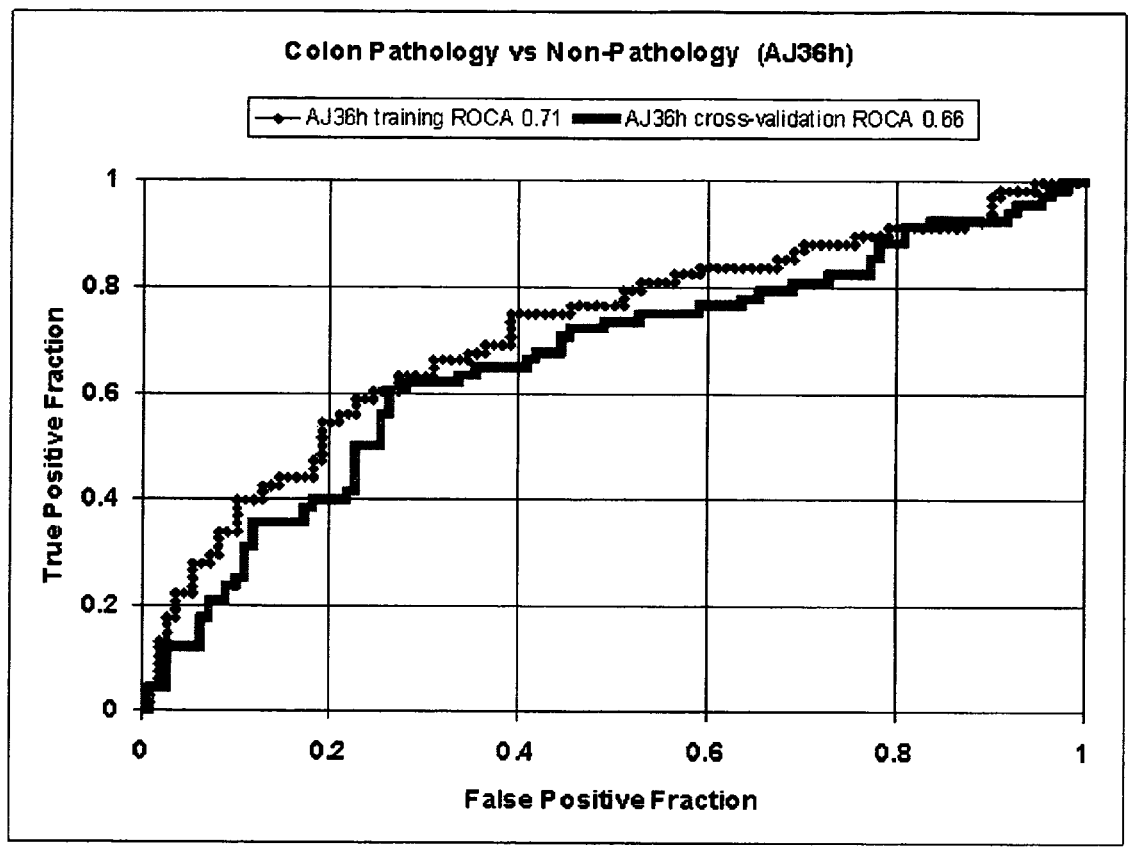
FIG. 4 depicts an ROC curve for a selected biomarker combination from combinations of pairs of the eight biomarkers tested and shown in FIG. 3. Experimental details are as described in Example 5. Combinations of a selection of the biomarkers identified in Table 1 were tested to determine the ability of the combinations to screen test subjects for one or more colorectal pathologies more effectively than can be achieved using the biomarkers of Table 1 individually. QRT-PCR as described in Example 3 was performed to measure the level of the RNA products of a select group of individual biomarkers from Table 1. Selected combinations of biomarkers were tested by applying logistic regression analysis to the QRT-PCR results of the selected combination and the ROC curve for the resulting logistic regression equation (logit function) determined. Panel (A)—ROC curve (ROC Area 0.72) for logit function for one of the datasets tested (AJ36h). This function returned by Simple Logistic operator in WEKA (ROC Area 0.66).

The best equation gives an ROC area 0.72 as shown in FIG. 4. Ten top equations that gave ROC=0.72 were used for the blind test prediction. Table 8 lists the parameters for the 10 equations.

Cross-validation was done with the SimpleLogistic function in WEKA. 100 bootstrap replicates of dataset AJ36h were constructed and analyzed each with the WEKA SimpleLogistic function. The resultant set of 100 logistic equations was subjected to 10-fold cross-validation. The results for all equations were then averaged which gave an ROC Area=0.66, overall accuracy 65%, sensitivity (TPF) 41%, specificity (TNF) 83%.

Prediction of Blind Samples

A blind test was conducted on an additional set of 80 samples (40 samples without pathology and 40 samples with colorectal pathology). A committee vote was taken over the ten (10) best logit equations from Reference Dataset AJ36h, to predict a state of either "colorectal pathology present" or "colorectal pathology absent (control)". For the set of blind samples the sensitivity (true positive fraction, TPF) is 43% (17/40), and the specificity (true negative fraction, TNF) is 80% (32/40), with an overall accuracy of 61. % (49/80, Table 9).

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

Example 6

Testing of Combinations of Biomarkers Using Logistic Regression and Application of Said Combinations to Screen for One or More Types of Colorectal Pathology or One or More Pathologies A selection of seven genes were chosen including: LIM domain containing preferred translocation partner in lipoma (LPP) Gene ID 4026; cytidine deaminase (CDA) Gene ID 978; sarcoma antigen NY-SAR-48 (MGC20553) Gene ID 93323; serine (or cysteine) proteinase inhibitor, Glade E (nexin, plasminogen activator inhibitor type 1), member 2 (SERPINE 2) Gene ID 5270; B-cell novel protein 1 (BCNP1) Gene ID 199786; hypothetical protein MGC45871 (MGC45871) Gene ID 359845; membrane-bound transcription factor protease, site 1 (MBTPS1) Gene ID 8720. Genes were chosen from either Table 1 or other similar experiments.

Clinical Question—Polyp v. No Pathology

A reference (training) data set was constructed containing $\Delta$Ct values for the above seven genes assayed against a total of 185 subjects having any type of polyp and 239 subjects not having polyps.

Logistic regression was used to analyze the dependence of the binary variable Y (0=control, 1=disease) on the $\Delta$Ct values from the reference data set. If P=probability that a patient sample is identified as "diseased", then a function X=Logit(p) can be defined as follows:

$$X=\text{Logit}(P)=\ln(P/(1-P))=b_0+b_1\Delta Ct_1+b_2\Delta Ct_2+\ldots+b_n\Delta Ct_n \quad (\text{Eq 1})$$

If X$\geq$threshold then Y=1 (diagnosis="has polyps"), and if X<threshold then Y=0 (diagnosis=does not have polyps). The (empirical) coefficients {bi} that define the relationship between X and the experimental measurements {$\Delta$Cti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (LPP; CDA; MBTPS1; SERPINE2; BCNP1) and shown as follows:

$$X=\text{Logit}(P)=\ln(P/(1-P))=-4.9104-0.4278\Delta Ct\text{-}MGC20553-0.6164\Delta CtCDA+0.8230\Delta CtMBTPS1+0.3961\Delta CtSERPINE2+0.1641\Delta CtBCNP1$$

gave an ROC=0.73 with a sensitivity of 80% and a specificity of 50%.

Clinical Question—High Risk Pathology v. Other

Using the same selection of seven biomarkers, but this time tested against a reference (training) data set with $\Delta$Ct values for the above seven genes assayed against a total of 129 subjects having "high risk" polyp and 295 subjects either having a polyp not classified as high risk or having no pathology, where subjects where classified as having "high risk polyps" if they had one of the following categories of polyps: Tubulovillous Adenoma; Villous Adenoma; High Grade Dysplasia and Tubular Adenoma where the diameter of the Tubular Adenoma polyp is greater than 10 mm and cancer Logistic regression was used to analyze the dependence of the binary variable Y (0=control, 1=disease) on the $\Delta$Ct values from the reference data set. If P=probability that a patient sample is identified as "diseased", then a function X=Logit(p) can be defined as follows:

$$X=\text{Logit}(P)=\ln(P/(1-P))=b_0+b_1\Delta Ct_1+b_2\Delta Ct_2+\ldots+b_n\Delta Ct_n \quad (\text{Eq 1})$$

If X$\geq$threshold then Y=1 (diagnosis="has high risk polyps"), and if X<threshold then Y=0 (diagnosis=does not have high risk polyps). The (empirical) coefficients {bi} that define the relationship between X and the experimental measurements {$\Delta$Cti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (CDA; MGC20553; MBTPS1; SERPINE2; BCNP1;) and shown as follows:

$$X=\text{Logit}(P)=\ln(P/(1-P))=-5.2981-0.5433\Delta CtCDA-0.4958\Delta CtMGC20553+0.8551\Delta CtMBTPS1+0.3554\Delta CtBCNP1+0.2438\Delta CtSERPINE2$$

gave an ROC=0.74 with a sensitivity of 83% and a specificity of 46%.

Clinical Question—Cancer v. Other

Finally the same seven genes were tested in combinations using a reference (training) data set containing $\Delta$Ct values for the above seven genes assayed against a total of 80 subjects having cancerous polyps and 344 subjects having other types of polyps or having no pathology.

Logistic regression was used to analyze the dependence of the binary variable Y (0=control, 1=disease) on the ΔCt values from the reference data set. If P=probability that a patient sample is identified as "diseased", then a function X=Logit(p) can be defined as follows:

$$X = \text{Logit}(P) = \ln(P/(1-P)) = b_0 + b_1 \Delta Ct_2 + b_2 \Delta Ct_2 + \ldots + b_n \Delta Ct_n \quad (Eq\ 1)$$

If X≧threshold then Y=1 (diagnosis="has cancerous polyps"), and if X<threshold then Y=0 (diagnosis=does not have cancerous polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (MGC20553, CDA, MBTPS1, SERPINE2, MGC45871; BCNP1) and shown as follows:

$$X = \text{Logit}(P) = \ln(P/(1-P)) = -12.9149 - 0.5378\Delta CtCDA - 0.5398\Delta CtMGC20553 + 1.0386\Delta CtMBTPS1 + + 0.7405\Delta CtBCNP1 + 0.4002\Delta CtMGC45871 + 0.2074\Delta CtSERPINE2$$

gave an ROC=0.83 with a sensitivity of 90% and a specificity of 55%.

Clinical Question—High Risk Pathology v. Other

A reference (training) data set was constructed containing ΔCt values for the above seven genes assayed against a total of 252 subjects having high risk polyps and 272 subjects having other types of polyps or having no pathology where by high risk polyps is meant Tubulovillous Adenoma, Villous Adenoma, High Grade Dysplasia and Tubular Adenoma—regardless of diameter of polyp.

Logistic regression was used to analyze the dependence of the binary variable Y (0=control, 1=disease) on the ΔCt values from the reference data set. If P=probability that a patient sample is identified as "diseased", then a function X=Logit(p) can be defined as follows:

$$X = \text{Logit}(P) = \ln(P/(1-P)) = b_0 + b_1 \Delta Ct_1 + b_2 \Delta Ct_2 + \ldots + b_n \Delta Ct_n \quad (Eq\ 1)$$

If X≧threshold then Y=1 (diagnosis="has high risk polyps"), and if X<threshold then Y=0 (diagnosis=does not have high risk polyps). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The best equation used the following genes (MGC20553; CDA; MBTPS1; SERPINE2; BCNP1;) and shown as follows:

$$X = \text{Logit}(P) = \ln(P/(1-P)) = -3.5819 - 0.7625\Delta CtCDA - 0.6117\Delta CtMGC20553 + 1.15\Delta CtMBTPS1 + 0.2174\Delta CtBCNP1 + 0.2439\Delta CtSERPINE2$$

gave an ROC=0.76 with a sensitivity of 82% and a specificity of 52%.

Example 7

Biomarkers to Screen for Presence of Colorectal Cancer. Deriving Classifiers to be Used with Combinations of Biomarkers and Application of Said Classifiers to Determine Presence of Colorectal Cancer QRT-PCR was performed on a selection of the genes identified from one or more microarray analyses (data not shown) as being able to differentiate as between individuals having colorectal cancer and individuals not having colorectal cancer. Some of genes selected for QRT-PCR were selected from microarray data performed on samples collected from three regions of China for over 593 samples including 61 samples from individuals having been diagnosed with colorectal cancer and 532 from individuals not having colorectal cancer (data not shown). Other genes were selected from other similar microarray experiments with individuals from North America and/or Asia. Among the individuals not having colorectal cancer was a mixture of individuals having breast cancer, kidney cancer, prostate cancer, bladder cancer, and individuals having other subtypes of colorectal pathology which were not colorectal cancer.

QRT-PCR was done on each individual gene across a population of individuals having colorectal cancer and a population of individuals not having colorectal cancer. QRT-PCR experiments were done using either the SYBR® Green Kit from Qiagen (Product Number 204143) and/or using Applied Biosystems PCR reagent kits (Cat 4334973) and/or using TaqMan Assay using the QuantiTect® Probe PCR Kit (Qiagen, Cat. #204345). TaqMan® probes were developed for each gene of interest and labelled with FAM and the Black Hole Quencher® from Biosearch Technologies. Beta-actin was used as a housekeeping gene in the duplexed assays and labelled using HEX and Black Hole Quencher®. Amplicons were detected in real time using a Prism 7500 instrument (Applied Biosystems). Results of the QRT-PCR for each gene across the population tested are shown in Table 12.

Rather than testing all possible combinations of the biomarkers noted in Table 12, in other embodiments, all possible combinations of biomarkers with a p value of less than 0.05 can be chosen and all or a portion of combinations of biomarkers tested. Discussed below is representative classifiers identified for selected combinations tested.

Classifiers were derived for all two gene combinations of the biomarkers identified in Table 12 using QRT-PCR for 28 of the genes identified in Table 12 across 58 individuals having colorectal cancer and 57 individuals not having colorectal cancer. The 28 genes utilized are represented by the following gene symbols and are described in more detail herein: OSBPL10, LOC283130, BANK1, COBLL1, MGC24039, C9orf85, BLNK, BCNP1, PDE3B, AKAP13, WDFY1, CDA, AGTRAP, ACTR2, UTS2, MS4A1, SPAP1, ANK3, KIAA1559, GBP5, MGC20553, CEACAM1, HIST1H4H, PRG1, BRD2, LTBP3, MAP4K3, and NIPA2 Primers utilized for the real time RT-PCR are further described in Table 16. Classifiers derived for selection combinations of two genes are shown as follows:

Table A: Table showing Resulting Classifiers for a Selection of Two Gene Combinations Wherein the Combinations are in the Form of Ratios and the Biomarkers Are Selected from the 28 Genes Selected from Table 12. Shown is the resulting ROC area of the Classifiers, the Sensitivity (at the noted cutoff Sens) and Specificity (at the noted cutoff Spec) are shown. The constant, and the coefficient for the selected two gene ratio are noted.

TABLE A

|  | ROC-area | Sensitivity at 90% Specificity | Specificity at 90% Sensitivity | Constant | Coeffic for Ratio |
| --- | --- | --- | --- | --- | --- |
| BANK1/CDA | 0.8621 | 46.55 | 68.42 | −3.7808 | 1.256 |
| BCNP1/CDA | 0.8451 | 43.10 | 57.89 | −2.7251 | 1.2554 |
| CDA/MS4A | 0.8430 | 43.10 | 63.16 | −1.3171 | −1.0944 |

TABLE A-continued

| | ROC-area | Sensitivity at 90% Specificity | Specificity at 90% Sensitivity | Constant | Coeffic for Ratio |
|---|---|---|---|---|---|
| C9orf85/CDA | 0.8382 | 44.83 | 52.63 | −16.482 | 2.2374 |
| CDA/OSBPL10 | 0.8367 | 56.90 | 47.37 | −5.9699 | −1.2875 |
| CDA/SPAP1 | 0.8364 | 48.28 | 59.65 | −3.3047 | −0.9384 |
| BLNK/CDA | 0.8361 | 50.00 | 68.42 | −4.8603 | 1.2367 |
| CDA/LOC283130 | 0.8339 | 67.24 | 52.63 | −3.9388 | −1.6368 |
| CDA/COBLL1 | 0.8321 | 53.45 | 56.14 | −6.9371 | −1.3126 |
| BANK1/PRG1 | 0.8306 | 55.17 | 54.39 | −8.6282 | 1.2825 |
| BANK1/CEACAM1 | 0.8291 | 56.9 | 56.14 | −1.7783 | 1.1225 |
| BCNP1/PRG1 | 0.8224 | 60.34 | 45.61 | −7.4478 | 1.2631 |
| BANK1/MGC20553 | 0.8197 | 44.83 | 59.65 | 2.2412 | 0.9436 |
| BANK1/NIPA2 | 0.8176 | 58.62 | 50.88 | −2.2946 | 1.6015 |
| ACTR2/BANK1 | 0.8155 | 41.38 | 54.39 | −9.1667 | −1.4596 |

Example 8

Classifiers were also derived for all possible combinations of a selection of nine of the biomarkers identified in Table 12. Data for use in generating the classifiers for the combinations were obtained using real time RT-PCR for each of the nine genes tested across the same 58 individuals having colorectal cancer and 57 individuals not having colorectal cancer described in Example 7. The 9 genes utilized are represented by the following gene symbols and are described in more detail herein: CDA, MGC20553, MS4A1, BCNP1, BANK1, GBP5, OSBPL10, SPAP1, LOC283130. Primers utilized for the real time RT-PCR are further described in Table 16. A selection of the resulting classifiers are described below in Table B below:

TABLE B

| # | ROC area | Constant | CDA | MGC20553 | MS4A1 | BCNP1 | BANK1 | GBP5 | OSBPL10 | SPAP1 | LOC283130 |
|---|---|---|---|---|---|---|---|---|---|---|---|
| 1 | 0.8364 | −14.48 | | | | | 1.61 | | | | |
| 1 | 0.8197 | −10.07 | | | 1.25 | | | | | | |
| 1 | 0.8091 | −10.56 | | | | | | | | 1.02 | |
| 2 | 0.8681 | −21.35 | | | | 1.39 | | | 0.77 | | |
| 2 | 0.8648 | −7.58 | −0.93 | | | | 1.41 | | | | |
| 2 | 0.8594 | −21.80 | | | | | 1.27 | | 0.81 | | |
| 3 | 0.8839 | −12.85 | −1.26 | | | 1.20 | | | 0.93 | | |
| 3 | 0.8811 | −13.04 | −1.25 | | | | 1.06 | | 0.97 | | |
| 3 | 0.8757 | −10.48 | −1.20 | | | 1.11 | | | | | 0.94 |
| 4 | 0.8963 | −9.09 | −1.47 | | | 1.34 | | −0.72 | 0.93 | | |
| 4 | 0.8917 | −7.25 | −1.29 | −0.51 | | 1.17 | | | 1.02 | | |
| 4 | 0.8902 | −5.32 | −1.59 | | | 1.11 | | −0.88 | | | 1.14 |
| 5 | 0.8987 | −10.60 | −1.42 | | | 0.99 | 0.43 | −0.71 | 0.92 | | |
| 5 | 0.8984 | −8.84 | −1.63 | | | 1.16 | | −0.80 | 0.75 | | 0.52 |
| 5 | 0.8969 | −9.34 | −1.65 | | | | 0.94 | −0.72 | 0.69 | | 0.75 |
| 6 | 0.9035 | −10.25 | −1.57 | | | 0.82 | 0.43 | −0.78 | 0.73 | | 0.52 |
| 6 | 0.9005 | −10.91 | −1.42 | | −0.32 | 1.13 | 0.62 | −0.72 | 0.91 | | |
| 6 | 0.9005 | −10.64 | −1.41 | | | 1.19 | 0.57 | −0.71 | 0.88 | −0.26 | |
| 7 | 0.9053 | −10.60 | −1.57 | | −0.31 | 0.96 | 0.61 | −0.79 | 0.73 | | 0.51 |
| 7 | 0.9020 | −10.31 | −1.55 | | | 0.98 | 0.53 | −0.77 | 0.71 | −0.20 | 0.49 |
| 7 | 0.9014 | −11.32 | −1.59 | 0.14 | | 0.82 | 0.46 | −0.87 | 0.71 | | 0.52 |
| 8 | 0.9056 | −10.57 | −1.57 | | −0.27 | 0.99 | 0.62 | −0.79 | 0.72 | −0.06 | 0.50 |
| 8 | 0.9044 | −11.30 | −1.59 | 0.09 | −0.29 | 0.95 | 0.62 | −0.85 | 0.71 | | 0.51 |
| 8 | 0.9026 | −11.17 | −1.57 | 0.11 | | 0.96 | 0.55 | −0.85 | 0.70 | −0.18 | 0.49 |
| 9 | 0.9041 | −11.26 | −1.58 | 0.09 | −0.25 | 0.98 | 0.63 | −0.85 | 0.71 | −0.06 | 0.50 |

TABLE A-continued

| | ROC-area | Sensitivity at 90% Specificity | Specificity at 90% Sensitivity | Constant | Coeffic for Ratio |
|---|---|---|---|---|---|
| CDA/HIST1H4H | 0.8134 | 51.72 | 47.37 | 1.6688 | −1.5062 |
| AKAP13/GBP5 | 0.7012 | 22.41 | 22.81 | −0.7784 | 0.6743 |
| BCNP1/CEACAM1 | 0.8131 | 44.83 | 52.63 | −0.8916 | 1.1843 |
| CEACAM1/SPAP1 | 0.8128 | 34.48 | 56.14 | −1.8563 | −0.88 |
| CDA/MAP4K3 | 0.8128 | 39.66 | 45.61 | −9.7566 | −1.7304 |
| BCNP1/GBP5 | 0.8107 | 36.21 | 57.89 | −4.611 | 1.1411 |

As noted for each two gene combination the ROC area is provided in addition to the specificity (when sensitivity is set at 90%) and sensitivity (when specificity is set at 90%). The cutoff utilized to generate the sensitivity and specificity as noted are provided in the two righthand most columns. The classifier for each of the two gene combinations can be generically described as follows:

$$X \text{(having colorectal cancer)} = \text{Logit}(P) = \ln(P/(1-P)) = b_0 + b_1(\Delta Ct_1 - \Delta Ct_2)$$

Where $b_0$ is identified as the coefficient and $b_1$ is noted as the coefficient for the ratio.

The classifiers shown above can be generically described in the following equation.

$$X \text{(possibility of having colorectal cancer)} = \text{Logit}(P) = \ln(P/(1-P)) = b_0 + b_1 \Delta Ct_1 + b_2 \Delta Ct_2 + \ldots + b_n \Delta Ct_n$$

Noted above are selected classifiers for combinations of 1, 2, 3, 4, 5, 6, 7, 8 or all 9 of the selected genes. The area under the curve is noted (ROC Area). Also provided is the constant $b_0$ and the coefficient for each biomarker (e.g. $b_n$) required for the selected classifier to be applied to the delta Ct of the noted gene for a test sample. As would be understood, where no coefficient is noted, that biomarker is not required for the classifier. Additional sensitivity and specificity determinations can be made for each classifier, and will vary depending upon the threshold set.

Figure 5:
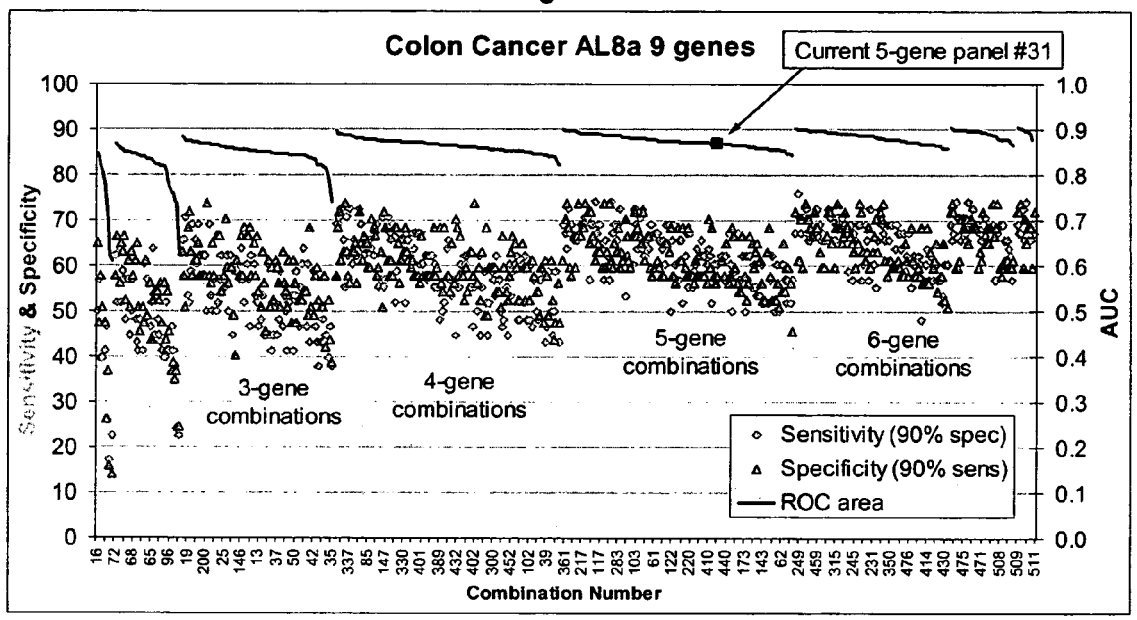
FIG. 5 depicts the graphical output results of the analysis of all possible combinations of 9 genes selected from the genes depicted in Table 12 and further described in Example 8. Shown is a graphical depiction of ROC area, sensitivity (specificity is set at the 90% threshold) and specificity (sensitivity is set at the 90% threshold) for each possible combination of 1, 2, 3, 4, 5, 6, 7, 8 or all 9 genes. Further details are described in Example 8.
Figure 6:
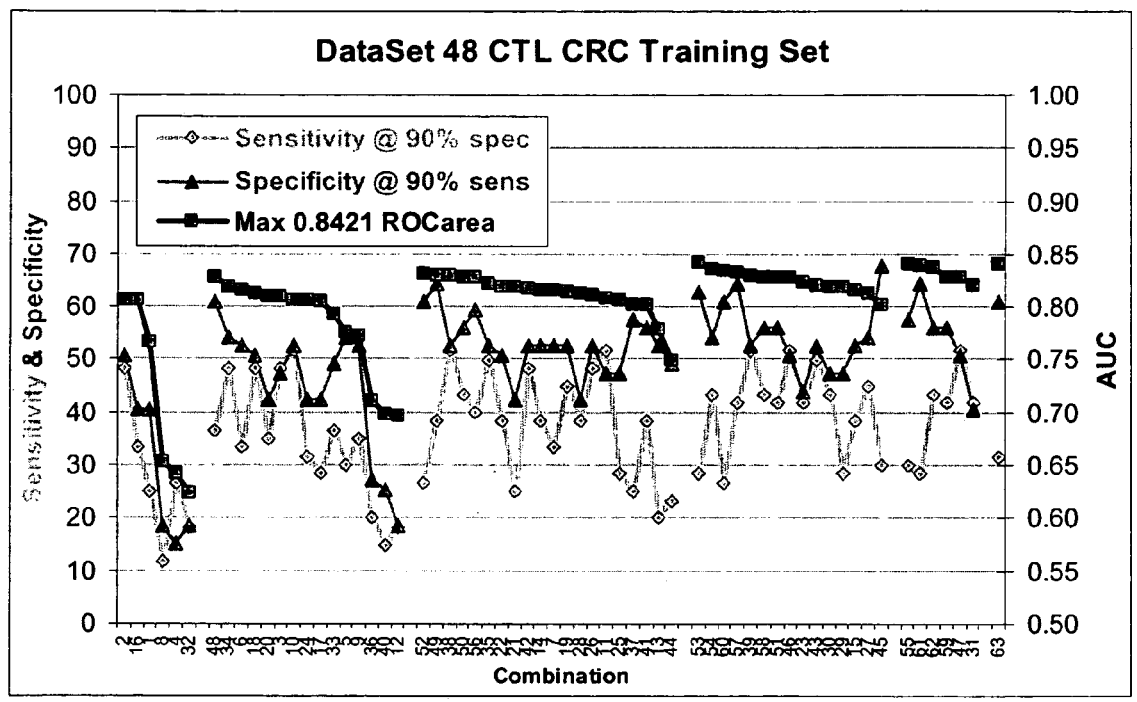
FIG. 6 depicts the graphical output results of the analysis of all possible combinations of 6 genes as further described in Example 11. Shown is a graphical depiction of the ROC area, sensitivity (specificity is set at the 90% threshold) and specificity (sensitivity is set at the 90% threshold) for each possible combination of 1, 2, 3, 4, 5 and all 6 of the genes noted in Example 11.

The results of all of the combinations of the 9 genes is graphically represented in FIG. 5.

Example 9

All possible combinations of biomarkers identified in Table 12 are tested by applying logistic regression to data corresponding to level of product of the biomarkers noted. QRT-PCR is conducted on each of the genes noted in Table 12 for a population of individuals who have been diagnosed as having colorectal cancer or not having colorectal cancer. A matrix containing the ΔCt for RNA corresponding to each gene for each individual of the two populations is created and classifiers derived for each possible combination of biomarkers of those listed in Table 12 (whether individually statistically significant or not) using techniques as described herein. For each classifier the ROC curve is plotted and the area under the curve determined. Classifiers are chosen depending on the specific sensitivity and specificity requirements of the specific intended use of the biomarkers (for example, if may be desirable to have a high sensitivity and fewer false negatives so as to miss less colorectal cancers); (alternatively high specificity resulting in lower false positives is also desirable as it can decrease costs of additional unnecessary medical interventions). A blind test is conducted on one or more of the resulting classifiers so as to demonstrate the utility of the classifier to test for colorectal cancer in a test individual. One or more the classifiers is applied to test an individual to determine the likelihood of said test subject having colorectal cancer.

Example 10

Blind Testing of One of the Combinations of the Genes in Table 12 Using the Derived Classifier A five gene combination encompassing B-cell scaffold protein with ankyrin repeats (BANK1), B-cell novel protein 1 (BCNP1), cytidine deaminase (CDA) membrane-spanning 4-domains, subfamily A, member 1 (MS4A1) and FERM domain containing 3 (MGC20553 aka FRMD3) was selected to pursue further blind sample testing.

The reference (training) data set was constructed containing ΔCt values for the above five genes assayed against a total of 57 subjects having colorectal cancer and 58 subjects not having colorectal cancer as described in more detail in Example 7.

Logistic regression was used to analyze the dependence of the binary variable Y (0=control, 1=disease) on the ΔCt values from the reference data set. If P probability that a patient sample is identified as "having colorectal cancer), then a function X Logit(p) can be defined as follows:

$$X = \text{Logit}(P) = \ln(P/(1-P)) = b_0 + b_1 \Delta Ct_1 + b_2 \Delta Ct_2 + \ldots + b_n \Delta Ct_n \quad \text{(Eq 1)}$$

If X≧threshold then Y=1 (diagnosis="has colorectal cancer"), and if X<threshold then Y=0 (diagnosis=does not have colorectal cancer). The (empirical) coefficients {bi} that define the relationship between X and the experimental measurements {ΔCti, where i represents a sample} were obtained by a maximum-likelihood (ML) fitting method. Identical {bi} values were obtained using several different commercial software programs: MedCalc (MedCalc Software, Mariakerke, Belgium) and XL-Stat (Addinsoft Software, Paris, France). ROC curve analysis was then used to evaluate the discriminatory power of the combinations. The classifier derived using the selected genes (BANK1, BCNP1, CDA, MS4A1, and MGC20553) and shown as follows:

$$X = \text{Logit}(P) = \ln(P/(1-P)) = -5.1338 - 0.8399(\Delta CtCDA) - 0.3314(\Delta CtMGC20553) - 0.3245(\Delta CtMS4A1) + 1.0903(\Delta CtBCNP1) + 0.7842(\Delta CtBANK1)$$

gave an area under the curve of 0.883±0.032. One can adjust the sensitivity or specificity by adjusting the testing cut off point as follows:

| Cut-off | Sens. (95% C.I.) | Spec. (95% C.I.) |
|---|---|---|
| −0.53 | 89.7 (78.8-96.1) | 78.9 (66.1-88.6) |
| −0.31 | 86.2 (74.6-93.8) | 80.7 (68.1-89.9) |
| −0.04 | 81.0 (68.6-90.1) | 82.5 (70.1-91.2) |
| 0.47 | 72.4 (59.1-83.3) | 87.7 (76.3-94.9) |
| 0.59 | 67.2 (53.7-79.0) | 89.5 (78.5-96.0) |
| 1.46 | 43.1 (30.2-56.8) | 94.7 (85.4-98.8) |

Using a cutoff of −1.1 gives a sensitivity of 98.3% and a specificity 50.9%.

A first blind test was performed using a scoring population comprised of 15 individuals not having colorectal cancer and 6 individuals having colorectal cancer. This blind test utilized individuals selected from a single site in Penang. The first blind test resulted in a sensitivity of 100% and a specificity of 43%. A second blind test was performed using a second scoring population (non overlapping with the first scoring population) of 31 non colorectal patients and 23 colorectal patients. Patient samples were collected from three different sites in Asia. The test resulted in a sensitivity of 100% (all samples with colorectal cancer properly identified) and a specificity of 47% (almost half of the samples without colorectal cancer properly identified). A final blind test was performed utilizing samples obtained from two clinics in North America including 15 colorectal cancer patients and 16 non colorectal cancer patients resulting in a sensitivity of 88% and a specificity of 33%.

Example 11

Selection of 6 Biomarkers (BCNP1, CD163, CDA, MS4A1, BANK1, MGC20553) to Derive Classifiers which are Particularly Useful in Screening for the Presence of Colorectal Cancer and Application of the Classifiers with the Combinations Selected to Determine Presence of Colorectal Cancer QRT-PCR was performed on the selection of genes BCNP1, CD163, CDA, MS4A1, BANK1, MGC20553 identified from one or more microarray analyses (selected from Table 12 and Table 11). QRT-PCR data was most recently collected on RNA samples from centrifuged lysed blood from 109 samples, 60 individuals having colorectal cancer and 59 individuals not having colorectal cancer. QRT-PCR was performed using a duplexed TaqMan Assay using the QuantiTect® Probe PCR Kit (Qiagen, Cat. #204345). TaqMan® probes were developed for each gene of interest and labelled with FAM and the Black Hole Quencher® from Biosearch Technologies. Beta-actin was used as a housekeeping gene in the duplexed assays and labelled using HEX and Black Hole Quencher®. ΔCts (Ct gene of interest−Ct Beta-actin) were calculated.

Results of the average QRT-PCR results for each gene across the population tested are shown in Table C below. The average ΔCt (Ct gene−Ct Beta-actin) of each gene in both the control population and the population having colorectal cancer (CRC) are shown, as is the standard deviation (SD) as amongst the data from the population. The p value for each gene individually is shown. The change in ΔCt as between the ΔCt of the Control samples for each gene and the ΔCt for the CRC samples for each gene are shown as ΔΔCt and the standard deviation are shown. Also shown is the fold change for each individual marker.

TABLE C

|  |  | BANK1 | BCNP1 | CDA | MGC20553 | MS4A1 | CD163 |
|---|---|---|---|---|---|---|---|
| Control |  Avg ΔCt of Control (non CRC) | 7.5998 | 6.5558 | 3.4814 | 9.7375 | 3.9940 | 5.2012 |
|  | SD | 0.767 | 0.907 | 0.491 | 1.036 | 0.974 | 0.381 |
| Colorectal Cancer (CRC) | CRC Avg | 8.3398 | 7.6368 | 3.2070 | 9.3773 | 5.1298 | 5.3896 |
|  | Standard Deviation | 0.708 | 0.893 | 0.539 | 0.867 | 1.041 | 0.482 |
|  | p-value (CRC v. Control) | 2.6E−07 | 1.6E−09 | 4.4E−03 | 4.2E−02 | 1.1E−08 | 2.0E−02 |
|  | ΔΔCt(ΔCtCont-ΔCtCRC) | −0.7400 | −1.0810 | 0.2743 | 0.3602 | −1.1359 | −0.1884 |
|  | Standard Deviation | 1.044 | 1.273 | 0.729 | 1.351 | 1.425 | 0.614 |
|  | Regulation (direction of regulation comparing CRC v. Control) | Down regulated | Down Regulated | Up regulated | Up regulated | Down regulated | Down regulated |
|  | Fold change (CRC v. Control) | 1.67 | 2.12 | 1.21 | 1.28 | 2.20 | 1.14 |
|  | Standard Deviation (Fold change) | 2.06 | 2.42 | 1.66 | 2.55 | 2.69 | 1.53 |

A matrix of the individual QRT-PCR data corresponding to each of the six biomarkers across a population comprising 60 individuals having colorectal cancer and 59 individuals not having colorectal cancer was generated using the same methods noted above. The matrix of data was used to generate classifiers for all possible combinations of the six biomarkers by applying logistic regression to the data of each possible combination. A listing of all of the combinations and the biomarkers which make up each combination are noted in Table D below. The ROC curve for each resulting classifier was measured to determine the ability of each derived classifier to properly identify a test patient as having colorectal cancer. The given sensitivity (at a pre-defined specificity) and the specificity (at a pre-defined sensitivity) can be determined from the ROC curve. The resulting classifiers from this analysis is shown in Table E and the results of these classifiers are shown graphically in FIG. 5.

TABLE D

Each combination is noted as a unique combination number ranging from 1 to 63. Presence of the number 1 in a column below a noted Gene indicates the presence of that gene within the generated classifier.

| Combination # | BANK1Gene01 | BCNP1Gene02 | CDAGene03 | MS4A1Gene04 | MGC20553Gene05 | CD163Gene06 |
|---|---|---|---|---|---|---|
| 1 | 1 |  |  |  |  |  |
| 2 |  | 1 |  |  |  |  |
| 3 | 1 | 1 |  |  |  |  |
| 4 |  |  | 1 |  |  |  |
| 5 | 1 |  | 1 |  |  |  |
| 6 |  | 1 | 1 |  |  |  |
| 7 | 1 | 1 | 1 |  |  |  |
| 8 |  |  |  | 1 |  |  |
| 9 | 1 |  |  | 1 |  |  |
| 10 |  | 1 |  | 1 |  |  |
| 11 | 1 | 1 |  | 1 |  |  |
| 12 |  |  | 1 | 1 |  |  |
| 13 | 1 |  | 1 | 1 |  |  |
| 14 |  | 1 | 1 | 1 |  |  |
| 15 | 1 | 1 | 1 | 1 |  |  |
| 16 |  |  |  |  | 1 |  |
| 17 | 1 |  |  |  | 1 |  |
| 18 |  | 1 |  |  | 1 |  |
| 19 | 1 | 1 |  |  | 1 |  |
| 20 |  |  | 1 |  | 1 |  |
| 21 | 1 |  | 1 |  | 1 |  |
| 22 |  | 1 | 1 |  | 1 |  |
| 23 | 1 | 1 | 1 |  | 1 |  |
| 24 |  |  |  | 1 | 1 |  |
| 25 | 1 |  |  | 1 | 1 |  |
| 26 |  | 1 |  | 1 | 1 |  |
| 27 | 1 | 1 |  | 1 | 1 |  |
| 28 |  |  | 1 | 1 | 1 |  |

TABLE D-continued

Each combination is noted as a unique combination number ranging from 1 to 63. Presence of the number 1 in a column below a noted Gene indicates the presence of that gene within the generated classifier.

| Combination # | BANK1Gene01 | BCNP1Gene02 | CDAGene03 | MS4A1Gene04 | MGC20553Gene05 | CD163Gene06 |
|---|---|---|---|---|---|---|
| 29 | 1 |   | 1 | 1 | 1 |   |
| 30 |   | 1 | 1 | 1 | 1 |   |
| 31 | 1 | 1 | 1 | 1 | 1 |   |
| 32 |   |   |   |   |   | 1 |
| 33 | 1 |   |   |   |   | 1 |
| 34 |   | 1 |   |   |   | 1 |
| 35 | 1 | 1 |   |   |   | 1 |
| 36 |   |   | 1 |   |   | 1 |
| 37 | 1 |   | 1 |   |   | 1 |
| 38 |   | 1 | 1 |   |   | 1 |
| 39 | 1 | 1 | 1 |   |   | 1 |
| 40 |   |   |   | 1 |   | 1 |
| 41 | 1 |   |   | 1 |   | 1 |
| 42 |   | 1 |   | 1 |   | 1 |
| 43 | 1 | 1 |   | 1 |   | 1 |
| 44 |   |   | 1 | 1 |   | 1 |
| 45 | 1 |   | 1 | 1 |   | 1 |
| 46 |   | 1 | 1 | 1 |   | 1 |
| 47 | 1 | 1 | 1 | 1 |   | 1 |
| 48 |   |   |   |   | 1 | 1 |
| 49 | 1 |   |   |   | 1 | 1 |
| 50 |   | 1 |   |   | 1 | 1 |
| 51 | 1 | 1 |   |   | 1 | 1 |
| 52 |   |   | 1 |   | 1 | 1 |
| 53 | 1 |   | 1 |   | 1 | 1 |
| 54 |   | 1 | 1 |   | 1 | 1 |
| 55 | 1 | 1 | 1 |   | 1 | 1 |
| 56 |   |   |   | 1 | 1 | 1 |
| 57 | 1 |   |   | 1 | 1 | 1 |
| 58 |   | 1 |   | 1 | 1 | 1 |
| 59 | 1 | 1 |   | 1 | 1 | 1 |
| 60 |   |   | 1 | 1 | 1 | 1 |
| 61 | 1 |   | 1 | 1 | 1 | 1 |
| 62 |   | 1 | 1 | 1 | 1 | 1 |
| 63 | 1 | 1 | 1 | 1 | 1 | 1 |

In preferred embodiments, data representing levels of products of any combination of two of the six biomarkers in a sample isolated or derived from a test subject are input to a formula as further described herein, for the purpose of providing a probability that the test subject has one or more colorectal pathologies. In certain other embodiments, data representing levels of products of any combination of three, four, or five of the six biomarkers are input to a formula as further described herein. It is also consistent with the methods described herein that data representing levels of products of all six of the six biomarkers are input to a formula to provide a probability that a test subject has one or more colorectal pathologies.

TABLE E

Classifiers resulting from each possible combination of the six biomarkers are noted. The Combination number corresponds to the combinations as noted in Table D. The number of genes contributing to the combination is noted, and the coefficient for that biomarker are noted within the row. Where 0 is noted as a coefficient, this biomarker does not contribute to the resulting classifier. The area under the curve (ROC area) is noted as is the sensitivity at 90% specificity and the specificity at 90% sensitivity.

| Comb # | # of genes | ROC area | Sensitivity @ 90% spec | Specificity @ 90% sens | Constant | BANK1 | BCNP1 | CDA | MGC20553 | MS4A1 | CD163 |
|---|---|---|---|---|---|---|---|---|---|---|---|
| 2 | 1 | 0.8065 | 48.33 | 50.85 | −9.4336 | 0 | 1.3378 | 0 | 0 | 0 | 0 |
| 16 | 1 | 0.8062 | 33.33 | 40.68 | −5.1508 | 0 | 0 | 0 | 0 | 1.1456 | 0 |
| 1 | 1 | 0.7664 | 25.00 | 40.68 | −10.646 | 1.3395 | 0 | 0 | 0 | 0 | 0 |
| 8 | 1 | 0.6531 | 11.67 | 18.64 | 3.9001 | 0 | 0 | 0 | −0.40595 | 0 | 0 |
| 4 | 1 | 0.6421 | 26.67 | 15.25 | 3.5585 | 0 | 0 | −1.0592 | 0 | 0 | 0 |
| 32 | 1 | 0.6232 | 18.33 | 18.64 | −5.4467 | 0 | 0 | 0 | 0 | 0 | 1.0322 |
| 48 | 2 | 0.8285 | 36.67 | 61.02 | −10.284 | 0 | 0 | 0 | 1.1534 | 0 | 0.96391 |
| 34 | 2 | 0.8184 | 48.33 | 54.24 | −14.22 | 0 | 1.3294 | 0 | 0 | 0 | 0.91273 |
| 6 | 2 | 0.8155 | 33.33 | 52.54 | −6.6582 | 0 | 1.2559 | −0.65891 | 0 | 0 | 0 |
| 18 | 2 | 0.8130 | 48.33 | 50.85 | −8.6118 | 0 | 1 | 0 | 0 | 0.3475 | 0 |
| 20 | 2 | 0.8102 | 35.00 | 42.37 | −2.2241 | 0 | 0 | −0.78667 | 0 | 1.0765 | 0 |
| 3 | 2 | 0.8093 | 48.33 | 47.46 | −10.046 | 0.18289 | 1.2184 | 0 | 0 | 0 | 0 |
| 10 | 2 | 0.8068 | 51.67 | 52.54 | −11.01 | 0 | 1.3885 | 0 | 0.12681 | 0 | 0 |

TABLE E-continued

Classifiers resulting from each possible combination of the six biomarkers are noted. The Combination number corresponds to the combinations as noted in Table D. The number of genes contributing to the combination is noted, and the coefficient for that biomarker are noted within the row. Where 0 is noted as a coefficient, this biomarker does not contribute to the resulting classifier. The area under the curve (ROC area) is noted as is the sensitivity at 90% specificity and the specificity at 90% sensitivity.

| Comb # | # of genes | ROCarea | Sensitivity @ 90% spec | Specificity @ 90% sens | Constant | BANK1 | BCNP1 | CDA | MGC20553 | MS4A1 | CD163 |
|---|---|---|---|---|---|---|---|---|---|---|---|
| 24 | 2 | 0.8065 | 31.67 | 42.37 | −4.3207 | 0 | 0 | 0 | −7.84E−02 | 1.1282 | 0 |
| 17 | 2 | 0.8048 | 28.33 | 42.37 | −3.938 | −0.24835 | 0 | 0 | 0 | 1.3149 | 0 |
| 33 | 2 | 0.7921 | 36.67 | 49.15 | −16.106 | 1.3541 | 0 | 0 | 0 | 0 | 1.0097 |
| 5 | 2 | 0.7754 | 30.00 | 54.24 | −7.6711 | 1.2227 | 0 | −0.61344 | 0 | 0 | 0 |
| 9 | 2 | 0.7718 | 35.00 | 52.54 | −8.8519 | 1.2937 | 0 | 0 | −0.14952 | 0 | 0 |
| 36 | 2 | 0.7113 | 20.00 | 27.12 | −2.8691 | 0 | 0 | −1.391 | 0 | 0 | 1.4243 |
| 40 | 2 | 0.6983 | 15.00 | 25.42 | −1.5982 | 0 | 0 | 0 | −0.47483 | 0 | 1.1646 |
| 12 | 2 | 0.6961 | 18.33 | 18.64 | 7.3191 | 0 | 0 | −1.0488 | −0.39666 | 0 | 0 |
| 52 | 3 | 0.8319 | 26.67 | 61.02 | −8.1557 | 0 | 0 | −1.0734 | 0 | 1.0665 | 1.3105 |
| 49 | 3 | 0.8299 | 38.33 | 64.41 | −9.4457 | −0.16237 | 0 | 0 | 0 | 1.2638 | 0.95548 |
| 38 | 3 | 0.8291 | 51.67 | 52.54 | −11.787 | 0 | 1.2127 | −0.90702 | 0 | 0 | 1.1775 |
| 50 | 3 | 0.8288 | 43.33 | 55.93 | −13.395 | 0 | 0.96662 | 0 | 0 | 0.38068 | 0.91813 |
| 56 | 3 | 0.8285 | 40.00 | 59.32 | −8.8677 | 0 | 0 | 0 | −0.16768 | 1.1205 | 1.0282 |
| 35 | 3 | 0.8226 | 50.00 | 52.54 | −15.171 | 0.2494 | 1.1715 | 0 | 0 | 0 | 0.92838 |
| 22 | 3 | 0.8192 | 38.33 | 50.85 | −5.7441 | 0 | 0.90176 | −0.66762 | 0 | 0.35836 | 0 |
| 21 | 3 | 0.8192 | 25.00 | 42.37 | 1.8168 | −0.71915 | 0 | −0.9327 | 0 | 1.5568 | 0 |
| 42 | 3 | 0.8178 | 48.33 | 52.54 | −14.643 | 0 | 1.3458 | 0 | 4.17E−02 | 0 | 0.89513 |
| 14 | 3 | 0.8158 | 38.33 | 52.54 | −8.2509 | 0 | 1.3096 | −0.66151 | 0.1273 | 0 | 0 |
| 7 | 3 | 0.8155 | 33.33 | 52.54 | −6.6677 | 2.33E−03 | 1.2544 | −0.65841 | 0 | 0 | 0 |
| 19 | 3 | 0.8147 | 45.00 | 52.54 | −7.7027 | −0.18144 | 0.99459 | 0 | 0 | 0.47486 | 0 |
| 28 | 3 | 0.8124 | 38.33 | 42.37 | −1.6155 | 0 | 0 | −0.78053 | −5.87E−02 | 1.0615 | 0 |
| 26 | 3 | 0.8116 | 48.33 | 52.54 | −9.8432 | 0 | 1.0675 | 0 | 9.36E−02 | 0.31563 | 0 |
| 11 | 3 | 0.8085 | 51.67 | 47.46 | −11.398 | 0.15545 | 1.2828 | 0 | 0.11619 | 0 | 0 |
| 25 | 3 | 0.8068 | 28.33 | 47.46 | −3.1168 | −0.24726 | 0 | 0 | −7.82E−02 | 1.2971 | 0 |
| 37 | 3 | 0.8020 | 25.00 | 57.63 | −13.206 | 1.1841 | 0 | −0.93208 | 0 | 0 | 1.3051 |
| 41 | 3 | 0.8017 | 38.33 | 55.93 | −13.824 | 1.2908 | 0 | 0 | −0.23193 | 0 | 1.0935 |
| 13 | 3 | 0.7788 | 20.00 | 52.54 | −5.7872 | 1.1714 | 0 | −0.61629 | −0.15341 | 0 | 0 |
| 44 | 3 | 0.7500 | 23.33 | 49.15 | 0.93831 | 0 | 0 | −1.3775 | −0.46832 | 0 | 1.5416 |
| 53 | 4 | 0.8421 | 28.33 | 62.71 | −4.0963 | −0.72824 | 0 | −1.2159 | 0 | 1.5557 | 1.3112 |
| 54 | 4 | 0.8359 | 43.33 | 54.24 | −10.864 | 0 | 0.79246 | −0.93889 | 0 | 0.43542 | 1.215 |
| 60 | 4 | 0.8345 | 26.67 | 61.02 | −6.7979 | 0 | 0 | −1.0645 | −0.16209 | 1.0289 | 1.3733 |
| 57 | 4 | 0.8322 | 41.67 | 64.41 | −8.0548 | −0.15788 | 0 | 0 | −0.16741 | 1.2282 | 1.0198 |
| 39 | 4 | 0.8294 | 51.67 | 52.54 | −11.969 | 4.28E−02 | 1.1857 | −0.89948 | 0 | 0 | 1.179 |
| 58 | 4 | 0.8288 | 43.33 | 55.93 | −13.371 | 0 | 0.96496 | 0 | −2.24E−03 | 0.38154 | 0.91909 |
| 51 | 4 | 0.8285 | 41.67 | 55.93 | −12.968 | −7.93E−02 | 0.9637 | 0 | 0 | 0.43635 | 0.91323 |
| 46 | 4 | 0.8285 | 51.67 | 50.85 | −12.048 | 0 | 1.2235 | −0.90636 | 2.49E−02 | 0 | 1.1669 |
| 23 | 4 | 0.8237 | 41.67 | 44.07 | −1.9249 | −0.65485 | 0.87804 | −0.81254 | 0 | 0.81182 | 0 |
| 43 | 4 | 0.8212 | 50.00 | 52.54 | −15.382 | 0.2432 | 1.1845 | 0 | 2.32E−02 | 0 | 0.91822 |
| 30 | 4 | 0.8195 | 43.33 | 47.46 | −6.9954 | 0 | 0.97268 | −0.669 | 9.40E−02 | 0.32588 | 0 |
| 29 | 4 | 0.8192 | 28.33 | 47.46 | 2.3538 | −0.71624 | 0 | −0.92591 | −5.37E−02 | 1.5416 | 0 |
| 15 | 4 | 0.8164 | 38.33 | 52.54 | −8.1437 | −3.34E−02 | 1.3322 | −0.66871 | 0.12965 | 0 | 0 |
| 27 | 4 | 0.8124 | 45.00 | 54.24 | −8.9424 | −0.1764 | 1.0611 | 0 | 9.25E−02 | 0.43969 | 0 |
| 45 | 4 | 0.8014 | 30.00 | 67.80 | −10.66 | 1.1055 | 0 | −0.93995 | −0.24668 | 0 | 1.3918 |
| 55 | 5 | 0.8410 | 30.00 | 57.63 | −6.9559 | −0.67682 | 0.76786 | −1.0879 | 0 | 0.9056 | 1.2208 |
| 61 | 5 | 0.8393 | 28.33 | 64.41 | −2.722 | −0.73359 | 0 | −1.2079 | −0.16199 | 1.523 | 1.3754 |
| 62 | 5 | 0.8379 | 43.33 | 55.93 | −10.555 | 0 | 0.76996 | −0.94059 | −2.76E−02 | 0.44682 | 1.228 |
| 59 | 5 | 0.8285 | 41.67 | 55.93 | −12.939 | −7.94E−02 | 0.96171 | 0 | −2.68E−03 | 0.43746 | 0.91437 |
| 47 | 5 | 0.8277 | 51.67 | 50.85 | −12.173 | 3.61E−02 | 1.1995 | −0.90005 | 2.22E−02 | 0 | 1.1693 |
| 31 | 5 | 0.8212 | 41.67 | 40.68 | −3.1633 | −0.65384 | 0.94851 | −0.81521 | 9.32E−02 | 0.77795 | 0 |
| 63 | 6 | 0.8407 | 31.67 | 61.02 | −6.5754 | −0.67929 | 0.74043 | −1.0901 | −3.29E−02 | 0.92168 | 1.2365 |

Primers and probes which were utilized for the QRT-PCR) are further described in Table 17.

Example 12

Testing a Test Subject for One or More Colorectal Pathologies Using the 6 Biomarkers (BCNP1, CD163, CDA, MS4A1, BANK1, MGC20553)

A reference population of 200 individuals is used to generate a formula which will be used to test the test subject. 100 of said individuals are confirmed to have colorectal cancer by colonoscopy. The remaining 100 individuals are screened for colorectal cancer by colonoscopy and are confirmed to be negative for colorectal cancer. Blood Samples are obtained for each of the 200 individuals and total RNA isolated from each isolated blood sample. RNA from each sample is reverse transcribed using an oligo dT primer and cDNA corresponding to the total mRNA is obtained. QRT-PCR is performed on each of the six genes in each of the samples derived from the blood sample and a ΔCt generated for each gene in reference to a Beta-actin control. A data matrix is generated of all of the data across the population. A classifier is developed using each of the following methods (a) logistic regression, (b) linear regression (c) neural networks and (d) principle component analysis. A formula consisting of each of the classifiers, wherein each classifier itself is given a weighting of equal value is generated (ie the results of each classifier when applied to a test subject will give an indication of whether the test subject has a colorectal pathology, and then the results of each classifier are tallied such that if, for example, 3 of the 4 classifiers indicate the test subject has colorectal pathology, the results of the formula indicate the test subject has colorectal pathology).

A blood sample is isolated from a test subject. Total RNA from the blood sample is isolated and cDNA derived using an oligo dT primer. QRT-PCR is performed in each of the six genes in the sample and a ΔCt generated for each gene in reference to a Beta-actin control. The data from the test subject's sample is input into the formula consisting of the four classifiers and a result of each classifier determined, along with the results of the sum of the four classifiers to provide an indication of whether said test subject has colorectal pathology, and in particular colorectal cancer.

FULL CITATIONS FOR REFERENCES REFERRED TO BY NUMBER IN THE SPECIFICATION

1] Ogawa M. Differentiation and proliferation of hematopoietic stem cells. Blood 1993; 81:2844-53.
2] Liew, C C. Method for the detection of gene transcripts in blood and uses thereof. U.S. Patent Application No. 2002000268730.
3] Ma J, Liew C C. Gene profiling identifies secreted protein transcripts from peripheral blood cells in coronary artery disease. J Mol Cell Cardiol 2003; 35:993-8.
4] Tsuang M T, Nossova N, Yager T D, Tsuang M M, Guo S C, Shyu K G, et. al. Assessing the validity of blood-based gene expression profiles for the classification of schizophrenia and bipolar disorder: A preliminary report. Am J Med Genet B Neuropsychiatr Genet 2005; 133B: 1-5.
5] K. Wayne Marshal, Hongwei Zhang, Thomas D. Yager, Nadine Nossova, Adam Dempsey, Run Zheng, Mark Han, Hongchang Tang, Samuel Chao., C. C. Liew. Blood-Based Biomarkers for Detecting Mild Osteoarthritis in the Human Knee. Osteoarthritis and Cartilage 2005; 13: 861-871.
6] Whistler T, Unger E R, Nisenbaum R, Vernon S D. Integration of gene expression, clinical, and epidemiologic data to characterize Chronic Fatigue Syndrome. J Transl Med. 2003; 1:10.
7] Bennett L, Palucka A K, Arce E., Cantrell V, Borvak J, Banchereau J, et al. Interferon and granulopoiesis signatures in systemic lupus erythematosus blood. J Exp Med 2003; 197:711-23.
8] Zhang H Q, Lu H, Enosawa S, Takahara S, Sakamoto K, Nakajima T, et al. Microarray analysis of gene expression in peripheral blood mononuclear cells derived from long-surviving renal recipients. Transplantation Proceedings 2002; 34:1757-9.
9] Tang Y, Nee A C, Lu A, Ran R, Sharp F R. Blood genomic expression profile for neuronal injury. J Cereb Blood Flow Metab. 2003; 23:310-9.
10] Tang Y, Gilbert D L, Glauser T A, Hershey A D, Sharp F R. Blood Gene Expression Profiling of Neurologic Diseases: A Pilot Microarray Study. Arch Neurol. 2005; 62:210-5.
[11] Imperiale T F, Wagner D R, Lin C Y, Larkin G N, Rogge J D, Ransohoff D F. Results of screening colonoscopy among persons 40 to 49 years of age. N Engl J. Med. 2002 Jun. 6; 346(23): 1781-5.
12] Ransohoff D F. Colorectal cancer screening in 2005: status and challenges. Gastroenterology. 2005 May; 128 (6):1685-95
13] Ahluwalia I B, Mack K A, Murphy W, Mokdad A H, Bales V S. State-specific prevalence of selected chronic disease-related characteristics—Behavioral Risk Factor Surveillance System, 2001. MMWR Surveill Summ. 2003 Aug. 22; 52(8):1-80.
14] Whitney A R, Diehn M, Popper S J, Alizadeh A A, Boldrick J C, Relman D A, et. al. Individuality and variation in gene expression patterns in human blood. Proc Natl Acad Sci U S A. 2003; 100:1896-901.
15] Pepe M S. The Statistical Evaluation of Medical Tests for Classification and Prediction. Oxford, England: Oxford University Press; 2003.
16] Dupont W D. Statistical Modeling for Biomedical Researchers. Cambridge, England: Cambridge University Press; 2002.
17] Pampel F C. Logistic regression: A Primer. Publication #07-132, Sage Publications: Thousand Oaks, Calif. 2000.
18] King E N, Ryan T P. A preliminary investigation of maximum likelihood logistic regression versus exact logistic regression. Am Statistician 2002; 56:163-170.
19] Metz C E. Basic principles of ROC analysis. Semin Nucl Med 1978; 8:283-98.
20] Swets J A. Measuring the accuracy of diagnostic systems. Science 1988; 240:1285-93.
21] Zweig M H, Campbell G. Receiver-operating characteristic (ROC) plots: a fundamental evaluation tool in clinical medicine. Clin Chem 1993; 39:561-77.
22] Witten I H, Frank Eibe. Data Mining: Practical Machine Learning Tools and Techniques (second edition). Morgan Kaufman 2005.
23] Deutsch J M. Evolutionary algorithms for finding optimal gene sets in microarray prediction. Bioinformatics 2003; 19:45-52.
24] Citarda F, Tomaselli G, Capocaccia R, Barcherini S, Crespi M; Italian Multicentre Study Group. Efficacy in standard clinical practice of colonoscopic polypectomy in reducing colorectal cancer incidence. Gut. 2001 June; 48(6):812-5.
25] Niels Landwehr, Mark Hall and Eibe Frank (2003) Logistic Model Trees. pp 241-252 in Machine Learning: ECML 2003: 14th European Conference on Machine Learning, Cavtat-Dubrovnik, Croatia, Sep. 22-26, 2003, Proceedings Publisher: Springer-Verlag GmbH, ISSN: 0302-9743
26] Tonkin, E. T.; Wang, T.-J.; Lisgo, S.; Bamshad, M. J.; Strachan, T. NIPBL, encoding a homolog of fungal Scc2-type sister chromatid cohesion proteins and fly Nipped-B, is mutated in Cornelia de Lange syndrome. *Nature Genet.* 36: 636-641, 2004. PubMed ID 15146185.
27] Krantz, I. D.; McCallum, J.; DeScipio, C.; Kaur, M.; Gillis, L. A.; Yaeger, D.; Jukofsky, L.; Wasserman, N.; Bottani, A.; Morris, C. A.; Nowaczyk, M. J. M.; Toriello, H.; and 9 others. Cornelia de Lange syndrome is caused by mutations in NIPBL, the human homolog of *Drosophila melanogaster* Nipped-B. *Nature Genet.* 36: 631-635, 2004. PubMed ID 15146186.
28] Nadel M R, Shapiro J A, Klabunde C N, Seeff L C, Uhler R, Smith R A, Ransohoff D F. A national survey of primary care physicians' methods for screening for fecal occult blood. Ann Intern Med. 2005 Jan. 18; 142(2):86-94.
29] Scaloni A, Jones W, Pospischil M, Sassa S, Schneewind O, Popowicz A M, Bossa F, Graziano S L, Manning J M. Deficiency of acylpeptide hydrolase in small-cell lung carcinoma cell lines. J Lab Clin Med. 1992 October; 120(4): 546-52.
30] Erlandsson R, Boldog F, Persson B, Zabarovsky E R, Allikmets R, Sumegi J, Klein G, Jornvall H. The gene from the short arm of chromosome 3, at D3F15S2, frequently deleted in renal cell carcinoma, encodes acylpeptide hydrolase. Oncogene. 1991 July; 6(7):1293-5.

31] Brown M S, Goldstein J L. A proteolytic pathway that controls the cholesterol content of membranes, cells, and blood. Proc Natl Acad Sci USA. 1999 Sep. 28; 96(20): 11041-8.

32] Adams J C, Seed B, Lawler J. Muskelin, a novel intracellular mediator of cell adhesive and cytoskeletal responses to thrombospondin-1. EMBO J. 1998 Sep. 1; 17(17):4964-74.

33] Gillis L A, McCallum J, Kaur M, DeScipio C, Yaeger D, Mariani A, Kline A D, Li H H, Devoto M, Jackson L G, Krantz I D. NIPBL mutational analysis in 120 individuals with Cornelia de Lange syndrome and evaluation of genotype-phenotype correlations. Am J Hum Genet. 2004 October; 75(4):610-23. Epub 2004 Aug. 18.

34] Takakura S, Kohno T, Manda R, Okamoto A, Tanaka T, Yokota J. Genetic alterations and expression of the protein phosphatase 1 genes in human cancers. Int J Oncol. 2001 April; 18(4):817-24.

35] Periale T F, Ransohoff D F, Itzkowitz S H, Turnbull B A, Ross M E; Colorectal Cancer Study Group. Fecal DNA versus fecal occult blood for colorectal-cancer screening in an average-risk population. N Engl J Med. 2004 Dec. 23; 351(26):2704-14.

All patents, patent applications, and published references cited herein are hereby incorporated by reference in their entirety.

One skilled in the art will readily appreciate that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

While this invention has been particularly shown and described with references to preferred embodiments thereof, it will be understood by those skilled in the art that various changes in form and details may be made therein without departing from the scope of the invention encompassed by the appended claims.

TABLES

Table 1 is found on CD-R filed herewith, identified as file Table01.txt.

TABLE 2

| Gene Symbol | AffySpot | p-value (MW) | p-value (t-test) | Fold change | Direction | Gene Description |
|---|---|---|---|---|---|---|
| APEH | 201284_s_at | | 6.0e-03 | 0.91 | downregulated | N-acylaminoacyl-pept |
| C1orf22 | 220342_x_at | <0.001 | 3.15049390173162e-03 | 1.07 | upregulated | chromosome 1 open re |
| ESR1 | 215551_at | 0.058 | 0.03 | 0.87 | downregulated | estrogen receptor 1 |
| ETS1 | 214447_at | 0.132 | 0.15 | 0.93 | downregulated | v-ets erythroblastos |
| FLJ14624 | 225666_at | | 0.01 | 0.76 | downregulated | hypothetical protein |
| FLJ20701 | | | 0.01 | 0.76 | downregulated | hypothetical protein |
| FLJ23091 | 221958_s_at | | 0.05 | 0.83 | downregulated | putative NFkB activa |
| G2 | 234784_at | 0.182 | 0.18 | 0.78 | downregulated | G2 protein |
| ICOS | 210439_at | | 0.07 | 0.88 | downregulated | inducible T-cell co- |
| ITCH | 235057_at | <0.001 | 1.73049856446377e-06 | 1.13 | upregulated | itchy homolog E3 ubi |
| MBTPS1 | 217543_s_at | | 8.0e-03 | 1.21 | upregulated | membrane-bound trans |
| MGC40157 | 225065_x_at | 0.301 | 0.04 | 1.19 | downregulated | hypothetical protein |
| MGC45871 | 226905_at | | 0.11 | 1.35 | upregulated | hypothetical protein |
| MKLN1 | 242984_at | 0.003 | 0.04 | 1.06 | upregulated | muskelin 1, intracel |
| MMP9 | 203936_s_at | 0.006 | 7.80154116715436e-03 | 1.24 | upregulated | matrix metalloprotei |
| NIPBL | 1560474_at | 0.005 | 0.01 | 1.07 | upregulated | Nipped-B homolog (Dr |
| RPS24 | 1555878_at | | 0.05 | 0.88 | downregulated | ribosomal protein S2 |
| SMARCA1 | 203874_s_at | 0.077 | 0.06 | 0.82 | downregulated | SWI/SNF related, mat |

TABLE 3

| Gene Symbol | RNA Accession No. | Protein Accession No. | Description |
|---|---|---|---|
| FLJ14624 | NM_032813 | NP_116202 | *Homo sapiens* hypothetical protein FLJ14624 (FLJ14624), mRNA |
| FLJ14624 | NM_032813 | NP_116202 | *Homo sapiens* hypothetical protein FLJ14624 (FLJ14624), mRNA |
| ETS1 | NM_005238 | NP_005229 | *Homo sapiens* v-ets erythroblastosis virus E26 oncogene homolog 1 (avian) (ETS1), mRNA |
| RPS24 | NM_033022 | NP_148982 | *Homo sapiens* ribosomal protein S24 (RPS24), transcript variant 1, mRNA |
| RPS24 | NM_001026 | NP_001017 | *Homo sapiens* ribosomal protein S24 (RPS24), transcript variant 2, mRNA |
| FLJ20701 | NM_017933 | NP_060403 | *Homo sapiens* hypothetical protein FLJ20701 (FLJ20701), mRNA |
| MKLN1 | NM_013255 | NP_037387 | *Homo sapiens* muskelin 1, intracellular mediator containing kelch motifs (MKLN1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| FLJ20701 | NM_017933 | NP_060403 | *Homo sapiens* hypothetical protein FLJ20701 (FLJ20701), mRNA |
| RPS24 | NM_033022 | NP_148982 | *Homo sapiens* ribosomal protein S24 (RPS24), transcript variant 1, mRNA |
| RPS24 | NM_001026 | NP_001017 | *Homo sapiens* ribosomal protein S24 (RPS24), transcript variant 2, mRNA |
| APEH | NM_001640 | NP_001631 | *Homo sapiens* N-acylaminoacyl-peptide hydrolase (APEH), mRNA |
| MBTPS1 | NM_003791 | NP_003782 | *Homo sapiens* membrane-bound transcription factor protease, site 1 (MBTPS1), transcrip |
| MBTPS1 | NM_201268 | NP_957720 | *Homo sapiens* membrane-bound transcription factor protease, site 1 (MBTPS1), transcrip |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| MMP9 | NM_004994 | NP_004985 | *Homo sapiens* matrix metalloproteinase 9 (gelatinase B, 92 kDa gelatinase, 92 kDa type I |

TABLE 3-continued

| Gene Symbol | RNA Accession No. | Protein Accession No. | Description |
|---|---|---|---|
| MKLN1 | NM_013255 | NP_037387 | *Homo sapiens* muskelin 1, intracellular mediator containing kelch motifs (MKLN1), mRNA |
| ESR1 | NM_000125 | NP_000116 | *Homo sapiens* estrogen receptor 1 (ESR1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| ITCH | NM_031483 | NP_113671 | *Homo sapiens* itchy homolog E3 ubiquitin protein ligase (mouse) (ITCH), mRNA |
| ITCH | NM_031483 | NP_113671 | *Homo sapiens* itchy homolog E3 ubiquitin protein ligase (mouse) (ITCH), mRNA |
| ICOS | NM_012092 | NP_036224 | *Homo sapiens* inducible T-cell co-stimulator (ICOS), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| ETS1 | NM_005238 | NP_005229 | *Homo sapiens* v-ets erythroblastosis virus E26 oncogene homolog 1 (avian) (ETS1), mRNA |
| SMARCA1 | NM_003069 | NP_003060 | *Homo sapiens* SWI/SNF related, matrix associated, actin dependent regulator of chromat |
| SMARCA1 | NM_139035 | NP_620604 | *Homo sapiens* SWI/SNF related, matrix associated, actin dependent regulator of chromat |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| ITCH | NM_031483 | NP_113671 | *Homo sapiens* itchy homolog E3 ubiquitin protein ligase (mouse) (ITCH), mRNA |
| ESR1 | NM_000125 | NP_000116 | *Homo sapiens* estrogen receptor 1 (ESR1), mRNA |
| ESR1 | NM_000125 | NP_000116 | *Homo sapiens* estrogen receptor 1 (ESR1), mRNA |
| MBTPS1 | NM_003791 | NP_003782 | *Homo sapiens* membrane-bound transcription factor protease, site 1 (MBTPS1), transcrip |
| MBTPS1 | NM_201268 | NP_957720 | *Homo sapiens* membrane-bound transcription factor protease, site 1 (MBTPS1), transcrip |
| FLJ20701 | NM_017933 | NP_060403 | *Homo sapiens* hypothetical protein FLJ20701 (FLJ20701), mRNA |
| C1orf22 | NM_025191 | NP_079467 | *Homo sapiens* chromosome 1 open reading frame 22 (C1orf22), mRNA |
| C1orf22 | NM_025191 | NP_079467 | *Homo sapiens* chromosome 1 open reading frame 22 (C1orf22), mRNA |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| C1orf22 | NM_025191 | NP_079467 | *Homo sapiens* chromosome 1 open reading frame 22 (C1orf22), mRNA |
| ETS1 | NM_005238 | NP_005229 | *Homo sapiens* v-ets erythroblastosis virus E26 oncogene homolog 1 (avian) (ETS1), mRNA |
| MGC40157 | NM_152350 | NP_689563 | *Homo sapiens* hypothetical protein MGC40157 (MGC40157), mRNA |
| MKLN1 | NM_013255 | NP_037387 | *Homo sapiens* muskelin 1, intracellular mediator containing kelch motifs (MKLN1), mRNA |
| FLJ14624 | NM_032813 | NP_116202 | *Homo sapiens* hypothetical protein FLJ14624 (FLJ14624), mRNA |
| MGC45871 | NM_182705 | NP_874364 | *Homo sapiens* hypothetical protein MGC45871 (MGC45871), mRNA |
| MGC45871 | NM_182705 | NP_874364 | *Homo sapiens* hypothetical protein MGC45871 (MGC45871), mRNA |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| FLJ23091 | NM_024911 | NP_079187 | *Homo sapiens* putative NFkB activating protein 373 (FLJ23091), transcript variant 1, m |
| FLJ23091 | NM_001002292 | NP_001002292 | *Homo sapiens* putative NFkB activating protein 373 (FLJ23091), transcript variant 2, m |
| MKLN1 | NM_013255 | NP_037387 | *Homo sapiens* muskelin 1, intracellular mediator containing kelch motifs (MKLN1), mRNA |
| ESR1 | NM_000125 | NP_000116 | *Homo sapiens* estrogen receptor 1 (ESR1), mRNA |
| ITCH | NM_031483 | NP_113671 | *Homo sapiens* itchy homolog E3 ubiquitin protein ligase (mouse) (ITCH), mRNA |
| MKLN1 | NM_013255 | NP_037387 | *Homo sapiens* muskelin 1, intracellular mediator containing kelch motifs (MKLN1), mRNA |
| FLJ20701 | NM_017933 | NP_060403 | *Homo sapiens* hypothetical protein FLJ20701 (FLJ20701), mRNA |
| FLJ20701 | NM_017933 | NP_060403 | *Homo sapiens* hypothetical protein FLJ20701 (FLJ20701), mRNA |
| ITCH | NM_031483 | NP_113671 | *Homo sapiens* itchy homolog E3 ubiquitin protein ligase (mouse) (ITCH), mRNA |
| NIPBL | NM_133433 | NP_597677 | *Homo sapiens* Nipped-B homolog (*Drosophila*) (NIPBL), transcript variant A, mRNA |
| NIPBL | NM_015384 | NP_056199 | *Homo sapiens* Nipped-B homolog (*Drosophila*) (NIPBL), transcript variant B, mRNA |
| MKLN1 | NM_013255 | NP_037387 | *Homo sapiens* muskelin 1, intracellular mediator containing kelch motifs (MKLN1), mRNA |
| MKLN1 | NM_013255 | NP_037387 | *Homo sapiens* muskelin 1, intracellular mediator containing kelch motifs (MKLN1), mRNA |

TABLE 4

| Gene Symbol | SensePrimer | SEQ ID NO | AntisensePrimer | SEQ ID NO | TaqManProbe | SEQ ID NO |
|---|---|---|---|---|---|---|
| APEH | GCCCTGTATTATGTGGACCT | 54 | AGATGGGTACTGCAGGTAGA | 55 | CCGGCTGAGCCCAGACCAAT | 56 |
| APEH | CACTCGGAGACACACTTGTT | 57 | CTTGGTCTGGCTTCTTCAG | 58 | CATCGCTGGCACTGACGTCCA | 59 |
| APEH | ACTCGGAGACACACTTGTTG | 60 | CTTGGTCTGGCTTCTTCAG | 61 | CATCGCTGGCACTGACGTCCA | 62 |
| APEH | AGTGGTGGTAGATGTTGTGC | 63 | AGACCACTCTCTGGCTGTC | 64 | TGCAGCCTTCTGCCTTTGGGA | 65 |
| APEH | CACTTGTTGTATGTGGCAGA | 66 | GCCTGGCTATCTCATCATC | 67 | | |
| C1orf22 | TAGGGAGGAGAAACAGAAGC | 68 | GGCCTCTAACTCGACCTCTA | 69 | TGGAACATGCTTACCCTGCTGATGA | 70 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| C1orf22 | TGTGGTGGATAAGAGCTGTC | 71 | CCCATCTTCTTCAGGATTTC | 72 | TGGCCATGAAATCTCTGGCTCTCA | 73 |
| C1orf22 | GAGGAGAGTTTCAGGAGTGG | 74 | CTCCCATCTTTGAGGTGAAT | 75 | TGGCCATGAAATCTCTGGCTCTCA | 76 |
| C1orf22 | TTGCTTGGAGATGACAGTTT | 77 | AGCATTGGTTTGTGGATATG | 78 | | |
| ESR1 | GGCACATCTTCTGTCTTCTG | 79 | CTGTGAAGAGCTACGGGAAT | 80 | TGGAATCCCTTTGGCTGTTCCC | 81 |
| ESR1 | TGGCACATCTTCTGTCTTCT | 82 | CTGTGAAGAGCTACGGGAAT | 83 | TGGAATCCCTTTGGCTGTTCCC | 84 |
| ESR1 | CCCTACTACCTGGAGAACGA | 85 | ATTGGTACTGGCCAATCTTT | 86 | CTGCCACCCTGGCGTCGATT | 87 |
| ESR1 | CACCATTCCCAAGTTAATCC | 88 | GAAATGCAGTTGGAAACAGA | 89 | TGGGACCAAAGTTCATTTGCTCCA | 90 |
| ESR1 | TGCCCTACTACCTGGAGAAC | 91 | ATTGGTACTGGCCAATCTTT | 92 | AGCCCAGCGGCTACACGGTG | 93 |
| ESR1 | GTGCCCTACTACCTGGAGAA | 94 | ATTGGTACTGGCCAATCTTT | 95 | AGCCCAGCGGCTACACGGTG | 96 |
| ESR1 | TGTGCAATGACTATGCTTCA | 97 | TTATCAATGGTGCACTGGTT | 98 | | |
| ESR1 | TGTGCAATGACTATGCTTCA | 99 | TTTATCAATGGTGCACTGGT | 100 | | |
| ETS1 | TGGGTGGTTTATACACTGGA | 101 | ATAAGGGTTTCACCCAGCTA | 102 | CCAGATTTGCCCATCCTTCCTCTG | 103 |
| ETS1 | GAGCTCCTCTCCCTCAAGTA | 104 | GGTGACGACTTCTTGTTTGA | 105 | CCTGGGTCATTCTCCGAGACCC | 106 |
| ETS1 | GGATGTCAGGTGAGACTGTG | 107 | GCCTTCAAGTCATTCCTCTC | 108 | CCCTGGCATCACCTGTGCCA | 109 |
| ETS1 | TCAAACAAGAAGTCGTCACC | 110 | GCGATCACAACTATCGTAGC | 111 | CCCGAGTTTACCACGACTGGTCCTC | 112 |
| ETS1 | CCGCTATACCTCGGATTACT | 113 | GCGTCTGATAGGACTCTGTG | 114 | CCCAGTGTGTTCCACCATCGGA | 115 |
| FLJ14624 | ACAGCTGCCATCAGAAACTA | 116 | GCTTCCTGTAGCTCATTCCT | 117 | CCGGGAAGCTGTAAGATTAAATCCCAA | 118 |
| FLJ14624 | TGATAAAGGCAACCAGACAG | 119 | AGCTTCCTGTAGCTCATTCC | 120 | TGCCATCAGAAACTACCGGGAAGC | 121 |
| FLJ14624 | GGATTTCTCGTTATCCCATT | 122 | TCTTGGTATGTTTGCTCAGG | 123 | AGGACACGCTCCGCGACCAC | 124 |
| FLJ14624 | CAAATACAGCCAGACTTTGC | 125 | TTTAATTGCTGTCCGGTAAC | 126 | TGCTGGTTCAAACCGTTTCAGGC | 127 |
| FLJ14624 | CAAATACAGCCAGACTTTGC | 128 | GTTTAATTGCTGTCCGGTAA | 129 | TGCTGCTTCAAACCGTTTCAGGC | 130 |
| FLJ14624 | CTTGGTGATAGGCAAATTCA | 131 | AGCAGGGTCATTCTGAAGAG | 132 | CCCGTTCCTGAGCATGCCGA | 133 |
| FLJ14624 | TTTGGCTGTGCTTTATCATC | 134 | CAGCAGACCGTAATTCTCCT | 135 | TGTTTCTTGGCCAAGTCTAGATGTCCC | 136 |
| FLJ20701 | ATTGGAGGACAAGAGCAGAT | 137 | CCATCGCTCTCTAGATTGG | 138 | TTCTTAGGTGCCGCAGTGCCC | 139 |
| FLJ20701 | CCTTCAGGAAGACTTTCCAC | 140 | CTCAAGTTCATTCAGCCATC | 141 | ACGGGCGGATCCACAGCAAC | 142 |
| FLJ20701 | TGATCAGCAAGTGAACACAC | 143 | CTCGGTGATAGCAAATCAGA | 144 | TGCATCCTTGATGGCAAGCTTCA | 145 |
| FLJ20701 | GTGATCAGCAAGTGAACACA | 146 | CTCGGTGATAGCAAATCAGA | 147 | TGCATCCTTGATGGCAAGCTTCA | 148 |
| FLJ20701 | TTAATGGTCCTGTCTGATGC | 149 | GGGTCTCTAGACAAGCCAAG | 150 | | |
| FLJ20701 | AGATTTGCAGACACAGAAGC | 151 | TTCTAACATCAGGTGGTTGC | 152 | | |
| FLJ23091 | TACAACTCACGAATCCCTTCT | 153 | ACAGGAAGTAGAGGCAGAGG | 154 | | |
| FLJ23091 | CAACTCACGAATCCCTTCTAC | 155 | ACAGGAAGTAGAGGCAGAGG | 156 | | |
| FLJ23091 | ACAACTCACGAATCCCTTCTA | 157 | ACAGGAAGTAGAGGCAGAGG | 158 | | |
| FLJ23091 | AACTCACGAATCCCTTCTACA | 159 | ACAGGAAGTAGAGGCAGAGG | 160 | | |
| FLJ23091 | GGGATTTCCATGACCTTTAT | 161 | ATCCAGAAGGACAGAAGCAT | 162 | TGCCCTGTCGGATGTCACCA | 163 |
| FLJ23091 | ATTGAAGAGGCAATTCCAAG | 164 | TTTAGCTTGAAGGCAATGTC | 165 | CCACATGGAGATGAGTCCTTGGTTCC | 166 |
| ICOS | CATGTGTAATGCTGGATGTG | 167 | AAACAACTCAGGGAACACCT | 168 | TGGACAACCTGACTGGCTTTGCA | 169 |
| ICOS | CAGGCCTCTGGTATTTCTTT | 170 | ATTTGTACACCTCCGTTGTG | 171 | TTGGCAGAACCATTGATTTCTCCTGTT | 172 |
| ICOS | AAACATGAAGTCAGGCCTCT | 173 | GTACACCTCCGTTGTGAAAT | 174 | TTGGCAGAACCATTGATTTCTCCTGTT | 175 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| ICOS | GTCAGGCCTCTGGTATTTCT | 176 | ATTTGTACACCTCCGTTGTG | 177 | TTGGCAGAACCATTGATTTCTCCTGTT | 178 |
| ICOS | GAAGTCAGGCCTCTGGTATT | 179 | ATTTGTACACCTCCGTTGTG | 180 | TTGGCAGAACCATTGATTTCTCCTGTT | 181 |
| ITCH | CAGATCCAAGGATGAAACAA | 182 | ACCACCATTTGAGAGTGATG | 183 | CACCAGCTCCTGCATCTTCAGGG | 184 |
| ITCH | TCAATCCAGATCACCTGAAA | 185 | AATCCTTGAGTCCAACTGGT | 186 | CCCATGGAACAGAGCCATGGC | 187 |
| ITCH | AAGCTGTTGTTTGCCATAGA | 188 | CAGAGAAGGACAAACATTGC | 189 | TGCCCATTCATGGTGCAAGTTCTC | 190 |
| ITCH | AAGCTGTTGTTTGCCATAGA | 191 | GCAGAGAAGGACAAACATTG | 192 | TGCCCATTCATGGTGCAAGTTCTC | 193 |
| ITCH | GCTGTTGTTTGCCATAGAAG | 194 | CAGAGAAGGACAAACATTGC | 195 | TGCCCATTCATGGTGCAAGTTCTC | 196 |
| ITCH | GCTGTTGTTTGCCATAGAAG | 197 | GCAGAGAAGGACAAACATTG | 198 | TGCCCATTCATGGTGCAAGTTCTC | 199 |
| MBTPS1 | CAATGACGGACCTCTTTATG | 200 | GGTAGCTCCCAGGTAGTCAT | 201 | TGCCGCCTACTCCAATCACATCC | 202 |
| MBTPS1 | TCTGTGGGAAGAAACATCTG | 203 | TGATGAGAATTCCACCTTCA | 204 | | |
| MBTPS1 | AATCCATCCAGTGACTACCC | 205 | ACTTGAGGGAACGAAAGACT | 206 | AACATCAAACGGGTCACGCCC | 207 |
| MBTPS1 | CAGCCAAAGCTAGAAATTCA | 208 | TAGGGTAGTCACTGGATGGA | 209 | TTCACTGCTCTTCAGGGCACTTGAA | 210 |
| MBTPS1 | GCAATGACGGACCTCTTTAT | 211 | GGTAGCTCCCAGGTAGTCAT | 212 | TGCCGCCTACTCCAATCACATCC | 213 |
| MGC40157 | AGAATCAGCATCATGTTTGG | 214 | ATAACCTTCTCTTGGGCTGA | 215 | CCTCATGGCAGGCTCCTGGC | 216 |
| MGC40157 | TCAGCCCAAGAGAAGGTTAT | 217 | TGAGCATGTCCTCTGATACA | 218 | TCCCAAGGACCAGTAGCTGCCA | 219 |
| MGC40157 | GACTACAGCTCACAGCACAC | 220 | AAAGCTACAACTTGGCCTGT | 221 | TGCCCAGGCTGGTCTCAGGC | 222 |
| MGC40157 | TCAGCCCAAGAGAAGGTTAT | 223 | AGGCAAGCATGTTTCTACAC | 224 | TCCCAAGGACCAGTAGCTGCCA | 225 |
| MGC40157 | ACTACAGCTCACAGCACACC | 226 | AAAGCTACAACTTGGCCTGT | 227 | TGCCCAGGCTGGTCTCAGGC | 228 |
| MGC40157 | TCAGCCCAAGAGAAGGTTAT | 229 | CATAAGGCAAGCATGTTTCT | 230 | TCCCAAGGACCAGTAGCTGCCA | 231 |
| MGC40157 | AGGCTCATGGATCACTCTTT | 232 | GGTACGCAATCCAGTTCTCT | 233 | CCGGCCTTCGCAGACTCCAG | 234 |
| MCG45871 | GACCTCTCTGATGAATGCTG | 235 | AATGACGTGAAGGGTAAGGT | 236 | ACCGGCTCTCCCGCTGTCCT | 237 |
| MCG45872 | GACCTCTCTGATGAATGCTG | 238 | GAATGACGTGAAGGGTAAGG | 239 | ACCGGCTCTCCCGCTGTCCT | 240 |
| MCG4S873 | GACCTCTCTGATGAATGCTG | 241 | GAATGACGTGAAGGGTAAGGT | 242 | ACCGGCTCTCCCGCTGTCCT | 243 |
| MCG45874 | GACCTCTCTGATGAATGCTG | 244 | GGAATGACGTGAAGGGTAAG | 245 | ACCGGCTCTCCCGCTGTCCT | 246 |
| MCG45875 | CCTCTCTGATGAATGCTGAC | 247 | GAATGACGTGAAGGGTAAGG | 248 | ACCGGCTCTCCCGCTGTCCT | 249 |
| MCG45876 | ACCTCTCTGATGAATGCTGA | 250 | GAATGACGTGAAGGGTAAGG | 251 | ACCGGCTCTCCCGCTGTCCT | 252 |
| MKLN1 | CCAGTGAACCACAATTCAGT | 253 | ATGCAGTGTCCTATTCGAGA | 254 | TGGATGTCCTCAGGCCCAGCA | 255 |
| MKLN1 | GGATCACACCTATGCTCAAA | 256 | CCATTTCTGTGTCCAGTGAC | 257 | TGACAGCATGACTCCTCCTAAAGGCA | 258 |
| MKLN1 | ATTTGAGAGGAGGCTGAG | 259 | AATGAAATGCCTGTCAGTTG | 260 | CCACTGGACAACCACAAACCATTTCTC | 261 |
| MKLN1 | GACTTGTAATGGCAGCGTAG | 262 | CTCGAAGAAGTTTCCAGGTT | 263 | TGACAGCAGAGCCAGTGAACCACA | 264 |
| MKLN1 | ACTTGTAATGGCAGCGTAGA | 265 | CTCGAAGAAGTTTCCAGGTT | 266 | TGACAGCAGAGCCAGTGAACCACA | 267 |
| MMP9 | ACTTTGACAGCGACAAGAAGT | 268 | GCGGTACATAGGGTACATGA | 269 | CGCCGCCACGAGGAACAAAC | 270 |
| MMP9 | AACTTTGACAGCGACAAGAA | 271 | GAAGCGGTACATAGGGTACAT | 272 | CGCCGCCACGAGGAACAAAC | 273 |
| MMP9 | CAGTACCACGGCCAACTAC | 274 | TGGAAGATGAATGGAAACTG | 275 | CCCATCAGCATTGCCGTCCC | 276 |
| MMP9 | CCACTACTGTGCCTTTGAGT | 277 | GTACTTCCCATCCTTGAACA | 278 | TTCCCAATCTCCGCGATGGC | 279 |
| MMP9 | CCACTAGTGTGCCTTTGAGT | 280 | CTTCCCATCCTTGAACAAA | 281 | TTCCCAATCTCCGCGATGGC | 282 |
| NIPBL | CACGAATAGCAGAAGAGGTG | 283 | GTATGTCACCTTCTGGGTCA | 284 | CAGCTTGTCCATAGCCTCAACGAGG | 285 |
| NIPBL | CCCATCCTTCAAGTTACACA | 286 | ATTAGCTGAATTGCCAGACA | 287 | TCCACAGATGCAACAAGCATCGG | 288 |

TABLE 4-continued

| Gene Symbol | SensePrimer | SEQ ID NO | AntisensePrimer | SEQ ID NO | TaqManProbe | SEQ ID NO |
|---|---|---|---|---|---|---|
| NIPBL | GGGATTGCTAGTCTCACAGA | 289 | TCTTCTGCTATTCGTGCATT | 290 | TCCTGAACCAGCTGCCTCTTCCA | 291 |
| NIPBL | CCCATCCTTCAAGTTACACA | 292 | AGACAACGGACCAGAAACTT | 293 | TCCACAGATGCAACAAGCATCGG | 294 |
| NIPBL | GCACAGGCTAAGTAGTGACG | 295 | AGGTGGTCTTGAGCCTTTAG | 296 | TTTCCCTTGAGATCTCCACAGCCA | 297 |
| NIPBL | CACGAATAGCAGAAGAGGTG | 298 | GTATGTCACCTTCTGGGTCA | 299 | CAGCTTGTCCATAGCCTCAACCAGG | 300 |
| NIPBL | CCCATCCTTCAAGTTACACA | 301 | ATTAGCTGAATTGCCAGACA | 302 | TCCACAGATGCAACAAGCATCGG | 303 |
| NIPBL | GGGATTGCTAGTCTCACAGA | 304 | TCTTCTGCTATTCGTGCATT | 305 | TCCTGAACCAGCTGCCTCTTCCA | 306 |
| NIPBL | CCCATCCTTCAAGTTACACA | 307 | AGACAACGGACCAGAAACTT | 308 | TCCACAGATGCAACAAGCATCGG | 309 |
| NIPBL | GCACAGGCTAAGTAGTGACG | 310 | AGGTGGTCTTGAGCCTTTAG | 311 | TTTCCCTTGAGATCTCCACAGCCA | 312 |
| RPS24 | CACCGTAACTATCCGCACTA | 313 | CGGTGTGGTCTTGTACATTT | 314 | AGGCACTGTCGCCTTCCCGG | 315 |
| RPS24 | AAGAAAGCAACGAAAGGAAC | 316 | TCATTGCAGCACCTTTACTC | 317 | TGCCAGCACCAACATTGGCC | 318 |
| RPS24 | AGACATGGCCTGTATGAGAA | 319 | ATCCAATCTCCAGCTCACTT | 320 | TGCCAGCACCAACATTGGCC | 321 |
| RPS24 | AAGACATGGCCTGTATGAGA | 322 | ATCCAATCTCCAGCTCACTT | 323 | TGCCAGCACCAACATTGGCC | 324 |
| RPS24 | GACATGGCCTGTATGAGAAG | 325 | ATCCAATCTCCAGCTCACTT | 326 | TGCCAGCACCAACATTGGCC | 327 |
| RPS24 | AAGGAACGCAAGAACAGAAT | 328 | ATTGCAGCACCTTTACTCCT | 329 | TGCCAGCACCAACATTGGCC | 330 |
| SMARCA1 | TACCTGGTCATTGATGAAGC | 331 | CAAAGGTGTTCCAGTTAGGA | 332 | CGTGAGTTCAAGTCGACTAACCGCTTG | 333 |
| SMARCA1 | TACCTGGTCATTGATGAAGC | 334 | TTATTCTGCAAAGGTGTTCC | 335 | TTCAAGTCGACTAACCGCTTGCTCC | 336 |
| SMARCA1 | TGGACCCAGAATATGAAGAG | 337 | ATGTTCAGTGGAGATGTTGG | 338 | TCTCTTTGCTCGGTCGGCTTTCA | 339 |
| SMARCA1 | CTTTGCTTGGTTACCTGAAA | 340 | AAACAAATGACACGGAGAGA | 341 | CCGAAATATTCCTGGACCTCACATGG | 342 |
| SMARCA1 | GGAAATGGACCCAGAATATG | 343 | GTTGGAGATTTCTGTGCTGA | 344 | TCTCTTTGCTCGGTCGGCTTTCA | 345 |
| SMARCA1 | AAGGAAATGGACCCAGAATA | 346 | CTGAAGGCTGAATGAAATGT | 347 | TCTCTTTGCTCGGTCGGCTTTCA | 348 |
| SMARCA1 | AGTGGGATGTTTGCGTTACT | 349 | CACGAACAATCTCTGAAAGC | 350 | TCATCAATGACCAGGTATCGCCAGTG | 351 |

TABLE 5

| Gene Symbol | Description | Commercially Available Antibody Reference | Scientific Reference |
|---|---|---|---|
| APEH | N-acylaminoacyl-peptide hydrolase | | |
| C1orf22 | chromosome 1 open reading frame 22 | | |
| ESR1 | estrogen receptor 1 | Ab2746 (Abcam) | Shevde NK & Pike JW Estrogen modulates the recruitment of myelopoietic cell progenitors in rat through a stromal cell-independent mechanism involving apoptosis. *Blood* 87: 2683-92 (1996). Yang NN et al. Identification of an estrogen response element activated by metabolites of 17beta-estradiol and raloxifene. *Science* 273: 1222-5 (1996). |
| ETS1 | v-ets erythroblastosis virus E26 oncogene homolog 1 (avian) | Ab10936 (Abcam) | Pande P et al. Ets-1: a plausible marker of invasive potential and lymph node metastasis in human oral squamous cell carcinomas. *J Pathol* 189: 40-5 (1999). Nakayama T et al. Expression of the Ets-1 proto-oncogene in human gastric carcinoma: correlation with tumor invasion. *Am J Pathol* 149: 1931-9 (1996). |

TABLE 5-continued

| Gene Symbol | Description | Commercially Available Antibody Reference | Scientific Reference |
|---|---|---|---|
| | | | Bories JC et al. Increased T-cell apoptosis and terminal B-cell differentiation induced by inactivation of the Ets-1 proto-oncogene. *Nature* 377: 635-8 (1995).<br>Wernert N et al. Stromal expression of c-Ets1 transcription factor correlates with tumor invasion. *Cancer Res* 54: 5683-8 (1994). |
| FLJ14624 | | | |
| FLJ20701 | putative NFkB activating protein 373 | | |
| FLJ23091 | inducible T-cell co-stimulator | | |
| G2 | G2 protein | | |
| ICOS | inducible T-cell co-stimulator | Ab3744 (Abcam) | |
| ITCH | itchy homolog E3 ubiquitin protein ligase (mouse) | | |
| MBTPS1 | membrane-bound transcription factor protease, site 1 | | |
| MGC40157 | hypothetical protein MGC40157 | | |
| MGC45871 | hypothetical protein MGC45871 | | |
| MKLN1 | muskelin 1, intracellular mediator containing kelch motifs | | |
| MMP9 | matrix metalloproteinase 9 (gelatinase B, 92 kDa gelatinase, 92 kDa type IV collagenase) | Ab5707 | |
| NIPBL | Nipped-B homolog (Drosophila) | | |
| RPS24 | ribosomal protein S24 | | |
| SMARCA1 | SWI/SNF related, matrix associated, actin dependent regulator of chromatin, subfamily a, member 1 | Ab21924 (Abcam) | Lazzaro MA & Picketts DJ Cloning and characterization of the murine Imitation Switch (ISWI) genes: differential expression patterns suggest distinct developmental roles for Snf2h and Snf2l. *J Neurochem* 77: 1145-56 (2001). |

TABLE 6

| | | 5' Primer | | | 3' Primer | | | |
|---|---|---|---|---|---|---|---|---|
| Symbol | Ref. ID | Primer Sequence | Position | SEQ ID NO: | Primer Sequence | Position | SEQ ID NO: | Product Length |
| APEH | NM_001640 | AAGGATGTCCAGTTTGCAGTGG | 2081 | 878 | TGGCAGGAAATGAAGCCACCAT | 2184 | 886 | 104 |
| FLJ23091 | NM_024911 | ACAGGCATCTATGGGATGTGGA | 1694 | 879 | AGATCGCCATTGGACTGGTCTT | 1794 | 887 | 101 |
| MBTPS1 | NM_003791 | TCGGTACTCCAAGGTTCTGGA | 3220 | 880 | TGTTTCCAAAGGTTACTGGGCG | 3348 | 888 | 129 |
| MGC40157 | NM_152350 | ACCCGAGAGAACTGGATTGCGT | 359 | 881 | GCTCCAATACTCAGCTGCCAAA | 469 | 889 | 111 |
| MGC45871 | NM_182705 | CCACCAAAGGAAGTAAGGTACAC | 362 | 882 | TAGTTGCGCCACGTGCCATT | 507 | 890 | 146 |
| MKLN1 | NM_013255 | GAGGGCCGAAATTGGTGTTTGA | 1169 | 883 | ATTGTGGTTCACTGGCTCTGCT | 1297 | 891 | 129 |
| NIPBL | NM_015384 | AGTGTACGCCACTTTGCCCTAA | 6886 | 884 | ATCAGCCTTGTTCCGCATAGCA | 7017 | 892 | 132 |
| PPP1R2 | NM_006241 | AAGATGCCTGTAGTGACACCGA | 250 | 885 | ATCCGATACTTTGGCTCCAAGC | 349 | 893 | 100 |

TABLE 7

| | AJ36h | | Blind test | |
|---|---|---|---|---|
| | No Polyp | Polyp | No Polyp | Polyp |
| Sample Size | 110 | 68 | 40 | 40 |
| Gender (F/M) | 55/54* | 22/45* | 21/19 | 13/27 |
| Age mean (range) | 57 (23~83) | 57 (38~82) | 57 (40~79) | 60 (38~76) |
| Polyp Subtype | | | | |
| Tubular adenoma | | 21 (31%) | | 14 (35%) |
| Hyperplastic | | 18 (27%) | | 15 (38%) |
| High risk pathology | | 7 (10%) | | 3 (7.5%) |
| Others | | 22 (32%) | | 8 (20%) |

*one sample missing information

TABLE 8

| Equ # | # ratios | ROC area | Constant | MGC45871-APEH | MKLN1-APEH | MGC45871-FLJ23091 | MKLN1-FLJ23091 | NIPBL-FLJ23091 |
|---|---|---|---|---|---|---|---|---|
| 26692 | 5 | 0.718 | −2.483 | 0 | 0.173 | 0 | −0.291 | 0 |
| 26690 | 5 | 0.718 | −2.483 | 0.173 | 0 | 0 | −0.291 | 0 |
| 26658 | 5 | 0.718 | −2.483 | 0.173 | 0 | −0.291 | 0 | 0 |
| 26660 | 5 | 0.718 | −2.483 | 0 | 0.173 | −0.291 | 0 | 0 |
| 25732 | 5 | 0.718 | −3.284 | 0 | 0.441 | 0 | 0 | −0.230 |
| 25218 | 5 | 0.718 | −3.285 | 0.441 | 0 | 0 | 0 | −0.230 |
| 25730 | 5 | 0.718 | −3.284 | 0.441 | 0 | 0 | 0 | −0.230 |
| 25220 | 5 | 0.718 | −3.285 | 0 | 0.441 | 0 | 0 | −0.230 |
| 17030 | 5 | 0.718 | −3.285 | −0.279 | 0.720 | 0 | 0 | −0.230 |
| 18052 | 5 | 0.718 | −3.284 | 0 | 0.441 | 0 | 0 | −0.230 |

| Equ # | MGC45871-MGC40157 | MKLN1-MGC40157 | NIPBL-MGC40157 | MGC45871-PPP1R2 | MKLN1-PPP1R2 | Thresh |
|---|---|---|---|---|---|---|
| 26692 | 0 | 0 | −0.173 | −0.863 | −0.929 | −0.481 |
| 26690 | 0 | 0 | −0.173 | −1.036 | −0.756 | −0.481 |
| 26658 | 0 | 0 | −0.173 | −0.745 | −1.047 | −0.481 |
| 26660 | 0 | 0 | −0.173 | −0.572 | −1.220 | −0.481 |
| 25732 | 0 | −0.514 | 0 | −0.793 | −0.916 | −0.014 |
| 25218 | −0.514 | 0 | 0 | −0.720 | −0.989 | −0.014 |
| 25730 | 0 | −0.514 | 0 | −1.234 | −0.475 | −0.014 |
| 25220 | −0.514 | 0 | 0 | −0.279 | −1.430 | −0.014 |
| 17030 | −0.514 | 0 | 0 | 0 | −1.709 | −0.014 |
| 18052 | −0.793 | 0.279 | 0 | 0 | −1.709 | −0.014 |

TABLE 9

| Parameter | Blind |
|---|---|
| Number of Samples | 80 |
| Number of Equations | 10 |
| Sensitivity (TPF) | 43% (17/40) |
| Specificity (TNF) | 80% (32/40) |
| Overall accuracy | 61% (49/80) |

TABLE 10

| Reporter Gene | Protein Activity & Measurement |
|---|---|
| CAT (chloramphenicol acetyltransferase) | Transfers radioactive acetyl groups to chloramphenicol and detection by thin layer chromatography and autoradiography |
| GAL (beta-galactosidase) | Hydrolyzes colorless galactosides to yield colored products. |
| GUS (beta-glucuronidase) | Hydrolyzes colorless glucuronides to yield colored products. |
| LUC (luciferase) | Oxidizes luciferin, emitting photons |
| GFP (green fluorescent protein) | Fluorescent protein without substrate |

TABLE 10-continued

| Reporter Gene | Protein Activity & Measurement |
|---|---|
| SEAP (secreted alkaline phosphatase) | Luminescence reaction with suitable substrates or with substrates that generate chromophores |
| HRP (horseradish peroxidase) | In the presence of hydrogen oxide, oxidation of 3,3',5,5'-tetramethylbenzidine to form a colored complex |
| AP (alkaline phosphatase) | Luminescence reaction with suitable substrates or with substrates that generate chromophores |

Table 11 is found on CD-R filed herewith, identified as file Table11.txt.

TABLE 12

| AffySpotID | Gene | GENE ID | p value | CCa/Ctrl | direction | DEFAULTGENEDESCRIPTION |
|---|---|---|---|---|---|---|
| 219073_s_at | OSBPL10 | 114884 | 3.8499E-08 | 0.451209844 | downregulated | oxysterol binding protein-like 10 |
| 1563498_s_at | LOC283130 | 283130 | 8.1224E-06 | 0.628849872 | downregulated | hypothetical protein LOC283130 |
| 219667_s_at | BANK1 | 55024 | 1.0668E-10 | 0.430259207 | downregulated | B-cell scaffold protein with ankyrin repeats 1 |
| 205547_s_at | TAGLN | 6876 | 0.40991641 | 0.889953014 | downregulated | transgelin |
| 203642_s_at | COBLL1 | 22837 | 5.3941E-07 | 0.474077388 | downregulated | COBL-like 1 |
| 228551_at | MGC24039 | 160518 | 0.05283113 | 0.695785002 | downregulated | hypothetical protein MGC24039 |
| 235866_at | C9orf85 | 138241 | 4.2656E-06 | 0.649259289 | downregulated | chromosome 9 open reading frame 85 |
| 207655_s_at | BLNK | 29760 | 4.7146E-09 | 0.508654531 | downregulated | B-cell linker |
| 230983_at | BCNP1 | 199786 | 1.8615E-11 | 0.422871727 | downregulated | B-cell novel protein 1 |
| 208591_s_at | PDE3B | 5140 | 0.05166031 | 0.826542405 | downregulated | phosphodiesterase 3B, cGMP-inhibited |
| 201340_s_at | ENC1 | 8507 | 0.62995039 | 0.93326798 | downregulated | ectodermal-neural cortex (with BTB-like domain) |
| 208325_s_at | AKAP13 | 11214 | 0.00033172 | 0.80202517 | downregulated | A kinase (PRKA) anchor protein 13 |
| 233559_s_at | WDFY1 | 57590 | 0.00920709 | 0.845905759 | downregulated | WD repeat and FYVE domain containing 1 |
| 205627_at | CDA | 978 | 9.2103E-05 | 1.343547864 | upregulated | cytidine deaminase |
| 1555736_a_at | AGTRAP | 57085 | 0.09637521 | 0.906895763 | downregulated | angiotensin II receptor-associated protein |
| 1554390_s_at | ACTR2 | 10097 | 0.03306275 | 0.892740407 | downregulated | ARP2 actin-related protein 2 homolog (yeast) |
| 201554_x_at | GYG | 2992 | 0.51537492 | 1.055438457 | upregulated | glycogenin 1 |
| 1559051_s_at | C6orf150 | 115004 | 0.97824175 | 1.002133453 | upregulated | chromosome 6 open reading frame 150 |
| 207795_s_at | KLRD1 | 3824 | 0.19904885 | 0.861882517 | downregulated | killer cell lectin-like receptor subfamily D, member 1 |
| 220784_s_at | UTS2 | 10911 | 0.04243446 | 0.627549503 | downregulated | urotensin 2 |
| 217418_x_at | MS4A1 | 931 | 1.3139E-09 | 0.423617526 | downregulated | membrane-spanning 4-domains, subfamily A, member 1 |
| 1563674_at | SPAP1 | 79368 | 9.3602E-09 | 0.400736546 | downregulated | Fc receptor-like 2 |
| 1570259_at | LIMS1 | 3987 | 0.92270088 | 0.990561902 | downregulated | LIM and senescent cell antigen-like domains 1 |
| 228988_at | ZNF6 | 7552 | 0.26569378 | 0.691253833 | downregulated | zinc finger protein 6 (CMPX1) |
| 215314_at | ANK3 | 288 | 0.03458547 | 0.655571614 | downregulated | ankyrin 3, node of Ranvier (ankyrin G) |
| 232911_at | KIAA1559 | 57677 | 2.7111E-07 | 0.640258188 | downregulated | mouse zinc finger protein 14-like |
| 200661_at | PPGB | 5476 | 0.6034369 | 1.039669304 | upregulated | protective protein for beta-galactosidase (galactosialidosis) |
| 238581_at | GBP5 | 115362 | 0.03263835 | 1.323760479 | upregulated | guanylate binding protein 5 |
| 212859_x_at | MT1E | 4493 | 0.46242859 | 0.892029229 | downregulated | metallothionein 1E (functional) |
| 229893_at | MGC20553 (FRMD3) | 257019 | 0.02322844 | 1.294641476 | upregulated | FERM domain containing 3 |
| 204415_at | G1P3 | 2537 | 0.98563356 | 1.003662309 | upregulated | interferon, alpha-inducible protein (clone IFI-6-16) |
| 211889_x_at | CEACAM1 | 634 | 0.12181619 | 1.155086057 | upregulated | carcinoembryonic antigen-related cell adhesion molecule 1 (biliary glycoprotein) |
| 1558733_at | FLJ35036 | 253461 | 0.9989125 | 1.000149237 | ¾ | zinc finger and BTB domain containing 38 |
| 235885_at | P2RY12 | 64805 | 0.64527963 | 1.061974664 | upregulated | purinergic receptor P2Y, G-protein coupled, 12 |
| 208180_s_at | HIST1H4H | 8365 | 1.275E-05 | 0.673893846 | downregulated | histone 1, H4h |
| 204627_s_at | ITGB3 | 3690 | 0.27856391 | 1.238694854 | upregulated | integrin, beta 3 (platelet glycoprotein IIIa, antigen CD61) |
| 1554676_at | PRG1 | 5552 | 0.14822954 | 1.10791216 | upregulated | proteoglycan 1, secretory granule |
| 208685_x_at | BRD2 | 6046 | 0.01411177 | 0.840822417 | downregulated | bromodomain containing 2 |
| 219922_s_at | LTBP3 | 4054 | 0.00028011 | 0.553407885 | downregulated | latent transforming growth factor beta binding protein 3 |
| 218311_at | MAP4K3 | 8491 | 5.0346E-06 | 0.680583549 | downregulated | mitogen-activated protein kinase kinase kinase kinase 3 |

TABLE 12-continued

| AffySpotID | Gene | GENE ID | p value | CCa/Ctrl | direction | DEFAULTGENEDESCRIPTION |
|---|---|---|---|---|---|---|
| 212129_at | NIPA2 | 81614 | 0.00333649 | 0.8287373 | downregulated | non imprinted in Prader-Willi/Angelman syndrome 2 |
| 229039_at | SYN2 | 6854 | 0.3194711 | 1.139160086 | upregulated | synapsin II |
| 203645_s_at | CD163 | 9332 | 0.76 | 0.98 | downregulated | CD163 molecule |
| 221557_s_at | LEF1 | 51176 | 0.28 | 0.87 | downregulated | lymphoid enhancer-binding factor 1 |
| 1552772_at | CLEC4D | 362432 | 0.01 | 1.31 | upregulated | C-type lectin domain family 4, member d |
| 220001_at | PADI4 | 23569 | 0.06 | 1.18 | upregulated | peptidyl arginine deiminase, type IV |
| 206026_s_a | TNFAIP6 | 460097 | 0.03 | 1.29 | upregulated | tumor necrosis factor, alpha-induced protein 6 |
| 202431_s_at | MYC | 4609 | 0.06 | 0.84 | downregulated | v-myc myelocytomatosis viral oncogene homolog (avian) |

TABLE 13

| AffySpotID | GeneSymbolCG | RNA Sequence | RNA Acc'n | Protein Acc'n |
|---|---|---|---|---|
| 1554390_s_at | ACTR2 | SEQ ID NO 1 | NM_001005386 | NP_001005386 |
| 1554390_s_at | ACTR2 | SEQ ID NO 2 | NM_005722 | NP_005713 |
| 1555736_a_at | AGTRAP | SEQ ID NO 3 | NM_020350 | NP_065083 |
| 1559051_s_at | C6orf150 | SEQ ID NO 4 | NM_138441 | NP_612450 |
| 1563674_at | SPAP1 | SEQ ID NO 5 | NM_030764 | NP_110391 |
| 200661_at | PPGB | SEQ ID NO 6 | NM_000308 | NP_000299 |
| 201340_s_at | ENC1 | SEQ ID NO 7 | NM_003633 | NP_003624 |
| 201554_x_at | GYG | SEQ ID NO 8 | NM_004130 | NP_004121 |
| 203642_s_at | COBLL1 | SEQ ID NO 9 | NM_014900 | NP_055715 |
| 203645_s_at | CD163 | SEQ ID NO 10 | NM_004244 | NP_004235 |
| 203645_s_at | CD163 | SEQ ID NO 11 | NM_203416 | NP_981961 |
| 204415_at | G1P3 | SEQ ID NO 12 | NM_002038 | NP_002029 |
| 204415_at | G1P3 | SEQ ID NO 13 | NM_022872 | NP_075010 |
| 204415_at | G1P3 | SEQ ID NO 14 | NM_022873 | NP_075011 |
| 204627_s_at | ITGB3 | SEQ ID NO 15 | NM_000212 | NP_000203 |
| 205547_s_at | TAGLN | SEQ ID NO 16 | NM_001001522 | NP_001001522 |
| 205547_s_at | TAGLN | SEQ ID NO 17 | NM_003186 | NP_003177 |
| 205627_at | CDA | SEQ ID NO 18 | NM_001785 | NP_001776 |
| 207655_s_at | BLNK | SEQ ID NO 19 | NM_013314 | NP_037446 |
| 207795_s_at | KLRD1 | SEQ ID NO 20 | NM_002262 | NP_002253 |
| 207795_s_at | KLRD1 | SEQ ID NO 21 | NM_007334 | NP_031360 |
| 208180_s_at | HIST1H4H | SEQ ID NO 22 | NM_003543 | NP_003534 |
| 208325_s_at | AKAP13 | SEQ ID NO 23 | NM_006738 | NP_006729 |
| 208325_s_at | AKAP13 | SEQ ID NO 24 | NM_007200 | NP_009131 |
| 208325_s_at | AKAP13 | SEQ ID NO 25 | NM_144767 | NP_658913 |
| 208591_s_at | PDE3B | SEQ ID NO 26 | NM_000922 | NP_000913 |
| 208685_x_at | BRD2 | SEQ ID NO 27 | NM_005104 | NP_005095 |

TABLE 13-continued

| AffySpotID | GeneSymbolCG | RNA Sequence | RNA Acc'n | Protein Acc'n |
|---|---|---|---|---|
| 211889_x_at | CEACAM1 | SEQ ID NO 28 | NM_001712 | NP_001703 |
| 212129_at | NIPA2 | SEQ ID NO 29 | NM_001008860 | NP_001008860 |
| 212129_at | NIPA2 | SEQ ID NO 30 | NM_001008892 | NP_001008892 |
| 212129_at | NIPA2 | SEQ ID NO 31 | NM_001008894 | NP_001008894 |
| 212129_at | NIPA2 | SEQ ID NO 32 | NM_030922 | NP_112184 |
| 217418_x_at | MS4A1 | SEQ ID NO 33 | NM_021950 | NP_068769 |
| 217418_x_at | MS4A1 | SEQ ID NO 34 | NM_152866 | NP_690605 |
| 218311_at | MAP4K3 | SEQ ID NO 35 | NM_003618 | NP_003609 |
| 219073_s_at | OSBPL10 | SEQ ID NO 36 | NM_017784 | NP_060254 |
| 219667_s_at | BANK1 | SEQ ID NO 37 | NM_017935 | NP_060405 |
| 219922_s_at | LTBP3 | SEQ ID NO 38 | NM_021070 | NP_066548 |
| 220784_s_at | UTS2 | SEQ ID NO 39 | NM_006786 | NP_006777 |
| 220784_s_at | UTS2 | SEQ ID NO 40 | NM_021995 | NP_068835 |
| 228988_at | ZNF6 | SEQ ID NO 41 | NM_021998 | NP_068838 |
| 229039_at | SYN2 | SEQ ID NO 42 | NM_003178 | NP_003169 |
| 230983_at | BCNP1 | SEQ ID NO 43 | NM_173544 | NP_775815 |
| 232911_at | KIAA1559 | SEQ ID NO 44 | NM_020917 | NP_065968 |
| 233559_s_at | WDFY1 | SEQ ID NO 45 | NM_020830 | NP_065881 |
| 235885_at | P2RY12 | SEQ ID NO 46 | NM_022788 | NP_073625 |
| 235885_at | P2RY12 | SEQ ID NO 47 | NM_176876 | NP_795345 |
| 229893_at | MGC20553 (FRMD3) | SEQ ID NO 48 | NM_174938 | NP_777598 |
| 221557_s_at | LEF1 | SEQ ID NO 49 | NM_016269 | NP_057353 |
| 1552772_at | CLEC4D | SEQ ID NO 50 | NM_080387 | NP_525126 |
| 220001_at | PADI4 | SEQ ID NO 51 | NM_012387 | NP_036519 |
| 206026_s_a | TNFAIP6 | SEQ ID NO 52 | NM_007115 | NP_009046 |
| 202431_s_at | MYC | SEQ ID NO 53 | NM_002467 | NP_002458 |

TABLE 14

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| OSBPL10 | 114884 | NM_017784 | GCTGGTGGTGTACTCTGCTA | 352 | CATTTCCATGTGGTATTTGG | 496 | CAAGCTCGAAGCTGAGTCACCCA | 640 |
| OSBPL10 | 114884 | NM_017784 | GTGCCTCAACTTGTTACAGC | 353 | CTGCTCTGTGGAATGTGACT | 497 | CAGCCCAGCCAGAAGCCAGG | 641 |
| OSBPL10 | 114884 | NM_017784 | TCTATGGAGGGAAAGTCCAC | 354 | TGACTTTGGTTTCTCCATTG | 498 | CCGCAGAAGTGAAGCACAACCC | 642 |
| LOC283130 | 283130 | NM_182556 | TGGTCTTGATCTCCTGACTT | 355 | AGGGACTCTCAGAAGTGGAG | 499 | | 642 |
| LOC283130 | 283130 | NM_182556 | TTCTTCAAGGGAATGAGCTT | 356 | GGAAGATGTGCATGTAGCTG | 500 | CTGCTGGTGCTCACGGCCAC | 643 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| LOC283130 | 283130 | NM_182556 | TCAACTCTGTCTCCTCTGCT | 357 | TTACAGTGTCAAACGGGTGT | 501 | CCAGTTCCCGCAAGCCCAGA | 644 |
| BANK1 | 55024 | AK091523 | ACAGGCATCACTACTTCCAA | 358 | ACCATCTTCACCATATGCAA | 502 | TGAGGATCCCACATCCTGAGATCAA | 645 |
| BANK1 | 55024 | AK091523 | TGAAAGCAGGAAGACATACG | 359 | ACCTCTAGTGGGCTGTGTTT | 503 | CATTTGCCTCAGCTCCATCTGCA | 646 |
| BANK1 | 55024 | AK091523 | TATCCAGCTTCACTTTCTGC | 360 | TGTCAAGTACAGAGCCCATT | 504 | CCCATGGTCAACTGCCATCTGAA | 647 |
| TAGLN | 6876 | NM_003186 | AACCCAGACACAAGTCTTCA | 361 | TCCAGCTCCTCGTCATACTT | 505 | CTGCACTTCGCGGCTCATGC | 648 |
| TAGLN | 6876 | NM_003186 | AGCAATGGTAACTGCACCT | 362 | CCAGGGAGGAGACAGTAGAG | 506 | | |
| TAGLN | 6876 | NM_003186 | TGACATGTTCCAGACTGTTG | 363 | GCGCTTTCTTCATAAACCA | 507 | CTGCCAAGCTGCCCAAAGCC | 649 |
| COBLL1 | 22837 | NM_014900 | ATGGCTAGATGTCCCAAGTT | 364 | AATGACACAGCCAGTAGTGC | 508 | | |
| COBLL1 | 22837 | NM_014900 | GCTTGGTGTGTCTGATAAGG | 365 | ACTCTGTCGCATCTGTTCTG | 509 | ACCAACTCCAACTGATGGCCCA | 650 |
| COBLL1 | 22837 | NM_014900 | CAGAACAGATGCGACAGAGT | 366 | AATGGCTGAGTCTTGACCTT | 510 | | |
| MGC24039 | 160518 | AK125323 | TTGACAAAGCTTCCTTCTG | 367 | TTTCTCTTCCCACTGAGACA | 511 | CCAGCCTGAGCCTTACCTGCCA | 651 |
| MGC24039 | 160518 | AK125323 | ACCTTTGAGTGCCAGAACTT | 368 | TCATTTCTGACCATGACACA | 512 | | |
| MGC24039 | 160518 | AK125323 | GGACACAAACGGACAATAAA | 369 | GCTGTGCAGATTTGCTTACT | 513 | CCAGGGAAGATGGTTCTCGCACC | 652 |
| C9orf85 | 138241 | NM_182505 | GCACCAGAATACGTTTAGCTT | 370 | TTTACACGCCACTCAAGAAC | 514 | CAGCGCTGACATACTCCATCATGAAG | 653 |
| C9orf85 | 138241 | NM_182505 | CTGGGAGTAGTTCGTTGGTT | 371 | CGTATTCTGGTGCTTCTGAG | 515 | TCTGGAACGAGCCACGTTGCC | 654 |
| C9orf85 | 138241 | NM_182505 | GGAGATTGAAGTGAGCTGAG | 372 | AAGGTGGTCAGAATTTCACA | 516 | CGTGCCATTACACTCCAGCCTGG | 655 |
| BLNK | 29760 | NM_013314 | CTTGAGACCAGAGGCTTACC | 373 | AAGCTTGTCCATTCTGTTTG | 517 | CACGTCAGCAGTTCCTGGCCC | 656 |
| BLNK | 29760 | NM_013314 | GCTATTGAAGTGGTCATCCA | 374 | CATGATAACTCAACCTCACCA | 518 | CAGGTCAGGCAATAGAACAAGTCCACA | 657 |
| BLNK | 29760 | NM_013314 | CCGTGGAAGATAATGATGAA | 375 | GAATTTGGCTTGGTTGATCT | 519 | TCCCACAGAAAGCAGTTCACCTCCA | 658 |
| BCNP1 | 199786 | NM_173544 | ACTGGATATTGGCAGCTTCT | 376 | TCTCCAGGGAGTGTGAAAG | 520 | CCCACTCCGGAAGCAGCTGC | 659 |
| BCNP1 | 199786 | NM_173544 | GCAGCTCCAAATCTTAACTTG | 377 | AGAAGCTGCCAATATCCAGT | 521 | CCGACTTCCTCTGCTTGCCAGC | 660 |
| BCNP1 | 199786 | NM_173544 | TTTCCTCCCATTCTGTCTG | 378 | AGCAAATGTATTTCGGAAGG | 522 | TGCCCTTTCCTCCTATTTCCCTCCA | 661 |
| PDE3B | 5140 | NM_000922 | AATGGCTATCGAGACATTCC | 379 | TTCATTTCCTGTTCCACAAC | 523 | CAACACGGCCAGTTCCTGGC | 662 |
| PDE3B | 5140 | NM_000922 | CTTCCACCACAAGTCATTTC | 380 | CTCAGCTGGGTCCTCTATTT | 524 | TGCTTTCTCAGGTTCCTGTAGGCCA | 663 |
| PDE3B | 5140 | NM_000922 | AGGTGGGATCGTAATAATGG | 381 | TGCTTCGGGATAGTCAGTAG | 525 | AAAGGCCTCACCAAGAATTTGGCA | 664 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| ENC1 | 8507 | NM_003633 | TGCCGTCGTAGGTATTAGTG | 382 | GTGAGAAACATGGACGAAAG | 526 | TCGAGTTGCAAACTTTGGTCTTCCC | 665 |
| ENC1 | 8507 | NM_003633 | TGTGCCGTCGTAGGTATTAG | 383 | GTGAGAAACATGGACGAAAG | 527 | TCGAGTTGCAAACTTTGGTCTTCCC | 666 |
| ENC1 | 8507 | NM_003633 | CAAACCATCAGGAAGAATGA | 384 | TCCAGTTAATTGCAGACTCG | 528 | CAAGCCTTTCATCCTCTGTCTCCAGC | 667 |
| AKAP13 | 11214 | NM_006738 | CTCCTGGTCATGATTGTTGT | 385 | ATCCTGGACGAAATGAAAGT | 529 | CCACAAACACGGGAAGGCCC | 668 |
| AKAP13 | 11214 | NM_006738 | AGGTTCTGGTTGGACAAGTT | 386 | GGGAAGAGAGATGACAAAGG | 530 | | |
| AKAP13 | 11214 | NM_006738 | GTTGCACAGACTGAAAGTCC | 387 | TCCAGAGTCCACAATAGGTG | 531 | CAGGAACGGTCTGTATTCTCCTCCTCA | 669 |
| WDFY1 | 57590 | NM_020830 | GACAAGTGTGTGAGCTGGAT | 388 | TGATCTGCCCAGAATAATCA | 532 | TGCCTCCCGAGCATGTTCCC | 670 |
| WDFY1 | 57590 | NM_020830 | GCTGAAGCTTGAACAGAACA | 389 | TCAGATGCTCCTGAGAAGAG | 533 | TCGCCTGCCTCTGGTGGAC | 671 |
| WDFY1 | 57590 | NM_020830 | CTGTGCTACCTTCAGCTCAC | 390 | ACTTTCCAACCACTGAGGAG | 534 | TTCCGCCGTCCGAGGAACAG | 672 |
| CDA | 978 | NM_001785 | CAAAGGGTGCAACATAGAAA | 391 | TTGCCCTGAAATCCTTGTA | 535 | ACCCGCTGGGCATCTGTGCT | 673 |
| CDA | 978 | NM_001785 | TACAAGGATTTCAGGGCAAT | 392 | AGTTGGTGCCAAACTCTCTC | 536 | TGCTATCGCCAGTGACATGCAAGA | 674 |
| CDA | 978 | NM_001785 | TGCCTTGGGACTTAGAACAC | 393 | CAGGATAGAACCTTGGGAAG | 537 | TCCTTTCCTTCCTGTGGGCCC | 675 |
| AGTRAP | 57085 | NM_020350 | GTTCTAGGGATGCTCCTGAC | 394 | GGAGTGTGCATGGTACTGG | 538 | CCCAGCTCAGGGATTGCCTGA | 676 |
| AGTRAP | 57085 | NM_020350 | CTCCTGCTGCTTCGTCTAC | 395 | CCTCTGCTGAGTCAATCGT | 539 | CCGCGCTCCCGGTACATGTG | 677 |
| AGTRAP | 57085 | NM_020350 | CACCATCTTCCTGGACATC | 396 | CTCCCGGTACATGTGGTAG | 540 | CTACCCGCGGGTCAGCCTCA | 678 |
| ACTR2 | 10097 | NM_005722 | GTGCTTTCTGGAGGGTCTAC | 397 | TCTTCAATGCGGATCTTAAA | 541 | ATCCTGGCCTGCCATCACGG | 679 |
| ACTR2 | 10097 | NM_005722 | AGACTCTGGAGATGGTGTGA | 398 | CTCGCAACAGAAGTAGCTTG | 542 | TCCCTCCCAGCAATATCCAGTCTCC | 680 |
| ACTR2 | 10097 | NM_005722 | AGAGCAGAAACTGGCCTTAG | 399 | GGCTGAAATAAAGCTTCTGG | 543 | CCCAACTTTGATGATACGTCCATCTGG | 681 |
| GYG1 | 2992 | NM_004130 | TGTGTACCTTTCACGAGACC | 400 | TGGGTTAATGCTATTGGTTG | 544 | TCACTCTGGCAGCACTGGGCA | 682 |
| GYG1 | 2992 | NM_004130 | CCAAAGTTGTGCATTTCCT | 401 | GGTAAAGATGTTCCACCACA | 545 | TGAGGCCCATGATCCCAACATG | 683 |
| GYG1 | 2992 | NM_004130 | TGTGGCTTCTGTAGAAAGGA | 402 | TCTGCTCCCATATAATCAGC | 546 | TCCCAGCTATGGCACAGCCG | 684 |
| C6orf150 | 115004 | NM_138441 | TATAACCCTGGCTTTGGAAT | 403 | ATGGCTTTAGTCGTAGTTGCT | 547 | AGCACCCAAGAAGGCCTGCG | 685 |
| C6orf150 | 115004 | NM_138441 | GATATAACCCTGGCTTTGGA | 404 | ATGCTTGGGTACAAGGTAAA | 548 | AGCACCCAAGAAGGCCTGCG | 686 |
| C6orf150 | 115004 | NM_138441 | ACTGCCTTCTTTCACGTATG | 405 | CCTGAGGCACTGAAGAAAG | 549 | CCCAGGTCTTTGCGGTCCCA | 687 |
| KLRD1 | 3824 | AF498040 | ACAATTCAACGCTGTTCTTT | 406 | TTATCCCTAAGGTCCCAGAA | 550 | CGTGCCTTCTCTACTTCGCTCTTGGA | 688 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| KLRD1 | 3824 | NM_007334 | CGGTGCAACTGTTACTTCAT | 407 | AATTGTTGACTGGAGCTCAT | 551 | TGTGCTTCTCAGAAATCCAGCCTGC | 689 |
| KLRD1 | 3824 | NM_007334 | CACATCGTGCCTTCTCTACT | 408 | TCTATGTTGGGTCCTGGAGT | 552 | CGCTCTTGGAACATAATTTCTCATGGC | 690 |
| UTS2 | 10911 | NM_021995 | TTATGCTCTGCGTCACTTCT | 409 | GAGGTGCTGAGAGTTGAAAG | 553 | TCCACGTCTCTTTGCTTTGGCCA | 691 |
| UTS2 | 10911 | NM_021995 | CACTTCTGCTCGGACTCATA | 410 | GTCTTCATGAGGTGCTGAGA | 554 | TCCACGTCTCTTTGCTTTGGCCA | 692 |
| UTS2 | 10911 | NM_021995 | CTTTCAACTCTCAGCACCTC | 411 | TGAGTCTGCTTTCCTGAGAA | 555 | | |
| MS4A1 | 931 | NM_021950 | TCGTTGAGAATGAATGGAAA | 412 | ATGTTTCAGTTAGCCCAACC | 556 | | |
| MS4A1 | 931 | NM_021950 | ACCCATCTGTGTGACTGTGT | 413 | CTTTGACCAAACACTTCCTG | 557 | CCGGATCACTCCTGGCAGCA | 693 |
| MS4A1 | 931 | NM_021950 | GTGTTGTCACGCTTCTTCTT | 414 | AAAGCCTATCCAAGGAACAG | 558 | TCACATTCTGAAGCACTCATTCTGCCT | 694 |
| SPATA1 | 64173 | NM_022354 | AAGTCACAGCATCAATGGAG | 415 | AGTCTGTGATGTTTGCCAGA | 559 | CCCTGGCTTCAAGTTGCATGAGC | 695 |
| SPATA1 | 64173 | NM_022354 | CTGATGGAACAATCCACAGA | 416 | CCAGCTTCTTCCTGATTCTT | 560 | TGGGATCTCTTCCAAGTTCCTCCTTGA | 696 |
| SPATA1 | 64173 | NM_022354 | CGATATCATGCCTACAATGG | 417 | CTTCAAGTTGCATGAGCAGT | 561 | CCTCCTCCATTGATGCTGTGACTTTC | 697 |
| LIMS1 | 3987 | NM_004987 | AGCTGTACCATGAGCAGTGT | 418 | GGCAAAGAGCATCTGAAAG | 562 | TGCGCTCAGTGCTTCCAGCA | 698 |
| LIMS1 | 3987 | NM_004987 | TATCGGGTTTGTCAAGAATG | 419 | TGAATATCAGAGGCTGCTCA | 563 | TGGGAGACACCTGTGTCGCCC | 699 |
| LIMS1 | 3987 | NM_004987 | GTGATGTGGTCTCTGCTCTT | 420 | TACAGACTGGCTTCATGTCA | 564 | AGCAGTTCACGCACCAGGCC | 700 |
| ZNF6 | 7552 | NM_021998 | GATGGGTTTGGTTCTGAAGT | 421 | CTCCAGCTACTGAATGTCCA | 565 | TTCAACATCATCTTCAGCCTCCGC | 701 |
| ZNF6 | 7552 | NM_021998 | TCAGCTTGAGGACTCTGATG | 422 | TTTGAAGGTACTGTGCTGCT | 566 | TGCCGCAGCCCAGACAACAG | 702 |
| ZNF6 | 7552 | NM_021998 | AAGACCCATACTGGAAGGAA | 423 | CCTTCTTGCAGAATTCACAC | 567 | TCACATGTCGTTTAAAGCCAGATGCA | 703 |
| ANK3 | 288 | NM_001149 | TTGATCATCCAAGCCTAGTG | 424 | GAATCATCACCCAATTCCTT | 568 | CGGTCATTGCATCTTCACTCTGCG | 704 |
| ANK3 | 288 | NM_001149 | AATTCACCGAGAAGTGTGTG | 425 | TGAAAGTGATTTCCATGCTC | 569 | CGCTGCTTCCACACATTAATGGCA | 705 |
| ANK3 | 288 | NM_001149 | ATGGACCTCCAGTCGTAACT | 426 | CTGGCTCTCATCTACATCCA | 570 | TGCCTTTAACAGAAATGCCTGAAGCA | 706 |
| KIAA1559 | 57677 | NM_020917.1 | AAAATTAGCCAGGCATGGTG | 427 | GCGATCTCAACTCACCACAA | 571 | TCCGCCTCCTGGATTCAAGTGA | 707 |
| KIAA1559 | 57677 | NM_020917.1 | ACCAAATTTCAGGGTCACCA | 428 | CTCAAACTCCTGGCCTCAAG | 572 | CCCTGTGCCAGGCCAAATTCA | 708 |
| KIAA1559 | 57677 | NM_020917.1 | ACCAAATTTCAGGGTCACCA | 429 | CTCAAGTGATCCACCCACCT | 573 | CCCTGTGCCAGGCCAAATTCA | 709 |
| PPGB | 5476 | NM_000308 | GAGAGCTATGCTGGCATCTA | 430 | GACCAGGGAGTTGTCATTCT | 573 | TCCTGCATGACCAGCACGGC | 710 |
| PPGB | 5476 | NM_000308 | ACAGGCTTTGGTCTTCTCTC | 431 | TTGTAGATGTTGAGGCCAGA | 575 | CACGATGCGGGCCACTTCCT | 711 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| PPGB | 5476 | NM_000308 | AACAAGCAGCCATACT GATG | 432 | GGCACTTTGCTTAGAA GAGG | 576 | CAGCTCCACGGCCTGA TGCA | 712 |
| GBP5 | 115362 | NM_052942 | CCTACCTGATGAACAA GCTG | 433 | GATGAGGCACACACCA TATC | 577 | CGGTGCAGTCTCACACC AAGGG | 713 |
| GBP5 | 115362 | NM_052942 | ACCAAGGGAATTTGGA TATG | 434 | AGTAAGAGTGCCAGTG CAAA | 578 | CTCCCAGGCCCTCGGT GTCA | 714 |
| GBP5 | 115362 | NM_052942 | GAAGAAAGAGGCACAA GTGA | 435 | TGTTTGGCTATCTCCA TTTG | 579 | TCTGCCTTTGAATCGC CGCC | 715 |
| MT1E | 4493 | NM_175617 | AAGTCTACTGCCACCT CTCAC | 436 | AAGAGCTGTTCCCACA TCA | 580 | CCCTGGGCACACTTGG CACA | 716 |
| MT1E | 4493 | NM_175617 | CCTATGGTTTCAGAAC AGAGC | 437 | AGTGAGAGGTGGCAGT AGAC | 581 | CGGGCACCTCCCTGCC CTAA | 717 |
| MT1E | 4493 | NM_175617 | ACTGCCACCTCTCACT CTC | 438 | AGAGCTGTTCCCACAT CAG | 582 | CCCTGGGCACACTTGG CACA | 718 |
| FRMD3 | 257019 | NM_174938 | GAACCCACTGGTCAAG AGTT | 439 | ACTGCTCAAACTCTGG TGTC | 583 | CCAGGCCCACCACAAG GAGC | 719 |
| FRMD3 | 257019 | NM_174938 | TTGTGGTCTTTCAGGG AAAT | 440 | AGTATTGAATGCCAAC ATGG | 584 | TCTCCTTCTGGGTGCCA ATCACA | 720 |
| FRMD3 | 257019 | NM_174938 | AACATTTCTGCTCCCT TGAT | 441 | GGCACTTGGGTTGTAC ACTA | 585 | CTCCCGGGCTGCCTTCA CTG | 721 |
| G1P3 | 2537 | NM_022873 | GGTAATATTGGTGCCC TGA | 442 | TTAGGCCAAGAAGGAA GAAG | 586 | TGGGCTACGCCACCCAC AAG | 722 |
| G1P3 | 2537 | NM_022873 | TATTGTCCAGGCTAGA GTGC | 443 | CTACTTGGGAGGTTGA GACA | 587 | TGCAGCCTCCAACTCCT AGCCTCA | 723 |
| G1P3 | 2537 | NM_022873 | TCTTCTCTCCTCCAAG GTCT | 444 | TCTTACCTGCATCCTT ACCC | 588 | TACCGCCTTCTGCCGCA TGG | 724 |
| CEACAM1 | 634 | NM_001712 | CAACCTACCTGTGGTG GATA | 445 | TTCACACTCATAGGGT CCTG | 589 | TCCCAGGCTGCAGCTGT CCA | 725 |
| CEACAM1 | 634 | NM_001712 | CACTTCACAGAGTGCG TGTA | 446 | GAATGGCATGGATTCA GTAG | 590 | CTTCTGGAACCCGCCCA CCA | 726 |
| CEACAM1 | 634 | NM_001712 | AGGTTCTTCTCCTTGT CCAC | 447 | GGGTAGCTTGTTGAGT TCCT | 591 | CGGTTGCCATCCACTCT TTCCC | 727 |
| ZBTB38 | 253461 | XM_172341.5 | AGGGACCTCAAGGACG ACTT | 448 | TTGAAGCTGCCAGAAC ATTG | 592 | CCCGAATGCGCTGCTCA TTTAA | 728 |
| ZBTB38 | 253461 | XM_172341.5 | ACCAACGCTGAATTTC CAAG | 449 | TCCATTTTCAATGCCT CCTC | 593 | CAACAGTCCAGCCATCC CATTGG | 729 |
| ZBTB38 | 253461 | XM_172341.5 | ATGGAGGAGGTTCACA CCAG | 450 | GGATTATGGGCTCAT GCTA | 594 | TCATGCTGCACCCTGAC CGG | 730 |
| P2RY12 | 64805 | NM_176876 | TGGTAACACCAGTCTG TGC | 451 | GCCATTTGTGATAAGT CCAA | 595 | CACCCAGGTCCTCTTCCC ACTGC | 731 |
| P2RY12 | 64805 | NM_022788 | GCTGCAGAACAGAACA CTTT | 452 | TGCCAAACCTCTTTGT GATA | 596 | TGCTCTTGTAATCTGAC CCTGGACATG | 732 |
| P2RY12 | 64805 | NM_022788 | ACATTCAAACCCTCCA GAAT | 453 | GGTGCACAGACTGGTG TTAC | 597 | CGACAACCTCACCTCTG CGCC | 733 |
| HIST1H4H | 8365 | NM_003543 | GTGTTCTGAAGGTGTT CCTG | 454 | GTAAAGAGTGCGTCCC TGTC | 598 | CGCCAAACGCAAGACCG TGA | 734 |
| HIST1H4H | 8365 | NM_003543 | TAACATCCAGGGCATC ACTA | 455 | GAACACCTTCAGAACA CCAC | 599 | TATCCGGCGCCTTGCTC GTC | 735 |
| HIST1H4H | 8365 | NM_003543 | ATAACATCCAGGGCAT CACT | 456 | AGAACACCACGAGTCT CCTC | 600 | TATCCGGCGCCTTGCTC GTC | 736 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| ITGB3 | 3690 | NM_000212 | GACTCAAGATTGGAGACACG | 457 | AGGCACAGTCACAATCAAAG | 601 | TGTCCTTGAAGCCCACGGGC | 737 |
| ITGB3 | 3690 | NM_000212 | TTACCACTGATGCCAAGACT | 458 | TGGAGGCAGAGTAATGATTG | 602 | CCTGCCAGCCTTCCGTCCAA | 738 |
| ITGB3 | 3690 | NM_000212 | AACCCTTCAGATTTGCCTTA | 459 | CAGTGAGGGTGTGGAATTAG | 603 | TGTCACCCTTAGGCCAGCACCA | 739 |
| PRG1 | 5552 | NM_002727 | CTTCCCACTTTCTGAGGACT | 460 | ATCCTGTTCCATTTCCGTTA | 604 | CGGCTCCGGCTCTGGATCAG | 740 |
| PRG1 | 5552 | NM_002727 | GGTTCTGGAATCCTCAGTTC | 461 | TTGGATTCACCTGGAAGTAG | 605 | TCTGGATTGCAGCGCACCCA | 741 |
| PRG1 | 5552 | NM_002727 | TCGAACTACTTCCAGGTGAA | 462 | GTCCTCAGAAAGTGGGAAGA | 606 | TCCAAAGACGAGAATCCAGGACTTGA | 742 |
| BRD2 | 6046 | NM_005104 | GATTCAGAGGAGGAGGAAGA | 463 | TGGGTTTGAATCACGTAAAG | 607 | TCCAGGCTCAGCTGCCGCTT | 743 |
| BRD2 | 6046 | NM_005104 | ATGCCAGATGAACCACTAGA | 464 | ATCTTCCTCCTCCTCTTCCT | 608 | CCCTGGCTTGGCCAAATCGTC | 744 |
| BRD2 | 6046 | NM_005104 | ACGGCTTATGTTCTCCAACT | 465 | CCCTGGTTCTAGTGGTTCAT | 609 | CGTGCCATTGCCACAACATCG | 745 |
| LTBP3 | 4054 | AF318354 | ACCTTCAGGGCTCCTATGT | 466 | CACTGTGTCATCGAAGTTCA | 610 | CCACCCAGGACCAGCACGGT | 746 |
| LTBP3 | 4054 | AF318354 | GGACMCAACATCGTCAACT | 467 | GCTTGCAGTAGCACTCGTAG | 611 | CCAGCCCACCGTGACATCGA | 747 |
| LTBP3 | 4054 | AF318354 | CTCTGGCTACCATCTGTCC | 468 | TGTAGGAGCCATTGGTATTG | 612 | TCCTCGCAGTGGCTCCGGTC | 748 |
| MAP4K3 | 8491 | NM_003618 | TGAAATTTGATCCACCCTTA | 469 | TGGTGTCCTTGTCCATATTC | 613 | CCACATCATGAACTTCCCGACAGTG | 749 |
| MAP4K3 | 8491 | NM_003618 | TAAAGTGCATATGGGTGCAT | 470 | TCGGCACCAAATATCAAGTA | 614 | CACTGTGCATCATCATGGATAAACCCA | 750 |
| MAP4K3 | 8491 | NM_003618 | CTGGAATATGGACAAGGACA | 471 | CTTCTAAATGTGCGACGTGT | 615 | CCTCGCTGATGCAATTCTTCTTCAACA | 751 |
| NIPA2 | 81614 | NM_030922 | TATCAAGGAGCTGTTTGCAG | 472 | TGGAGTCACAATGGAAGTGT | 616 | AAGCCTGTGCTGCGGCATCC | 752 |
| NIPA2 | 81614 | NM_030922 | AACACTTCCATTGTGACTCC | 473 | GCCACTCAAAGTACCAATGA | 617 | CATCGTCAACAGGCATATCTTGCCA | 753 |
| NIPA2 | 81614 | NM_030922 | CTCACAAGCTAGGTGATCCA | 474 | CCGATTACAGAGCAGATTGT | 618 | CCATGGCGAGGACCCACCAC | 754 |
| SYN2 | 6854 | NM_003178 | GAACTGGAAGACGAACACTG | 475 | TACAGCTTTGACAGCACAGA | 619 | CCAGGCCGCCAAACATCTCA | 755 |
| SYN2 | 6854 | NM_003178 | CATAATGGGAGACCAAATCA | 476 | GGAAAGAGAAAGCTCCTCAA | 620 | CCACAGCCCTCCAGGGTCCA | 756 |
| SYN2 | 6854 | NM_003178 | TCTGTGCTGTCAAAGCTGTA | 477 | CTAGTTCGGTGATGAGTTGC | 621 | TGGCATGCTACAGTCCATGACCTCA | 757 |
| LEF1 | 51176 | NM_016269 | GATGTCAACTCCAAACAAGGC | 478 | AGTGAGGATGGGTAGGGTTG | 622 | TTATCCCTTGTCTCCGGGTGGT | 758 |
| LEF1 | 51176 | NM_016269 | TGGATTCAGGCAACCCTAC | 479 | TGTGGGGATGTTCCTGTTTG | 623 | ATGTCCAGGTTTTCCCATCA | 759 |
| LEF1 | 51176 | NM_016269 | AGGCTGGTCTGCAAGAGACA | 480 | GAATGAGCTTCGTTTTCCACC | 624 | TGCATCAGGTACAGGTCCAAGA | 760 |
| CLEC4D | 362432 | NM_080387 | TTCACGCTGTAAGAGAGGCAC | 481 | AGTTGGACTGGAAGGCTCTC | 625 | GAACTGAAAGTGCTGAAGGGA | 761 |

TABLE 14-continued

| Gene | GeneID | RNA Acc'n | Sense Primer (5' Primer) | SEQ ID NO: | Antisense Primer (3' Primer) | SEQ ID NO: | TaqMan Probe | SEQ ID NO: |
|---|---|---|---|---|---|---|---|---|
| CLEC4D | 362432 | NM_080387 | GAACTGAAAAGTGCTGAAGGG | 482 | TCCTTTCACTCTCAGCCCAC | 626 | AGCACCTGGAACTGTTGTCCT | 762 |
| CLEC4D | 362432 | NM_080387 | GGGCTGAGAGTGAAAGGAAC | 483 | CCACTGACCTTTGGCATTC | 627 | ATGACCATCAGCACGGAAGC | 763 |
| PADI4 | 23569 | NM_012387 | CTCCACCAGTCAAAGCTCTA | 484 | TCCAGGTCCTCTGATCTTTC | 628 | CTACATCCAAGCCCCACACAAAAC | 764 |
| PADI4 | 23569 | NM_012387 | ATGCAGGATGAAATGGAGAT | 485 | GTTTGATGGGAAACTCCTTC | 629 | CTACATCCAAGCCCCACACAAAA | 764 |
| PADI4 | 23569 | NM_012387 | GAAAGATCAGAGGACCTGGA | 486 | TCAAGCACTTCATCATCCTC | 630 | TACATCCAAGCCCCACACAAAA | 766 |
| TNFAIP6 | 23569 | NM_007115 | CAGGTTGCTTGGCTGATTATG | 487 | TTGATTTGGAAACCTCCAGC | 631 | TGGCTTTGTGGGAAGATACTGTGG | 767 |
| TNFAIP6 | 23569 | NM_007115 | CATTAGACTCAAGTATGGTGCAGC | 488 | TCCACAGTATCTTCCCACAAAG | 632 | CAGGTTGCTTGGCTGATTATGT | 768 |
| TNFAIP6 | 23569 | NM_007115 | TACCACAGAGAAGCACGGTC | 489 | ATCCATCCAGCAGCACAGA | 633 | GCAGAAGCTAAGGCGGTGTGTGAA | 769 |
| MYC | 4609 | NM_002467 | GAGGCTATTCTGCCCATTTG | 490 | TCCTGTTGGTGAAGCTAACG | 634 | TTTCGGGTAGTGGAAAACCA | 770 |
| MYC | 4609 | NM_002467 | TTTCGGGTAGTGGAAAACCAG | 491 | CGTCGCAGTAGAAATACGGCT | 635 | CTATGACCTCGACTACGACTCGGT | 771 |
| MYC | 4609 | NM_002467 | AGTGGAAAACCAGCAGCCTC | 492 | CGTCGCAGTAGAAATACGGCT | 636 | ATGACCTCGACTACGACTCGGT | 772 |
| CD163 | 9332 | NM_203416 | TGAGTCTTCCTTGTGGGATTGT | 493 | CGACCTGTTGTGGCTTTTT | 637 | TTCAGTGCAGAAAACCCCACA | 773 |
| CD163 | 9332 | NM_203416 | TCTTCCTTGTGGGATTGTCC | 494 | AGGATGACTGACGGGATGA | 638 | CAGTGCAGAAAACCCCACAAA | 774 |
| CD163 | 9332 | NM_203416 | CCCACAAAAAGCCACAACA | 495 | CTTGAGGAAACTGCAAGCC | 639 | TCATCCCGTCAGTCATCCTTTATTGC | 775 |

TABLE 15

| Gene Symbol | Protein Description | Commercially Available Antibody Reference | Scientific Reference |
|---|---|---|---|
| OSBPL10 | oxysterol binding protein-like 10 | | |
| LOC283130 | hypothetical protein LOC283130 | | |
| BANK1 | B-cell scaffold protein with ankyrin repeats 1 | | |
| TAGLN | Transgelin (alternative name smooth muscle 22 Protein SM22) | Abcam Ab14106 AntiHuman Rabbit Polyclonal Antibody | Nishida W *et al.* Gene cloning and nucleotide sequence of SM22 alpha from the chicken gizzard smooth muscle. *Biochem Int* 23: 663-8 (1991). |
| COBLL1 | COBL-like 1 | | |
| MGC24039 | hypothetical protein MGC24039 | | |
| C9orf85 | chromosome 9 open reading frame 85 | | |

TABLE 15-continued

| Gene Symbol | Protein Description | Commercially Available Antibody Reference | Scientific Reference |
|---|---|---|---|
| BLNK | B-cell linker | Abcam Ab4474 AntiHuman Rabbit Polyclonal Antibody | Kabak S et al. The direct recruitment of BLNK to immunoglobulin alpha couples the B-cell antigen receptor to distal signaling pathways. *Mol Cell Biol* 22: 2524-35 (2002). |
| BCNP1 | B-cell novel protein 1 | | |
| PDE3B | phosphodiesterase 3B, cGMP-inhibited | SantaCruz Biotechnology AntiHuman Rabbit Polyclonal Antibody | Liu H, and Maurel D. H. 1998 Expression of cyclic GMP-Inhibited phosphodiesterase 3A and 3B (PDE3A and PDE 3B) in rat tissues: differential subcellular localization and regulated expression Br. J. Pharmacol 125 1501:1510. |
| ENC1 | ectodermal-neural cortex (with BTB-like domain) | | |
| AKAP13 | A kinase (PRKA) anchor protein 13 | | Other Family Antibodies Available including: Abcam Ab10346 AKAP12 AntiRat Rabbit Polyclonal Antibody Abcam Ab 25805 AKAP 9 AntiHuman Rabbit Polyclonal Antibody Abcam AB14096 AKAP 3 Goat Polyclonal Antibody |
| WDFY1 | WD repeat and FYVE domain containing 1 (aka FENS-1) | Abcam Ab21695 AntiHuman Goat Polyclonal Antibody | |
| CDA | cytidine deaminase | Abcam Ab5197 Antihuman Rabbit Polyclonal Antibody | Duquette ML *et al*. AID binds to transcription-induced structures in c-MYC that map to regions associated with translocation and hypermutation. *Oncogene* 24: 5791-8 (2005). |
| AGTRAP | angiotensin II receptor-associated protein | | |
| ACTR2 | ARP2 actin-related protein 2 homolog (yeast) | | |
| GYG | glycogenin 1 | | |
| C6orf150 | chromosome 6 open reading frame 150 | | |
| KLRD1 | killer cell lectin-like receptor subfamily D, member 1 | Abcam Ab19740 CD94 Ab (aka KLRD1 Ab) AntiHuman Mouse Monoclonal Antibody | Moretta A *et al*. Human natural killer cell receptors for HLA-class I molecules. Evidence that the Kp43 (CD94) molecule functions as receptor for HLA-B alleles. *J Exp Med* 180: 545-55 (1994). |
| UTS2 | urotensin 2 | Abcam Ab14200 Antihuman Rabbit Polyclonal Antibody | |
| MS4A1 | membrane-spanning 4-domains, subfamily A, member 1 | Abcam Ab9475 AntiHuman Mouse Monoclonal Antibody | Mason DY *et al*. Antibody L26 recognizes an intracellular epitope on the B-cell-associated CD20 antigen. *Am J Pathol* 136: 1215-22 (1990). |
| SPAP1 | Fc receptor-like 2 | | |
| LIMS1 | LIM and senescent cell antigen-like domains 1 | | |
| ZNF6 | zinc finger protein 6 (CMPX1) | | |
| ANK3 | ankyrin 3, node of Ranvier (ankyrin G) | | |
| KIAA1559 | mouse zinc finger protein 14-like | | |

TABLE 15-continued

| Gene Symbol | Protein Description | Commercially Available Antibody Reference | Scientific Reference |
|---|---|---|---|
| PPGB | protective protein for beta-galactosidase (galactosialidosis) | | |
| GBP5 | guanylate binding protein 5 | | |
| MT1E | metallothionein 1E (functional) | | |
| MGC20553 (FRMD3) | FERM domain containing 3 | | |
| G1P3 | interferon, alpha-inducible protein (clone IFI-6-16) | | |
| CEACAM1 | carcinoembryonic antigen-related cell adhesion molecule 1 (biliary glycoprotein) | Abcam Ab26279 Antihuman mouse monoclonal Antibody | |
| FLJ35036 (ZBTB38) | zinc finger and BTB domain containing 38 | | |
| P2RY12 | purinergic receptor P2Y, G-protein coupled, 12 | Alamone Labs #APR-012 AntiHuman Mouse Polyclonal Antibody | Queiroz, G. et al. (2003) J. Pharmacol. Exp. Ther. 307, 809. |
| HIST1H4H | histone 1, H4h | | |
| ITGB3 | integrin, beta 3 (platelet glycoprotein IIIa, antigen CD61) | Abcam Ab7167 AntiHumanMouse Monoclonal Antibody | Pittier R et al. Neurite extension and in vitro myelination within three-dimensional modified fibrin matrices. J Neurobiol 63: 1-14 (2005).; Soldi R et al. Role of alphavbeta3 integrin in the activation of vascular endothelial growth factor receptor-2. EMBO J 18: 882-92 (1999). |
| PRG1 | proteoglycan 1, secretory granule | | |
| BRD2 | bromodomain containing 2 | Abcam Ab19276 Antihuman Rabbit PolyClonal Antibody | |
| LTBP3 | latent transforming growth factor beta binding protein 3 | Abcam Ab21621 Antibovine Rabbit Polyclonal | |
| MAP4K3 | mitogen-activated protein kinase kinase kinase kinase 3 | | |
| NIPA2 | non imprinted in Prader-Willi/Angelman syndrome 2 | | |
| SYN2 | synapsin II | Abcam Ab12240 Antihuman Rabbit Monoclonal | |
| LEF1 | Lymphoid enhancer-binding factor 1 | Abcam Ab22884 Antihuman Rabbit Polyclonal; Ab12037 Antihuman Mouse Monoclonal; | |
| CLEC4D | C-type lectin domain family 4, member d | | |

TABLE 15-continued

| Gene Symbol | Protein Description | Commercially Available Antibody Reference | Scientific Reference |
|---|---|---|---|
| PADI4 | peptidyl arginine deiminase, type IV | Abcam AB26071 Anithuman goat polyclonal | |
| TNFAIP6 | tumor necrosis factor, alpha-induced protein 6 | Abcam Ab36380 Antihuman chicken polyclonal | |
| MYC | v-myc myelocytomatosis viral oncogene homolog (avian) | Abcam Ab1383 Antihuman rabbit polyclonal | |

TABLE 16

| Symbol | 5' Primer (Sense Primer) Primer Sequence | SEQ ID NO: | 3' Primer (Antisense Primer) Primer Sequence | Position | SEQ ID NO: | Product |
|---|---|---|---|---|---|---|
| LOC283130 | AAGGCCAGAATCCCAGCTCAG | 934 | 776 ATCCATCTGCATCCGGGACT-TGAT | 1044 | 818 | 111 |
| MGC24039 | AACAAGGGATCGCCTGCTCC | 3717 | 777 ATAAGGGAGTTGACAGTCAT-GCGG | 3833 | 819 | 117 |
| ACTR2 | ACCGGGTTTGTGAAGTGTGGAT | 109 | 778 CACTTGCCTCATCACCAACCAT | 253 | 820 | 145 |
| AGTRAP | CATGGCCATCCTCAGCTTGC | 325 | 779 AAGACCCAAGGAAACCAGT-GTGGA | 434 | 821 | 110 |
| AKAP13 | TCTCAGCCCGGTGATGGTC | 8562 | 780 TGTAAGAGACTTGTGCACGCGG | 8710 | 822 | 149 |
| ANK3 | ATACGCCATTACATCAAGCAGCAC | | 781 CCAAGGGCAGTATTCCCAT-TCACA | | 823 | |
| BANK1 | TGCTGAAAGGCATGGTCACAAAG | 1303 | 782 GCTGGGTTCTGTGTGGAAG-GAATA | 1449 | 824 | 147 |
| BCNP1 | GGCGCGTGCTGAAGAAATTCAA | 1664 | 783 TTTGCAGCCTGGCTCGAGTTG | 1782 | 825 | 119 |
| BLNK | TTTCAGAACAGGAAGCTGGCGT | 1172 | 784 GTTGTTTGGAATCATGGCCA-GAGC | 1315 | 826 | 144 |
| BRD2 | TGCCTATGCTTGGCCTTTCT | 2799 | 785 ATCTTCCGCTTGACAGTGCTGA | 2909 | 827 | 111 |
| C6orf150 | CAAGAAGGCCTGCGCATTCAAA | 1098 | 786 AGCCGCCATGTTTCTTCTTGGA | 1225 | 828 | 128 |
| C9orf85 | TTATTCCGTTGAATAAAGAAACAGA | 545 | 787 TTTGATGGTCTCCTCCTGTG | 694 | 829 | 150 |
| CDA | ATCGCCAGTGACATGCAAGA | 376 | 788 TACCATCCGGCTTGGTCATGTA | 484 | 830 | 109 |
| CEACAM1 | ATTGGAGTAGTGGCCCTGGTTG | | 789 ATTGGAGTGGTCCTGAGTGTGGT | | 831 | |
| COBLL1 | AGGAAGAGTGAGGGCAGGTTCA | 375 | 790 GCTGTAAGGCAGTCACACGAC-TAT | 523 | 832 | 149 |
| ENC1 | CATGAGCTCACTCCATCACTCGAT | 2196 | 791 AGCATTTACAAGGTGCAGCAGAT | 2325 | 833 | 130 |
| FLJ35036 | CTCCGAGTTGTCTTGAAGTGAGG | | 792 TTGGCAAAGATTGGGCAGCAAG | | 834 | |
| G1P3 | CCTCCAAGGTCTAGTGACGGA | 68 | 793 CCCACTGCAAGTGAAGAGCA | 167 | 835 | 100 |
| GBP5 | CTGACTCTGCGAGCTTCTTCC | | 794 GATCACTACCTTGCTTTGGCCTT | | 836 | |
| GYG | GGGACCAAGGCATACTGAACACA | 538 | 795 TGGCACTTGCACCAAACACTTT | 678 | 837 | 141 |
| HIST1H4H | CACTTACACAGAGCACGCCAAA | | 796 TTAGCCACCGAAGCCGTAAAGA | | 838 | |

TABLE 16-continued

| | 5' Primer (Sense Primer) | | 3' Primer (Antisense Primer) | | | |
|---|---|---|---|---|---|---|
| Symbol | Primer Sequence | SEQ ID NO: | Primer Sequence | Position | SEQ ID NO: | Product |
| ITGB3 | AGCTCATTGTTGATGCTTATGGGA | 1118 | 797 ATACAAGACTTGAGGCCAGGGA | 1232 | 839 | |
| KIAA1559 | TGTGGGAGAACTACAGCAAC | 95 | 798 TGGACTCCAAATCAGGGCAGTA | 238 | 840 | 144 |
| KLRD1 | cccagtatctatttccatcattg | 670 | 799 tctctgccccaagaaacatt | 819 | 841 | 150 |
| LIMS1 | AGGTGATGTGGTCTCTGCTCTT | | 800 CAGACTGGCTTCATGT-CAAACTCC | | 842 | |
| LTBP3 | TCTGCATCAACTTTCCCGGTCA | 2024 | 801 TTGTTCTCGCATTTGCCATCCG | 2162 | 843 | 139 |
| MAP4K3 | TGAACTTCCCGACAGTGATGGT | 1141 | 802 AACCACCTTGGTGTCCTTGT | 1250 | 844 | 110 |
| MGC20553 | AGGTGCACAGAGCCAACATTAC | | 803 AATGGAACACCCTCACCCAGA | | 845 | |
| MS4A1 | AAAGAACGTGCTCCAGACCC | | 804 TTCAGTTAGCCCAACCACT-TCTTC | | 846 | |
| MT1E | CTTGTTCGTCTCACTGGTGT | 1 | 805 ACTCTTCTTGCAGGAGGTGCAT | 142 | 847 | 142 |
| NIPA2 | CTGGACTGCTGTCAATGGGA | 471 | 806 ACTTACTAGCACGCTGAGAGC | 577 | 848 | 107 |
| OSBPL10 | ATGGAGTCCAGGAACCTCTGG | 2467 | 807 TTTGGGCTTCCATGGTGTGC | 2616 | 849 | 150 |
| P2RY12 | GAACACTTTCTCATGTCCAGGGT | | 808 CCTGCAGAGTGGCATCTGG-TATTT | | 850 | |
| PDE3B | TGAGCAGGGAGATGAAGAAGCAA | 3171 | 809 GCAAACCAGCAGCATCATAGGAG | 3316 | 851 | 146 |
| PPGB | GACACTGTTGTGGTCCAGGATTTG | | 810 TGGAAGCAGCTGTTGTGTTGG | | 852 | |
| PRG1 | TACTCAAATGCAGTCGGCTTGTCC | | 811 ACCCATTGGTACCTGGCTCTCT | | 853 | |
| SPAP1 | AGCCAGTGTATGTCAATGTGGG | | 812 GGAGTCCTTGTTCTCCA-GAAGTGT | | 854 | |
| SYN2 | ACAGCTCAACAAGTCGCAGT | 1470 | 813 AAAGAGGCTGGCAAAGGACT | 1605 | 855 | 136 |
| TAGLN | TGAAGGCAAAGACATGGCAG | 429 | 814 TTCCCTCTTATGCTCCTGCG | 561 | 856 | 133 |
| UTS2 | AAGCCGTCTATCTTGTGGCGAT | 10 | 815 CGTCTTCATGAGGTGCT-GAGAGTT | 150 | 857 | 141 |
| WDFY1 | AAGGACATGAAGGTAGTGTCGCCT | 632 | 816 ATGGCCCTGAAGTAACAGCGT | 768 | 858 | 137 |
| ZNF6 | TGCAGGGCTGATCTGGGTCT | | 817 CTTCCACCGCCTGAATCCAT-ACTT | | 859 | |

TABLE 17

| Symbol | RefSeq | Affy ID | 5' Primer Primer Sequence | SEQ ID NO: | Taqman Probe | SEQ ID NO: | 3' Primer Primer Sequence | SEQ ID NO: |
|---|---|---|---|---|---|---|---|---|
| BANK1 | NM_017935 | 219667_s_at | CTGAAAGGCATGGTCACAAA | 860 | TCCTTCCACACAGAACCCAGCA | 866 | TCAGCTCCATCTGCACTCTG | 872 |
| BCNP1 | NM_173544 NM_004244 | 230983_at; 203645_s_at | CGCGTGCTGAAGAAATTCAA | 861 | TTGGCGCAGAGGAGGTTCAT | 867 | ACTCAGGCAGCTCCTTTTTG | 873 |
| CD163 | NM_203416 | 215049_x_at | GCAGCACATGGGAGATTGTCCTGTAA | 862 | AGCAAGTGGCCTCTGTAATCTGCTCA | 868 | ATTGCACGAGGACAGTGTTTGGGA | 874 |
| CDA | NM_001785 | 205627_at | GCCGTCTCAGAAGGGTACAA | 863 | CAGGGCAATTGCTATCGCCA | 869 | CCAGTTGGTGCCAAACTCTC | 875 |
| MGC 20553 | NM_174938 | 229893_at | AGGTGCACAGAGCCAACATTAC | 864 | CTCATCATTAACATGGAACCCCTGC | 870 | AATGGAACACCCTCACCCAGA | 876 |
| MS4A1 | NM_152866 | 217418_x_at | AAAGAACGTGCTCCAGACCC | 865 | CATAGTTCTCCTGTCAGCAGAAGA | 871 | TTCAGTTAGCCCAACCACTTCTTC | 877 |

We claim:

1. A method of determining a probability that a test subject has colorectal cancer, the method comprising (a) determining the gene-specific levels of mRNA transcribed from each gene of a set of genes consisting of BCNP1, CD163, CDA, MS4A1, BANK1, and MGC20553 in blood of the test subject, thereby obtaining a set of test levels; and (b) applying to the set of test levels a classifier for determining a probability that the gene-specific levels of mRNA transcribed from each gene of the set of genes in blood of a subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, thereby determining a probability that the test subject has colorectal cancer.

2. A computer-implemented method of determining a probability that a test subject has colorectal cancer, the method comprising:

using a suitably programmed computer, applying a classifier to data representing the gene-specific levels of mRNA transcribed from each gene of a set of genes consisting of BCNP1, CD163, CDA, MS4A1, BANK1 and MGC20553 in blood of a test subject, the classifier being for determining a probability that the gene-specific levels of mRNA transcribed from each gene of the set of genes in blood of a subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, thereby determining a probability that the test subject has colorectal cancer.

3. The method of claim 1, wherein the classifier has a form:

$$Y=C+\Sigma\beta_i X_i,$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$ is a level of mRNA transcribed from an ith gene of the set of genes in blood of the test subject, wherein $\beta_i$ is a logistic regression equation coefficient, wherein C is a logistic regression equation constant, and wherein $\beta_i$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

4. A non-transitory computer-readable medium comprising instructions for applying a classifier to data representing the gene-specific levels of mRNA transcribed from each gene of a set of genes consisting of BCNP1, CD163, CDA, MS4A1, BANK1, and MGC20553 in blood of a test subject, the classifier being for determining a probability that the gene-specific levels of mRNA transcribed from each gene of the set of genes in blood of a test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer.

5. The computer-readable medium of claim 4, wherein the classifier has a form:

$$Y=C+\Sigma\beta_i X_i,$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$ is a level of mRNA transcribed from an ith gene of the set of genes in blood of the test subject, wherein $\beta_i$ is a logistic regression equation coefficient, wherein C is a logistic regression equation constant, and wherein $\beta_i$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

6. A computer system for determining a probability that a test subject has colorectal cancer, the computer system comprising
   a processor; and
   a memory configured with instructions that cause said processor to (i) apply a classifier to data representing the gene-specific levels of mRNA transcribed from each gene of a set of genes consisting of BCNP1, CD163, CDA, MS4A1, BANK1, and MGC20553 in blood of a test subject, the classifier being for determining a probability that the gene-specific levels of mRNA transcribed from each gene of the set of genes in blood of a test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer.

7. The computer system of claim 6, wherein the classifier has a form:

$$Y=C+\Sigma\beta_i X_i,$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein $X_i$ is a level of mRNA transcribed from an ith gene of the set of genes in blood of the test subject, wherein $\beta_i$ is a logistic regression equation coefficient, wherein C is a logistic regression equation constant, and wherein $\beta_i$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

8. The method of claim 2, wherein the classifier has a form:

$$Y=C+\Sigma\beta_i X_i,$$

wherein Y is a value indicating a probability that the gene-specific levels of mRNA transcribed from each gene of the set of genes in blood of the test subject classify with the gene-specific levels of mRNA transcribed from each gene of the set of genes in blood of subjects having colorectal cancer as opposed to the gene-specific levels of mRNA transcribed from each gene of the set of genes in blood of subjects not having colorectal cancer, wherein Xi is a level of mRNA transcribed from an ith gene of the set of genes in blood of the test subject, wherein $\beta_i$ is a logistic regression equation coefficient, wherein C is a logistic regression equation constant, and wherein $\beta_i$ and C are the result of applying logistic regression analysis to the gene-specific levels of mRNA transcribed from each gene of the set of genes in blood of subjects having colorectal cancer, and to the gene-specific levels of mRNA transcribed from each gene of the set of genes in blood of subjects not having colorectal cancer.

9. The method of claim 1, wherein the levels of mRNA are determined using amplification.

10. The method of claim 2, wherein the levels of mRNA are determined using amplification.

11. The computer-readable medium of claim 4, wherein the levels of mRNA are determined using amplification.

12. The computer system of claim 6, wherein the levels of mRNA are determined using amplification.

13. The method of claim 1, wherein the levels of mRNA are determined relative to levels of mRNA transcribed from a beta-actin gene.

14. The method of claim 2, wherein the levels of mRNA are determined relative to levels of mRNA transcribed from a beta-actin gene.

15. The computer-readable medium of claim 4, wherein the levels of mRNA are determined relative to levels of mRNA transcribed from a beta-actin gene.

16. The computer system of claim 6, wherein the levels of mRNA are determined relative to levels of mRNA transcribed from a beta-actin gene.

* * * * *

SEQUENCE LISTING

<160> NUMBER OF SEQ ID NOS: 893

<210> SEQ ID NO 1
<211> LENGTH: 3878
<212> TYPE: DNA
<213> ORGANISM: Homo sapiens
<300> PUBLICATION INFORMATION:
<308> DATABASE ACCESSION NUMBER: NM_001005386
<309> DATABASE ENTRY DATE: 2006-09-24
<313> RELEVANT RESIDUES: (1)..(3878)

<400> SEQUENCE: 1

```
ggagcccggc ggcggcttcc ggtcggggga aaaaagttgg gccgaaggag gggccgggaa      60
gacgcaagag gaagaagaga aaacggccgg gcggcggtgg ctgtaggttg tgcggctgca     120
gcggctcttc cctgggcgga cgatggacag ccagggcagg aaggtggtgg tgtgcgacaa     180
cggcaccggg tttgtgaagt gtggatatgc aggctctaac tttccagaac acatcttccc     240
agctttggtt ggaagaccta ttatcagatc aaccaccaaa gtgggaaaca ttgaaatcaa     300
gaataacaaa aagatggatc ttatggttgg tgatgaggca agtgaattac gatcaatgtt     360
agaagttaac taccctatgg aaaatggcat agtacgaaat tgggatgaca tgaaacacct     420
gtgggactac acatttggac cagagaaact taatatagat accagaaatt gtaaaatctt     480
actcacagaa cctcctatga acccaaccaa aaacagagag aagattgtag aggtaatgtt     540
tgaaacttac cagttttccg gtgtatatgt agccatccag gcagttctga ctttgtacgc     600
tcaaggttta ttgactggtg tagtggtaga ctctggagat ggtgtgactc acatttgccc     660
agtatatgaa ggcttttctc tccctcatct taccaggaga ctggatattg ctgggaggga     720
tataactaga tatcttatca agctacttct gttgcgagga tacgccttca accactctgc     780
tgattttgaa acggttcgca tgattaaaga aaaactgtgt tacgtgggat ataatattga     840
gcaagagcag aaactggcct tagaaaccac agtattagtt gaatcttata cactcccaga     900
tggacgtatc atcaaagttg ggggagagag atttgaagca ccagaagctt tatttcagcc     960
tcacttgatc aatgttgaag gagttggtgt tgctgaattg cttttttaaca caattcaggc    1020 agctgacatt gataccagat ctgaattcta caaacacatt gtgctttctg gagggtctac    1080
tatgtatcct ggcctgccat cacgttgga acgagaactc aaacagcttt acttagaacg    1140
agttttgaag ggtgatgtgg aaaaacttc taaatttaag atccgcattg aagacccacc    1200
ccgcagaaag cacatggtat tcctgggtgg tgcagttcta gcggatatca tgaaagacaa    1260
agacaacttt tggatgaccc cacaagagta ccaagaaaag ggtgtccgtg tgctagagaa    1320
acttggtgtg actgttcgat aaactccaaa gcttgttccc gtcatacccg taatgctttc    1380 tttttttcctt tattgccaat ctttgaactc attcaactcc aggacatgga agaggcctct    1440
ctctgccctt tgactggaaa ggtcaagttt tattctggtg tcttgggaa gctttgttaa    1500 atttttgtta atgtgggtaa atctgagttt aattcaactg cttccctaca tagactagag    1560
ggctaaggat tctgtctgct gctttgtttc ttctaagtag gcatttagat cattcctgta    1620
ggcttcctat tttcactttta ctgctctaat gctgctagtc gtagtcttta gcacactagg    1680
tggtatgcct ttattagcat aaaacaaaaa aaactttaac aggagctttt acatattact    1740
gggatggggg gtggttcggg atgggtgggc agctgctgaa ccctttaggg catttcctct    1800
gtaatgtggc gctttcaact gtactgctgc agctttaagt accttaaagc ttctcctgtg    1860
aacttcttag ggaaatgtta ggttcagaac taaagtgttt tgggtgggtt ttgttgcggg    1920
```

```
gggagggta   acaatgggtg   gtcttctgat   ttttatttt    gaggttttgt   caactggagt      1980
acgtagagga   actttattta   cagtactttg   atttggcagg   ttttcttcta   cttgtgctct      2040
gcctggagct   gtttccatat   gatataaaaa   gcaagtgtag   tattccatta   ctatgtggct      2100
tagggattta   tttgttttt    aaaatcaacc   atgttagctg   ggattagact   ccctacagtc      2160
cttcaatgga   aaagtaacat   ttaaaaatcc   tttgggtaat   tcgaattaca   gatttaaaag      2220
agcttaagat   ctggtgtttt   gttaatgctt   ctgtttattc   cagaagcatt   aaggtaaccc      2280
attgccaagt   atcattcttg   caaattattc   ttttatataa   ctgaccagtg   cttaataaaa      2340
caagcaggta   cttacaaata   attactggca   gtaggtata    attggtggtt   taaaaataac      2400
attggaatac   aggacttgtt   gccaattggg   taattttcat   tagttgtttt   gtttgttttg      2460
atttgaaacc   tggaaataca   gtaaaatttg   actgtttaaa   atgttggcca   aaaaaatcaa      2520
gatttaattt   ttttatttgt   actgaaaaac   taatcataac   tgttaattct   cagccatctt      2580
tgaagcttga   aagaagagtc   tttggtattt   tgtaaacgtt   agcagacttt   cctgccagtg      2640
tcagaaaatc   ctatttatga   atcctgtcgg   tattccttgg   tatctgaaaa   aaataccaaa      2700
tagtaccata   catgagttat   ttctaagttt   gaaaaataaa   aagaaattgc   atcacactaa      2760
ttacaaaata   caagttctgg   aaaaaatatt   tttcttcatt   ttaaaacttt   ttttaacta       2820
ataatggctt   tgaaagaaga   ggcttaattt   ggggtggta    actaaaatca   aagaaatga       2880
ttgacttgag   ggtctctgtt   tggtaagaat   acatcattag   cttaaataag   cagcagaagg      2940
ttagttttaa   ttatgtagct   tctgttaata   ttaagtgttt   tttgtctgtt   ttacctcaat      3000
ttgaacagat   aagtttgcct   gcatgctgga   catgcctcag   aaccatgaat   agcccgtact      3060
agatcttggg   aacatggatc   ttagagtcac   tttggaataa   gttcttatat   aaataccccc      3120
agcctttga   gaacggggct    tgttaaagga   cgcgtatgta   gggcccgtac   ctactggcag      3180
ttgggttcag   ggaaatggga   ttgacttggc   cttcaggctc   ctttggtcat   aattttaaaa      3240
tatgggagta   gaaaacaaca   aagaatggaa   tggactctta   aaacaatgaa   agagcattta      3300
tcgtttgtcc   cttgaatgta   gaatttgttt   ttgatttcat   aattctgctg   gtaaatgtga      3360
cagttaaaat   ggtgcattat   gtatatatat   taaattag    aaataccatt   ttataatttt      3420
actattccag   ggtgacataa   tgcatttaaa   tttgggattt   gggtggagta   ttatgtttaa      3480
ctggagttgt   caagtatgag   tccctcagga   aaaaaaaaa   ttctgtttta   aaagcaatc       3540
tgattcttag   ctcttgaaac   tattgctact   taaatttcca   ataattaaaa   atttaaaatt      3600
tttaaattag   aattgccaat   acttctacat   ttgagaaggg   ttttttttaga  aatacattta      3660
gtaaagtccc   caagacatta   gtcttacatt   taaactttt    tctttaaaac   atggttttgg      3720
tggttaactt   ttacacagtt   ctgagtactg   ttaatatctg   gaaagtatct   tgagatatca      3780
gtggaaagct   aaacagtcta   aattaacatg   aaatacttca   ttttgattga   gaaaataaaa      3840
tcagattttt   tcaaagtcaa   aaaaaaaaaa   aaaaaaaa                                  3878
```

<210> SEQ ID NO 2
<211> LENGTH: 3863
<212> TYPE: DNA
<213> ORGANISM: Homo sapiens
<300> PUBLICATION INFORMATION:
<308> DATABASE ACCESSION NUMBER: NM_005722
<309> DATABASE ENTRY DATE: 2006-09-24
<313> RELEVANT RESIDUES: (1)..(3863)

<400> SEQUENCE: 2

```
ggagcccggc   ggcggcttcc   ggtcggggga   aaaaagttgg   gccgaaggag   gggccgggaa       60
```

-continued

```
gacgcaagag gaagaagaga aaacggccgg gcggcggtgg ctgtaggttg tgcggctgca    120
gcggctcttc cctgggcgga cgatggacag ccagggcagg aaggtggtgg tgtgcgacaa    180
cggcaccggg tttgtgaagt gtggatatgc aggctctaac tttccagaac acatcttccc    240
agctttggtt ggaagaccta ttatcagatc aaccaccaaa gtgggaaaca ttgaaatcaa    300
ggatcttatg gttggtgatg aggcaagtga attacgatca atgttagaag ttaactaccc    360
tatggaaaat ggcatagtac gaaattggga tgacatgaaa cacctgtggg actacacatt    420
tggaccagag aaacttaata tagataccag aaattgtaaa atcttactca cagaacctcc    480
tatgaaccca accaaaaaca gagagaagat tgtagaggta atgtttgaaa cttaccagtt    540
ttccggtgta tatgtagcca tccaggcagt tctgactttg tacgctcaag gtttattgac    600
tggtgtagtg gtagactctg gagatggtgt gactcacatt tgcccagtat atgaaggctt    660
ttctctccct catcttacca ggagactgga tattgctggg agggatataa ctagatatct    720
tatcaagcta cttctgttgc gaggatacgc cttcaaccac tctgctgatt ttgaaacggt    780
tcgcatgatt aaagaaaaac tgtgttacgt gggatataat attgagcaag agcagaaact    840
ggccttagaa accacagtat tagttgaatc ttatacactc ccagatggac gtatcatcaa    900
agttggggga gagagatttg aagcaccaga agctttattt cagcctcact tgatcaatgt    960
tgaaggagtt ggtgttgctg aattgctttt taacacaatt caggcagctg acattgatac   1020
cagatctgaa ttctacaaac acattgtgct ttctggaggg tctactatgt atcctggcct   1080
gccatcacgg ttggaacgag aacttaaaca gctttactta gaacgagttt tgaagggtga   1140
tgtggaaaaa ctttctaaat ttaagatccg cattgaagac ccaccccgca gaaagcacat   1200
ggtattcctg ggtggtgcag ttctagcgga tatcatgaaa gacaaagaca acttttggat   1260
gacccgacaa gagtaccaag aaaagggtgt ccgtgtgcta gagaaacttg gtgtgactgt   1320
tcgataaact ccaaagcttg ttcccgtcat acccgtaatg ctttcttttt tcctttattg   1380
ccaatctttg aactcattca actccaggac atggaagagg cctctctctg ccctttgact   1440
ggaaaggtca agtttattc tggtgtcttg gggaagcttt gttaaatttt tgttaatgtg   1500
ggtaaatctg agtttaattc aactgcttcc ctacatagac tagagggcta aggattctgt   1560
ctgctgcttt gtttcttcta agtaggcatt tagatcattc ctgtaggctt cctattttca   1620
ctttactgct ctaatgctgc tagtcgtagt ctttagcaca ctaggtggta tgcctttatt   1680
agcataaaac aaaaaaaact ttaacaggag cttttacata ttactgggat gggggtggt    1740 tcgggatggg tgggcagctg ctgaacccctt tagggcattt cctctgtaat gtggcgcttt   1800
caactgtact gctgcagctt taagtacctt aaagcttctc ctgtgaactt cttagggaaa   1860
tgttaggttc agaactaaag tgttttgggt gggttttgtt gcgggggga gggtaacaat    1920 gggtggtctt ctgattttta ttttgaggt tttgtcaact ggagtacgta gaggaacttt    1980
atttacagta ctttgatttg gcaggttttc ttctacttgt gctctgcctg gagctgtttc   2040
catatgatat aaaaagcaag tgtagtattc cattactatg tggcttaggg atttatttgt   2100
tttttaaaat caaccatgtt agctgggatt agactcccta cagtccttca atggaaaagt   2160
aacatttaaa aatcctttgg gtaattcgaa ttacagattt aaaagagctt aagatctggt   2220
gttttgttaa tgcttctgtt tattccagaa gcattaaggt aacccattgc caagtatcat   2280
tcttgcaaat tattctttta tataactgac cagtgcttaa taaaacaagc aggtacttac   2340
aaataattac tggcagtagg ttataattgg tggtttaaaa ataacattgg aatacaggac   2400
ttgttgccaa ttgggtaatt ttcattagtt gttttgtttg ttttgatttg aaacctggaa   2460
```

-continued

```
atacagtaaa atttgactgt ttaaaatgtt ggccaaaaaa atcaagattt aattttttta    2520
tttgtactga aaaactaatc ataactgtta attctcagcc atctttgaag cttgaaagaa    2580
gagtctttgg tattttgtaa acgttagcag actttcctgc cagtgtcaga aaatcctatt    2640
tatgaatcct gtcggtattc cttggtatct gaaaaaaata ccaaatagta ccatacatga    2700
gttatttcta agtttgaaaa ataaaaagaa attgcatcac actaattaca aaatacaagt    2760
tctggaaaaa atattttttct tcattttaaa actttttttt aactaataat ggctttgaaa    2820
gaagaggctt aatttggggg tggtaactaa aatcaaaaga aatgattgac ttgagggtct    2880
ctgtttggta agaatacatc attagcttaa ataagcagca aaggttagt tttaattatg      2940
tagcttctgt taatattaag tgttttttgt ctgttttacc tcaatttgaa cagataagtt    3000
tgcctgcatg ctggacatgc ctcagaacca tgaatagccc gtactagatc ttgggaacat    3060
ggatcttaga gtcactttgg aataagttct tatataaata cccccagcct tttgagaacg    3120
gggcttgtta aaggacgcgt atgtagggcc cgtacctact ggcagttggg ttcagggaaa    3180
tgggattgac ttggccttca ggctcctttg gtcataattt taaaatatgg gagtagaaaa    3240
caacaaagaa tggaatggac tcttaaaaca atgaaagagc atttatcgtt tgtcccttga    3300
atgtagaatt tgttttttgat ttcataattc tgctggtaaa tgtgacagtt aaaatggtgc    3360
attatgtata tatattataa tttagaaata ccatttttata attttactat tccagggtga    3420
cataatgcat ttaaatttgg gatttgggtg gagtattatg tttaactgga gttgtcaagt    3480
atgagtccct caggaaaaaa aaaaattctg ttttaaaaag caatctgatt cttagctctt    3540
gaaactattg ctacttaaat ttccaataat taaaaattta aaatttttaa attagaattg    3600
ccaatacttc tacatttgag aagggttttt ttagaaatac atttagtaaa gtccccaaga    3660
cattagtctt acatttaaac tttttctttt aaaacatggt tttggtggtt aacttttaca    3720
cagttctgag tactgttaat atctggaaag tatcttgaga tatcagtgga aagctaaaca    3780
gtctaaatta acatgaaata cttcattttg attgagaaaa taaaatcaga ttttttcaaa    3840
gtcaaaaaaa aaaaaaaaaa aaa                                             3863
```

<210> SEQ ID NO 3
<211> LENGTH: 1200
<212> TYPE: DNA
<213> ORGANISM: Homo sapiens
<300> PUBLICATION INFORMATION:
<308> DATABASE ACCESSION NUMBER: NM_020350
<309> DATABASE ENTRY DATE: 2006-05-07
<313> RELEVANT RESIDUES: (1)..(1200)

<400> SEQUENCE: 3

```
ctgcgctggg gttggagtgg ccgcaacggg cggggcgggg cggggccggg caagtttgtt      60
ccccgagttc ggagcctagg agcccccgc ggctgcggcg caggtgccct cggcctgagt      120
cgggatggag ctgcctgctg tgaacctgaa ggtgattctc ctaggtcact ggctgctgac     180
aacctgggc tgcattgtat tctcaggctc ctatgcctgg ccaacttca ccatcctggc      240
cttgggcgtg tgggctgtgg ctcagcggga ctccatcgac gccataagca tgtttctggg    300
tggcttgctg ccaccatct tcctggacat cgtgcacatc agcatcttct acccgcgggt     360
cagcctcacg gacacgggcc gctttggcgt gggcatggcc atcctcagct tgctgctcaa    420
gccgctctcc tgctgcttcg tctaccacat gtaccggag cgcggggtg agctcctggt     480
ccacactggt ttccttgggt cttctcagga ccgtagtgcc taccagacga ttgactcagc    540
agaggcgccc gcagatccct ttgcagtccc agagggcagg agtcaagatg cccgagggta   600
```

-continued

| | |
|---|---|
| ctgaagccag ccacgctgcg cccggccctg ccccgggcct tcctcgtgcc tgggaggtcg | 660 |
| ttctagggat gctcctgacc tccgtctctt ggacctaaga tggaatgtgt ccccagctca | 720 |
| gggattgcct gaaccaagag gccaggagcc ccatgggcc gcccagtacc atgcacactc | 780 |
| ctgtcccgaa ctccctgagg cctccctcc cttcagggca ccactggtt cccaggctgg | 840 |
| aaccagggtc tctctttacc tcctacccca tggtggcacc acagaggccc tcagccgagt | 900 |
| cctgcctgag tgttgcaagc tcaggccttt aaggactgct gatgcccct caggcctccc | 960 |
| ccaagtttgc tgggctttgg tggaagccct gagagcttca ggtcctgctc agcccgagga | 1020 |
| gcagtctgga tgggagtga ggccccgtcc ttctcactgc ctggtcacat ggtgcctagg | 1080 |
| gatgcagggc tggaggccag aggtgtcagc aacactgtgt cccaccacaa cctccagcct | 1140 |
| cccttttcag agcacagcat taaagtttgg ggaattctgt agaaaaaaaa aaaaaaaaa | 1200 |

<210> SEQ ID NO 4
<211> LENGTH: 1802
<212> TYPE: DNA
<213> ORGANISM: Homo sapiens
<300> PUBLICATION INFORMATION:
<308> DATABASE ACCESSION NUMBER: NM_138441
<309> DATABASE ENTRY DATE: 2006-10-04
<313> RELEVANT RESIDUES: (1)..(1802)

<400> SEQUENCE: 4

| | |
|---|---|
| agcctggggt tccccttcgg gtcgcagact cttgtgtgcc cgccagtagt gcttggtttc | 60 |
| caacagctgc tgctggctct tcctcttgcg gccttttcct gaaacggatt cttctttcgg | 120 |
| ggaacagaaa gcgccagcca tgcagccttg cacggaaag gccatgcaga gagcttccga | 180 |
| ggccggagcc actgccccca aggcttccgc acggaatgcc aggggcgccc cgatggatcc | 240 |
| caccgagtct ccggctgccc ccgaggccgc cctgcctaag gcgggaaagt tcggccccgc | 300 |
| caggaagtcg ggatcccggc agaaaaagag cgccccggac acccaggaga ggccgccccgt | 360 |
| ccgcgcaact ggggcccgcg ccaaaaaggc ccctcagcgc gcccaggaca cgcagccgtc | 420 |
| tgacgccacc agcgcccctg ggcagagggg gctgcagcct cctgcggctc gggagccggc | 480 |
| tctttccagg gctggttctt gccgccagag gggcgcgcgc tgctccacga agccaagacc | 540 |
| tccgcccggg ccctgggacg tgcccagccc cggcctgccg gtctcggccc ccattctcgt | 600 |
| acggagggat gcgcgcctg gggctcgaa gctccgggcg gttttggaga agttgaagct | 660 |
| cagccgcgat gatatctcca cggcggcggg gatggtgaaa ggggttgtgg accacctgct | 720 |
| gctcagactg aagtgcgact ccgcgttcag aggcgtcggg ctgctgaaca ccgggagcta | 780 |
| ctatgagcac gtgaagattt ctgcacctaa tgaatttgat gtcatgttta aactggaagt | 840 |
| ccccagaatt caactagaag aatattccaa cactcgtgca tattactttg tgaaatttaa | 900 |
| aagaaatccg aaagaaaatc tctgagtca gttttttagaa ggtgaaatat tatcagcttc | 960 |
| taagatgctg tcaaagtttta ggaaaatcat taaggaagaa attaacgaca ttaaagatac | 1020 |
| agatgtcatc atgaagagga aagaggagg gagccctgct gtaacacttc ttattagtga | 1080 |
| aaaaatatct gtggatataa ccctggcttt ggaatcaaaa agtagctggc ctgctagcac | 1140 |
| ccaagaaggc ctgcgcattc aaaactggct ttcagcaaaa gttaggaagc aactacgact | 1200 |
| aaagccattt taccttgtac ccaagcatgc aaaggaagga aatggtttcc aagaagaaac | 1260 |
| atggcggcta tccttctctc acatcgaaaa ggaaattttg aacaatcatg gaaaatctaa | 1320 |
| aacgtgctgt gaaaacaaag aagagaaatg ttgcaggaaa gattgtttaa aactaatgaa | 1380 |
| ataccttttta gaacagctga agaaaggtt taaagacaaa aaacatctgg ataaattctc | 1440 |

-continued

| | |
|---|---|
| ttcttatcat gtgaaaactg ccttctttca cgtatgtacc cagaaccctc aagacagtca | 1500 |
| gtgggaccgc aaagacctgg gcctctgctt tgataactgc gtgacatact ttcttcagtg | 1560 |
| cctcaggaca gaaaaacttg agaattattt tattcctgaa ttcaatctat tctctagcaa | 1620 |
| cttaattgac aaaagaagta aggaatttct gacaaagcaa attgaatatg aaagaaacaa | 1680 |
| tgagtttcca gttttgatg aattttgaga ttgtattttt agaaagatct aagaactaga | 1740 |
| gtcaccctaa atcctggaga atacaagaaa aatttgaaaa ggggccagac gctgtggctc | 1800 |
| ac | 1802 |

<210> SEQ ID NO 5
<211> LENGTH: 2573
<212> TYPE: DNA
<213> ORGANISM: Homo sapiens
<300> PUBLICATION INFORMATION:
<308> DATABASE ACCESSION NUMBER: NM_030764
<309> DATABASE ENTRY DATE: 2006-04-09
<313> RELEVANT RESIDUES: (1)..(2573)

<400> SEQUENCE: 5

| | |
|---|---|
| ggtgaccaag agtacatctc ttttcaaata gctggattag gtcctcatgc tgctgtggtc | 60 |
| attgctggtc atctttgatg cagtcactga acaggcagat tcgctgaccc ttgtggcgcc | 120 |
| ctcttctgtc ttcgaaggag acagcatcgt tctgaaatgc cagggagaac agaactggaa | 180 |
| aattcagaag atggcttacc ataaggataa caaagagtta tctgttttca aaaaattctc | 240 |
| agatttcctt atccaaagtg cagttttaag tgacagtggt aactattcct gtagtaccaa | 300 |
| aggacaactc tttctctggg ataaaacttc aaatatagta aagataaaag tccaagagct | 360 |
| ctttcaacgt cctgtgctga ctgccagctc cttccagccc atcgaagggg gtccagtgag | 420 |
| cctgaaatgt gagacccggc tctctccaca gaggttggat gttcaactcc agttctgctt | 480 |
| cttcagagaa aaccaggtcc tggggtcagg ctggagcagc tctccggagc tccagatttc | 540 |
| tgccgtgtgg agtgaagaca cagggtctta ctggtgcaag gcagaaacgg tgactcacag | 600 |
| gatcagaaaa cagagcctcc aatcccagat tcacgtgcag agaatcccca tctctaatgt | 660 |
| aagcttggag atccgggccc ccgggggaca ggtgactgaa ggacaaaaac tgatcctgct | 720 |
| ctgctcagtg gctggggta caggaaatgt cacattctcc tggtacagag aggccacagg | 780 |
| aaccagtatg ggaaagaaaa cccagcgttc cctgtcagca gagctggaga tcccagctgt | 840 |
| gaaagagagt gatgccggca atatattctg tagagctgac aacggccatg tgcctatcca | 900 |
| gagcaaggtg gtgaatatcc ctgtgagaat tccagtgtct cgccctgtcc tcaccctcag | 960 |
| gtctcctggg gcccaggctg cagtggggga cctgctggag cttcactgtg aggccctgag | 1020 |
| aggctctccc ccaatcttgt accaattta tcatgaggat gtcacccttg gaacagctc | 1080 |
| ggccccctct ggaggagggg cctccttcaa cctctctttg actgcagaac attctggaaa | 1140 |
| ctactcctgt gaggccaaca acggcctggg gcccagtgc agtgaggcag tgccagtctc | 1200 |
| catctcagga cctgatggct atagaagaga cctcatgaca gctggagttc tctggggact | 1260 |
| gtttggtgtc cttggtttca ctggtgttgc tttgctgttg tatgccttgt tccacaagat | 1320 |
| atcaggagaa agttctgcca ctaatgaacc cagagggct tccaggccaa atcctcaaga | 1380 |
| gttcacctat tcaagcccaa ccccagacat ggaggagctg cagccagtgt atgtcaatgt | 1440 |
| gggctctgta gatgtggatg tggtttattc tcaggtctgg agcatgcagc agccagaaag | 1500 |
| ctcagcaaac atcaggacac ttctggagaa caaggactcc caagtcatct actcttctgt | 1560 |
| gaagaaatca taacacttgg aggaatcaga agggaagatc aacagcaagg atggggcatc | 1620 |

-continued

```
attaagactt gctataaaac cttatgaaaa tgcttgaggc ttatcacctg ccacagccag    1680
aacgtgcctc aggaggcacc tcctgtcatt tttgtcctga tgatgtttct tctccaatat    1740
cttcttttac ctatcaatat tcattgaact gctgctacat ccagacactg tgcaaataaa    1800
ttatttctgc taccttctct taagcaatca gtgtgtaaag atttgaggga agaatgaata    1860
agagatacaa ggtctcacct tcatctactg tgaagtgatg agaacaggac ttgatagtgg    1920
tgtattaact tatttatgtg ctgctggata cagtttgcta atattttgtt gagaattttt    1980
gcaaatatgt tcattgggaa tattggcctg aaattttctt ttccactgtg tctctgccag    2040
aatgtttgta tcaggctgat gctggcttca tagaatgagt taggcaggag cccttcctcc    2100
ttgatttttt ggcatagttt cagcaggatt ggtaccagtt attctttctg catcttgtag    2160
aattcagcta tgaatccatc tggtctaggg cttttgtgtt ggttggtaag ttttttatta    2220
ctaattcaac ttcagcgctt gatattggtc taggaggggt ttctgtctct tcctggttca    2280
atcttgggag attgtgtgtt tccaggaatt tagccgtttc ctccagattt tcttctttat    2340
gtgcatcgac ttgagtgtaa acataactta tatgcactgg gaaaccaaaa aatctgtgtg    2400
acttgcttta ttgcagcatt tgtttttattt tggtagtctg gaactgaacc tgcaatatca    2460
ccaaagtatg catatagttg caaaaatgtg attttttgaca tagtaaatat gagtatttgc    2520
aataaactat gatattactt ttgtaagtat atagaataaa atgtaaataa tct           2573
```

<210> SEQ ID NO 6
<211> LENGTH: 1815
<212> TYPE: DNA
<213> ORGANISM: Homo sapiens
<300> PUBLICATION INFORMATION:
<308> DATABASE ACCESSION NUMBER: NM_000308
<309> DATABASE ENTRY DATE: 2006-08-20
<313> RELEVANT RESIDUES: (1)..(1815)

<400> SEQUENCE: 6

```
ggggagatga tccgagccgc gccgccgccg ctgttcctgc tgctgctgct gctgctgctg      60
ctagtgtcct gggcgtcccg aggcgaggca gcccccgacc aggacgagat ccagcgcctc     120
cccgggctgg ccaagcagcc gtctttccgc cagtactccg gctacctcaa aagctccggc     180
tccaagcacc tccactactg gtttgtggag tcccagaagg atcccgagaa cagccctgtg     240
gtgctttggc tcaatggggg tcccggctgc agctcactag atgggctcct cacagagcat     300
ggccccttcc tggtccagcc agatggtgtc accctggagt acaaccccta ttcttggaat     360
ctgattgcca atgtgttata cctggagtcc ccagctgggg tgggcttctc ctactccgat     420
gacaagtttt atgcaactaa tgacactgag gtcgcccaga gcaattttga ggcccttcaa     480
gatttcttcc gcctctttcc ggagtacaag aacaacaaac ttttcctgac cggggagagc     540
tatgctggca tctacatccc caccctggcc gtgctggtca tgcaggatcc cagcatgaac     600
cttcaggggc tggctgtggg caatggactc tcctcctatg agcagaatga caactccctg     660
gtctactttg cctactacca tggccttctg gggaacaggc tttggtcttc tctccagacc     720
cactgctgct ctcaaaacaa agtgtaactt catgacaaca aagacctgga atgcgtgacc     780
aatcttcagg aagtggcccg catcgtgggc aactctggcc tcaacatcta caatctctat     840
gccccgtgtg ctgagggggt gcccagccat tttaggtatg agaaggacac tgttgtggtc     900
caggatttgg gcaacatctt cactcgcctg ccactcaagc ggatgtggca tcaggcactg     960
ctgcgctcag gggataaagt gcgcatggac cccccctgca ccaacacaac agctgcttcc    1020
acctacctca caaacccgta cgtgcggaag gccctcaaca tcccggagca gctgccacaa    1080
```

-continued

| | |
|---|---|
| tgggacatgt gcaactttct ggtaaactta cagtaccgcc gtctctaccg aagcatgaac | 1140 |
| tcccagtatc tgaagctgct tagctcacag aaataccaga tcctattata taatggagat | 1200 |
| gtagacatgg cctgcaattt catgggggat gagtggtttg tggattccct caaccagaag | 1260 |
| atggaggtgc agcgccggcc ctggttagtg aagtacgggg acagcgggga gcagattgcc | 1320 |
| ggcttcgtga aggagttctc ccacatcgcc tttctcacga tcaagggcgc cggccacatg | 1380 |
| gttcccaccg acaagcccct cgctgccttc accatgttct cccgcttcct gaacaagcag | 1440 |
| ccatactgat gaccacagca accagctcca cggcctgatg cagcccctcc cagcctctcc | 1500 |
| cgctaggaga gtcctcttct aagcaaagtg cccctgcagg cgggttctgc cgccaggact | 1560 |
| gcccccttcc cagagccctg tacatcccag actgggccca gggtctccca tagacagcct | 1620 |
| gggggcaagt tagcactttta ttcccgcagc agttcctgaa tggggtggcc tggcccccttc | 1680 |
| tctgcttaaa gaatgccctt tatgatgcac tgattccatc ccaggaaccc aacagagctc | 1740 |
| aggacagccc acaggaggt ggtggacgga ctgtaattga tagattgatt atggaattaa | 1800 |
| attgggtaca gcttc | 1815 |

<210> SEQ ID NO 7
<211> LENGTH: 4827
<212> TYPE: DNA
<213> ORGANISM: Homo sapiens
<300> PUBLICATION INFORMATION:
<308> DATABASE ACCESSION NUMBER: NM_003633
<309> DATABASE ENTRY DATE: 2006-08-20
<313> RELEVANT RESIDUES: (1)..(4827)

<400> SEQUENCE: 7

| | |
|---|---|
| gcggtggcgc tgcggagacc cggtccagac gcctggcggc cgccggcaca caaggcgctt | 60 |
| tctagctccc tcccccgagc gcacagcccg cctccttccg cggcgcctgc agtggcaggc | 120 |
| ttgctctgcc ctaccgtgac gcgctccgga gacgctctgc gggtcctgga caccgggtcc | 180 |
| gcggcgtggg gacgacagac ggaggcgaac gccatcggta gccggtccgc gagccatcgt | 240 |
| tcggggcgca gtcctctccc cggctggccc tcctttctcc ggggcattcg ccaccgcttc | 300 |
| cctgggctga cgaccgggt tcgtcgcctc cttgcccgtg accgtcgcta gaactcagtt | 360 |
| gtgcgttgcg ccagtcgcc actgctgagt ggaagcaaaa tgtcagtcag tgtgcatgag | 420 |
| aaccgcaagt ccagggccag cagcggctcc attaacatct atctgtttca caagtcctcc | 480 |
| tacgctgaca gcgtcctcac tcacctgaat cttttacgcc agcagcgtct cttcactgac | 540 |
| gtccttctcc atgccggaaa taggaccttc ccttgccacc gggcagtgct ggctgcatgc | 600 |
| agtcgctact ttgaggccat gttcagtggt ggcctgaaag agagccagga cagtgaggtc | 660 |
| aactttgaca attccatcca cccagaagtc ttggagctgc tgcttgacta tgcgtactcc | 720 |
| tcccgggtca tcatcaatga agaaaatgca gaatcgctcc tggaagctgg tgacatgctg | 780 |
| gagtttcaag acatccggga tgcatgtgca gagttcctgg aaaagaacct gcatcccacc | 840 |
| aactgcctgg gcatgctgct gctgtctgat gcacaccagt gcaccaagct gtacgaacta | 900 |
| tcttggagaa tgtgtctcag caacttccaa accatcagga gaatgaaga tttcctccag | 960 |
| ctgccccagg acatggtagt gcaactcttg tccagtgaag agctggagac agaggatgaa | 1020 |
| aggcttgtgt acgagtctgc aattaactgg atcagctatg acctgaagaa gcgctattgc | 1080 |
| tacctcccag aactgttgca gacagtaagg ctggcacttc tgccagccat ctatctcatg | 1140 |
| gagaatgtgg ccatggagga actcatcacc aagcagagaa agagtaagga aattgtggaa | 1200 |
| gaggccatca ggtgcaaact gaaaatcctg cagaatgacg gtgtggtaac cagcctctgt | 1260 |

```
gcccgacctc ggaaaactgg ccatgccctc ttccttctgg gaggacagac tttcatgtgt    1320
gacaagttgt atctggtaga ccagaaggcc aaagaaatca ttcccaaggc tgacattccc    1380
agcccaagaa aagagtttag tgcatgtgcg attggctgca aagtgtacat tactgggggg    1440
cgggggtctg aaaatggggt ctcgaaagat gtctgggttt atgataccct gcacgaggag    1500
tggtccaagg ctgcccccat gctggtggcc aggtttggcc atggctctgc tgaactgaag    1560
cactgcctgt atgtggttgg ggggcacacg gccgcaactg gctgcctccc ggcctccccc    1620
tcagtctctc taaagcaggt agaacattat gaccccacaa tcaacaaatg gaccatggtg    1680
gccccactcc gagaaggcgt tagcaacgcc gcagtagtga gtgccaaact taagttattt    1740
gctttcggag gtaccagtgt cagtcatgac aagctcccca agttcagtg ttacgatcag    1800 tgtgaaaaca ggtggactgt accggccacc tgtccccagc cctggcgtta cacagcagca    1860
gctgtgctgg ggaaccagat ttttattatg gggggtgata cagaattctc tgcctgctct    1920
gcttataaat tcaacagtga gacttaccag tggaccaaag tgggagatgt gacagcaaag    1980
cgcatgagct gccatgctgt ggcctctgga aacaaactct acgtggttgg aggatacttt    2040
ggcattcagc gatgcaagac tttggactgc tacgatccaa cattagacgt gtggaacagc    2100
atcaccactg tcccgtactc gctgattcct actgcatttg tcagcacctg gaaacatctg    2160
ccttcttaaa tgcagtacat tctaaagaga gtgagcatga gctcactcca tcactcgatg    2220
agataatatg agatttctac ttcggagagg ccaagtctaa tgaagagaaa aaaaggaaaa    2280
gaagttgcaa gactcgaata aaatctgctg caccttgtaa atgctctaac tggacatgaa    2340
ggaaaggggc gagggagggg ggtgggattt ttggtgcaag tagcacatgg tttaaatatg    2400
aatgaacaaa cctgtgatct agtccttgtc ttgtaattgt ggattaatgt caatgttaat    2460
cagcccctca aagggagaga aaagctggac cttttccctt gctgtaccat attcagcatt    2520
tgatttccat gggccccacc atttatgtgt agaatttgaa atggttgtca cctctctctg    2580
aggacagagc ttgaagcctc cacaccagct gctgctggag attcaaagcc caactgtggg    2640
tccgagaggg aagctggctg ggctggctga agaatgaaga ccactggact ctccgttaat    2700
ctctaagggg tctgctcccc aggaacgttt ctgaacaatg gggactttgt tggtagccat    2760
ttggtagatg ttcttttcta tttataagtg actttaaact ttcccttggc tgttaagaag    2820
tttgttatag atttagctat ttattgttcg atgcctgcat gctgaaacaa tgcctacagc    2880
tgtcttcaca tgtatggacg tgtgtgaatg gttgtacgtt ttgcacattt tgtggctgtt    2940
gagatgtgct ttgctgcaca aacatgaaaa tttttgagtt acaatttgga gcataactgg    3000
agggtgggct gggagggggt ggattttaa aatgtcaaga cagggaagga tgacaaaatg    3060
gaaatttaaa tgacatccta gaggtagaga accgtggag atcgcttttc tcagactcac    3120
caacttttaa tgggatttca tggggtttgg ttgtgctgat agggtaaggg gaggctgctt    3180
tctgcccttc tccccactcc catctgattt acttaattca gtctcagctg ctgaaatttg    3240
gaaaggacca aattgcttta cagttttttt ctttgtgtag tatcttgaaa tcctggaaaa    3300
ttctatggaa tagttctgta tagggcac aagtaaaggc attgtccaaa gtttatttat    3360
ttatttatta ccctaagaat gctttgccat aaccacattt aatgggaaaa acggcatgta    3420
tcacagatgt aaattaactc accagattta ctgggcctga actcattctc ttcttgctat    3480
atgatttagc aagttctaga aggtctccaa gacaataatt acattggcac aatgtatact    3540
tcagtgctca cccgtagcaa atctcttttt aaaaaactct ttggtgcaca agtaacacat    3600
ttggccacaa acaccaaag aattgtaggc agtggcccct attgagaagt tttccggtag    3660
```

-continued

| | |
|---|---|
| agttggaaat cagttgtgaa tacattcttt gctagttgga gtgcttgttt actaagcatg | 3720 |
| tgccgtcgta ggtattagtg ctagtctcaa ataggtgctt cccctgaggt gcagggggaag | 3780 |
| accaaagttt gcaactcgaa ctgctttcgt ccatgtttct cacattgctg tattttagaa | 3840 |
| aatagggggtt aagactgata acaaccttt acattgtgac tgtgtttgca ttgtctaatg | 3900 |
| acagataaat ccttaacatt tctctccacc ttagtacttt agactaattg tgtttgtccg | 3960 |
| tccatgccat gaatgagtgg gctgtagttg ggcctaaata aatgagctgt tggaagaaaa | 4020 |
| gaatcacagt actttccagc agtcagtccc tggttcctag atgtgttcta agcaatgcaa | 4080 |
| atgtctaatt gtcccccagt gggcatagtc agtgtcgttt atattgtagc agttacagct | 4140 |
| ctgtagttta tgatgcaaat ctgccaagag agatgtatgt gtcactgcat ggcttctgaa | 4200 |
| agcaggatga atttttctgca gctgtttcaa agttggggtc tgttcttgaa tcctctatta | 4260 |
| attactgtgt gtgagccaga gggagctgtg gtaagggttg ggcccccagc ctgtagggaa | 4320 |
| ctttctggac tcccactctt tgaatcgata taggcatttg gtctcactac ttgaccattc | 4380 |
| tcaccctgtg aaacgtccca cactttgaag caaatacaat tcacagcaca gtacacacaa | 4440 |
| aaaccttggc ataagacaga gaaggttctt cttattttgt gggctggttg ctgtagaaac | 4500 |
| atataacaaa gggcagccct ccacttctgg tataattgtg tagccccttt tctttgggct | 4560 |
| tgacacctgt cttgaataag agtgattaga gctgcataat gtccctctct tggctattga | 4620 |
| ccatgtggtt cacgtacaaa actctgtata agttgaagga aaatgttcat gttcatatgt | 4680 |
| acttgtttgc tatgactaca ttttgaggtt ttgtaaaact gttatttttt tttttttcac | 4740 |
| aatgtgaaac tgaaggtcaa taaattatta gagattttct cttcaaaaaa aaaaaaaaaa | 4800 |
| aaaaaaaaaa aaaaaaaaaa aaaaaaa | 4827 |

<210> SEQ ID NO 8
<211> LENGTH: 1807
<212> TYPE: DNA
<213> ORGANISM: Homo sapiens
<300> PUBLICATION INFORMATION:
<308> DATABASE ACCESSION NUMBER: NM_004130
<309> DATABASE ENTRY DATE: 2006-09-17
<313> RELEVANT RESIDUES: (1)..(1807)

<400> SEQUENCE: 8

| | |
|---|---|
| ctctgagtca ccaacctgag gctgccccgg ccgcctgcgc acccggcagc accatgacag | 60 |
| atcaggcctt tgtgacacta accacaaacg atgcctacgc caaaggtgcc ctggtcctgg | 120 |
| gatcatctct gaaacagcac aggaccacca ggaggctggt cgtgctcgcc acccctcagg | 180 |
| tctcagactc catgagaaaa gttttagaga cagtctttga tgaagtcatc atggtagatg | 240 |
| tcttggacag tggcgattct gctcatctaa ccttaatgaa gaggccagag ttgggtgtca | 300 |
| cgctgacaaa gctccactgc tggtcgctta cacagtattc aaaatgtgta ttcatggatg | 360 |
| cagatactct ggtcctagca aatattgatg atcttttga cagagaagaa ttgtcagcag | 420 |
| caccagaccc agggtggcct gactgcttca attccggagt cttcgtttat cagccttcag | 480 |
| ttgaaacata caatcagctg ttgcatcttg cttctgagca aggtagtttt gatggtgggg | 540 |
| accaaggcat actgaacaca tttttagca gctgggcaac aacagatatc agaaaacacc | 600 |
| tgccgtttat ttataaccta agcagcatct ctatatactc ctacctcccg gcatttaaag | 660 |
| tgtttggtgc aagtgccaaa gttgtgcatt tcctgggacg agtcaaacca tggaattata | 720 |
| cttatgatcc caaaacaaaa agtgtcaaaa gtgaggccca tgatcccaac atgactcatc | 780 |
| cagagtttct catcctgtgg tggaacatct ttaccaccaa cgttttacct ctgcttcaac | 840 |

-continued

| | | |
|---|---|---|
| aatttggcct tgtcaaagac acctgctcat atgtaaatgt gctttcagac ttggtctata | 900 | |
| cactggcttt ctcttgtggc ttctgtagaa aggaagatgt ctcaggagcc atatcacatc | 960 | |
| tgtcccttgg ggagatccca gctatggcac agccgtttgt atcctcggaa gaacggaagg | 1020 | |
| aacgatggga acagggccag gctgattata tgggagcaga ttcctttgac aacatcaaga | 1080 | |
| ggaaacttga cacttacctc cagtagaaac actgcatttt tctgtgaaca catccacttc | 1140 | |
| acaagccttg tttctgatac ttagtatcta gagctgggtt gagaaaagtc tgttacagtt | 1200 | |
| gctagaggtt ttcattaaaa cttatcagat gagaggcttt tttaggataa gaggtgagaa | 1260 | |
| ctgggcaaaa gttgtgaagc agcaattctg ttatatggac agtgttctgc tttttaatcc | 1320 | |
| tatttagctt gtttcagaaa ttctcacttt tgttgactgc caacatacaa agtaagggaa | 1380 | |
| actcaagata ttaagatggc tgtatcagtt cttaaaatct gcagagcctg gttcaaaatc | 1440 | |
| agtcactccc ttcagaagca gacatggcat ctgttccttg cttgcttgtt ggttgtgtac | 1500 | |
| cttttcacgag acctgaattt tagaattgcc cagtgctgcc agagtgagtg agtgtaattc | 1560 | |
| tcctttcagg taaagatagg ctatctcaac actgctgagt gattcataaa catatcaacc | 1620 | |
| aatagcatta acccatttta tttcctgtcc ttagtgtctg aagatgctca ccagttttct | 1680 | |
| gtgtacagta aggcagcatg ctaaaatgct tttgttcagt tctggatatt tgaaaatagc | 1740 | |
| agtgtgttct ctgatggtta cctgcagtgg caccctgtac aaaaaataaa agacttattg | 1800 | |
| gtgtaaa | 1807 | |

<210> SEQ ID NO 9
<211> LENGTH: 4923
<212> TYPE: DNA
<213> ORGANISM: Homo sapiens
<300> PUBLICATION INFORMATION:
<308> DATABASE ACCESSION NUMBER: NM_014900
<309> DATABASE ENTRY DATE: 2006-10-15
<313> RELEVANT RESIDUES: (1)..(4923)

<400> SEQUENCE: 9

| | | |
|---|---|---|
| cggcggcggc gcccgcgggc tgggagccgg ggcccgcagg tggaagcgca cccgggaggc | 60 | |
| gggccggccg gggctggagc ggctcgggcg ggctcttgac gctcagccag cttcgctccg | 120 | |
| gcctcgggaa ggcgcgcgtc ccgccctgac ccgccggcct ctcccacccc agcagtgacg | 180 | |
| cgccgcctgg gagctggagc ccgcgcagcg ccccgcaggg cgatggacgg ccgaaccccg | 240 | |
| cgcccgcagg acgccccagc caggagaaaa ccaaaagcca aggcaccact tcctccagct | 300 | |
| gagaccaaat atactgatgt ctcttcagct gctgattctg tagaatccac tgctttcatc | 360 | |
| atggaacaga agaaaacat gatagataaa gacgttgaac tctcagtggt cctacctggg | 420 | |
| gatattatca aatctactac tgttcatggc agtaaaccta tgatggactt gttgatattc | 480 | |
| ctttgtgcac agtatcactt aaatccatca agttacacaa tcgatctgtt gtcagctgaa | 540 | |
| cagaaccaca ttaaatttaa gccaaacaca ccaataggaa tgttggaggt agagaaggta | 600 | |
| attttaaagc caaaaatgtt ggataagaaa aaacctacac ctataatacc agagaaaact | 660 | |
| gtgagagtag tgattaattt taagaaaaca cagaagacca tagtgagagt gagtccacat | 720 | |
| gcatcgcttc aagagcttgc ccctattata tgtagcaaat gtgagtttga tccgttgcat | 780 | |
| acactattgt tgaaagatta tcaatcgcag gagcctcttg acttgacaaa atctcttaat | 840 | |
| gacctgggac taagagaatt atatgcgatg gatgtcaaca gagagtcctg ccaaatatca | 900 | |
| caaaacctag atattatgaa ggagaaagaa aataaagggt ttttcagttt ttttcaacgc | 960 | |
| agtaagaaaa agcgagacca aactgcaagt gcccctgcaa cccctctagt aaataagcac | 1020 | |

```
cgcccaactt ttacaaggtc caataccatt tccaaaccat atatttccaa caccctgccg    1080
tcggatgcac ccaagaagag gcgggctcca ctgcccccga tgccagcatc tcagagtgtc    1140
ccccaagacc ttgcacacat ccaggagagg cctgcttctt gtatagtgaa atccatgagc    1200
gtggatgaga cagataagag tccctgtgaa gcaggaagag tgagggcagg ttcactgcag    1260
ctcagcagca tgtctgcagg gaattcatct ttgagaagga caaagcgaaa agcaccttcc    1320
ccaccctcca aaataccccc gcatcaaagt gatgaaaata gtcgtgtgac tgccttacag    1380
ccagtagatg gagttcctcc agacagtgct tcagaagcaa actctcctga ggagctatcc    1440
agcccagaaa cctttcaccc tgggctttcc agtcaggagc agtgcactgc gcccaaactg    1500
atggaggaaa cctctgtctt tgagtgccct gggacacctg aggcagccat aacatcattg    1560
acatctggaa taagctctga ttatagcctt gaagagatat atgaaaagga agaactgagt    1620
gaagtgccta agttgaagc tgaaaatatt tctccgaagt cacaagatat tccttttgta    1680
tctactgata aataaatac actgaaaaat gatcctgact cagcccttgg caatggtagt    1740
ggagagttct cacaaaactc catggaagaa aaacaagaaa ctaaaagcac agatggacaa    1800
gaaccacaca gtgtagtata tgatacaagc aatggaaaga aggtagttga cagtataaga    1860
aacttgaagt cgttgggccc aaaccaagag aatgttcaaa atgaaataat tgtctatcca    1920
gagaacacag aagacaatat gaaaaatgga gtgaagaaaa cagaaatcaa tgtagaaggt    1980
gttgccaaaa ataacaacat tgatatggaa gttgagagac catcaaactc tgaggcacat    2040
gaaactgata ctgctataag ttacaaggaa accatctag cagcttcatc agtaccagat     2100
caaaaactga atcaacccag tgcagaaaag acaaaagatg cagcaattca gacaacccct    2160
tcttgtaaca gttttgatgg gaaacaccaa gatcataatt tatctgactc caaagttgaa    2220
gaatgtgtgc aaacttcaaa taacaacata tcaactcaac actcatgctt aagttcacaa    2280
gattctgtaa ataccctcaag ggaattcagg agtcaaggca ccctaattat acattcagaa    2340
gatccgctta ccgtaaaaga tccaatttgt gcacatggta atgatgatct tttgcctcct    2400
gtagatagga ttgacaaaaa ttccactgct tcttacctaa agaattaccc actttataga    2460
caggactaca atcccaagcc aaaaccttca aatgaaatta cacgagagta tatcccaaa     2520 attggcatga ctacttataa aatagtgcct cccaaatcct tggaaatatc gaaagactgg    2580
caatcagaaa ccatagagta taagatgat caggacatgc atgctttagg gaaaaagcac     2640
actcatgaga atgtgaaaga aactgccatc caaacagaag attctgctat ttctgaaagc    2700
ccagaagagc cactgccaaa ccttaaaccg aagcctaacc tgagaacaga gcatcaagtg    2760
cccagttctg tgagctcacc tgatgatgcc atggttagtc ctctgaaacc tgctcccaaa    2820
atgacaagag acactggcac agctcctttt gcaccaaatt tggaagaaat aaacaatatt    2880
ttggaatcaa aatttaaatc tcgggcttca aatgcccagg ccaaacccag ctctttttt     2940 ttgcagatgc agaagagagt atcgggtcac tatgtgacat ctgcagctgc caagagtgtc    3000
catgctgccc ctaatcctgc tccaaaagaa ctgacaaata agaggcaga aagggatatg     3060 ctgccttctc cggagcagac tctttctccc ttaagtaaaa tgcctcactc tgttccacaa    3120
ccccttgttg aaaaaactga tgatgatgtc atcggtcagg ctcctgctga gcctcccct    3180 cctcccatag ctccaaaacc tgtgacaatt cctgctagtc aggtatccac acaaaatctg    3240
aagactttga aaacttttgg tgccccacga ccatactcaa gttctggtcc ttcaccgttt    3300
gctcttgctg tagtgaaaag gtcacagtct ttcagtaaag agcgcaccga gtcacctagt    3360
gccagtgcat tggtccaacc tccagccaac acagaggaag ggaagactca ttctgtaaat    3420
```

| | | | | |
|---|---|---|---|---|
| aaatttgtgg | acatcccaca | gcttggtgtg | tctgataagg | aaaataactc tgcacataat | 3480 |
| gaacagaatt | cccaaatacc | aactccaact | gatgggcccat | cattcactgt tatgagacaa | 3540 |
| agttctttaa | cattccaaag | ctctgaccca | gaacagatgc | gacagagttt gctgactgca | 3600 |
| atccgttcgg | gagaggctgc | tgccaaattg | aaaaggggtta | ccattccatc aaatacaata | 3660 |
| tctgtgaatg | gaaggtcaag | actcagccat | tccatgtccc | ctgatgccca ggacggccat | 3720 |
| taaatgttac | cctgccacac | cactgcactt | cacttccact | tcagaccaac ttcatactaa | 3780 |
| tggaacattt | tggcaaatgt | atattcagat | gtacactaat | atattatcta ttaaaatatt | 3840 |
| agaatttgtg | ttgtggcttt | taatgccaga | agaaaagtta | ccagaattta taatttatag | 3900 |
| taattttttg | atctttttt | tgccttaaga | gttgaatatg | ctgctttaga actttaaaac | 3960 |
| aaggtgtaaa | tgattttcat | ttttttacaaa | tgaaaaataa | ttcctttgta ttgatttcac | 4020 |
| ttaccagcac | attctctaca | atggtgactt | agacaaaagt | ataagattca tagactttat | 4080 |
| atttgtatga | catacaacta | ggacaaacat | agatatgaca | tttgctgcct cagtgtagca | 4140 |
| attggaaata | tttataagtt | atatgaaagc | ctgttttggg | ctgaaagaat gatttagaaa | 4200 |
| actagtgata | ccaaataagt | atattcagtt | caataattat | tttcaatgat gaatcactta | 4260 |
| gtgtgaaaga | cttgccttgt | gtattcttta | tgtaattaca | aatcactgtc aattttatgg | 4320 |
| gaagctcata | gtattttaat | attttattaa | catggaactc | ttgttttttt aatctttaga | 4380 |
| acttaaattc | tacaagaatt | ttaaatattt | tctgtatata | attatgacat tgtcacacag | 4440 |
| aaattacaca | ttttatgtgc | cagaagccctt | aaacatcttt | ctgtgaaaat gctgatatat | 4500 |
| tgtgacagtt | atttcacatt | tgatatgtag | agaggaatag | gggttagttt atgtttatat | 4560 |
| tgaaaaactt | taaagactat | ttggaagttc | cagaaattct | ggttttaatt caagtaaaat | 4620 |
| gataaaatag | tcattatata | gttcagatgc | taatattcta | agtaataata tatatttaca | 4680 |
| ttgaagctaa | aactgttaag | caaaacaatg | cccatttgtc | ggcttacagc tcttccggag | 4740 |
| tctagagcct | gttggtgttc | tgtccctact | ttaagaattt | aattgctcac ttattctgaa | 4800 |
| agctttgttc | aaacaagatg | atattaaatt | tgttttcact | aaaactactg ggatatctgc | 4860 |
| ctcttgggga | ttttttttttc | aatttaataa | agcaagttg | tatatttggg gtgcttttta | 4920 |
| aaa | | | | | 4923 |

<210> SEQ ID NO 10
<211> LENGTH: 3806
<212> TYPE: DNA
<213> ORGANISM: Homo sapiens
<300> PUBLICATION INFORMATION:
<308> DATABASE ACCESSION NUMBER: NM_004244
<309> DATABASE ENTRY DATE: 2006-10-15
<313> RELEVANT RESIDUES: (1)..(3806)

<400> SEQUENCE: 10

| | | | | |
|---|---|---|---|---|
| gaattcttag | ttgttttctt | tagaagaaca | tttctaggga | ataatacaag aagatttagg | 60 |
| aatcattgaa | gttataaatc | tttggaatga | gcaaactcag | aatggtgcta cttgaagact | 120 |
| ctggatctgc | tgacttcaga | agacattttg | tcaacttgag | tcccttcacc attactgtgg | 180 |
| tcttacttct | cagtgcctgt | tttgtcacca | gttctcttgg | aggaacagac aaggagctga | 240 |
| ggctagtgga | tggtgaaaac | aagtgtagcg | ggagagtgga | agtgaaagtc caggaggagt | 300 |
| ggggaacggt | gtgtaataat | ggctggagca | tggaagcggt | ctctgtgatt tgtaaccagc | 360 |
| tgggatgtcc | aactgctatc | aaagcccctg | gatgggctaa | ttccagtgca ggttctggac | 420 |
| gcatttggat | ggatcatgtt | tcttgtcgtg | ggaatgagtc | agctctttgg gattgcaaac | 480 |

-continued

```
atgatggatg gggaaagcat agtaactgta ctcaccaaca agatgctgga gtgacctgct    540
cagatggatc caatttggaa atgaggctga cgcgtggagg gaatatgtgt tctggaagaa    600
tagagatcaa attccaagga cggtggggaa cagtgtgtga tgataacttc aacatagatc    660
atgcatctgt catttgtaga caacttgaat gtggaagtgc tgtcagtttc tctggttcat    720
ctaattttgg agaaggctct ggaccaatct ggtttgatga tcttatatgc aacggaaatg    780
agtcagctct ctggaactgc aaacatcaag gatgggaaa gcataactgt gatcatgctg     840
aggatgctgg agtgatttgc tcaaagggag cagatctgag cctgagactg gtagatggag    900
tcactgaatg ttcaggaaga ttagaagtga gattccaagg agaatggggg acaatatgtg    960
atgacggctg ggacagttac gatgctgctg tggcatgcaa gcaactggga tgtccaactg   1020
ccgtcacagc cattggtcga gttaacgcca gtaaggggatt tggacacatc tggcttgaca   1080
gcgtttcttg ccagggacat gaacctgctg tctggcaatg taaacaccat gaatggggaa   1140
agcattattg caatcacaat gaagatgctg gcgtgacatg ttctgatgga tcagatctgg   1200
agctaagact tagaggtgga ggcagccgct gtgctgggac agttgaggtg gagattcaga   1260
gactgttagg gaaggtgtgt gacagaggct ggggactgaa agaagctgat gtggtttgca   1320
ggcagctggg atgtggatct gcactcaaaa catcttatca agtgtactcc aaaatccagg   1380
caacaaacac atggctgttt ctaagtagct gtaacggaaa tgaaacttct ctttgggact   1440
gcaagaactg gcaatggggt ggacttacct gtgatcacta tgaagaagcc aaaattacct   1500
gctcagccca cagggaaccc agactggttg gaggggacat tccctgttct ggacgtgttg   1560
aagtgaagca tggtgacacg tggggctcca tctgtgattc ggacttctct ctggaagctg   1620
ccagcgttct atgcagggaa ttacagtgtg gcacagttgt ctctatcctg ggggagctc    1680 actttggaga gggaaatgga cagatctggg ctgaagaatt ccagtgtgag ggacatgagt   1740
cccatctttc actctgccca gtagcacccc gcccagaagg aacttgtagc cacagcaggg   1800
atgttggagt agtctgctca agatacacag aaattcgctt ggtgaatggc aagacccgt    1860 gtgagggcag agtggagctc aaaacgcttg gtgcctgggg atccctctgt aactctcact   1920
gggacataga agatgcccat gttctttgcc agcagcttaa atgtggagtt gccctttcta   1980
ccccaggagg agcacgtttt ggaaaaggaa atggtcagat ctggaggcat atgtttcact   2040 gcactggac tgagcagcac atgggagatt gtcctgtaac tgctctaggt gcttcattat    2100
gtccttcaga gcaagtggcc tctgtaatct gctcaggaaa ccagtcccaa acactgtcct   2160
cgtgcaattc atcgtctttg ggcccaacaa ggcctaccat tccagaagaa agtgctgtgg   2220
cctgcataga gagtggtcaa cttcgcctgg taaatggagg aggtcgctgt gctgggagag   2280
tagagatcta tcatgagggc tcctggggca ccatctgtga tgacagctgg gacctgagtg   2340
atgcccacgt ggtttgcaga cagctgggct gtggagaggc cattaatgcc actggttctg   2400
ctcattttgg ggaaggaaca gggcccatct ggctggatga gatgaatgc aatggaaaag    2460 aatcccgcat ttggcagtgc cattcacacg gctgggggca gcaaaattgc aggcacaagg   2520
aggatgcgga agttatctgc tcagaattca tgtctctgag actgaccagt gaagccagca   2580
gagaggcctg tgcagggcgt ctggaagttt tttacaatgg agcttggggc actgttggca   2640
agagtagcat gtctgaaacc actgggggtg tggtgtgcag gcagctgggc tgtgcagaca   2700
aagggaaaat caaccctgca tctttagaca aggccatgtc cattcccatg tgggtggaca   2760
atgttcagtg tccaaaagga cctgacacgc tgtggcagtg cccatcatct ccatgggaga   2820
agagactggc cagcccctcg gaggagacct ggatcacatg tgacaacaag ataagacttc   2880
```

```
aggaaggacc cacttcctgt tctggacgtg tggagatctg gcatggaggt tcctgggggra    2940 cagtgtgtga tgactcttgg gacttggacg atgctcaggt ggtgtgtcaa caacttggct    3000
gtggtccagc tttgaaagca ttcaagaag cagagtttgg tcaggggact ggaccgatat     3060
ggctcaatga agtgaagtgc aaagggaatg agtcttcctt gtgggattgt cctgccagac    3120 gctgggggcca tagtgagtgt gggcacaagg aagacgctgc agtgaattgc acagatattt   3180
cagtgcagaa aaccccacaa aaagccacaa caggtcgctc atcccgtcag tcatccttta    3240
ttgcagtcgg gatccttggg gttgttctgt tggccatttt cgtcgcatta ttcttcttga    3300
ctaaaaagcg aagacagaga cagcggcttg cagtttcctc aagaggagag aacttagtcc    3360
accaaattca ataccgggag atgaattctt gcctgaatgc agatgatctg gacctaatga    3420
attcctcaga aaattcccat gagtcagctg atttcagtgc tgctaaacta atttctgtgt    3480
ctaaatttct tcctatttct ggaatggaaa aggaggccat tctgagccac actgaaaagg    3540
aaaatgggaa tttataaccc agtgagttca gcctttaaga taccttgatg aagacctgga    3600
ctattgaatg gagcagaaat tcacctctct cactgactat tacagttgca tttttatgga    3660
gttcttcttc tcctaggatt cctaagactg ctgctgaatt tataaaaatt aagtttgtga    3720
atgtgactac ttagtggtgt atatgagact ttcaagggaa ttaaataaat aataagaat    3780 gttattgatt tgagtttgct ttaatt                                         3806

<210> SEQ ID NO 11
<211> LENGTH: 3728
<212> TYPE: DNA
<213> ORGANISM: Homo sapiens
<300> PUBLICATION INFORMATION:
<308> DATABASE ACCESSION NUMBER: NM_203416
<309> DATABASE ENTRY DATE: 2006-10-15
<313> RELEVANT RESIDUES: (1)..(3728)

<400> SEQUENCE: 11
gaattcttag ttgttttctt tagaagaaca tttctaggga ataatacaag aagatttagg      60
aatcattgaa gttataaatc tttggaatga gcaaactcag aatggtgcta cttgaagact     120
ctggatctgc tgacttcaga agacattttg tcaacttgag tcccttcacc attactgtgg     180
tcttacttct cagtgcctgt tttgtcacca gttctcttgg aggaacagac aaggagctga     240
ggctagtgga tggtgaaaac aagtgtagcg ggagagtgga agtgaaagtc caggaggagt     300
ggggaacggt gtgtaataat ggctggagca tggaagcggt ctctgtgatt tgtaaccagc     360
tgggatgtcc aactgctatc aaagcccctg gatgggctaa ttccagtgca ggttctggac    420
gcatttggat ggatcatgtt tcttgtcgtg ggaatgagtc agctctttgg gattgcaaac    480
atgatggatg gggaaagcat agtaactgta ctcaccaaca agatgctgga gtgacctgct    540
cagatggatc caatttggaa atgaggctga cgcgtggagg gaatatgtgt tctggaagaa    600
tagagatcaa attccaagga cggtggggaa cagtgtgtga tgataacttc aacatagatc    660
atgcatctgt catttgtaga caacttgaat gtggaagtgc tgtcagtttc tctggttcat    720
ctaattttgg agaaggctct ggaccaatct ggtttgatga tcttatatgc aacgaaatg    780 agtcagctct ctggaactgc aaacatcaag gatggggaaa gcataactgt gatcatgctg    840
aggatgctgg agtgatttgc tcaaagggag cagatctgag cctgagactg gtagatggag    900
tcactgaatg ttcaggaaga ttagaagtga gattccaagg agaatggggg acaatatgtg    960 atgacgctg ggacagttac gatgctgctg tggcatgcaa gcaactggga tgtccaactg   1020
ccgtcacagc cattggtcga gttaacgcca gtaagggatt tggacacatc tggcttgaca   1080
```

```
gcgtttcttg ccagggacat gaacctgctg tctggcaatg taaacaccat gaatggggaa    1140
agcattattg caatcacaat gaagatgctg gcgtgacatg ttctgatgga tcagatctgg    1200
agctaagact tagaggtgga ggcagccgct gtgctggcac agttgaggtg gagattcaga    1260
gactgttagg gaaggtgtgt gacagaggct ggggactgaa agaagctgat gtggtttgca    1320
ggcagctggg atgtggatct gcactcaaaa catcttatca agtgtactcc aaaatccagg    1380
caacaaacac atggctgttt ctaagtagct gtaacgaaaa tgaaacttct ctttgggact    1440
gcaagaactg gcaatggggt ggacttacct gtgatcacta tgaagaagcc aaaattacct    1500
gctcagccca cagggaaccc agactggttg gaggggacat tccctgttct ggacgtgttg    1560
aagtgaagca tggtgacacg tggggctcca tctgtgattc ggacttctct ctggaagctg    1620
ccagcgttct atgcagggaa ttacagtgtg cacagttgt ctctatcctg ggggagctc      1680 actttggaga gggaaatgga cagatctggg ctgaagaatt ccagtgtgag ggacatgagt    1740
cccatctttc actctgccca gtagcacccc gcccagaagg aacttgtagc cacagcaggg    1800
atgttggagt agtctgctca agatacacag aaattcgctt ggtgaatggc aagacccgt     1860 gtgagggcag agtggagctc aaaacgcttg gtgcctgggg atccctctgt aactctcact    1920
gggacataga agatgcccat gttctttgcc agcagcttaa atgtggagtt gcccttttcta   1980 ccccaggagg agcacgtttt ggaaaaggaa atggtcagat ctggaggcat atgtttcact    2040
gcactgggac tgagcagcac atgggagatt gtcctgtaac tgctctaggt gcttcattat    2100
gtccttcaga gcaagtggcc tctgtaatct gctcaggaaa ccagtcccaa acactgtcct    2160
cgtgcaattc atcgtctttg ggcccaacaa ggcctaccat tccagaagaa agtgctgtgg    2220
cctgcataga gagtggtcaa cttcgcctgg taaatggagg aggtcgctgt gctgggagag    2280
tagagatcta tcatgagggc tcctggggca ccatctgtga tgacagctgg gacctgagtg    2340
atgcccacgt ggtttgcaga cagctgggct gtggagaggc cattaatgcc actggttctg    2400 ctcatttttgg ggaaggaaca gggcccatct ggctggatga gatgaaatgc aatggaaaag   2460
aatcccgcat ttggcagtgc cattcacacg gctgggggca gcaaaattgc aggcacaagg    2520
aggatgcggg agttatctgc tcagaattca tgtctctgag actgaccagt gaagccagca    2580
gagaggcctg tgcagggcgt ctggaagttt tttacaatgg agcttggggc actgttggca    2640
agagtagcat gtctgaaacc actgtgggtg tggtgtgcag gcagctgggc tgtgcagaca    2700
aagggaaaat caaccctgca tctttagaca aggccatgtc cattcccatg tgggtggaca    2760
atgttcagtg tccaaaagga cctgacacgc tgtggcagtg cccatcatct ccatgggaga    2820
agagactggc cagcccctcg gaggagacct ggatcacatg tgacaacaag ataagacttc    2880
aggaaggacc cacttcctgt tctggacgtg tggagatctg gcatggaggt tcctggggga    2940
cagtgtgtga tgactcttgg gacttggacg atgctcaggt ggtgtgtcaa caacttggct    3000
gtggtccagc tttgaaagca ttcaaagaag cagagtttgg tcaggggact ggaccgatat    3060
ggctcaatga agtgaagtgc aaagggaatg agtcttcctt gtgggattgt cctgccagac    3120
gctgggccca tagtgagtgt gggcacaagg aagacgctgc agtgaattgc acagatattt    3180
cagtgcagaa aaccccacaa aaagccacaa caggtcgctc atcccgtcag tcatccttta    3240
ttgcagtcgg gatccttggg gttgttctgt tggccatttt cgtcgcatta ttcttcttga    3300
ctaaaaagcg aagacagaga cagcggcttg cagtttcctc aagaggagag aacttagtcc    3360
accaaattca ataccgggag atgaattctt gcctgaatgc agatgatctg gacctaatga    3420
attcctcagg aggccattct gagccacact gaaaaggaaa atgggaattt ataacccagt    3480
```

```
gagttcagcc tttaagatac cttgatgaag acctggacta ttgaatggag cagaaattca    3540
cctctctcac tgactattac agttgcattt ttatggagtt cttcttctcc taggattcct    3600
aagactgctg ctgaatttat aaaaattaag tttgtgaatg tgactactta gtggtgtata    3660
tgagactttc aagggaatta aataaataaa taagaatgtt attgatttga gtttgcttta    3720
attacttg                                                             3728
```

<210> SEQ ID NO 12
<211> LENGTH: 836
<212> TYPE: DNA
<213> ORGANISM: Homo sapiens
<300> PUBLICATION INFORMATION:
<308> DATABASE ACCESSION NUMBER: NM_002038
<309> DATABASE ENTRY DATE: 2006-08-20
<313> RELEVANT RESIDUES: (1)..(836)

<400> SEQUENCE: 12

```
ccagccttca gccggagaac cgtttactcg ctgctgtgcc catctatcag caggctccgg      60
gctgaagatt gcttctcttc tcctccaa ggtctagtga cggagcccgc gcgcggcgcc       120
accatgcggc agaaggcggt atcgcttttc ttgtgctacc tgctgctctt cacttgcagt     180
ggggtggagg caggtaagaa aaagtgctcg agagctcgg acagcggctc cgggttctgg      240
aaggccctga ccttcatggc cgtcggagga ggactcgcag tcgccgggct gcccgcgctg    300
ggcttcaccg gcgccggcat cgcggccaac tcggtggctg cctcgctgat gagctggtct    360
gcgatcctga atgggggcgg cgtgcccgcc ggggggctag tggccacgct gcagagcctc    420
ggggctggtg gcagcagcgt cgtcataggt aatattggtg ccctgatggg ctacgccacc    480
cacaagtatc tcgatagtga ggaggatgag gagtagccag cagctcccag aacctcttct    540
tccttcttgg cctaactctt ccagttagga tctagaactt tgcctttttt tttttttttt    600
tttttttgag atgggttctc actatattgt ccaggctaga gtgcagtggc tattcacaga    660
tgcgaacata gtacactgca gcctccaact cctagcctca agtgatcctc ctgtctcaac    720
ctcccaagta ggattacaag catgcgccga cgatgcccag aatccagaac tttgtctatc    780
actctcccca caaacctaga tgtgaaaaca gaataaactt cacccagaaa acactt        836
```

<210> SEQ ID NO 13
<211> LENGTH: 848
<212> TYPE: DNA
<213> ORGANISM: Homo sapiens
<300> PUBLICATION INFORMATION:
<308> DATABASE ACCESSION NUMBER: NM_022872
<309> DATABASE ENTRY DATE: 2006-08-20
<313> RELEVANT RESIDUES: (1)..(848)

<400> SEQUENCE: 13

```
ccagccttca gccggagaac cgtttactcg ctgctgtgcc catctatcag caggctccgg      60
gctgaagatt gcttctcttc tcctccaa ggtctagtga cggagcccgc gcgcggcgcc       120
accatgcggc agaaggcggt atcgcttttc ttgtgctacc tgctgctctt cacttgcagt     180
ggggtggagg caggtgagaa tgcgggtaag aaaaagtgct cggagagctc ggacagcggc    240
tccgggttct ggaaggccct gaccttcatg gccgtcggag gaggactcgc agtcgccggg    300
ctgcccgcgc tgggcttcac cggcgccggc atcgcggcca actcggtggc tgcctcgctg    360
atgagctggt ctgcgatcct gaatgggggc ggcgtgcccg ccggggggct agtggccacg    420
ctgcagagcc tcggggctgg tggcagcagc gtcgtcatag gtaatattgg tgccctgatg    480
ggctacgcca cccacaagta tctcgatagt gaggaggatg aggagtagcc agcagctccc    540
```

```
agaacctctt cttccttctt ggcctaactc ttccagttag gatctagaac tttgcctttt      600 ttttttttt tttttttttg agatgggttc tcactatatt gtccaggcta gagtgcagtg      660
gctattcaca gatgcgaaca tagtacactg cagcctccaa ctcctagcct caagtgatcc     720
tcctgtctca acctcccaag taggattaca agcatgcgcc gacgatgccc agaatccaga     780
actttgtcta tcactctccc caacaaccta gatgtgaaaa cagaataaac ttcacccaga     840
aaacactt                                                              848

<210> SEQ ID NO 14
<211> LENGTH: 860
<212> TYPE: DNA
<213> ORGANISM: Homo sapiens
<300> PUBLICATION INFORMATION:
<308> DATABASE ACCESSION NUMBER: NM_022873
<309> DATABASE ENTRY DATE: 2006-08-20
<313> RELEVANT RESIDUES: (1)..(860)

<400> SEQUENCE: 14
ccagccttca gccggagaac cgtttactcg ctgctgtgcc catctatcag caggctccgg      60
gctgaagatt gcttctcttc tctcctccaa ggtctagtga cggagcccgc gcgcggcgcc     120
accatgcggc agaaggcggt atcgcttttc ttgtgctacc tgctgctctt cacttgcagt     180
ggggtggagg caggtgagaa tgcgggtaag gatgcaggta agaaaaagtg ctcggagagc     240
tcggacagcg gctccgggtt ctggaaggcc ctgaccttca tggccgtcgg aggaggactc     300
gcagtcgccg gctgcccgc gctgggcttc accggcgccg gcatcgcggc caactcggtg     360
gctgcctcgc tgatgagctg gtctgcgatc ctgaatgggg gcggcgtgcc cgccggggg      420 ctagtggcca cgctgcagag cctcggggct ggtggcagca gcgtcgtcat aggtaatatt     480
ggtgccctga tgggctacgc cacccacaag tatctcgata gtgaggagga tgaggagtag     540
ccagcagctc ccagaacctc ttcttccttc ttggcctaac tcttccagtt aggatctaga     600
actttgcctt ttttttttt ttttttttt tgagatgggt tctcactata ttgtccaggc     660
tagagtgcag tggctattca cagatgcgaa catagtacac tgcagcctcc aactcctagc     720
ctcaagtgat cctcctgtct caacctccca agtaggatta caagcatgcg ccgacgatgc     780
ccagaatcca gaactttgtc tatcactctc cccaacaacc tagatgtgaa aacagaataa     840 acttcacccca gaaaacactt                                                 860

<210> SEQ ID NO 15
<211> LENGTH: 4894
<212> TYPE: DNA
<213> ORGANISM: Homo sapiens
<300> PUBLICATION INFORMATION:
<308> DATABASE ACCESSION NUMBER: NM_000212
<309> DATABASE ENTRY DATE: 2006-10-08
<313> RELEVANT RESIDUES: (1)..(4894)

<400> SEQUENCE: 15
cgccgcggga ggcggacgag atgcgagcgc ggccgcggcc ccggccgctc tgggcgactg      60
tgctggcgct gggggcgctg gcgggcgttg gcgtaggagg gcccaacatc tgtaccacgc     120
gaggtgtgag ctcctgccag cagtgcctgg ctgtgagccc catgtgtgcc tggtgctctg     180
atgaggccct gctctggcgg tcacctcgct gtgacctgaa ggagaatctg ctgaaggata     240
actgtgcccc agaatccatc gagttcccag tgagtgaggc ccgagtacta gaggacaggc     300
ccctcagcga caagggctct ggagacagct cccaggtcac tcaagtcagt ccccagagga     360
ttgcactccg gctccggcca gatgattcga agaatttctc catccaagtg cggcaggtgg     420
```

-continued

```
aggattaccc tgtggacatc tactacttga tggacctgtc ttactccatg aaggatgatc    480
tgtggagcat ccagaacctg ggtaccaagc tggccaccca gatgcgaaag ctcaccagta    540
acctgcggat tggcttcggg gcatttgtgg acaagcctgt gtcaccatac atgtatatct    600
ccccaccaga ggccctcgaa acccctgct atgatatgaa gaccacctgc ttgcccatgt     660
ttggctacaa acacgtgctg acgctaactg accaggtgac ccgcttcaat gaggaagtga    720
agaagcagag tgtgtcacgg aaccgagatg ccccagaggg tggctttgat gccatcatgc    780
aggctacagt ctgtgatgaa aagattggct ggaggaatga tgcatcccac ttgctggtgt    840
ttaccactga tgccaagact catatagcat ggacggaaag gctggcaggc attgtccagc    900
ctaatgacgg gcagtgtcat gttggtagtg acaatcatta ctctgcctcc actaccatgg    960
attatccctc tttggggctg atgactgaga agctatccca gaaaaacatc aatttgatct   1020
ttgcagtgac tgaaaatgta gtcaatctct atcagaacta tagtgagctc atcccaggga   1080
ccacagttgg ggttctgtcc atggattcca gcaatgtcct ccagctcatt gttgatgctt   1140
atgggaaaat ccgttctaaa gtagagctgg aagtgcgtga cctccctgaa gagttgtctc   1200
tatccttcaa tgccacctgc ctcaacaatg aggtcatccc tggcctcaag tcttgtatgg   1260
gactcaagat tggagacacg gtgagcttca gcattgaggc caaggtgcga ggctgtcccc   1320
aggagaagga gaagtccttt accataaagc ccgtgggctt caaggacagc ctgatcgtcc   1380
aggtcacctt tgattgtgac tgtgcctgcc aggcccaagc tgaacctaat agccatcgct   1440
gcaacaatgg caatgggacc tttgagtgtg gggtatgccg ttgtgggcct ggctggctgg   1500
gatcccagtg tgagtgctca gaggaggact atcgcccttc ccagcaggac gaatgcagcc   1560
cccgggaggg tcagcccgtc tgcagccagc ggggcgagtg cctctgtggt caatgtgtct   1620
gccacagcag tgactttggc aagatcacgg gcaagtactg cgagtgtgac gacttctcct   1680
gtgtccgcta caaggggag atgtgctcag ccatggcca gtgcagctgt ggggactgcc    1740
tgtgtgactc cgactggacc ggctactact gcaactgtac cacgcgtact gacacctgca   1800
tgtccagcaa tgggctgctg tgcagcggcc gcggcaagtg tgaatgtggc agctgtgtct   1860
gtatccagcc gggctcctat ggggacacct gtgagaagtg ccccacctgc ccagatgcct   1920 gcaccttta gaaagaatgt gtggagtgta agaagtttga ccggggagcc ctacatgacg    1980
aaaatacctg caaccgttac tgccgtgacg agattgagtc agtgaaagag cttaaggaca   2040
ctggcaagga tgcagtgaat tgtacctata gaatgagga tgactgtgtc gtcagattcc    2100
agtactatga agattctagt ggaaagtcca tcctgtatgt ggtagaagag ccagagtgtc   2160
ccaagggccc tgacatcctg gtggtcctgc tctcagtgat gggggccatt ctgctcattg   2220
gccttgccgc cctgctcatc tggaaactcc tcatcaccat ccacgaccga aaagaattcg   2280
ctaaatttga ggaagaacgc gccagagcaa atgggacac agccaacaac ccactgtata   2340
aagaggccac gtctaccttc accaatatca cgtaccgggg cacttaatga taagcagtca   2400
tcctcagatc attatcagcc tgtgccacga ttgcaggagt ccctgccatc atgtttacag   2460
aggacagtat ttgtggggag ggatttgggg ctcagagtgg ggtaggttgg gagaatgtca   2520
gtatgtggaa gtgtgggtct gtgtgtgtgt atgtgggggt ctgtgtgttt atgtgtgtgt   2580
gttgtgtgtg ggagtgtgta atttaaaatt gtgatgtgtc ctgataagct gagctcctta   2640
gcctttgtcc cagaatgcct cctgcaggga ttcttcctgc ttagcttgag ggtgactatg   2700
gagctgagca ggtgttcttc attacctcag tgagaagcca gctttcctca tcaggccatt   2760
gtccctgaag agaagggcag ggctgaggcc tctcattcca gaggaaggga caccaagcct   2820
```

```
tggctctacc ctgagttcat aaatttatgg ttctcaggcc tgactctcag cagctatggt    2880
aggaactgct gggcttggca gcccgggtca tctgtacctc tgcctccttt ccctccctc    2940
aggccgaagg aggagtcagg gagagctgaa ctattagagc tgcctgtgcc ttttgccatc    3000
ccctcaaccc agctatggtt ctctcgcaag ggaagtcctt gcaagctaat tctttgacct    3060
gttgggagtg aggatgtctg ggccactcag gggtcattca tggcctgggg gatgtaccag    3120
catctcccag ttcataatca caaccctttca gatttgcctt attggcagct ctactctgga    3180
ggtttgttta aagaagtgt gtcacccctta ggccagcacc atctctttac ctcctaattc    3240
cacaccctca ctgctgtaga catttgctat gagctgggga tgtctctcat gaccaaatgc    3300
ttttcctcaa agggagagag tgctattgta gagccagagg tctggcccta tgcttccggc    3360
ctcctgtccc tcatccatag cacctccaca tacctggccc tgtgccttgg tgtgctgtat    3420
ccatccatgg ggctgattgt atttaccttc tacctcttgg ctgccttgtg aaggaattat    3480
tcccatgagt tggctgggaa taagtgccag gatggaatga tgggtcagtt gtatcagcac    3540
gtgtggcctg ttcttctatg ggttggacaa cctcatttta actcagtctt taatctgaga    3600
ggccacagtg caattttatt ttattttcct catgatgagg ttttcttaac ttaaaagaac    3660
atgtatataa acatgcttgc attatatttg taaatttatg tgatggcaaa gaaggagagc    3720
ataggaaacc acacagactt gggcagggta cagacactcc cacttggcat cattcacagc    3780
aagtcactgg ccagtggctg gatctgtgag gggctctctc atgatagaag gctatgggga    3840
tagatgtgtg gacacattgg accttttcctg aggaagaggg actgttcttt tgtcccagaa    3900
aagcagtggc tccattggtg ttgacataca tccaacatta aaagccaccc ccaaatgccc    3960
aagaaaaaaa gaaagactta tcaacatttg ttccatgagc agaaaactgg agctctggcc    4020
tcagtgttac agctaaataa tctttaatta aggcaagtca ctttcttctt cttaaagctg    4080
ttttctagtt tgagaaatga tgggatttta gcagccagtc ttgaaggtct ctttcagtat    4140
caacattcta agatgctggg acttactgtg tcatcaaatg tgcggttaag attctctggg    4200
atattgatac tgtttgtgtt tttagttggg agatctgaga gacctggctt tggcaagagc    4260
agatgtcatt ccatatcacc tttctcaatg aaagtctcat tctatcctct ctccaaaccc    4320
gttttccaac atttgttaat agttacgtct ctcctgatgt agcacttaag cttcatttag    4380
ttattatttc tttcttcact ttgcacacat ttgcatccac atattaggga agaggaatcc    4440
ataagtagct gaaatatcta ttctgtatta ttgtgttaac attgagaata agccttggaa    4500
ttagatatgg ggcaatgact gagccctgtc tcacccatgg attactcctt actgtaggga    4560
atggcagtat ggtagaggga taaataggggg gcggggaggg atagtcatgg atccaagaag    4620
tccttagaaa tagtggcagg gaacaggtgt ggaagctcat gcctgtaatt ataaccttca    4680
gctactaaga caggtgtggt ggctcacgcc tgtgattata atcttcagtt actaagacag    4740
agtccatgag agtgttaatg ggacatttt tttagataag atgtttttata tgaagaaact    4800
gtatcaaagg gggaagaaaa tgtatttaac aggtgaatca aatcaggaat cttgtctgag    4860
ctactggaat gaagttcaca ggtcttgaag acca                              4894
```

<210> SEQ ID NO 16
<211> LENGTH: 1574
<212> TYPE: DNA
<213> ORGANISM: Homo sapiens
<300> PUBLICATION INFORMATION:
<308> DATABASE ACCESSION NUMBER: NM_001001522
<309> DATABASE ENTRY DATE: 2006-10-15
<313> RELEVANT RESIDUES: (1)..(1574)

<400> SEQUENCE: 16

```
tcaccacggc ggcagccctt taaacccctc acccagccag cgccccatcc tgtctgtccg      60
aacccagaca caagtcttca ctccttcctg cgagccctga ggaagccttg tgagtgcatt     120
ggctggggct tggagggaag ttgggctgga gctggacagg agcagtgggt gcatttcagg     180
caggctctcc tgaggtccca ggcgccagct ccagctccct ggctagggaa acccacccctc    240
tcagtcagca tgggggccca agctccaggc agggtgggct ggatcactag cgtcctggat     300
ctctctcaga ctgggcagcc ccgggctcat tgaaatgccc cggatgactt ggctagtgca     360
gaggaattga tggaaaccac cggggtgaga gggaggctcc ccatctcagc cagccacatc     420
cacaaggtgt gtgtaagggt gcaggcgccg gccggttagg ccaaggctct actgtctgtt     480
gcccctccag gagaacttcc aaggagcttt cccagacat  ggccaacaag ggtccttcct     540
atggcatgag ccgcgaagtg cagtccaaaa tcgagaagaa gtatgacgag gagctggagg     600
agcggctggt ggagtggatc atagtgcagt gtggccctga tgtgggccgc ccagaccgtg     660
ggcgcttggg cttccaggtc tggctgaaga tggcgtgat  tctgagcaag ctggtgaaca     720
gcctgtaccc tgatggctcc aagccggtga aggtgcccga gaaccacccc tccatggtct     780
tcaagcagat ggagcaggtg gctcagttcc tgaaggcggc tgaggactat ggggtcatca     840
agactgacat gttccagact gttgacctct tgaaggcaa  agacatggca gcagtgcaga     900
ggaccctgat ggctttgggc agcttggcag tgaccaagaa tgatgggcac taccgtggag     960
atcccaactg gtttatgaag aaagcgcagg agcataagag ggaattcaca gagagccagc    1020
tgcaggaggg aaagcatgtc attggccttc agatgggcag caacagaggg gcctcccagg    1080
ccggcatgac aggctacgga cgacctcggc agatcatcag ttagagcgga gagggctagc    1140
cctgagcccg gccctccccc agctccttgg ctgcagccat cccgcttagc ctgcctcacc    1200
cacacccgtg tggtaccttc agccctggcc aagctttgag gctctgtcac tgagcaatgg    1260
taactgcacc tgggcagctc ctccctgtgc cccagcctc  agcccaactt cttacccgaa    1320
agcatcactg ccttggcccc tccctcccgg ctgcccccat cacctctact gtctcctccc    1380
tgggctaagc aggggagaag cgggctgggg gtagcctgga tgtgggccaa gtccactgtc    1440
ctccttggcg gcaaaagccc attgaagaag aaccagccca gcctgccccc tatcttgtcc    1500
tggaatattt ttgggggttgg aactcaaaaa aaaaaaaaaa aaatcaatct tttctcaaaa    1560
aaaaaaaaaa aaaa                                                       1574
```

<210> SEQ ID NO 17
<211> LENGTH: 1177
<212> TYPE: DNA
<213> ORGANISM: Homo sapiens
<300> PUBLICATION INFORMATION:
<308> DATABASE ACCESSION NUMBER: NM_003186
<309> DATABASE ENTRY DATE: 2006-10-15
<313> RELEVANT RESIDUES: (1)..(1177)

<400> SEQUENCE: 17

```
tcaccacggc ggcagccctt taaacccctc acccagccag cgccccatcc tgtctgtccg      60
aacccagaca caagtcttca ctccttcctg cgagccctga ggaagccttc tttccccaga     120
catggccaac aagggtcctt cctatggcat gagccgcgaa gtgcagtcca aaatcgagaa     180
gaagtatgac gaggagctgg aggagcggct ggtggagtgg atcatagtgc agtgtggccc     240
tgatgtgggc cgcccagacc gtgggcgctt gggcttccag gtctggctga agaatggcgt    300
gattctgagc aagctggtga acagcctgta ccctgatggc tccaagccgg tgaaggtgcc    360
```

```
cgagaaccca ccctccatgg tcttcaagca gatggagcag gtggctcagt tcctgaaggc      420
ggctgaggac tatggggtca tcaagactga catgttccag actgttgacc tctttgaagg      480
caaagacatg gcagcagtgc agaggaccct gatggctttg gcagcttgg cagtgaccaa       540 gaatgatggg cactaccgtg agatcccaa ctggtttatg aagaaagcgc aggagcataa       600
gagggaattc acagagagcc agctgcagga gggaaagcat gtcattggcc ttcagatggg      660
cagcaacaga ggggcctccc aggccggcat gacaggctac ggacgacctc ggcagatcat      720
cagttagagc ggagagggct agccctgagc ccggccctcc cccagctcct tggctgcagc      780
catcccgctt agcctgcctc acccacaccc gtgtggtacc ttcagccctg ccaagctttt     840
gaggctctgt cactgagcaa tggtaactgc acctgggcag ctcctccctg tgccccagc      900 ctcagcccaa cttcttaccc gaaagcatca ctgccttggc cctccctcc cggctgcccc     960 catcacctct actgtctcct ccctgggcta agcaggggag aagcgggctg ggggtagcct    1020
ggatgtgggc caagtccact gtcctccttg gcggcaaaag cccattgaag aagaaccagc    1080
ccagcctgcc ccctatcttg tcctggaata ttttttgggt tggaactcaa aaaaaaaaa     1140 aaaaaatcaa tcttttctca aaaaaaaaaa aaaaaa                              1177
```

<210> SEQ ID NO 18
<211> LENGTH: 985
<212> TYPE: DNA
<213> ORGANISM: Homo sapiens
<300> PUBLICATION INFORMATION:
<308> DATABASE ACCESSION NUMBER: NM_001785
<309> DATABASE ENTRY DATE: 2006-08-20
<313> RELEVANT RESIDUES: (1)..(985)

<400> SEQUENCE: 18

```
caaaccatgg gaggctcctc tcctagaccc tgcatcctga aagctgcgta cctgagagcc       60
tgcggtctgg ctgcagggac acacccaagg ggaggagctg caatcgtgtc tggggcccca      120
gcccaggctg gccggagctc ctgtttccg ctgctctgct gcctgccgg ggtaccaaca        180 tggcccagaa gcgtcctgcc tgcaccctga gcctgagtg tgtccagcag ctgctggttt      240
gctcccagga ggccaagaag tcagcctact gccctacag tcactttcct gtggggctg       300 ccctgctcac ccaggagggg agaatcttca aagggtgcaa catagaaaat gcctgctacc     360
cgctgggcat ctgtgctgaa cggaccgcta tccagaaggc cgtctcagaa gggtacaagg     420
atttcagggc aattgctatc gccagtgaca tgcaagatga tttatctct ccatgtgggg      480 cctgcaggca agtcatgaga gagttttggca ccaactggcc cgtgtacatg accaagccgg    540
atggtacgta tattgtcatg acggtccagg agctgctgcc ctcctccttt gggcctgagg     600
acctgcagaa gacccagtga cagccagaga atgcccactg cctgtaacag ccacctggag     660
aacttcataa agatgtctca cagccctggg gacacctgcc cagtgggccc cagccctaca     720
gggactgggc aaagatgatg tttccagatt acactccagc ctgagtcagc accctcctg      780 gcaacctgcc ttgggactta gaacaccgcc gccccctgcc ccacctttcc tttccttcct    840
gtgggccctc tttcaaagtc cagcctagtc tggactgctt ccccatcagc cttcccaagg    900
ttctatcctg ttccgagcaa cttttctaat tataaacatc acagaacatc ctggatcaaa    960
aaaaaaaaaa aaaaaaaaa aaaaa                                            985
```

<210> SEQ ID NO 19
<211> LENGTH: 1828
<212> TYPE: DNA
<213> ORGANISM: Homo sapiens
<300> PUBLICATION INFORMATION:

<308> DATABASE ACCESSION NUMBER: NM_013314
<309> DATABASE ENTRY DATE: 2006-10-15
<313> RELEVANT RESIDUES: (1)..(1828)

<400> SEQUENCE: 19

```
acttctccct agagcagggg tgtttgccag cagcctgcac tctcagaaat cagacttgag      60
tggccggaac ccttgagacc agaggcttac catgctgctc cctaggaggg ccaggaactg     120
ctgacgtgac cactgacag ttattcgtgt ctcttacaat taccaaacag aatggacaag     180
cttaataaaa taaccgtccc cgccagtcag aagttgaggc agcttcaaaa gatggtccat     240
gatattaaaa acaatgaagg tggaataatg aataaaatca aaaagctaaa agtcaaagca     300
cctccaagtg ttcctcgaag ggactacgct tcagagagcc ctgctgacga agaggagcag     360
tggtccgatg actttgacag cgactatgaa atccagatg agcactcgga ctcagagatg     420
tacgtgatgc ccgccgagga gaacgctgat gacagctacg agccgcctcc agtagagcag     480
gaaaccaggc cggttcaccc agccctgccc ttcgccagag gcgagtatat agacaatcga     540
tcaagccaga ggcattcccc acccttcagc aagacacttc ccagtaagcc cagctggcct     600
tcagagaaag caaggctcac ctccacctg ccggccctga ctgctttgca gaaacctcaa     660
gtcccaccca acccaaagg cctccttgag gatgaggctg attatgtggt ccccgtggaa     720
gataatgatg aaaactatat tcatcccaca gaaagcagtt cacctccacc tgaaaaagct     780
cccatggtga atagatcaac caagccaaat tcctcaacgc ccgcctctcc tccaggaaca     840
gcttcaggtc gaaacagtgg ggcctgggaa accaagtcac ctccaccagc tgcaccatcc     900
ccgttgccac gggccgggaa aaaccaacg acaccactga agacaactcc agttgcctct     960
caacagaatg cttcaagtgt tgtgaagaa aaacctatac ctgctgaacg ccaccgaggg    1020
tcaagtcaca gacaagaagc tgtgcagtca ccagtgtttc ctcctgccca gaaacaaatc    1080
caccaaaaac ccatacctct gccaagattt acagaagggg gaaacccaac tgtggatggg    1140
ccctacccca gcttttcatc taattccact atttcagaac aggaagctgg cgttctctgc    1200
aagccatggt atgctggagc ctgtgatcga agtctgctg aagaggcatt gcacagatca    1260
aacaaggatg gatcatttct tattcggaaa agctctggcc atgattccaa caaccatat    1320
acactagttg tattctttaa taagcgagta tataatattc ctgtgcgatt tattgaagca    1380
acaaaacaat atgccttggg cagaaagaaa atggtgaag agtactttgg aagtgttgct    1440
gaaatcatca ggaatcatca acatagtcct ttggttctta ttgacagtca gaataacaca    1500
aaagattcca ccagactgaa gtatgcagtt aaagtttcat aaaggggaa aaaaagatc    1560
aataccattg cttcagacac tttcccaaag tttctccttt tgagaaaaag tcccaaaact    1620
tcatattttg gattatgaat catccagtaa taaaatggaa gatggagtca gctattgaag    1680
tggtcatcca tttcttttta agaagctcat gtggacttgt tctattgcct gacctgatga    1740
actgttaata tctggtgagg ttgagttatc atgctactaa tattttccaa ataaatattt    1800
ttattttaa aaataaaaa aaaaaaaa                                         1828
```

<210> SEQ ID NO 20
<211> LENGTH: 1364
<212> TYPE: DNA
<213> ORGANISM: Homo sapiens
<300> PUBLICATION INFORMATION:
<308> DATABASE ACCESSION NUMBER: NM_002262
<309> DATABASE ENTRY DATE: 2006-08-20
<313> RELEVANT RESIDUES: (1)..(1364)

<400> SEQUENCE: 20

```
ctgtattgtg gttcctggaa cactttagag gcttgtgatt ctactgcttc ttattcacac      60
tataatacat gtctcaccaa tagatgattc aagaacatca tttaaataca caattttca      120
ttctctattt ttgctaaatt tcttcatact caactttcag attctttaat ctccagctca     180
gcttcaacaa ttcaacgctg ttctttctga aaaagtacac atcgtgcctt ctctacttcg     240
ctcttggaac ataatttctc atggcagtgt ttaagaccac tctgtggagg ttaatttctg     300
ggacctttagg gataatatgc ctttcgttga tggctacgtt gggaattttg ttgaaaaatt    360
cttttactaa actgagtatt gagccagcat ttactccagg acccaacata gaactccaga     420
aagactctga ctgctgttct tgccaagaaa aatgggttgg gtaccggtgc aactgttact     480
tcatttccag tgaacagaaa acttggaacg aaagtcggca tctctgtgct tctcagaaat     540
ccagcctgct tcagcttcaa aacacagatg aactggattt tatgagctcc agtcaacaat     600
tttactggat tggactctct tacagtgagg agcacaccgc ctggttgtgg gagaatggct     660
ctgcactctc ccagtatcta tttccatcat ttgaaacttt taatacaaag aactgcatag     720
cgtataatcc aaatggaaat gctttagatg aatcctgtga agataaaaat cgttatatct     780
gtaagcaaca gctcatttaa atgtttcttg gggcagagaa ggtggagagt aaagacccaa     840
cattactaac aatgatacag ttgcatgtta tattattact aattgtctac ttctggagtc     900
tataaaatgt ttttaaacag tgtcatatac aattgtcatg tatgtgaaac aatgtgtttt     960
aaaattgatg aaattcgttc acctacattt gagaattata aaattaacat aaagaatttt    1020
gtattttcat ttaatgtata taatgttaaa ttcaatgtag ttttattaca catttatgta    1080
attttattta cattcttgct aattctcagc agaaatttaa ataagattta attcacatca    1140
aataaaattt agaaaataaa atttaactca cactgcccag gctggagcat agtggcaaga    1200
tcatagctca ttgcaagctc aagtgatcct cctgactcag cctcccaagt agctaggact    1260
gcaggcacca tgtcactatg cccgactaat ttttaatttt taattttttg tcaagacaag    1320
gtcttgctat gttgcccagg ctggtcttga actcctggcc tcaa                     1364

<210> SEQ ID NO 21
<211> LENGTH: 1271
<212> TYPE: DNA
<213> ORGANISM: Homo sapiens
<300> PUBLICATION INFORMATION:
<308> DATABASE ACCESSION NUMBER: NM_007334
<309> DATABASE ENTRY DATE: 2006-08-20
<313> RELEVANT RESIDUES: (1)..(1271)

<400> SEQUENCE: 21
ctgtattgtg gttcctggaa cactttagag gcttgtgatt ctactgcttc ttattcacac      60
tataatacat gtctcaccaa tagatgattc aagaacatca tttaaataca caattttca      120
ttctctattt ttgctaaatt tcttcatact caactttcag attctttaat ctccagctca     180
gcttcaacaa ttcaacgctg ttctttctga aaaagtacac atcgtgcctt ctctacttcg     240
ctcttggaac ataatttctc atggcagctt ttactaaact gagtattgag ccagcattta     300
ctccaggacc caacatagaa ctccagaaag actctgactg ctgttcttgc caagaaaat     360
gggttgggta ccggtgcaac tgttacttca tttccagtga acagaaaact tggaacgaaa     420
gtcggcatct ctgtgcttct cagaaatcca gcctgcttca gcttcaaaac acagatgaac     480
tggattttat gagctccagt caacaatttt actggattgg actctcttac agtgaggagc     540
acaccgcctg gttgtgggag aatggctctg cactctccca gtatctattt ccatcatttg     600
aaactttta tacaaagaac tgcatagcgt ataatccaaa tggaaatgct ttagatgaat     660
```

```
cctgtgaaga taaaaatcgt tatatctgta agcaacagct catttaaatg tttcttgggg    720
cagagaaggt ggagagtaaa gacccaacat tactaacaat gatacagttg catgttatat    780
tattactaat tgtctacttc tggagtctat aaaatgtttt taaacagtgt catatacaat    840
tgtcatgtat gtgaaacaat gtgttttaaa attgatgaaa ttcgttcacc tacatttgag    900
aattataaaa ttaacataaa gaattttgta ttttcattta atgtatataa tgttaaattc    960
aatgtagttt tattacacat ttatgtaatt ttatttacat tcttgctaat tctcagcaga   1020
aatttaaata agatttaatt cacatcaaat aaaatttaga aaataaaatt taactcacac   1080
tgcccaggct ggagcatagt ggcaagatca tagctcattg caagctcaag tgatcctcct   1140
gactcagcct cccaagtagc taggactgca ggcaccatgt cactatgccc gactaatttt   1200 taattttttaa ttttttgtca agacaaggtc ttgctatgtt gcccaggctg gtcttgaact   1260
cctggcctca a                                                        1271

<210> SEQ ID NO 22
<211> LENGTH: 374
<212> TYPE: DNA
<213> ORGANISM: Homo sapiens
<300> PUBLICATION INFORMATION:
<308> DATABASE ACCESSION NUMBER: NM_003543
<309> DATABASE ENTRY DATE: 2006-10-18
<313> RELEVANT RESIDUES: (1)..(374)

<400> SEQUENCE: 22
atgtctggcc gtggtaaagg tggaaaaggt tgggtaagg gaggagctaa gcgtcatcgc     60
aaggttttgc gcgataacat ccagggcatc actaagccag ctatccggcg ccttgctcgt   120
cgcggcggtg tcaagcgaat ttctggcctt atctatgagg agactcgtgg tgttctgaag   180
gtgttcctgg agaacgtgat tcgtgacgct gtcacttaca cagagcacgc caaacgcaag   240
accgtgacag caatggatgt ggtctacgcg ctgaagcgac agggacgcac tctttacggc   300
ttcggtggct aaggctcctg cttgctgcac tcttattttc attttcaacc aaaggccctt   360
ttcagggccg ccca                                                     374

<210> SEQ ID NO 23
<211> LENGTH: 13302
<212> TYPE: DNA
<213> ORGANISM: Homo sapiens
<300> PUBLICATION INFORMATION:
<308> DATABASE ACCESSION NUMBER: NM_006738
<309> DATABASE ENTRY DATE: 2006-08-20
<313> RELEVANT RESIDUES: (1)..(13302)

<400> SEQUENCE: 23
gaagcgcctg tgctctgccg agactgccgt gcccattgct cgcctcggtc gccgccgctt     60
tagccgcctc cgggggagcg gccgcctatt gtctttctcc gcggcgaagg tgaagagttg    120
tcccagctcg gcccgcgggg gagccccggg agccgcacgt gtcctgggtc atgaaactta    180
atccacagca agctccctta tatggtgatt gtgttgttac agtgctgctt gctgaagagg    240
acaaagctga agatgatgta gtgttttact tggtattttt gggttccacc ctccgtcact    300
gtacaagtac tcggaaggtc agttctgata cattggagac cattgctcct ggtcatgatt    360
gttgtgaaac agtgaaggtg cagctctgtg cttccaaaga gggccttccc gtgtttgtgg    420
tggctgaaga agactttcat ttcgtccagg atgaagcgta tgatgcagct caattcctag    480
caaccagtgc tggaaatcag caggctttga acttttacccg ttttcttgac cagtcaggac    540
ccccatctgg ggatgtgaat tcccttgata agaagttggt gctggcattc aggcacctga    600
```

```
agctgcccac ggagtggaat gtattgggga cagatcagag tttgcatgat gctggcccgc    660
gagagacatt gatgcatttt gctgtgcggc tgggactgct gaggttgacg tggttcctgt    720
tgcagaagcc aggtggccgc ggagctctca gtatccacaa ccaggaaggg gcgacgcctg    780
tgagcttggc cttggagcga ggctatcaca agctgcacca gcttctaacc gaggagaatg    840
ctggagaacc agactcctgg agcagtttat cctatgaaat accgtatgga gactgttctg    900
tgaggcatca tcgagagttg gacatctata cattaacctc tgagtctgat tcacatcatg    960
aacacccatt tcctggagac ggttgcactg gaccaatttt taaacttatg aacatccaac   1020
agcaactaat gaaaacaaac ctcaagcaga tggacagtct tatgccctta atgatgacag   1080
cacaggatcc ttccagtgcc ccagagacag atggccagtt tcttccctgt gcaccggagc   1140
ccacggaccc tcagcgactt tcttcttctg aagagactga gagcactcag tgctgcccag   1200
ggagccctgt tgcacagact gaaagtccct gtgatttgtc aagcatagtt gaggaggaga   1260
atacagaccg ttcctgtagg aagaaaaata aaggcgtgga agaaaaaggg gaagaggtgg   1320
agccagcacc tattgtggac tctggaactg tatctgatca agacagctgc cttcagagct   1380
tgcctgattg tggagtaaag ggcacggaag gcctttcgtc ctgtggaaac agaaatgaag   1440
aaactggaac aaaatcttct ggaatgccca cagaccagga gtccctgagc agtggagatg   1500
ctgtgcttca gagagacttg gtcatggagc caggcacagc ccagtattcc tctgagggtg   1560
aactgggagg catttcaaca acaaatgtca gtaccccaga cactgcaggg gaaatggaac   1620
atgggctcat gaacccagat gccactgttt ggaagaatgt gcttcaggga ggggaaagta   1680
caaaggaaag atttgagaac tctaatattg gcacagctgg agcctctgac gtgcacgtca   1740
caagtaagcc tgtggataaa atcagtgttc caaactgtgc ccctgctgcc agttccctgg   1800
atggtaacaa acctgctgag tcttcacttg catttagtaa tgaagaaacc tccactgaaa   1860
aaacagcaga aacggaaact tcacgaagtc gtgaggagag tgctgatgct ccagtagatc   1920
agaattctgt ggtgattcca gctgctgcaa aagacaagat ttcagatgga ttagaacctt   1980
atactctctt agcagcaggc ataggtgagg caatgtcacc ctcagattta gcccttcttg   2040
ggctggaaga agatgtaatg ccacaccaga actcagaaac aaattcatct catgctcaaa   2100
gccaaaaggg caaatcctca cccatttgtt ctacaactgg agacgataaa ctttgtgcag   2160
actctgcatg tcaacagaac acagtgactt ctagtgcgga tttggttgca aaactgtgtg   2220
ataacatagt tagcgagtcc gaaagcacca cagcaaggca acccagctca caagatccac   2280
ccgatgcctc ccactgtgaa gacccacagg ctcatacagt cacctctgac cctgtaaggg   2340
atacccagga acgtgcggat ttttgtcctt tcaaagtggt ggataacaaa ggccaacgaa   2400
aagatgtgaa actagataaa cctttaacaa atatgcttga ggtggtttca catccacatc   2460
cagttgtccc taaaatggag aaagaactgg tgccagacca ggcagtaata tcagacagta   2520
cttttctctct ggcaaacagt ccaggcagtg aatcagtaac caaggatgac gcactttctt   2580
ttgtcccctc ccagaaagaa aagggaacag caactcctga actacataca gctacagatt   2640
atagagatgg cccagatgga aattcgaatg agcctgatac gcggccacta gaagacaggg   2700
cagtaggcct gtccacatcc tccactgctg cagagcttca gcacgggatg gggaatacca   2760
gtctcacagg acttggtgga gagcatgagg tcccgccccc tccagcaatc ccagaagctc   2820
tgaatatcaa ggggaacact gactcttccc tgcaaagtgt gggtaaggcc actttggctt   2880
tagattcagt tttgactgaa gaaggaaaac ttctggtggt tcagaaagc tctgcagctc   2940
aggaacaaga taaggataaa gcggtgacct gttcctctat taaggaaaat gctctctctt   3000
```

```
caggaacttt gcaggaagag cagagaacac cacctcctgg acaagatact caacaatttc    3060
atgaaaaatc aatctcagct gactgtgcca aggacaaagc acttcagcta agtaattcac    3120
cgggtgcatc ctctgccttt cttaaggcag aaactgaaca taacaaggaa gtggcccac     3180 aagtctcact gctgactcaa ggtggggctg cccagagcct ggtgccacca ggagcaagtc    3240
tggccacaga gtcaaggcag gaagccttgg gggcagagca caacagctcc gctctgttgc    3300
catgtctgtt gccagatggg tctgatgggt ccgatgctct taactgcagt cagccttctc    3360
ctctggatgt tggagtgaag aacactcaat cccagggaaa aactagtgcc tgtgaggtga    3420
gtggagatgt gacggtggat gttacagggg ttaatgctct acaaggtatg gctgagccca    3480
gaagagagaa tatatcacac aacacccaag acatcctgat tccaaacgtc ttgttgagcc    3540
aagagaagaa tgccgttcta ggtttgccag tggctctaca ggacaaagct gtgactgacc    3600
cacagggagt tggaacccca gagatgatac ctcttgattg ggagaaaggg aagctggagg    3660
gagcagacca cagctgtacc atgggtgacg ctgaggaagc ccaaatagac gatgaagcac    3720
atcctgtcct actgcagcct gttgccaagg agctccccac agacatggag ctctcagccc    3780
atgatgatgg ggccccagct ggtgtgaggg aagtcatgcg agcccgcct tcaggcaggg     3840 aaaggagcac tccctctcta ccttgcatgg tctctgccca ggacgcacct ctgcctaagg    3900
gggcagactt gatagaggag gctgccagcc gtatagtgga tgctgtcatc gaacaagtca    3960
aggccgctgg agcactgctt actgagggg aggcctgtca catgtcactg tccagccctg      4020
agttgggtcc tctcactaaa ggactagaga gtgcttttac agaaaaagtg agtactttcc    4080
cacctgggga gagcctacca atgggcagta ctcctgagga agccacgggg agccttgcag    4140
gatgttttgc tggaagggag gagccagaga agatcatttt acctgtccag gggcctgagc    4200
cagcagcaga aatgccagac gtgaaagctg aagatgaagt ggattttaga gcaagttcaa    4260
tttctgaaga agtggctgta gggagcatag ctgctacact gaagatgaag caaggcccaa    4320
tgacccaggc gataaaccga gaaaactggt gtacaataga gccatgccct gatgcagcat    4380
ctcttctggc ttccaagcag agcccagaat gtgagaactt cctggatgtt ggactgggca    4440
gagagtgtac ctcaaaacaa ggtgtactta aaagagaatc tggagtgat tctgacctct       4500 ttcactcacc cagtgatgac atggacagca tcatcttccc aaagccagag gaagagcatt    4560
tggcctgtga tatcaccgga tccagttcat ccaccgatga cacggcttca ctggaccgac    4620
attcttctca tggcagtgat gtgtctctct cccagatttt aaagccaaac aggtcaagag    4680
atcggcaaag ccttgatgga ttctacagcc atgggatggg agctgagggt cgagaaagtg    4740
agagtgagcc tgctgaccca ggcgacgtgg aggaggagga gatggacagt atcactgaag    4800
tgcctgcaaa ctgctctgtc ctaaggagct ccatgcgctc tctttctccc ttccggaggc    4860
acagctgggg gctgggaaa aatgcagcca gcgatgcaga aatgaaccac cggagtatga      4920
gctggtgccc ctctggtgtg cagtactctg ctggcctgag tgctgacttt aattacagaa    4980
gtttcagtct agaaggcttg acaggaggag ctggtgtcgg aaacaagcca tcctcatctc    5040
tagaagtaag ctctgcaaat gccgaagagc tcagacaccc attcagtggt gaggaacggg    5100
ttgactcttt ggtgtcactt tcagaagagg atctggagtc agaccagaga gaacatagga    5160
tgtttgatca gcagatatgt cacagatcta agcagcaggg atttaattac tgtacatcag    5220
ccatttcctc tccattgaca aaatccatct cattaatgac aatcagccat cctggattgg    5280
acaattcacg gcccttccac agtacctttcc acaataccag tgctaatctg actgagagta    5340
taacagaaga gaactataat ttcctgccac atagcccctc caagaaagat tctgaatgga    5400
```

```
agagtggaac aaaagtcagt cgtacattca gctacatcaa gaataaaatg tctagcagca    5460
agaagagcaa agaaaaggaa aaagaaaaag ataagattaa ggagaaggag aaagattcta    5520
aagacaagga gaaagataag aagactgtca acgggcacac tttcagttcc attcctgttg    5580
tgggtcccat cagctgtagc cagtgtatga agcccttcac caacaaagat gcctatactt    5640
gtgcaaattg cagtgctttt gtccacaaag gctgccgaga agtctagcc tcctgtgcaa     5700 aggtcaaaat gaagcagccc aaagggagcc ttcaggcaca tgacacatca tcactgccca    5760
cggtcattat gagaaacaag ccctcacagc ccaaggagcg tcctcggtcc gcagtcctcc    5820
tggtggatga aaccgctacc accccaatat ttgccaatag acgatcccag cagagtgtct    5880
cgctctccaa aagtgtctcc atacagaaca ttactggagt tggcaatgat gagaacatgt    5940
caaacacctg gaaattcctg tctcattcaa cagactcact aaataaaatc agcaaggtca    6000
atgagtcaac agaatcactt actgatgagg gagtaggtac agacatgaat gaaggacaac    6060
tactgggaga cttgagatt gagtccaaac agctggaagc agagtcttgg agtcggataa       6120
tagacagcaa gtttctaaaa cagcaaaaga aagatgtggt caaacggcaa gaagtaatat    6180
atgagttgat gcagacagag tttcatcatg tccgcactct caagatcatg agtggtgtgt    6240
acagccaggg gatgatggcg gatctgcttt ttgagcagca gatggtagaa aagctgttcc    6300
cctgtttgga tgagctgatc agtatccata gccaattctt ccagaggatt ctggagcgga    6360
agaaggagtc tctggtggat aaaagtgaaa agaactttct catcaagagg ataggggatg    6420
tgcttgtaaa tcagttttca ggtgagaatg cagaacgttt aaagaagaca tatggcaagt    6480
tttgtgggca acataaccag tctgtaaact acttcaaaga cctttatgcc aaggataagc    6540
gttttcaagc ctttgtaaag aagaagatga gcagttcagt tgttagaagg cttggaattc    6600
cagagtgcat attgcttgta actcagcgga ttaccaagta cccagttta ttccaaagaa      6660 tattgcagtg taccaaagac aatgaagtgg agcaggaaga tctagcacag tccttgagcc    6720
tggtgaagga tgtgattgga gctgtagaca gcaaagtggc aagttatgaa aagaaagtgc    6780
gtctcaatga gatttataca aagacagata gcaagtcaat catgaggatg aagagtggtc    6840
agatgtttgc caaggaagat ttgaaacgga agaagcttgt acgtgatggg agtgtgtttc    6900
tgaagaatgc agcaggaagg ttgaaagagg ttcaagcagt tcttctcact gacatttag      6960 ttttccttca agaaaaagac cagaagtaca tctttgcatc attggaccag aagtcaacag    7020
tgatctcttt aaagaagctg attgtgagag aagtggcaca tgaggagaaa ggtttattcc    7080
tgatcagcat ggggatgaca gatccagaga tggtagaagt ccatgccagc tccaaagagg    7140
aacgaaacag ctggattcag atcattcagg acacaatcaa caccctgaac agagatgaag    7200
atgaaggaat tcctagtgag aatgaggaag aaaagaaaat gttggacacc agagcccgag    7260
aattaaaaga acaacttcac cagaaggacc aaaaaatcct actcttgttg gaagagaagg    7320
agatgatttt ccgggacatg gctgagtgca gcacccctct cccagaggat tgctccccaa    7380
cacatagccc tagagttctc ttccgctcca acacagaaga ggctctcaaa ggaggacctt    7440
taatgaaaag tgcaataaat gaggtggaga tccttcaggg tttggtgagt ggaaatctgg    7500
gaggcacact tgggccgact gtcagcagcc ccattgagca agatgtggtc ggtcccgttt    7560
ccctgccccg gagagcagag acctttggag gatttgacag ccatcagatg aatgcttcaa    7620
aaggaggcga gaaggaagag ggagatgatg gccaagatct taggagaacg gaatcagata    7680
gtggcctaaa aaagggtgga aatgctaacc tggtatttat gcttaaaaga aacagtgagc    7740
aggttgtcca gagcgttgtt catctctacg agctcctcag cgctctgcag ggtgtggtgc    7800
```

```
tgcagcagga cagctacatt gaggaccaga aactggtgct gagcgagagg gcgctcactc    7860
gcagcttgtc ccgcccgagc tccctcattg agcaggagaa gcagcgcagc ctggagaagc    7920
agcgccagga cctggccaac ctgcagaagc agcaggccca gtacctcgag gagaagcgca    7980
ggcgcgagcg tgagtgggaa gctcgtgaga gggagctgcg ggagcgggag gccctcctgg    8040
cccagcgcga ggaggaggtg cagcaggggc agcaggacct ggaaaaggag cgggaggagc    8100
tccagcagaa gaagggcaca taccagtatg acctggagcg actgcgtgct gcccagaaac    8160
agcttgagag ggaacaggag cagctgcgcc gggaggcaga gcggctcagc cagcggcaga    8220
cagaacggga cctgtgtcag gtttcccatc cacataccaa gctgatgagg atcccatcgt    8280
tcttccccag tcctgaggag cccccctcgc catctgcacc ttccatagcc aaatcagggt    8340
cattggactc agaactttca gtgtcccaa aaaggaacag catctctcgg acacacaaag     8400
ataaggggcc ttttcacata ctgagttcaa ccagccagac aaacaaagga ccagaagggc    8460
agagccaggc ccctgcgtcc acctctgcct ctacccgcct gtttgggtta acaaagccaa    8520
aggaaaagaa ggagaaaaaa aagaagaaca aaaccagccg ctctcagccc ggtgatggtc    8580
ccgcgtcaga agtatcagca gagggtgaag agatcttctg ctgaccctct tcctctctgc    8640
tgaggcagct gcctcctgat cctggccagc ccacctctcc tgctgtcccc gcgtgcacaa    8700
gtctcttaca ctggacgccc actgctcctc agcgtccagt cctcctgggc ggccccaggt    8760
cctggacaat aagcaacaga tgatattgag tgtcgggtgg ggaaggaggc ccagactctg    8820
cttcggccat gatttgtgac tgcccaggac tctcaggttg ggctggccct actcaggatt    8880
acactgaaag taatggcctc gtaagtacag gtgatggttt tggacacgtc aggaattcct    8940
aaaggctgaa agagtgtatc caagtaaggt ctgaacctcc gaatgccttt tatttggggg    9000
aacacaaaac caaacagcag atgttttgga cttgatctgt gtacgtacat ggggacctgt    9060
ctgcatatac acacgggaa tgccagaaga aggcccagtc tgcaccaggc gtctggtcaa     9120
cttagcacaa gggcagtgcc tggacggacc cggagccccc gcatatcagc agttcaccca    9180
gtactcctca gagactggtt tccctctaaa cccatcccgg gcacatacca cccgtgtttt    9240
gcatgtattt ctcatttcat tttagggatg acaaacattt gtgaaaccag tgagagaagg    9300
cttgatgtgt ataaaagacg tgatgtgcac cacctcgatc tcggtgtttc aggcactaaa    9360
gcaacaaaac aacccatagt atctcattct gtcatcagat ccagaagaaa tatcctggtt    9420
ttccagcatg tttacccaca tgttttggcc atggataaag tgaagaggcc tactcaccat    9480
tatccctgca gcgtgacacc ttttgattgt cactgaccac tcagaagggg ccacggcctc    9540
ctggctgtgt tcctgagccc ccgtcgtgcc tctcccagac agcagctgtc tggcccttgc    9600
tgggtgaggg cacaccactg ccaggggtca gcctcgcacc caggccaggc agaagctgtg    9660
ctctgaagct aggacagctg gctgagaagt gggttcaggc gaagggtgaa gccatgtgta    9720
gcagttcctg ccagtgcaga tctggagagg agctggcccg gaaggcgtgg ttgtgaaagc    9780
gcccttctta tgttaggagg ccttggcaaa attggatttc ttcaaaaata catgtaaagg    9840
tctgttgttg aattgtactc tgcccctgga agcagataca gatggctgcc tgctgctcgg    9900
ctttgctttt gcttttccca ccgtgttttc atctttgttc acttgaggct ttccccagct    9960
ggtgtgtgca ggacagttca tggtaatgtt gccctgag gccccgtaca ccagaaggga    10020
ggccctggaa aattttgtgc ttccaacgtg gccttcaatt cttgcttttt tgcccctcgg    10080
aagcatgggg cttttgagca cacttaaaaa aagaaaatc tgtaacttgg tgcttattga    10140
tgaattgcaa gctggccttg cagatggaga tatttatctt tcagtttatt tgaaagaggt    10200
```

```
ctggtttaaa atttgtagcc tacatttgtt ttatttattg tatttgtgtg tttgtgtttg   10260 tttttttta agggtgagcc aggtctagcc caacagtcta aactatccag tcaataccga   10320
gtgaagtggc agccagcact gttcactctg tgtcttttga agtgccttga aggcccagat   10380
gaaattttaa agggagggg tccatgtcct tccctccccc accccgcctc attctttaat   10440
caaaggatgt cttctccctt gtttgagaat aagaaactc gccacctctg acctaccttt   10500 gccttttct gtcatggaga atactcaccc ttcagaaaca gaccaaaggc caaacctgc   10560 tgattttct attgaaaata tgtccccttg caaagaccct aaacaaaaag ttaagtttct   10620
ttctttcacc tatttgtaca actccaagtt acagctgaat ctgtcgtgac tttcctgaga   10680
tctacccggg gcttggctgt ctgttctggg cactggctcc gagttcccct cctgggattt   10740
gcaggagggc agtactgaac ctgcattctt ctccttgtaa atgtaggccg ggtgcccctg   10800
ttctccgggt ttggaacaat acgaggttgg tgctgatggg atttacttgc gtacgtgctc   10860
ttcacaaaaa caccgtggat gctgaagtta gagcacgtcg ccacagagct tgacatcaat   10920
gttagagggt ctcttactcc ccgcccagct gtgatgtttc atctgctttg gttgttttgg   10980
tggtcttttt taaaaataga gatttcacat ctgcccagac cccactcaaa acgatttggt   11040
caggttctgg ttggacaagt ttaaaatcaa agtagtgccc ggaattccct caaaccaccc   11100
aacttcatcc aggaatacag tctgcagtgc agcaacagaa ccgcttacca agaactgtgc   11160
ttacatacct ttgtcatctc tcttccccc ttggaagttg tcctcagggg gatttgttcc   11220
tgtcctgggg atttacctgg gatggtggct gcctgtgctt ttgctcatgg ccttgacagt   11280
gctctagttg ctggatctaa tggcctgtct tggtttctat cacatgagaa ggggttgttt   11340
ttttggggtg actcggactg aattccccat actgtttcca cgccgggaca ccatgttctc   11400
catcaagcta aagaaatcac gtgcctgaaa ctgtgcttaa gttttggggg aaagatggag   11460
ttcctatcca gagcccccag atttccgaaa tcgagtgagc ttcctggaag gagactgcgt   11520
cttctctcaa ttccagtcat ctcagtcgtt gtcgttaggt gacatgtgca ctttaaatgc   11580
tctcatcggt tggcttcatt ttcaagacaa tcaaatgtat tgactgtgtt ttcttcttag   11640
aaaatggaga gggttaaaaa catgcaaact gccactttca accttgcca gtattccctc   11700 tacccccgtg agagctatct gggggaaga atccttacca aggttttttt ggaaaggtac   11760
gaatcttaac ttttttcccc ttctgtgtct cagggtaata ctattcagag tcgccccttt   11820
gctcattttc tcccgtattt gttaccttcc tgaggcctca gtattagtcg tgagcacaaa   11880
gttttgagac ctttggcgtt gtttcttgat gtgggagggg aggtgttagt gcatgcaagg   11940
gttgaactag atagaccctg ccttagtaga gggtgggact ataaccttag aggccagaac   12000
ttgatccaga agttgctgtc cacagaagtg cttttctattt catcattttt gtttctaggg   12060
ctctttttct gtagccaggt cttcccaagg attttagtat ttgcattgga gttgaggttt   12120
actctaatga tggtggccca gctgtgccca gaggacagcc aggcaggccc tgggagggag   12180
tttagaaaga cagtcctggt gaatgggctt caagtggtca caaagagggt ggctgtgagg   12240
tgaccccaga cactgcagaa cgatgtgcac cctctgcgtt ttggatgtcc ttggaatgtg   12300
ggagcctaga ataaccctg tggatggaat tggggcagcg gctgctggag atctgtgtgc   12360
cttgccttcc ttcagcagga ccgtctaggt gcgcagccac ctatggatgc gtcccagcca   12420
gccccgtcgc tctcgtccat cctcagagac aaagaagagg gcagggagtt tgggcttggt   12480
tttgaacttt cctttcaatg tagcaaagca ttcctagtta accagagcct tggaatctac   12540
tgcctgctgg ccaggcttta aaatgaaaag tgttttaatg ctgccataaa agggaggcgg   12600
```

```
ggggaggaa gggaaaataa aggcatcttt ccaagtactc atctaattta attgtcaaaa    12660
gattgatagg ccatgaatta cttctccatc tcactaaggg ttaaaggcgt gcaaccccc    12720
actggctgtg tccctgcca ccgaagtgag tgacctgccc tacaaccagg tgggaccacc    12780
tgtgctgcag tccggagggg cttctgcagg aagcactcac cccccacacc ttccccggcc    12840
tgagcttccc ctacctttcg tcaccacctg agggcatgag cacaggccat ggggcgtgcc    12900
tggtgagtct gcctgtggtt caggcttagc ctgtggtctc ctgtgtgctg ctgcccgcat    12960
gggatgcgca ggggaggcgt ggggatccgc aggagggtgg ttgggataca ccggatacct    13020
ctgctctcat tgcttgtttg caaatgtctc atggacattt gtgtgctaaa tcctattaaa    13080
taaaaagac gggttaaaac ccagatgctg tatattcatt tgtaattatg tataaagtga    13140
agcagtttta aactgtaaag atttttttca gtgtgtttc tcgaattttg ccacaacata    13200
ctggcttcgt attttattta tctttctttc tagttaccag cttcagaccc ttgtaaagtc    13260
tccctcagcc ctttcaaaaa ataataaatt tcctgtgaag tt                      13302
```

<210> SEQ ID NO 24
<211> LENGTH: 13290
<212> TYPE: DNA
<213> ORGANISM: Homo sapiens
<300> PUBLICATION INFORMATION:
<308> DATABASE ACCESSION NUMBER: NM_007200
<309> DATABASE ENTRY DATE: 2006-08-20
<313> RELEVANT RESIDUES: (1)..(13290)

<400> SEQUENCE: 24

```
gaagcgcctg tgctctgccg agactgccgt gcccattgct cgcctcggtc gccgccgctt      60
tagccgcctc cggggagcg gccgcctatt gtctttctcc gcggcgaagg tgaagagttg     120
tcccagctcg gcccgcgggg gagccccggg agccgcacgt gtcctgggtc atgaaactta     180
atccacagca agctcccta tatggtgatt gtgttgttac agtgctgctt gctgaagagg     240
acaaagctga agatgatgta gtgttttact tggtattttt gggttccacc ctccgtcact     300
gtacaagtac tcggaaggtc agttctgata cattggagac cattgctcct ggtcatgatt     360
gttgtgaaac agtgaaggtg cagctctgtg cttccaaaga gggccttccc gtgtttgtgg     420
tggctgaaga agactttcat ttcgtccagg atgaagcgta tgatgcagct caattcctag     480
caaccagtgc tggaaatcag caggctttga acttttacccg ttttcttgac cagtcaggac     540
ccccatctgg ggatgtgaat tcccttgata agaagttggt gctggcattc aggcacctga     600
agctgcccac ggagtggaat gtattgggga cagatcagag tttgcatgat gctggcccgc     660
gagagacatt gatgcatttt gctgtgcggc tgggactgct gaggttgacg tggttcctgt     720
tgcagaagcc aggtggccgc ggagctctca gtatccacaa ccaggaaggg gcgacgcctg     780
tgagcttggc cttggagcga ggctatcaca agctgcacca gcttctaacc gaggagaatg     840
ctggagaacc agactcctgg agcagtttat cctatgaaat accgtatgga gactgttctg     900
tgaggcatca tcgagagttg gacatctata cattaacctc tgagtctgat tcacatcatg     960
aacacccatt tcctggagac ggttgcactg gaccaatttt taaacttatg aacatccaac    1020
agcaactaat gaaaacaaac ctcaagcaga tggacagtct tatgcccctta atgatgacag    1080
cacaggatc ttccagtgcc ccagagacag atggccagtt tcttccctgt gcaccggagc    1140
ccacggaccc tcagcgactt tcttcttctg aagagactga gagcactcag tgctgcccag    1200
ggagccctgt tgcacagact gaaagtccct gtgatttgtc aagcatagtt gaggaggaga    1260
atacagaccg ttcctgtagg aagaaaaata aaggcgtgga aagaaagggg aagaggtgg    1320
```

```
agccagcacc tattgtggac tctggaactg tatctgatca agacagctgc cttcagagct    1380
tgcctgattg tggagtaaag ggcacggaag gcctttcgtc ctgtggaaac agaaatgaag    1440
aaactggaac aaaatcttct ggaatgccca cagaccagga gtccctgagc agtggagatg    1500
ctgtgcttca gagagacttg gtcatggagc caggcacagc ccagtattcc tctggaggtg    1560
aactgggagg catttcaaca acaaatgtca gtaccccaga cactgcaggg gaaatggaac    1620
atgggctcat gaacccagat gccactgttt ggaagaatgt gcttcaggga ggggaaagta    1680
caaaggaaag atttgagaac tctaatattg gcacagctgg agcctctgac gtgcacgtca    1740
caagtaagcc tgtggataaa atcagtgttc caaactgtgc ccctgctgcc agttccctgg    1800
atggtaacaa acctgctgag tcttcacttg catttagtaa tgaagaaacc tccactgaaa    1860
aaacagcaga aacggaaact tcacgaagtc gtgaggagag tgctgatgct ccagtagatc    1920
agaattctgt ggtgattcca gctgctgcaa aagacaagat ttcagatgga ttagaacctt    1980
atactctctt agcagcaggc ataggtgagg caatgtcacc ctcagattta gcccttcttg    2040
ggctggaaga agatgtaatg ccacaccaga actcagaaac aaattcatct catgctcaaa    2100
gccaaaaggg caaatcctca cccatttgtt ctacaactgg agacgataaa ctttgtgcag    2160
actctgcatg tcaacagaac acagtgactt ctagtggcga tttggttgca aaactgtgtg    2220
ataacatagt tagcgagtcc gaaagcacca cagcaaggca acccagctca caagatccac    2280
ccgatgcctc ccactgtgaa gacccacagg ctcatacagt cacctctgac cctgtaaggg    2340
atacccagga acgtgcggat ttttgtcctt tcaaagtggt ggataacaaa ggccaacgaa    2400
aagatgtgaa actagataaa cctttaacaa atatgcttga ggtggtttca catccacatc    2460
cagttgtccc taaaatggag aaagaactgg tgccagacca ggcagtaata tcagacagta    2520 cttttctctct ggcaaacagt ccaggcagtg aatcagtaac caaggatgac gcactttctt    2580
ttgtcccctc ccagaaagaa aagggaacag caactcctga actacataca gctacagatt    2640
atagagatgg cccagatgga aattcgaatg agcctgatac gcggccacta aagacaggg    2700 cagtaggcct gtccacatcc tccactgctg cagagcttca gcacgggatg gggaatacca    2760
gtctcacagg acttggtgga gagcatgagg gtcccgcccc tccagcaatc ccagaagctc    2820
tgaatatcaa ggggaacact gactcttccc tgcaaagtgt gggtaaggcc actttggctt    2880
tagattcagt tttgactgaa gaaggaaaac ttctggtggt ttcagaaagc tctgcagctc    2940
aggaacaaga taaggataaa gcggtgacct gttcctctat taaggaaaat gctctctctt    3000
caggaacttt gcaggaagag cagagaacac cacctcctgg acaagatact caacaatttc    3060
atgaaaaatc aatctcagct gactgtgcca aggacaaagc acttcagcta agtaattcac    3120
cgggtgcatc ctctgccttt cttaaggcag aaactgaaca taacaaggaa gtggccccac    3180
aagtctcact gctgactcaa ggtggggctg cccagagcct ggtgccacca ggagcaagtc    3240
tggccacaga gtcaaggcag gaagccttgg gggcagagca caacagctcc gctctgttgc    3300
catgtctgtt gccagatggg tctgatgggt ccgatgctct taactgcagt cagccttctc    3360
ctctggatgt tggagtgaag aacactcaat cccaggaaaa aactagtgcc tgtgaggtga    3420
gtggagatgt gacggtggat gttacagggg ttaatgctct acaaggtatg gctgagccca    3480
gaagagagaa tatatcacac aacacccaag acatcctgat tccaaacgtc ttgttgagcc    3540
aagagaagaa tgccgttcta ggtttgccag tggctctaca ggacaaagct gtgactgacc    3600
cacagggagt tggaacccca gagatgatac ctcttgattg ggagaaaggg aagctggagg    3660
gagcagacca cagctgtacc atgggtgacg ctgaggaagc ccaaatagac gatgaagcac    3720
```

```
atcctgtcct actgcagcct gttgccaagg agctccccac agacatggag ctctcagccc      3780
atgatgatgg ggccccagct ggtgtgaggg aagtcatgcg agcccgcct tcaggcaggg       3840 aaaggagcac tccctctcta ccttgcatgg tctctgccca ggacgcacct ctgcctaagg      3900
gggcagactt gatagaggag gctgccagcc gtatagtgga tgctgtcatc gaacaagtca      3960
aggccgctgg agcactgctt actgaggggg aggcctgtca catgtcactg tccagccctg      4020
agttgggtcc tctcactaaa ggactagaga gtgcttttac agaaaaagtg agtactttcc      4080
cacctgggga gagcctacca atgggcagta ctcctgagga agccacgggg agccttgcag      4140
gatgttttgc tggaagggag gagccagaga agatcatttt acctgtccag gggcctgagc      4200
cagcagcaga aatgccagac gtgaaagctg aagatgaagt ggattttaga gcaagttcaa      4260
tttctgaaga agtggctgta gggagcatag ctgctacact gaagatgaag caaggcccaa      4320
tgacccaggc gataaaccga gaaaactggt gtacaataga gccatgccct gatgcagcat      4380
ctcttctggc ttccaagcag agcccagaat gtgagaactt cctggatgtt ggactgggca      4440
gagagtgtac ctcaaaacaa ggtgtactta aaagagaatc tgggagtgat tctgacctct      4500
ttcactcacc cagtgatgac atggacagca tcatcttccc aaagccagag gaagagcatt      4560
tggcctgtga tatcaccgga tccagttcat ccaccgatga cacggcttca ctggaccgac      4620
attcttctca tggcagtgat gtgtctctct cccagatttt aaagccaaac aggtcaagag      4680
atcggcaaag ccttgatgga ttctacagcc atgggatggg agctgagggt cgagaaagtg      4740
agagtgagcc tgctgaccca ggcgacgtgg aggaggagga gatggacagt atcactgaag      4800
tgcctgcaaa ctgctctgtc ctaaggagct ccatgcgctc tctttctccc ttccggaggc      4860
acagctgggg gcctgggaaa aatgcagcca gcgatgcaga aatgaaccac cggagttcaa      4920
tgcgagttct tggggatgtt gtcaggagac ctcccattca taggagaagt ttcagtctag      4980
aaggcttgac aggaggagct ggtgtcggaa acaagccatc ctcatctcta gaagtaagct      5040
ctgcaaatgc cgaagagctc agacacccat tcagtggtga ggaacgggtt gactctttgg      5100
tgtcactttc agaagaggat ctggagtcag accagagaga acataggatg tttgatcagc      5160
agatatgtca cagatctaag cagcagggat ttaattactg tacatcagcc atttcctctc      5220
cattgacaaa atccatctca ttaatgacaa tcagccatcc tggattggac aattcacggc      5280
ccttccacag taccttccac aataccagtg ctaatctgac tgagagtata acagaagaga      5340
actataattt cctgccacat agcccctcca gaaagattc tgaatggaag agtggaacaa      5400
aagtcagtcg tacattcagc tacatcaaga ataaaatgtc tagcagcaag aagagcaaag      5460
aaaaggaaaa agaaaaagat aagattaagg agaaggagaa agattctaaa gacaaggaga      5520
aagataagaa gactgtcaac gggcacactt tcagttccat tcctgttgtg ggtcccatca      5580
gctgtagcca gtgtatgaag cccttcacca acaaagatgc ctatacttgt gcaaattgca      5640
gtgcttttgt ccacaaaggc tgccgagaaa gtctagcctc ctgtgcaaag gtcaaaatga      5700
agcagcccaa agggagcctt caggcacatg acacatcatc actgcccacg tcattatga       5760 gaaacaagcc ctcacagccc aaggagcgtc ctcggtccgc agtcctcctg gtggatgaaa      5820
ccgctaccac cccaatattt gccaatagac gatcccagca gagtgtctcg ctctccaaaa      5880
gtgtctccat acagaacatt actggagttg gcaatgatga aacatgtca aacacctgga       5940 aattcctgtc tcattcaaca gactcactaa ataaaatcag caaggtcaat gagtcaacag      6000
aatcacttac tgatgaggga gtaggtacag acatgaatga aggacaacta ctgggagact      6060
ttgagattga gtccaaacag ctggaagcag agtcttggag tcggataata gacagcaagt      6120
```

```
ttctaaaaca gcaaaagaaa gatgtggtca aacggcaaga agtaatatat gagttgatgc    6180
agacagagtt tcatcatgtc cgcactctca agatcatgag tggtgtgtac agccagggga    6240
tgatggcgga tctgcttttt gagcagcaga tggtagaaaa gctgttcccc tgtttggatg    6300
agctgatcag tatccatagc caattcttcc agaggattct ggagcggaag aaggagtctc    6360
tggtggataa aagtgaaaag aactttctca tcaagaggat aggggatgtg cttgtaaatc    6420
agttttcagg tgagaatgca gaacgtttaa agaaagacata tggcaagttt tgtgggcaac    6480
ataaccagtc tgtaaactac ttcaaagacc tttatgccaa ggataagcgt tttcaagcct    6540
ttgtaaagaa gaagatgagc agttcagttg ttagaaggct tggaattcca gagtgcatat    6600
tgcttgtaac tcagcggatt accaagtacc cagtttttatt ccaaagaata ttgcagtgta    6660
ccaaagacaa tgaagtggag caggaagatc tagcacagtc cttgagcctg gtgaaggatg    6720
tgattggagc tgtagacagc aaagtggcaa gttatgaaaa gaaagtgcgt ctcaatgaga    6780
tttatacaaa gacagatagc aagtcaatca tgaggatgaa gagtggtcag atgtttgcca    6840
aggaagattt gaaacggaag aagcttgtac gtgatgggag tgtgtttctg aagaatgcag    6900
caggaaggtt gaaagaggtt caagcagttc ttctcactga cattttagtt ttccttcaag    6960
aaaaagacca gaagtacatc tttgcatcat tggaccagaa gtcaacagtg atctctttaa    7020
agaagctgat tgtgagagaa gtggcacatg aggagaaagg tttattcctg atcagcatgg    7080
ggatgacaga tccagagatg gtagaagtcc atgccagctc caaagaggaa cgaaacagct    7140
ggattcagat cattcaggac acaatcaaca ccctgaacag agatgaagat gaaggaattc    7200
ctagtgagaa tgaggaagaa aagaaaatgt tggacaccag agcccgagaa ttaaaagaac    7260
aacttcacca gaaggaccaa aaaatcctac tcttgttgga agagaaggag atgatttttcc    7320 gggacatggc tgagtgcagc accctctccc agaggattg ctccccaaca catagcccta    7380
gagttctctt ccgctccaac acagaagagg ctctcaaagg aggacctta atgaaaagtg    7440 caataaatga ggtggagatc cttcagggtt tggtgagtgg aaatctggga ggcacacttg    7500
ggccgactgt cagcagcccc attgagcaag atgtggtcgg tcccgtttcc ctgccccgga    7560
gagcagagac ctttggagga tttgacagcc atcagatgaa tgcttcaaaa ggaggcgaga    7620
aggaagaggg agatgatggc caagatctta ggagaacgga atcagatagt ggcctaaaaa    7680
agggtggaaa tgctaacctg gtatttatgc ttaaaagaaa cagtgagcag gttgtccaga    7740
gcgttgttca tctctacgag ctcctcagcg ctctgcaggg tgtggtgctg cagcaggaca    7800
gctacattga ggaccagaaa ctggtgctga gcgagagggc gctcactcgc agcttgtccc    7860
gcccgagctc cctcattgag caggagaagc agcgcagcct ggagaagcag cgccaggacc    7920
tggccaacct gcagaagcag caggcccagt acctcgagga gaagcgcagg cgcgagcgtg    7980
agtgggaagc tcgtgagagg gagctgcggg agcgggaggc cctcctggcc cagcgcgagg    8040
aggaggtgca gcaggggcag caggacctgg aaaaggagcg ggaggagctc cagcagaaga    8100
agggcacata ccagtatgac ctggagcgac tgcgtgctgc ccagaaacag cttgagaggg    8160
aacaggagca gctgcgccgg gaggcagagc ggctcagcca gcggcagaca gaacgggacc    8220
tgtgtcaggt ttcccatcca cataccaagc tgatgaggat cccatcgttc ttccccagtc    8280
ctgaggagcc ccctcgcca tctgcacctt ccatagccaa atcagggtca ttggactcag    8340
aactttcagt gtccccaaaa aggaacagca tctctcggac acacaaagat aaggggcctt    8400
ttcacatact gagttcaacc agccagacaa acaaaggacc agaagggcag agccaggccc    8460
ctgcgtccac ctctgcctct acccgcctgt ttgggttaac aaagccaaag gaaaagaagg    8520
```

```
agaaaaaaaa gaagaacaaa accagccgct ctcagcccgg tgatggtccc gcgtcagaag   8580
tatcagcaga gggtgaagag atcttctgct gaccctcttc ctctctgctg aggcagctgc   8640
ctcctgatcc tggccagccc acctctcctg ctgtccccgc gtgcacaagt ctcttacact   8700
ggacgcccac tgctcctcag cgtccagtcc tcctgggcgg ccccaggtcc tggacaataa   8760
gcaacagatg atattgagtg tcgggtgggg aaggaggccc agactctgct tcggccatga   8820
tttgtgactg cccaggactc tcaggttggg ctggccctac tcaggattac actgaaagta   8880
atggcctcgt aagtacaggt gatggttttg gacacgtcag gaattcctaa aggctgaaag   8940
agtgtatcca agtaaggtct gaacctccga atgccttta tttgggggaa cacaaaacca    9000
aacagcagat gttttggact tgatctgtgt acgtacatgg ggacctgtct gcatatacac   9060
acggggaatg ccagaagaag gcccagtctg caccaggcgt ctggtcaact tagcacaagg   9120
gcagtgcctg gacggacccg gagccccgc atatcagcag ttcacccagt actcctcaga    9180
gactggtttc cctctaaacc catcccgggc acataccacc cgtgttttgc atgtatttct   9240
catttcattt tagggatgac aaacatttgt gaaaccagtg agagaaggct tgatgtgtat   9300
aaaagacgtg atgtgcacca cctcgatctc ggtgtttcag gcactaaagc aacaaaacaa   9360
cccatagtat ctcattctgt catcagatcc agaagaaata tcctggtttt ccagcatgtt   9420
tacccacatg ttttggccat ggataaagtg aagaggccta ctcaccatta tccctgcagc   9480
gtgacacctt ttgattgtca ctgaccactc agaaggggcc acggcctcct ggctgtgttc   9540
ctgagccccc gtcgtgcctc tcccagacag cagctgtctg gcccttgctg ggtgagggca   9600
caccactgcc aggggtcagc ctcgcaccca ggccaggcag aagctgtgct ctgaagctag   9660
gacagctggc tgagaagtgg gttcaggcga agggtgaagc catgtgtagc agttcctgcc   9720
agtgcagatc tggagaggag ctggcccgga aggcgtggtt gtgaaagcgc ccttcttatg   9780
ttaggaggcc ttggcaaaat tggatttctt caaaaataca tgtaaaggtc tgttgttgaa   9840
ttgtactctg cccctggaag cagatacaga tggctgcctg ctgctcggct ttgcttttgc   9900
ttttcccacc gtgttttcat cttgttcac ttgaggcttt ccccagctgg tgtgtgcagg    9960
acagttcatg gtaatgttgc cctctgaggc cccgtacacc agaagggagg ccctggaaaa  10020
ttttgtgctt ccaacgtggc cttcaattct tgcttttttg cccctcggaa gcatggggct  10080
tttgagcaca cttaaaaaaa gaaaaatctg taacttggtg cttattgatg aattgcaagc  10140
tggccttgca gatggagata tttatctttc agtttatttg aaagaggtct ggtttaaaat  10200
ttgtagccta catttgtttt atttattgta tttgtgtgtt tgtgtttgtt ttttttaag    10260 ggtgagccag gtctagccca acagtctaaa ctatccagtc aataccgagt gaagtggcag  10320
ccagcactgt tcactctgtg tcttttgaag tgccttgaag gccagatga aattttaaag    10380 ggaggggtc catgtccttc cctcccccac cccgcctcat tctttaatca aggatgtct     10440 tctcccttgt ttgagaatga agaaactcgc cacctctgac ctacctttgc cttttctgt    10500 catggagaat actcacccctt cagaaacaga ccaaaggcca aaacctgctg atttttctat  10560
tgaaaatatg tccccttgca aagaccctaa acaaaaagtt aagttctttt ctttcaccta  10620
tttgtacaac tccaagttac agctgaatct gtcgtgactt tcctgagatc tacccggggc  10680
ttggctgtct gttctgggca ctggctccga gttccctcc tggatttgc aggagggcag     10740 tactgaacct gcattcttct ccttgtaaat gtaggccggg tgccctgtt ctcgggttt     10800 ggaacaatac gaggttggtg ctgatgggat ttacttgcgt acgtgctctt cacaaaaaca  10860
ccgtggatgc tgaagttaga gcacgtcgcc acagagcttg acatcaatgt tagagggtct  10920
```

```
cttactcccc gcccagctgt gatgtttcat ctgctttggt tgttttggtg gtcttttta    10980 aaaatagaga tttcacatct gcccagaccc cactcaaaac gatttggtca ggttctggtt    11040
ggacaagttt aaaatcaaag tagtgcccgg aattccctca aaccacccaa cttcatccag    11100
gaatacagtc tgcagtgcag caacagaacc gcttaccaag aactgtgctt acatacctt    11160 gtcatctctc ttccccctt ggaagttgtc ctcagggga tttgttcctg tcctggggat    11220
ttacctggga tggtggctgc ctgtgctttt gctcatggcc ttgacagtgc tctagttgct    11280
ggatctaatg gcctgtcttg gtttctatca catgagaagg ggttgttttt ttggggtgac    11340
tcggactgaa ttccccatac tgtttccacg ccgggacacc atgttctcca tcaagctaaa    11400
gaaatcacgt gcctgaaact gtgcttaagt tttgggggaa agatggagtt cctatccaga    11460 gccccagat ttccagaatc gagtgagctt cctggaagga gactgcgtct tctctcaatt    11520
ccagtcatct cagtcgttgt cgttaggtga catgtgcact ttaaatgctc tcatcggttg    11580
gcttcatttt caagacaatc aaatgtattg actgtgtttt cttcttagaa aatggagagg    11640
gttaaaaaca tgcaaactgc cactttcaac ctttgccagt attccctcta cccccgtgag    11700
agctatctgg ggggaagaat ccttaccaag gttttttttgg aaaggtacga atcttaactt    11760
ttttcccctt ctgtgtctca gggtaatact attcagagtc gcccctttgc tcatttctc    11820 ccgtatttgt taccttcctg aggcctcagt attagtcgtg agcacaaagt tttgagacct    11880
ttggcgttgt ttcttgatgt ggggagggag gtgttagtgc atgcaagggt tgaactagat    11940
agaccctgcc ttagtagagg gtgggactat aaccttagag gccagaactt gatccagaag    12000
ttgctgtcca cagaagtgct ttctatttca tcatttttgt ttctagggct cttttctgt    12060 agccaggtct tcccaaggat tttagtattt gcattggagt tgaggtttac tctaatgatg    12120
gtggcccagc tgtgcccaga ggacagccag gcaggccctg ggagggagtt tagaaagaca    12180
gtcctggtga atgggcttca agtggtcaca aagagggtgg ctgtgaggtg accccagaca    12240
ctgcagaacg atgtgcaccc tctgcgtttt ggatgtcctt ggaatgtggg agcctagaaa    12300
taaccctgtg gatggaattg gggcagcggc tgctggagat ctgtgtgcct tgccttcctt    12360
cagcaggacc gtctaggtgc gcagccacct atggatgcgt cccagccagc cccgtcgctc    12420
tcgtccatcc tcagagacaa agaagagggc agggagtttg ggcttggttt tgaactttcc    12480
tttcaatgta gcaaagcatt cctagttaac cagagccttg gaatctactg cctgctggcc    12540
aggctttaaa atgaaaagtg tttaatgct gccataaaag gggaggcgggg gggaggaagg    12600 gaaaataaag gcatctttcc aagtactcat ctaatttaat tgtcaaaaga ttgataggcc    12660
atgaattact tctccatctc actaaggggtt aaaggcgtgc aaccccccac tggctgtgtc    12720
ccctgccacc gaagtgagtg acctgcccta caaccaggtg ggaccacctg tgctgcagtc    12780 cggagggct tctgcaggaa gcactcaccc cccacacctt ccccggcctg agcttcccct    12840 accttcgtc accacctgag ggcatgagca caggccatgg ggcgtgcctg gtgagtctgc    12900
ctgtggttca ggcttagcct gtggtctcct gtgtgctgct gcccgcatgg gatgcgcagg    12960
ggaggcgtgg ggatccgcag gagggtggtt gggatacacc ggatacctct gctctcattg    13020
cttgtttgca aatgctctat ggacatttgt gtgctaaatc ctattaaata aaaaagacgg    13080
gttaaaaccc agatgctgta tattcatttg taattatgta taagtgaag cagttttaaa    13140 ctgtaaagat tttttcagt gtgttttctc gaattttgcc acaacatact ggcttcgtat    13200
tttatttatc tttctttcta gttaccagct tcagacccctt gtaaagtctc cctcagccct    13260
ttcaaaaaat aataaatttc ctgtgaagtt                                   13290
```

<210> SEQ ID NO 25
<211> LENGTH: 8081
<212> TYPE: DNA
<213> ORGANISM: Homo sapiens
<300> PUBLICATION INFORMATION:
<308> DATABASE ACCESSION NUMBER: NM_144767
<309> DATABASE ENTRY DATE: 2006-08-20
<313> RELEVANT RESIDUES: (1)..(8081)

<400> SEQUENCE: 25

```
gtctaaaact ctcttttctc ttggctcttc ttattcgagt gatgaggagg aggagttgca      60
taattcacgg cccttccaca gtaccttcca caataccagt gctaatctga ctgagagtat     120
aacagaagag aactataatt tcctgccaca tagcccctcc aagaaagatt ctgaatggaa     180
gagtggaaca aaagtcagtc gtacattcag ctacatcaag aataaaatgt ctagcagcaa     240
gaagagcaaa gaaaaggaaa agaaaaagag taagattaag gagaaggaga agattctaa     300
agacaaggag aaagataaga agactgtcaa cgggcacact ttcagttcca ttcctgttgt     360
gggtcccatc agctgtagcc agtgtatgaa gcccttcacc aacaaagatg cctatacttg     420
tgcaaattgc agtgcttttg tccacaaagg ctgccgagaa agtctagcct cctgtgcaaa     480
ggtcaaaatg aagcagccca agggagcct tcaggcacat gacacatcat cactgcccac     540
ggtcattatg agaaacaagc cctcacagcc caaggagcgt cctcggtccg cagtcctcct     600
ggtggatgaa accgctacca ccccaatatt tgccaataga cgatcccagc agagtgtctc     660
gctctccaaa agtgtctcca tacagaacat tactggagtt ggcaatgatg agaacatgtc     720
aaacacctgg aaattcctgt ctcattcaac agactcacta aataaaatca gcaaggtcaa     780
tgagtcaaca gaatcactta ctgatgaggg agtaggtaca gacatgaatg aaggacaact     840
actgggagac tttgagattg agtccaaaca gctggaagca gagtcttgga gtcggataat     900
agacagcaag tttctaaaac agcaaaagaa agatgtggtc aaacggcaag aagtaatata     960
tgagttgatg cagacagagt ttcatcatgt ccgcactctc aagatcatga gtggtgtgta    1020
cagccagggg atgatggcgg atctgctttt tgagcagcag atggtagaaa agctgttccc    1080
ctgtttggat gagctgatca gtatccatag ccaattcttc cagaggattc tggagcggaa    1140
gaaggagtct ctggtggata aaagtgaaaa gaactttctc atcaagagga taggggatgt    1200
gcttgtaaat cagttttcag gtgagaatgc agaacgttta agaagacat atggcaagtt    1260
ttgtgggcaa cataaccagt ctgtaaacta cttcaaagac ctttatgcca aggataagcg    1320
tttttcaagcc tttgtaaaga agaagatgag cagttcagtt gttagaaggc ttggaattcc    1380
agagtgcata ttgcttgtaa ctcagcggat taccaagtac ccagttttat tccaaagaat    1440
attgcagtgt accaaagaca atgaagtgga gcaggaagat ctagcacagt ccttgagcct    1500
ggtgaaggat gtgattggag ctgtagacag caaagtggca agttatgaaa agaaagtgcg    1560
tctcaatgag atttatacaa agacagatag caagtcaatc atgaggatga gagtggtca    1620
gatgtttgcc aaggaagatt tgaaacggaa gaagcttgta cgtgatggga gtgtgtttct    1680
gaagaatgca gcaggaaggt tgaaagaggt tcaagcagtt cttctcactg acattttagt    1740
tttccttcaa gaaaaagacc agaagtacat ctttgcatca ttggaccaga agtcaacagt    1800
gatctcttta aagaagctga ttgtgagaga agtggcacat gaggagaaag gtttattcct    1860
gatcagcatg gggatgacag atccagagat ggtagaagtc catgccagct ccaaagagga    1920
acgaaacagc tggattcaga tcattcagga cacaatcaac accctgaaca gagatgaaga    1980
tgaaggaatt cctagtgaga atgaggaaga aagaaaatg ttggacacca gagcccgaga    2040
```

```
attaaaagaa caacttcacc agaaggacca aaaaatccta ctcttgttgg aagagaagga    2100
gatgattttc cgggacatgg ctgagtgcag caccectctc ccagaggatt gctcccaac     2160
acatagccct agagttctct tccgctccaa cacagaagag gctctcaaag gaggaccttt    2220
aatgaaaagt gcaataaatg aggtggagat ccttcagggt ttggtgagtg gaaatctggg    2280
aggcacactt gggccgactg tcagcagccc cattgagcaa gatgtggtcg gtcccgtttc    2340
cctgccccgg agagcagaga cctttggagg atttgacagc catcagatga atgcttcaaa    2400
aggaggcgag aaggaagagg gagatgatgg ccaagatctt aggagaacgg aatcagatag    2460
tggcctaaaa aagggtggaa atgctaacct ggtatttatg cttaaaagaa acagtgagca    2520
ggttgtccag agcgttgttc atctctacga gctcctcagc gctctgcagg gtgtggtgct    2580
gcagcaggac agctacattg aggaccagaa actggtgctg agcgagaggg cgctcactcg    2640
cagcttgtcc cgcccgagct ccctcattga gcaggagaag cagcgcagcc tggagaagca    2700
gcgccaggac ctggccaacc tgcagaagca gcaggcccag tacctcgagg agaagcgcag    2760
gcgcgagcgt gagtgggaag ctcgtgagag ggagctgcgg gagcgggagg ccctcctggc    2820
ccagcgcgag gaggaggtgc agcaggggca gcaggacctg gaaaaggagc gggaggagct    2880
ccagcagaag aagggcacat accagtatga cctggagcga ctgcgtgctg cccagaaaca    2940
gcttgagagg gaacaggagc agctgcgccg ggaggcagag cggctcagcc agcggcagac    3000
agaacgggac ctgtgtcagg tttcccatcc acataccaag ctgatgagga tcccatcgtt    3060
cttccccagt cctgaggagc cccctcgcc atctgcacct tccatagcca aatcagggtc     3120
attggactca gaactttcag tgtccccaaa aaggaacagc atctctcgga cacacaaaga    3180
taagggccct tttcacatac tgagttcaac cagccagaca aacaaaggac cagaagggca    3240
gagccaggcc cctgcgtcca cctctgcctc tacccgcctg tttgggttaa caaagccaaa    3300
ggaaaagaag gagaaaaaaa agaagaacaa aaccagccgc tctcagcccg gtgatggtcc    3360
cgcgtcagaa gtatcagcag agggtgaaga gatcttctgc tgaccctctt cctctctgct    3420
gaggcagctg cctcctgatc ctggccagcc cacctctcct gctgtccccg cgtgcacaag    3480
tctcttacac tggacgccca ctgctcctca gcgtccagtc ctcctgggcg ccccaggtc     3540
ctggacaata agcaacagat gatattgagt gtcgggtggg aaggaggcc cagactctgc     3600
ttcggccatg atttgtgact gcccaggact ctcaggttgg gctggcccta ctcaggatta    3660
cactgaaagt aatggcctcg taagtacagg tgatggtttt ggacacgtca ggaattccta    3720
aaggctgaaa gagtgtatcc aagtaaggtc tgaacctccg aatgcctttt atttggggga    3780
acacaaaacc aaacagcaga tgttttggac ttgatctgtg tacgtacatg gggacctgtc    3840
tgcatataca cacggggaat gccagaagaa ggcccagtct gcaccaggcg tctggtcaac    3900
ttagcacaag ggcagtgcct ggacggaccc ggagcccccg catatcagca gttcacccag    3960
tactcctcag agactggttt ccctctaaac ccatcccggg cacataccac ccgtgttttg    4020
catgtatttc tcatttcatt ttagggatga caaacatttg tgaaaccagt gagagaaggc    4080
ttgatgtgta taaagacgt gatgtgcacc acctcgatct cggtgtttca ggcactaaag     4140
caacaaaaca acccatagta tctcattctg tcatcagatc cagaagaaat atcctggttt    4200
tccagcatgt ttacccacat gttttggcca tggataaagt gaagaggcct actcaccatt    4260
atccctgcag cgtgacacct tttgattgtc actgaccact cagaaggggc cacggcctcc    4320
tggctgtgtt cctgagcccc cgtcgtgcct ctcccagaca gcagctgtct ggcccttgct    4380
gggtgagggc acaccactgc caggggtcag cctcgcaccc aggccaggca gaagctgtgc    4440
```

```
tctgaagcta ggacagctgg ctgagaagtg ggttcaggcg aagggtgaag ccatgtgtag   4500
cagttcctgc cagtgcagat ctggagagga gctggcccgg aaggcgtggt tgtgaaagcg   4560
cccttcttat gttaggaggc cttggcaaaa ttggatttct tcaaaaatac atgtaaaggt   4620
ctgttgttga attgtactct gcccctggaa gcagatacag atggctgcct gctgctcggc   4680
tttgcttttg cttttcccac cgtgttttca tctttgttca cttgaggctt tccccagctg   4740
gtgtgtgcag gacagttcat ggtaatgttg ccctctgagg ccccgtacac cagaagggag   4800
gccctggaaa attttgtgct tccaacgtgg ccttcaattc ttgctttttt gcccctcgga   4860
agcatggggc ttttgagcac acttaaaaaa agaaaaatct gtaacttggt gcttattgat   4920
gaattgcaag ctggccttgc agatggagat atttatcttt cagtttattt gaaagaggtc   4980
tggtttaaaa tttgtagcct acatttgttt tatttattgt atttgtgtgt tgtgtttgt    5040 tttttttttaa gggtgagcca ggtctagccc aacagtctaa actatccagt caataccgag   5100
tgaagtggca gccagcactg ttcactctgt gtcttttgaa gtgccttgaa ggcccagatg   5160
aaattttaaa gggagggggt ccatgtcctt ccctccccca ccccgcctca ttctttaatc   5220
aaaggatgtc ttctcccttg tttgagaatg aagaaactcg ccacctctga cctacctttg   5280
cctttttctg tcatggagaa tactcaccct tcagaaacag accaaaggcc aaaacctgct   5340
gattttctca ttgaaaatat gtccccttgc aaagacccta aacaaaaagt taagtttctt   5400
tctttcacct atttgtacaa ctccaagtta cagctgaatc tgtcgtgact ttcctgagat   5460
ctacccgggg cttggctgtc tgttctgggc actggctccg agttcccctc ctgggatttg   5520
caggagggca gtactgaacc tgcattcttc tccttgtaaa tgtaggccgg gtgcccctgt   5580
tctccgggtt tggaacaata cgaggttggt gctgatggga tttacttgcg tacgtgctct   5640
tcacaaaaac accgtggatg ctgaagttag agcacgtcgc cacagagctt gacatcaatg   5700
ttagagggtc tcttactccc cgcccagctg tgatgtttca tctgctttgg ttgttttggt   5760
ggtctttttt aaaatagag atttcacatc tgcccagacc ccactcaaaa cgatttggtc   5820
aggttctggt tggacaagtt taaaatcaaa gtagtgcccg gaattcccct caaaccaccca   5880 acttcatcca ggaatacagt ctgcagtgca gcaacagaac cgcttaccaa gaactgtgct   5940 tacataccctt tgtcatctct cttccccccct tggaagttgt cctcagggggg atttgttcct   6000 gtcctgggga tttacctggg atggtggctg cctgtgcttt tgctcatggc cttgacagtg   6060
ctctagttgc tggatctaat ggcctgtctt ggtttctatc acatgagaag gggttgtttt   6120
tttggggtga ctcggactga attccccata ctgtttccac gccgggacac catgttctcc   6180
atcaagctaa agaaatcacg tgcctgaaac tgtgcttaag ttttggggga aagatggagt   6240
tcctatccag agcccccaga tttccagaat cgagtgagct tcctggaagg agactgcgtc   6300
ttctctcaat tccagtcatc tcagtcgttg tcgttaggtg acatgtgcac tttaaatgct   6360
ctcatcggtt ggcttcattt tcaagacaat caaatgtatt gactgtgttt tcttcttaga   6420
aaatggagag ggttaaaaac atgcaaactg ccactttcaa cctttgccag tattccctct   6480 accccccgtga gagctatctg gggggaagaa tccttaccaa ggttttttttg gaaaggtacg   6540 aatcttaact ttttttccccct tctgtgtctc agggtaatac tattcagagt cgccccctttg   6600 ctcatttttct cccgtatttg ttaccttcct gaggcctcag tattagtcgt gagcacaaag   6660
ttttgagacc tttggcgttg tttcttgatg tgggaggggga ggtgttagtg catgcaaggg   6720
ttgaactaga tagaccctgc cttagtagag ggtgggacta taaccttaga ggccagaact   6780
tgatccagaa gttgctgtcc acagaagtgc tttctatttc atcattttttg tttctagggc   6840
```

-continued

| | |
|---|---|
| tcttttctg tagccaggtc ttcccaagga ttttagtatt tgcattggag ttgaggttta | 6900 |
| ctctaatgat ggtggcccag ctgtgcccag aggacagcca ggcaggccct gggagggagt | 6960 |
| ttagaaagac agtcctggtg aatgggcttc aagtggtcac aaagagggtg gctgtgaggt | 7020 |
| gaccccagac actgcagaac gatgtgcacc ctctgcgttt tggatgtcct tggaatgtgg | 7080 |
| gagcctagaa ataaccctgt ggatggaatt ggggcagcgg ctgctggaga tctgtgtgcc | 7140 |
| ttgccttcct tcagcaggac cgtctaggtg cgcagccacc tatggatgcg tcccagccag | 7200 |
| ccccgtcgct ctcgtccatc ctcagagaca agaagaggg cagggagttt gggcttggtt | 7260 |
| ttgaactttc ctttcaatgt agcaaagcat tcctagttaa ccagagcctt ggaatctact | 7320 |
| gcctgctggc caggctttaa aatgaaaagt gttttaatgc tgccataaaa gggaggcggg | 7380 |
| ggggaggaag ggaaaataaa ggcatctttc caagtactca tctaatttaa ttgtcaaaag | 7440 |
| attgataggc catgaattac ttctccatct cactaagggt taaaggcgtg caaccccca | 7500 |
| ctggctgtgt cccctgccac cgaagtgagt gacctgccct acaaccaggt gggaccacct | 7560 |
| gtgctgcagt ccggaggggc ttctgcagga agcactcacc ccccacacct tccccggcct | 7620 |
| gagcttcccc tacctttcgt caccacctga gggcatgagc acaggccatg gggcgtgcct | 7680 |
| ggtgagtctg cctgtggttc aggcttagcc tgtggtctcc tgtgtgctgc tgcccgcatg | 7740 |
| ggatgcgcag gggaggcgtg gggatccgca ggagggtggt tgggatacac cggataccct | 7800 |
| tgctctcatt gcttgtttgc aaatgctcta tggacatttg tgtgctaaat cctattaaat | 7860 |
| aaaaagacg ggttaaaacc cagatgctgt atattcattt gtaattatgt ataaagtgaa | 7920 |
| gcagttttaa actgtaaaga ttttttttcag tgtgttttct cgaattttgc cacaacatac | 7980 |
| tggcttcgta ttttatttat ctttctttct agttaccagc ttcagacccct tgtaaagtct | 8040 |
| ccctcagccc tttcaaaaaa taataaattt cctgtgaagt t | 8081 |

<210> SEQ ID NO 26
<211> LENGTH: 4784
<212> TYPE: DNA
<213> ORGANISM: Homo sapiens
<300> PUBLICATION INFORMATION:
<308> DATABASE ACCESSION NUMBER: NM_000922
<309> DATABASE ENTRY DATE: 2006-07-30
<313> RELEVANT RESIDUES: (1)..(4784)

<400> SEQUENCE: 26

| | |
|---|---|
| gaggcgacac tgagtctcca agtccggaga ggtgcccgag ggaaaagagg cggcagctaa | 60 |
| actggtcctg gagagaagcc ccttccgccc ctctcctcag ccagcatgtc ccggactccg | 120 |
| ccgctcctca gtccgcgcgg tggggacccc gggccgtggc ggccggcgca gccctgacgg | 180 |
| gttgcgaacc aggggcgcc ccgaacgcgg gggttgggt ctgggagcgc gagcggccgc | 240 |
| tacggtacga gcggggtgtg ctgagtcccg tggccacccc cggccccagc catgaggagg | 300 |
| gacgagcgag acgccaaagc catgcggtcc ctgcagccgc cggatgggc cggctcgccc | 360 |
| cccgagagtc tgaggaacgg ctacgtgaag agctgcgtga gccccttgcg gcaggaccct | 420 |
| ccgcgcggct tcttcttcca cctctgccgc ttctgcaacg tggagctgcg gccgccgccg | 480 |
| gcctctcccc agcagccgcg gcgctgctcc cccttctgcc gggcgcgcct ctcgctgggc | 540 |
| gccctggctc cctttgtcct cgccctgctg ctgggcgcgg aacccgagag ctgggctgcc | 600 |
| ggggccgcct ggctgcggac gctgctgagc gtgtgttcgc acagcttgag ccccctcttc | 660 |
| agcatcgcct gtgccttctt cttcctcacc tgcttcctca cccggaccaa gcggggaccc | 720 |
| ggcccgggcc ggagctgcgg ctcctggtgg ctgctggcgc tgcccgcctg ctgttacctg | 780 |

```
ggggacttct tggtgtggca gtggtggtct tggccttggg gggatggcga cgcagggtcc     840
gcggccccgc acacgccccc ggaggcggca gcgggcaggt tgctgctggt gctgagctgc     900
gtagggctgc tgctgacgct cgcgcacccg ctgcggctcc ggcactgcgt tctggtgctg     960
ctcctggcca gcttcgtctg gtgggtctcc ttcaccagcc tcgggtcgct gccctccgcc    1020
ctcaggccgc tgctctccgg cctggtgggg ggcgctggct gcctgctggc cctggggttg    1080
gatcacttct ttcaaatcag ggaagcgcct cttcatcctc gactgtccag tgccgccgaa    1140
gaaaaagtgc ctgtgatccg accccggagg aggtccagct gcgtgtcgtt aggagaaact    1200
gcagccagtt actatggcag ttgcaaaata ttcaggagac cgtcgttgcc ttgtatttcc    1260
agagaacaga tgattctttg ggattgggac ttaaaacaat ggtataagcc tcattatcaa    1320
aattctggag gtgaaatgg agttgatctt cagtgctaa atgaggctcg caatatggtg    1380
tcagatcttc tgactgatcc aagccttcca ccacaagtca tttcctctct acggagtatt    1440
agtagcttaa tgggtgcttt ctcaggttcc tgtaggccaa agattaatcc tctcacacca    1500
tttcctggat tttaccccctg ttctgaaata gaggacccag ctgagaaagg ggatagaaaa    1560
cttaacaagg gactaaatag gaatagtttg ccaactccac agctgaggag aagctcagga    1620
acttcaggat tgctacctgt tgaacagtct tcaaggtggg atcgtaataa tggcaaaagg    1680
cctcaccaag aatttggcat ttcaagtcaa ggatgctatc taaatgggcc ttttaattca    1740
aatctactga ctatcccgaa gcaaaggtca tcttctgtat cactgactca ccatgtaggt    1800
ctcagaagag ctggtgtttt gtccagtctg agtcctgtga attcttccaa ccatggacca    1860
gtgtctactg gctctctaac taatcgatca cccatagaat ttcctgatac tgctgatttt    1920
cttaataagc caagcgttat cttgcagaga tctctgggca atgcacctaa tactccagat    1980
ttttatcagc aacttagaaa ttctgatagc aatctgtgta acagctgtgg acatcaaatg    2040
ctgaaatatg tttcaacatc tgaatcagat ggtacagatt gctgcagtgg aaaatcaggt    2100
gaagaagaaa acatttctc gaaagaatca ttcaaactta tggaaactca acaagaagag    2160
gaaacagaga agaagacag cagaaaatta tttcaggaag gtgataagtg gctaacagaa    2220
gaggcacaga gtgaacagca aacaaatatt gaacaggaag tatcactgga cctgatttta    2280
gtagaagagt atgactcatt aatagaaaag atgagcaact ggaattttcc aatttttgaa    2340
cttgtagaaa agatgggaga gaaatcagga aggattctca gtcaggttat gtataccta    2400
tttcaagaca ctggtttatt ggaaatattt aaaattccca ctcaacaatt tatgaactat    2460
tttcgtgcat tagaaaatgg ctatcgagac attccttatc acaatcgtat acatgccaca    2520
gatgtgctac atgcagtttg gtatctgaca acacggccag ttcctggctt acagcagatc    2580
cacaatggtt gtgaacagg aaatgaaaca gattctgatg gtagaattaa ccatgggcga    2640
attgcttata tttcttcgaa gagctgctct aatcctgatg agagttatgg ctgcctgtct    2700
tcaaacattc ctgcattaga attgatggct ctatacgtgg cagctgccat gcatgattat    2760
gatcacccag ggaggacaaa tgcatttcta gtggctacaa tgcccctca ggcagtttta    2820
tacaatgaca gatctgttct ggaaaatcat catgctgcgt cagcttggaa tctatatctt    2880
tctcgcccag aatacaactt ccttcttcat cttgatcatg tggaattcaa gcgctttcgt    2940
ttttagtca ttgaagcaat ccttgctacg gatcttaaaa agcattttga ttttctcgca    3000
gaattcaatg ccaaggcaaa tgatgtaaat agtaatggca tagaatggag taatgaaaat    3060
gatcgcctct tggtatgcca ggtgtgcatc aaactggcag atataaatgg cccagcaaaa    3120
gttcgagact tgcatttgaa atggacagaa ggcattgtca atgaatttta tgagcaggga    3180
```

```
gatgaagaag caaatcttgg tctgcccatc agtccattca tggatcgttc ttctcctcaa    3240
ctagcaaaac tccaagaatc ttttatcacc cacatagtgg gtcccctgtg taactcctat    3300
gatgctgctg gtttgctacc aggtcagtgg ttagaagcag aagaggataa tgatactgaa    3360
agtggtgatg atgaagacgg tgaagaatta gatacagaag atgaagaaat ggaaaacaat    3420
ctaaatccaa aaccaccaag aaggaaaagc agacggcgaa tattttgtca gctaatgcac    3480
cacctcactg aaaaccacaa gatatggaag gaaatcgtag aggaagaaga aaaatgtaaa    3540
gctgatggga ataaactgca ggtggagaat tcctccttac ctcaagcaga tgagattcag    3600
gtaattgaag aggcagatga agaggaatag cgacagtttg agtaaaagaa aagtcatatt    3660
gaagaagccc agagggttgt gcccaggggc agaaatcatt gcctagtgtt caccggctga    3720
ctctcaactg accattccca tgtggacagg ccttaatact gtgagaggat ccttgctctg    3780
ctggcagttt cccactccta tgcactttca caggaactag aaaactattc ttaaaccaaa    3840
aataccatcc gtgttgaccc catgttgcaga gcccttactt aaatccttca ctggtgtatg    3900
aatactttgt cataatgctg ctttgctggg tagtgagctc ttattttca ctgggggtca    3960 gctataacta aaaactcaag tgacatattt cagttaccaa agtggccagg aacttttgc    4020 ttttatgaaa atagattcat attgtatttc ccagtgtgtc ttttatgtct ttgaatgttt    4080
tggagaaaag tctatgcctg tctaaaaatg aatccagtgt tgcctttctg agggatttct    4140
gctcaatgca atacactgtt cagtgctatt ctcccagcta ggtttatcca tgaaggactg    4200
agtgaccttt gttgtattta acaaaatcca ggtgcatcaa tttctgatgc ttttactat     4260 tgtgtattat ctactatgtg tgttttattt ctgctgagag tattcaggtt tgccatggac    4320
atcagaagtt tgaattccag tcttatctta tgttccatgg ctgaattta aagctgttta     4380 ggtttaacaa tgaagggatt tattctttag tcaaaattgt tgttttact ctagctcagg     4440 attcgtattt ttaaagattt agttaatata acacagcac agatttgtca gaagaaaaaa    4500
aatttgctgt aataccaaaa ctaacctcat caaagataca gaaaaaaga aatatagtga    4560 gccctaaagg acacatacat tgaataaata attggaacat gtggttatct ttagatccac    4620
atcttagctg tcatttgttc actctaaaac tgatgttcat ctttctgtta atttccctct    4680
gcctaaagag tacatgacag aaatgaccta tcactactta ttatttctga agcctaactg    4740
caagagtgat ttcttgagaa caagtaaaga actggctcgt gccg                    4784
```

<210> SEQ ID NO 27
<211> LENGTH: 4693
<212> TYPE: DNA
<213> ORGANISM: Homo sapiens
<300> PUBLICATION INFORMATION:
<308> DATABASE ACCESSION NUMBER: NM_005104
<309> DATABASE ENTRY DATE: 2006-08-20
<313> RELEVANT RESIDUES: (1)..(4693)

<400> SEQUENCE: 27

```
ggactgcggg ataggaagct ggggatatgg acaagcagca gcgttatagc gctctgggtt      60
tcgggacata ggcctgggcc atgcggcccc cttggcccct tggcgcgacc cccaggaacg     120
ttcggaaagc tggtcctcgt ggctggggga aaggcggggg gtgggggga agcgggcacg      180 tgaccccggt cagccaatct gggtgctgct gacgtggccg cgcggccccg atgctctccc     240 cacccccca gcccgttccg gaagggaggg gctgggggct acgccccctc cccagcacg      300 gcttcgtttt ctgggggggg gttgacaccc cggattacat accccgtacc aagccgaggg    360
caactttgga ggcccctggg aaggcttag gatccagatt cttcgctgct gctgccttac     420
```

```
cgccgagaac caccacccgc caggcgtctt gcggccacac ccctggcggg ttcaggcagg   480
ctacgcccac gcgacccctc ccgtttccct gctttggcca atggaggagc tacgaatggc   540
acgacctgct cgagcttggc agtctccagt tgggctgtgc atggaagctt gggaagactt   600
tgttggaagg ggaggcgggg agagagtgct ggaggctctg gggcgatggc ttccgcacct   660
cttccaacca ccctctttcc ctggagtcgg cggaccacag ctcagccaat tggcttggag   720
atgtggcggg ttgccacttc cctgtgggtc tctgcgcac tcttctgcct ggtgactgac    780
accttggaaa tgaagtttat gacgtcatcg ctgcggctgg ccaatagaaa aagctcccgc   840
ggagaggtgt tccttcccct tcgactcagc ttcttcaccc gcgtgagcga gcgcgcgcgc   900
gcggaggggg tggggaaaat ctcaagcagg gtggcgcgca tgagcggcga agctcctcct   960
ccccgcctat atataaaggg ctggcgcggg gctcggcggc gccatttcgt gctggagtgg  1020
agcagcctct agaacgagct ggaggattct gcctaccgat acagagcctt cgagtcgtcc  1080
ggggccgcca ttacaatcca cctccatccg cttggaaatg ccttcgtcc cggcctatga   1140 ctggtcccag cgggcagtac agacccccta gaagccctg gagctcccct ttttcgggcc   1200
ccgcccaatc ctcggagtct gtccacccc tctactccgc cctcaagagg atttcaaaga   1260
tggaggcggc ggctccctaa accactttc gtgttcatcc gcctccatcc gagatcgaaa    1320
cgggacctcg tcggcccgt aggggcccga caagaagagg gaatccctgc agaccaacag   1380
cgggctatat tgacgacggt gtctgagatc ggggaccgtc ttttgaagag tcagtccctc   1440
cttagttgcc cgcctcagct gaggccgccg ccatttcttt gctgtccgcc gtctgcagag   1500
cgcgccaagc tgcccggagc tctccgagag gccccaaaga gactgctttc gtgccggcca   1560
ggcagggggt tgtcgcctg gaggcccaag aggaacggcc tcccccaac ttagcgggtt    1620 atgctggacc gggcggtgag ggaaaccgag gccacccgga cttccgcgg ctgagggcag    1680 cgccggttcc ttgcggtcaa gatgctgcaa aacgtgactc cccacaataa gctccctggg   1740
gaagggaatg cagggttgct ggggctgggc ccagaagcag cagcaccagg gaaaaggatt   1800
cgaaaaccct ctctcttgta tgagggcttt gagagcccca caatggcttc ggtgcctgct   1860
ttgcaactta cccctgccaa cccaccaccc ccggaggtgt ccaatcccaa aaagccagga   1920
cgagttacca accagctgca atacctacac aaggtagtga tgaaggctct gtggaaacat   1980
cagttcgcat ggccattccg gcagcctgtg gatgctgtca aactgggtct accggattat   2040
cacaaaatta taaaacagcc tatggacatg ggtactatta agaggagact tgaaaacaat   2100
tattattggg ctgcttcaga gtgtatgcaa gattttaata ccatgttcac caactgttac   2160
atttacaaca agcccactga tgatattgtc ctaatggcac aaacgctgga aaagatattc   2220
ctacagaagg ttgcatcaat gccacaagaa gaacaagagc tggtagtgac catccctaag   2280
aacagccaca agaaggggc caagttggca gcgctccagg gcagtgttac cagtgcccat   2340
caggtgcctg ccgtctcttc tgtgtcacac acagccctgt atactcctcc acctgagata   2400
cctaccactg tcctcaacat tccccaccca tcagtcattt cctctccact tctcaagtcc   2460
ttgcactctg ctggacccc gctccttgct gttactgcag ctcctccagc ccagccctt    2520 gccaagaaaa aaggcgtaaa gcggaaagca gatactacca ccctacacc tacagccatc    2580 ttggctcctg gttctccagc tagccctcct gggagtcttg agcctaaggc agcacggctt   2640
ccccctatgc gtagagagag tggtcgcccc atcaagcccc cacgcaaaga cttgcctgac   2700
tctcagcaac aacaccagag ctctaagaaa ggaaagcttt cagaacagtt aaaacattgc   2760
aatggcattt tgaaggagtt actctctaag aagcatgctg cctatgcttg gcctttctat   2820
```

```
aaaccagtgg atgcttctgc acttggcctg catgactacc atgacatcat taagcacccc    2880
atggacctca gcactgtcaa gcggaagatg gagaaccgtg attaccggga tgcacaggag    2940
tttgctgctg atgtacggct tatgttctcc aactgctata agtacaatcc cccagatcac    3000
gatgttgtgg caatggcacg aaagctacag gatgtatttg agttccgtta tgccaagatg    3060
ccagatgaac cactagaacc agggccttta ccagtctcta ctgccatgcc cctggcttg     3120 gccaaatcgt cttcagagtc ctccagtgag gaaagtagca gtgagagctc ctctgaggaa    3180
gaggaggagg aagatgagga ggacgaggag gaagaagaga gtgaaagctc agactcagag    3240
gaagaaaggg ctcatcgctt agcagaacta caggaacagc ttcgggcagt acatgaacaa    3300
ctggctgctc tgtcccaggg tccaatatcc aagcccaaga ggaaaagaga gaaaaaagag    3360
aaaaagaaga acggaaggc agagaagcat cgaggccgag ctggggccga tgaagatgac    3420 aagggggccta gggcaccccg cccacctcaa cctaagaagt ccagaaaagc aagtggcagt    3480
gggggtggca gtgctgcttt aggcccttct ggctttggac cttctggagg aagtggcacc    3540
aagctcccca aaaggccac aaagacagcc ccacctgccc tgcctacagg ttatgattca    3600
gaggaggagg aagagagcag gcccatgagt tacgatgaga gcggcagct gagcctggac    3660 atcaacaaat tacctgggga gaagctgggc cgagttgtgc atataatcca agccagggag    3720
ccctctttac gtgattcaaa cccagaagag attgagattg attttgaaac actcaagcca    3780
tccacactta gagagcttga gcgctatgtc ctttcctgcc tacgtaagaa accccggaag    3840
ccctacacca ttaagaagcc tgtgggaaag acaaaggagg aactggcttt ggagaaaaag    3900
cgggaattag aaaagcggtt acaagatgtc agcggacagc tcaattctac taaaaagccc    3960
cccaagaaag cgaatgagaa aacagagtca tcctctgcac agcaagtagc agtgtcacgc    4020
cttagcgctt ccagctccag ctcagattcc agctcctcct cttcctcgtc gtcgtcttca    4080
gacaccagtg attcagactc aggctaaggg gtcaggccag atgggcagg aaggctccgc    4140 aggaccggac ccctagacca ccctgcccca cctgccccctt cccccttgc tgtgacactt    4200 cttcatctca cccccccccg cccccctcta ggagagctgg ctctgcagtg gggggagggat    4260 gcagggacat ttactgaagg agggacatgg acaaaacaac attgaattcc cagccccatt    4320
ggggagtgat ctcttggaca cagagccccc attcaaaatg gggcagggca agggtgggag    4380
tgtgcaaagc cctgatctgg agttacctga ggccatagct gccctattca cttctaaggg    4440
ccctgttttg agattgtttg ttctaattta ttttaagcta ggtaaggctg gggggagggt    4500
ggggccgtgt cccctcagc ctccatgggg agggaagaag ggggagctct tttttttacgt    4560 tgatttttt ttttctactc tgtttttccct tttccttcc gctccatttg gggccctggg    4620
ggtttcagtc atctccccat ttggtcccct ggactgtctt tgttgattct aacttgtaaa    4680
taaagaaaat att                                                       4693

<210> SEQ ID NO 28
<211> LENGTH: 3497
<212> TYPE: DNA
<213> ORGANISM: Homo sapiens
<300> PUBLICATION INFORMATION:
<308> DATABASE ACCESSION NUMBER: NM_001712
<309> DATABASE ENTRY DATE: 2006-08-20
<313> RELEVANT RESIDUES: (1)..(3497)

<400> SEQUENCE: 28
aggctcagca cagagagtgg aaaacagcag aggtgacaga gcagccgtgc tcgaagcgtt      60
cctggagccc aagctctcct ccacaggtga agacaggggcc agcaggagac accatggggc    120
```

```
acctctcagc cccacttcac agagtgcgtg taccctggca ggggcttctg ctcacagcct    180
cacttctaac cttctggaac ccgcccacca ctgcccagct cactactgaa tccatgccat    240
tcaatgttgc agaggggaag gaggttcttc tccttgtcca caatctgccc cagcaacttt    300
ttggctacag ctggtacaaa gggggaaagag tggatggcaa ccgtcaaatt gtaggatatg    360
caataggaac tcaacaagct accccagggc ccgcaaacag cggtcgagag acaatatacc    420
ccaatgcatc cctgctgatc cagaacgtca cccagaatga cacaggattc tacaccctac    480
aagtcataaa gtcagatctt gtgaatgaag aagcaactgg acagttccat gtatacccgg    540
agctgcccaa gccctccatc tccagcaaca actccaaccc tgtggaggac aaggatgctg    600
tggccttcac ctgtgaacct gagactcagg acacaaccta cctgtggtgg ataaacaatc    660
agagcctccc ggtcagtccc aggctgcagc tgtccaatgg caacaggacc ctcactctac    720
tcagtgtcac aaggaatgac acaggaccct atgagtgtga aatacagaac ccagtgagtg    780
cgaaccgcag tgacccagtc accttgaatg tcacctatgg cccggacacc cccaccattt    840 cccccttcaga cacctattac cgtccagggg caaacctcag cctctcctgc tatgcagcct    900
ctaacccacc tgcacagtac tcctggctta tcaatggaac attccagcaa agcacacaag    960
agctctttat ccctaacatc actgtgaata atagtggatc ctataccctgc cacgccaata   1020 actcagtcac tggctgcaac aggaccacag tcaagacgat catagtcact gagctaagtc   1080
cagtagtagc aaagccccaa atcaaagcca gcaagaccac agtcacagga gataaggact   1140
ctgtgaacct gacctgctcc acaaatgaca ctggaatctc catccgttgg ttcttcaaaa   1200
accagagtct cccgtcctcg gagaggatga agctgtccca gggcaacacc accctcagca   1260
taaaccctgt caagagggag gatgctggga cgtattggtg tgaggtcttc aacccaatca   1320
gtaagaacca aagcgacccc atcatgctga acgtaaacta taatgctcta ccacaagaaa   1380
atggcctctc acctgggcc attgctggca ttgtgattgg agtagtggcc ctggttgctc   1440
tgatagcagt agccctggca tgttttctgc atttcgggaa gaccggcagg gcaagcgacc   1500
agcgtgatct cacagagcac aaaccctcag tctccaacca cactcaggac cactccaatg   1560
acccacctaa caagatgaat gaagttactt attctaccct gaactttgaa gcccagcaac   1620
ccacacaacc aacttcagcc tccccatccc taacagccac agaaataatt tattcagaag   1680
taaaaaagca gtaatgaaac ctgtcctgct cactgcagtg ctgatgtatt tcaagtctct   1740
caccctcatc actaggagat tccttttccc tgtaggggta gaggggtggg gacagaaaca   1800
actttctcct actcttcctt cctaataggc atctccaggc tgcctggtca ctgcccctct   1860
ctcagtgtca atagatgaaa gtacattggg agtctgtagg aaacccaacc ttcttgtcat   1920
tgaaatttgg caaagctgac tttgggaaag agggaccaga acttccctc ccttccctt   1980 ttcccaacct ggacttgttt taaacttgcc tgttcagagc actcattcct tcccaccccc   2040
agtcctgtcc tatcactcta attcggattt gccatagcct tgaggttatg tccttttcca   2100
ttaagtacat gtgccaggaa acaagagaga gagaaagtaa aggcagtaat gccttctcct   2160
atttctccaa agccttgtgt gaactcacca aacacaagaa aatcaaatat ataaccaata   2220
gtgaaatgcc acacctttgt ccactgtcag ggttgtctac ctgtaggatc agggtctaag   2280
caccttggtg cttagctaga ataccaccta atccttctgg caagcctgtc ttcagagaac   2340
ccactagaag caactaggaa aatcacttgc caaaatccaa ggcaattcct gatggaaaat   2400
gcaaaagcac atatatgttt taatatcttt atgggctctg ttcaaggcag tgctgagagg   2460
gaggggttat agcttcagga gggaaccagc ttctgataaa cacaatctgc taggaacttg   2520
```

```
ggaaaggaat cagagagctg cccttcagcg attatttaaa ttattgttaa agaatacaca    2580
atttggggta ttgggatttt tctccttttc tctgagacat tccaccattt taattttttgt   2640 aactgcttat ttatgtgaaa agggttattt ttacttagct tagctatgtc agccaatccg    2700
attgccttag gtgaaagaaa ccaccgaaat ccctcaggtc ccttggtcag gagcctctca    2760
agattttttt tgtcagaggc tccaaataga aaataagaaa aggttttctt cattcatggc    2820
tagagctaga tttaactcag tttctaggca cctcagacca atcatcaact accattctat    2880
tccatgtttg cacctgtgca ttttctgttt gcccccattc actttgtcag gaaaccttgg    2940
cctctgctaa ggtgtatttg gtccttgaga agtgggagca ccctacaggg acactatcac    3000
tcatgctggt ggcattgttt acagctagaa agctgcactg gtgctaatgc cccttgggga    3060
aatggggctg tgaggaggag gattataact taggcctagc ctcttttaac agcctctgaa    3120
atttatcttt tcttctatgg ggtctataaa tgtatcttat aataaaaagg aaggacagga    3180
ggaagacagg caaatgtact tctcacccag tcttctacac agatgaaatc tctttggggc    3240
taagagaaag gttttattct atattgctta cctgatctca tgttaggcct aagaggcttt    3300
ctccaggagg attagcttgg agttctctat actcaggtac ctctttcagg gttttctaac    3360
cctgacacgg actgtgcata ctttccctca tccatgctgt gctgtgttat ttaattttc    3420 ctggctaaga tcatgtctga attatgtatg aaaattattc tatgtttta taataaaaat    3480 aatatatcag acatcga                                                   3497

<210> SEQ ID NO 29
<211> LENGTH: 2466
<212> TYPE: DNA
<213> ORGANISM: Homo sapiens
<300> PUBLICATION INFORMATION:
<308> DATABASE ACCESSION NUMBER: NM_001008860
<309> DATABASE ENTRY DATE: 2006-08-15
<313> RELEVANT RESIDUES: (1)..(2466)

<400> SEQUENCE: 29
gttttccggc gccggcccta ggtcccggca gcggtggtga cggcggtgcc ggaggttgtc      60
cttggcaggt tttcctcggc gcttctccat ggaggaggcg gtgcgaacgg cttcagcccc     120
gaatgctcgc atctcccact ggacggcgac gaaggcggtg gccgtgcgag cgcaggactg     180
ggcggcctgt gtgggggtgt gagccgcggt gcccaaggct gcgccggcga ggggaagccg     240
cgcggccggc cggccgacta gggctggagc tactcggcca gggtttaaga ctttaaatga     300
gaataaaggt tggtatttac gaggaaatga gagtgaataa gtcatctcta acctctccca     360 gcctttttt cataagagag accatattaa acttacatgt ttgaagactg cttcattctg     420
cctctagtac cagcggtttc tctgttctgt gatcaatgtg attcacagga actccttaag     480
taacaaacga aatgagccag gggcgtggaa aatatgactt ctatattggt ctgggattgg     540
ctatgagctc cagcattttc attggaggaa gttcatttt gaaaaaaaag ggcctccttc     600
gacttgccag gaaaggctct atgagagcag gtcaaggtgg ccatgcatat cttaaggaat     660
ggttgtggtg ggctggactg ctgtcaatgg gagctggtga ggtggccaac ttcgctgcgt     720
atgcgtttgc accagccact ctagtgactc cactaggagc tctcagcgtg ctagtaagtg     780
ccattctttc ttcatacttt ctcaatgaaa gacttaatct tcatgggaaa attgggtgtt     840
tgctaagtat tctaggatct acagttatgg tcattcatgc tccaaaggaa gaggagattg     900
agactttaaa tgaaatgtct cacaagctag gtgatccagg ttttgtggtc tttgcaaccc     960
ttgtggtcat tgtggccttg atattaatct tcgtggtggg tcctcgccat ggacagacaa    1020
```

| | | |
|---|---|---|
| acattcttgt gtacataaca atctgctctg taatcggcgc gttttcagtc tcctgtgtga | 1080 | |
| agggcctggg cattgctatc aaggagctgt ttgcagggaa gcctgtgctg cggcatcccc | 1140 | |
| tggcttggat tctgctgctg agcctcatcg tctgtgtgag cacacagatt aattacctaa | 1200 | |
| atagggccct ggatatattc aacacttcca ttgtgactcc aatatattat gtattcttta | 1260 | |
| caacatcagt tttaacttgt tcagctattc ttttaagga gtggcaagat atgcctgttg | 1320 | |
| acgatgtcat tggtactttg agtggcttct ttacaatcat tgtggggata ttcttgttgc | 1380 | |
| atgcctttaa agacgtcagc tttagtctag caagtctgcc tgtgtctttt cgaaaagacg | 1440 | |
| agaaagcaat gaatggcaat ctctctaata tgtatgaagt tcttaataat aatgaagaaa | 1500 | |
| gcttaacctg tggaatcgaa caacacactg gtgaaaatgt ctcccgaaga atggaaatc | 1560 | |
| tgacagcttt ttaagaaagg tgtaattaaa ggttaatctg tgattgttat gaagtgaatt | 1620 | |
| tgaatatcat cagaatgtgt ctgaaaaaac attgtcctca ataatgttc tttaaaggca | 1680 | |
| atctttttaa agatttcact aatttggacc aagaaattac ttttcttgta tttaaacaaa | 1740 | |
| caatggtagc tcactaaaat gacctcagca catgacgatt tctattaaca ttttattgtt | 1800 | |
| gtagaagtat tttacatttt catcccttct ccaaaagccg aatgcactaa tgacagtttt | 1860 | |
| aagtctatga aaatgcttta ttttttcatt ggtgatgaaa gtctgaaatg tgcatttgtc | 1920 | |
| atccccactc catcaatccc tgaccatgta aggctttttt attttaaaaa aacagagtta | 1980 | |
| tcccaataca ttatcctgtg atttaccta cctacaaaag tggctcctgt ttgtttgatg | 2040 | |
| atgattggtt ttattttga aatatttatt aagggaaaac taagttactg aatgaaggaa | 2100 | |
| cctcttctt acaaaacaaa aaaaagggca gaaatcaccc caaggaacga tttctcaggt | 2160 | |
| tgagatgatc accgtgaatc cggcttcctc tgagcattcg atggccttag cacctcatca | 2220 | |
| agccagcaca tcctgcctgc tgttgcagcc tggctgggtt tattcttcag ttaccctaat | 2280 | |
| cccatgatgc ctggaaccttg gattaccgtt tacatcagc tcttgtactt tcagtatat | 2340 | |
| tttcataatg agttatattg tcatttagac tttgaacagc tctgggaaat agaagactag | 2400 | |
| ggttgtttct taaatttagc tcatgttata ataaaaagtt gaaatgaaaa aaaaaaaaa | 2460 | |
| aaaaaa | 2466 | |

<210> SEQ ID NO 30
<211> LENGTH: 2330
<212> TYPE: DNA
<213> ORGANISM: Homo sapiens
<300> PUBLICATION INFORMATION:
<308> DATABASE ACCESSION NUMBER: NM_001008892
<309> DATABASE ENTRY DATE: 2006-10-15
<313> RELEVANT RESIDUES: (1)..(2330)

<400> SEQUENCE: 30

| | | |
|---|---|---|
| gttttccggc gccggcccta ggtcccggca gcggtggtga cggcggtgcc ggaggttgtc | 60 | |
| cttggcaggt tttcctcggc gcttctccat ggaggaggcg gtgcgaacgg cttcagcccc | 120 | |
| gaatgctcgc atctcccact ggacggcgac gaaggcggtg gccgtgcgag cgcaggactg | 180 | |
| ggcggcctgt gtggggtgt gagccgcggt gcccaaggct gcgccggcga ggggaagccg | 240 | |
| cgcggccggc cggccgacta gggtttgaag actgcttcat tctgcctcta gtaccagcgg | 300 | |
| tttctctgtt ctgtgatcaa tgtgattcac aggaactcct taagtaacaa acgaaatgag | 360 | |
| ccaggggcgt ggaaaatatg acttctatat tggtctggga ttggctatga gctccagcat | 420 | |
| tttcattgga ggaagtttca ttttgaaaaa aagggcctc cttcgacttg ccaggaaagg | 480 | |
| ctctatgaga gcaggtcaag gtggccatgc atatcttaag gaatggttgt ggtgggctgg | 540 | |

-continued

| | |
|---|---|
| actgctgtca atgggagctg gtgaggtggc caacttcgct gcgtatgcgt ttgcaccagc | 600 |
| cactctagtg actccactag gagctctcag cgtgctagta agtgccattc tttcttcata | 660 |
| cttctcaat gaaagactta atcttcatgg gaaaattggg tgtttgctaa gtattctagg | 720 |
| atctacagtt atggtcattc atgctccaaa ggaagaggag attgagactt aaatgaaat | 780 |
| gtctcacaag ctaggtgatc caggttttgt ggtcttttgca acccttgtgg tcattgtggc | 840 |
| cttgatatta atcttcgtgg tgggtcctcg ccatggacag acaaacattc ttgtgtacat | 900 |
| aacaatctgc tctgtaatcg gcgcgttttc agtctcctgt gtgaagggcc tgggcattgc | 960 |
| tatcaaggag ctgtttgcag ggaagcctgt gctgcggcat cccctggctt ggattctgct | 1020 |
| gctgagcctc atcgtctgtg tgagcacaca gattaattac ctaaataggg ccctggatat | 1080 |
| attcaacact tccattgtga ctccaatata ttatgtattc tttacaacat cagttttaac | 1140 |
| ttgttcagct attctttta aggagtggca agatatgcct gttgacgatg tcattggtac | 1200 |
| tttgagtggc ttcttacaa tcattgtggg gatattcttg ttgcatgcct ttaaagacgt | 1260 |
| cagctttagt ctagcaagtc tgcctgtgtc ttttcgaaaa gacgagaaag caatgaatgg | 1320 |
| caatctctct aatatgtatg aagttcttaa taataatgaa gaaagcttaa cctgtggaat | 1380 |
| cgaacaacac actggtgaaa atgtctcccg aagaaatgga atctgacag cttttaagaa | 1440 |
| aagtgtaat taaaggttaa tctgtgattg ttatgaagtg aatttgaata tcatcagaat | 1500 |
| gtgtctgaaa aaacattgtc ctcaaataat gttctttaaa ggcaatcttt ttaaagattt | 1560 |
| cactaatttg gaccaagaaa ttactttct tgtatttaaa caaacaatgg tagctcacta | 1620 |
| aaatgacctc agcacatgac gatttctatt aacatttat tgttgtagaa gtattttaca | 1680 |
| ttttcatccc ttctccaaaa gccgaatgca ctaatgacag ttttaagtct atgaaaatgc | 1740 |
| tttatttttt cattggtgat gaaagtctga atgtgcatt tgtcatcccc actccatcaa | 1800 |
| tccctgacca tgtaaggctt ttttatttta aaaaaacaga gttatcccaa tacattatcc | 1860 |
| tgtgatttac cttacctaca aaagtggctc ctgtttgttt gatgatgatt ggttttatt | 1920 |
| ttgaaatatt tattaaggga aaactaagtt actgaatgaa ggaacctctt tcttacaaaa | 1980 |
| caaaaaaaag ggcagaaatc accccaagga acgatttctc aggttgagat gatcaccgtg | 2040 |
| aatccggctt cctctgagca ttcgatggcc ttagcacctc atcaagccag cacatcctgc | 2100 |
| ctgctgttgc agcctggctg ggtttattct tcagttaccc taatcccatg atgcctggaa | 2160 |
| ccttgattac cgttttacat cagctcttgt acttttcagt atattttcat aatgagttat | 2220 |
| attgtcattt agactttgaa cagctctggg aaatagaaga ctagggttgt ttcttaaatt | 2280 |
| tagctcatgt tataataaaa agttgaaatg aaaaaaaaaa aaaaaaaaa | 2330 |

<210> SEQ ID NO 31
<211> LENGTH: 2273
<212> TYPE: DNA
<213> ORGANISM: Homo sapiens
<300> PUBLICATION INFORMATION:
<308> DATABASE ACCESSION NUMBER: NM_001008894
<309> DATABASE ENTRY DATE: 2006-10-15
<313> RELEVANT RESIDUES: (1)..(2273)

<400> SEQUENCE: 31

| | |
|---|---|
| gttttccggc gccggcccta ggtcccggca gcggtggtga cggcggtgcc ggaggttgtc | 60 |
| cttggcaggt tttcctcggc gcttctccat ggaggaggcg gtgcgaacgg cttcagcccc | 120 |
| gaatgctcgc atctcccact ggacggcgac gaaggcggtg gccgtgcgag cgcaggactg | 180 |
| ggcggcctgt gtggggggtgt gagccgcggt gcccaaggct gcgccggcga ggggaagccg | 240 |

-continued

| | | | | |
|---|---|---|---|---|
| cgcggccggc | cggccgacta | gggtttgaag | actgcttcat | tctgcctcta | gtaccagcgg | 300 |
| tttctctgtt | ctgtgatcaa | tgtgattcac | aggaactcct | taagtaacaa | acgaaatgag | 360 |
| ccagggggcgt | ggaaaatatg | acttctatat | tggtctggga | ttggctatga | gctccagcat | 420 |
| tttcattgga | ggaagtttca | ttttgaaaaa | aaagggcctc | cttcgacttg | ccaggaaagg | 480 |
| ctctatgaga | gcagtgggag | ctggtgaggt | ggccaacttc | gctgcgtatg | cgtttgcacc | 540 |
| agccactcta | gtgactccac | taggagctct | cagcgtgcta | gtaagtgcca | ttctttcttc | 600 |
| atactttctc | aatgaaagac | ttaatcttca | tgggaaaatt | gggtgtttgc | taagtattct | 660 |
| aggatctaca | gttatggtca | ttcatgctcc | aaaggaagag | gagattgaga | ctttaaatga | 720 |
| aatgtctcac | aagctaggtg | atccaggttt | tgtggtcttt | gcaacccttg | tggtcattgt | 780 |
| ggccttgata | ttaatcttcg | tggtgggtcc | tcgccatgga | cagacaaaca | ttcttgtgta | 840 |
| cataacaatc | tgctctgtaa | tcggcgcgtt | ttcagtctcc | tgtgtgaagg | gcctgggcat | 900 |
| tgctatcaag | gagctgtttg | cagggaagcc | tgtgctgcgg | catcccctgg | cttggattct | 960 |
| gctgctgagc | ctcatcgtct | gtgtgagcac | acagattaat | tacctaaata | gggccctgga | 1020 |
| tatattcaac | acttccattg | tgactccaat | atattatgta | ttctttacaa | catcagtttt | 1080 |
| aacttgttca | gctattcttt | ttaaggagtg | gcaagatatg | cctgttgacg | atgtcattgg | 1140 |
| tactttgagt | ggcttcttta | caatcattgt | ggggatattc | ttgttgcatg | cctttaaaga | 1200 |
| cgtcagcttt | agtctagcaa | gtctgcctgt | gtcttttcga | aaagacgaga | aagcaatgaa | 1260 |
| tggcaatctc | tctaatatgt | atgaagttct | taataataat | gaagaaagct | taacctgtgg | 1320 |
| aatcgaacaa | cacactggtg | aaaatgtctc | ccgaagaaat | ggaaatctga | cagcttttta | 1380 |
| agaaaggtgt | aattaaaggt | taatctgtga | ttgttatgaa | gtgaatttga | atatcatcag | 1440 |
| aatgtgtctg | aaaaaacatt | gtcctcaaat | aatgttcttt | aaaggcaatc | ttttttaaaga | 1500 |
| tttcactaat | ttggaccaag | aaattacttt | tcttgtattt | aaacaaacaa | tggtagctca | 1560 |
| ctaaaatgac | ctcagcacat | gacgatttct | attaacattt | tattgttgta | gaagtatttt | 1620 |
| acattttcat | cccttctcca | aaagccgaat | gcactaatga | cagttttaag | tctatgaaaa | 1680 |
| tgctttattt | tttcattggt | gatgaaagtc | tgaaatgtgc | atttgtcatc | cccactccat | 1740 |
| caatccctga | ccatgtaagg | ctttttttatt | taaaaaaac | agagttatcc | caatacatta | 1800 |
| tcctgtgatt | taccttacct | acaaaagtgg | ctcctgtttg | tttgatgatg | attggtttta | 1860 |
| tttttgaaat | atttattaag | ggaaaactaa | gttactgaat | gaaggaacct | ctttcttaca | 1920 |
| aaacaaaaaa | aagggcagaa | atcaccccaa | ggaacgattt | tcaggttgaa | gatgatcacc | 1980 |
| gtgaatccgg | cttcctctga | gcattcgatg | gccttagcac | ctcatcaagc | cagcacatcc | 2040 |
| tgcctgctgt | tgcagcctgg | ctgggtttat | tcttcagtta | ccctaatccc | atgatgcctg | 2100 |
| gaaccttgat | taccgtttta | catcagctct | tgtactttc | agtatatttt | cataatgagt | 2160 |
| tatattgtca | tttagacttt | gaacagctct | gggaaataga | agactagggt | tgtttcttaa | 2220 |
| atttagctca | tgttataata | aaaagttgaa | atgaaaaaaa | aaaaaaaaa | aaa | 2273 |

<210> SEQ ID NO 32
<211> LENGTH: 2588
<212> TYPE: DNA
<213> ORGANISM: Homo sapiens
<300> PUBLICATION INFORMATION:
<308> DATABASE ACCESSION NUMBER: NM_030922
<309> DATABASE ENTRY DATE: 2006-10-15
<313> RELEVANT RESIDUES: (1)..(2588)

<400> SEQUENCE: 32

```
gttttccggc gccggccctu ggtcccggca gcggtggtga cggcggtgcc ggaggttgtc    60
cttggcaggt tttcctcggc gcttctccat ggaggaggcg gtgcgaacgg cttcagcccc   120
gaatgctcgc atctcccact ggacggcgac gaaggcggtg gccgtgcgag cgcaggactg   180
ggcggcctgt gtgggggtgt gagccgcggt gcccaaggct gcgccggcga ggggaagccg   240
cgcggccggc cggccgacta gggctggagc tactcggcca gggtttaaga ctttaaatga   300
gaataaaggg tggtatttac gaggaaatga gagtgaataa gtcatctcta acctctccca   360
gccttttttt cataagagag accatattaa acttacatgc tctcccggct gtgatagacc   420
ttcagttaca gagagaggga gcagagtggg accaggtctg agaatagtga agcaactcat   480
tcctttcagg acattccctc tgatgtccta ttttcaaact gtttgaagac tgcttcattc   540
tgcctctagt accagcggtt tctctgttct gtgatcaatg tgattcacag gaactcctta   600
agtaacaaac gaaatgagcc aggggcgtgg aaaatatgac ttctatattg gtctgggatt   660
ggctatgagc tccagcattt tcattggagg aagtttcatt ttgaaaaaaa agggcctcct   720
tcgacttgcc aggaaaggct ctatgagagc aggtcaaggt ggccatgcat atcttaagga   780
atggttgtgg tgggctggac tgctgtcaat gggagctggt gaggtggcca acttcgctgc   840
gtatgcgttt gcaccagcca ctctagtgac tccactagga gctctcagcg tgctagtaag   900
tgccattctt tcttcatact ttctcaatga aagacttaat cttcatggga aaattgggtg   960
tttgctaagt attctaggat ctacagttat ggtcattcat gctccaaagg aagaggagat  1020
tgagacttta aatgaaatgt ctcacaagct aggtgatcca ggttttgtgg tctttgcaac  1080
ccttgtggtc attgtggcct tgatattaat cttcgtggtg ggtcctcgcc atggacagac  1140
aaacattctt gtgtacataa caatctgctc tgtaatcggc gcgttttcag tctcctgtgt  1200
gaagggcctg ggcattgcta tcaaggagct gttttgcaggg aagcctgtgc tgcggcatcc  1260
cctggcttgg attctgctgc tgagcctcat cgtctgtgtg agcacacaga ttaattacct  1320
aaatagggcc ctggatatat tcaacacttc cattgtgact ccaatatatt atgtattctt  1380
tacaacatca gttttaactt gttcagctat tcttttttaag gagtggcaag atatgcctgt  1440
tgacgatgtc attggtactt tgagtggctt ctttacaatc attgtgggga tattcttgtt  1500
gcatgccttt aaagacgtca gctttagtct agcaagtctg cctgtgtctt ttcgaaaaga  1560
cgagaaagca atgaatggca atctctctaa tatgtatgaa gttcttaata ataatgaaga  1620
aagcttaacc tgtggaatcg aacaacacac tggtgaaaat gtctcccgaa gaaatggaaa  1680
tctgacagct ttttaagaaa ggtgtaatta aaggttaatc tgtgattgtt atgaagtgaa  1740
tttgaatatc atcagaatgt gtctgaaaaa acattgtcct caaataatgt tctttaaagg  1800
caatcttttt aaagatttca ctaatttgga ccaagaaatt acttttcttg tatttaaaca  1860
aacaatggta gctcactaaa atgaccctcag cacatgacga tttctattaa cattttattg  1920
ttgtagaagt attttacatt ttcatcccctt ctccaaaagc cgaatgcact aatgacagtt  1980
ttaagtctat gaaaatgctt tattttttca ttggtgatga agtctgaaa tgtgcatttg  2040
tcatccccac tccatcaatc cctgaccatg taaggctttt ttatttttaa aaaacagagt  2100
tatcccaata cattatcctg tgatttacct tacctacaaa agtggctcct gtttgtttga  2160
tgatgattgg ttttatttttt gaaatattta ttaagggaaa actaagttac tgaatgaagg  2220
aacctctttc ttacaaaaca aaaaaaaggg cagaaatcac cccaaggaac gatttctcag  2280
gttgagatga tcaccgtgaa tccggcttcc tctgagcatt cgatggcctt agcacctcat  2340
caagccagca catcctgcct gctgttgcag cctggctggg tttattcttc agttacccta  2400
```

-continued

| | |
|---|---|
| atcccatgat gcctggaacc ttgattaccg ttttacatca gctcttgtac ttttcagtat | 2460 |
| attttcataa tgagttatat tgtcatttag actttgaaca gctctgggaa atagaagact | 2520 |
| agggttgttt cttaaattta gctcatgtta taataaaaag ttgaaatgaa aaaaaaaaa | 2580 |
| aaaaaaaa | 2588 |

<210> SEQ ID NO 33
<211> LENGTH: 3331
<212> TYPE: DNA
<213> ORGANISM: Homo sapiens
<300> PUBLICATION INFORMATION:
<308> DATABASE ACCESSION NUMBER: NM_021950
<309> DATABASE ENTRY DATE: 2006-10-15
<313> RELEVANT RESIDUES: (1)..(3331)

<400> SEQUENCE: 33

| | |
|---|---|
| gtctatcagc gatttcatct tcaggcctgg actacaccac tcaccctccc agtgtgcttg | 60 |
| agaaacaaac tgcacccact gaactccgca gctagcatcc aaatcagccc ttgagatttg | 120 |
| aggccttgga gactcaggag ttttgagagc aaaatgacaa cacccagaaa ttcagtaaat | 180 |
| gggactttcc cggcagagcc aatgaaaggc cctattgcta tgcaatctgg tccaaaacca | 240 |
| ctcttcagga ggatgtcttc actggtgggc cccacgcaaa gcttcttcat gagggaatct | 300 |
| aagactttgg gggctgtcca gattatgaat gggctcttcc acattgccct gggggtctt | 360 |
| ctgatgatcc cagcagggat ctatgcaccc atctgtgtga ctgtgtggta ccctctctgg | 420 |
| ggaggcatta tgtatattat ttccggatca ctcctggcag caacggagaa aaactccagg | 480 |
| aagtgtttgg tcaaggaaa atgataatg aattcattga gcctctttgc tgccatttct | 540 |
| ggaatgattc tttcaatcat ggacatactt aatattaaaa tttcccattt tttaaaaatg | 600 |
| gagagtctga attttattag agctcacaca ccatatatta acatatacaa ctgtgaacca | 660 |
| gctaatccct ctgagaaaaa ctccccatct acccaatact gttacagcat acaatctctg | 720 |
| ttcttgggca ttttgtcagt gatgctgatc tttgccttct tccaggaact tgtaatagct | 780 |
| ggcatcgttg agaatgaatg gaaagaacg tgctccagac ccaaatctaa catagttctc | 840 |
| ctgtcagcag aagaaaaaaa agaacagact attgaaataa agaagaagt ggttgggcta | 900 |
| actgaaacat cttcccaacc aaagaatgaa gaagacattg aaattattcc aatccaagaa | 960 |
| gaggaagaag aagaaacaga gacgaacttt ccagaacctc cccaagatca ggaatcctca | 1020 |
| ccaatagaaa atgacagctc tccttaagtg atttcttctg ttttctgttt cctttttaa | 1080 |
| acattagtgt tcatagcttc caagagacat gctgactttc atttcttgag gtactctgca | 1140 |
| catacgcacc acatctctat ctggcctttg catggagtga ccatagctcc ttctctctta | 1200 |
| cattgaatgt agagaatgta gccattgtag cagcttgtgt tgtcacgctt cttcttttga | 1260 |
| gcaactttct tacactgaag aaaggcagaa tgagtgcttc agaatgtgat ttcctactaa | 1320 |
| cctgttcctt ggataggctt tttagtatag tattttttt tgtcattttc tccatcaaca | 1380 |
| accagggaga ctgcacctga tggaaaagat atatgactgc ttcatgacat tcctaaacta | 1440 |
| tcttttttt attccacatc tacgttttg gtggagtccc ttttgcatca ttgttttaag | 1500 |
| gatgataaaa aaaaataaca actagggaca atacagaacc cattccattt atctttctac | 1560 |
| agggctgaca ttgtggcaca ttcttagagt taccacaccc catgagggaa gctctaaata | 1620 |
| gccaacaccc atctgttttt tgtaaaaaca gcatagctta tacatggaca tgtctctgcc | 1680 |
| ttaactttc ctaactccca ctctaggcta ttgtttgcat gtctacctac ttttagccat | 1740 |
| tatgcgagaa aagaaaaaaa tgaccataga aaatgccacc atgaggtgcc caaatttcaa | 1800 |

-continued

| | |
|---|---|
| ataataatta acatttagtt atatttataa tttccagatg acaaagtatt tcatcaaata | 1860 |
| acttcatttg atgttccatg atcaagaaag aatccctatc tctattttac aagtaattca | 1920 |
| aagaggccaa ataacttgta aacaagaaaa ggtaacttgt caacagtcat aactagtaat | 1980 |
| tatgagagcc ttgtttcata accaggtctt cttactcaaa tcctgtgatg tttgaaataa | 2040 |
| ccaaattgtc tctccaatgt ctgcataaac tgtgagagcc aagtcaacag cttttatcaa | 2100 |
| gaatttactc tctgaccagc aataaacaag cactgagaga cacagagagc cagattcaga | 2160 |
| ttttacccat ggggataaaa agactcagac tttcaccaca tttggaaaac tacttgcatc | 2220 |
| ataaatatat aataactggt agtttatatg aagcagacac taagtgctat agacactctc | 2280 |
| agaatatcat acttggaaac aatgtaatta aaatgccgaa tctgagtcaa cagctgccct | 2340 |
| actttttcaat tcagatatac tagtacctta cctagaaata atgttaacct agggtgaagt | 2400 |
| cactataatc tgtagtctat tatttgggca tttgctacat gatgagtgct gccagattgt | 2460 |
| ggcaggtaaa gagacaatgt aatttgcact ccctatgata tttctacatt tttagcgacc | 2520 |
| actagtggaa gacattcccc aaaattagaa aaaaggaga tagaagattt ctgtctatgt | 2580 |
| aaagttctca aaatttgttc taaattaata aaactatctt tgtgttcttt tctgcaacag | 2640 |
| atgattccaa catgggtgtt tgtctattct tctttactct tgaaacatta gaccatggga | 2700 |
| ggctcttaca gccttgagtt gatatttata caacccaaat ctaggtttga acggtgaggt | 2760 |
| gtcaggtcat caaatattca tgtctatata gtcttacaca ggttctcaaa aaaaatgttc | 2820 |
| atgggatagg tcattgataa tggattcctt attctgagaa ctccagacga ctgaaatata | 2880 |
| tgagagaagg aaaaggacat agtaggagca ggcctgagaa aaaaatgaaa gtcagaaatc | 2940 |
| tttaaaaaaa tacaagatct tatttctatc ttattttttc tcctcttctg aaatatatat | 3000 |
| gaggattcct ctccaaaccc atggtttctc taagaatttt gagtcatttg tatgacctca | 3060 |
| aataattagt tttagctgac ctcacataac tccttataat aggagacatc tttaatgtct | 3120 |
| gctattaaag aaggatgaaa attcctatga ccttctcccc gattatccct ttggcaatat | 3180 |
| agagtcaaat aataacattg accaatagta aacatgcttt gccaagaagt agaagatata | 3240 |
| ttctctagcc ttagtttttc ctcccaattt gcattttgt aaaaataatg ttgtatccac | 3300 |
| aaaggaaata aactttaaaa acccaagtgc a | 3331 |

<210> SEQ ID NO 34
<211> LENGTH: 3594
<212> TYPE: DNA
<213> ORGANISM: Homo sapiens
<300> PUBLICATION INFORMATION:
<308> DATABASE ACCESSION NUMBER: NM_152866
<309> DATABASE ENTRY DATE: 2006-10-15
<313> RELEVANT RESIDUES: (1)..(2594)

<400> SEQUENCE: 34

| | |
|---|---|
| gtctatcagc gatttcatct tcaggcctgg actacaccac tcaccctccc agtgtgcttg | 60 |
| agaaacaaac tgcacccact gaactccgca gctagcatcc aaatcagccc ttgagatttg | 120 |
| aggccttgga gactcagatc ctgaacaaga gagaacaaaa tctctacttt gatggaactt | 180 |
| ccattctgtg gggaagagac tgacaataag caattaaata aataagaact cagcagtagg | 240 |
| ccttgcctca gatccaaggt cactcggaag aggccatgtc tacccctcaat gacactcatg | 300 |
| gaggaaatgc tgagagaagc attcagatgc atgacacaag gtaagactgc caaaaatctt | 360 |
| gttcttgctc tcctcatttt gttatttgtt ttatttttag gagttttgag agcaaaatga | 420 |
| caacacccag aaaattcagta aatgggactt tcccggcaga gccaatgaaa ggccctattg | 480 |

```
ctatgcaatc tggtccaaaa ccactcttca ggaggatgtc ttcactggtg ggccccacgc    540
aaagcttctt catgagggaa tctaagactt tgggggctgt ccagattatg aatgggctct    600
tccacattgc cctgggggt cttctgatga tcccagcagg gatctatgca cccatctgtg    660
tgactgtgtg gtaccctctc tggggaggca ttatgtatat tatttccgga tcactcctgg    720
cagcaacgga gaaaaactcc aggaagtgtt tggtcaaagg aaaaatgata atgaattcat    780
tgagcctctt tgctgccatt tctggaatga ttctttcaat catggacata cttaatatta    840
aaatttccca tttttaaaa atggagagtc tgaatttat tagagctcac acaccatata    900
ttaacatata caactgtgaa ccagctaatc cctctgagaa aaactcccca tctacccaat    960
actgttacag catacaatct ctgttcttgg gcattttgtc agtgatgctg atctttgcct   1020
tcttccagga acttgtaata gctggcatcg ttgagaatga atggaaaaga acgtgctcca   1080
gacccaaatc taacatagtt ctcctgtcag cagaagaaaa aaagaacag actattgaaa   1140 taaaagaaga agtggttggg ctaactgaaa catcttccca accaaagaat gaagaagaca   1200
ttgaaattat tccaatccaa gaagaggaag aagaagaaac agagacgaac tttccagaac   1260
ctccccaaga tcaggaatcc tcaccaatag aaaatgacag ctctccttaa gtgatttctt   1320
ctgttttctg tttcctttt taaacattag tgttcatagc ttccaagaga catgctgact   1380
ttcatttctt gaggtactct gcacatacgc accacatctc tatctggcct ttgcatggag   1440
tgaccatagc tccttctctc ttacattgaa tgtagagaat gtagccattg tagcagcttg   1500
tgttgtcacg cttcttcttt tgagcaactt tcttacactg aagaaggca gaatgagtgc   1560 ttcagaatgt gatttcctac taacctgttc cttggatagg cttttagta tagtattttt   1620 ttttgtcatt ttctccatca acaaccaggg agactgcacc tgatggaaaa gatatatgac   1680
tgcttcatga cattcctaaa ctatctttt tttattccac atctacgttt ttggtggagt   1740
cccttttgca tcattgtttt aaggatgata aaaaaaaata caactaggg acaatacaga   1800 acccattcca tttatctttc tacagggctg acattgtggc acattcttag agttaccaca   1860
ccccatgagg gaagctctaa atagccaaca cccatctgtt ttttgtaaaa acagcatagc   1920
ttatacatgg acatgtctct gccttaactt ttcctaactc ccactctagg ctattgtttg   1980
catgtctacc tacttttagc cattatgcga gaaaagaaaa aaatgaccat agaaaatgcc   2040
accatgaggt gcccaaattt caaataataa ttaacattg gttatattta aatttccag    2100 atgacaaagt atttcatcaa ataacttcat ttgatgttcc atgatcaaga aagaatccct   2160
atctctattt tacaagtaat tcaaagaggc caaataactt gtaaacaaga aaaggtaact   2220
tgtcaacagt cataactagt aattatgaga gccttgtttc ataaccaggt cttcttactc   2280
aaatcctgtg atgtttgaaa taaccaaatt gtctctccaa tgtctgcata aactgtgaga   2340
gccaagtcaa cagcttttat caagaattta ctctctgacc agcaataaac aagcactgag   2400
agacacagag agccagattc agattttacc catggggata aaaagactca gactttcacc   2460
acatttggaa aactacttgc atcataaata tataataact ggtagtttat atgaagcaga   2520
cactaagtgc tatagacact ctcagaatat catacttgga aacaatgtaa ttaaaatgcc   2580
gaatctgagt caacagctgc cctacttttc aattcagata tactagtacc ttacctagaa   2640
ataatgttaa cctagggtga agtcactata atctgtagtc tattatttgg gcatttgcta   2700
catgatgagt gctgccagat tgtggcaggt aaagagacaa tgtaatttgc actccctatg   2760
atatttctac atttttagcg accactagtg aagacattc cccaaaatta gaaaaaagg    2820 agatagaaga tttctgtcta tgtaaagttc tcaaaatttg ttctaaatta ataaaactat   2880
```

| | |
|---|---|
| ctttgtgttc ttttctgcaa cagatgattc aacatgggt gtttgtctat tcttctttac | 2940 |
| tcttgaaaca ttagaccatg ggaggctctt acagccttga gttgatattt atacaaccca | 3000 |
| aatctaggtt tgaacggtga ggtgtcaggt catcaaatat tcatgtctat atagtcttac | 3060 |
| acaggttctc aaaaaaaatg ttcatgggat aggtcattga taatgattc cttattctga | 3120 |
| gaactccaga cgactgaaat atatgagaga aggaaaagga catagtagga gcaggcctga | 3180 |
| gaaaaaaatg aaagtcagaa atcttaaaa aaatacaaga tcttatttct atcttatttt | 3240 |
| ttctcctctt ctgaaatata tatgaggatt cctctccaaa cccatggttt ctctaagaat | 3300 |
| tttgagtcat ttgtatgacc tcaaataatt agttttagct gacctcacat aactccttat | 3360 |
| aataggagac atctttaatg tctgctatta agaaggatg aaaattccta tgaccttctc | 3420 |
| cccgattatc cctttggcaa tatagagtca aataataaca ttgaccaata gtaaacatgc | 3480 |
| tttgccaaga agtagaagat atattctcta gccttagttt ttcctcccaa tttgcattt | 3540 |
| tgtaaaaata atgttgtatc cacaaaggaa ataaacttta aaaacccaag tgca | 3594 |

<210> SEQ ID NO 35
<211> LENGTH: 4141
<212> TYPE: DNA
<213> ORGANISM: Homo sapiens
<300> PUBLICATION INFORMATION:
<308> DATABASE ACCESSION NUMBER: NM_003618
<309> DATABASE ENTRY DATE: 2006-08-20
<313> RELEVANT RESIDUES: (1)..(4141)

<400> SEQUENCE: 35

| | |
|---|---|
| gagccggccg cggcgccctc tctccgtgtg gcccctgag cggccccct ccctgcccg | 60 |
| ggagggaggc gggggcacc tggggcccgc catgaacccc ggcttcgatt tgtcccgccg | 120 |
| gaacccgcag gaggacttcg agctgattca gcgcatcggc agcggcacct acggcgacgt | 180 |
| ctacaaggca cggaatgtta acactggtga attagcagca attaaagtaa taaaattgga | 240 |
| accaggagaa gactttgcag ttgtgcagca agaaattatt atgatgaaag actgtaaaca | 300 |
| cccaaatatt gttgcttatt ttggaagcta tctcaggcga gataagcttt ggatttgcat | 360 |
| ggagttttgt ggaggtggtt ctttacagga tatttatcac gtaactggac ctctgtcaga | 420 |
| actgcaaatt gcatatgtta gcagagaaac actgcaggga ttatattatc ttcacagtaa | 480 |
| aggaaaaatg cacagagata taagggagc taacattcta ttaacggata atggtcatgt | 540 |
| gaaattggct gattttggag tatctgcaca gataacagct acaattgcca acggaagtc | 600 |
| tttcattggc acaccatatt ggatggctcc agaagttgca gctgttgaga ggaaggggg | 660 |
| ttacaatcaa ctctgtgatc tctgggcagt gggaatcact gccatagaac ttgcagagct | 720 |
| tcagcctcct atgtttgact acacccaat gagagcatta tttctaatga caaaagcaa | 780 |
| ttttcagcct cctaaactaa aggataaaat gaaatggtca atagttttc atcactttgt | 840 |
| gaaaatggca cttaccaaaa atccgaaaaa agacctact gctgaaaaat tattacagca | 900 |
| tcctttttgta acacaacatt tgacacggtc tttggcaatc gagctgttgg ataaagtaaa | 960 |
| taatccagat cattccactt accatgattt cgatgatgat gatcctgagc tcttgttgc | 1020 |
| tgtaccacat agaattcact caacaagtag aaacgtgaga aagaaaaaa cacgctcaga | 1080 |
| gataaccttt ggccaagtga aatttgatcc accccttaaga aaggagacag aaccacatca | 1140 |
| tgaacttccc gacagtgatg gttttttgga cagttcagaa gaaatatact acactgcaag | 1200 |
| atctaatctg gatctgcaac tggaatatgg acaaggacac caaggtggtt acttttagg | 1260 |
| tgcaaacaag agtcttctca gtctgttga agaagaattg catcagcgag gacacgtcgc | 1320 |

```
acatttagaa gatgatgaag gagatgatga tgaatctaaa cactcaactc tgaaagcaaa    1380
aattccacct cctttgccac caaagcctaa gtctatcttc ataccacagg aaatgcattc    1440
tactgaggat gaaaatcaag gaacaatcaa gagatgtccc atgtcaggga gcccagcaaa    1500
gccatcccaa gttccaccta gaccaccacc tcccagatta cccccacaca aacctgttgc    1560
cttaggaaat ggaatgagct ccttccagtt aaatggtgaa cgagatggct cattatgtca    1620
acaacagaat gaacatagag gcacaaacct ttcaagaaaa gaaaagaaag atgtaccaaa    1680
gcctattagt aatggtcttc ctccaacacc taaagtgcat atgggtgcat gttttcaaa     1740 agtttttaat gggtgtccct tgaaaattca ctgtgcatca tcatggataa acccagatac    1800
aagagatcag tacttgatat ttggtgccga agaagggatt tatacc ctca atcttaatga   1860 acttcatgaa acatcaatgg aacagctatt ccctcgaagg tgtacatggt tgtatgtaat    1920
gaacaattgc ttgctatcaa tatctggtaa agcttctcag ctttattccc ataatttacc    1980
agggcttttt gattatgcaa gacaaatgca aaagttacct gttgctattc cagcacacaa    2040
actccctgac agaatactgc caaggaaatt ttctgtatca gcaaaatcc ctgaaaccaa     2100 atggtgccag aagtgttgtg ttgtaagaaa tccttacacg ggccataaat acctatgtgg    2160
agcacttcag actagcattg ttctattaga atgggttgaa ccaatgcaga aatttatgtt    2220
aattaagcac atagattttc ctataccatg tccacttaga atgtttgaaa tgctggtagt    2280
tcctgaacag gagtacccctt tagtttgtgt tggtgtcagt agaggtagag acttcaacca    2340
agtggttcga tttgagacgg tcaatccaaa ttctacctct tcatggttta cagaatcaga    2400
taccccacag acaaatgtta ctcatgtaac ccaactggag agagatacca tccttgtatg    2460
cttggactgt tgtataaaaa tagtaaatct ccaaggaaga ttaaaatcta gcaggaaatt    2520
gtcatcagaa ctcaccttg atttccagat tgaatcaata gtgtgcctac aagacagtgt     2580
gctagctttc tggaaacatg gaatgcaagg tagaagtttt agatctaatg aggtaacaca    2640
agaaatttca gatagcacaa gaattttcag gctgcttgga tctgacaggg tcgtggtttt    2700
ggaaagtagg ccaactgata accccacagc aaatagcaat ttgtcatcc tggcgggtca     2760 tgaaaacagt tactgagaat tgttgtgctt tgacagttaa ctctagaaag aaagaacact    2820
accactgcaa cattaatgga tgcttgaagc tgtacaaaag ctgcagtaac ctgtcttcag    2880
ttactttgta atttattgtg gcatgagata agatggggaa aattttgttt taagtggtat    2940
ggatatattt agcatattga accacacaag tgcttaattc attgttatgt aatctttgta    3000
catataggca gtattttttc tgtgaaactt catattgctg aagacataca ctaagaattt    3060
atgtagataa tgtactttta tgagatgtac aagtaagtgt cttatctgta cagatgtaaa    3120
tgttgatgaa aatgcaattg gggttaatat tttaagaatt cttagtata ttcttgggtg     3180 tggctatatt acaaaatggg atgctggcaa tgaaacaata catttaacac tattgtatt     3240 ttattatatg taatttagta atatgaatat aaatcttgta acttttaaaa ttgtaatgga    3300
ggctgtaatc attttataat ctttttaatt ttaatgcaag tacactggtg tttatatttg    3360
cacaaagtat tgatatgtga tgtattaagt cacaaaagta agctgtgaca ttgtctataa    3420
gcatttggct ccacaaatgt atttggattg ttttctatgt gaagcaaacc aattataatt    3480
aaccacatgt tgtagtaact ggtctttta tatttaagca gaatcctgta agattgcttg     3540
tctttgctta aaaacaatac ctttgaacat ttttgaatca cagaatagcg gtaccatgat    3600
agaatactgc aattgtggtc agaattacag tatgcacaaa gaattaatta gcattattaa    3660
agagtcctca ctaaacattt catatgatca cactgaagaa ctgtaacatt ccatagagtg    3720
```

| | |
|---|---|
| aagtggttca aatttctctt ggaatttta cttttgttgg ccttatttta tgatccttt | 3780 |
| catattctt ttgacttaga gtattaatac atggccaaaa taattagtt actacctcat | 3840 |
| acaaacaata taatggttac tacacatcac aggaacttag ttttggttta agtcatttt | 3900 |
| gattgctttt ttccaatgga atatgtatat accaggtttt agcaaaatgc cacttttgg | 3960 |
| ctcttttgg tatatgttct ttatattta atgtgagtat atacactaag aacaaactaa | 4020 |
| attgtgattt atgatcttca tttatttaa tgataatggt tttaaaatat gttcctgatt | 4080 |
| gtacatattg taaataaac atgtttttta acaaaaaaaa aaaaaaaaa aaaaaaaaa | 4140 |
| a | 4141 |

<210> SEQ ID NO 36
<211> LENGTH: 3938
<212> TYPE: DNA
<213> ORGANISM: Homo sapiens
<300> PUBLICATION INFORMATION:
<308> DATABASE ACCESSION NUMBER: NM_017784
<309> DATABASE ENTRY DATE: 2005-09-24
<313> RELEVANT RESIDUES: (1)..(3938)

<400> SEQUENCE: 36

| | |
|---|---|
| tgagcctgtc aggctgggcg ggtccatatc cgggtggacc gggtgggtga ggctgcccct | 60 |
| ccctccaggt cccgaggtgg ataaggggtg gggagtgacg tgcagagatt ccctttcgcc | 120 |
| ccttcggatc caagagaggg tggcagaagg aatgcgtggg tgacttggcg tggatttagg | 180 |
| gcgtgcccac cctgcagatc ggcctcctag agtgtcccga gggcctgaga ggccgcaggg | 240 |
| acacgaagga agagaaggca tttcccgggg atttggagca ggcacgcgcg gcccgggcgt | 300 |
| ccggagctgt agcagcagca gcagccgccg tgccggggcc gccaccgcgg cgggcacccg | 360 |
| cgtcccgggc gcccacggac catggagagg gcagtccagg gcacagacgg cggcgggggt | 420 |
| agcaacagca gcagccgcag cagcagccgt gctacctcgg cgggctcctc gccctcctgc | 480 |
| tctctggcgg gccgggggt ctccagccgg tcggcggcgg ccgggctcgg cggcggggga | 540 |
| agccgcagca gccgggctc tgtggccgct agccgtccg ggggaggcgg ccgcaggagg | 600 |
| gagccggcgc tcgagggcgt gctcagcaaa tacaccaacc tcctccaggg ctggcagaac | 660 |
| aggtacttcg tactggattt cgaggctggc atcctgcagt attttgtgaa tgagcaaagc | 720 |
| aaacaccaga agcctcgagg agtcctgtct ttatctggag ccatagtgtc cctgagcgat | 780 |
| gaagctcccc acatgctggt ggtgtactct gctaatggag agatgtttaa actgagagct | 840 |
| gctgatgcaa aagagaaaca attctgggtg actcagcttc gagcttgtgc caaataccac | 900 |
| atggaaatga attctaagag tgctccaagc tcccgaagcc gaagtctcac tttgctccca | 960 |
| catgaacac ccaattctgc gtctcccctgt agccagagac acctcagtgt gggggccccc | 1020 |
| ggtgttgtca caatcacgca tcacaagtcg cctgcagccg cccgaagagc caagagtcag | 1080 |
| tattccggcc agcttcacga agtcagagag atgatgaacc aggtggaagg gcagcagaag | 1140 |
| aaccttgtgc acgccattga gtccctgcca gggtccggcc ccctcactgc cttggaccag | 1200 |
| gacctgctgc tcctgaaagc tacctctgct gccaccctca gctgccttgg ggagtgcctc | 1260 |
| aacttgttac agcagagtgt gcaccaggcg ggccagccca gccagaagcc aggagcctcg | 1320 |
| gaaaacatcc tgggatggca cgggtccaag tcacattcca cagagcagct gaaaaatggg | 1380 |
| acacttggct ctttgccatc agccagtgcc aacataaccct gggcaatttt accaaaactct | 1440 |
| gctgaagacg aacaaacctc acagccagag ccagagccaa actcaggctc tgaattggtt | 1500 |
| ttgtctgaag atgaaaaaag tgacaatgaa gataaggaag agacggaatt gggcgtcatg | 1560 |

```
gaggatcagc gtagtataat tcttcatctc atttcacaac tcaaacttgg aatggatttg    1620
accaaggtgt tgcttcccac ctttatcctg gagaagcgat ctttgctgga gatgtatgca    1680
gatttcatgg cgcacccaga cctactgctg gccatcaccg ctggggccac accagaggag    1740
agagtcattt gcttcgttga gtattatctc acagcctttc acgagggccg caagggcgct    1800
ttagccaaga agccctacaa ccccatcata ggcgagacat ttcactgctc ctgggaagtt    1860
cccaaggaca gggtcaagcc taagaggact gcttcccgct ctcctgccag ctgtcacgaa    1920
cacccaatgg ccgatgaccc ttccaaaagc tacaaactaa ggtttgtggc tgagcaagtg    1980
tcccatcacc cacccatctc ctgcttctac tgtgagtgcg aggagaagag actgtgcgtc    2040
aacactcatg tatggaccaa aagcaagttc atgggcatgt ccgtgggggt ctctatgata    2100
ggggaaggtg tgttgaggct cctggaacac ggggaggagt acgtattcac cctgcctagt    2160
gcctacgccc ggtccattct caccatcccg tgggtggagc tcggaggaaa agtcagcatc    2220
aactgtgcca agactgggta ctcagcgaca gtgatattcc acacgaagcc tttctatgga    2280
gggaaagtcc acagggttac cgcagaagtg aagcacaacc caaccaacac cattgtttgt    2340
aaagcccatg gggaatggaa tggtacttta gagttcacct acaacaatgg agaaaccaaa    2400
gtcatcgaca caaccacact gccagtgtat cccaagaaga tcagacctct tgagaagcag    2460
ggacccatgg agtccaggaa cctctggcgg gaggtgaccc gatacctgcg gctgggggac    2520
attgacgcag ccaccgagca gaagcggcac ctggaggaga gcaacgggt ggaggaacgg    2580 aagcgcgaga acctccgcac accatggaag cccaaatatt ttatccagga gggcgatggc    2640
tgggtatact tcaatcccct ctggaaagca cactgatggg gtggaggtgc agagctttcc    2700
agtatagccc tgttttttgta ggaatattaa agtagtagag tatcagggtt ttgttggcat    2760
tcactgagac cttgtattag catccaagaa atgatgagag agagagaaat tatatactat    2820
gaaaagtgca cccccacact ctgctagagg aatgaattta ttcaagagcc attcggggca    2880
cgtgtgtgta cacaccgtat acgttcacac acatgcacta tgtaaacatc tgagtatgat    2940
tacacattta aatactgcac tcaccaaggt taaagtgggt aatcataagc tccttttat    3000 caatgaagtt tgaagttttt ctatttttca ctttgccaaa aatgttttac actcacaaag    3060
atattctcac ttagtcaact cctgtcaaaa tgaaggtgaa ctggcatggc ccgatcactg    3120
tccataaggg agaaagtggc tcattcctgg tagaagtatg ggtggttatc atttcaaaat    3180
tattgtgatt ctcacctccc tccccacctc agtgttttgt ctgtccgcgc caagaaaga    3240 taagcaagta tttcctgctg gatgggggtt ggcaggaagc tgttaaagat ttatgccaga    3300
gccttgcagg atggagcacc tctgggacaa ctaagagcca aggcccacca aggagttttc    3360
cacccgtctc tcatggtcac agcgctagtc attcattttt gagaagttgc ttctttttaca    3420 tcagaaaacc agtcaatcat atggagactt cttttgtgat gaaaaagggc tttagaagtt    3480
aaatacatgc atgcacatga aaacatgcac aaccacagcc tcaatcttgt atttagtttg    3540
gggaaagaga agagaatttc ctgtggatta ttttttcctc aagtgcacct ctctggttaa    3600
cccaaactct gcaagaaagc actgtgacta aaacatacat aacgcctgca taaatattcc    3660
atggtttcag ttaaatttca gttttttagcc tttacacatg aggtcaaagg agtgacgaaa    3720
atacaaagca aggaaaaaat gaaatatctg gttttgctg aatgcttaat ttattttta    3780 ctgtgccact ccaatatttta tcaaatccaa atagcatgaa tgcttctctg tagtaatact    3840
aattttgtgc cttttgtctg ctttcttaag accagttgtt cacactttgt agatattaga    3900
caaatatatt tcgattgaat acaaaaaaaa aaaaaaaa                           3938
```

<210> SEQ ID NO 37
<211> LENGTH: 3239
<212> TYPE: DNA
<213> ORGANISM: Homo sapiens
<300> PUBLICATION INFORMATION:
<308> DATABASE ACCESSION NUMBER: NM_017935
<309> DATABASE ENTRY DATE: 2006-08-20
<313> RELEVANT RESIDUES: (1)..(3239)

<400> SEQUENCE: 37

| | | | | | |
|---|---|---|---|---|---|
| ccgcagcctc | cgcgggtggc | aagcgggctg | gggagagccg | agggccaaag | gaagagaaaa | 60 |
| tcgcggggag | tctctggccg | ggagagtcca | ggtagcgctc | ggcgggcagc | agtgcgcagg | 120 |
| cccctcggct | tcaaccgcca | caatgctgcc | agcagcgcca | ggcaaggggc | ttgggagccc | 180 |
| ggaccccgcc | ccctgcggcc | cagcgccccc | aggaaataca | aaagatataa | taatgatata | 240 |
| tgaagaagat | gctgaggaat | gggctctgta | cttgacagaa | gtattttac | atgttgtgaa | 300 |
| aagggaagcc | atcctgttat | atcgcttgga | gaatttctct | tttcggcatt | tggagttgct | 360 |
| gaacttaacg | tcttacaaat | gtaaacttt | gatattatca | aatagcctgc | ttagagacct | 420 |
| aactccaaag | aaatgtcagt | ttctggaaaa | gatacttcat | tcaccaaaaa | gtgtagttac | 480 |
| tttgctttgt | ggagtgaaga | gttcagatca | gctctatgaa | ttactaaata | tctctcaaag | 540 |
| cagatgggag | atctcaactg | aacaggaacc | tgaagactac | atctctgtaa | tccagagtat | 600 |
| catattcaaa | gattctgaag | actactttga | ggtcaacatt | ccaacagacc | tacgagcaaa | 660 |
| acattctggg | gaaataagtg | agagaaagga | aattgaagaa | ctatcagaag | cttcaagaaa | 720 |
| caccatacca | ctagcagtgg | tgcttcccac | tgaaattcca | tgtgagaatc | ctggtgaaat | 780 |
| attcataatt | ttgagagatg | aagtaattgg | tgatactgta | gaggttgaat | ttacatcaag | 840 |
| taataagcgc | attagaacac | ggccagccct | ttggaataag | aaagtctggt | gcatgaaagc | 900 |
| tttagagttt | cctgctggtt | cagtccatgt | caatgtctac | tgtgatggaa | tcgttaaagc | 960 |
| tacaaccaaa | attaagtact | acccaacagc | aaaggcaaag | gaatgcctat | tcagaatggc | 1020 |
| agattcagga | gagagtttgt | gccagaatag | cattgaagaa | cttgatggtg | tccttacatc | 1080 |
| catattcaaa | catgagatac | catattatga | gttccagtct | cttcaaactg | aaatttgttc | 1140 |
| tcaaaacaaa | tatactcatt | tcaaagaact | tccaactctt | ctccactgtg | cagcaaaatt | 1200 |
| tggcttaaag | aacctggcta | ttcatttgct | tcaatgttca | ggagcaacct | gggcatctaa | 1260 |
| gatgaaaaat | atggagggtt | cagaccccgc | acatattgct | gaaaggcatg | gtcacaaaga | 1320 |
| actcaagaaa | atcttcgaag | acttttcaat | ccaagaaatt | gacataaata | atgagcaaga | 1380 |
| aaatgattat | gaagaggata | ttgcctcatt | ttccacatat | attccttcca | cacagaaccc | 1440 |
| agcatttcat | catgaaagca | ggaagacata | cgggcagagt | gcagatggag | ctgaggcaaa | 1500 |
| tgaaatggaa | ggggaaggaa | aacagaatgg | atcaggcatg | gagaccaaac | acagcccact | 1560 |
| agaggttggc | agtgagagtt | ctgaagacca | gtatgatgac | ttgtatgtgt | tcattcctgg | 1620 |
| tgctgatcca | gaaaataatt | cacaagagcc | actcatgagc | agcagacctc | ctctccccc | 1680 |
| gccgcgacct | gtagctaatg | ccttccaact | ggaaagacct | cacttcacct | taccagggac | 1740 |
| aatggtggaa | ggccaaatgg | aaagaagtca | aaactgggt | catcctggtg | ttagacaaga | 1800 |
| aacaggagat | gaacccaaag | gagaaaaaga | gaagaaagaa | gaggaaaaag | agcaggagga | 1860 |
| ggaagaagac | ccatatactt | ttgctgagat | tgatgacagt | gaatatgaca | tgatattggc | 1920 |
| caatctgagt | ataaagaaaa | aaactggagg | tcggtctttc | attataaata | gacctcctgc | 1980 |
| ccccacaccc | cgacccacaa | gtatacctcc | aaaagaggaa | actacacctt | acatagctca | 2040 |

| | |
|---|---|
| agtgtttcaa caaaagacag ccagaagaca atctgatgat gacaagttcc gtggtcttcc | 2100 |
| taagaaacaa gacagagctc ggatagagag tccagccttt tctactctca ggggctgtct | 2160 |
| aactgatggt caggaagaac tcatcctcct gcaggagaaa gtaaagaatg gaaaatgtc | 2220 |
| tatgatgaa gctctggaga aatttaaaca ctggcagatg ggaaaagtg gcctggaaat | 2280 |
| gattcagcag gagaaattac gacaactacg agactgcatt attgggaaaa ggccagaaga | 2340 |
| agaaaatgtc tataataaac tcaccattgt gcaccatcca ggtggtaagg aaactgccca | 2400 |
| caatgaaaat aagttttata atgtacactt cagcaataag cttcctgctc gaccccaagt | 2460 |
| tgaaaaggaa tttggtttct gttgcaagaa agatcattaa agaaggttat tataatgaaa | 2520 |
| ctcacgaatc tacggacatt ttgctttcag ggtgaagcaa gcttgaattt ggattgcctg | 2580 |
| ctctctttaa agcgaattca tactatgaca gcagaaacaa aacttcagat ttcagaattt | 2640 |
| gttattggca aaatttattc tcattatacc tgcttcatat gggtatatta ctattaaaac | 2700 |
| agaataccat agagtaattg cattatttga aaattctctc attttacaat gcacttcacc | 2760 |
| aatgaaacag ctaatttcca ttttgaaaat taaaagaaaa cagcacagag aagttaaatg | 2820 |
| cggtgtagca aagttatggg gtctgcttga gggcactaac ctcaacagat tattcctcct | 2880 |
| ctccttagaa taaccatgaa aatacaaatt tacttagcac attttgtctt tttaagtagc | 2940 |
| tggttcattt tctgaatttc tcacattcag agttccagtc attattgtta catcatgttt | 3000 |
| gcagaaacct tgtcttattt agtgtctatt tgcatataac cctgaaaaca ttattatttg | 3060 |
| aaaactttc tatatctcaa attaatatac attttcataa cctacctttg tattaagact | 3120 |
| tgcaattta tcaatctatt atttcttaga aacaatttac tagcttagaa tagaaagcaa | 3180 |
| tgttatcgtc atataatttt catgtacaaa tgccacaaat aaattgaatg tttaaagct | 3239 |

<210> SEQ ID NO 38
<211> LENGTH: 4064
<212> TYPE: DNA
<213> ORGANISM: Homo sapiens
<300> PUBLICATION INFORMATION:
<308> DATABASE ACCESSION NUMBER: NM_021070
<309> DATABASE ENTRY DATE: 2006-08-20
<313> RELEVANT RESIDUES: (1)..(4064)

<400> SEQUENCE: 38

| | |
|---|---|
| atgcccgggc cccgaggggc tgctggcggc ctggcccctg agatgcgcgg ggcgggggcg | 60 |
| gcggggctgc tggcgctgct gctgctgctg ctgctgctgc tgctgggcct gggcggcagg | 120 |
| gtcgaggggg ggccggccgg cgagcgggc gcaggcgggg gcgggcgct ggcccgcgag | 180 |
| cgcttcaagg tggtctttgc gccggtgatc tgcaagcgga cctgtctcaa gggccagtgt | 240 |
| cgggacagtt gtcagcaggg ctccaacatg acgctcatcg gagagaacgg ccacagcaca | 300 |
| gacacgctca cgggctccgg cttccgcgtg gtggtgtgcc ctctcccctg catgaatggc | 360 |
| ggccagtgct cctcgcgaaa ccagtgcctg tgtccccgg acttcactgg gcgcttctgc | 420 |
| caggtgcccg caggaggagc cggtgggggt accggcggct caggccccgg cctgagcagg | 480 |
| acagggccc tgtccacagg ggcgctgccg cccctggctc cggagggcga ctctgtggcc | 540 |
| agcaagcacg ccatctacgc cgtccaggtg atcgctgacc tcctgggcc cggggagggg | 600 |
| cctcctgccc agcacgcagc cttcctggtg ccctaggcc cgggacagat tcagcagaa | 660 |
| gtgcaggccc cgccccccgt ggtgaatgtg cgcgtccatc acccgcccga ggcctcagtc | 720 |
| caggtgcacc gcattgagag ctcgaacgcc gagagcgcag ccccctccca gcacctgctg | 780 |
| ccgcacccca gccctcgca cccccggccg cccacccaga agcccctggg ccgctgcttt | 840 |

-continued

```
caggacactc tgcccaagca gccgtgtggc agcaacccccc tccccggcct caccaagcag   900
gaagactgct gcggtagcat cggcactgcc tggggccaga gcaagtgcca caagtgtccc    960
cagctgcagt acacaggagt gcagaagcca gggcctgtac gtggggaagt gggcgctgac  1020
tgtccccagg gctacaagag gcttaacagc acccactgcc aggacatcaa cgagtgcgca  1080
atgccgggcg tgtgtcgcca tggtgactgc ctcaacaacc ctggctccta tcgctgtgtc  1140
tgcccacctg gccatagttt aggccccttcc cgtacacagt gcattgcaga caaaccggag  1200
gagaagagcc tgtgtttccg cctggtgagc cctgagcacc agtgccagca cccactgacc  1260
acccgcctga cccgccagct ctgctgctgc agtgtcggca aggcctgggg cgcgcggtgt  1320
cagcgctgcc aacagatgg caccgctgcg ttcaaggaga tctgcccagc tgggaaggga  1380
taccacattc tcacctccca ccagacgctc accattcagg gcgagagtga cttttccctt  1440
ttcctgcacc ctgacgggcc acccaagccc cagcagcttc cggagagccc tagccaggct  1500
ccaccacctg aggacacaga ggaagagaga ggggtgacca cggactcacc ggtgagtgag  1560
gagaggtcag tgcagcagag ccacccaact gccaccacga ctcctgcccg ccctaccccc  1620
gagctgatct cccgtccctc gccccccgacc atgcgctggt tcctgccgga cttgcctcct  1680
tcccgcagcg ccgtagagat cgctcccact caggtcacag agactgatga gtgccgactg  1740
aaccagaaca tctgtggcca cggagagtgc gtgccgggcc ccctgactta ctcctgccac  1800
tgcaaccccg gctaccggtc acatccccag caccgctact gcgtggatgt gaacgagtgc  1860
gaggcagagc cctgtggccc ggggagggggc atctgcatga acaccggcgg ctcctacaat  1920
tgccactgca accgcggcta ccgcctgcac gtgggcgccg gggggcgctc gtgcgtggac  1980
ctgaacgaat gcgccaagcc ccacctgtgc ggcgacggcg gcttctgcat caactttccc  2040
ggtcactaca agtgcaactg ctaccccggc taccggctca agcctcccg gcctcctgtg  2100
tgcgaagaca tcgacgagtg ccgggaccca agctcttgcc cggatggcaa atgcgagaac  2160
aagcccggga gcttcaagtg catcgcctgt cagcctggct accgcagcca ggggggcggg  2220
gcctgtcgcg acgtgaacga gtgcgccgag ggcagcccct gctcgcctgg ctggtgcgag  2280
aacctccccgg gctccttccg ctgcacctgt gcccagggct acgcgcccgc gcccgacggc  2340
cgcagttgct tggatgtgga cgagtgtgag gctggggacg tgtgtgacaa tggcatctgc  2400
agcaacacgc caggatcttt ccagtgtcag tgcctctctg gctaccatct gtccagggac  2460
cggagccact gcgaggacat tgatgagtgt gacttccctg cagcctgcat tgggggtgac  2520
tgcatcaata ccaatggctc ctacagatgt ctttgcccccc aggggcatcg gctggtgggt  2580
ggcaggaaat gccaagacat agatgagtgc agccaggacc cgagcctgtg ccttccccat  2640
ggggcctgca agaaccttca gggctcctat gtgtgtgtct gcgatgaggg cttcactccc  2700
acccaggacc agcacggttg tgaggaggtg gagcagcccc accacaagaa ggagtgctac  2760
ctgaacttcg atgacacagt gttctgcgac agcgtattgg ccaccaacgt gacccagcag  2820
gagtgctgct gctctctggg ggccggctgg ggcgaccact gcgaaatcta ccctgccca   2880
gtctacagtc cagccgagtt ccacagcctc tgcccagacg gaaagggcta cacccaggac  2940
aacaacatcg tcaactacgg catcccagcc caccgtgaca tcgacgagtg catgttgttc  3000
gggtcggaga tttgcaagga gggcaagtgc gtgaacacgc agcctggcta cgagtgctac  3060
tgcaagcagg gcttctacta cgacgggaac ctgctggaat gcgtggacgt ggacgagtgc  3120
ctggacgagt ccaactgccg gaacggagtg tgtgagaaca cgcgcggcgg ctaccgctgt  3180
gcctgcacgc cccctgccga gtacagtccc gcgcagcgcc agtgcctgag cccggaagag  3240
```

```
atggagcgtg ccccggagcg gcgcgacgtg tgctggagcc agcgcggaga ggacggcatg    3300
tgcgctggcc ccctggccgg gcctgccctc accttcgacg actgctgctg ccgccagggc    3360
cgcggctggg gcgcccaatg ccgaccgtgc ccgccgcgcg gcgcggggtc ccattgcccg    3420
acatcgcaga gcgagagcaa ttccttctgg gacacaagcc ccctgctgtt ggggaagccc    3480
ccaagagatg aggacagttc agaggaggat tcagacgagt gtcgctgcgt gagtggccgc    3540
tgcgtgccgc ggccgggcgg cgccgtgtgc gagtgtcccg gcggcttcca gctcgacgcc    3600
tcccgcgccc gctgcgtgga tatcgacgag tgccgagagc tgaaccagcg cgggctgctg    3660
tgcaagagcg agcgctgcgt gaacaccagc ggctccttcc gctgcgtctg caaagccggc    3720
ttcgcgcgca ccgcccgca cggggcctgc gttccccagc gccgccgctg acgccgccga    3780
cgccgccctc ggcccagacc tcggtgatca ctgagggatt ccgcgagct cggcctcact    3840 tctgccccga cttgtggctc ggacccaggg accttcaggg cccgcagacc ctcccggcgc    3900
cttgagaccc gaggcgcccc taccggcccc cctcccggt tagcgggcgg ttgtaaggtc    3960
tccggcgggc gctgcctgcc ttcctcccag agggtgtttc ctagaaactg ataaatcaga    4020
tcgtgcctct ttaccttggg ctttcgaaaa aaaaaaaaaa aaaa                      4064
```

<210> SEQ ID NO 39
<211> LENGTH: 558
<212> TYPE: DNA
<213> ORGANISM: Homo sapiens
<300> PUBLICATION INFORMATION:
<308> DATABASE ACCESSION NUMBER: NM_006786
<309> DATABASE ENTRY DATE: 2006-10-08
<313> RELEVANT RESIDUES: (1)..(558)

<400> SEQUENCE: 39

```
ccaagaagga agccgtctat cttgtggcga tcatgtataa gctggcctcc tgctgtttgc      60
ttttcatagg attcttaaat cctctcttat ctcttcctct ccttgactcc agggaaatat     120
cctttcaact ctcagcacct catgaagacg cgcgcttaac tccggaggag ctagaaagag     180
cttcccttct acagatactg ccagagatgc tgggtgcaga agagggggat attctcagga     240
aagcagactc aagtaccaac attttttaacc caagaggaaa tttgagaaag ttcaggatt     300 tctctggaca agatcctaac attttactga gtcatctttt ggccagaatc tggaaaccat     360
acaagaaacg tgagactcct gattgcttct ggaaatactg tgtctgaagt gaaataagca     420
tctgttagtc agctcagaaa cacccatctt agaatatgaa aaataacaca atgcttgatt     480
tgaaaacagt gtgagaaaa actaggcaaa ctacaccctg ttcattgtta cctggaaaat     540
aaatcctcta tgttttgc                                                   558
```

<210> SEQ ID NO 40
<211> LENGTH: 652
<212> TYPE: DNA
<213> ORGANISM: Homo sapiens
<300> PUBLICATION INFORMATION:
<308> DATABASE ACCESSION NUMBER: NM_021995
<309> DATABASE ENTRY DATE: 2006-10-08
<313> RELEVANT RESIDUES: (1)..(652)

<400> SEQUENCE: 40

```
tccccagatt gtcattcttc agggatggca gccctaaaca cagcatggca actcatctac      60
tcactcatga aagattaaaa aatggaaacc aacgtatttc atcttatgct ctgcgtcact     120
tctgctcgga ctcataaatc cacgtctctt tgctttggcc acttcaactc atatccaagc     180
cttcctttaa ttcatgattt attgctggaa atatcctttc aactctcagc acctcatgaa     240
```

-continued

| | |
|---|---|
| gacgcgcgct taactccgga ggagctagaa agagcttccc ttctacagat actgccagag | 300 |
| atgctgggtg cagaaagagg ggatattctc aggaaagcag actcaagtac caacattttt | 360 |
| aacccaagag gaaatttgag aaagtttcag gatttctctg gacaagatcc taacatttta | 420 |
| ctgagtcatc ttttggccag aatctggaaa ccatacaaga aacgtgagac tcctgattgc | 480 |
| ttctggaaat actgtgtctg aagtgaaata agcatctgtt agtcagctca gaaacaccca | 540 |
| tcttagaata tgaaaaataa cacaatgctt gatttgaaaa cagtgtggag aaaaactagg | 600 |
| caaactacac cctgttcatt gttacctgga aaataaatcc tctatgtttt gc | 652 |

<210> SEQ ID NO 41
<211> LENGTH: 4182
<212> TYPE: DNA
<213> ORGANISM: Homo sapiens
<300> PUBLICATION INFORMATION:
<308> DATABASE ACCESSION NUMBER: NM_021998
<309> DATABASE ENTRY DATE: 2006-07-07
<313> RELEVANT RESIDUES: (1)..(4182)

<400> SEQUENCE: 41

| | |
|---|---|
| agacgcagag tagattgtga ttggctcggg ctgcggaacc tcggaaaccc gaatgtgagg | 60 |
| accttaaggg atccacagct gccgcccccc gcagccatcc agagcgcggt cacagtccga | 120 |
| ctggcggcac ggaggcggcg gcggcggcgg cggcggcagc ggcggcggca gcggcggcgg | 180 |
| cagctgtagc tgcagcagca ggtaaagaga gcgttttccc aaagaaaata acatagcaca | 240 |
| gaaggaaaaa taaaagaaa ttgctgcaga ttttacttta tgtgagaaaa tctacaattt | 300 |
| cttcgagaca ctcatataaa gatattggtg aatgaacttt gctaagtatg gattcaggcg | 360 |
| gtggaagtct tggattgcac acgccagact ctagaatggc ccataccatg attatgcaag | 420 |
| attttgtggc tggaatggct ggtactgcac atatcgatgg agaccatatt gttgtttcag | 480 |
| ttcctgaagc tgttttagtt tctgatgttg tcacagatga tgggataact cttgatcatg | 540 |
| gccttgcagc tgaagttgtc catggacctg atatcatcac agagactgat gtagtaacag | 600 |
| aaggtgtgat tgttcctgaa gcggtacttg aagctgatgt tgccattgaa gaggatttag | 660 |
| aggaagatga tggtgatcac atcttgactt ctgaactaat tacagaaacc gttagggtac | 720 |
| cagagcaggt tttcgtggct gaccttgtta ctggtcctaa tggacactta gaacatgtgg | 780 |
| tccaagattg tgtttcagga gtcgactctc ccacaatggt atcagaggag gttcttgtaa | 840 |
| ctaattcaga tacagaaact gtgattcaag cagctggagg tgttcctggt tctacagtta | 900 |
| ctataaaaac cgaagatgat gatgatgatg atgtcaagag cacttctgaa gactacttaa | 960 |
| tgatatcttt ggatgatgtt ggagaaaaat tagagcatat ggggaataca ccattaaaaa | 1020 |
| ttggcagtga tggttcacaa gaagatgcta agaagatgg gtttggttct gaagttataa | 1080 |
| aagtgtatat atttaaagcg gaggctgaag atgatgttga aataggtgga acagaaattg | 1140 |
| tcacagagag tgagtacacc agtggacatt cagtagctgg agtgcttgac cagagccgaa | 1200 |
| tgcagcggga gaagatggtt tacatggcag ttaaagattc ttctcaagaa gaagatgata | 1260 |
| tcagagatga aagaagagtt tcccgaaggt atgaagattg tcaagcatca ggaaatactt | 1320 |
| tggactcagc attagaaagc agaagtagta cagcagcaca gtaccttcaa atttgtgacg | 1380 |
| gcattaatac aaataaagta cttaaacaaa agccaaaaaa gaggagaagg ggagaaacca | 1440 |
| ggcagtggca aacagctgtt ataataggtc ctgatggaca gccctcaca gtgtacccct | 1500 |
| gccatatttg cacaaaaaag tttaaatcca gggattctt aaaagacac atgaagaatc | 1560 |
| atcctgatca tttaatgaga aaaaaatatc agtgtacaga ttgtgacttt acaactaaca | 1620 |

```
agaaagtgag tttccataac cacttagaaa gccataagct cataaacaaa gtcgacaaaa   1680
cccatgaatt tacagaatac acacgaagat acagagaggc tagtccactg agttccaata   1740
aacttatttt aagagacaag gagccgaaga tgcacaagtg caaatactgt gactatgaaa   1800
ctgcagaaca aggactgtta aacaggcatt tgttggccgt tcacagcaag aattttcctc   1860
atgtttgtgt tgagtgtggg aagggttttc gacatccttc tgaactcaag aaacatatga   1920
gaacccatac tggtgagaag ccatatcagt gtcagtattg tattttcagg tgtgcagatc   1980
aatcaaatct gaaaactcac attaagtcta acatggtaa caatttgcca tataaatgtg   2040
agcattgtcc ccaagcattt ggtgatgaga gggagcttca acgccatctg gatttgtttc   2100
aaggacataa gacacaccag tgtcctcatt gtgaccataa gagcaccaat tcaagtgacc   2160
ttaagcggca catcatatct gtccatacta aggattttcc tcacaaatgt gaggtctgtg   2220
ataaaggttt tcatcgtcct tctgagctca aaaagcatag tgatatccat aagggtagga   2280
agattcatca gtgcaggcac tgtgacttta aaacatccga tccatttatt cttagtggcc   2340
atatcctttc agttcatact aaagatcagc cattgaaatg taaaaggtgc aagagaggat   2400
tcagacaaca aaatgagcta aaaaaacata tgaagaccca tactggaagg aagatttacc   2460
aatgtgagta ttgtgaatac agcactacag atgcatctgg ctttaaacga catgtgatat   2520
caatacatac aaaagactat ccacacaggt gtgaattctg caagaaggga ttccgaagac   2580
catcagaaaa aaatcagcat attatgaggc accacaaaga ggctcttatg taataagatc   2640
aatataaaga aagaagctat ttaggagata tgatatgcta cttgggagaa aactctcact   2700
aactgtctca ccgggtttca aagcttgata ctaaaccatg actttacatt ctttgtatta   2760
aagatcttaa atatttgaa ttcacagggg atcccatagc cctttgaaaa ttacttaaag   2820
aatttaagaa gcactataga atggttacag aaaaacttct taagtatctg tgtaatagta   2880
ttatatgcat acttaaacta cagaggggaa aagcaaagac aaatacttta tttggctgat   2940
tatgttagat acaaatgttt ctgagaagag aatacataat tgagtttagt gatgctttgc   3000
tatagcaagc aaacccactt ttatgcaatt ttagaaatgg ggcagggaaa caaaatgtgg   3060
tcattcatca gtcacttagt cattgagcct tttatattgt acctggaaat taaattccag   3120
caatgacaaa agttttgtgt attcattaaa agaaaactaa ctggaaaaca ggttagatta   3180
attcagtact attaaaaaag aattcagagc tgttaatatt ttatcacagg ataggatact   3240
taaaatatag cattctgtgc tgagatctaa ggtgaagtct ataaagatta aagttccctt   3300
ttttctgatg ttcaagttga ttgttgttca gtatggcata tatgacaaaa gtatatttga   3360
gtcaaatgtg gctttctaaa atggatgcaa cattagcgtt gcaaacaaaa tcagcactat   3420
atttcttaat gatctaaaga ttaatttgag agaacacagt tttcttaaat attataatgt   3480
ctagagtttt tttaggacag tcttagcaag tatgattgtt ctagtcttac ttgctctaat   3540
gtttaaaggt gcaattttat gccattattg aaattgattt ttaaaatcta tataccatat   3600
gattaacatg catttcaat atgaggcagt gtttatgcag tatttaacag agcaatctgc   3660
tgccaataga gttggaggt ggatatttag tttacagtgt ataaacttaa aatatgcatc   3720
cctttaacaa cgctttgtgt tagcatgctg caaatcaaaa tggcacttaa tattaaaagc   3780
tggtttaggg aaattttatg aaaatcctgt tcataaatgt aatgcatatg atatgtactt   3840
ttaagtttta gttgcttcat gtttacattc agctgttcaa cataattaaa atgtaatttt   3900
acttcatgct atattgtggc tttgtgtttc aaataatgtt cacctttctg tttttgcacc   3960
agataagaat cagttccttg agaataaatt ttttatcttt cttaacttca gaatattaaa   4020
```

-continued

| | |
|---|---|
| tttggaatat ctactaaaat tgtgtgttat gtggctgtaa atgatgtaca cgctgtaaaa | 4080 |
| taagatcgct actgttatgt gggattatta tttctaaatg ttactcattg aaatgagcat | 4140 |
| acaataaaaa gcatttattg cacttaaaaa aaaaaaaaa aa | 4182 |

<210> SEQ ID NO 42
<211> LENGTH: 3899
<212> TYPE: DNA
<213> ORGANISM: Homo sapiens
<300> PUBLICATION INFORMATION:
<308> DATABASE ACCESSION NUMBER: NM_003178
<309> DATABASE ENTRY DATE: 2006-08-20
<313> RELEVANT RESIDUES: (1)..(3899)

<400> SEQUENCE: 42

| | |
|---|---|
| tccgccgctg ctgtctgcgg ggtctggcgc cggggtctga gtctctgctg gctaagccgc | 60 |
| cgcctcagcc gcctcagtcg cctcaatctc gccttccgcc ctcgctctcc ctccgcgcca | 120 |
| ccagaccccg tagccccgcg cgcccccagc cctttaagcc agatgatgaa cttcctgcgg | 180 |
| cgccggctgt cggacagcag cttcatcgcc aacctgccca acggctacat gaccgacctg | 240 |
| cagcggcccg agccccagca gccgccgccc ccgccgcccc ccggtccggg cgccgcctcg | 300 |
| gcctcggcgg cgcccccgac cgcctcgccg ggcccggagc ggaggccgcc gcccgcctcg | 360 |
| gcgcccgcgc cgcagcccgc gccgacgccg tcggtgggca gcagcttctt cagctcgctg | 420 |
| tcccaagccg tgaagcagac ggccgcctcg gctggcctgg tggacgcgcc cgctcccgcg | 480 |
| cccgcagccg ccaggaaggc caaggtgctg ctggtggtcg acgagccgca cgccgactgg | 540 |
| gccaagtgct tcggggcaa aaaagtcctt ggagattatg atatcaaggt ggaacaggca | 600 |
| gaattttcag agctcaacct ggtggccat gcagatggca cctatgctgt ggatatgcag | 660 |
| gttctccgga atggcacaaa ggttgtccgg tccttccggc cagacttcgt gctcatccgg | 720 |
| cagcatgcat ttggcatggc ggagaatgag gacttccgcc acctgatcat tggtatgcag | 780 |
| tatgcaggcc tccccagcat caactcactg gaatccatat acaacttctg tgacaagcca | 840 |
| tgggtgtttg cccagctggt cgctatctat aagacactgg gaggagaaaa gttccctctc | 900 |
| attgaacaga catactaccc caaccacaaa gagatgctga cactgccccac gttccctgtg | 960 |
| gtggtgaaga ttggccacgc tcactcaggc atgggcaagg tcaaagtgga aaaccactac | 1020 |
| gacttccagg acattgccag cgtggtggct ctcacccaga cctatgccac tgcagagcct | 1080 |
| ttcattgact ccaagtatga catccgggtc cagaagattg caacaactca aaggcttac | 1140 |
| atgaggacat cgatctcagg gaactggaag acgaacactg ctctgcgat gctggagcag | 1200 |
| attgccatgt cagacaggta caactgtgg gtggacacct gctctgagat gtttggcggc | 1260 |
| ctggacatct gtgctgtcaa agctgtacat ggcaaagatg ggaaagacta catttttgag | 1320 |
| gtcatggact gtagcatgcc actgattggg gaacatcagg tggaggacag gcaactcatc | 1380 |
| accgaactag tcatcagcaa gatgaaccag ctgctgtcca ggactcctgc cctgtctcct | 1440 |
| cagagacccc taacaaccca gcagccacag agcggaacac ttaaggatcc ggactcaagc | 1500 |
| aagacccca ctcagcggcc acccctcaa ggttgtttac agtatattct cgactgtaat | 1560 |
| ggcattgcag tagggccaaa acaagtccaa gcttcttaaa atgattggtg gttaattttt | 1620 |
| caaagcagaa attttaagcc aaaaacaaac gaaaggaaag cggggagggg aaaacagacc | 1680 |
| ctcccactgg tgccgttgct gcgttctttc aatgctgact ggactgtgtt tttcctatgc | 1740 |
| agtgtcagct cctctgtctg gttgtttacc tgttcctgtt cgtgcttgta atgctcactt | 1800 |
| atgttttctc tgtataactt gtgattccag ggctgtttgt caacagtata caaaagaatt | 1860 |

| | | | | |
|---|---|---|---|---|
| gtgcctctcc | caagtccagt | gtgactttat | cttctgggtg | gtttgatagt gttttttaaaa | 1920 |
| gtaatatata | atgtggggtg | aaatgggagt | aggggggtgg | acaggggaga aacgaaaacc | 1980 |
| acaaaaagaa | aacccaactc | ctctcctccc | cccaagctca | gttaaatccc ccacctccaa | 2040 |
| ctttccctcc | accagtgtgc | ttgggatctt | caatgaactg | tgcttttcgc tttctttctg | 2100 |
| catgactatt | gtaactagat | agaacattaa | gagattttca | agatcaaact tccatagctt | 2160 |
| catccactga | atttgaaggc | atccaccttt | ttctccattt | gctaaaattt ggtgcagttt | 2220 |
| gagtttatgt | gaataggctg | gctgtgcctg | tagagctctt | gtgtttttag tgatgacatg | 2280 |
| aaatacaaag | aacaagctat | ttccaggaat | gtgttctgta | ttttacatcc cagtgtaccc | 2340 |
| tttattttat | tattaactaa | ttaactatga | gattttaaa | aaatgggggcc gctgatgtgc | 2400 |
| aatatcaaag | tgaacttgtg | agtattttgt | gtgtgttgat | ctcagttgtt tcttcattgt | 2460 |
| tgctgtttct | ggatccagcc | atgtgtgcgc | ttgtgtggac | ctgaggctgc tttctgttcc | 2520 |
| caaagcttga | cctgtgtaca | gagataattc | cttggcaatg | ttggacatag aatgcaggga | 2580 |
| gctactgaag | gtctgtcagg | gatttgtcca | ttctgctctt | ggcctctcct gaggcctcat | 2640 |
| aatgggagac | caaatcaaaa | atgtcccatg | tcacttgagt | gggtacactg cctacagaac | 2700 |
| cttgaggttg | actcctgctt | cagttctcag | ctgtttacca | cagccctcca gggtccaaag | 2760 |
| attgaggagc | tttctctttc | ctgggaggaa | ctgtctcaga | tttagcttgt gtgtgttttg | 2820 |
| gacagaggct | ccacagcggt | ggctcttgag | gaatcctcac | cagtttgttc tcttccctct | 2880 |
| gacaagcagc | acctgagcag | atgctgaggc | agttcattaa | accaggcctc agcttcagtg | 2940 |
| cctcatcttg | ccatctcccg | gccaggctgg | gaacgggcac | caagcagccg cctctaacaa | 3000 |
| acaccatggt | ccgtggaagt | tcatgccagc | agcttgcctt | tgagaagaaa tgctgctggc | 3060 |
| tctattttta | cattcccttc | cacctctata | ctgtcatgtc | accgttctga actcccagat | 3120 |
| ctgagaagga | actagtgttg | gtggtatgta | acaagagtta | cgtatccagg ggcttgtgcc | 3180 |
| ttggtttctc | ctttgattgc | tggtaaattc | tgaggccaca | gagaaatgca ttgagtgtga | 3240 |
| atgttgtcat | ctgtaatccc | tccctcagct | gataatggta | gttgatctgt tgtaaatata | 3300 |
| tacatatatg | catatttgca | cttccagatg | ggttgcataa | gaatcaggtc cttaaatacc | 3360 |
| tcccaatctg | atgaaacgat | agaataaagt | aacatttccc | agaatggagg aatacattat | 3420 |
| tttatcgtat | atttttgtcc | aagcgataag | ctgacggtgg | tattgcttct ctgcatgtta | 3480 |
| tcagtgtgta | catctggtgc | ttttcatgtg | tcatttgtga | gccacaaatg caaagttgcc | 3540 |
| atttgaattc | agtcaggcta | cagggtggtg | tcagtcaagg | tctttcaggt gggggagaaa | 3600 |
| ttggttaggg | ctcccactgc | caaatgcaag | cagatagcat | aacctgactg ttatgtgccc | 3660 |
| tcaggcagca | tgcttaggga | caactctgtg | gcctggggga | catctgtgtc acagtatagg | 3720 |
| attgccattc | aggtgttttg | tacctatttc | tttcctgacg | ttgtcccctt tttttgtact | 3780 |
| gatccaactg | ggagaacctc | agccaatgct | ggaagtatga | ttgaagtacc tctcttttgt | 3840 |
| gactcttgta | cagcttaatg | tgcaataaag | gaaaagttat | atctgaaaaa aaaaaaaaa | 3899 |

<210> SEQ ID NO 43
<211> LENGTH: 2340
<212> TYPE: DNA
<213> ORGANISM: Homo sapiens
<300> PUBLICATION INFORMATION:
<308> DATABASE ACCESSION NUMBER: NM_173544
<309> DATABASE ENTRY DATE: 2006-03-17
<313> RELEVANT RESIDUES: (1)..(2340)

<400> SEQUENCE: 43

```
gctgagcagg agatgggaat tgaaacctgc gcagaggcgg ctgtgcaggg tgagagtgga      60
gccgaaacca cagaaagtga agtttgcttc aacgtcttgt cccggcaggc cactcagatg     120
tgagagtgag gaagtgggat ggggcctgac cggaaggagg tgccctgag ccgaggaacg      180 caggcggtgg tcgtggggaa gggaagagga gccccgggag acgacagcag catgggtggg     240
cggccttcga gccctctgga caagcagcag cggcagcacc taagggtca ggtggacacc      300 ctgctgagga acttcctgcc ttgctaccgt gggcagctgg cagcgtctgt cctgcggcag     360
atctctcgag agctgggccc tcaggagccg accggaagcc agttgctacg cagcaaaaag     420
ctgccccgag tccgtgagca ccgaggaccc ctgacccagc ttcggggcca cccaccccgg     480
tggcagccga tcttctgtgt tctgcgtggg acggccgcc tagagtggtt cagccacaag      540
gaggaatatg aaaacggggg ccactgcctt ggctcaacag ccctgacagg atacacgctc     600
ctgacttccc agcgagaata tctccgcctt ttggatgctc tctgccctga atccttggga     660
gaccatactc aggaagagcc tgactccctc ttggaagtgc ctgtgagctt cccgctgttc     720
ctgcagcacc ccttccgccg gcacctctgc ttctctgcag ccaccaggga ggcacagcat     780
gcctggaggc tggccctgca gggtggcatc cggcttcagg gcacagtcct gcagcgaagc     840
caggcccctg ctgcccgggc cttcctggac gccgtccgac tctaccggca gcaccaaggc     900
cactttggcg acgacgacgt gaccctaggc tcagacgccg aggtgctgac cgcggtgctg     960
atgcgggagc aacttcccgc gctgcgagcc cagaccCttc ctggcctgcg gggggcaggc    1020
cgcgcccgcg cctgggcctg gaccgagctt ctagacgccg ttcacgcagc tgtcctggcc    1080
ggggcctccg ccgggctctg cgccttccag cccgaaaagg acgagctgct tgcgtcgctg    1140
gagaagacga tccgcccgga cgtggaccag ctgctgcggc agcgggcgcg tgtggcgggg    1200
cggctgagga cggatatcag gggaccgctc gagtcgtgcc tgcgccggga ggtggacccg    1260
cagctgcccc gggtcgtgca gaccctgctg cgcaccgtgg aagcctcgct cgaggcggtg    1320
cggaccctcc tggctcaagg catggaccga ctgtcccacc gcctgcgcca gagcccctca    1380
ggcacgcggc tgcgcaggga ggtttactca ttggggaga tgccgtggga cttggcgctg     1440
atgcagacat gctaccgtga ggccgagcgg agccgggggc gcttggggca gctggcagca    1500
ccgtttggct ttctggggat gcagagcctc gtgtttgggg cccaagatct tgcacagcag    1560
ctcatggctg acgccgtggc caccttcctg cagctggctg accagtgtct gacgacggcc    1620
ctcaactgtg accaggctgc ccagaggctg gagagagtca gggggcgcgt gctgaagaaa    1680
ttcaaatcgg acacgcgggt tggcgcagagg aggttcatcc gaggctgggg tctctgcatc    1740 ttttttacctt ttgtgctgag ccaactcgag ccaggctgca aaaggagct gcctgagttc     1800 gaggggatg tccttgccgt gggcagccag gctctgacca ctgagggcat ctatgaggac     1860
gtcatccggg ggtgcttgct gcagaggatt gaccaagaat tgaaaaagac ccttggtgcc    1920
aatgatgtat cctgcactct ggacggctgc ttggaggtcc catgggaaca ggagggagca    1980
gctccaaatc ttaacttggt gtcaagtttc ctggctggga caagctttt taccgacttc     2040 ctctgcttgc cagcaaagtc atctgctaac tggatattgg cagcttctct gctgtcttgc    2100
agctgcttcc ggagtggggt tccacaggga tcccgtgtgt tcttggttca gcttgcagag    2160
ggactttcac actccctgga gaccgtttcc tcccattctg tctggagttt tcggcctacc    2220
ccaagacaat gagatattcc tgccctttcc tcctatttcc ctccaacccc ccttccgaa     2280 atacatttgc tcaatcattt gcacttcata ggccaaaaaa aaaaaaaaaa aaaaaaaaa     2340
```

<210> SEQ ID NO 44

```
<211> LENGTH: 5659
<212> TYPE: DNA
<213> ORGANISM: Homo sapiens
<300> PUBLICATION INFORMATION:
<308> DATABASE ACCESSION NUMBER: NM_020917
<309> DATABASE ENTRY DATE: 2006-07-07
<313> RELEVANT RESIDUES: (1)..(5659)

<400> SEQUENCE: 44
```

| | | | | | |
|---|---|---|---|---|---|
| gtcggctccg | agagctctgg | cttatcagga | ctccatagtt | ctccaacaga | gaaatcttga | 60 |
| aaaggactga | ccagttttg | cagttctaaa | accatggccc | atggttcagt | gacattcagg | 120 |
| gatgtggcca | tagacttctc | acaggaagaa | tgggaattcc | tggatcctgc | tcagagggac | 180 |
| ttatataggg | atgtaatgtg | ggagaactac | agcaacttca | tttcactagg | accttccatt | 240 |
| tctaaaccag | atgtgattac | cttattggat | gaagaaagga | aggaacctgg | gatggttgtg | 300 |
| agggaaggga | caagaagata | ctgccctgat | ttggagtcca | gatacaggac | caatacttta | 360 |
| tctccagaaa | aggacatttta | tgaaatatat | tcatttcagt | gggatataat | ggaaagaatt | 420 |
| aaaagctata | gccttcaggg | ttccatttttt | aggaatgatt | gggaatgcaa | aagcaagatt | 480 |
| gaggggggaaa | aggaacaaca | agagggatat | tttgggcaag | tgaaaattac | ctctgaaaaa | 540 |
| atgaccactt | acaaaaggca | caattttctt | actgagtatc | agatcgttca | taatggagaa | 600 |
| aaggtgtatg | agtgtaagga | gtgtaggaag | acctttattc | gtcgctcaac | acttagtcaa | 660 |
| cacctgagaa | ttcatactgg | tgagaaaccct | tataagtgta | aggaatgtgg | gcaggccttt | 720 |
| agacagcgtg | cacatcttat | tcgacatcac | aaacttcaca | ccggtgagaa | acctatgaa | 780 |
| tgtaaggagt | gtgggaaggc | ctttacagtg | ctccaagaac | ttactcaaca | tcagagactt | 840 |
| catacgggtg | aaaaacccta | tgaatgtaag | gaatgtggaa | aggcctttag | agtacatcag | 900 |
| caactggctc | gacatcagag | aattcacact | ggtgagaaac | cctatgaatg | taaggactgt | 960 |
| ggaaagacct | ttagacagtg | tacacacctt | acacgccatc | agagacttca | tactgctgaa | 1020 |
| aagctctatg | aatgtaagga | atgtgggaaa | gccttcgtat | gtggtccaga | ccttagagta | 1080 |
| catcagaaaa | ttcattttgg | tgagaaaccc | tatgaatgta | aggagtgtgg | aaaggctttt | 1140 |
| agaatatgcc | aacaacttac | tgttcatcag | agtattcata | ctggtgagaa | acctacgaa | 1200 |
| tgtaaggaat | gtgggaagac | ttttagatta | agacaacaac | tagttcgcca | tcagagaata | 1260 |
| catactcgtg | agaaacccta | tgaatgtatg | gaatgttgga | agacctttag | tagttactca | 1320 |
| cagcttatt | cacaccagag | cattcatatt | ggtgagagac | cctatgaatg | tgaagagtgt | 1380 |
| ggaaaggcct | ttagactgct | ctcacaactt | actcagcatc | aaagtattca | cactggtgag | 1440 |
| aaaccttatg | aatgtaagga | atgtagaaaa | ccttttagac | tgctctcaca | acttacccaa | 1500 |
| catcagagta | ttcacactgg | tgagaaacct | tatgaatgta | aggaatgtgg | taaggctttt | 1560 |
| agactttatt | catttcttac | tcaacaccag | agaattcata | ctggtgagaa | gccctacaag | 1620 |
| tgtaaggagt | gtaagaaggc | ctttagacag | cattcacacc | ttactcagca | tcagaagatt | 1680 |
| cataatggaa | tttaatagaa | gaaagccttc | aaatgtatat | gatgttacag | aacatcagaa | 1740 |
| aattcattttt | tgagaaaatg | tgtttcatgc | tcaattccaa | gcataataaa | ttttatatta | 1800 |
| gagaaagaat | atgttgattt | aaaagccttc | caacaccatt | taaacatggt | ttatcttcag | 1860 |
| caaattccta | tgagagaata | atgtaatgaa | tgtaggaaaa | tctttagcct | tatctgtcat | 1920 |
| tatctcccttt | tctccacttg | attaccagtt | tgatttattg | gacaagatac | taagcttctg | 1980 |
| tgcctcatttt | tgctgacttg | taaaatggta | ataatagtac | ttatatgtat | tagttatttta | 2040 |
| ttgctgcgta | ataaattacc | acagacttag | tagcataaaa | taacatataa | ttatatctta | 2100 |

```
taatttggat caggagtata ggcatgactt agttgggtcc tctgcttcag ggtctcttgc   2160
aaggctacag atttcagcca gggctgaggt ctcatctgaa ggctcaactg gggaaggatc   2220
cacatccaga ctaacatagt tgttacccaa tgtatttccg tgaggcctgt tgcattgaga   2280
ttctcagttt ctagctggct gttggctgaa cgctgactgc agctcctggc cacaatagcc   2340
tcatcaacat ggctgcttgc ttcatcaagg catgcaagcc aaaagggagg acagtctgct   2400
agcaagatgg aagttaccat cttgtgtaat ctaatcatgg aagtaacatt ccctcacctt   2460
ctactggtag aagtaagtta ctaggatagt ccacactcaa gagaacggga tgatacaaga   2520
gtgtgaataa gtcctggaga caggaccact gggggcctg tttagagtca gcctgccaca   2580
ctgtggaata ggattgttgc aaggagtaag tagttaatac ttggaggaat cacagtcata   2640
tagcatgtat tctgtaaata ttatctgtaa ttgttattat tgtcattagt attagtgaat   2700
tcacgtaaaa ggaagatctg tagacataat aaatgtagaa atgcctcctg tcacctctca   2760
gaaattatta aacataattt attctaggta aaatttagat tgtagtgaat gtaggaagtt   2820
cttcagcact tgagctgcat tagaaatttc atgccaaaaa tgaatttcat gaatgtgagg   2880
tcactagtaa tacagctgtt gaagaattag agggaaatag gaaatgattt tcccataatt   2940
ccagaaagca aaaggcttac aatccctgtt gtctgaccac agtttaaaat taattagaaa   3000
ctatcaaaaa tgtggcttaa aagaaattaa ccacctagga atttaatatt gttgtgtata   3060
tttatgtgtg tgtataaaac tcctgtggga agaaacaaa acatcattct ataagtcagt    3120
atacttttgg atgctcaaaa tgccatatct tcaaccagta ggagttgttt caagttgagt   3180
ttttgatgtg atcccaccaa taatttgata gtttacttga ttgtggctgc ataatttggt   3240
aacctatgaa agatgctaga gcaccaatgt ataatttttt tgagacaggg tgtcactttg   3300
tcccccaggc tggagtgcag tggtacgagc acagttcact gtaccctgtt cctcctgggc   3360
tcaagtgatt cttccaccta aatttttttt ttttttttag agaaagggtc tcactatgtt   3420
gcccaggctg gtcttgaact tctgggctca agtgatcctc cctccttggc ctccaaaggt   3480
gctggggtta caggtgtgag ccaccacacc cggcccaact cattattctt gaaatcaata   3540
aatcagagga aaaattgtca tttagtttcc ttttcccatg tgaaccaaat ttcagggtca   3600
ccagaagttc atcaaattca aatgaatttg gcctggcaca ggggtcacac ctgtaatccc   3660
agcactttgg gaggacaagg tgggtggatc acttgaggcc aggagtttga gaccaacctg   3720
gttaacatgg tgaaaccctg tctgtactaa aaatacaaaa tttagccggg cgtggtggca   3780 cacctgta gtcccaggct gaggtgggag gatcacttga gcccaggagg cagagtttgc   3840
agtgagctgg gatcgtgcca ctgcactcca gcctgggtga cggagtgaga ccctgtctca   3900 aaaaaaaat tgttttttg aatgggtttt tctttttga agaagtctaa taaatctaga    3960
aggaattaga ggattagaaa aatcaccatt ttctggacct taatggaata atgggtccag   4020
aaaacatgat cttcaatggg tactacaact aataggtgaa atattttata gcagagttt    4080 tatggtggat ctatcaaact ggccacctct gaacccttg atctgtttta accttaataa    4140
aaatgggtct atcagacaac acacttcctg acgtaatgca ataggaagtc cacaccacca   4200
tctacaaagc cttattgctg gaataatgaa ctgaaagcag acagggacta gatgaacagt   4260
atatggtcat cccttggtat ccatggggaa ttggttccag gatcctccac tgatggtaaa   4320
atctgaggat gctcaagtcc cttgtataaa atggcatagt atgtatttgc atattaccta   4380
ctcacatctt cctgtatact ttaaattatc tttagatcac ttatacctat cacaatgtaa   4440
atactatgta aatagttgtt atactgtatt tttcaatttg cattatttt attgtatttt    4500
```

-continued

| | |
|---|---|
| attttttattg ttttttttg agtattttct atttgagatt ggttgaatct gcacatatgg | 4560 |
| agggctggct ataaagggca ccacaaggaa gaagccaaac agatccagaa tgtgtgaaat | 4620 |
| tctacagagc aaattacctg atttcttcaa ctaacaggta gcatgaaaat acaaggggaa | 4680 |
| gggcaaccat taacagatta aaagagactt aagagacat atcaactaaa ttcagtatgt | 4740 |
| tggcattact tggacctggt ttgaacaaaa cataaaaagc cattttggag acagtgaggg | 4800 |
| aagtgtggac atggactaaa tattaaatga tatttacata tattaatttg gttagggatt | 4860 |
| atgtcagtgt gattataaaa aataaaagat cgtatgatat gagatacata ctatgaaatg | 4920 |
| aagatagaca catttggatt aaaatattct agcaaaagaa ataattggca agagagctg | 4980 |
| gaaactaaat tggcaacatg ttgataattt aagtggagtg ttttgttcat ggagacttat | 5040 |
| tgttctaata tttctacttt tgtatgtgtt tgaaatttca ataataaaat gtttaaaatc | 5100 |
| aaaaccaaaa ttatagacta tgtagaaatg aatgacagtg agatgcctgc acatctaacc | 5160 |
| ttgtcagata taatcaaagt tctgttcagt gacaaattaa tgccctgtaa tgtggtaagg | 5220 |
| aaatcttatt tgtggataca gtcttcatct tcttcactta cccacagcag caacaccagg | 5280 |
| cctgtcacac agatgaatgt gttgaggaa tgaataagta tttccgtcaa gaaaaaggaa | 5340 |
| acaacaaaat aaaaccaacc caagtaaaga acagccaagt ggccaggtgc ggtggctcat | 5400 |
| gcctgtaatc ccagcacttt gggaggccat ggcaggtgga tcacctgagg tcgggatttt | 5460 |
| gagaccagcc tgaccaacac tgagaaaccc catctctatt aaagatacaa aattagccag | 5520 |
| gcatggtggt gcatgcctgt aatcccagct acttgggagg ctaaggcagg agaatcactt | 5580 |
| gaatccagga ggcggagttt gtggtgagtt gagatcgcgc cactgcactc cagcctgggt | 5640 |
| aacagagcaa gagtctgtc | 5659 |

<210> SEQ ID NO 45
<211> LENGTH: 4607
<212> TYPE: DNA
<213> ORGANISM: Homo sapiens
<300> PUBLICATION INFORMATION:
<308> DATABASE ACCESSION NUMBER: NM_020830
<309> DATABASE ENTRY DATE: 2006-09-24
<313> RELEVANT RESIDUES: (1)..(4607)

<400> SEQUENCE: 45

| | |
|---|---|
| gtcagctgat gggctgcctg ccgaggaggc cgcagcagtc gccgcgcgaa catggcggcc | 60 |
| gaaatccact ccaggccgca gagcagccgc ccggtgctgc tgagcaagat cgaggggcac | 120 |
| caggacgccg tcacggccgc gctgctcatc cccaaggagg acggcgtgat cacggccagc | 180 |
| gaggacagaa ccatccgggt atggctgaaa agagacagtg gtcaatactg gcccagcatt | 240 |
| taccacacaa tggcctctcc ttgctctgct atggcttacc atcatgacag cagacggata | 300 |
| tttgtgggcc aggataatgg agctgtaatg gaatttcacg tttctgaaga ttttaataaa | 360 |
| atgaacttta tcaagaccta cccagctcat cagaaccggg tgtctgcgat tatcttcagc | 420 |
| ttggccacag agtgggtgat cagtaccggc cacgacaagt gtgtgagctg atgtgcacg | 480 |
| cggagcggga acatgctcgg gaggcacttc ttcacgtcct gggcttcgtg tctgcaatat | 540 |
| gactttgaca ctcagtatgc tttcgttggt gattattctg ggcagatcac cctgctgaag | 600 |
| cttgaacaga acacgtgttc agtcatcaca accctcaaag acatgaagg tagtgtcgcc | 660 |
| tgcctctggt gggaccctat tcagcggtta ctcttctcag gagcatctga caacagcatc | 720 |
| atcatgtggg acatcggagg aaggaaaggc cggacgctgt acttcagggg ccatcatgac | 780 |
| aaggtgcagt cgctgtgcta ccttcagctc accaggcagc tcgtctcctg ttcctcggac | 840 |

```
ggcggaattg cagtgtggaa catggatgtt agcagagaag aggctcctca gtggttggaa    900
agtgattctt gtcagaaatg tgagcagcca tttttctgga acataaagca gatgtgggac    960
accaagacgc tggggctaag acaacatcac tgcaggaaat gcgggcaggc tgtctgcggg   1020
aagtgcagca gcaagcgctc aagttaccca gtcatgggct tcgagttcca agtccgggtt   1080
tgtgattctt gttacgactc catcaaagat gaagatcgga cttctctagc gacctttcat   1140
gaaggaaaac ataacatttc ccacatgtcc atggacattg ccggggact gatggtgacc    1200
tgtgggaccg accgcattgt aaagatctgg gacatgacac tgtggtggg ctgcagtctg    1260
gcgactgggt tttctccgca ctgatctgag agctgggcgg cgtccacacc taagaacagc   1320
agctccacca aatgaagtcc ctctcacgca gctccacagc gctgtctcgt gaatggacag   1380
tagccactta caaacaaatc aacatttta aaagaaaat gtaaggtgt gttttggggc      1440
atttgtggaa cttacccatg gggactaata tggaaaaggt ctgtccatag tggttccctg   1500
aagactggaa ttacttcagc aaaacttccc catgaacagc taatgtgtag tgaaagaatg   1560
agctagcaaa tgagttttag cgggacaaa aaatcaaaca aaaagtgaa tgcttagaac    1620
cttctcaaag cagtcacaag tacagacact tcacttagcc tagggggcct tccagggttc   1680
ttgtggctgt tgtcagagca ggagctgggg gagggaagac ttgttctctc tttcttgagg   1740
ggtggcatta ggaacttacg aaaccagaga cctttcccta tgacttggca gtatgtgaat   1800
atcctctaca cttagttatt gataaacttc ttaaagagat ctgttatttt caggtagtgc   1860
cataatctgc acttagcatt ggcttgcttc agttgtttct cttcccagcc agtatgccac   1920
aggtgaactt tcggggttgt cattaagtaa gttgtgaaat ttctgtaata acaaaggcag   1980
tccgcattct tcccttttccc ccaaattcct agggcaaaac ttttttatgg tgctgttaac   2040
atgggagtca cacaagccgc tgacttttt ctcattgcca ttagtaatga ctgatggaaa    2100
acccagccac cactgtgatg cgaaatgatc agtctgttgc ctgaaacagc ccagtcctct   2160
taactgaaac agcattctac ttcttgttcc aagatgagcc tctgcaatat tctggcaatt   2220
taatatacccc cctacaaaag cactccacag ctttttacact attttgactt tgagttataa  2280
ctagtattat tcatgttttc ataaaaagaa gttagtgacc cagagctata atcatccatc   2340
aagtcttcca caataattcc caactcataa attgctttcc taacaactag caaaagctat   2400
tgttcataat ggcatttcta aagcttttgg gcactgtgta ccaggatgag gaagagaaga   2460
aatgaggagc ctgtcttta atattccagt atttgtgtgt ttgatttttt ttgacaacag    2520
tacatatatc tatttctcta gggatatgga agtaagtgga gaagggccta cctttttaaa   2580
ggacaaatat aaaaatagca acagtatctt tgctaatctt actaatagat attgattaaa   2640
aaaaaaaac ctcagtactg catcactgtg ttgggatcgt accaggacaa tagggtcatt   2700
ccatatgata aaactaaagg actaaatttg ttttataatg atgtcttaga gggactgaaa   2760
agtttaagga ggcgatcaaa ctaaaatgtc ttaatggctg tgtgacacac gtaaggaaag   2820
gaaaggggt cacgcacatc atgtactgga atgatctgca ttaaacattg acttgtcttc    2880
agaaataaga ctgaagggtt tgttgttcc ttagagtttt cgtgttacat cacctaaaga    2940
gatttctttt aaaaactttc tagactcttt gcaaaatgta tattactaac atagtttgga   3000
agaaaaattg agtagtggta agttttgttc aagcacaatg ttgaatgtta agcttcctgt   3060
attaattta gttcagttaa tggttcagcc catacaaagg tgctatccta gggattttat    3120
gaattcctga aaggaaaata gaatatgatc aattccttgc cctgtggaag agtgcagaac   3180
tgtggttttg ttttcctttg acttctgtaa aatgtgaccg tttgacatct gtggtagatt   3240
```

```
gaacggaata tcacagctgc tgagtttact ccatagcttt caaacctttt ttattttaag   3300
aaattcttga aaaaccctat gttccatggg aacataaagt tattatagtg cctcctaagg   3360
ggttaatata aatcaaggag gaagtttata tttaaggaag aattggagtg acgtatctta   3420
gaaaaggaaa ggctgatgtt tccatatagc ttgctctcca ccaggcctat cattttctt    3480 tttagagaca aacgtgacag gctagtcttg tctctctcat atgctaggta gcaaatgggg   3540 tgatatttt atagaagtgg gcaaaaatta ttttctcaat tttactgagt aggcacagaa    3600
gaaaagtaca gataggctga tggttattgc cttatttga ctgcatttct cttaaatgga    3660
tcatttaaat tagttcttca agtaacagtt tactggttgt tccattcctg aatatgcagg   3720
ctaatttgta cagataggga ttaaggaata cagactatta gagaagatcc ttatatttac   3780
atctagtata tatgtggtaa ggaaatgccg attcttcatt ataaacaagt tttaaaattg   3840
ttctttctta gttcaaatga tagcaatacc cctatagcat taggtagaaa caaattattc   3900
attacatcgt aaatctcttt actatgtcct agctctgtcc tgctacctaa aggatataaa   3960
gaaatactat tgctctagaa tgtattactt tgttctccca tgaaagaatt cagtttgtta   4020
gtacctatat ttttaaactg gtgaaactga cccaaatatg taataaatac catagtagct   4080
cagacccaag gagatatttt tctaaaatca gttttcgtta aagtacttct acttccgtta   4140
ttggatatgg tatctcctaa agtgtaaaaa aaatctgtta ctatatagtg ataaaccatc   4200
tgctcatcgt aagtgtaagg cttaacaaat aagtaataca tgctatattt attcaagtgt   4260
ctattgctta attgttaatt gtgagcagat ttattgaatg cctattctat tttctgcagt   4320
ttacaataca ataactcttt gagtaagttg aagtttaatt gtgcaacaaa tttgtattag   4380
agtacaattt aaagtgtttt tctctatagc cttttttgac tggggaagca agggggtaatg  4440 ttaattagta cactttgttc ttgtactagc tatgtttcta taagatatgg tgccctgtgt   4500
atcccagaga tgctagaaaa ctgttctttg ctcctatttg tgggttctgt ttttgtgggt   4560
tttttttttt gagaaaatgt acacaataaa acattccttg cttgtta              4607

<210> SEQ ID NO 46
<211> LENGTH: 1502
<212> TYPE: DNA
<213> ORGANISM: Homo sapiens
<300> PUBLICATION INFORMATION:
<308> DATABASE ACCESSION NUMBER: NM_022788
<309> DATABASE ENTRY DATE: 2006-10-01
<313> RELEVANT RESIDUES: (1)..(1502)

<400> SEQUENCE: 46
atcacaatca gaagacagga gctgcagaac agaacacttt ctcatgtcca gggtcagatt    60
acaagagcac tcaagacttt actgacgaaa actcaggaaa tcctctatca caaagaggtt   120
tggcaactaa actaagacat taaaaggaaa ataccagatg ccactctgca ggttgcaata   180
actactactt actggataca ttcaaaccct ccagaatcaa cagttatcag gtaaccaaca   240
agaaatgcaa gccgtcgaca acctcacctc tgcgcctggt aacaccagtc tgtgcaccag   300
agactacaaa atcacccagg tcctcttccc actgctctac actgtcctgt ttttgttgg    360 acttatcaca aatggcctgg cgatgaggat tttctttcaa atccggagta aatcaaactt   420 tattatttt cttaagaaca cagtcatttc tgatcttctc atgattctga cttttccatt    480
caaaattctt agtgatgcca aactgggaac aggaccactg agaactttg tgtgtcaagt    540 tacctccgtc atattttatt tcacaatgta tatcagtatt tcattcctgg gactgataac   600
tatcgatcgc taccagaaga ccaccaggcc atttaaaaca tccaaccccca aaaatctctt   660
```

-continued

| | |
|---|---|
| gggggctaag attctctctg ttgtcatctg ggcattcatg ttcttactct ctttgcctaa | 720 |
| catgattctg accaacaggc agccgagaga caagaatgtg aagaaatgct ctttccttaa | 780 |
| atcagagttc ggtctagtct ggcatgaaat agtaaattac atctgtcaag tcattttctg | 840 |
| gattaatttc ttaattgtta ttgtatgtta tacactcatt acaaaagaac tgtaccggtc | 900 |
| atacgtaaga acgaggggtg taggtaaagt ccccaggaaa aaggtgaacg tcaaagtttt | 960 |
| cattatcatt gctgtattct ttatttgttt tgttcctttc cattttgccc gaattcctta | 1020 |
| caccctgagc caaacccggg atgtctttga ctgcactgct gaaaatactc tgttctatgt | 1080 |
| gaaagagagc actctgtggt taacttcctt aaatgcatgc ctggatccgt tcatctattt | 1140 |
| tttcctttgc aagtccttca gaaattcctt gataagtatg ctgaagtgcc ccaattctgc | 1200 |
| aacatctctg tcccaggaca ataggaaaaa agaacaggat ggtggtgacc caaatgaaga | 1260 |
| gactccaatg taaacaaatt aactaaggaa atatttcaat ctctttgtgt tcagaactcg | 1320 |
| ttaaagcaaa gcgctaagta aaatattaa ctgacgaaga agcaactaag ttaataataa | 1380 |
| tgactctaaa gaaacagaag attacaaaag caattttcat ttacctttcc agtatgaaaa | 1440 |
| gctatcttaa aatatagaaa actaatctaa actgtagctg tattagcagc aaaacaaacg | 1500 |
| ac | 1502 |

<210> SEQ ID NO 47
<211> LENGTH: 1474
<212> TYPE: DNA
<213> ORGANISM: Homo sapiens
<300> PUBLICATION INFORMATION:
<308> DATABASE ACCESSION NUMBER: NM_176876
<309> DATABASE ENTRY DATE: 2006-10-01
<313> RELEVANT RESIDUES: (1)..(1474)

<400> SEQUENCE: 47

| | |
|---|---|
| tgaagccctc ttttctctc cttctatttc tctctagagc actcaagact ttactgacga | 60 |
| aaactcagga aatcctctat cacaaagagg tttggcaact aaactaagac attaaaagga | 120 |
| aaataccaga tgccactctg caggttgcaa taactactac ttactggata cattcaaacc | 180 |
| ctccagaatc aacagttatc aggtaaccaa caagaaatgc aagccgtcga caacctcacc | 240 |
| tctgcgcctg gtaacaccag tctgtgcacc agagactaca aaatcaccca ggtcctcttc | 300 |
| ccactgctct acactgtcct gttttttgtt ggacttatca caaatggcct ggcgatgagg | 360 |
| attttctttc aaatccggag taaatcaaac tttattattt ttcttaagaa cacagtcatt | 420 |
| tctgatcttc tcatgattct gacttttcca ttcaaaattc ttagtgatgc caaactggga | 480 |
| acaggaccac tgagaacttt tgtgtgtcaa gttacctccg tcatatttta tttcacaatg | 540 |
| tatatcagta tttcattcct gggactgata actatcgatc gctaccagaa gaccaccagg | 600 |
| ccatttaaaa catccaaccc caaaaatctc ttggggcta agattctctc tgttgtcatc | 660 |
| tgggcattca tgttcttact ctctttgcct aacatgattc tgaccaacag gcagccgaga | 720 |
| gacaagaatg tgaagaaatg ctctttcctt aaatcagagt tcggtctagt ctggcatgaa | 780 |
| atagtaaatt acatctgtca agtcattttc tggattaatt tcttaattgt tatttgtatgt | 840 |
| tatacactca ttacaaaaga actgtaccgg tcatacgtaa gaacgagggg tgtaggtaaa | 900 |
| gtccccagga aaaggtgaa cgtcaaagtt tcattatca ttgctgtatt ctttatttgt | 960 |
| tttgttcctt tccattttgc ccgaattcct tacaccctga gccaaacccg ggatgtcttt | 1020 |
| gactgcactg ctgaaaatac tctgttctat gtgaaagaga gcactctgtg gttaacttcc | 1080 |
| ttaaatgcat gcctggatcc gttcatctat ttttcctttt gcaagtcctt cagaaattcc | 1140 |

| | |
|---|---:|
| ttgataagta tgctgaagtg cccccaattct gcaacatctc tgtcccagga caataggaaa | 1200 |
| aaagaacagg atggtggtga cccaaatgaa gagactccaa tgtaaacaaa ttaactaagg | 1260 |
| aaatatttca atctctttgt gttcagaact cgttaaagca aagcgctaag taaaaatatt | 1320 |
| aactgacgaa gaagcaacta agttaataat aatgactcta aagaaacaga agattacaaa | 1380 |
| agcaattttc atttaccttt ccagtatgaa aagctatctt aaaatataga aaactaatct | 1440 |
| aaactgtagc tgtattagca gcaaaacaaa cgac | 1474 |

<210> SEQ ID NO 48
<211> LENGTH: 2537
<212> TYPE: DNA
<213> ORGANISM: Homo sapiens
<300> PUBLICATION INFORMATION:
<308> DATABASE ACCESSION NUMBER: NM_174938
<309> DATABASE ENTRY DATE: 2006-10-15
<313> RELEVANT RESIDUES: (1)..(2537)

<400> SEQUENCE: 48

| | |
|---|---:|
| gaggtggagg cgagcgaaca gagggaggga cccgcccgcc gcgccccggc cgctgggcat | 60 |
| gtgtgtccgc aggcgcccga cgctgccgat gtcccggggc tgagcagcgc ccaggtgtcc | 120 |
| cggacagtgc gtgcgagcgt gtgtgtccgc gcaggcgagc accgcgccgg ccctgagcct | 180 |
| cccgctcgct ccccacggcc gcggtgcatg ttcgcctcct gccactgtgt gccgagaggc | 240 |
| aggaggacca tgaaatgatc cactttcgga gctccagcgt caaatcgctc agccaggaga | 300 |
| tgagatgcac catccggctg ctggacgact cggagatctc ctgccacatc cagagggaaa | 360 |
| ccaaagggca gtttctcatt gaccacatct gcaactacta cagcctgctg agaaggact | 420 |
| actttggcat tcgctatgtg gacccagaga agcaaaggca ctggcttgaa cctaacaagt | 480 |
| ccatcttcaa gcaaatgaaa actcatccac catacaccat gtgctttaga gtgaaattct | 540 |
| acccacatga accccttgaag attaaagaag agctcacaag atacctttta taccttcaga | 600 |
| ttaaaaggga cattttttcat ggccacctgc tgtgctcctt ttctgatgct gcctacctgg | 660 |
| gtgcctgtat tgttcaagct gagcttggtg attacgatcc taatgagcat cctgagaatt | 720 |
| acatcagtga gtttgagatt ttccccaagc agtcacagaa gctggaaaga aaatagtgg | 780 |
| aaattcataa aaatgaactc aggggggcaga gcccaccagt tgctgaattt aacttgctcc | 840 |
| tgaaagctca cactttggaa acctacgggg tggatcctca cccatgcaag gattcaacag | 900 |
| gcacaacaac attttttagga ttcacagctg caggctttgt ggtctttcag ggaaataaga | 960 |
| gaatccattt gataaaatgg ccagatgtct gcaaattgaa gtttgaaggg aagacatttt | 1020 |
| atgtgattgg cacccagaag gagaaaaaag ccatgttggc attcaatact tcaacaccag | 1080 |
| ctgcctgcaa acatctttgg aagtgtgagg tggaaaacca ggcctttttat aagtatgcaa | 1140 |
| aatccagtca gatcaagact gtatcaagca gcaagatatt ttttaaagga agtagatttc | 1200 |
| gatatagtgg gaaagttgcc aaagaggtgg tggaggccag ttccaagatc cagggggagc | 1260 |
| ctcctgaggt gcacagagcc aacattactc agagccgcag ttcccactcc ttgaacaaac | 1320 |
| agctcatcat taacatggaa cccctgcagc ccctgcttcc ttcccccagc gagcaagaag | 1380 |
| aagaacttcc tctgggtgag ggtgttccat tgcctaaaga ggagaacatt tctgctccct | 1440 |
| tgatctccag ctccccagtg aaggcagccc gggagtatga agatcccccct agtgaagagg | 1500 |
| aagataaaat aaaagaagaa cctttaacca tctctgaact agtgtacaac ccaagtgcca | 1560 |
| gcctgctccc caccccctgtg gatgacgatg agattgacat gctctttgac tgtccttcta | 1620 |
| ggcttgagtt ggaaagagaa gacacagatt catttgagga tctggaagca gatgaaaacg | 1680 |

```
cctttttgat tgctgaagaa gaggagctga aggaggctcg ccgtgctttg tcgtggagct   1740
acgacattct gactggccat attcgggtga acccactggt caagagtttt tccaggctcc   1800
ttgtggtggg cctgggactg ctgctctttg tatttcccct gctcctcctc cttttggagt   1860
caggtattga tctctccttc ttatgcgaaa tccgccagac accagagttt gagcagtttc   1920
actatgaata ctactgtccc ctcaaggagt gggtggctgg gaaagtccac ctcatcctct   1980
acatgctggg ttgctcatga agttaatctc tcacgtgact aagggctata ttcaatgcta   2040
gtgatttctt ttttcagca aatgcctggt tctgaagggt cacggggctg tcaacaggtg   2100
ttccttactc ataattgatt attcaaacct ttaagttagc tttccataat tcactgcact   2160
taaataagtt taaatcaaat acagttattt tagttacagg ttaggaagat ggtctttaaa   2220
taaccaaaaa tatgtttatt ttttattata gtgtagacat acccttcatc tattatatca   2280
taatacatgt tacattggac tgaattagat tttcccattt ctaatagttg gcaccattat   2340
aagctataag gttcagaatc agaattttag taacaactca agagaaagtt gttgaatata   2400
atccttagtg aagacagtgt cctctaacca atgcctatac aactaaattt atgctgggtt   2460
tttggttttg tttttttaaa aatattttta tgtgttcaaa ctattttggt aaattttag   2520 caaaaaaaaa aaaaaaa                                                 2537
```

<210> SEQ ID NO 49
<211> LENGTH: 3084
<212> TYPE: DNA
<213> ORGANISM: Homo sapiens

<400> SEQUENCE: 49

```
aagatctaaa aacggacatc tccaccgtgg gtggctcctt tttcttttc tttttttccc     60 acccttcagg aagtggacgt ttcgttatct tctgatcctt gcaccttctt ttggggaaac    120
ggggcccttc tgcccagatc ccctctcttt tctcggaaaa caaactacta agtcggcatc    180
cggggtaact acagtggaga gggtttccgc ggagacgcgc cgccggaccc tcctctgcac    240 tttgggagg cgtgctccct ccagaaccgg cgttctccgc gcgcaaatcc ggcgacgcg     300 gggtcgcggg gtggccgccg gggcagcctc gtctagcgcg cgccgcgcag acgccccgg    360 agtcgccagc taccgcagcc ctcgccgccc agtgcccttc ggcctcgggg cgggcgcctg    420
cgtcggtctc cgcgaagcgg gaaagcgcgg cggccgccgg gattcgggcg ccgcggcagc    480
tgctccggct gccggccggc ggccccgcgc tcgcccgccc cgcttccgcc cgctgtcctg    540
ctgcacgaac ccttccaact ctcctttcct cccccaccct tgagttaccc ctctgtcttt    600
cctgctgttg cgcgggtgct cccacagcgg agcggagatt acagagccgc cgggatgccc    660
caactctccg gaggaggtgg cggcggcggg ggacccgg aactctgcgc cacgacgag     720 atgatcccct tcaaggacga gggcgatcct cagaaggaaa agatcttcgc cgagatcagt    780
catcccgaag aggaaggcga tttagctgac atcaagtctt ccttggtgaa cgagtctgaa    840
atcatcccgg ccagcaacgg acacgaggtg gccagacaag cacaaacctc tcaggagccc    900
taccacgaca aggccagaga caccccgat gacgaaaagc atccagatgg aggcctctac    960
aacaagggac cctcctactc gagttattcc gggtacataa tgatgccaaa tatgaataac   1020
gacccataca tgtcaaatgg atctctttct ccacccatcc cgagaacatc aaataaagtg   1080
cccgtggtgc agccatccca tgcggtccat cctctcaccc cctcatcac ttacagtgac   1140 gagcactttt ctccaggatc acaccgtca cacatcccat cagatgtcaa ctccaaacaa   1200
ggcatgtcca gacatcctcc agctcctgat atccctactt tttatcccct gtctccgggt   1260
```

-continued

| | |
|---|---|
| ggtgttggac agatcacccc acctcttggc tggcaaggtc agcctgtata tcccatcacg | 1320 |
| ggtggattca ggcaacccta cccatcctca ctgtcagtcg acacttccat gtccaggttt | 1380 |
| tcccatcata tgattcccgg tcctcctggt ccccacacaa ctggcatccc tcatccagct | 1440 |
| attgtaacac ctcaggtcaa acaggaacat ccccacactg acagtgacct aatgcacgtg | 1500 |
| aagcctcagc atgaacagag aaaggagcag gagccaaaaa gacctcacat taagaagcct | 1560 |
| ctgaatgctt ttatgttata catgaaagaa atgagagcga atgtcgttgc tgagtgtact | 1620 |
| ctaaaagaaa gtgcagctat caaccagatt cttggcagaa ggtggcatgc cctctcccgt | 1680 |
| gaagagcagg ctaaatatta tgaattagca cggaaagaaa gacagctaca tatgcagctt | 1740 |
| tatccaggct ggtctgcaag agacaattat ggtaagaaaa agaagaggaa gagagagaaa | 1800 |
| ctacaggaat ctgcatcagg tacaggtcca agaatgacag ctgcctacat ctgaaacatg | 1860 |
| gtggaaaacg aagctcattc ccaacgtgca aagccaaggc agcgacccca ggacctcttc | 1920 |
| tggagatgga agcttgttga aaacccagac tgtctccacg gcctgcccag tcgacgccaa | 1980 |
| aggaacactg acatcaattt taccctgagg tcactgctag agacgctgat ccataaagac | 2040 |
| aatcactgcc aaccctcttt tcgtctactg caagagccaa gttccaaaat aaagcataaa | 2100 |
| aaggtttttt aaaaggaaat gtaaaagcac atgagaatgc tagcaggctg tggggcagct | 2160 |
| gagcagcttt tctcccccca tatctgcgtg cacttcccag agcatcttgc atccaaacct | 2220 |
| gtaacctttc ggcaaggacg gtaacttggc tgcatttgcc tgtcatgcgc aactggagcc | 2280 |
| agcaaccagc tatccatcag cacccagtg gaggagttca tggaagagtt ccctctttgt | 2340 |
| ttctgcttca ttttctttc ttttcttttc tcctaaagct tttatttaac agtgcaaaag | 2400 |
| gatcgttttt ttttgctttt ttaaacttga attttttaa tttacacttt ttagttttaa | 2460 |
| ttttcttgta tattttgcta gctatgagct tttaaataaa attgaaagtt ctggaaaagt | 2520 |
| ttgaaataat gacataaaaa gaagccttct ttttctgaga cagcttgtct ggtaagtggc | 2580 |
| ttctctgtga attgcctgta acacatagtg gcttctccgc ccttgtaagg tgttcagtag | 2640 |
| agctaaataa atgtaatagc caaaccccac tctgttggta gcaattggca gccctatttc | 2700 |
| agtttatttt ttcttctgtt ttcttctttt cttttttaa acagtaaacc ttaacagatg | 2760 |
| cgttcagcag actggtttgc agtgaatttt catttctttc cttatcaccc ccttgttgta | 2820 |
| aaaagcccag cacttgaatt gttattactt taaatgttct gtatttgtat ctgttttat | 2880 |
| tagccaatta gtgggatttt atgccagttg ttaaaatgag cattgatgta cccattttt | 2940 |
| aaaaaagcaa gcacagcctt tgcccaaaac tgtcatccta acgtttgtca ttccagtttg | 3000 |
| agttaatgtg ctgagcattt ttttaaaaga agctttgtaa taaaacattt ttaaaaattg | 3060 |
| tcatttaaaa aaaaaaaaaa aaaa | 3084 |

<210> SEQ ID NO 50
<211> LENGTH: 1973
<212> TYPE: DNA
<213> ORGANISM: Homo sapiens
<300> PUBLICATION INFORMATION:
<308> DATABASE ACCESSION NUMBER: NM_080387
<309> DATABASE ENTRY DATE: 2006-04-19
<313> RELEVANT RESIDUES: (1)..(1973)

<400> SEQUENCE: 50

| | |
|---|---|
| ctttgaaaaa gacttctttt gagctaactt tcttatactg gtacctttct aatctcacta | 60 |
| caatatgtaa cattggtgtt cgatctcaag tatttctgaa tatattcccc tatccacaga | 120 |
| aatatactct gggggaaaaa aaatagaaca aattcttgcc gtcctgacca ttgaacaaga | 180 |

```
gactaattag acaatggggc tagaaaaacc tcaaagtaaa ctggaaggag gcatgcatcc    240
ccagctgata ccttcggtta ttgctgtagt tttcatctta cttctcagtg tctgttttat    300
tgcaagttgt ttggtgactc atcacaactt ttcacgctgt aagagaggca caggagtgca    360
caagttagag caccatgcaa agctcaaatg catcaaagag aaatcagaac tgaaaagtgc    420
tgaagggagc acctggaact gttgtcctat tgactggaga gccttccagt ccaactgcta    480
ttttcctctt actgacaaca agacgtgggc tgagagtgaa aggaactgtt cagggatggg    540
ggcccatctg atgaccatca gcacggaagc tgagcagaac tttattattc agtttctgga    600
tagacggctt tcctatttcc ttggacttag agatgagaat gccaaaggtc agtggcgttg    660
ggtggaccag acgccattta acccacgcag agtattctgg cataagaatg aacccgacaa    720
ctctcaggga gaaaactgtg ttgttcttgt ttataaccaa gataaatggg cctggaatga    780
tgttccttgt aactttgaag caagtaggat ttgtaaaata cctggaacaa cattgaacta    840
gaaactcaga aagtggtcct tgtgatggaa agagaaaaga aaaccaatt agaataaggc    900 agaatgtacg tgcgtcattg aacacagaa acatgctgg ttcatacagc gttttagtc    960 ataatggtct ttttattt gtttgattca ttcgagacaa catgtgtgta tgtgtgtgtg    1020
tgtgtgtgta gataatgtgg ttttgtatg gtgtttgatg gaaggaataa tctttctttg    1080
ctttcttagt agtatttcaa ggtgtttact tttcaattgg tgtgcactga atgcatgtat    1140
ggaagaatag cgtgaataat gcaatctctt tgtcatttt cccctctca gactcttagc    1200 tcttaaaatt caaagatggg atattctaac tggtagtggt gcatcatttt taacccaaat    1260
attgcaagca ctttaaagat ttgaaaccac attttattg tttgatgttt cattttcaga    1320
ctttttaatg tcagtcatta caattacatt gcatgaggaa aattttttcca gaacaacagt    1380 gtggaatagt tctgaattat gctgttctac agatagaaaa aaagtccaaa tgcctttaaa    1440
aatttacttc ttactccacc caacacgttt ttgcaaagca agaagtcttt gtaagacacc    1500
ttaaacaaag tccttcaatt ctacagcaga ggaaataaaa tcccccagaa gccaagggc    1560 tcaccttcac attgttagtt catgacagac ccaggtgtgc ttcattagag ataacataca    1620
ttccctttgg tatcacagga agttactggg gattactcga cctcattact tagctaacga    1680
ctggataaaa tttcttaatt gtttgaagta acattgtatt cgtgtttgca ttattaattt    1740
gaatagaaaa taatcacatt ttcaacccat ttatacaaat tgttaatgtt tctttagagc    1800
tgtataacta tagtttgaac tagcaaggaa gttattgttt tgacaaccag aaattatgct    1860
tttctggtgc atgaaacatt aattgcaaag ggcagtcaca tccaacttta ataaaatatg    1920
gtggtctttc ttaaaaaaaa aaaaaaaaaa aaaaaaaaaa aaaaaaaaaa aaa          1973
```

<210> SEQ ID NO 51
<211> LENGTH: 2263
<212> TYPE: DNA
<213> ORGANISM: Homo sapiens
<300> PUBLICATION INFORMATION:
<308> DATABASE ACCESSION NUMBER: NM_012387
<309> DATABASE ENTRY DATE: 2006-08-13
<313> RELEVANT RESIDUES: (1)..(2263)

<400> SEQUENCE: 51

```
agccagaggg acgagctagc ccgacgatgg cccaggggac attgatccgt gtgacccccag     60 agcagcccac ccatgccgtg tgtgtgctgg gcaccttgac tcagcttgac atctgcagct    120
ctgcccctga ggactgcacg tccttcagca tcaacgcctc cccaggggtg gtcgtggata    180
ttgcccacag ccctccagcc aagaagaaat ccacaggttc ctccacatgg cccctggacc    240
```

-continued

```
ctggggtaga ggtgaccctg acgatgaaag cggccagtgg tagcacaggc gaccagaagg    300
ttcagatttc atactacgga cccaagactc caccagtcaa agctctactc tacctcaccg    360
cggtggaaat ctccctgtgc gcagacatca cccgcaccgg caaagtgaag ccaaccagag    420
ctgtgaaaga tcagaggacc tggacctggg gcccttgtgg acagggtgcc atcctgctgg    480
tgaactgtga cagagacaat ctcgaatctt gccatggaa ctgcgaggat gatgaagtgc    540
ttgacagcga agacctgcag gacatgtcgc tgatgaccct gagcacgaag accccaagg    600 acttcttcac aaaccataca ctggtgctcc acgtggccag gtctgagatg acaaagtga    660 gggtgttca ggccacacgg ggcaaactgt cctccaagtg cagcgtagtc ttgggtccca    720
agtggccctc tcactacctg atggtccccg gtggaaagca caacatggac ttctacgtgg    780
aggccctcgc tttcccggac accgacttcc cggggctcat taccctcacc atctccctgc    840
tggacacgtc caacctggag ctccccgagg ctgtggtgtt ccaagacagc gtggtcttcc    900
gcgtggcgcc ctggatcatg accccccaaca cccagccccc gcaggaggtg tacgcgtgca    960
gtatttttga aaatgaggac ttcctgaagt cagtgactac tctggccatg aaagccaagt   1020
gcaagctgac catctgccct gaggaggaga acatggatga ccgtggatg caggatgaaa   1080 tggagatcgg ctacatccaa gccccacaca aaacgctgcc cgtggtcttc gactctccaa   1140
ggaacagagg cctgaaggag tttccatca acgagtgat gggtccagat tttggctatg   1200
taactcgagg gccccaaaca gggggtatca gtggactgga ctccttggg aacctggaag   1260 tgagccccc agtcacagtc aggggcaagg aataccccgct gggcaggatt ctcttcgggg   1320
acagctgtta tcccagcaat gacagccggc agatgcacca ggccctgcag gacttcctca   1380
gtgcccagca ggtgcaggcc cctgtgaagc tctattctga ctggctgtcc gtgggccacg   1440
tggacgagtt cctgagcttt gtgccagcac cgacaggaa gggcttccgg ctgctcctgg   1500
ccagccccag gtcctgctac aaactgttcc aggagcagca gaatgaggc cacggggagg   1560 ccctgctgtt cgaagggatc aagaaaaaa aacagcagaa aataaagaac attctgtcaa   1620
acaagacatt gagagaacat aattcatttg tggagagatg catcgactgg aaccgcgagc   1680
tgctgaagcg ggagctgggc ctggccgaga gtgacatcat tgacatcccg cagctcttca   1740
agctcaaaga gttctctaag gcggaagctt ttttccccaa catggtgaac atgctggtgc   1800
tagggaagca cctgggcatc cccaagccct tcgggcccgt catcaacggc cgctgctgcc   1860
tggaggagaa ggtgtgttcc ctgctggagc cactgggcct ccagtgcacc ttcatcaacg   1920
acttcttcac ctaccacatc aggcatgggg aggtgcactg cggcaccaac gtgcgcagaa   1980
agcccttctc cttcaagtgg tggaacatgg tgccctgagc ccatcttccc tggcgtcctc   2040
tccctcctgg ccagatgtcg ctgggtcctc tgcagtgtgg caagcaagag ctcttgtgaa   2100
tattgtggct ccctgggggc ggccagccct cccagcagtg gcttgctttc ttctcctgtg   2160
atgtcccagt ttcccactct gaagatccca acatggtcct agcactgcac actcagttct   2220
gctctaagaa gctgcaataa agttttttta agtcactttg tac                     2263
```

<210> SEQ ID NO 52
<211> LENGTH: 1440
<212> TYPE: DNA
<213> ORGANISM: Homo sapiens
<300> PUBLICATION INFORMATION:
<308> DATABASE ACCESSION NUMBER: NM_007115
<309> DATABASE ENTRY DATE: 2006-09-24
<313> RELEVANT RESIDUES: (1)..(1440)

<400> SEQUENCE: 52

```
cagtcacatt tcagccactg ctctgagaat ttgtgagcag cccctaacag gctgttactt    60
cactacaact gacgatatga tcatcttaat ttacttattt ctcttgctat gggaagacac   120
tcaaggatgg ggattcaagg atggaatttt tcataactcc atatggcttg aacgagcagc   180
cggtgtgtac cacagagaag cacggtctgg caaatacaag ctcacctacg cagaagctaa   240
ggcggtgtgt gaatttgaag gcggccatct cgcaacttac aagcagctag aggcagccag   300
aaaaattgga tttcatgtct gtgctgctgg atggatggct aagggcagag ttggataccc   360
cattgtgaag ccagggccca actgtggatt tggaaaaact ggcattattg attatggaat   420
ccgtctcaat aggagtgaaa gatgggatgc ctattgctac aacccacacg caaaggagtg   480
tggtggcgtc tttacagatc caaagcaaat ttttaaatct ccaggcttcc caaatgagta   540
cgaagataac caaatctgct actggcacat tagactcaag tatggtcagc gtattcacct   600
gagttttttta gattttgacc ttgaagatga cccaggttgc ttggctgatt atgttgaaat   660
atatgacagt tacgatgatg tccatggctt tgtgggaaga tactgtggag atgagcttcc   720
agatgacatc atcagtacag gaaatgtcat gaccttgaag tttctaagtg atgcttcagt   780
gacagctgga ggtttccaaa tcaaatatgt tgcaatggat cctgtatcca atccagtca   840
aggaaaaaat acaagtacta cttctactgg aaataaaaac tttttagctg gaagatttag   900
ccacttataa aaaaaaaaaa aaggatgatc aaaacacaca gtgtttatgt tggaatcttt   960
tggaactcct ttgatctcac tgttattatt aacatttatt tattattttt ctaaatgtga  1020
aagcaataca taatttaggg aaaattggaa aatataggaa actttaaacg agaaaatgaa  1080
acctctcata atcccactgc atagaaataa caagcgttaa cattttcata ttttttttctt  1140
tcagtcattt ttctatttgt ggtatatgta tatatgtacc tatatgtatt tgcatttgaa  1200
attttggaat cctgctctat gtacagtttt gtattatact ttttaaatct tgaactttat  1260
aaacattttc tgaaatcatt gattattcta caaaaacatg attttaaaca gctgtaaaat  1320
attctatgat atgaatgttt tatgcattat ttaagcctgt ctctattgtt ggaatttcag  1380
gtcattttca taaatattgt tgcaataaat atccttgaac acaaaaaaaa aaaaaaaaa   1440
```

<210> SEQ ID NO 53
<211> LENGTH: 2377
<212> TYPE: DNA
<213> ORGANISM: Homo sapiens
<300> PUBLICATION INFORMATION:
<308> DATABASE ACCESSION NUMBER: NM_002467
<309> DATABASE ENTRY DATE: 2006-10-15
<313> RELEVANT RESIDUES: (1)..(2377)

<400> SEQUENCE: 53

```
acccccgagc tgtgctgctc gcggccgcca ccgccgggcc ccggccgtcc ctggctcccc    60
tcctgcctcg agaagggcag ggcttctcag aggcttggcg ggaaaaagaa cggagggagg   120
gatcgcgctg agtataaaag ccggttttcg gggctttatc taactcgctg tagtaattcc   180
agcgagaggc agagggagcg agcgggcggc cggctagggt ggaagagccg ggcgagcaga   240
gctgcgctgc gggcgtcctg ggaagggaga tccggagcga ataggggct tcgcctctgg   300
cccagccctc ccgctgatcc cccagccagc ggtccgcaac ccttgccgca tccacgaaac   360
tttgcccata gcagcgggcg ggcactttgc actggaactt acaacacccg agcaaggacg   420
cgactctccc gacgcgggga ggctattctg cccatttggg gacacttccc cgccgctgcc   480
aggacccgct tctctgaaag gctctccttg cagctgctta gacgctggat ttttttcggg   540
tagtggaaaa ccagcagcct cccgcgacga tgcccctcaa cgttagcttc accaacagga   600
```

-continued

```
actatgacct cgactacgac tcggtgcagc cgtatttcta ctgcgacgag gaggagaact    660
tctaccagca gcagcagcag agcgagctgc agccccggc gcccagcgag gatatctgga    720
agaaattcga gctgctgccc accccgcccc tgtccctag ccgccgctcc gggctctgct    780
cgccctccta cgttgcggtc acaccttct cccttcgggg agacaacgac ggcggtggcg    840
ggagcttctc cacggccgac cagctggaga tggtgaccga gctgctggga ggagacatgg    900
tgaaccagag tttcatctgc gacccggacg acgagacctt catcaaaaac atcatcatcc    960
aggactgtat gtggagcggc ttctcggccg ccgccaagct cgtctcagag aagctggcct   1020
cctaccagge tgcgcgcaaa gacagcggca gcccgaaccc cgcccgcggc cacagcgtct   1080
gctccacctc cagcttgtac ctgcaggatc tgagcgccgc cgcctcagag tgcatcgacc   1140
cctcggtggt cttccctac cctctcaacg acagcagctc gcccaagtcc tgcgcctcgc   1200
aagactccag cgccttctct ccgtcctcgg attctctgct ctcctcgacg gagtcctccc   1260
cgcagggcag ccccgagccc ctggtgctcc atgaggagac accgcccacc accagcagcg   1320
actctgagga ggaacaagaa gatgaggaag aaatcgatgt tgtttctgtg gaaagaggc   1380
aggctcctgg caaaaggtca gagtctggat caccttctgc tggaggccac agcaaacctc   1440
ctcacagccc actggtcctc aagaggtgcc acgtctccac acatcagcac aactacgcag   1500
cgcctccctc cactcggaag gactatcctg ctgccaagag ggtcaagttg gacagtgtca   1560
gagtcctgag acagatcagc aacaaccgaa aatgcaccag ccccaggtcc tcggacaccg   1620
aggagaatgt caagaggcga acacacaacg tcttggagcg ccagaggagg aacgagctaa   1680
aacggagctt ttttgccctg cgtgaccaga tcccggagtt ggaaacaat gaaaaggccc   1740
ccaaggtagt tatccttaaa aaagccacag catacatcct gtccgtccaa gcagaggagc   1800
aaaagctcat ttctgaagag gacttgttgc ggaaacgacg agaacagttg aaacacaaac   1860
ttgaacagct acggaactct tgtgcgtaag gaaaagtaag gaaaacgatt ccttctaaca   1920
gaaatgtcct gagcaatcac ctatgaactt gtttcaaatg catgatcaaa tgcaacctca   1980
caaccttggc tgagtcttga gactgaaaga tttagccata atgtaaactg cctcaaattg   2040
gactttgggc ataaaagaac ttttttatgc ttaccatctt ttttttttct ttaacagatt   2100
tgtatttaag aattgttttt aaaaaatttt aagatttaca caatgtttct ctgtaaatat   2160
tgccattaaa tgtaaataac tttaataaaa cgtttatagc agttacacag aatttcaatc   2220
ctagtatata gtacctagta ttataggtac tataaaccct aattttttt atttaagtac   2280
attttgcttt ttaaagttga tttttttcta ttgttttag aaaaaataaa ataactggca   2340
aatatatcat tgagccaaaa aaaaaaaaaa aaaaaaa                            2377
```

<210> SEQ ID NO 54
<211> LENGTH: 20
<212> TYPE: DNA
<213> ORGANISM: Artificial Sequence
<220> FEATURE:
<223> OTHER INFORMATION: Primer

<400> SEQUENCE: 54
gccctgtatt atgtggacct                                                 20

<210> SEQ ID NO 55
<211> LENGTH: 20
<212> TYPE: DNA
<213> ORGANISM: Artificial Sequence
<220> FEATURE:
<223> OTHER INFORMATION: Primer

```
<400> SEQUENCE: 55
agatgggtac tgcaggtaga                                            20

<210> SEQ ID NO 56
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 56
ccggctgagc ccagaccaat                                            20

<210> SEQ ID NO 57
<211> LENGTH: 20
<212> TYPE: DNA
<213> ORGANISM: Artificial Sequence
<220> FEATURE:
<223> OTHER INFORMATION: Primer

<400> SEQUENCE: 57
cactcggaga cacacttgtt                                            20

<210> SEQ ID NO 58
<211> LENGTH: 19
<212> TYPE: DNA
<213> ORGANISM: Artificial Sequence
<220> FEATURE:
<223> OTHER INFORMATION: Primer

<400> SEQUENCE: 58
cttggtctgg cttcttcag                                             19

<210> SEQ ID NO 59
<211> LENGTH: 21
<212> TYPE: DNA
<213> ORGANISM: Artificial Sequence
<220> FEATURE:
<223> OTHER INFORMATION: TaqManp probe sequence

<400> SEQUENCE: 59
catcgctggc actgacgtcc a                                          21

<210> SEQ ID NO 60
<211> LENGTH: 20
<212> TYPE: DNA
<213> ORGANISM: Artificial Sequence
<220> FEATURE:
<223> OTHER INFORMATION: Primer

<400> SEQUENCE: 60
actcggagac acacttgttg                                            20

<210> SEQ ID NO 61
<211> LENGTH: 19
<212> TYPE: DNA
<213> ORGANISM: Artificial Sequence
<220> FEATURE:
<223> OTHER INFORMATION: Primer

<400> SEQUENCE: 61
cttggtctgg cttcttcag                                             19

<210> SEQ ID NO 62
<211> LENGTH: 21
<212> TYPE: DNA
```

```
<213> ORGANISM: Artificial Sequence
<220> FEATURE:
<223> OTHER INFORMATION: TaqManp probe sequence

<400> SEQUENCE: 62
catcgctggc actgacgtcc a                                              21

<210> SEQ ID NO 63
<211> LENGTH: 20
<212> TYPE: DNA
<213> ORGANISM: Artificial Sequence
<220> FEATURE:
<223> OTHER INFORMATION: Primer

<400> SEQUENCE: 63
agtggtggta gatgttgtgc                                                20

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
agaccactct ctggctgtc                                                 19

<210> SEQ ID NO 65
<211> LENGTH: 21
<212> TYPE: DNA
<213> ORGANISM: Artificial Sequence
<220> FEATURE:
<223> OTHER INFORMATION: TaqManp probe sequence

<400> SEQUENCE: 65
tgcagccttc tgcctttggg a                                              21

<210> SEQ ID NO 66
<211> LENGTH: 20
<212> TYPE: DNA
<213> ORGANISM: Artificial Sequence
<220> FEATURE:
<223> OTHER INFORMATION: Primer

<400> SEQUENCE: 66
cacttgttgt atgtggcaga                                                20

<210> SEQ ID NO 67
<211> LENGTH: 19
<212> TYPE: DNA
<213> ORGANISM: Artificial Sequence
<220> FEATURE:
<223> OTHER INFORMATION: Primer

<400> SEQUENCE: 67
gcctggctat ctcatcatc                                                 19

<210> SEQ ID NO 68
<211> LENGTH: 20
<212> TYPE: DNA
<213> ORGANISM: Artificial Sequence
<220> FEATURE:
<223> OTHER INFORMATION: Primer

<400> SEQUENCE: 68
tagggaggag aaacagaagc                                                20
```

-continued

```
<210> SEQ ID NO 69
<211> LENGTH: 20
<212> TYPE: DNA
<213> ORGANISM: Artificial Sequence
<220> FEATURE:
<223> OTHER INFORMATION: Primer

<400> SEQUENCE: 69
ggcctctaac tcgacctcta                                              20

<210> SEQ ID NO 70
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 70
tggaacatgc ttaccctgct gatga                                        25

<210> SEQ ID NO 71
<211> LENGTH: 20
<212> TYPE: DNA
<213> ORGANISM: Artificial Sequence
<220> FEATURE:
<223> OTHER INFORMATION: Primer

<400> SEQUENCE: 71
tgtggtggat aagagctgtc                                              20

<210> SEQ ID NO 72
<211> LENGTH: 20
<212> TYPE: DNA
<213> ORGANISM: Artificial Sequence
<220> FEATURE:
<223> OTHER INFORMATION: Primer

<400> SEQUENCE: 72
cccatcttct tcaggatttc                                              20

<210> SEQ ID NO 73
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 73
tggccatgaa atctctggct ctca                                         24

<210> SEQ ID NO 74
<211> LENGTH: 20
<212> TYPE: DNA
<213> ORGANISM: Artificial Sequence
<220> FEATURE:
<223> OTHER INFORMATION: Primer

<400> SEQUENCE: 74
gaggagagtt tcaggagtgg                                              20

<210> SEQ ID NO 75
<211> LENGTH: 20
<212> TYPE: DNA
<213> ORGANISM: Artificial Sequence
<220> FEATURE:
<223> OTHER INFORMATION: Primer
```

-continued

```
<400> SEQUENCE: 75
ctcccatctt tgaggtgaat                                              20

<210> SEQ ID NO 76
<211> LENGTH: 24
<212> TYPE: DNA
<213> ORGANISM: Artificial Sequence
<220> FEATURE:
<223> OTHER INFORMATION: aqManp probe sequence

<400> SEQUENCE: 76
tggccatgaa atctctggct ctca                                         24

<210> SEQ ID NO 77
<211> LENGTH: 20
<212> TYPE: DNA
<213> ORGANISM: Artificial Sequence
<220> FEATURE:
<223> OTHER INFORMATION: Primer

<400> SEQUENCE: 77
ttgcttggag atgacagttt                                              20

<210> SEQ ID NO 78
<211> LENGTH: 20
<212> TYPE: DNA
<213> ORGANISM: Artificial Sequence
<220> FEATURE:
<223> OTHER INFORMATION: Primer

<400> SEQUENCE: 78
agcattggtt tgtggatatg                                              20

<210> SEQ ID NO 79
<211> LENGTH: 20
<212> TYPE: DNA
<213> ORGANISM: Artificial Sequence
<220> FEATURE:
<223> OTHER INFORMATION: Primer

<400> SEQUENCE: 79
ggcacatctt ctgtcttctg                                              20

<210> SEQ ID NO 80
<211> LENGTH: 20
<212> TYPE: DNA
<213> ORGANISM: Artificial Sequence
<220> FEATURE:
<223> OTHER INFORMATION: Primer

<400> SEQUENCE: 80
ctgtgaagag ctacgggaat                                              20

<210> SEQ ID NO 81
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 81
tggaatccct ttggctgttc cc                                           22

<210> SEQ ID NO 82
<211> LENGTH: 20
<212> TYPE: DNA
```

```
<213> ORGANISM: Artificial Sequence
<220> FEATURE:
<223> OTHER INFORMATION: Primer

<400> SEQUENCE: 82
tggcacatct tctgtcttct                                              20

<210> SEQ ID NO 83
<211> LENGTH: 20
<212> TYPE: DNA
<213> ORGANISM: Artificial Sequence
<220> FEATURE:
<223> OTHER INFORMATION: Primer

<400> SEQUENCE: 83
ctgtgaagag ctacgggaat                                              20

<210> SEQ ID NO 84
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 84
tggaatccct ttggctgttc cc                                           22

<210> SEQ ID NO 85
<211> LENGTH: 20
<212> TYPE: DNA
<213> ORGANISM: Artificial Sequence
<220> FEATURE:
<223> OTHER INFORMATION: Primer

<400> SEQUENCE: 85
ccctactacc tggagaacga                                              20

<210> SEQ ID NO 86
<211> LENGTH: 20
<212> TYPE: DNA
<213> ORGANISM: Artificial Sequence
<220> FEATURE:
<223> OTHER INFORMATION: Primer

<400> SEQUENCE: 86
attggtactg gccaatcttt                                              20

<210> SEQ ID NO 87
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 87
ctgccaccct ggcgtcgatt                                              20

<210> SEQ ID NO 88
<211> LENGTH: 20
<212> TYPE: DNA
<213> ORGANISM: Artificial Sequence
<220> FEATURE:
<223> OTHER INFORMATION: Primer

<400> SEQUENCE: 88
caccattccc aagttaatcc                                              20
```

<210> SEQ ID NO 89
<211> LENGTH: 20
<212> TYPE: DNA
<213> ORGANISM: Artificial Sequence
<220> FEATURE:
<223> OTHER INFORMATION: Primer

<400> SEQUENCE: 89
gaaatgcagt tggaaacaga                                                    20

<210> SEQ ID NO 90
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 90
tgggaccaaa gttcatttgc tcca                                               24

<210> SEQ ID NO 91
<211> LENGTH: 20
<212> TYPE: DNA
<213> ORGANISM: Artificial Sequence
<220> FEATURE:
<223> OTHER INFORMATION: Primer

<400> SEQUENCE: 91
tgccctacta cctggagaac                                                    20

<210> SEQ ID NO 92
<211> LENGTH: 20
<212> TYPE: DNA
<213> ORGANISM: Artificial Sequence
<220> FEATURE:
<223> OTHER INFORMATION: Primer

<400> SEQUENCE: 92
attggtactg gccaatcttt                                                    20

<210> SEQ ID NO 93
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 93
agcccagcgg ctacacggtg                                                    20

<210> SEQ ID NO 94
<211> LENGTH: 20
<212> TYPE: DNA
<213> ORGANISM: Artificial Sequence
<220> FEATURE:
<223> OTHER INFORMATION: Primer

<400> SEQUENCE: 94
gtgccctact acctggagaa                                                    20

<210> SEQ ID NO 95
<211> LENGTH: 20
<212> TYPE: DNA
<213> ORGANISM: Artificial Sequence
<220> FEATURE:
<223> OTHER INFORMATION: Primer

```
<400> SEQUENCE: 95
attggtactg gccaatcttt                                              20

<210> SEQ ID NO 96
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 96
agcccagcgg ctacacggtg                                              20

<210> SEQ ID NO 97
<211> LENGTH: 20
<212> TYPE: DNA
<213> ORGANISM: Artificial Sequence
<220> FEATURE:
<223> OTHER INFORMATION: Primer

<400> SEQUENCE: 97
tgtgcaatga ctatgcttca                                              20

<210> SEQ ID NO 98
<211> LENGTH: 20
<212> TYPE: DNA
<213> ORGANISM: Artificial Sequence
<220> FEATURE:
<223> OTHER INFORMATION: Primer

<400> SEQUENCE: 98
ttatcaatgg tgcactggtt                                              20

<210> SEQ ID NO 99
<211> LENGTH: 20
<212> TYPE: DNA
<213> ORGANISM: Artificial Sequence
<220> FEATURE:
<223> OTHER INFORMATION: Primer

<400> SEQUENCE: 99
tgtgcaatga ctatgcttca                                              20

<210> SEQ ID NO 100
<211> LENGTH: 20
<212> TYPE: DNA
<213> ORGANISM: Artificial Sequence
<220> FEATURE:
<223> OTHER INFORMATION: Primer

<400> SEQUENCE: 100
tttatcaatg gtgcactggt                                              20

<210> SEQ ID NO 101
<211> LENGTH: 20
<212> TYPE: DNA
<213> ORGANISM: Artificial Sequence
<220> FEATURE:
<223> OTHER INFORMATION: Primer

<400> SEQUENCE: 101
tgggtggttt atacactgga                                              20

<210> SEQ ID NO 102
<211> LENGTH: 20
<212> TYPE: DNA
```

<213> ORGANISM: Artificial Sequence
<220> FEATURE:
<223> OTHER INFORMATION: Primer

<400> SEQUENCE: 102
ataagggttt cacccagcta                                               20

<210> SEQ ID NO 103
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 103
ccagatttgc ccatccttcc tctg                                          24

<210> SEQ ID NO 104
<211> LENGTH: 20
<212> TYPE: DNA
<213> ORGANISM: Artificial Sequence
<220> FEATURE:
<223> OTHER INFORMATION: Primer

<400> SEQUENCE: 104
gagctcctct ccctcaagta                                               20

<210> SEQ ID NO 105
<211> LENGTH: 20
<212> TYPE: DNA
<213> ORGANISM: Artificial Sequence
<220> FEATURE:
<223> OTHER INFORMATION: Primer

<400> SEQUENCE: 105
ggtgacgact tcttgtttga                                               20

<210> SEQ ID NO 106
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 106
cctcggtcat tctccgagac cc                                            22

<210> SEQ ID NO 107
<211> LENGTH: 20
<212> TYPE: DNA
<213> ORGANISM: Artificial Sequence
<220> FEATURE:
<223> OTHER INFORMATION: Primer

<400> SEQUENCE: 107
ggatgtcagg tgagactgtg                                               20

<210> SEQ ID NO 108
<211> LENGTH: 20
<212> TYPE: DNA
<213> ORGANISM: Artificial Sequence
<220> FEATURE:
<223> OTHER INFORMATION: Primer

<400> SEQUENCE: 108
gccttcaagt cattcctctc                                               20

```
<210> SEQ ID NO 109
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 109
ccctggcatc acctgtgcca                                                     20

<210> SEQ ID NO 110
<211> LENGTH: 20
<212> TYPE: DNA
<213> ORGANISM: Artificial Sequence
<220> FEATURE:
<223> OTHER INFORMATION: Primer

<400> SEQUENCE: 110
tcaaacaaga agtcgtcacc                                                     20

<210> SEQ ID NO 111
<211> LENGTH: 20
<212> TYPE: DNA
<213> ORGANISM: Artificial Sequence
<220> FEATURE:
<223> OTHER INFORMATION: Primer

<400> SEQUENCE: 111
gcgatcacaa ctatcgtagc                                                     20

<210> SEQ ID NO 112
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 112
cccgagttta ccacgactgg tcctc                                               25

<210> SEQ ID NO 113
<211> LENGTH: 20
<212> TYPE: DNA
<213> ORGANISM: Artificial Sequence
<220> FEATURE:
<223> OTHER INFORMATION: Primer

<400> SEQUENCE: 113
ccgctatacc tcggattact                                                     20

<210> SEQ ID NO 114
<211> LENGTH: 20
<212> TYPE: DNA
<213> ORGANISM: Artificial Sequence
<220> FEATURE:
<223> OTHER INFORMATION: Primer

<400> SEQUENCE: 114
gcgtctgata ggactctgtg                                                     20

<210> SEQ ID NO 115
<211> LENGTH: 22
<212> TYPE: DNA
<213> ORGANISM: Artificial Sequence
<220> FEATURE:
<223> OTHER INFORMATION: TaqManp probe sequence
```

```
<400> SEQUENCE: 115
cccagtgtgt tccaccatcg ga                                        22

<210> SEQ ID NO 116
<211> LENGTH: 20
<212> TYPE: DNA
<213> ORGANISM: Artificial Sequence
<220> FEATURE:
<223> OTHER INFORMATION: Primer

<400> SEQUENCE: 116
acagctgcca tcagaaacta                                           20

<210> SEQ ID NO 117
<211> LENGTH: 20
<212> TYPE: DNA
<213> ORGANISM: Artificial Sequence
<220> FEATURE:
<223> OTHER INFORMATION: Primer

<400> SEQUENCE: 117
gcttcctgta gctcattcct                                           20

<210> SEQ ID NO 118
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 118
ccgggaagct gtaagattaa atcccaa                                   27

<210> SEQ ID NO 119
<211> LENGTH: 20
<212> TYPE: DNA
<213> ORGANISM: Artificial Sequence
<220> FEATURE:
<223> OTHER INFORMATION: Primer

<400> SEQUENCE: 119
tgataaaggc aaccagacag                                           20

<210> SEQ ID NO 120
<211> LENGTH: 20
<212> TYPE: DNA
<213> ORGANISM: Artificial Sequence
<220> FEATURE:
<223> OTHER INFORMATION: Primer

<400> SEQUENCE: 120
agcttcctgt agctcattcc                                           20

<210> SEQ ID NO 121
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 121
tgccatcaga aactaccggg aagc                                      24

<210> SEQ ID NO 122
<211> LENGTH: 20
<212> TYPE: DNA
```

```
<213> ORGANISM: Artificial Sequence
<220> FEATURE:
<223> OTHER INFORMATION: Primer

<400> SEQUENCE: 122
ggatttctcg ttatcccatt                                                    20

<210> SEQ ID NO 123
<211> LENGTH: 20
<212> TYPE: DNA
<213> ORGANISM: Artificial Sequence
<220> FEATURE:
<223> OTHER INFORMATION: Primer

<400> SEQUENCE: 123
tcttggtatg tttgctcagg                                                    20

<210> SEQ ID NO 124
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 124
aggacacgct ccgcgaccac                                                    20

<210> SEQ ID NO 125
<211> LENGTH: 20
<212> TYPE: DNA
<213> ORGANISM: <213>   Artificial Sequence
<220> FEATURE:
<223> OTHER INFORMATION: Primer

<400> SEQUENCE: 125
caaatacagc cagactttgc                                                    20

<210> SEQ ID NO 126
<211> LENGTH: 20
<212> TYPE: DNA
<213> ORGANISM: Artificial Sequence
<220> FEATURE:
<223> OTHER INFORMATION: Primer

<400> SEQUENCE: 126
tttaattgct gtccggtaac                                                    20

<210> SEQ ID NO 127
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 127
tgctgcttca aaccgtttca ggc                                                23

<210> SEQ ID NO 128
<211> LENGTH: 20
<212> TYPE: DNA
<213> ORGANISM: Artificial Sequence
<220> FEATURE:
<223> OTHER INFORMATION: Primer

<400> SEQUENCE: 128
caaatacagc cagactttgc                                                    20
```

```
<210> SEQ ID NO 129
<211> LENGTH: 20
<212> TYPE: DNA
<213> ORGANISM: Artificial Sequence
<220> FEATURE:
<223> OTHER INFORMATION: Primer

<400> SEQUENCE: 129
gtttaattgc tgtccggtaa                                               20

<210> SEQ ID NO 130
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 130
tgctgcttca aaccgtttca ggc                                           23

<210> SEQ ID NO 131
<211> LENGTH: 20
<212> TYPE: DNA
<213> ORGANISM: Artificial Sequence
<220> FEATURE:
<223> OTHER INFORMATION: Primer

<400> SEQUENCE: 131
cttggtgata ggcaaattca                                               20

<210> SEQ ID NO 132
<211> LENGTH: 20
<212> TYPE: DNA
<213> ORGANISM: Artificial Sequence
<220> FEATURE:
<223> OTHER INFORMATION: Primer

<400> SEQUENCE: 132
agcagggtca ttctgaagag                                               20

<210> SEQ ID NO 133
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 133
cccgttcctg agcatgccga                                               20

<210> SEQ ID NO 134
<211> LENGTH: 20
<212> TYPE: DNA
<213> ORGANISM: Artificial Sequence
<220> FEATURE:
<223> OTHER INFORMATION: Primer

<400> SEQUENCE: 134
tttggctgtg ctttatcatc                                               20

<210> SEQ ID NO 135
<211> LENGTH: 20
<212> TYPE: DNA
<213> ORGANISM: Artificial Sequence
<220> FEATURE:
<223> OTHER INFORMATION: Primer
```

```
<400> SEQUENCE: 135
cagcagaccg taattctcct                                          20

<210> SEQ ID NO 136
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 136
tgtttcttgg ccaagtctag atgtccc                                  27

<210> SEQ ID NO 137
<211> LENGTH: 20
<212> TYPE: DNA
<213> ORGANISM: Artificial Sequence
<220> FEATURE:
<223> OTHER INFORMATION: Primer

<400> SEQUENCE: 137
attggaggac aagagcagat                                          20

<210> SEQ ID NO 138
<211> LENGTH: 19
<212> TYPE: DNA
<213> ORGANISM: Artificial Sequence
<220> FEATURE:
<223> OTHER INFORMATION: Primer

<400> SEQUENCE: 138
ccatcgctct ctagattgg                                           19

<210> SEQ ID NO 139
<211> LENGTH: 21
<212> TYPE: DNA
<213> ORGANISM: Artificial Sequence
<220> FEATURE:
<223> OTHER INFORMATION: TaqManp probe sequence

<400> SEQUENCE: 139
ttcttaggtg ccgcagtgcc c                                        21

<210> SEQ ID NO 140
<211> LENGTH: 20
<212> TYPE: DNA
<213> ORGANISM: Artificial Sequence
<220> FEATURE:
<223> OTHER INFORMATION: Primer

<400> SEQUENCE: 140
ccttcaggaa gactttccac                                          20

<210> SEQ ID NO 141
<211> LENGTH: 20
<212> TYPE: DNA
<213> ORGANISM: Artificial Sequence
<220> FEATURE:
<223> OTHER INFORMATION: Primer

<400> SEQUENCE: 141
ctcaagttca ttcagccatc                                          20

<210> SEQ ID NO 142
<211> LENGTH: 20
<212> TYPE: DNA
```

```
<213> ORGANISM: Artificial Sequence
<220> FEATURE:
<223> OTHER INFORMATION: TaqManp probe sequence

<400> SEQUENCE: 142
acgggcggat ccacagcaac                                            20

<210> SEQ ID NO 143
<211> LENGTH: 20
<212> TYPE: DNA
<213> ORGANISM: Artificial Sequence
<220> FEATURE:
<223> OTHER INFORMATION: Primer

<400> SEQUENCE: 143
tgatcagcaa gtgaacacac                                            20

<210> SEQ ID NO 144
<211> LENGTH: 20
<212> TYPE: DNA
<213> ORGANISM: Artificial Sequence
<220> FEATURE:
<223> OTHER INFORMATION: Primer

<400> SEQUENCE: 144
ctcggtgata gcaaatcaga                                            20

<210> SEQ ID NO 145
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 145
tgcatccttg atggcaagct tca                                        23

<210> SEQ ID NO 146
<211> LENGTH: 20
<212> TYPE: DNA
<213> ORGANISM: Artificial Sequence
<220> FEATURE:
<223> OTHER INFORMATION: Primer

<400> SEQUENCE: 146
gtgatcagca agtgaacaca                                            20

<210> SEQ ID NO 147
<211> LENGTH: 20
<212> TYPE: DNA
<213> ORGANISM: Artificial Sequence
<220> FEATURE:
<223> OTHER INFORMATION: Primer

<400> SEQUENCE: 147
ctcggtgata gcaaatcaga                                            20

<210> SEQ ID NO 148
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 148
tgcatccttg atggcaagct tca                                        23
```

<210> SEQ ID NO 149
<211> LENGTH: 20
<212> TYPE: DNA
<213> ORGANISM: Artificial Sequence
<220> FEATURE:
<223> OTHER INFORMATION: Primer

<400> SEQUENCE: 149
ttaatggtcc tgtctgatgc                                              20

<210> SEQ ID NO 150
<211> LENGTH: 20
<212> TYPE: DNA
<213> ORGANISM: Artificial Sequence
<220> FEATURE:
<223> OTHER INFORMATION: Primer

<400> SEQUENCE: 150
gggtctctag acaagccaag                                              20

<210> SEQ ID NO 151
<211> LENGTH: 20
<212> TYPE: DNA
<213> ORGANISM: Artificial Sequence
<220> FEATURE:
<223> OTHER INFORMATION: Primer

<400> SEQUENCE: 151
agatttgcag acacagaagc                                              20

<210> SEQ ID NO 152
<211> LENGTH: 20
<212> TYPE: DNA
<213> ORGANISM: Artificial Sequence
<220> FEATURE:
<223> OTHER INFORMATION: Primer

<400> SEQUENCE: 152
ttctaacatc aggtggttgc                                              20

<210> SEQ ID NO 153
<211> LENGTH: 21
<212> TYPE: DNA
<213> ORGANISM: Artificial Sequence
<220> FEATURE:
<223> OTHER INFORMATION: Primer

<400> SEQUENCE: 153
tacaactcac gaatcccttc t                                            21

<210> SEQ ID NO 154
<211> LENGTH: 20
<212> TYPE: DNA
<213> ORGANISM: Artificial Sequence
<220> FEATURE:
<223> OTHER INFORMATION: Primer

<400> SEQUENCE: 154
acaggaagta gaggcagagg                                              20

<210> SEQ ID NO 155
<211> LENGTH: 21
<212> TYPE: DNA
<213> ORGANISM: Artificial Sequence
<220> FEATURE:
<223> OTHER INFORMATION: Primer

```
<400> SEQUENCE: 155
caactcacga atcccttcta c                                             21

<210> SEQ ID NO 156
<211> LENGTH: 20
<212> TYPE: DNA
<213> ORGANISM: Artificial Sequence
<220> FEATURE:
<223> OTHER INFORMATION: Primer

<400> SEQUENCE: 156
acaggaagta gaggcagagg                                               20

<210> SEQ ID NO 157
<211> LENGTH: 21
<212> TYPE: DNA
<213> ORGANISM: Artificial Sequence
<220> FEATURE:
<223> OTHER INFORMATION: Primer

<400> SEQUENCE: 157
acaactcacg aatcccttct a                                             21

<210> SEQ ID NO 158
<211> LENGTH: 20
<212> TYPE: DNA
<213> ORGANISM: Artificial Sequence
<220> FEATURE:
<223> OTHER INFORMATION: Primer

<400> SEQUENCE: 158
acaggaagta gaggcagagg                                               20

<210> SEQ ID NO 159
<211> LENGTH: 21
<212> TYPE: DNA
<213> ORGANISM: Artificial Sequence
<220> FEATURE:
<223> OTHER INFORMATION: Primer

<400> SEQUENCE: 159
aactcacgaa tcccttctac a                                             21

<210> SEQ ID NO 160
<211> LENGTH: 20
<212> TYPE: DNA
<213> ORGANISM: Artificial Sequence
<220> FEATURE:
<223> OTHER INFORMATION: Primer

<400> SEQUENCE: 160
acaggaagta gaggcagagg                                               20

<210> SEQ ID NO 161
<211> LENGTH: 20
<212> TYPE: DNA
<213> ORGANISM: Artificial Sequence
<220> FEATURE:
<223> OTHER INFORMATION: Primer

<400> SEQUENCE: 161
gggatttcca tgacctttat                                               20

<210> SEQ ID NO 162
<211> LENGTH: 20
<212> TYPE: DNA
```

```
<213> ORGANISM: Artificial Sequence
<220> FEATURE:
<223> OTHER INFORMATION: Primer

<400> SEQUENCE: 162
atccagaagg acagaagcat                                              20

<210> SEQ ID NO 163
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 163
tgccctgtcg gatgtcacca                                              20

<210> SEQ ID NO 164
<211> LENGTH: 20
<212> TYPE: DNA
<213> ORGANISM: Artificial Sequence
<220> FEATURE:
<223> OTHER INFORMATION: Primer

<400> SEQUENCE: 164
attgaagagg caattccaag                                              20

<210> SEQ ID NO 165
<211> LENGTH: 20
<212> TYPE: DNA
<213> ORGANISM: Artificial Sequence
<220> FEATURE:
<223> OTHER INFORMATION: Primer

<400> SEQUENCE: 165
tttagcttga aggcaatgtc                                              20

<210> SEQ ID NO 166
<211> LENGTH: 26
<212> TYPE: DNA
<213> ORGANISM: Artificial Sequence
<220> FEATURE:
<223> OTHER INFORMATION: TaqManp probe sequence

<400> SEQUENCE: 166
ccacatggag atgagtcctt ggttcc                                       26

<210> SEQ ID NO 167
<211> LENGTH: 20
<212> TYPE: DNA
<213> ORGANISM: Artificial Sequence
<220> FEATURE:
<223> OTHER INFORMATION: Primer

<400> SEQUENCE: 167
catgtgtaat gctggatgtg                                              20

<210> SEQ ID NO 168
<211> LENGTH: 20
<212> TYPE: DNA
<213> ORGANISM: Artificial Sequence
<220> FEATURE:
<223> OTHER INFORMATION: Primer

<400> SEQUENCE: 168
aaacaactca gggaacacct                                              20
```

<210> SEQ ID NO 169
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 169
tggacaacct gactggcttt gca                                              23

<210> SEQ ID NO 170
<211> LENGTH: 20
<212> TYPE: DNA
<213> ORGANISM: Artificial Sequence
<220> FEATURE:
<223> OTHER INFORMATION: Primer

<400> SEQUENCE: 170
caggcctctg gtatttcttt                                                  20

<210> SEQ ID NO 171
<211> LENGTH: 20
<212> TYPE: DNA
<213> ORGANISM: Artificial Sequence
<220> FEATURE:
<223> OTHER INFORMATION: Primer

<400> SEQUENCE: 171
atttgtacac ctccgttgtg                                                  20

<210> SEQ ID NO 172
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 172
ttggcagaac cattgatttc tcctgtt                                          27

<210> SEQ ID NO 173
<211> LENGTH: 20
<212> TYPE: DNA
<213> ORGANISM: Artificial Sequence
<220> FEATURE:
<223> OTHER INFORMATION: Primer

<400> SEQUENCE: 173
aaacatgaag tcaggcctct                                                  20

<210> SEQ ID NO 174
<211> LENGTH: 20
<212> TYPE: DNA
<213> ORGANISM: Artificial Sequence
<220> FEATURE:
<223> OTHER INFORMATION: Primer

<400> SEQUENCE: 174
gtacacctcc gttgtgaaat                                                  20

<210> SEQ ID NO 175
<211> LENGTH: 27
<212> TYPE: DNA
<213> ORGANISM: Artificial Sequence
<220> FEATURE:
<223> OTHER INFORMATION: TaqManp probe sequence

```
<400> SEQUENCE: 175
ttggcagaac cattgatttc tcctgtt                                         27

<210> SEQ ID NO 176
<211> LENGTH: 20
<212> TYPE: DNA
<213> ORGANISM: Artificial Sequence
<220> FEATURE:
<223> OTHER INFORMATION: Primer

<400> SEQUENCE: 176
gtcaggcctc tggtatttct                                                 20

<210> SEQ ID NO 177
<211> LENGTH: 20
<212> TYPE: DNA
<213> ORGANISM: Artificial Sequence
<220> FEATURE:
<223> OTHER INFORMATION: Primer

<400> SEQUENCE: 177
atttgtacac ctccgttgtg                                                 20

<210> SEQ ID NO 178
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 178
ttggcagaac cattgatttc tcctgtt                                         27

<210> SEQ ID NO 179
<211> LENGTH: 20
<212> TYPE: DNA
<213> ORGANISM: Artificial Sequence
<220> FEATURE:
<223> OTHER INFORMATION: Primer

<400> SEQUENCE: 179
gaagtcaggc ctctggtatt                                                 20

<210> SEQ ID NO 180
<211> LENGTH: 20
<212> TYPE: DNA
<213> ORGANISM: Artificial Sequence
<220> FEATURE:
<223> OTHER INFORMATION: Primer

<400> SEQUENCE: 180
atttgtacac ctccgttgtg                                                 20

<210> SEQ ID NO 181
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 181
ttggcagaac cattgatttc tcctgtt                                         27

<210> SEQ ID NO 182
<211> LENGTH: 20
<212> TYPE: DNA
```

```
<213> ORGANISM: Artificial Sequence
<220> FEATURE:
<223> OTHER INFORMATION: Primer

<400> SEQUENCE: 182
cagatccaag gatgaaacaa                                                      20

<210> SEQ ID NO 183
<211> LENGTH: 20
<212> TYPE: DNA
<213> ORGANISM: Artificial Sequence
<220> FEATURE:
<223> OTHER INFORMATION: Primer

<400> SEQUENCE: 183
accaccattt gagagtgatg                                                      20

<210> SEQ ID NO 184
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 184
caccagctcc tgcatcttca ggg                                                  23

<210> SEQ ID NO 185
<211> LENGTH: 20
<212> TYPE: DNA
<213> ORGANISM: Artificial Sequence
<220> FEATURE:
<223> OTHER INFORMATION: Primer

<400> SEQUENCE: 185
tcaatccaga tcacctgaaa                                                      20

<210> SEQ ID NO 186
<211> LENGTH: 20
<212> TYPE: DNA
<213> ORGANISM: Artificial Sequence
<220> FEATURE:
<223> OTHER INFORMATION: Primer

<400> SEQUENCE: 186
aatccttgag tccaactggt                                                      20

<210> SEQ ID NO 187
<211> LENGTH: 21
<212> TYPE: DNA
<213> ORGANISM: Artificial Sequence
<220> FEATURE:
<223> OTHER INFORMATION: TaqManp probe sequence

<400> SEQUENCE: 187
cccatggaac agagccatgg c                                                    21

<210> SEQ ID NO 188
<211> LENGTH: 20
<212> TYPE: DNA
<213> ORGANISM: Artificial Sequence
<220> FEATURE:
<223> OTHER INFORMATION: Primer

<400> SEQUENCE: 188
aagctgttgt ttgccataga                                                      20
```

```
<210> SEQ ID NO 189
<211> LENGTH: 20
<212> TYPE: DNA
<213> ORGANISM: Artificial Sequence
<220> FEATURE:
<223> OTHER INFORMATION: Primer

<400> SEQUENCE: 189
cagagaagga caaacattgc                                               20

<210> SEQ ID NO 190
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 190
tgcccattca tggtgcaagt tctc                                          24

<210> SEQ ID NO 191
<211> LENGTH: 20
<212> TYPE: DNA
<213> ORGANISM: Artificial Sequence
<220> FEATURE:
<223> OTHER INFORMATION: Primer

<400> SEQUENCE: 191
aagctgttgt ttgccataga                                               20

<210> SEQ ID NO 192
<211> LENGTH: 20
<212> TYPE: DNA
<213> ORGANISM: Artificial Sequence
<220> FEATURE:
<223> OTHER INFORMATION: Primer

<400> SEQUENCE: 192
gcagagaagg acaaacattg                                               20

<210> SEQ ID NO 193
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 193
tgcccattca tggtgcaagt tctc                                          24

<210> SEQ ID NO 194
<211> LENGTH: 20
<212> TYPE: DNA
<213> ORGANISM: Artificial Sequence
<220> FEATURE:
<223> OTHER INFORMATION: Primer

<400> SEQUENCE: 194
gctgttgttt gccatagaag                                               20

<210> SEQ ID NO 195
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 195
cagagaagga caaacattgc                                              20

<210> SEQ ID NO 196
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 196
tgcccattca tggtgcaagt tctc                                         24

<210> SEQ ID NO 197
<211> LENGTH: 20
<212> TYPE: DNA
<213> ORGANISM: Artificial Sequence
<220> FEATURE:
<223> OTHER INFORMATION: Primer

<400> SEQUENCE: 197
gctgttgttt gccatagaag                                              20

<210> SEQ ID NO 198
<211> LENGTH: 20
<212> TYPE: DNA
<213> ORGANISM: Artificial Sequence
<220> FEATURE:
<223> OTHER INFORMATION: Primer

<400> SEQUENCE: 198
gcagagaagg acaaacattg                                              20

<210> SEQ ID NO 199
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 199
tgcccattca tggtgcaagt tctc                                         24

<210> SEQ ID NO 200
<211> LENGTH: 20
<212> TYPE: DNA
<213> ORGANISM: Artificial Sequence
<220> FEATURE:
<223> OTHER INFORMATION: Primer

<400> SEQUENCE: 200
caatgacgga cctctttatg                                              20

<210> SEQ ID NO 201
<211> LENGTH: 20
<212> TYPE: DNA
<213> ORGANISM: Artificial Sequence
<220> FEATURE:
<223> OTHER INFORMATION: Primer

<400> SEQUENCE: 201
ggtagctccc aggtagtcat                                              20

<210> SEQ ID NO 202
<211> LENGTH: 23
<212> TYPE: DNA

```
<213> ORGANISM: Artificial Sequence
<220> FEATURE:
<223> OTHER INFORMATION: TaqManp probe sequence

<400> SEQUENCE: 202
tgccgcctac tccaatcaca tcc                                          23

<210> SEQ ID NO 203
<211> LENGTH: 20
<212> TYPE: DNA
<213> ORGANISM: Artificial Sequence
<220> FEATURE:
<223> OTHER INFORMATION: Primer

<400> SEQUENCE: 203
tctgtgggaa gaaacatctg                                              20

<210> SEQ ID NO 204
<211> LENGTH: 20
<212> TYPE: DNA
<213> ORGANISM: Artificial Sequence
<220> FEATURE:
<223> OTHER INFORMATION: Primer

<400> SEQUENCE: 204
tgatgagaat tccaccttca                                              20

<210> SEQ ID NO 205
<211> LENGTH: 20
<212> TYPE: DNA
<213> ORGANISM: Artificial Sequence
<220> FEATURE:
<223> OTHER INFORMATION: Primer

<400> SEQUENCE: 205
aatccatcca gtgactaccc                                              20

<210> SEQ ID NO 206
<211> LENGTH: 20
<212> TYPE: DNA
<213> ORGANISM: Artificial Sequence
<220> FEATURE:
<223> OTHER INFORMATION: Primer

<400> SEQUENCE: 206
acttgaggga acgaaagact                                              20

<210> SEQ ID NO 207
<211> LENGTH: 21
<212> TYPE: DNA
<213> ORGANISM: Artificial Sequence
<220> FEATURE:
<223> OTHER INFORMATION: TaqManp probe sequence

<400> SEQUENCE: 207
aacatcaaac gggtcacgcc c                                            21

<210> SEQ ID NO 208
<211> LENGTH: 20
<212> TYPE: DNA
<213> ORGANISM: Artificial Sequence
<220> FEATURE:
<223> OTHER INFORMATION: Primer

<400> SEQUENCE: 208
cagccaaagc tagaaattca                                              20
```

```
<210> SEQ ID NO 209
<211> LENGTH: 20
<212> TYPE: DNA
<213> ORGANISM: Artificial Sequence
<220> FEATURE:
<223> OTHER INFORMATION: Primer

<400> SEQUENCE: 209
tagggtagtc actggatgga                                              20

<210> SEQ ID NO 210
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 210
ttcactgctc ttcagggcac ttgaa                                        25

<210> SEQ ID NO 211
<211> LENGTH: 20
<212> TYPE: DNA
<213> ORGANISM: Artificial Sequence
<220> FEATURE:
<223> OTHER INFORMATION: Primer

<400> SEQUENCE: 211
gcaatgacgg acctctttat                                              20

<210> SEQ ID NO 212
<211> LENGTH: 20
<212> TYPE: DNA
<213> ORGANISM: Artificial Sequence
<220> FEATURE:
<223> OTHER INFORMATION: Primer

<400> SEQUENCE: 212
ggtagctccc aggtagtcat                                              20

<210> SEQ ID NO 213
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 213
tgccgcctac tccaatcaca tcc                                          23

<210> SEQ ID NO 214
<211> LENGTH: 20
<212> TYPE: DNA
<213> ORGANISM: Artificial Sequence
<220> FEATURE:
<223> OTHER INFORMATION: Primer

<400> SEQUENCE: 214
agaatcagca tcatgtttgg                                              20

<210> SEQ ID NO 215
<211> LENGTH: 20
<212> TYPE: DNA
<213> ORGANISM: Artificial Sequence
<220> FEATURE:
<223> OTHER INFORMATION: Primer
```

```
<400> SEQUENCE: 215
ataaccttct cttgggctga                                        20

<210> SEQ ID NO 216
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 216
cctcatggca ggctcctggc                                        20

<210> SEQ ID NO 217
<211> LENGTH: 20
<212> TYPE: DNA
<213> ORGANISM: Artificial Sequence
<220> FEATURE:
<223> OTHER INFORMATION: Primer

<400> SEQUENCE: 217
tcagcccaag agaaggttat                                        20

<210> SEQ ID NO 218
<211> LENGTH: 20
<212> TYPE: DNA
<213> ORGANISM: Artificial Sequence
<220> FEATURE:
<223> OTHER INFORMATION: Primer

<400> SEQUENCE: 218
tgagcatgtc ctctgataca                                        20

<210> SEQ ID NO 219
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 219
tcccaaggac cagtagctgc ca                                     22

<210> SEQ ID NO 220
<211> LENGTH: 20
<212> TYPE: DNA
<213> ORGANISM: Artificial Sequence
<220> FEATURE:
<223> OTHER INFORMATION: Primer

<400> SEQUENCE: 220
gactacagct cacagcacac                                        20

<210> SEQ ID NO 221
<211> LENGTH: 19
<212> TYPE: DNA
<213> ORGANISM: Artificial Sequence
<220> FEATURE:
<223> OTHER INFORMATION: Primer

<400> SEQUENCE: 221
aaagctacaa cttggcctt                                         19

<210> SEQ ID NO 222
<211> LENGTH: 20
<212> TYPE: DNA
```

```
<213> ORGANISM: Artificial Sequence
<220> FEATURE:
<223> OTHER INFORMATION: TaqManp probe sequence

<400> SEQUENCE: 222
tgcccaggct ggtctcaggc                                              20

<210> SEQ ID NO 223
<211> LENGTH: 20
<212> TYPE: DNA
<213> ORGANISM: Artificial Sequence
<220> FEATURE:
<223> OTHER INFORMATION: Primer

<400> SEQUENCE: 223
tcagcccaag agaaggttat                                              20

<210> SEQ ID NO 224
<211> LENGTH: 20
<212> TYPE: DNA
<213> ORGANISM: Artificial Sequence
<220> FEATURE:
<223> OTHER INFORMATION: Primer

<400> SEQUENCE: 224
aggcaagcat gtttctacac                                              20

<210> SEQ ID NO 225
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 225
tcccaaggac cagtagctgc ca                                           22

<210> SEQ ID NO 226
<211> LENGTH: 20
<212> TYPE: DNA
<213> ORGANISM: Artificial Sequence
<220> FEATURE:
<223> OTHER INFORMATION: Primer

<400> SEQUENCE: 226
actacagctc acagcacacc                                              20

<210> SEQ ID NO 227
<211> LENGTH: 20
<212> TYPE: DNA
<213> ORGANISM: Artificial Sequence
<220> FEATURE:
<223> OTHER INFORMATION: Primer

<400> SEQUENCE: 227
aaagctacaa cttggcctgt                                              20

<210> SEQ ID NO 228
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 228
tgcccaggct ggtctcaggc                                              20
```

```
<210> SEQ ID NO 229
<211> LENGTH: 20
<212> TYPE: DNA
<213> ORGANISM: Artificial Sequence
<220> FEATURE:
<223> OTHER INFORMATION: Primer

<400> SEQUENCE: 229
tcagcccaag agaaggttat                                                   20

<210> SEQ ID NO 230
<211> LENGTH: 20
<212> TYPE: DNA
<213> ORGANISM: Artificial Sequence
<220> FEATURE:
<223> OTHER INFORMATION: Primer

<400> SEQUENCE: 230
cataaggcaa gcatgtttct                                                   20

<210> SEQ ID NO 231
<211> LENGTH: 22
<212> TYPE: DNA
<213> ORGANISM: Artificial Sequence
<220> FEATURE:
<223> OTHER INFORMATION: TaqManp probe sequence

<400> SEQUENCE: 231
tcccaaggac cagtagctgc ca                                                22

<210> SEQ ID NO 232
<211> LENGTH: 20
<212> TYPE: DNA
<213> ORGANISM: Artificial Sequence
<220> FEATURE:
<223> OTHER INFORMATION: Primer

<400> SEQUENCE: 232
aggctcatgg atcactcttt                                                   20

<210> SEQ ID NO 233
<211> LENGTH: 20
<212> TYPE: DNA
<213> ORGANISM: Artificial Sequence
<220> FEATURE:
<223> OTHER INFORMATION: Primer

<400> SEQUENCE: 233
ggtacgcaat ccagttctct                                                   20

<210> SEQ ID NO 234
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 234
ccggccttcg cagactccag                                                   20

<210> SEQ ID NO 235
<211> LENGTH: 20
<212> TYPE: DNA
<213> ORGANISM: Artificial Sequence
<220> FEATURE:
<223> OTHER INFORMATION: Primer
```

```
<400> SEQUENCE: 235
gacctctctg atgaatgctg                                            20

<210> SEQ ID NO 236
<211> LENGTH: 20
<212> TYPE: DNA
<213> ORGANISM: Artificial Sequence
<220> FEATURE:
<223> OTHER INFORMATION: Primer

<400> SEQUENCE: 236
aatgacgtga agggtaaggt                                            20

<210> SEQ ID NO 237
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 237
accggctctc ccgctgtcct                                            20

<210> SEQ ID NO 238
<211> LENGTH: 20
<212> TYPE: DNA
<213> ORGANISM: Artificial Sequence
<220> FEATURE:
<223> OTHER INFORMATION: Primer

<400> SEQUENCE: 238
gacctctctg atgaatgctg                                            20

<210> SEQ ID NO 239
<211> LENGTH: 20
<212> TYPE: DNA
<213> ORGANISM: Artificial Sequence
<220> FEATURE:
<223> OTHER INFORMATION: Primer

<400> SEQUENCE: 239
gaatgacgtg aagggtaagg                                            20

<210> SEQ ID NO 240
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 240
accggctctc ccgctgtcct                                            20

<210> SEQ ID NO 241
<211> LENGTH: 20
<212> TYPE: DNA
<213> ORGANISM: Artificial Sequence
<220> FEATURE:
<223> OTHER INFORMATION: Primer

<400> SEQUENCE: 241
gacctctctg atgaatgctg                                            20

<210> SEQ ID NO 242
<211> LENGTH: 21
<212> TYPE: DNA
```

```
<213> ORGANISM: Artificial Sequence
<220> FEATURE:
<223> OTHER INFORMATION: Primer

<400> SEQUENCE: 242
gaatgacgtg aagggtaagg t                                       21

<210> SEQ ID NO 243
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 243
accggctctc ccgctgtcct                                         20

<210> SEQ ID NO 244
<211> LENGTH: 20
<212> TYPE: DNA
<213> ORGANISM: Artificial Sequence
<220> FEATURE:
<223> OTHER INFORMATION: Primer

<400> SEQUENCE: 244
gacctctctg atgaatgctg                                         20

<210> SEQ ID NO 245
<211> LENGTH: 20
<212> TYPE: DNA
<213> ORGANISM: Artificial Sequence
<220> FEATURE:
<223> OTHER INFORMATION: Primer

<400> SEQUENCE: 245
ggaatgacgt gaagggtaag                                         20

<210> SEQ ID NO 246
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 246
accggctctc ccgctgtcct                                         20

<210> SEQ ID NO 247
<211> LENGTH: 20
<212> TYPE: DNA
<213> ORGANISM: Artificial Sequence
<220> FEATURE:
<223> OTHER INFORMATION: Primer

<400> SEQUENCE: 247
cctctctgat gaatgctgac                                         20

<210> SEQ ID NO 248
<211> LENGTH: 20
<212> TYPE: DNA
<213> ORGANISM: Artificial Sequence
<220> FEATURE:
<223> OTHER INFORMATION: Primer

<400> SEQUENCE: 248
gaatgacgtg aagggtaagg                                         20
```

-continued

```
<210> SEQ ID NO 249
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 249
accggctctc ccgctgtcct                                                    20

<210> SEQ ID NO 250
<211> LENGTH: 20
<212> TYPE: DNA
<213> ORGANISM: Artificial Sequence
<220> FEATURE:
<223> OTHER INFORMATION: Primer

<400> SEQUENCE: 250
acctctctga tgaatgctga                                                    20

<210> SEQ ID NO 251
<211> LENGTH: 20
<212> TYPE: DNA
<213> ORGANISM: Artificial Sequence
<220> FEATURE:
<223> OTHER INFORMATION: Primer

<400> SEQUENCE: 251
gaatgacgtg aagggtaagg                                                    20

<210> SEQ ID NO 252
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 252
accggctctc ccgctgtcct                                                    20

<210> SEQ ID NO 253
<211> LENGTH: 20
<212> TYPE: DNA
<213> ORGANISM: Artificial Sequence
<220> FEATURE:
<223> OTHER INFORMATION: Primer

<400> SEQUENCE: 253
ccagtgaacc acaattcagt                                                    20

<210> SEQ ID NO 254
<211> LENGTH: 20
<212> TYPE: DNA
<213> ORGANISM: Artificial Sequence
<220> FEATURE:
<223> OTHER INFORMATION: Primer

<400> SEQUENCE: 254
atgcagtgtc ctattcgaga                                                    20

<210> SEQ ID NO 255
<211> LENGTH: 21
<212> TYPE: DNA
<213> ORGANISM: Artificial Sequence
<220> FEATURE:
<223> OTHER INFORMATION: TaqManp probe sequence
```

```
<400> SEQUENCE: 255
tggatgtcct caggcccagc a                                           21

<210> SEQ ID NO 256
<211> LENGTH: 20
<212> TYPE: DNA
<213> ORGANISM: Artificial Sequence
<220> FEATURE:
<223> OTHER INFORMATION: Primer

<400> SEQUENCE: 256
ggatcacacc tatgctcaaa                                             20

<210> SEQ ID NO 257
<211> LENGTH: 20
<212> TYPE: DNA
<213> ORGANISM: Artificial Sequence
<220> FEATURE:
<223> OTHER INFORMATION: Primer

<400> SEQUENCE: 257
ccatttctgt gtccagtgac                                             20

<210> SEQ ID NO 258
<211> LENGTH: 26
<212> TYPE: DNA
<213> ORGANISM: Artificial Sequence
<220> FEATURE:
<223> OTHER INFORMATION: TaqManp probe sequence

<400> SEQUENCE: 258
tgacagcatg actcctccta aaggca                                      26

<210> SEQ ID NO 259
<211> LENGTH: 20
<212> TYPE: DNA
<213> ORGANISM: Artificial Sequence
<220> FEATURE:
<223> OTHER INFORMATION: Primer

<400> SEQUENCE: 259
atttgagaga ggaggctgag                                             20

<210> SEQ ID NO 260
<211> LENGTH: 20
<212> TYPE: DNA
<213> ORGANISM: Artificial Sequence
<220> FEATURE:
<223> OTHER INFORMATION: Primer

<400> SEQUENCE: 260
aatgaaatgc ctgtcagttg                                             20

<210> SEQ ID NO 261
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 261
ccactggaca accacaaacc atttctc                                     27

<210> SEQ ID NO 262
<211> LENGTH: 20
<212> TYPE: DNA
```

```
<213> ORGANISM: Artificial Sequence
<220> FEATURE:
<223> OTHER INFORMATION: Primer

<400> SEQUENCE: 262
gacttgtaat ggcagcgtag                                              20

<210> SEQ ID NO 263
<211> LENGTH: 20
<212> TYPE: DNA
<213> ORGANISM: Artificial Sequence
<220> FEATURE:
<223> OTHER INFORMATION: Primer

<400> SEQUENCE: 263
ctcgaagaag tttccaggtt                                              20

<210> SEQ ID NO 264
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 264
tgacagcaga gccagtgaac caca                                         24

<210> SEQ ID NO 265
<211> LENGTH: 20
<212> TYPE: DNA
<213> ORGANISM: Artificial Sequence
<220> FEATURE:
<223> OTHER INFORMATION: Primer

<400> SEQUENCE: 265
acttgtaatg gcagcgtaga                                              20

<210> SEQ ID NO 266
<211> LENGTH: 20
<212> TYPE: DNA
<213> ORGANISM: Artificial Sequence
<220> FEATURE:
<223> OTHER INFORMATION: Primer

<400> SEQUENCE: 266
ctcgaagaag tttccaggtt                                              20

<210> SEQ ID NO 267
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 267
tgacagcaga gccagtgaac caca                                         24

<210> SEQ ID NO 268
<211> LENGTH: 21
<212> TYPE: DNA
<213> ORGANISM: Artificial Sequence
<220> FEATURE:
<223> OTHER INFORMATION: Primer

<400> SEQUENCE: 268
actttgacag cgacaagaag t                                            21
```

```
<210> SEQ ID NO 269
<211> LENGTH: 20
<212> TYPE: DNA
<213> ORGANISM: Artificial Sequence
<220> FEATURE:
<223> OTHER INFORMATION: Primer

<400> SEQUENCE: 269
gcggtacata gggtacatga                                                 20

<210> SEQ ID NO 270
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 270
cgccgccacg aggaacaaac                                                 20

<210> SEQ ID NO 271
<211> LENGTH: 20
<212> TYPE: DNA
<213> ORGANISM: Artificial Sequence
<220> FEATURE:
<223> OTHER INFORMATION: Primer

<400> SEQUENCE: 271
aactttgaca gcgacaagaa                                                 20

<210> SEQ ID NO 272
<211> LENGTH: 21
<212> TYPE: DNA
<213> ORGANISM: Artificial Sequence
<220> FEATURE:
<223> OTHER INFORMATION: Primer

<400> SEQUENCE: 272
gaagcggtac atagggtaca t                                               21

<210> SEQ ID NO 273
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 273
cgccgccacg aggaacaaac                                                 20

<210> SEQ ID NO 274
<211> LENGTH: 19
<212> TYPE: DNA
<213> ORGANISM: Artificial Sequence
<220> FEATURE:
<223> OTHER INFORMATION: Primer

<400> SEQUENCE: 274
cagtaccacg gccaactac                                                  19

<210> SEQ ID NO 275
<211> LENGTH: 20
<212> TYPE: DNA
<213> ORGANISM: Artificial Sequence
<220> FEATURE:
<223> OTHER INFORMATION: Primer
```

<400> SEQUENCE: 275
tggaagatga atggaaactg                                                    20

<210> SEQ ID NO 276
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 276
cccatcagca ttgccgtccc                                                    20

<210> SEQ ID NO 277
<211> LENGTH: 20
<212> TYPE: DNA
<213> ORGANISM: Artificial Sequence
<220> FEATURE:
<223> OTHER INFORMATION: Primer

<400> SEQUENCE: 277
ccactactgt gcctttgagt                                                    20

<210> SEQ ID NO 278
<211> LENGTH: 20
<212> TYPE: DNA
<213> ORGANISM: Artificial Sequence
<220> FEATURE:
<223> OTHER INFORMATION: Primer

<400> SEQUENCE: 278
gtacttccca tccttgaaca                                                    20

<210> SEQ ID NO 279
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 279
ttcccaatct ccgcgatggc                                                    20

<210> SEQ ID NO 280
<211> LENGTH: 20
<212> TYPE: DNA
<213> ORGANISM: Artificial Sequence
<220> FEATURE:
<223> OTHER INFORMATION: Primer

<400> SEQUENCE: 280
ccactactgt gcctttgagt                                                    20

<210> SEQ ID NO 281
<211> LENGTH: 19
<212> TYPE: DNA
<213> ORGANISM: Artificial Sequence
<220> FEATURE:
<223> OTHER INFORMATION: Primer

<400> SEQUENCE: 281
cttcccatcc ttgaacaaa                                                     19

<210> SEQ ID NO 282
<211> LENGTH: 20
<212> TYPE: DNA

```
<213> ORGANISM: Artificial Sequence
<220> FEATURE:
<223> OTHER INFORMATION: TaqManp probe sequence

<400> SEQUENCE: 282
ttcccaatct ccgcgatggc                                                  20

<210> SEQ ID NO 283
<211> LENGTH: 20
<212> TYPE: DNA
<213> ORGANISM: Artificial Sequence
<220> FEATURE:
<223> OTHER INFORMATION: Primer

<400> SEQUENCE: 283
cacgaatagc agaagaggtg                                                  20

<210> SEQ ID NO 284
<211> LENGTH: 20
<212> TYPE: DNA
<213> ORGANISM: Artificial Sequence
<220> FEATURE:
<223> OTHER INFORMATION: Primer

<400> SEQUENCE: 284
gtatgtcacc ttctgggtca                                                  20

<210> SEQ ID NO 285
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 285
cagcttgtcc atagcctcaa ccagg                                            25

<210> SEQ ID NO 286
<211> LENGTH: 20
<212> TYPE: DNA
<213> ORGANISM: Artificial Sequence
<220> FEATURE:
<223> OTHER INFORMATION: Primer

<400> SEQUENCE: 286
cccatccttc aagttacaca                                                  20

<210> SEQ ID NO 287
<211> LENGTH: 20
<212> TYPE: DNA
<213> ORGANISM: Artificial Sequence
<220> FEATURE:
<223> OTHER INFORMATION: Primer

<400> SEQUENCE: 287
attagctgaa ttgccagaca                                                  20

<210> SEQ ID NO 288
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 288
tccacagatg caacaagcat cgg                                              23
```

```
<210> SEQ ID NO 289
<211> LENGTH: 20
<212> TYPE: DNA
<213> ORGANISM: Artificial Sequence
<220> FEATURE:
<223> OTHER INFORMATION: Primer

<400> SEQUENCE: 289
gggattgcta gtctcacaga                                               20

<210> SEQ ID NO 290
<211> LENGTH: 20
<212> TYPE: DNA
<213> ORGANISM: Artificial Sequence
<220> FEATURE:
<223> OTHER INFORMATION: Primer

<400> SEQUENCE: 290
tcttctgcta ttcgtgcatt                                               20

<210> SEQ ID NO 291
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 291
tcctgaacca gctgcctctt cca                                           23

<210> SEQ ID NO 292
<211> LENGTH: 20
<212> TYPE: DNA
<213> ORGANISM: Artificial Sequence
<220> FEATURE:
<223> OTHER INFORMATION: Primer

<400> SEQUENCE: 292
cccatccttc aagttacaca                                               20

<210> SEQ ID NO 293
<211> LENGTH: 20
<212> TYPE: DNA
<213> ORGANISM: Artificial Sequence
<220> FEATURE:
<223> OTHER INFORMATION: Primer

<400> SEQUENCE: 293
agacaacgga ccagaaactt                                               20

<210> SEQ ID NO 294
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 294
tccacagatg caacaagcat cgg                                           23

<210> SEQ ID NO 295
<211> LENGTH: 20
<212> TYPE: DNA
<213> ORGANISM: Artificial Sequence
<220> FEATURE:
<223> OTHER INFORMATION: Primer
```

```
<400> SEQUENCE: 295
gcacaggcta agtagtgacg                                              20

<210> SEQ ID NO 296
<211> LENGTH: 20
<212> TYPE: DNA
<213> ORGANISM: Artificial Sequence
<220> FEATURE:
<223> OTHER INFORMATION: Primer

<400> SEQUENCE: 296
aggtggtctt gagcctttag                                              20

<210> SEQ ID NO 297
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 297
tttcccttga gatctccaca gcca                                         24

<210> SEQ ID NO 298
<211> LENGTH: 20
<212> TYPE: DNA
<213> ORGANISM: Artificial Sequence
<220> FEATURE:
<223> OTHER INFORMATION: Primer

<400> SEQUENCE: 298
cacgaatagc agaagaggtg                                              20

<210> SEQ ID NO 299
<211> LENGTH: 20
<212> TYPE: DNA
<213> ORGANISM: Artificial Sequence
<220> FEATURE:
<223> OTHER INFORMATION: Primer

<400> SEQUENCE: 299
gtatgtcacc ttctgggtca                                              20

<210> SEQ ID NO 300
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 300
cagcttgtcc atagcctcaa ccagg                                        25

<210> SEQ ID NO 301
<211> LENGTH: 20
<212> TYPE: DNA
<213> ORGANISM: Artificial Sequence
<220> FEATURE:
<223> OTHER INFORMATION: Primer

<400> SEQUENCE: 301
cccatccttc aagttacaca                                              20

<210> SEQ ID NO 302
<211> LENGTH: 20
<212> TYPE: DNA
```

<213> ORGANISM: Artificial Sequence
<220> FEATURE:
<223> OTHER INFORMATION: Primer

<400> SEQUENCE: 302
attagctgaa ttgccagaca    20

<210> SEQ ID NO 303
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 303
tccacagatg caacaagcat cgg    23

<210> SEQ ID NO 304
<211> LENGTH: 20
<212> TYPE: DNA
<213> ORGANISM: Artificial Sequence
<220> FEATURE:
<223> OTHER INFORMATION: Primer

<400> SEQUENCE: 304
gggattgcta gtctcacaga    20

<210> SEQ ID NO 305
<211> LENGTH: 20
<212> TYPE: DNA
<213> ORGANISM: Artificial Sequence
<220> FEATURE:
<223> OTHER INFORMATION: Primer

<400> SEQUENCE: 305
tcttctgcta ttcgtgcatt    20

<210> SEQ ID NO 306
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 306
tcctgaacca gctgcctctt cca    23

<210> SEQ ID NO 307
<211> LENGTH: 20
<212> TYPE: DNA
<213> ORGANISM: Artificial Sequence
<220> FEATURE:
<223> OTHER INFORMATION: Primer

<400> SEQUENCE: 307
cccatccttc aagttacaca    20

<210> SEQ ID NO 308
<211> LENGTH: 20
<212> TYPE: DNA
<213> ORGANISM: Artificial Sequence
<220> FEATURE:
<223> OTHER INFORMATION: Primer

<400> SEQUENCE: 308
agacaacgga ccagaaactt    20

```
<210> SEQ ID NO 309
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 309
tccacagatg caacaagcat cgg                                              23

<210> SEQ ID NO 310
<211> LENGTH: 20
<212> TYPE: DNA
<213> ORGANISM: Artificial Sequence
<220> FEATURE:
<223> OTHER INFORMATION: Primer

<400> SEQUENCE: 310
gcacaggcta agtagtgacg                                                  20

<210> SEQ ID NO 311
<211> LENGTH: 20
<212> TYPE: DNA
<213> ORGANISM: Artificial Sequence
<220> FEATURE:
<223> OTHER INFORMATION: Primer

<400> SEQUENCE: 311
aggtggtctt gagcctttag                                                  20

<210> SEQ ID NO 312
<211> LENGTH: 24
<212> TYPE: DNA
<213> ORGANISM: Artificial Sequence
<220> FEATURE:
<223> OTHER INFORMATION: TaqManp probe sequence

<400> SEQUENCE: 312
tttcccttga gatctccaca gcca                                             24

<210> SEQ ID NO 313
<211> LENGTH: 20
<212> TYPE: DNA
<213> ORGANISM: Artificial Sequence
<220> FEATURE:
<223> OTHER INFORMATION: Primer

<400> SEQUENCE: 313
caccgtaact atccgcacta                                                  20

<210> SEQ ID NO 314
<211> LENGTH: 20
<212> TYPE: DNA
<213> ORGANISM: Artificial Sequence
<220> FEATURE:
<223> OTHER INFORMATION: Primer

<400> SEQUENCE: 314
cggtgtggtc ttgtacattt                                                  20

<210> SEQ ID NO 315
<211> LENGTH: 20
<212> TYPE: DNA
<213> ORGANISM: Artificial Sequence
<220> FEATURE:
<223> OTHER INFORMATION: TaqManp probe sequence
```

```
<400> SEQUENCE: 315
aggcactgtc gccttcccgg                                          20

<210> SEQ ID NO 316
<211> LENGTH: 20
<212> TYPE: DNA
<213> ORGANISM: Artificial Sequence
<220> FEATURE:
<223> OTHER INFORMATION: Primer

<400> SEQUENCE: 316
aagaaagcaa cgaaaggaac                                          20

<210> SEQ ID NO 317
<211> LENGTH: 20
<212> TYPE: DNA
<213> ORGANISM: Artificial Sequence
<220> FEATURE:
<223> OTHER INFORMATION: Primer

<400> SEQUENCE: 317
tcattgcagc acctttactc                                          20

<210> SEQ ID NO 318
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 318
tgccagcacc aacattggcc                                          20

<210> SEQ ID NO 319
<211> LENGTH: 20
<212> TYPE: DNA
<213> ORGANISM: Artificial Sequence
<220> FEATURE:
<223> OTHER INFORMATION: Primer

<400> SEQUENCE: 319
agacatggcc tgtatgagaa                                          20

<210> SEQ ID NO 320
<211> LENGTH: 20
<212> TYPE: DNA
<213> ORGANISM: Artificial Sequence
<220> FEATURE:
<223> OTHER INFORMATION: Primer

<400> SEQUENCE: 320
atccaatctc cagctcactt                                          20

<210> SEQ ID NO 321
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 321
tgccagcacc aacattggcc                                          20

<210> SEQ ID NO 322
<211> LENGTH: 20
<212> TYPE: DNA
```

```
<213> ORGANISM: Artificial Sequence
<220> FEATURE:
<223> OTHER INFORMATION: Primer

<400> SEQUENCE: 322
aagacatggc ctgtatgaga                                               20

<210> SEQ ID NO 323
<211> LENGTH: 20
<212> TYPE: DNA
<213> ORGANISM: Artificial Sequence
<220> FEATURE:
<223> OTHER INFORMATION: Primer

<400> SEQUENCE: 323
atccaatctc cagctcactt                                               20

<210> SEQ ID NO 324
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 324
tgccagcacc aacattggcc                                               20

<210> SEQ ID NO 325
<211> LENGTH: 20
<212> TYPE: DNA
<213> ORGANISM: Artificial Sequence
<220> FEATURE:
<223> OTHER INFORMATION: Primer

<400> SEQUENCE: 325
gacatggcct gtatgagaag                                               20

<210> SEQ ID NO 326
<211> LENGTH: 20
<212> TYPE: DNA
<213> ORGANISM: Artificial Sequence
<220> FEATURE:
<223> OTHER INFORMATION: Primer

<400> SEQUENCE: 326
atccaatctc cagctcactt                                               20

<210> SEQ ID NO 327
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 327
tgccagcacc aacattggcc                                               20

<210> SEQ ID NO 328
<211> LENGTH: 20
<212> TYPE: DNA
<213> ORGANISM: Artificial Sequence
<220> FEATURE:
<223> OTHER INFORMATION: Primer

<400> SEQUENCE: 328
aaggaacgca agaacagaat                                               20
```

```
<210> SEQ ID NO 329
<211> LENGTH: 20
<212> TYPE: DNA
<213> ORGANISM: Artificial Sequence
<220> FEATURE:
<223> OTHER INFORMATION: Primer

<400> SEQUENCE: 329
attgcagcac ctttactcct                                              20

<210> SEQ ID NO 330
<211> LENGTH: 20
<212> TYPE: DNA
<213> ORGANISM: Artificial Sequence
<220> FEATURE:
<223> OTHER INFORMATION: TaqManp probe sequence

<400> SEQUENCE: 330
tgccagcacc aacattggcc                                              20

<210> SEQ ID NO 331
<211> LENGTH: 20
<212> TYPE: DNA
<213> ORGANISM: Artificial Sequence
<220> FEATURE:
<223> OTHER INFORMATION: Primer

<400> SEQUENCE: 331
tacctggtca ttgatgaagc                                              20

<210> SEQ ID NO 332
<211> LENGTH: 20
<212> TYPE: DNA
<213> ORGANISM: Artificial Sequence
<220> FEATURE:
<223> OTHER INFORMATION: Primer

<400> SEQUENCE: 332
caaaggtgtt ccagttagga                                              20

<210> SEQ ID NO 333
<211> LENGTH: 27
<212> TYPE: DNA
<213> ORGANISM: Artificial Sequence
<220> FEATURE:
<223> OTHER INFORMATION: TaqManp probe sequence

<400> SEQUENCE: 333
cgtgagttca agtcgactaa ccgcttg                                      27

<210> SEQ ID NO 334
<211> LENGTH: 20
<212> TYPE: DNA
<213> ORGANISM: Artificial Sequence
<220> FEATURE:
<223> OTHER INFORMATION: Primer

<400> SEQUENCE: 334
tacctggtca ttgatgaagc                                              20

<210> SEQ ID NO 335
<211> LENGTH: 20
<212> TYPE: DNA
<213> ORGANISM: Artificial Sequence
<220> FEATURE:
<223> OTHER INFORMATION: Primer
```

```
<400> SEQUENCE: 335
ttattctgca aaggtgttcc                                                     20

<210> SEQ ID NO 336
<211> LENGTH: 25
<212> TYPE: DNA
<213> ORGANISM: Artificial Sequence
<220> FEATURE:
<223> OTHER INFORMATION: TaqManp probe sequence

<400> SEQUENCE: 336
ttcaagtcga ctaaccgctt gctcc                                               25

<210> SEQ ID NO 337
<211> LENGTH: 20
<212> TYPE: DNA
<213> ORGANISM: Artificial Sequence
<220> FEATURE:
<223> OTHER INFORMATION: Primer

<400> SEQUENCE: 337
tggacccaga atatgaagag                                                     20

<210> SEQ ID NO 338
<211> LENGTH: 20
<212> TYPE: DNA
<213> ORGANISM: Artificial Sequence
<220> FEATURE:
<223> OTHER INFORMATION: Primer

<400> SEQUENCE: 338
atgttcagtg gagatgttgg                                                     20

<210> SEQ ID NO 339
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 339
tctctttgct cggtcggctt tca                                                 23

<210> SEQ ID NO 340
<211> LENGTH: 20
<212> TYPE: DNA
<213> ORGANISM: Artificial Sequence
<220> FEATURE:
<223> OTHER INFORMATION: Primer

<400> SEQUENCE: 340
ctttgcttgg ttacctgaaa                                                     20

<210> SEQ ID NO 341
<211> LENGTH: 20
<212> TYPE: DNA
<213> ORGANISM: Artificial Sequence
<220> FEATURE:
<223> OTHER INFORMATION: Primer

<400> SEQUENCE: 341
aaacaaatga cacggagaga                                                     20

<210> SEQ ID NO 342
<211> LENGTH: 26
<212> TYPE: DNA
```

```
<213> ORGANISM: Artificial Sequence
<220> FEATURE:
<223> OTHER INFORMATION: TaqManp probe sequence

<400> SEQUENCE: 342
ccgaaatatt cctggacctc acatgg                                          26

<210> SEQ ID NO 343
<211> LENGTH: 20
<212> TYPE: DNA
<213> ORGANISM: Artificial Sequence
<220> FEATURE:
<223> OTHER INFORMATION: Primer

<400> SEQUENCE: 343
ggaaatggac ccagaatatg                                                 20

<210> SEQ ID NO 344
<211> LENGTH: 20
<212> TYPE: DNA
<213> ORGANISM: Artificial Sequence
<220> FEATURE:
<223> OTHER INFORMATION: Primer

<400> SEQUENCE: 344
gttggagatt tctgtgctga                                                 20

<210> SEQ ID NO 345
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 345
tctctttgct cggtcggctt tca                                             23

<210> SEQ ID NO 346
<211> LENGTH: 20
<212> TYPE: DNA
<213> ORGANISM: Artificial Sequence
<220> FEATURE:
<223> OTHER INFORMATION: Primer

<400> SEQUENCE: 346
aaggaaatgg acccagaata                                                 20

<210> SEQ ID NO 347
<211> LENGTH: 20
<212> TYPE: DNA
<213> ORGANISM: Artificial Sequence
<220> FEATURE:
<223> OTHER INFORMATION: Primer

<400> SEQUENCE: 347
ctgaaggctg aatgaaatgt                                                 20

<210> SEQ ID NO 348
<211> LENGTH: 23
<212> TYPE: DNA
<213> ORGANISM: Artificial Sequence
<220> FEATURE:
<223> OTHER INFORMATION: TaqManp probe sequence

<400> SEQUENCE: 348
tctctttgct cggtcggctt tca                                             23
```

<210> SEQ ID NO 349
<211> LENGTH: 20
<212> TYPE: DNA
<213> ORGANISM: Artificial Sequence
<220> FEATURE:
<223> OTHER INFORMATION: Primer

<400> SEQUENCE: 349
agtgggatgt ttgcgttact                                              20

<210> SEQ ID NO 350
<211> LENGTH: 20
<212> TYPE: DNA
<213> ORGANISM: Artificial Sequence
<220> FEATURE:
<223> OTHER INFORMATION: Primer

<400> SEQUENCE: 350
cacgaacaat ctctgaaagc                                              20

<210> SEQ ID NO 351
<211> LENGTH: 26
<212> TYPE: DNA
<213> ORGANISM: Artificial Sequence
<220> FEATURE:
<223> OTHER INFORMATION: TaqManp probe sequence

<400> SEQUENCE: 351
tcatcaatga ccaggtatcg ccagtg                                       26

<210> SEQ ID NO 352
<211> LENGTH: 20
<212> TYPE: DNA
<213> ORGANISM: Artificial Sequence
<220> FEATURE:
<223> OTHER INFORMATION: Primer

<400> SEQUENCE: 352
gctggtggtg tactctgcta                                              20

<210> SEQ ID NO 353
<211> LENGTH: 20
<212> TYPE: DNA
<213> ORGANISM: Artificial Sequence
<220> FEATURE:
<223> OTHER INFORMATION: Primer

<400> SEQUENCE: 353
gtgcctcaac ttgttacagc                                              20

<210> SEQ ID NO 354
<211> LENGTH: 20
<212> TYPE: DNA
<213> ORGANISM: Artificial Sequence
<220> FEATURE:
<223> OTHER INFORMATION: Primer

<400> SEQUENCE: 354
tctatggagg gaaagtccac                                              20

<210> SEQ ID NO 355
<211> LENGTH: 20
<212> TYPE: DNA
<213> ORGANISM: Artificial Sequence
<220> FEATURE:
<223> OTHER INFORMATION: Primer

<400> SEQUENCE: 355
tggtcttgat ctcctgactt                                           20

<210> SEQ ID NO 356
<211> LENGTH: 20
<212> TYPE: DNA
<213> ORGANISM: Artificial Sequence
<220> FEATURE:
<223> OTHER INFORMATION: Primer

<400> SEQUENCE: 356
ttcttcaagg gaatgagctt                                           20

<210> SEQ ID NO 357
<211> LENGTH: 20
<212> TYPE: DNA
<213> ORGANISM: Artificial Sequence
<220> FEATURE:
<223> OTHER INFORMATION: Primer

<400> SEQUENCE: 357
tcaactctgt ctcctctgct                                           20

<210> SEQ ID NO 358
<211> LENGTH: 20
<212> TYPE: DNA
<213> ORGANISM: Artificial Sequence
<220> FEATURE:
<223> OTHER INFORMATION: Primer

<400> SEQUENCE: 358
acaggcatca ctacttccaa                                           20

<210> SEQ ID NO 359
<211> LENGTH: 20
<212> TYPE: DNA
<213> ORGANISM: Artificial Sequence
<220> FEATURE:
<223> OTHER INFORMATION: Primer

<400> SEQUENCE: 359
tgaaagcagg aagacatacg                                           20

<210> SEQ ID NO 360
<211> LENGTH: 20
<212> TYPE: DNA
<213> ORGANISM: Artificial Sequence
<220> FEATURE:
<223> OTHER INFORMATION: Primer

<400> SEQUENCE: 360
tatccagctt cactttctgc                                           20

<210> SEQ ID NO 361
<211> LENGTH: 20
<212> TYPE: DNA
<213> ORGANISM: Artificial Sequence
<220> FEATURE:
<223> OTHER INFORMATION: Primer

<400> SEQUENCE: 361
aacccagaca caagtcttca                                           20

<210> SEQ ID NO 362
<211> LENGTH: 19
<212> TYPE: DNA

```
<213> ORGANISM: Artificial Sequence
<220> FEATURE:
<223> OTHER INFORMATION: Primer

<400> SEQUENCE: 362
agcaatggta actgcacct                                               19

<210> SEQ ID NO 363
<211> LENGTH: 20
<212> TYPE: DNA
<213> ORGANISM: Artificial Sequence
<220> FEATURE:
<223> OTHER INFORMATION: Primer

<400> SEQUENCE: 363
tgacatgttc cagactgttg                                              20

<210> SEQ ID NO 364
<211> LENGTH: 20
<212> TYPE: DNA
<213> ORGANISM: Artificial Sequence
<220> FEATURE:
<223> OTHER INFORMATION: Primer

<400> SEQUENCE: 364
atggctagat gtcccaagtt                                              20

<210> SEQ ID NO 365
<211> LENGTH: 20
<212> TYPE: DNA
<213> ORGANISM: Artificial Sequence
<220> FEATURE:
<223> OTHER INFORMATION: Primer

<400> SEQUENCE: 365
gcttggtgtg tctgataagg                                              20

<210> SEQ ID NO 366
<211> LENGTH: 20
<212> TYPE: DNA
<213> ORGANISM: Artificial Sequence
<220> FEATURE:
<223> OTHER INFORMATION: Primer

<400> SEQUENCE: 366
cagaacagat gcgacagagt                                              20

<210> SEQ ID NO 367
<211> LENGTH: 20
<212> TYPE: DNA
<213> ORGANISM: Artificial Sequence
<220> FEATURE:
<223> OTHER INFORMATION: Primer

<400> SEQUENCE: 367
ttgacaaagc ttcctttctg                                              20

<210> SEQ ID NO 368
<211> LENGTH: 20
<212> TYPE: DNA
<213> ORGANISM: Artificial Sequence
<220> FEATURE:
<223> OTHER INFORMATION: Primer

<400> SEQUENCE: 368
acctttgagt gccagaactt                                              20
```

```
<210> SEQ ID NO 369
<211> LENGTH: 20
<212> TYPE: DNA
<213> ORGANISM: Artificial Sequence
<220> FEATURE:
<223> OTHER INFORMATION: Primer

<400> SEQUENCE: 369
ggacacaaac ggacaataaa                                                   20

<210> SEQ ID NO 370
<211> LENGTH: 21
<212> TYPE: DNA
<213> ORGANISM: Artificial Sequence
<220> FEATURE:
<223> OTHER INFORMATION: Primer

<400> SEQUENCE: 370
gcaccagaat acgtttagct t                                                 21

<210> SEQ ID NO 371
<211> LENGTH: 20
<212> TYPE: DNA
<213> ORGANISM: Artificial Sequence
<220> FEATURE:
<223> OTHER INFORMATION: Primer

<400> SEQUENCE: 371
ctgggagtag ttcgttggtt                                                   20

<210> SEQ ID NO 372
<211> LENGTH: 20
<212> TYPE: DNA
<213> ORGANISM: Artificial Sequence
<220> FEATURE:
<223> OTHER INFORMATION: Primer

<400> SEQUENCE: 372
ggagattgaa gtgagctgag                                                   20

<210> SEQ ID NO 373
<211> LENGTH: 20
<212> TYPE: DNA
<213> ORGANISM: Artificial Sequence
<220> FEATURE:
<223> OTHER INFORMATION: Primer

<400> SEQUENCE: 373
cttgagacca gaggcttacc                                                   20

<210> SEQ ID NO 374
<211> LENGTH: 20
<212> TYPE: DNA
<213> ORGANISM: Artificial Sequence
<220> FEATURE:
<223> OTHER INFORMATION: Primer

<400> SEQUENCE: 374
gctattgaag tggtcatcca                                                   20

<210> SEQ ID NO 375
<211> LENGTH: 20
<212> TYPE: DNA
<213> ORGANISM: Artificial Sequence
<220> FEATURE:
<223> OTHER INFORMATION: Primer
```

```
<400> SEQUENCE: 375
ccgtggaaga taatgatgaa                                            20

<210> SEQ ID NO 376
<211> LENGTH: 20
<212> TYPE: DNA
<213> ORGANISM: Artificial Sequence
<220> FEATURE:
<223> OTHER INFORMATION: Primer

<400> SEQUENCE: 376
actggatatt ggcagcttct                                            20

<210> SEQ ID NO 377
<211> LENGTH: 21
<212> TYPE: DNA
<213> ORGANISM: Artificial Sequence
<220> FEATURE:
<223> OTHER INFORMATION: Primer

<400> SEQUENCE: 377
gcagctccaa atcttaactt g                                          21

<210> SEQ ID NO 378
<211> LENGTH: 19
<212> TYPE: DNA
<213> ORGANISM: Artificial Sequence
<220> FEATURE:
<223> OTHER INFORMATION: Primer

<400> SEQUENCE: 378
tttcctccca ttctgtctg                                             19

<210> SEQ ID NO 379
<211> LENGTH: 20
<212> TYPE: DNA
<213> ORGANISM: Artificial Sequence
<220> FEATURE:
<223> OTHER INFORMATION: Primer

<400> SEQUENCE: 379
aatggctatc gagacattcc                                            20

<210> SEQ ID NO 380
<211> LENGTH: 20
<212> TYPE: DNA
<213> ORGANISM: Artificial Sequence
<220> FEATURE:
<223> OTHER INFORMATION: Primer

<400> SEQUENCE: 380
cttccaccac aagtcatttc                                            20

<210> SEQ ID NO 381
<211> LENGTH: 20
<212> TYPE: DNA
<213> ORGANISM: Artificial Sequence
<220> FEATURE:
<223> OTHER INFORMATION: Primer

<400> SEQUENCE: 381
aggtgggatc gtaataatgg                                            20

<210> SEQ ID NO 382
<211> LENGTH: 20
<212> TYPE: DNA
```

```
<213> ORGANISM: Artificial Sequence
<220> FEATURE:
<223> OTHER INFORMATION: Primer

<400> SEQUENCE: 382
tgccgtcgta ggtattagtg                                          20

<210> SEQ ID NO 383
<211> LENGTH: 20
<212> TYPE: DNA
<213> ORGANISM: Artificial Sequence
<220> FEATURE:
<223> OTHER INFORMATION: Primer

<400> SEQUENCE: 383
tgtgccgtcg taggtattag                                          20

<210> SEQ ID NO 384
<211> LENGTH: 20
<212> TYPE: DNA
<213> ORGANISM: Artificial Sequence
<220> FEATURE:
<223> OTHER INFORMATION: Primer

<400> SEQUENCE: 384
caaaccatca ggaagaatga                                          20

<210> SEQ ID NO 385
<211> LENGTH: 20
<212> TYPE: DNA
<213> ORGANISM: Artificial Sequence
<220> FEATURE:
<223> OTHER INFORMATION: Primer

<400> SEQUENCE: 385
ctcctggtca tgattgttgt                                          20

<210> SEQ ID NO 386
<211> LENGTH: 20
<212> TYPE: DNA
<213> ORGANISM: Artificial Sequence
<220> FEATURE:
<223> OTHER INFORMATION: Primer

<400> SEQUENCE: 386
aggttctggt tggacaagtt                                          20

<210> SEQ ID NO 387
<211> LENGTH: 20
<212> TYPE: DNA
<213> ORGANISM: Artificial Sequence
<220> FEATURE:
<223> OTHER INFORMATION: Primer

<400> SEQUENCE: 387
gttgcacaga ctgaaagtcc                                          20

<210> SEQ ID NO 388
<211> LENGTH: 20
<212> TYPE: DNA
<213> ORGANISM: Artificial Sequence
<220> FEATURE:
<223> OTHER INFORMATION: Primer

<400> SEQUENCE: 388
gacaagtgtg tgagctggat                                          20
```

```
<210> SEQ ID NO 389
<211> LENGTH: 20
<212> TYPE: DNA
<213> ORGANISM: Artificial Sequence
<220> FEATURE:
<223> OTHER INFORMATION: Primer

<400> SEQUENCE: 389
gctgaagctt gaacagaaca                                              20

<210> SEQ ID NO 390
<211> LENGTH: 20
<212> TYPE: DNA
<213> ORGANISM: Artificial Sequence
<220> FEATURE:
<223> OTHER INFORMATION: Primer

<400> SEQUENCE: 390
ctgtgctacc ttcagctcac                                              20

<210> SEQ ID NO 391
<211> LENGTH: 20
<212> TYPE: DNA
<213> ORGANISM: Artificial Sequence
<220> FEATURE:
<223> OTHER INFORMATION: Primer

<400> SEQUENCE: 391
caaagggtgc aacatagaaa                                              20

<210> SEQ ID NO 392
<211> LENGTH: 20
<212> TYPE: DNA
<213> ORGANISM: Artificial Sequence
<220> FEATURE:
<223> OTHER INFORMATION: Primer

<400> SEQUENCE: 392
tacaaggatt tcagggcaat                                              20

<210> SEQ ID NO 393
<211> LENGTH: 20
<212> TYPE: DNA
<213> ORGANISM: Artificial Sequence
<220> FEATURE:
<223> OTHER INFORMATION: Primer

<400> SEQUENCE: 393
tgccttggga cttagaacac                                              20

<210> SEQ ID NO 394
<211> LENGTH: 20
<212> TYPE: DNA
<213> ORGANISM: Artificial Sequence
<220> FEATURE:
<223> OTHER INFORMATION: Primer

<400> SEQUENCE: 394
gttctaggga tgctcctgac                                              20

<210> SEQ ID NO 395
<211> LENGTH: 19
<212> TYPE: DNA
<213> ORGANISM: Artificial Sequence
<220> FEATURE:
<223> OTHER INFORMATION: Primer
```

```
<400> SEQUENCE: 395
ctcctgctgc ttcgtctac                                               19

<210> SEQ ID NO 396
<211> LENGTH: 19
<212> TYPE: DNA
<213> ORGANISM: Artificial Sequence
<220> FEATURE:
<223> OTHER INFORMATION: Primer

<400> SEQUENCE: 396
caccatcttc ctggacatc                                               19

<210> SEQ ID NO 397
<211> LENGTH: 20
<212> TYPE: DNA
<213> ORGANISM: Artificial Sequence
<220> FEATURE:
<223> OTHER INFORMATION: Primer

<400> SEQUENCE: 397
gtgctttctg gagggtctac                                              20

<210> SEQ ID NO 398
<211> LENGTH: 20
<212> TYPE: DNA
<213> ORGANISM: Artificial Sequence
<220> FEATURE:
<223> OTHER INFORMATION: Primer

<400> SEQUENCE: 398
agactctgga gatggtgtga                                              20

<210> SEQ ID NO 399
<211> LENGTH: 20
<212> TYPE: DNA
<213> ORGANISM: Artificial Sequence
<220> FEATURE:
<223> OTHER INFORMATION: Primer

<400> SEQUENCE: 399
agagcagaaa ctggccttag                                              20

<210> SEQ ID NO 400
<211> LENGTH: 20
<212> TYPE: DNA
<213> ORGANISM: Artificial Sequence
<220> FEATURE:
<223> OTHER INFORMATION: Primer

<400> SEQUENCE: 400
tgtgtacctt tcacgagacc                                              20

<210> SEQ ID NO 401
<211> LENGTH: 19
<212> TYPE: DNA
<213> ORGANISM: Artificial Sequence
<220> FEATURE:
<223> OTHER INFORMATION: Primer

<400> SEQUENCE: 401
ccaaagttgt gcatttcct                                               19

<210> SEQ ID NO 402
<211> LENGTH: 20
<212> TYPE: DNA
```

<213> ORGANISM: Artificial Sequence
<220> FEATURE:
<223> OTHER INFORMATION: Primer

<400> SEQUENCE: 402
tgtggcttct gtagaaagga                                          20

<210> SEQ ID NO 403
<211> LENGTH: 20
<212> TYPE: DNA
<213> ORGANISM: Artificial Sequence
<220> FEATURE:
<223> OTHER INFORMATION: Primer

<400> SEQUENCE: 403
tataaccctg gctttggaat                                          20

<210> SEQ ID NO 404
<211> LENGTH: 20
<212> TYPE: DNA
<213> ORGANISM: Artificial Sequence
<220> FEATURE:
<223> OTHER INFORMATION: Primer

<400> SEQUENCE: 404
gatataaccc tggctttgga                                          20

<210> SEQ ID NO 405
<211> LENGTH: 20
<212> TYPE: DNA
<213> ORGANISM: Artificial Sequence
<220> FEATURE:
<223> OTHER INFORMATION: Primer

<400> SEQUENCE: 405
actgccttct ttcacgtatg                                          20

<210> SEQ ID NO 406
<211> LENGTH: 20
<212> TYPE: DNA
<213> ORGANISM: Artificial Sequence
<220> FEATURE:
<223> OTHER INFORMATION: Primer

<400> SEQUENCE: 406
acaattcaac gctgttcttt                                          20

<210> SEQ ID NO 407
<211> LENGTH: 20
<212> TYPE: DNA
<213> ORGANISM: Artificial Sequence
<220> FEATURE:
<223> OTHER INFORMATION: Primer

<400> SEQUENCE: 407
cggtgcaact gttacttcat                                          20

<210> SEQ ID NO 408
<211> LENGTH: 20
<212> TYPE: DNA
<213> ORGANISM: Artificial Sequence
<220> FEATURE:
<223> OTHER INFORMATION: Primer

<400> SEQUENCE: 408
cacatcgtgc cttctctact                                          20

```
<210> SEQ ID NO 409
<211> LENGTH: 20
<212> TYPE: DNA
<213> ORGANISM: Artificial Sequence
<220> FEATURE:
<223> OTHER INFORMATION: Primer

<400> SEQUENCE: 409
ttatgctctg cgtcacttct                                                    20

<210> SEQ ID NO 410
<211> LENGTH: 20
<212> TYPE: DNA
<213> ORGANISM: Artificial Sequence
<220> FEATURE:
<223> OTHER INFORMATION: Primer

<400> SEQUENCE: 410
cacttctgct cggactcata                                                    20

<210> SEQ ID NO 411
<211> LENGTH: 20
<212> TYPE: DNA
<213> ORGANISM: Artificial Sequence
<220> FEATURE:
<223> OTHER INFORMATION: Primer

<400> SEQUENCE: 411
ctttcaactc tcagcacctc                                                    20

<210> SEQ ID NO 412
<211> LENGTH: 20
<212> TYPE: DNA
<213> ORGANISM: Artificial Sequence
<220> FEATURE:
<223> OTHER INFORMATION: Primer

<400> SEQUENCE: 412
tcgttgagaa tgaatggaaa                                                    20

<210> SEQ ID NO 413
<211> LENGTH: 20
<212> TYPE: DNA
<213> ORGANISM: Artificial Sequence
<220> FEATURE:
<223> OTHER INFORMATION: Primer

<400> SEQUENCE: 413
acccatctgt gtgactgtgt                                                    20

<210> SEQ ID NO 414
<211> LENGTH: 20
<212> TYPE: DNA
<213> ORGANISM: Artificial Sequence
<220> FEATURE:
<223> OTHER INFORMATION: Primer

<400> SEQUENCE: 414
gtgttgtcac gcttcttctt                                                    20

<210> SEQ ID NO 415
<211> LENGTH: 20
<212> TYPE: DNA
<213> ORGANISM: Artificial Sequence
<220> FEATURE:
<223> OTHER INFORMATION: Primer
```

<400> SEQUENCE: 415
aagtcacagc atcaatggag                                               20

<210> SEQ ID NO 416
<211> LENGTH: 20
<212> TYPE: DNA
<213> ORGANISM: Artificial Sequence
<220> FEATURE:
<223> OTHER INFORMATION: Primer

<400> SEQUENCE: 416
ctgatggaac aatccacaga                                               20

<210> SEQ ID NO 417
<211> LENGTH: 20
<212> TYPE: DNA
<213> ORGANISM: Artificial Sequence
<220> FEATURE:
<223> OTHER INFORMATION: Primer

<400> SEQUENCE: 417
cgatatcatg cctacaatgg                                               20

<210> SEQ ID NO 418
<211> LENGTH: 20
<212> TYPE: DNA
<213> ORGANISM: Artificial Sequence
<220> FEATURE:
<223> OTHER INFORMATION: Primer

<400> SEQUENCE: 418
agctgtacca tgagcagtgt                                               20

<210> SEQ ID NO 419
<211> LENGTH: 20
<212> TYPE: DNA
<213> ORGANISM: Artificial Sequence
<220> FEATURE:
<223> OTHER INFORMATION: Primer

<400> SEQUENCE: 419
tatcgggttt gtcaagaatg                                               20

<210> SEQ ID NO 420
<211> LENGTH: 20
<212> TYPE: DNA
<213> ORGANISM: Artificial Sequence
<220> FEATURE:
<223> OTHER INFORMATION: Primer

<400> SEQUENCE: 420
gtgatgtggt ctctgctctt                                               20

<210> SEQ ID NO 421
<211> LENGTH: 20
<212> TYPE: DNA
<213> ORGANISM: Artificial Sequence
<220> FEATURE:
<223> OTHER INFORMATION: Primer

<400> SEQUENCE: 421
gatgggtttg gttctgaagt                                               20

<210> SEQ ID NO 422
<211> LENGTH: 20
<212> TYPE: DNA

```
<213> ORGANISM: Artificial Sequence
<220> FEATURE:
<223> OTHER INFORMATION: Primer

<400> SEQUENCE: 422
tcagcttgag gactctgatg                                              20

<210> SEQ ID NO 423
<211> LENGTH: 20
<212> TYPE: DNA
<213> ORGANISM: Artificial Sequence
<220> FEATURE:
<223> OTHER INFORMATION: Primer

<400> SEQUENCE: 423
aagacccata ctggaaggaa                                              20

<210> SEQ ID NO 424
<211> LENGTH: 20
<212> TYPE: DNA
<213> ORGANISM: Artificial Sequence
<220> FEATURE:
<223> OTHER INFORMATION: Primer

<400> SEQUENCE: 424
ttgatcatcc aagcctagtg                                              20

<210> SEQ ID NO 425
<211> LENGTH: 20
<212> TYPE: DNA
<213> ORGANISM: Artificial Sequence
<220> FEATURE:
<223> OTHER INFORMATION: Primer

<400> SEQUENCE: 425
aattcaccga gaagtgtgtg                                              20

<210> SEQ ID NO 426
<211> LENGTH: 20
<212> TYPE: DNA
<213> ORGANISM: Artificial Sequence
<220> FEATURE:
<223> OTHER INFORMATION: Primer

<400> SEQUENCE: 426
atggacctcc agtcgtaact                                              20

<210> SEQ ID NO 427
<211> LENGTH: 20
<212> TYPE: DNA
<213> ORGANISM: Artificial Sequence
<220> FEATURE:
<223> OTHER INFORMATION: Primer

<400> SEQUENCE: 427
aaaattagcc aggcatggtg                                              20

<210> SEQ ID NO 428
<211> LENGTH: 20
<212> TYPE: DNA
<213> ORGANISM: Artificial Sequence
<220> FEATURE:
<223> OTHER INFORMATION: Primer

<400> SEQUENCE: 428
accaaatttc agggtcacca                                              20
```

<210> SEQ ID NO 429
<211> LENGTH: 20
<212> TYPE: DNA
<213> ORGANISM: Artificial Sequence
<220> FEATURE:
<223> OTHER INFORMATION: Primer

<400> SEQUENCE: 429
accaaatttc agggtcacca                                              20

<210> SEQ ID NO 430
<211> LENGTH: 20
<212> TYPE: DNA
<213> ORGANISM: Artificial Sequence
<220> FEATURE:
<223> OTHER INFORMATION: Primer

<400> SEQUENCE: 430
gagagctatg ctggcatcta                                              20

<210> SEQ ID NO 431
<211> LENGTH: 20
<212> TYPE: DNA
<213> ORGANISM: Artificial Sequence
<220> FEATURE:
<223> OTHER INFORMATION: Primer

<400> SEQUENCE: 431
acaggctttg gtcttctctc                                              20

<210> SEQ ID NO 432
<211> LENGTH: 20
<212> TYPE: DNA
<213> ORGANISM: Artificial Sequence
<220> FEATURE:
<223> OTHER INFORMATION: Primer

<400> SEQUENCE: 432
aacaagcagc catactgatg                                              20

<210> SEQ ID NO 433
<211> LENGTH: 20
<212> TYPE: DNA
<213> ORGANISM: Artificial Sequence
<220> FEATURE:
<223> OTHER INFORMATION: Primer

<400> SEQUENCE: 433
cctacctgat gaacaagctg                                              20

<210> SEQ ID NO 434
<211> LENGTH: 20
<212> TYPE: DNA
<213> ORGANISM: Artificial Sequence
<220> FEATURE:
<223> OTHER INFORMATION: Primer

<400> SEQUENCE: 434
accaagggaa tttggatatg                                              20

<210> SEQ ID NO 435
<211> LENGTH: 20
<212> TYPE: DNA
<213> ORGANISM: Artificial Sequence
<220> FEATURE:
<223> OTHER INFORMATION: Primer

```
<400> SEQUENCE: 435
gaagaaagag gcacaagtga                                          20

<210> SEQ ID NO 436
<211> LENGTH: 21
<212> TYPE: DNA
<213> ORGANISM: Artificial Sequence
<220> FEATURE:
<223> OTHER INFORMATION: Primer

<400> SEQUENCE: 436
aagtctactg ccacctctca c                                        21

<210> SEQ ID NO 437
<211> LENGTH: 21
<212> TYPE: DNA
<213> ORGANISM: Artificial Sequence
<220> FEATURE:
<223> OTHER INFORMATION: Primer

<400> SEQUENCE: 437
cctatggttt cagaacagag c                                        21

<210> SEQ ID NO 438
<211> LENGTH: 19
<212> TYPE: DNA
<213> ORGANISM: Artificial Sequence
<220> FEATURE:
<223> OTHER INFORMATION: Primer

<400> SEQUENCE: 438
actgccacct ctcactctc                                           19

<210> SEQ ID NO 439
<211> LENGTH: 20
<212> TYPE: DNA
<213> ORGANISM: Artificial Sequence
<220> FEATURE:
<223> OTHER INFORMATION: Primer

<400> SEQUENCE: 439
gaacccactg gtcaagagtt                                          20

<210> SEQ ID NO 440
<211> LENGTH: 20
<212> TYPE: DNA
<213> ORGANISM: Artificial Sequence
<220> FEATURE:
<223> OTHER INFORMATION: Primer

<400> SEQUENCE: 440
ttgtggtctt tcagggaaat                                          20

<210> SEQ ID NO 441
<211> LENGTH: 20
<212> TYPE: DNA
<213> ORGANISM: Artificial Sequence
<220> FEATURE:
<223> OTHER INFORMATION: Primer

<400> SEQUENCE: 441
aacatttctg ctcccttgat                                          20

<210> SEQ ID NO 442
<211> LENGTH: 19
<212> TYPE: DNA
```

```
<213> ORGANISM: Artificial Sequence
<220> FEATURE:
<223> OTHER INFORMATION: Primer

<400> SEQUENCE: 442
ggtaatattg gtgccctga                                               19

<210> SEQ ID NO 443
<211> LENGTH: 20
<212> TYPE: DNA
<213> ORGANISM: Artificial Sequence
<220> FEATURE:
<223> OTHER INFORMATION: Primer

<400> SEQUENCE: 443
tattgtccag gctagagtgc                                              20

<210> SEQ ID NO 444
<211> LENGTH: 20
<212> TYPE: DNA
<213> ORGANISM: Artificial Sequence
<220> FEATURE:
<223> OTHER INFORMATION: Primer

<400> SEQUENCE: 444
tcttctctcc tccaaggtct                                              20

<210> SEQ ID NO 445
<211> LENGTH: 20
<212> TYPE: DNA
<213> ORGANISM: Artificial Sequence
<220> FEATURE:
<223> OTHER INFORMATION: Primer

<400> SEQUENCE: 445
caacctacct gtggtggata                                              20

<210> SEQ ID NO 446
<211> LENGTH: 20
<212> TYPE: DNA
<213> ORGANISM: Artificial Sequence
<220> FEATURE:
<223> OTHER INFORMATION: Primer

<400> SEQUENCE: 446
cacttcacag agtgcgtgta                                              20

<210> SEQ ID NO 447
<211> LENGTH: 20
<212> TYPE: DNA
<213> ORGANISM: Artificial Sequence
<220> FEATURE:
<223> OTHER INFORMATION: Primer

<400> SEQUENCE: 447
aggttcttct ccttgtccac                                              20

<210> SEQ ID NO 448
<211> LENGTH: 20
<212> TYPE: DNA
<213> ORGANISM: Artificial Sequence
<220> FEATURE:
<223> OTHER INFORMATION: Primer

<400> SEQUENCE: 448
agggacctca aggacgactt                                              20
```

<210> SEQ ID NO 449
<211> LENGTH: 20
<212> TYPE: DNA
<213> ORGANISM: Artificial Sequence
<220> FEATURE:
<223> OTHER INFORMATION: Primer

<400> SEQUENCE: 449
accaacgctg aatttccaag                                              20

<210> SEQ ID NO 450
<211> LENGTH: 20
<212> TYPE: DNA
<213> ORGANISM: Artificial Sequence
<220> FEATURE:
<223> OTHER INFORMATION: Primer

<400> SEQUENCE: 450
atggaggagg ttcacaccag                                              20

<210> SEQ ID NO 451
<211> LENGTH: 19
<212> TYPE: DNA
<213> ORGANISM: Artificial Sequence
<220> FEATURE:
<223> OTHER INFORMATION: Primer

<400> SEQUENCE: 451
tggtaacacc agtctgtgc                                               19

<210> SEQ ID NO 452
<211> LENGTH: 20
<212> TYPE: DNA
<213> ORGANISM: Artificial Sequence
<220> FEATURE:
<223> OTHER INFORMATION: Primer

<400> SEQUENCE: 452
gctgcagaac agaacacttt                                              20

<210> SEQ ID NO 453
<211> LENGTH: 20
<212> TYPE: DNA
<213> ORGANISM: Artificial Sequence
<220> FEATURE:
<223> OTHER INFORMATION: Primer

<400> SEQUENCE: 453
acattcaaac cctccagaat                                              20

<210> SEQ ID NO 454
<211> LENGTH: 20
<212> TYPE: DNA
<213> ORGANISM: Artificial Sequence
<220> FEATURE:
<223> OTHER INFORMATION: Primer

<400> SEQUENCE: 454
gtgttctgaa ggtgttcctg                                              20

<210> SEQ ID NO 455
<211> LENGTH: 20
<212> TYPE: DNA
<213> ORGANISM: Artificial Sequence
<220> FEATURE:
<223> OTHER INFORMATION: Primer

<400> SEQUENCE: 455
taacatccag ggcatcacta                                              20

<210> SEQ ID NO 456
<211> LENGTH: 20
<212> TYPE: DNA
<213> ORGANISM: Artificial Sequence
<220> FEATURE:
<223> OTHER INFORMATION: Primer

<400> SEQUENCE: 456
ataacatcca gggcatcact                                              20

<210> SEQ ID NO 457
<211> LENGTH: 20
<212> TYPE: DNA
<213> ORGANISM: Artificial Sequence
<220> FEATURE:
<223> OTHER INFORMATION: Primer

<400> SEQUENCE: 457
gactcaagat tggagacacg                                              20

<210> SEQ ID NO 458
<211> LENGTH: 20
<212> TYPE: DNA
<213> ORGANISM: Artificial Sequence
<220> FEATURE:
<223> OTHER INFORMATION: Primer

<400> SEQUENCE: 458
ttaccactga tgccaagact                                              20

<210> SEQ ID NO 459
<211> LENGTH: 20
<212> TYPE: DNA
<213> ORGANISM: Artificial Sequence
<220> FEATURE:
<223> OTHER INFORMATION: Primer

<400> SEQUENCE: 459
aacccttcag atttgcctta                                              20

<210> SEQ ID NO 460
<211> LENGTH: 20
<212> TYPE: DNA
<213> ORGANISM: Artificial Sequence
<220> FEATURE:
<223> OTHER INFORMATION: Primer

<400> SEQUENCE: 460
cttcccactt tctgaggact                                              20

<210> SEQ ID NO 461
<211> LENGTH: 20
<212> TYPE: DNA
<213> ORGANISM: Artificial Sequence
<220> FEATURE:
<223> OTHER INFORMATION: Primer

<400> SEQUENCE: 461
ggttctggaa tcctcagttc                                              20

<210> SEQ ID NO 462
<211> LENGTH: 20
<212> TYPE: DNA

-continued

<213> ORGANISM: Artificial Sequence
<220> FEATURE:
<223> OTHER INFORMATION: Primer

<400> SEQUENCE: 462
tcgaactact tccaggtgaa                                              20

<210> SEQ ID NO 463
<211> LENGTH: 20
<212> TYPE: DNA
<213> ORGANISM: Artificial Sequence
<220> FEATURE:
<223> OTHER INFORMATION: Primer

<400> SEQUENCE: 463
gattcagagg aggaggaaga                                              20

<210> SEQ ID NO 464
<211> LENGTH: 20
<212> TYPE: DNA
<213> ORGANISM: Artificial Sequence
<220> FEATURE:
<223> OTHER INFORMATION: Primer

<400> SEQUENCE: 464
atgccagatg aaccactaga                                              20

<210> SEQ ID NO 465
<211> LENGTH: 20
<212> TYPE: DNA
<213> ORGANISM: Artificial Sequence
<220> FEATURE:
<223> OTHER INFORMATION: Primer

<400> SEQUENCE: 465
acggcttatg ttctccaact                                              20

<210> SEQ ID NO 466
<211> LENGTH: 19
<212> TYPE: DNA
<213> ORGANISM: Artificial Sequence
<220> FEATURE:
<223> OTHER INFORMATION: Primer

<400> SEQUENCE: 466
accttcaggg ctcctatgt                                               19

<210> SEQ ID NO 467
<211> LENGTH: 20
<212> TYPE: DNA
<213> ORGANISM: Artificial Sequence
<220> FEATURE:
<223> OTHER INFORMATION: Primer

<400> SEQUENCE: 467
ggacaacaac atcgtcaact                                              20

<210> SEQ ID NO 468
<211> LENGTH: 19
<212> TYPE: DNA
<213> ORGANISM: Artificial Sequence
<220> FEATURE:
<223> OTHER INFORMATION: Primer

<400> SEQUENCE: 468
ctctggctac catctgtcc                                               19

<210> SEQ ID NO 469
<211> LENGTH: 20
<212> TYPE: DNA
<213> ORGANISM: Artificial Sequence
<220> FEATURE:
<223> OTHER INFORMATION: Primer

<400> SEQUENCE: 469
tgaaatttga tccacccttca                                              20

<210> SEQ ID NO 470
<211> LENGTH: 20
<212> TYPE: DNA
<213> ORGANISM: Artificial Sequence
<220> FEATURE:
<223> OTHER INFORMATION: Primer

<400> SEQUENCE: 470
taaagtgcat atgggtgcat                                               20

<210> SEQ ID NO 471
<211> LENGTH: 20
<212> TYPE: DNA
<213> ORGANISM: Artificial Sequence
<220> FEATURE:
<223> OTHER INFORMATION: Primer

<400> SEQUENCE: 471
ctggaatatg gacaaggaca                                               20

<210> SEQ ID NO 472
<211> LENGTH: 20
<212> TYPE: DNA
<213> ORGANISM: Artificial Sequence
<220> FEATURE:
<223> OTHER INFORMATION: Primer

<400> SEQUENCE: 472
tatcaaggag ctgtttgcag                                               20

<210> SEQ ID NO 473
<211> LENGTH: 20
<212> TYPE: DNA
<213> ORGANISM: Artificial Sequence
<220> FEATURE:
<223> OTHER INFORMATION: Primer

<400> SEQUENCE: 473
aacacttcca ttgtgactcc                                               20

<210> SEQ ID NO 474
<211> LENGTH: 20
<212> TYPE: DNA
<213> ORGANISM: Artificial Sequence
<220> FEATURE:
<223> OTHER INFORMATION: Primer

<400> SEQUENCE: 474
ctcacaagct aggtgatcca                                               20

<210> SEQ ID NO 475
<211> LENGTH: 20
<212> TYPE: DNA
<213> ORGANISM: Artificial Sequence
<220> FEATURE:
<223> OTHER INFORMATION: Primer

```
<400> SEQUENCE: 475
gaactggaag acgaacactg                                           20

<210> SEQ ID NO 476
<211> LENGTH: 20
<212> TYPE: DNA
<213> ORGANISM: Artificial Sequence
<220> FEATURE:
<223> OTHER INFORMATION: Primer

<400> SEQUENCE: 476
cataatggga gaccaaatca                                           20

<210> SEQ ID NO 477
<211> LENGTH: 20
<212> TYPE: DNA
<213> ORGANISM: Artificial Sequence
<220> FEATURE:
<223> OTHER INFORMATION: Primer

<400> SEQUENCE: 477
tctgtgctgt caaagctgta                                           20

<210> SEQ ID NO 478
<211> LENGTH: 21
<212> TYPE: DNA
<213> ORGANISM: Artificial Sequence
<220> FEATURE:
<223> OTHER INFORMATION: Primer

<400> SEQUENCE: 478
gatgtcaact ccaaacaagg c                                         21

<210> SEQ ID NO 479
<211> LENGTH: 19
<212> TYPE: DNA
<213> ORGANISM: Artificial Sequence
<220> FEATURE:
<223> OTHER INFORMATION: Primer

<400> SEQUENCE: 479
tggattcagg caaccctac                                            19

<210> SEQ ID NO 480
<211> LENGTH: 20
<212> TYPE: DNA
<213> ORGANISM: Artificial Sequence
<220> FEATURE:
<223> OTHER INFORMATION: Primer

<400> SEQUENCE: 480
aggctggtct gcaagagaca                                           20

<210> SEQ ID NO 481
<211> LENGTH: 21
<212> TYPE: DNA
<213> ORGANISM: Artificial Sequence
<220> FEATURE:
<223> OTHER INFORMATION: Primer

<400> SEQUENCE: 481
ttcacgctgt aagagaggca c                                         21

<210> SEQ ID NO 482
<211> LENGTH: 21
<212> TYPE: DNA
```

```
<213> ORGANISM: Artificial Sequence
<220> FEATURE:
<223> OTHER INFORMATION: Primer

<400> SEQUENCE: 482
gaactgaaaa gtgctgaagg g                                              21

<210> SEQ ID NO 483
<211> LENGTH: 20
<212> TYPE: DNA
<213> ORGANISM: Artificial Sequence
<220> FEATURE:
<223> OTHER INFORMATION: Primer

<400> SEQUENCE: 483
gggctgagag tgaaaggaac                                                20

<210> SEQ ID NO 484
<211> LENGTH: 20
<212> TYPE: DNA
<213> ORGANISM: Artificial Sequence
<220> FEATURE:
<223> OTHER INFORMATION: Primer

<400> SEQUENCE: 484
ctccaccagt caaagctcta                                                20

<210> SEQ ID NO 485
<211> LENGTH: 20
<212> TYPE: DNA
<213> ORGANISM: Artificial Sequence
<220> FEATURE:
<223> OTHER INFORMATION: Primer

<400> SEQUENCE: 485
atgcaggatg aaatggagat                                                20

<210> SEQ ID NO 486
<211> LENGTH: 20
<212> TYPE: DNA
<213> ORGANISM: Artificial Sequence
<220> FEATURE:
<223> OTHER INFORMATION: Primer

<400> SEQUENCE: 486
gaaagatcag aggacctgga                                                20

<210> SEQ ID NO 487
<211> LENGTH: 21
<212> TYPE: DNA
<213> ORGANISM: Artificial Sequence
<220> FEATURE:
<223> OTHER INFORMATION: Primer

<400> SEQUENCE: 487
caggttgctt ggctgattat g                                              21

<210> SEQ ID NO 488
<211> LENGTH: 24
<212> TYPE: DNA
<213> ORGANISM: Artificial Sequence
<220> FEATURE:
<223> OTHER INFORMATION: Primer

<400> SEQUENCE: 488
cattagactc aagtatggtc agcg                                           24
```

<210> SEQ ID NO 489
<211> LENGTH: 20
<212> TYPE: DNA
<213> ORGANISM: Artificial Sequence
<220> FEATURE:
<223> OTHER INFORMATION: Primer

<400> SEQUENCE: 489
taccacagag aagcacggtc                                                    20

<210> SEQ ID NO 490
<211> LENGTH: 20
<212> TYPE: DNA
<213> ORGANISM: Artificial Sequence
<220> FEATURE:
<223> OTHER INFORMATION: Primer

<400> SEQUENCE: 490
gaggctattc tgcccatttg                                                    20

<210> SEQ ID NO 491
<211> LENGTH: 21
<212> TYPE: DNA
<213> ORGANISM: Artificial Sequence
<220> FEATURE:
<223> OTHER INFORMATION: Primer

<400> SEQUENCE: 491
tttcgggtag tggaaaacca g                                                  21

<210> SEQ ID NO 492
<211> LENGTH: 20
<212> TYPE: DNA
<213> ORGANISM: Artificial Sequence
<220> FEATURE:
<223> OTHER INFORMATION: Primer

<400> SEQUENCE: 492
agtggaaaac cagcagcctc                                                    20

<210> SEQ ID NO 493
<211> LENGTH: 22
<212> TYPE: DNA
<213> ORGANISM: Artificial Sequence
<220> FEATURE:
<223> OTHER INFORMATION: Primer

<400> SEQUENCE: 493
tgagtcttcc ttgtgggatt gt                                                 22

<210> SEQ ID NO 494
<211> LENGTH: 20
<212> TYPE: DNA
<213> ORGANISM: Artificial Sequence
<220> FEATURE:
<223> OTHER INFORMATION: Primer

<400> SEQUENCE: 494
tcttccttgt gggattgtcc                                                    20

<210> SEQ ID NO 495
<211> LENGTH: 19
<212> TYPE: DNA
<213> ORGANISM: Artificial Sequence
<220> FEATURE:
<223> OTHER INFORMATION: Primer

```
<400> SEQUENCE: 495
cccacaaaaa gccacaaca                                                    19

<210> SEQ ID NO 496
<211> LENGTH: 20
<212> TYPE: DNA
<213> ORGANISM: Artificial Sequence
<220> FEATURE:
<223> OTHER INFORMATION: Primer

<400> SEQUENCE: 496
ggtttatggt gtacctttac                                                   20

<210> SEQ ID NO 497
<211> LENGTH: 20
<212> TYPE: DNA
<213> ORGANISM: Artificial Sequence
<220> FEATURE:
<223> OTHER INFORMATION: Primer

<400> SEQUENCE: 497
tcagtgtaag gtgtctcgtc                                                   20

<210> SEQ ID NO 498
<211> LENGTH: 20
<212> TYPE: DNA
<213> ORGANISM: Artificial Sequence
<220> FEATURE:
<223> OTHER INFORMATION: Primer

<400> SEQUENCE: 498
gttacctctt tggtttcagt                                                   20

<210> SEQ ID NO 499
<211> LENGTH: 20
<212> TYPE: DNA
<213> ORGANISM: Artificial Sequence
<220> FEATURE:
<223> OTHER INFORMATION: Primer

<400> SEQUENCE: 499
gaggtgaaga ctctcaggga                                                   20

<210> SEQ ID NO 500
<211> LENGTH: 20
<212> TYPE: DNA
<213> ORGANISM: Artificial Sequence
<220> FEATURE:
<223> OTHER INFORMATION: Primer

<400> SEQUENCE: 500
gtcgatgtac gtgtagaagg                                                   20

<210> SEQ ID NO 501
<211> LENGTH: 20
<212> TYPE: DNA
<213> ORGANISM: Artificial Sequence
<220> FEATURE:
<223> OTHER INFORMATION: Primer

<400> SEQUENCE: 501
tgtgggcaaa ctgtgacatt                                                   20

<210> SEQ ID NO 502
<211> LENGTH: 20
<212> TYPE: DNA
```

```
<213> ORGANISM: Artificial Sequence
<220> FEATURE:
<223> OTHER INFORMATION: Primer

<400> SEQUENCE: 502
aacgtatacc acttctacca                                               20

<210> SEQ ID NO 503
<211> LENGTH: 20
<212> TYPE: DNA
<213> ORGANISM: Artificial Sequence
<220> FEATURE:
<223> OTHER INFORMATION: Primer

<400> SEQUENCE: 503
tttgtgtcgg gtgatctcca                                               20

<210> SEQ ID NO 504
<211> LENGTH: 20
<212> TYPE: DNA
<213> ORGANISM: Artificial Sequence
<220> FEATURE:
<223> OTHER INFORMATION: Primer

<400> SEQUENCE: 504
ttacccgaga catgaactgt                                               20

<210> SEQ ID NO 505
<211> LENGTH: 20
<212> TYPE: DNA
<213> ORGANISM: Artificial Sequence
<220> FEATURE:
<223> OTHER INFORMATION: Primer

<400> SEQUENCE: 505
ttcatactgc tcctcgacct                                               20

<210> SEQ ID NO 506
<211> LENGTH: 20
<212> TYPE: DNA
<213> ORGANISM: Artificial Sequence
<220> FEATURE:
<223> OTHER INFORMATION: Primer

<400> SEQUENCE: 506
gagatgacag aggagggacc                                               20

<210> SEQ ID NO 507
<211> LENGTH: 19
<212> TYPE: DNA
<213> ORGANISM: Artificial Sequence
<220> FEATURE:
<223> OTHER INFORMATION: Primer

<400> SEQUENCE: 507
accaaatact tctttcgcg                                                19

<210> SEQ ID NO 508
<211> LENGTH: 20
<212> TYPE: DNA
<213> ORGANISM: Artificial Sequence
<220> FEATURE:
<223> OTHER INFORMATION: Primer

<400> SEQUENCE: 508
cgtgatgacc gacacagtaa                                               20
```

<210> SEQ ID NO 509
<211> LENGTH: 20
<212> TYPE: DNA
<213> ORGANISM: Artificial Sequence
<220> FEATURE:
<223> OTHER INFORMATION: Primer

<400> SEQUENCE: 509
gtcttgtcta cgctgtctca                                              20

<210> SEQ ID NO 510
<211> LENGTH: 20
<212> TYPE: DNA
<213> ORGANISM: Artificial Sequence
<220> FEATURE:
<223> OTHER INFORMATION: Primer

<400> SEQUENCE: 510
ttccagttct gagtcggtaa                                              20

<210> SEQ ID NO 511
<211> LENGTH: 20
<212> TYPE: DNA
<213> ORGANISM: Artificial Sequence
<220> FEATURE:
<223> OTHER INFORMATION: Primer

<400> SEQUENCE: 511
acagagtcac ccttctcttt                                              20

<210> SEQ ID NO 512
<211> LENGTH: 20
<212> TYPE: DNA
<213> ORGANISM: Artificial Sequence
<220> FEATURE:
<223> OTHER INFORMATION: Primer

<400> SEQUENCE: 512
acacagtacc agtctttact                                              20

<210> SEQ ID NO 513
<211> LENGTH: 20
<212> TYPE: DNA
<213> ORGANISM: Artificial Sequence
<220> FEATURE:
<223> OTHER INFORMATION: Primer

<400> SEQUENCE: 513
tcattcgttt agacgtgtcg                                              20

<210> SEQ ID NO 514
<211> LENGTH: 20
<212> TYPE: DNA
<213> ORGANISM: Artificial Sequence
<220> FEATURE:
<223> OTHER INFORMATION: Primer

<400> SEQUENCE: 514
caagaactca ccgcacattt                                              20

<210> SEQ ID NO 515
<211> LENGTH: 20
<212> TYPE: DNA
<213> ORGANISM: Artificial Sequence
<220> FEATURE:
<223> OTHER INFORMATION: Primer -continued

<400> SEQUENCE: 515
gagtcttcgt ggtcttatgc                                           20

<210> SEQ ID NO 516
<211> LENGTH: 20
<212> TYPE: DNA
<213> ORGANISM: Artificial Sequence
<220> FEATURE:
<223> OTHER INFORMATION: Primer

<400> SEQUENCE: 516
acactttaag actggtggaa                                           20

<210> SEQ ID NO 517
<211> LENGTH: 20
<212> TYPE: DNA
<213> ORGANISM: Artificial Sequence
<220> FEATURE:
<223> OTHER INFORMATION: Primer

<400> SEQUENCE: 517
aagcttgtcc attctgtttg                                           20

<210> SEQ ID NO 518
<211> LENGTH: 21
<212> TYPE: DNA
<213> ORGANISM: Artificial Sequence
<220> FEATURE:
<223> OTHER INFORMATION: Primer

<400> SEQUENCE: 518
catgataact caacctcacc a                                         21

<210> SEQ ID NO 519
<211> LENGTH: 20
<212> TYPE: DNA
<213> ORGANISM: Artificial Sequence
<220> FEATURE:
<223> OTHER INFORMATION: Primer

<400> SEQUENCE: 519
tctagttggt tcggtttaag                                           20

<210> SEQ ID NO 520
<211> LENGTH: 19
<212> TYPE: DNA
<213> ORGANISM: Artificial Sequence
<220> FEATURE:
<223> OTHER INFORMATION: Primer

<400> SEQUENCE: 520
gaaagtgtga gggacctct                                            19

<210> SEQ ID NO 521
<211> LENGTH: 20
<212> TYPE: DNA
<213> ORGANISM: Artificial Sequence
<220> FEATURE:
<223> OTHER INFORMATION: Primer

<400> SEQUENCE: 521
tgacctataa ccgtcgaaga                                           20

<210> SEQ ID NO 522
<211> LENGTH: 20
<212> TYPE: DNA

-continued

<210> SEQ ID NO 522
<211> LENGTH: 20
<212> TYPE: DNA
<213> ORGANISM: Artificial Sequence
<220> FEATURE:
<223> OTHER INFORMATION: Primer

<400> SEQUENCE: 522
ggaaggcttt atgtaaacga                                              20

<210> SEQ ID NO 523
<211> LENGTH: 20
<212> TYPE: DNA
<213> ORGANISM: Artificial Sequence
<220> FEATURE:
<223> OTHER INFORMATION: Primer

<400> SEQUENCE: 523
caacaccttg tcctttactt                                              20

<210> SEQ ID NO 524
<211> LENGTH: 20
<212> TYPE: DNA
<213> ORGANISM: Artificial Sequence
<220> FEATURE:
<223> OTHER INFORMATION: Primer

<400> SEQUENCE: 524
tttatctcct gggtcgactc                                              20

<210> SEQ ID NO 525
<211> LENGTH: 20
<212> TYPE: DNA
<213> ORGANISM: Artificial Sequence
<220> FEATURE:
<223> OTHER INFORMATION: Primer

<400> SEQUENCE: 525
gatgactgat agggcttcgt                                              20

<210> SEQ ID NO 526
<211> LENGTH: 20
<212> TYPE: DNA
<213> ORGANISM: Artificial Sequence
<220> FEATURE:
<223> OTHER INFORMATION: Primer

<400> SEQUENCE: 526
gaaagcaggt acaaagagtg                                              20

<210> SEQ ID NO 527
<211> LENGTH: 20
<212> TYPE: DNA
<213> ORGANISM: Artificial Sequence
<220> FEATURE:
<223> OTHER INFORMATION: Primer

<400> SEQUENCE: 527
gaaagcaggt acaaagagtg                                              20

<210> SEQ ID NO 528
<211> LENGTH: 20
<212> TYPE: DNA
<213> ORGANISM: Artificial Sequence
<220> FEATURE:
<223> OTHER INFORMATION: Primer

<400> SEQUENCE: 528
gctcagacgt taattgacct                                              20

```
<210> SEQ ID NO 529
<211> LENGTH: 20
<212> TYPE: DNA
<213> ORGANISM: Artificial Sequence
<220> FEATURE:
<223> OTHER INFORMATION: Primer

<400> SEQUENCE: 529
tgaaagtaaa gcaggtccta                                               20

<210> SEQ ID NO 530
<211> LENGTH: 20
<212> TYPE: DNA
<213> ORGANISM: Artificial Sequence
<220> FEATURE:
<223> OTHER INFORMATION: Primer

<400> SEQUENCE: 530
ggaaacagta gagagaaggg                                               20

<210> SEQ ID NO 531
<211> LENGTH: 20
<212> TYPE: DNA
<213> ORGANISM: Artificial Sequence
<220> FEATURE:
<223> OTHER INFORMATION: Primer

<400> SEQUENCE: 531
gtggataaca cctgagacct                                               20

<210> SEQ ID NO 532
<211> LENGTH: 20
<212> TYPE: DNA
<213> ORGANISM: Artificial Sequence
<220> FEATURE:
<223> OTHER INFORMATION: Primer

<400> SEQUENCE: 532
actaataaga cccgtctagt                                               20

<210> SEQ ID NO 533
<211> LENGTH: 20
<212> TYPE: DNA
<213> ORGANISM: Artificial Sequence
<220> FEATURE:
<223> OTHER INFORMATION: Primer

<400> SEQUENCE: 533
gagaagagtc ctcgtagact                                               20

<210> SEQ ID NO 534
<211> LENGTH: 20
<212> TYPE: DNA
<213> ORGANISM: Artificial Sequence
<220> FEATURE:
<223> OTHER INFORMATION: Primer

<400> SEQUENCE: 534
gaggagtcac caacctttca                                               20

<210> SEQ ID NO 535
<211> LENGTH: 19
<212> TYPE: DNA
<213> ORGANISM: Artificial Sequence
<220> FEATURE:
<223> OTHER INFORMATION: Primer
```

```
<400> SEQUENCE: 535
atgttcctaa agtcccgtt                                              19

<210> SEQ ID NO 536
<211> LENGTH: 20
<212> TYPE: DNA
<213> ORGANISM: Artificial Sequence
<220> FEATURE:
<223> OTHER INFORMATION: Primer

<400> SEQUENCE: 536
ctctctcaaa ccgtggttga                                             20

<210> SEQ ID NO 537
<211> LENGTH: 20
<212> TYPE: DNA
<213> ORGANISM: Artificial Sequence
<220> FEATURE:
<223> OTHER INFORMATION: Primer

<400> SEQUENCE: 537
gaagggttcc aagataggac                                             20

<210> SEQ ID NO 538
<211> LENGTH: 19
<212> TYPE: DNA
<213> ORGANISM: Artificial Sequence
<220> FEATURE:
<223> OTHER INFORMATION: Primer

<400> SEQUENCE: 538
ggtcatggta cgtgtgagg                                              19

<210> SEQ ID NO 539
<211> LENGTH: 19
<212> TYPE: DNA
<213> ORGANISM: Artificial Sequence
<220> FEATURE:
<223> OTHER INFORMATION: Primer

<400> SEQUENCE: 539
tgctaactga gtcgtctcc                                              19

<210> SEQ ID NO 540
<211> LENGTH: 19
<212> TYPE: DNA
<213> ORGANISM: Artificial Sequence
<220> FEATURE:
<223> OTHER INFORMATION: Primer

<400> SEQUENCE: 540
gatggtgtac atggccctc                                              19

<210> SEQ ID NO 541
<211> LENGTH: 20
<212> TYPE: DNA
<213> ORGANISM: Artificial Sequence
<220> FEATURE:
<223> OTHER INFORMATION: Primer

<400> SEQUENCE: 541
aaattctagg cgtaacttct                                             20

<210> SEQ ID NO 542
<211> LENGTH: 20
<212> TYPE: DNA
```

```
<213> ORGANISM: Artificial Sequence
<220> FEATURE:
<223> OTHER INFORMATION: Primer

<400> SEQUENCE: 542
gttcgatgaa gacaacgctc                                          20

<210> SEQ ID NO 543
<211> LENGTH: 20
<212> TYPE: DNA
<213> ORGANISM: Artificial Sequence
<220> FEATURE:
<223> OTHER INFORMATION: Primer

<400> SEQUENCE: 543
ggtcttcgaa ataaagtcgg                                          20

<210> SEQ ID NO 544
<211> LENGTH: 20
<212> TYPE: DNA
<213> ORGANISM: Artificial Sequence
<220> FEATURE:
<223> OTHER INFORMATION: Primer

<400> SEQUENCE: 544
gttggttatc gtaattgggt                                          20

<210> SEQ ID NO 545
<211> LENGTH: 20
<212> TYPE: DNA
<213> ORGANISM: Artificial Sequence
<220> FEATURE:
<223> OTHER INFORMATION: Primer

<400> SEQUENCE: 545
acaccacctt gtagaaatgg                                          20

<210> SEQ ID NO 546
<211> LENGTH: 20
<212> TYPE: DNA
<213> ORGANISM: Artificial Sequence
<220> FEATURE:
<223> OTHER INFORMATION: Primer

<400> SEQUENCE: 546
cgactaatat accctcgtct                                          20

<210> SEQ ID NO 547
<211> LENGTH: 21
<212> TYPE: DNA
<213> ORGANISM: Artificial Sequence
<220> FEATURE:
<223> OTHER INFORMATION: Primer

<400> SEQUENCE: 547
tcgttgatgc tgatttcggt a                                        21

<210> SEQ ID NO 548
<211> LENGTH: 20
<212> TYPE: DNA
<213> ORGANISM: Artificial Sequence
<220> FEATURE:
<223> OTHER INFORMATION: Primer

<400> SEQUENCE: 548
aaatggaaca tgggttcgta                                          20
```

<210> SEQ ID NO 549
<211> LENGTH: 19
<212> TYPE: DNA
<213> ORGANISM: Artificial Sequence
<220> FEATURE:
<223> OTHER INFORMATION: Primer

<400> SEQUENCE: 549
gaaagaagtc acggagtcc                                                    19

<210> SEQ ID NO 550
<211> LENGTH: 20
<212> TYPE: DNA
<213> ORGANISM: Artificial Sequence
<220> FEATURE:
<223> OTHER INFORMATION: Primer

<400> SEQUENCE: 550
aagaccctgg aatccctatt                                                   20

<210> SEQ ID NO 551
<211> LENGTH: 20
<212> TYPE: DNA
<213> ORGANISM: Artificial Sequence
<220> FEATURE:
<223> OTHER INFORMATION: Primer

<400> SEQUENCE: 551
tactcgaggt cagttgttaa                                                   20

<210> SEQ ID NO 552
<211> LENGTH: 20
<212> TYPE: DNA
<213> ORGANISM: Artificial Sequence
<220> FEATURE:
<223> OTHER INFORMATION: Primer

<400> SEQUENCE: 552
tgaggtcctg ggttgtatct                                                   20

<210> SEQ ID NO 553
<211> LENGTH: 20
<212> TYPE: DNA
<213> ORGANISM: Artificial Sequence
<220> FEATURE:
<223> OTHER INFORMATION: Primer

<400> SEQUENCE: 553
gaaagttgag agtcgtggag                                                   20

<210> SEQ ID NO 554
<211> LENGTH: 20
<212> TYPE: DNA
<213> ORGANISM: Artificial Sequence
<220> FEATURE:
<223> OTHER INFORMATION: Primer

<400> SEQUENCE: 554
agagtcgtgg agtacttctg                                                   20

<210> SEQ ID NO 555
<211> LENGTH: 20
<212> TYPE: DNA
<213> ORGANISM: Artificial Sequence
<220> FEATURE:
<223> OTHER INFORMATION: Primer

```
<400> SEQUENCE: 555
aagagtcctt tcgtctgagt                                              20

<210> SEQ ID NO 556
<211> LENGTH: 20
<212> TYPE: DNA
<213> ORGANISM: Artificial Sequence
<220> FEATURE:
<223> OTHER INFORMATION: Primer

<400> SEQUENCE: 556
ccaacccgat tgactttgta                                              20

<210> SEQ ID NO 557
<211> LENGTH: 20
<212> TYPE: DNA
<213> ORGANISM: Artificial Sequence
<220> FEATURE:
<223> OTHER INFORMATION: Primer

<400> SEQUENCE: 557
gtccttcaca aaccagtttc                                              20

<210> SEQ ID NO 558
<211> LENGTH: 20
<212> TYPE: DNA
<213> ORGANISM: Artificial Sequence
<220> FEATURE:
<223> OTHER INFORMATION: Primer

<400> SEQUENCE: 558
gacaaggaac ctatccgaaa                                              20

<210> SEQ ID NO 559
<211> LENGTH: 20
<212> TYPE: DNA
<213> ORGANISM: Artificial Sequence
<220> FEATURE:
<223> OTHER INFORMATION: Primer

<400> SEQUENCE: 559
agaccgtttg tagtgtctga                                              20

<210> SEQ ID NO 560
<211> LENGTH: 20
<212> TYPE: DNA
<213> ORGANISM: Artificial Sequence
<220> FEATURE:
<223> OTHER INFORMATION: Primer

<400> SEQUENCE: 560
ttcttagtcc ttcttcgacc                                              20

<210> SEQ ID NO 561
<211> LENGTH: 20
<212> TYPE: DNA
<213> ORGANISM: Artificial Sequence
<220> FEATURE:
<223> OTHER INFORMATION: Primer

<400> SEQUENCE: 561
tgacgagtac gttgaacttc                                              20

<210> SEQ ID NO 562
<211> LENGTH: 19
<212> TYPE: DNA
```

```
<213> ORGANISM: Artificial Sequence
<220> FEATURE:
<223> OTHER INFORMATION: Primer

<400> SEQUENCE: 562
gaaagtctac gagaaacgg                                                19

<210> SEQ ID NO 563
<211> LENGTH: 20
<212> TYPE: DNA
<213> ORGANISM: Artificial Sequence
<220> FEATURE:
<223> OTHER INFORMATION: Primer

<400> SEQUENCE: 563
actcgtcgga gactataagt                                               20

<210> SEQ ID NO 564
<211> LENGTH: 20
<212> TYPE: DNA
<213> ORGANISM: Artificial Sequence
<220> FEATURE:
<223> OTHER INFORMATION: Primer

<400> SEQUENCE: 564
actgtacttc ggtcagacat                                               20

<210> SEQ ID NO 565
<211> LENGTH: 20
<212> TYPE: DNA
<213> ORGANISM: Artificial Sequence
<220> FEATURE:
<223> OTHER INFORMATION: Primer

<400> SEQUENCE: 565
acctgtaagt catcgacctc                                               20

<210> SEQ ID NO 566
<211> LENGTH: 20
<212> TYPE: DNA
<213> ORGANISM: Artificial Sequence
<220> FEATURE:
<223> OTHER INFORMATION: Primer

<400> SEQUENCE: 566
tcgtcgtgtc atggaagttt                                               20

<210> SEQ ID NO 567
<211> LENGTH: 20
<212> TYPE: DNA
<213> ORGANISM: Artificial Sequence
<220> FEATURE:
<223> OTHER INFORMATION: Primer

<400> SEQUENCE: 567
cacacttaag acgttcttcc                                               20

<210> SEQ ID NO 568
<211> LENGTH: 20
<212> TYPE: DNA
<213> ORGANISM: Artificial Sequence
<220> FEATURE:
<223> OTHER INFORMATION: Primer

<400> SEQUENCE: 568
ttccttaacc cactactaag                                               20
```

<210> SEQ ID NO 569
<211> LENGTH: 20
<212> TYPE: DNA
<213> ORGANISM: Artificial Sequence
<220> FEATURE:
<223> OTHER INFORMATION: Primer

<400> SEQUENCE: 569
ctcgtacctt tagtgaaagt                    20

<210> SEQ ID NO 570
<211> LENGTH: 20
<212> TYPE: DNA
<213> ORGANISM: Artificial Sequence
<220> FEATURE:
<223> OTHER INFORMATION: Primer

<400> SEQUENCE: 570
acctacatct actctcggtc                    20

<210> SEQ ID NO 571
<211> LENGTH: 20
<212> TYPE: DNA
<213> ORGANISM: Artificial Sequence
<220> FEATURE:
<223> OTHER INFORMATION: Primer

<400> SEQUENCE: 571
aacaccactc aactctagcg                    20

<210> SEQ ID NO 572
<211> LENGTH: 20
<212> TYPE: DNA
<213> ORGANISM: Artificial Sequence
<220> FEATURE:
<223> OTHER INFORMATION: Primer

<400> SEQUENCE: 572
gaactccggt cctcaaactc                    20

<210> SEQ ID NO 573
<211> LENGTH: 20
<212> TYPE: DNA
<213> ORGANISM: Artificial Sequence
<220> FEATURE:
<223> OTHER INFORMATION: Primer

<400> SEQUENCE: 573
tccacccacc tagtgaactc                    20

<210> SEQ ID NO 574
<211> LENGTH: 20
<212> TYPE: DNA
<213> ORGANISM: Artificial Sequence
<220> FEATURE:
<223> OTHER INFORMATION: Primer

<400> SEQUENCE: 574
tcttactgtt gagggaccag                    20

<210> SEQ ID NO 575
<211> LENGTH: 20
<212> TYPE: DNA
<213> ORGANISM: Artificial Sequence
<220> FEATURE:
<223> OTHER INFORMATION: Primer -continued

<400> SEQUENCE: 575
agaccggagt tgtagatgtt                                              20

<210> SEQ ID NO 576
<211> LENGTH: 20
<212> TYPE: DNA
<213> ORGANISM: Artificial Sequence
<220> FEATURE:
<223> OTHER INFORMATION: Primer

<400> SEQUENCE: 576
ggagaagatt cgtttcacgg                                              20

<210> SEQ ID NO 577
<211> LENGTH: 20
<212> TYPE: DNA
<213> ORGANISM: Artificial Sequence
<220> FEATURE:
<223> OTHER INFORMATION: Primer

<400> SEQUENCE: 577
ctataccaca cacggagtag                                              20

<210> SEQ ID NO 578
<211> LENGTH: 20
<212> TYPE: DNA
<213> ORGANISM: Artificial Sequence
<220> FEATURE:
<223> OTHER INFORMATION: Primer

<400> SEQUENCE: 578
aaacgtgacc gtgagaatga                                              20

<210> SEQ ID NO 579
<211> LENGTH: 20
<212> TYPE: DNA
<213> ORGANISM: Artificial Sequence
<220> FEATURE:
<223> OTHER INFORMATION: Primer

<400> SEQUENCE: 579
gtttacctct atcggtttgt                                              20

<210> SEQ ID NO 580
<211> LENGTH: 19
<212> TYPE: DNA
<213> ORGANISM: Artificial Sequence
<220> FEATURE:
<223> OTHER INFORMATION: Primer

<400> SEQUENCE: 580 actcaccct tgtcgagaa                                                19

<210> SEQ ID NO 581
<211> LENGTH: 20
<212> TYPE: DNA
<213> ORGANISM: Artificial Sequence
<220> FEATURE:
<223> OTHER INFORMATION: Primer

<400> SEQUENCE: 581
cagatgacgg tggagagtga                                              20

<210> SEQ ID NO 582
<211> LENGTH: 19
<212> TYPE: DNA

```
<213> ORGANISM: Artificial Sequence
<220> FEATURE:
<223> OTHER INFORMATION: Primer

<400> SEQUENCE: 582
gactacaccc ttgtcgaga                                                     19

<210> SEQ ID NO 583
<211> LENGTH: 20
<212> TYPE: DNA
<213> ORGANISM: Artificial Sequence
<220> FEATURE:
<223> OTHER INFORMATION: Primer

<400> SEQUENCE: 583
ctgtggtctc aaactcgtca                                                    20

<210> SEQ ID NO 584
<211> LENGTH: 20
<212> TYPE: DNA
<213> ORGANISM: Artificial Sequence
<220> FEATURE:
<223> OTHER INFORMATION: Primer

<400> SEQUENCE: 584
ggtacaaccg taagttatga                                                    20

<210> SEQ ID NO 585
<211> LENGTH: 20
<212> TYPE: DNA
<213> ORGANISM: Artificial Sequence
<220> FEATURE:
<223> OTHER INFORMATION: Primer

<400> SEQUENCE: 585
atcacatgtt gggttcacgg                                                    20

<210> SEQ ID NO 586
<211> LENGTH: 20
<212> TYPE: DNA
<213> ORGANISM: Artificial Sequence
<220> FEATURE:
<223> OTHER INFORMATION: Primer

<400> SEQUENCE: 586
gaagaaggaa gaaccggatt                                                    20

<210> SEQ ID NO 587
<211> LENGTH: 20
<212> TYPE: DNA
<213> ORGANISM: Artificial Sequence
<220> FEATURE:
<223> OTHER INFORMATION: Primer

<400> SEQUENCE: 587
acagagttgg agggttcatc                                                    20

<210> SEQ ID NO 588
<211> LENGTH: 20
<212> TYPE: DNA
<213> ORGANISM: Artificial Sequence
<220> FEATURE:
<223> OTHER INFORMATION: Primer

<400> SEQUENCE: 588
cccattccta cgtccattct                                                    20
```

```
<210> SEQ ID NO 589
<211> LENGTH: 20
<212> TYPE: DNA
<213> ORGANISM: Artificial Sequence
<220> FEATURE:
<223> OTHER INFORMATION: Primer

<400> SEQUENCE: 589
gtcctgggat actcacactt                                              20

<210> SEQ ID NO 590
<211> LENGTH: 20
<212> TYPE: DNA
<213> ORGANISM: Artificial Sequence
<220> FEATURE:
<223> OTHER INFORMATION: Primer

<400> SEQUENCE: 590
gatgacttag gtacggtaag                                              20

<210> SEQ ID NO 591
<211> LENGTH: 20
<212> TYPE: DNA
<213> ORGANISM: Artificial Sequence
<220> FEATURE:
<223> OTHER INFORMATION: Primer

<400> SEQUENCE: 591
tccttgagtt gttcgatggg                                              20

<210> SEQ ID NO 592
<211> LENGTH: 20
<212> TYPE: DNA
<213> ORGANISM: Artificial Sequence
<220> FEATURE:
<223> OTHER INFORMATION: Primer

<400> SEQUENCE: 592
gttacaagac cgtcgaagtt                                              20

<210> SEQ ID NO 593
<211> LENGTH: 20
<212> TYPE: DNA
<213> ORGANISM: Artificial Sequence
<220> FEATURE:
<223> OTHER INFORMATION: Primer

<400> SEQUENCE: 593
ctcctccgta acttttacct                                              20

<210> SEQ ID NO 594
<211> LENGTH: 20
<212> TYPE: DNA
<213> ORGANISM: Artificial Sequence
<220> FEATURE:
<223> OTHER INFORMATION: Primer

<400> SEQUENCE: 594
atcgtactcg gggtattagg                                              20

<210> SEQ ID NO 595
<211> LENGTH: 20
<212> TYPE: DNA
<213> ORGANISM: Artificial Sequence
<220> FEATURE:
<223> OTHER INFORMATION: Primer
```

```
<400> SEQUENCE: 595
aacctgaata gtgtttaccg                                          20

<210> SEQ ID NO 596
<211> LENGTH: 20
<212> TYPE: DNA
<213> ORGANISM: Artificial Sequence
<220> FEATURE:
<223> OTHER INFORMATION: Primer

<400> SEQUENCE: 596
atagtgtttc tccaaaccgt                                          20

<210> SEQ ID NO 597
<211> LENGTH: 20
<212> TYPE: DNA
<213> ORGANISM: Artificial Sequence
<220> FEATURE:
<223> OTHER INFORMATION: Primer

<400> SEQUENCE: 597
cattgtggtc agacacgtgg                                          20

<210> SEQ ID NO 598
<211> LENGTH: 20
<212> TYPE: DNA
<213> ORGANISM: Artificial Sequence
<220> FEATURE:
<223> OTHER INFORMATION: Primer

<400> SEQUENCE: 598
ctgtccctgc gtgagaaatg                                          20

<210> SEQ ID NO 599
<211> LENGTH: 20
<212> TYPE: DNA
<213> ORGANISM: Artificial Sequence
<220> FEATURE:
<223> OTHER INFORMATION: Primer

<400> SEQUENCE: 599
caccacaaga cttccacaag                                          20

<210> SEQ ID NO 600
<211> LENGTH: 20
<212> TYPE: DNA
<213> ORGANISM: Artificial Sequence
<220> FEATURE:
<223> OTHER INFORMATION: Primer

<400> SEQUENCE: 600
ctcctctgag caccacaaga                                          20

<210> SEQ ID NO 601
<211> LENGTH: 20
<212> TYPE: DNA
<213> ORGANISM: Artificial Sequence
<220> FEATURE:
<223> OTHER INFORMATION: Primer

<400> SEQUENCE: 601
gaaactaaca ctgacacgga                                          20

<210> SEQ ID NO 602
<211> LENGTH: 20
<212> TYPE: DNA
```

```
<213> ORGANISM: Artificial Sequence
<220> FEATURE:
<223> OTHER INFORMATION: Primer

<400> SEQUENCE: 602
gttagtaatg agacggaggt                                          20

<210> SEQ ID NO 603
<211> LENGTH: 20
<212> TYPE: DNA
<213> ORGANISM: Artificial Sequence
<220> FEATURE:
<223> OTHER INFORMATION: Primer

<400> SEQUENCE: 603
gattaaggtg tgggagtgac                                          20

<210> SEQ ID NO 604
<211> LENGTH: 20
<212> TYPE: DNA
<213> ORGANISM: Artificial Sequence
<220> FEATURE:
<223> OTHER INFORMATION: Primer

<400> SEQUENCE: 604 attgcctttα ccttgtccta                                          20

<210> SEQ ID NO 605
<211> LENGTH: 20
<212> TYPE: DNA
<213> ORGANISM: Artificial Sequence
<220> FEATURE:
<223> OTHER INFORMATION: Primer

<400> SEQUENCE: 605
gatgaaggtc cacttaggtt                                          20

<210> SEQ ID NO 606
<211> LENGTH: 20
<212> TYPE: DNA
<213> ORGANISM: Artificial Sequence
<220> FEATURE:
<223> OTHER INFORMATION: Primer

<400> SEQUENCE: 606
agaagggtga aagactcctg                                          20

<210> SEQ ID NO 607
<211> LENGTH: 20
<212> TYPE: DNA
<213> ORGANISM: Artificial Sequence
<220> FEATURE:
<223> OTHER INFORMATION: Primer

<400> SEQUENCE: 607
gaaatgcact aagtttgggt                                          20

<210> SEQ ID NO 608
<211> LENGTH: 20
<212> TYPE: DNA
<213> ORGANISM: Artificial Sequence
<220> FEATURE:
<223> OTHER INFORMATION: Primer

<400> SEQUENCE: 608
tccttctcct cctccttcta                                          20
```

<210> SEQ ID NO 609
<211> LENGTH: 20
<212> TYPE: DNA
<213> ORGANISM: Artificial Sequence
<220> FEATURE:
<223> OTHER INFORMATION: Primer

<400> SEQUENCE: 609
tacttggtga tcttggtccc                                                    20

<210> SEQ ID NO 610
<211> LENGTH: 20
<212> TYPE: DNA
<213> ORGANISM: Artificial Sequence
<220> FEATURE:
<223> OTHER INFORMATION: Primer

<400> SEQUENCE: 610
acttgaagct actgtgtcac                                                    20

<210> SEQ ID NO 611
<211> LENGTH: 20
<212> TYPE: DNA
<213> ORGANISM: Artificial Sequence
<220> FEATURE:
<223> OTHER INFORMATION: Primer

<400> SEQUENCE: 611
gatgctcacg atgacgttcg                                                    20

<210> SEQ ID NO 612
<211> LENGTH: 20
<212> TYPE: DNA
<213> ORGANISM: Artificial Sequence
<220> FEATURE:
<223> OTHER INFORMATION: Primer

<400> SEQUENCE: 612
gttatggtta ccgaggatgt                                                    20

<210> SEQ ID NO 613
<211> LENGTH: 20
<212> TYPE: DNA
<213> ORGANISM: Artificial Sequence
<220> FEATURE:
<223> OTHER INFORMATION: Primer

<400> SEQUENCE: 613
cttatacctg ttcctgtggt                                                    20

<210> SEQ ID NO 614
<211> LENGTH: 20
<212> TYPE: DNA
<213> ORGANISM: Artificial Sequence
<220> FEATURE:
<223> OTHER INFORMATION: Primer

<400> SEQUENCE: 614
atgaactata aaccacggct                                                    20

<210> SEQ ID NO 615
<211> LENGTH: 20
<212> TYPE: DNA
<213> ORGANISM: Artificial Sequence
<220> FEATURE:
<223> OTHER INFORMATION: Primer -continued

<400> SEQUENCE: 615
tgtgcagcgt gtaaatcttc    20

<210> SEQ ID NO 616
<211> LENGTH: 20
<212> TYPE: DNA
<213> ORGANISM: Artificial Sequence
<220> FEATURE:
<223> OTHER INFORMATION: Primer

<400> SEQUENCE: 616
tgtgaaggta acactgaggt    20

<210> SEQ ID NO 617
<211> LENGTH: 20
<212> TYPE: DNA
<213> ORGANISM: Artificial Sequence
<220> FEATURE:
<223> OTHER INFORMATION: Primer

<400> SEQUENCE: 617
agtaaccatg aaactcaccg    20

<210> SEQ ID NO 618
<211> LENGTH: 20
<212> TYPE: DNA
<213> ORGANISM: Artificial Sequence
<220> FEATURE:
<223> OTHER INFORMATION: Primer

<400> SEQUENCE: 618
tgttagacga gacattagcc    20

<210> SEQ ID NO 619
<211> LENGTH: 20
<212> TYPE: DNA
<213> ORGANISM: Artificial Sequence
<220> FEATURE:
<223> OTHER INFORMATION: Primer

<400> SEQUENCE: 619
agacacgaca gtttcgacat    20

<210> SEQ ID NO 620
<211> LENGTH: 20
<212> TYPE: DNA
<213> ORGANISM: Artificial Sequence
<220> FEATURE:
<223> OTHER INFORMATION: Primer

<400> SEQUENCE: 620
aactcctcga aagagaaagg    20

<210> SEQ ID NO 621
<211> LENGTH: 20
<212> TYPE: DNA
<213> ORGANISM: Artificial Sequence
<220> FEATURE:
<223> OTHER INFORMATION: Primer

<400> SEQUENCE: 621
cgttgagtag tggcttgatc    20

<210> SEQ ID NO 622
<211> LENGTH: 20
<212> TYPE: DNA

<210> SEQ ID NO 622
<211> LENGTH: 20
<212> TYPE: DNA
<213> ORGANISM: Artificial Sequence
<220> FEATURE:
<223> OTHER INFORMATION: Primer

<400> SEQUENCE: 622
gttgggatgg gtaggagtga                                           20

<210> SEQ ID NO 623
<211> LENGTH: 20
<212> TYPE: DNA
<213> ORGANISM: Artificial Sequence
<220> FEATURE:
<223> OTHER INFORMATION: Primer

<400> SEQUENCE: 623
gtttgtcctt gtagggtgt                                            20

<210> SEQ ID NO 624
<211> LENGTH: 21
<212> TYPE: DNA
<213> ORGANISM: Artificial Sequence
<220> FEATURE:
<223> OTHER INFORMATION: Primer

<400> SEQUENCE: 624
ccaccttttg cttcgagtaa g                                         21

<210> SEQ ID NO 625
<211> LENGTH: 20
<212> TYPE: DNA
<213> ORGANISM: Artificial Sequence
<220> FEATURE:
<223> OTHER INFORMATION: Primer

<400> SEQUENCE: 625
ctctcggaag gtcaggttga                                           20

<210> SEQ ID NO 626
<211> LENGTH: 20
<212> TYPE: DNA
<213> ORGANISM: Artificial Sequence
<220> FEATURE:
<223> OTHER INFORMATION: Primer

<400> SEQUENCE: 626
cacccgactc tcactttcct                                           20

<210> SEQ ID NO 627
<211> LENGTH: 19
<212> TYPE: DNA
<213> ORGANISM: Artificial Sequence
<220> FEATURE:
<223> OTHER INFORMATION: Primer

<400> SEQUENCE: 627
cttacggttt ccagtcacc                                            19

<210> SEQ ID NO 628
<211> LENGTH: 20
<212> TYPE: DNA
<213> ORGANISM: Artificial Sequence
<220> FEATURE:
<223> OTHER INFORMATION: Primer

<400> SEQUENCE: 628
ctttctagtc tcctggacct                                           20

<210> SEQ ID NO 629
<211> LENGTH: 20
<212> TYPE: DNA
<213> ORGANISM: Artificial Sequence
<220> FEATURE:
<223> OTHER INFORMATION: Primer

<400> SEQUENCE: 629
cttcctcaaa gggtagtttg                                           20

<210> SEQ ID NO 630
<211> LENGTH: 20
<212> TYPE: DNA
<213> ORGANISM: Artificial Sequence
<220> FEATURE:
<223> OTHER INFORMATION: Primer

<400> SEQUENCE: 630
ctcctactac ttcacgaact                                           20

<210> SEQ ID NO 631
<211> LENGTH: 20
<212> TYPE: DNA
<213> ORGANISM: Artificial Sequence
<220> FEATURE:
<223> OTHER INFORMATION: Primer

<400> SEQUENCE: 631
cgacctccaa aggtttagtt                                           20

<210> SEQ ID NO 632
<211> LENGTH: 22
<212> TYPE: DNA
<213> ORGANISM: Artificial Sequence
<220> FEATURE:
<223> OTHER INFORMATION: Primer

<400> SEQUENCE: 632
gaaacaccct tctatgacac ct                                        22

<210> SEQ ID NO 633
<211> LENGTH: 19
<212> TYPE: DNA
<213> ORGANISM: Artificial Sequence
<220> FEATURE:
<223> OTHER INFORMATION: Primer

<400> SEQUENCE: 633
agacacgacg acctaccta                                            19

<210> SEQ ID NO 634
<211> LENGTH: 20
<212> TYPE: DNA
<213> ORGANISM: Artificial Sequence
<220> FEATURE:
<223> OTHER INFORMATION: Primer

<400> SEQUENCE: 634
gcaatcgaag tggttgtcct                                           20

<210> SEQ ID NO 635
<211> LENGTH: 21
<212> TYPE: DNA
<213> ORGANISM: Artificial Sequence
<220> FEATURE:
<223> OTHER INFORMATION: Primer

```
<400> SEQUENCE: 635
tcggcataaa gatgacgctg c                                              21

<210> SEQ ID NO 636
<211> LENGTH: 21
<212> TYPE: DNA
<213> ORGANISM: Artificial Sequence
<220> FEATURE:
<223> OTHER INFORMATION: Primer

<400> SEQUENCE: 636
tcggcataaa gatgacgctg c                                              21

<210> SEQ ID NO 637
<211> LENGTH: 19
<212> TYPE: DNA
<213> ORGANISM: Artificial Sequence
<220> FEATURE:
<223> OTHER INFORMATION: Primer

<400> SEQUENCE: 637
tttttcggtg ttgtccagc                                                 19

<210> SEQ ID NO 638
<211> LENGTH: 19
<212> TYPE: DNA
<213> ORGANISM: Artificial Sequence
<220> FEATURE:
<223> OTHER INFORMATION: Primer

<400> SEQUENCE: 638
agtagggcag tcagtagga                                                 19

<210> SEQ ID NO 639
<211> LENGTH: 19
<212> TYPE: DNA
<213> ORGANISM: Artificial Sequence
<220> FEATURE:
<223> OTHER INFORMATION: Primer

<400> SEQUENCE: 639
ccgaacgtca aaggagttc                                                 19

<210> SEQ ID NO 640
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 640
caagctcgaa gctgagtcac cca                                            23

<210> SEQ ID NO 641
<211> LENGTH: 20
<212> TYPE: DNA
<213> ORGANISM: Artificial Sequence
<220> FEATURE:
<223> OTHER INFORMATION: Primer

<400> SEQUENCE: 641
cagcccagcc agaagccagg                                                20

<210> SEQ ID NO 642
<211> LENGTH: 22
<212> TYPE: DNA
```

```
<213> ORGANISM: Artificial Sequence
<220> FEATURE:
<223> OTHER INFORMATION: TaqMan probe sequenvce

<400> SEQUENCE: 642
ccgcagaagt gaagcacaac cc                                         22

<210> SEQ ID NO 643
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 643
ctgctggtgc tcacggccac                                            20

<210> SEQ ID NO 644
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 644
ccagttcccg caagcccaga                                            20

<210> SEQ ID NO 645
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 645
tgaggatccc acatcctgag atcaa                                      25

<210> SEQ ID NO 646
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 646
catttgcctc agctccatct gca                                        23

<210> SEQ ID NO 647
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 647
cccatggtca actgccatct gaa                                        23

<210> SEQ ID NO 648
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 648
ctgcacttcg cggctcatgc                                            20
```

<210> SEQ ID NO 649
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 649
ctgccaagct gcccaaagcc                                           20

<210> SEQ ID NO 650
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 650
accaactcca actgatggcc ca                                        22

<210> SEQ ID NO 651
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 651
ccagcctgag ccttacctgc ca                                        22

<210> SEQ ID NO 652
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 652
ccagggaaga tggttctcgc acc                                       23

<210> SEQ ID NO 653
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 653
cagcgctgac atactccatc atgaag                                    26

<210> SEQ ID NO 654
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 654
tctggaacga gccacgttgc c                                         21

<210> SEQ ID NO 655
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 655
cgtgccatta cactccagcc tgg                                              23

<210> SEQ ID NO 656
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 656
cacgtcagca gttcctggcc c                                                21

<210> SEQ ID NO 657
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 657
caggtcaggc aatagaacaa gtccaca                                          27

<210> SEQ ID NO 658
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 658
tcccacagaa agcagttcac ctcca                                            25

<210> SEQ ID NO 659
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 659
cccactccgg aagcagctgc                                                  20

<210> SEQ ID NO 660
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 660
ccgacttcct ctgcttgcca gc                                               22

<210> SEQ ID NO 661
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 661 tgcccttcc tcctatttcc ctcca                                             25

<210> SEQ ID NO 662
<211> LENGTH: 20
<212> TYPE: DNA

-continued

<213> ORGANISM: Artificial Sequence
<220> FEATURE:
<223> OTHER INFORMATION: TaqMan probe sequenvce

<400> SEQUENCE: 662
caacacggcc agttcctggc                                                    20

<210> SEQ ID NO 663
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 663
tgctttctca ggttcctgta ggcca                                              25

<210> SEQ ID NO 664
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 664
aaaggcctca ccaagaattt ggca                                               24

<210> SEQ ID NO 665
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 665
tcgagttgca aactttggtc ttccc                                              25

<210> SEQ ID NO 666
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 666
tcgagttgca aactttggtc ttccc                                              25

<210> SEQ ID NO 667
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 667
caagcctttc atcctctgtc tccagc                                             26

<210> SEQ ID NO 668
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 668
ccacaaacac gggaaggccc                                                    20

-continued

```
<210> SEQ ID NO 669
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 669
caggaacggt ctgtattctc ctcctca                                            27

<210> SEQ ID NO 670
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 670
tgcctcccga gcatgttccc                                                    20

<210> SEQ ID NO 671
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 671
tcgcctgcct ctggtgggac                                                    20

<210> SEQ ID NO 672
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 672
ttccgccgtc cgaggaacag                                                    20

<210> SEQ ID NO 673
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 673
acccgctggg catctgtgct                                                    20

<210> SEQ ID NO 674
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 674
tgctatcgcc agtgacatgc aaga                                               24

<210> SEQ ID NO 675
<211> LENGTH: 21
<212> TYPE: DNA
<213> ORGANISM: Artificial Sequence
<220> FEATURE:
<223> OTHER INFORMATION: TaqMan probe sequenvce
```

```
<400> SEQUENCE: 675
tcctttcctt cctgtgggcc c                                              21

<210> SEQ ID NO 676
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 676
cccagctcag ggattgcctg a                                              21

<210> SEQ ID NO 677
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 677
ccgcgctccc ggtacatgtg                                                20

<210> SEQ ID NO 678
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 678
ctacccgcgg gtcagcctca                                                20

<210> SEQ ID NO 679
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 679
atcctggcct gccatcacgg                                                20

<210> SEQ ID NO 680
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 680
tccctcccag caatatccag tctcc                                          25

<210> SEQ ID NO 681
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 681
cccaactttg atgatacgtc catctgg                                        27

<210> SEQ ID NO 682
<211> LENGTH: 21
<212> TYPE: DNA
```

```
<213> ORGANISM: Artificial Sequence
<220> FEATURE:
<223> OTHER INFORMATION: TaqMan probe sequenvce

<400> SEQUENCE: 682
tcactctggc agcactgggc a                                          21

<210> SEQ ID NO 683
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 683
tgaggcccat gatcccaaca tg                                         22

<210> SEQ ID NO 684
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 684
tcccagctat ggcacagccg                                            20

<210> SEQ ID NO 685
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 685
agcacccaag aaggcctgcg                                            20

<210> SEQ ID NO 686
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 686
agcacccaag aaggcctgcg                                            20

<210> SEQ ID NO 687
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 687
cccaggtctt tgcggtccca                                            20

<210> SEQ ID NO 688
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 688
cgtgccttct ctacttcgct cttgga                                     26
```

```
<210> SEQ ID NO 689
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 689
tgtgcttctc agaaatccag cctgc                                       25

<210> SEQ ID NO 690
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 690
cgctcttgga acataatttc tcatggc                                     27

<210> SEQ ID NO 691
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 691
tccacgtctc tttgctttgg cca                                         23

<210> SEQ ID NO 692
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 692
tccacgtctc tttgctttgg cca                                         23

<210> SEQ ID NO 693
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 693
ccggatcact cctggcagca                                             20

<210> SEQ ID NO 694
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 694
tcacattctg aagcactcat tctgcct                                     27

<210> SEQ ID NO 695
<211> LENGTH: 23
<212> TYPE: DNA
<213> ORGANISM: Artificial Sequence
<220> FEATURE:
<223> OTHER INFORMATION: TaqMan probe sequenvce
```

```
<400> SEQUENCE: 695
ccctggcttc aagttgcatg agc                                           23

<210> SEQ ID NO 696
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 696
tgggatctct tccaagttcc tccttga                                       27

<210> SEQ ID NO 697
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 697
cctcctccat tgatgctgtg actttc                                        26

<210> SEQ ID NO 698
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 698
tgcgctcagt gcttccagca                                               20

<210> SEQ ID NO 699
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 699
tgggagacac ctgtgtcgcc c                                             21

<210> SEQ ID NO 700
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 700
agcagttcac gcaccaggcc                                               20

<210> SEQ ID NO 701
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 701
ttcaacatca tcttcagcct ccgc                                          24

<210> SEQ ID NO 702
<211> LENGTH: 20
<212> TYPE: DNA
```

```
<213> ORGANISM: Artificial Sequence
<220> FEATURE:
<223> OTHER INFORMATION: TaqMan probe sequenvce

<400> SEQUENCE: 702
tgccgcagcc cagacaacag                                              20

<210> SEQ ID NO 703
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 703
tcacatgtcg tttaaagcca gatgca                                       26

<210> SEQ ID NO 704
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 704
cggtcattgc atcttcactc tgcg                                         24

<210> SEQ ID NO 705
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 705
cgctgcttcc acacattaat ggca                                         24

<210> SEQ ID NO 706
<211> LENGTH: 26
<212> TYPE: DNA
<213> ORGANISM: Artificial Sequence
<220> FEATURE:
<223> OTHER INFORMATION: TaqMan probe sequenvce

<400> SEQUENCE: 706
tgcctttaac agaaatgcct gaagca                                       26

<210> SEQ ID NO 707
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 707
tccgcctcct ggattcaagt ga                                           22

<210> SEQ ID NO 708
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 708
ccctgtgcca ggccaaattc a                                            21
```

```
<210> SEQ ID NO 709
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 709
ccctgtgcca ggccaaattc a                                              21

<210> SEQ ID NO 710
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 710
tcctgcatga ccagcacggc                                                20

<210> SEQ ID NO 711
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 711
cacgatgcgg gccacttcct                                                20

<210> SEQ ID NO 712
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 712
cagctccacg gcctgatgca                                                20

<210> SEQ ID NO 713
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 713
cggtgcagtc tcacaccaag gg                                             22

<210> SEQ ID NO 714
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 714
ctcccaggcc ctcggtgtca                                                20

<210> SEQ ID NO 715
<211> LENGTH: 20
<212> TYPE: DNA
<213> ORGANISM: Artificial Sequence
<220> FEATURE:
<223> OTHER INFORMATION: TaqMan probe sequenvce
```

```
<400> SEQUENCE: 715
tctgcctttg aatcgccgcc                                              20

<210> SEQ ID NO 716
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 716
ccctgggcac acttggcaca                                              20

<210> SEQ ID NO 717
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 717
cgggcacctc cctgccctaa                                              20

<210> SEQ ID NO 718
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 718
ccctgggcac acttggcaca                                              20

<210> SEQ ID NO 719
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 719
ccaggcccac cacaaggagc                                              20

<210> SEQ ID NO 720
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 720
tctccttctg ggtgccaatc aca                                          23

<210> SEQ ID NO 721
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 721
ctcccgggct gccttcactg                                              20

<210> SEQ ID NO 722
<211> LENGTH: 20
<212> TYPE: DNA
```

```
<213> ORGANISM: Artificial Sequence
<220> FEATURE:
<223> OTHER INFORMATION: TaqMan probe sequenvce

<400> SEQUENCE: 722
tgggctacgc cacccacaag                                                 20

<210> SEQ ID NO 723
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 723
tgcagcctcc aactcctagc ctca                                            24

<210> SEQ ID NO 724
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 724
taccgccttc tgccgcatgg                                                 20

<210> SEQ ID NO 725
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 725
tcccaggctg cagctgtcca                                                 20

<210> SEQ ID NO 726
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 726
cttctggaac ccgcccacca                                                 20

<210> SEQ ID NO 727
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 727
cggttgccat ccactctttc cc                                              22

<210> SEQ ID NO 728
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 728
cccgaatgcg ctgctcattt aa                                              22
```

```
<210> SEQ ID NO 729
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 729
caacagtcca gccatcccat tgg                                              23

<210> SEQ ID NO 730
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 730
tcatgctgca ccctgaccgg                                                  20

<210> SEQ ID NO 731
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 731
cacccaggtc ctcttcccac tgc                                              23

<210> SEQ ID NO 732
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 732
tgctcttgta atctgaccct ggacatg                                          27

<210> SEQ ID NO 733
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 733
cgacaacctc acctctgcgc c                                                21

<210> SEQ ID NO 734
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 734
cgccaaacgc aagaccgtga                                                  20

<210> SEQ ID NO 735
<211> LENGTH: 20
<212> TYPE: DNA
<213> ORGANISM: Artificial Sequence
<220> FEATURE:
<223> OTHER INFORMATION: TaqMan probe sequenvce
```

```
<400> SEQUENCE: 735
tatccggcgc cttgctcgtc                                          20

<210> SEQ ID NO 736
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 736
tatccggcgc cttgctcgtc                                          20

<210> SEQ ID NO 737
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 737
tgtccttgaa gcccacgggc                                          20

<210> SEQ ID NO 738
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 738
cctgccagcc ttccgtccaa                                          20

<210> SEQ ID NO 739
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 739 tgtcacccتt aggccagcac ca                                       22

<210> SEQ ID NO 740
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 740
cggctccggc tctggatcag                                          20

<210> SEQ ID NO 741
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 741
tctggattgc agcgcaccca                                          20

<210> SEQ ID NO 742
<211> LENGTH: 26
<212> TYPE: DNA
```

```
<213> ORGANISM: Artificial Sequence
<220> FEATURE:
<223> OTHER INFORMATION: TaqMan probe sequenvce

<400> SEQUENCE: 742
tccaaagacg agaatccagg acttga                                          26

<210> SEQ ID NO 743
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 743
tccaggctca gctgccgctt                                                 20

<210> SEQ ID NO 744
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 744
ccctggcttg gccaaatcgt c                                               21

<210> SEQ ID NO 745
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 745
cgtgccattg ccacaacatc g                                               21

<210> SEQ ID NO 746
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 746
ccacccagga ccagcacggt                                                 20

<210> SEQ ID NO 747
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 747
ccagcccacc gtgacatcga                                                 20

<210> SEQ ID NO 748
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 748
tcctcgcagt ggctccggtc                                                 20
```

```
<210> SEQ ID NO 749
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 749
ccacatcatg aacttcccga cagtg                                           25

<210> SEQ ID NO 750
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 750
cactgtgcat catcatggat aaaccca                                         27

<210> SEQ ID NO 751
<211> LENGTH: 27
<212> TYPE: DNA
<213> ORGANISM: Artificial Sequence
<220> FEATURE:
<223> OTHER INFORMATION: TaqMan probe sequenvce

<400> SEQUENCE: 751
cctcgctgat gcaattcttc ttcaaca                                         27

<210> SEQ ID NO 752
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 752
aagcctgtgc tgcggcatcc                                                 20

<210> SEQ ID NO 753
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 753
catcgtcaac aggcatatct tgcca                                           25

<210> SEQ ID NO 754
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 754
ccatggcgag gacccaccac                                                 20

<210> SEQ ID NO 755
<211> LENGTH: 20
<212> TYPE: DNA
<213> ORGANISM: Artificial Sequence
<220> FEATURE:
<223> OTHER INFORMATION: TaqMan probe sequenvce
```

<400> SEQUENCE: 755
ccaggccgcc aaacatctca                                              20

<210> SEQ ID NO 756
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 756
ccacagccct ccagggtcca                                              20

<210> SEQ ID NO 757
<211> LENGTH: 25
<212> TYPE: DNA
<213> ORGANISM: Artificial Sequence
<220> FEATURE:
<223> OTHER INFORMATION: TaqMan probe sequenvce

<400> SEQUENCE: 757
tggcatgcta cagtccatga cctca                                        25

<210> SEQ ID NO 758
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 758
ttatcccttg tctccgggtg gt                                           22

<210> SEQ ID NO 759
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 759
atgtccaggt tttcccatca                                              20

<210> SEQ ID NO 760
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 760
tgcatcaggt acaggtccaa ga                                           22

<210> SEQ ID NO 761
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 761
gaactgaaaa gtgctgaagg ga                                           22

<210> SEQ ID NO 762
<211> LENGTH: 21
<212> TYPE: DNA

```
<213> ORGANISM: Artificial Sequence
<220> FEATURE:
<223> OTHER INFORMATION: TaqMan probe sequenvce

<400> SEQUENCE: 762
agcacctgga actgttgtcc t                                              21

<210> SEQ ID NO 763
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 763
atgaccatca gcacggaagc                                                20

<210> SEQ ID NO 764
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 764
ctacatccaa gccccacaca aaac                                           24

<210> SEQ ID NO 765
<211> LENGTH: 23
<212> TYPE: DNA
<213> ORGANISM: Artificial Sequence
<220> FEATURE:
<223> OTHER INFORMATION: TaqMan probe sequenvce

<400> SEQUENCE: 765
ctacatccaa gccccacaca aaa                                            23

<210> SEQ ID NO 766
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 766
tacatccaag ccccacacaa aa                                             22

<210> SEQ ID NO 767
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 767
tggctttgtg ggaagatact gtgg                                           24

<210> SEQ ID NO 768
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 768
caggttgctt ggctgattat gt                                             22
```

```
<210> SEQ ID NO 769
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 769
gcagaagcta aggcggtgtg tgaa                                          24

<210> SEQ ID NO 770
<211> LENGTH: 20
<212> TYPE: DNA
<213> ORGANISM: Artificial Sequence
<220> FEATURE:
<223> OTHER INFORMATION: TaqMan probe sequenvce

<400> SEQUENCE: 770
tttcgggtag tggaaaacca                                               20

<210> SEQ ID NO 771
<211> LENGTH: 24
<212> TYPE: DNA
<213> ORGANISM: Artificial Sequence
<220> FEATURE:
<223> OTHER INFORMATION: TaqMan probe sequenvce

<400> SEQUENCE: 771
ctatgacctc gactacgact cggt                                          24

<210> SEQ ID NO 772
<211> LENGTH: 22
<212> TYPE: DNA
<213> ORGANISM: Artificial Sequence
<220> FEATURE:
<223> OTHER INFORMATION: TaqMan probe sequenvce

<400> SEQUENCE: 772
atgacctcga ctacgactcg gt                                            22

<210> SEQ ID NO 773
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 773
ttcagtgcag aaaacccac a                                              21

<210> SEQ ID NO 774
<211> LENGTH: 21
<212> TYPE: DNA
<213> ORGANISM: Artificial Sequence
<220> FEATURE:
<223> OTHER INFORMATION: TaqMan probe sequenvce

<400> SEQUENCE: 774
cagtgcagaa aaccccacaa a                                             21

<210> SEQ ID NO 775
<211> LENGTH: 26
<212> TYPE: DNA
<213> ORGANISM: Artificial Sequence
<220> FEATURE:
<223> OTHER INFORMATION: TaqMan probe sequenvce
```

```
<400> SEQUENCE: 775
tcatcccgtc agtcatcctt tattgc                                          26

<210> SEQ ID NO 776
<211> LENGTH: 21
<212> TYPE: DNA
<213> ORGANISM: Artificial Sequence
<220> FEATURE:
<223> OTHER INFORMATION: Primer

<400> SEQUENCE: 776
aaggccagaa tcccagctca g                                               21

<210> SEQ ID NO 777
<211> LENGTH: 20
<212> TYPE: DNA
<213> ORGANISM: Artificial Sequence
<220> FEATURE:
<223> OTHER INFORMATION: Primer

<400> SEQUENCE: 777
aacaagggat cgcctgctcc                                                 20

<210> SEQ ID NO 778
<211> LENGTH: 22
<212> TYPE: DNA
<213> ORGANISM: Artificial Sequence
<220> FEATURE:
<223> OTHER INFORMATION: Primer

<400> SEQUENCE: 778
accgggtttg tgaagtgtgg at                                              22

<210> SEQ ID NO 779
<211> LENGTH: 20
<212> TYPE: DNA
<213> ORGANISM: Artificial Sequence
<220> FEATURE:
<223> OTHER INFORMATION: Primer

<400> SEQUENCE: 779
catggccatc ctcagcttgc                                                 20

<210> SEQ ID NO 780
<211> LENGTH: 19
<212> TYPE: DNA
<213> ORGANISM: Artificial Sequence
<220> FEATURE:
<223> OTHER INFORMATION: Primer

<400> SEQUENCE: 780
tctcagcccg gtgatggtc                                                  19

<210> SEQ ID NO 781
<211> LENGTH: 24
<212> TYPE: DNA
<213> ORGANISM: Artificial Sequence
<220> FEATURE:
<223> OTHER INFORMATION: Primer

<400> SEQUENCE: 781
atacgccatt acatcaagca gcac                                            24

<210> SEQ ID NO 782
<211> LENGTH: 23
<212> TYPE: DNA
```

```
<213> ORGANISM: Artificial Sequence
<220> FEATURE:
<223> OTHER INFORMATION: Primer

<400> SEQUENCE: 782
tgctgaaagg catggtcaca aag                                            23

<210> SEQ ID NO 783
<211> LENGTH: 22
<212> TYPE: DNA
<213> ORGANISM: Artificial Sequence
<220> FEATURE:
<223> OTHER INFORMATION: Primer

<400> SEQUENCE: 783
ggcgcgtgct gaagaaattc aa                                             22

<210> SEQ ID NO 784
<211> LENGTH: 22
<212> TYPE: DNA
<213> ORGANISM: Artificial Sequence
<220> FEATURE:
<223> OTHER INFORMATION: Primer

<400> SEQUENCE: 784
tttcagaaca ggaagctggc gt                                             22

<210> SEQ ID NO 785
<211> LENGTH: 20
<212> TYPE: DNA
<213> ORGANISM: Artificial Sequence
<220> FEATURE:
<223> OTHER INFORMATION: Primer

<400> SEQUENCE: 785
tgcctatgct tggcctttct                                                20

<210> SEQ ID NO 786
<211> LENGTH: 22
<212> TYPE: DNA
<213> ORGANISM: Artificial Sequence
<220> FEATURE:
<223> OTHER INFORMATION: Primer

<400> SEQUENCE: 786
caagaaggcc tgcgcattca aa                                             22

<210> SEQ ID NO 787
<211> LENGTH: 25
<212> TYPE: DNA
<213> ORGANISM: Artificial Sequence
<220> FEATURE:
<223> OTHER INFORMATION: Primer

<400> SEQUENCE: 787
ttattccgtt gaataaagaa acaga                                          25

<210> SEQ ID NO 788
<211> LENGTH: 20
<212> TYPE: DNA
<213> ORGANISM: Artificial Sequence
<220> FEATURE:
<223> OTHER INFORMATION: Primer

<400> SEQUENCE: 788
atcgccagtg acatgcaaga                                                20
```

<210> SEQ ID NO 789
<211> LENGTH: 22
<212> TYPE: DNA
<213> ORGANISM: Artificial Sequence
<220> FEATURE:
<223> OTHER INFORMATION: Primer

<400> SEQUENCE: 789
attggagtag tggccctggt tg                                              22

<210> SEQ ID NO 790
<211> LENGTH: 22
<212> TYPE: DNA
<213> ORGANISM: Artificial Sequence
<220> FEATURE:
<223> OTHER INFORMATION: Primer

<400> SEQUENCE: 790
aggaagagtg agggcaggtt ca                                              22

<210> SEQ ID NO 791
<211> LENGTH: 24
<212> TYPE: DNA
<213> ORGANISM: Artificial Sequence
<220> FEATURE:
<223> OTHER INFORMATION: Primer

<400> SEQUENCE: 791
catgagctca ctccatcact cgat                                            24

<210> SEQ ID NO 792
<211> LENGTH: 23
<212> TYPE: DNA
<213> ORGANISM: Artificial Sequence
<220> FEATURE:
<223> OTHER INFORMATION: Primer

<400> SEQUENCE: 792
ctccgagttg tcttgaagtg agg                                             23

<210> SEQ ID NO 793
<211> LENGTH: 21
<212> TYPE: DNA
<213> ORGANISM: Artificial Sequence
<220> FEATURE:
<223> OTHER INFORMATION: Primer

<400> SEQUENCE: 793
cctccaaggt ctagtgacgg a                                               21

<210> SEQ ID NO 794
<211> LENGTH: 21
<212> TYPE: DNA
<213> ORGANISM: Artificial Sequence
<220> FEATURE:
<223> OTHER INFORMATION: Primer

<400> SEQUENCE: 794
ctgactctgc gagcttcttc c                                               21

<210> SEQ ID NO 795
<211> LENGTH: 23
<212> TYPE: DNA
<213> ORGANISM: Artificial Sequence
<220> FEATURE:
<223> OTHER INFORMATION: Primer

```
<400> SEQUENCE: 795
gggaccaagg catactgaac aca                                           23

<210> SEQ ID NO 796
<211> LENGTH: 22
<212> TYPE: DNA
<213> ORGANISM: Artificial Sequence
<220> FEATURE:
<223> OTHER INFORMATION: Primer

<400> SEQUENCE: 796
cacttacaca gagcacgcca aa                                            22

<210> SEQ ID NO 797
<211> LENGTH: 24
<212> TYPE: DNA
<213> ORGANISM: Artificial Sequence
<220> FEATURE:
<223> OTHER INFORMATION: Primer

<400> SEQUENCE: 797
agctcattgt tgatgcttat ggga                                          24

<210> SEQ ID NO 798
<211> LENGTH: 20
<212> TYPE: DNA
<213> ORGANISM: Artificial Sequence
<220> FEATURE:
<223> OTHER INFORMATION: Primer

<400> SEQUENCE: 798
tgtgggagaa ctacagcaac                                               20

<210> SEQ ID NO 799
<211> LENGTH: 24
<212> TYPE: DNA
<213> ORGANISM: Artificial Sequence
<220> FEATURE:
<223> OTHER INFORMATION: Primer

<400> SEQUENCE: 799
cccagtatct atttccatca tttg                                          24

<210> SEQ ID NO 800
<211> LENGTH: 22
<212> TYPE: DNA
<213> ORGANISM: Artificial Sequence
<220> FEATURE:
<223> OTHER INFORMATION: Primer

<400> SEQUENCE: 800
aggtgatgtg gtctctgctc tt                                            22

<210> SEQ ID NO 801
<211> LENGTH: 22
<212> TYPE: DNA
<213> ORGANISM: Artificial Sequence
<220> FEATURE:
<223> OTHER INFORMATION: Primer

<400> SEQUENCE: 801
tctgcatcaa ctttcccggt ca                                            22

<210> SEQ ID NO 802
<211> LENGTH: 22
<212> TYPE: DNA
```

```
<213> ORGANISM: Artificial Sequence
<220> FEATURE:
<223> OTHER INFORMATION: Primer

<400> SEQUENCE: 802
tgaacttccc gacagtgatg gt                                              22

<210> SEQ ID NO 803
<211> LENGTH: 22
<212> TYPE: DNA
<213> ORGANISM: Artificial Sequence
<220> FEATURE:
<223> OTHER INFORMATION: Primer

<400> SEQUENCE: 803
aggtgcacag agccaacatt ac                                              22

<210> SEQ ID NO 804
<211> LENGTH: 20
<212> TYPE: DNA
<213> ORGANISM: Artificial Sequence
<220> FEATURE:
<223> OTHER INFORMATION: Primer

<400> SEQUENCE: 804
aaagaacgtg ctccagaccc                                                 20

<210> SEQ ID NO 805
<211> LENGTH: 20
<212> TYPE: DNA
<213> ORGANISM: Artificial Sequence
<220> FEATURE:
<223> OTHER INFORMATION: Primer

<400> SEQUENCE: 805
cttgttcgtc tcactggtgt                                                 20

<210> SEQ ID NO 806
<211> LENGTH: 20
<212> TYPE: DNA
<213> ORGANISM: Artificial Sequence
<220> FEATURE:
<223> OTHER INFORMATION: Primer

<400> SEQUENCE: 806
ctggactgct gtcaatggga                                                 20

<210> SEQ ID NO 807
<211> LENGTH: 21
<212> TYPE: DNA
<213> ORGANISM: Artificial Sequence
<220> FEATURE:
<223> OTHER INFORMATION: Primer

<400> SEQUENCE: 807
atggagtcca ggaacctctg g                                               21

<210> SEQ ID NO 808
<211> LENGTH: 23
<212> TYPE: DNA
<213> ORGANISM: Artificial Sequence
<220> FEATURE:
<223> OTHER INFORMATION: Primer

<400> SEQUENCE: 808
gaacactttc tcatgtccag ggt                                             23
```

<210> SEQ ID NO 809
<211> LENGTH: 23
<212> TYPE: DNA
<213> ORGANISM: Artificial Sequence
<220> FEATURE:
<223> OTHER INFORMATION: Primer

<400> SEQUENCE: 809
tgagcaggga gatgaagaag caa                                      23

<210> SEQ ID NO 810
<211> LENGTH: 24
<212> TYPE: DNA
<213> ORGANISM: Artificial Sequence
<220> FEATURE:
<223> OTHER INFORMATION: Primer

<400> SEQUENCE: 810
gacactgttg tggtccagga tttg                                     24

<210> SEQ ID NO 811
<211> LENGTH: 24
<212> TYPE: DNA
<213> ORGANISM: Artificial Sequence
<220> FEATURE:
<223> OTHER INFORMATION: Primer

<400> SEQUENCE: 811
tactcaaatg cagtcggctt gtcc                                     24

<210> SEQ ID NO 812
<211> LENGTH: 22
<212> TYPE: DNA
<213> ORGANISM: Artificial Sequence
<220> FEATURE:
<223> OTHER INFORMATION: Primer

<400> SEQUENCE: 812
agccagtgta tgtcaatgtg gg                                       22

<210> SEQ ID NO 813
<211> LENGTH: 20
<212> TYPE: DNA
<213> ORGANISM: Artificial Sequence
<220> FEATURE:
<223> OTHER INFORMATION: Primer

<400> SEQUENCE: 813
acagctcaac aagtcgcagt                                          20

<210> SEQ ID NO 814
<211> LENGTH: 20
<212> TYPE: DNA
<213> ORGANISM: Artificial Sequence
<220> FEATURE:
<223> OTHER INFORMATION: Primer

<400> SEQUENCE: 814
tgaaggcaaa gacatggcag                                          20

<210> SEQ ID NO 815
<211> LENGTH: 22
<212> TYPE: DNA
<213> ORGANISM: Artificial Sequence
<220> FEATURE:
<223> OTHER INFORMATION: Primer

```
<400> SEQUENCE: 815
aagccgtcta tcttgtggcg at                                              22

<210> SEQ ID NO 816
<211> LENGTH: 24
<212> TYPE: DNA
<213> ORGANISM: Artificial Sequence
<220> FEATURE:
<223> OTHER INFORMATION: Primer

<400> SEQUENCE: 816
aaggacatga aggtagtgtc gcct                                            24

<210> SEQ ID NO 817
<211> LENGTH: 20
<212> TYPE: DNA
<213> ORGANISM: Artificial Sequence
<220> FEATURE:
<223> OTHER INFORMATION: Primer

<400> SEQUENCE: 817
tgcagggctg atctgggtct                                                 20

<210> SEQ ID NO 818
<211> LENGTH: 24
<212> TYPE: DNA
<213> ORGANISM: Artificial Sequence
<220> FEATURE:
<223> OTHER INFORMATION: Primer

<400> SEQUENCE: 818
tagttcaggg cctacgtcta ccta                                            24

<210> SEQ ID NO 819
<211> LENGTH: 24
<212> TYPE: DNA
<213> ORGANISM: Artificial Sequence
<220> FEATURE:
<223> OTHER INFORMATION: Primer

<400> SEQUENCE: 819
ggcgtactga cagttgaggg aata                                            24

<210> SEQ ID NO 820
<211> LENGTH: 22
<212> TYPE: DNA
<213> ORGANISM: Artificial Sequence
<220> FEATURE:
<223> OTHER INFORMATION: Primer

<400> SEQUENCE: 820
taccaaccac tactccgttc ac                                              22

<210> SEQ ID NO 821
<211> LENGTH: 24
<212> TYPE: DNA
<213> ORGANISM: Artificial Sequence
<220> FEATURE:
<223> OTHER INFORMATION: Primer

<400> SEQUENCE: 821
aggtgtgacc aaaggaaccc agaa                                            24

<210> SEQ ID NO 822
<211> LENGTH: 22
<212> TYPE: DNA
```

```
<213> ORGANISM: Artificial Sequence
<220> FEATURE:
<223> OTHER INFORMATION: Primer

<400> SEQUENCE: 822
ggcgcacgtg ttcagagaat gt                                    22

<210> SEQ ID NO 823
<211> LENGTH: 24
<212> TYPE: DNA
<213> ORGANISM: Artificial Sequence
<220> FEATURE:
<223> OTHER INFORMATION: Primer

<400> SEQUENCE: 823
acacttaccc ttatgacggg aacc                                  24

<210> SEQ ID NO 824
<211> LENGTH: 24
<212> TYPE: DNA
<213> ORGANISM: Artificial Sequence
<220> FEATURE:
<223> OTHER INFORMATION: Primer

<400> SEQUENCE: 824
ataaggaagg tgtgtcttgg gtcg                                  24

<210> SEQ ID NO 825
<211> LENGTH: 21
<212> TYPE: DNA
<213> ORGANISM: Artificial Sequence
<220> FEATURE:
<223> OTHER INFORMATION: Primer

<400> SEQUENCE: 825
gttgagctcg gtccgacgtt t                                     21

<210> SEQ ID NO 826
<211> LENGTH: 24
<212> TYPE: DNA
<213> ORGANISM: Artificial Sequence
<220> FEATURE:
<223> OTHER INFORMATION: Primer

<400> SEQUENCE: 826
cgagaccggt actaaggttt gttg                                  24

<210> SEQ ID NO 827
<211> LENGTH: 22
<212> TYPE: DNA
<213> ORGANISM: Artificial Sequence
<220> FEATURE:
<223> OTHER INFORMATION: Primer

<400> SEQUENCE: 827
agtcgtgaca gttcgccttc ta                                    22

<210> SEQ ID NO 828
<211> LENGTH: 22
<212> TYPE: DNA
<213> ORGANISM: Artificial Sequence
<220> FEATURE:
<223> OTHER INFORMATION: Primer

<400> SEQUENCE: 828
aggttcttct ttgtaccgcc ga                                    22
```

<210> SEQ ID NO 829
<211> LENGTH: 20
<212> TYPE: DNA
<213> ORGANISM: Artificial Sequence
<220> FEATURE:
<223> OTHER INFORMATION: Primer

<400> SEQUENCE: 829
gtgtcctcct ctggtagttt                                           20

<210> SEQ ID NO 830
<211> LENGTH: 22
<212> TYPE: DNA
<213> ORGANISM: Artificial Sequence
<220> FEATURE:
<223> OTHER INFORMATION: Primer

<400> SEQUENCE: 830
atgtactggt tcggcctacc at                                        22

<210> SEQ ID NO 831
<211> LENGTH: 23
<212> TYPE: DNA
<213> ORGANISM: Artificial Sequence
<220> FEATURE:
<223> OTHER INFORMATION: Primer

<400> SEQUENCE: 831
tggtgtgagt cctggtgagg tta                                       23

<210> SEQ ID NO 832
<211> LENGTH: 24
<212> TYPE: DNA
<213> ORGANISM: Artificial Sequence
<220> FEATURE:
<223> OTHER INFORMATION: Primer

<400> SEQUENCE: 832
tatcagcaca ctgacggaat gtcg                                      24

<210> SEQ ID NO 833
<211> LENGTH: 23
<212> TYPE: DNA
<213> ORGANISM: Artificial Sequence
<220> FEATURE:
<223> OTHER INFORMATION: Primer

<400> SEQUENCE: 833
tagacgacgt ggaacattta cga                                       23

<210> SEQ ID NO 834
<211> LENGTH: 22
<212> TYPE: DNA
<213> ORGANISM: Artificial Sequence
<220> FEATURE:
<223> OTHER INFORMATION: Primer

<400> SEQUENCE: 834
gaacgacggg ttagaaacgg tt                                        22

<210> SEQ ID NO 835
<211> LENGTH: 20
<212> TYPE: DNA
<213> ORGANISM: Artificial Sequence
<220> FEATURE:
<223> OTHER INFORMATION: Primer

```
<400> SEQUENCE: 835
acgagaagtg aacgtcaccc                                              20

<210> SEQ ID NO 836
<211> LENGTH: 23
<212> TYPE: DNA
<213> ORGANISM: Artificial Sequence
<220> FEATURE:
<223> OTHER INFORMATION: Primer

<400> SEQUENCE: 836
ttccggtttc gttccatcac tag                                          23

<210> SEQ ID NO 837
<211> LENGTH: 22
<212> TYPE: DNA
<213> ORGANISM: Artificial Sequence
<220> FEATURE:
<223> OTHER INFORMATION: Primer

<400> SEQUENCE: 837
tttcacaaac cacgttcacg gt                                           22

<210> SEQ ID NO 838
<211> LENGTH: 22
<212> TYPE: DNA
<213> ORGANISM: Artificial Sequence
<220> FEATURE:
<223> OTHER INFORMATION: Primer

<400> SEQUENCE: 838
agaaatgccg aagccaccga tt                                           22

<210> SEQ ID NO 839
<211> LENGTH: 22
<212> TYPE: DNA
<213> ORGANISM: Artificial Sequence
<220> FEATURE:
<223> OTHER INFORMATION: Primer

<400> SEQUENCE: 839
agggaccgga gttcagaaca ta                                           22

<210> SEQ ID NO 840
<211> LENGTH: 22
<212> TYPE: DNA
<213> ORGANISM: Artificial Sequence
<220> FEATURE:
<223> OTHER INFORMATION: Primer

<400> SEQUENCE: 840
atgacgggac taaacctcag gt                                           22

<210> SEQ ID NO 841
<211> LENGTH: 20
<212> TYPE: DNA
<213> ORGANISM: Artificial Sequence
<220> FEATURE:
<223> OTHER INFORMATION: Primer

<400> SEQUENCE: 841
ttacaaagaa ccccgtctct                                              20

<210> SEQ ID NO 842
<211> LENGTH: 24
<212> TYPE: DNA
```

```
<213> ORGANISM: Artificial Sequence
<220> FEATURE:
<223> OTHER INFORMATION: Primer

<400> SEQUENCE: 842
cctcaaactg tacttcggtc agac                                    24

<210> SEQ ID NO 843
<211> LENGTH: 22
<212> TYPE: DNA
<213> ORGANISM: Artificial Sequence
<220> FEATURE:
<223> OTHER INFORMATION: Primer

<400> SEQUENCE: 843
gcctaccgtt tacgctcttg tt                                      22

<210> SEQ ID NO 844
<211> LENGTH: 20
<212> TYPE: DNA
<213> ORGANISM: Artificial Sequence
<220> FEATURE:
<223> OTHER INFORMATION: Primer

<400> SEQUENCE: 844
tgttcctgtg gttccaccaa                                         20

<210> SEQ ID NO 845
<211> LENGTH: 21
<212> TYPE: DNA
<213> ORGANISM: Artificial Sequence
<220> FEATURE:
<223> OTHER INFORMATION: Primer

<400> SEQUENCE: 845
agacccactc ccacaaggta a                                       21

<210> SEQ ID NO 846
<211> LENGTH: 24
<212> TYPE: DNA
<213> ORGANISM: Artificial Sequence
<220> FEATURE:
<223> OTHER INFORMATION: Primer

<400> SEQUENCE: 846
cttcttcacc aacccgattg actt                                    24

<210> SEQ ID NO 847
<211> LENGTH: 22
<212> TYPE: DNA
<213> ORGANISM: Artificial Sequence
<220> FEATURE:
<223> OTHER INFORMATION: Primer

<400> SEQUENCE: 847
tacgtggagg acgttcttct ca                                      22

<210> SEQ ID NO 848
<211> LENGTH: 21
<212> TYPE: DNA
<213> ORGANISM: Artificial Sequence
<220> FEATURE:
<223> OTHER INFORMATION: Primer

<400> SEQUENCE: 848
cgagagtcgc acgatcattc a                                       21
```

<210> SEQ ID NO 849
<211> LENGTH: 20
<212> TYPE: DNA
<213> ORGANISM: Artificial Sequence
<220> FEATURE:
<223> OTHER INFORMATION: Primer

<400> SEQUENCE: 849
cgtgtggtac cttcgggttt                                              20

<210> SEQ ID NO 850
<211> LENGTH: 24
<212> TYPE: DNA
<213> ORGANISM: Artificial Sequence
<220> FEATURE:
<223> OTHER INFORMATION: Primer

<400> SEQUENCE: 850
tttatggtct acggtgagac gtcc                                         24

<210> SEQ ID NO 851
<211> LENGTH: 23
<212> TYPE: DNA
<213> ORGANISM: Artificial Sequence
<220> FEATURE:
<223> OTHER INFORMATION: Primer

<400> SEQUENCE: 851
gaggatacta cgacgaccaa acg                                          23

<210> SEQ ID NO 852
<211> LENGTH: 21
<212> TYPE: DNA
<213> ORGANISM: Artificial Sequence
<220> FEATURE:
<223> OTHER INFORMATION: Primer

<400> SEQUENCE: 852
ggttgtgttg tcgacgaagg t                                            21

<210> SEQ ID NO 853
<211> LENGTH: 22
<212> TYPE: DNA
<213> ORGANISM: Artificial Sequence
<220> FEATURE:
<223> OTHER INFORMATION: Primer

<400> SEQUENCE: 853
tctctcggtc catggttacc ca                                           22

<210> SEQ ID NO 854
<211> LENGTH: 24
<212> TYPE: DNA
<213> ORGANISM: Artificial Sequence
<220> FEATURE:
<223> OTHER INFORMATION: Primer

<400> SEQUENCE: 854
tgtgaagacc tcttgttcct gagg                                         24

<210> SEQ ID NO 855
<211> LENGTH: 20
<212> TYPE: DNA
<213> ORGANISM: Artificial Sequence
<220> FEATURE:
<223> OTHER INFORMATION: Primer

```
<400> SEQUENCE: 855
tcaggaaacg gtcggagaaa                                          20

<210> SEQ ID NO 856
<211> LENGTH: 20
<212> TYPE: DNA
<213> ORGANISM: Artificial Sequence
<220> FEATURE:
<223> OTHER INFORMATION: Primer

<400> SEQUENCE: 856
gcgtcctcgt attctccctt                                          20

<210> SEQ ID NO 857
<211> LENGTH: 24
<212> TYPE: DNA
<213> ORGANISM: Artificial Sequence
<220> FEATURE:
<223> OTHER INFORMATION: Primer

<400> SEQUENCE: 857
ttgagagtcg tggagtactt ctgc                                     24

<210> SEQ ID NO 858
<211> LENGTH: 21
<212> TYPE: DNA
<213> ORGANISM: Artificial Sequence
<220> FEATURE:
<223> OTHER INFORMATION: Primer

<400> SEQUENCE: 858
tgcgacaatg aagtcccggt a                                        21

<210> SEQ ID NO 859
<211> LENGTH: 24
<212> TYPE: DNA
<213> ORGANISM: Artificial Sequence
<220> FEATURE:
<223> OTHER INFORMATION: Primer

<400> SEQUENCE: 859
ttcataccta agtccgccac cttc                                     24

<210> SEQ ID NO 860
<211> LENGTH: 20
<212> TYPE: DNA
<213> ORGANISM: Artificial Sequence
<220> FEATURE:
<223> OTHER INFORMATION: Primer

<400> SEQUENCE: 860
ctgaaaggca tggtcacaaa                                          20

<210> SEQ ID NO 861
<211> LENGTH: 20
<212> TYPE: DNA
<213> ORGANISM: Artificial Sequence
<220> FEATURE:
<223> OTHER INFORMATION: Primer

<400> SEQUENCE: 861
cgcgtgctga agaaattcaa                                          20

<210> SEQ ID NO 862
<211> LENGTH: 26
<212> TYPE: DNA
```

```
<213> ORGANISM: Artificial Sequence
<220> FEATURE:
<223> OTHER INFORMATION: Primer

<400> SEQUENCE: 862
gcagcacatg ggagattgtc ctgtaa                                           26

<210> SEQ ID NO 863
<211> LENGTH: 20
<212> TYPE: DNA
<213> ORGANISM: Artificial Sequence
<220> FEATURE:
<223> OTHER INFORMATION: Primer

<400> SEQUENCE: 863
gccgtctcag aagggtacaa                                                  20

<210> SEQ ID NO 864
<211> LENGTH: 22
<212> TYPE: DNA
<213> ORGANISM: Artificial Sequence
<220> FEATURE:
<223> OTHER INFORMATION: Primer

<400> SEQUENCE: 864
aggtgcacag agccaacatt ac                                               22

<210> SEQ ID NO 865
<211> LENGTH: 20
<212> TYPE: DNA
<213> ORGANISM: Artificial Sequence
<220> FEATURE:
<223> OTHER INFORMATION: Primer

<400> SEQUENCE: 865
aaagaacgtg ctccagaccc                                                  20

<210> SEQ ID NO 866
<211> LENGTH: 22
<212> TYPE: DNA
<213> ORGANISM: Artificial Sequence
<220> FEATURE:
<223> OTHER INFORMATION: Taqman probe sequence

<400> SEQUENCE: 866
tccttccaca cagaacccag ca                                               22

<210> SEQ ID NO 867
<211> LENGTH: 20
<212> TYPE: DNA
<213> ORGANISM: Artificial Sequence
<220> FEATURE:
<223> OTHER INFORMATION: Taqman probe sequence

<400> SEQUENCE: 867
ttggcgcaga ggaggttcat                                                  20

<210> SEQ ID NO 868
<211> LENGTH: 26
<212> TYPE: DNA
<213> ORGANISM: Artificial Sequence
<220> FEATURE:
<223> OTHER INFORMATION: Taqman probe sequence

<400> SEQUENCE: 868
agcaagtggc ctctgtaatc tgctca                                           26
```

```
<210> SEQ ID NO 869
<211> LENGTH: 20
<212> TYPE: DNA
<213> ORGANISM: Artificial Sequence
<220> FEATURE:
<223> OTHER INFORMATION: Taqman probe sequence

<400> SEQUENCE: 869
cagggcaatt gctatcgcca                                              20

<210> SEQ ID NO 870
<211> LENGTH: 25
<212> TYPE: DNA
<213> ORGANISM: Artificial Sequence
<220> FEATURE:
<223> OTHER INFORMATION: Taqman probe sequence

<400> SEQUENCE: 870
ctcatcatta acatggaacc cctgc                                        25

<210> SEQ ID NO 871
<211> LENGTH: 24
<212> TYPE: DNA
<213> ORGANISM: Artificial Sequence
<220> FEATURE:
<223> OTHER INFORMATION: Taqman probe sequence

<400> SEQUENCE: 871
catagttctc ctgtcagcag aaga                                         24

<210> SEQ ID NO 872
<211> LENGTH: 20
<212> TYPE: DNA
<213> ORGANISM: Artificial Sequence
<220> FEATURE:
<223> OTHER INFORMATION: Primer

<400> SEQUENCE: 872
gtctcacgtc tacctcgact                                              20

<210> SEQ ID NO 873
<211> LENGTH: 20
<212> TYPE: DNA
<213> ORGANISM: Artificial Sequence
<220> FEATURE:
<223> OTHER INFORMATION: Primer

<400> SEQUENCE: 873
gtttttcctc gacggactca                                              20

<210> SEQ ID NO 874
<211> LENGTH: 24
<212> TYPE: DNA
<213> ORGANISM: Artificial Sequence
<220> FEATURE:
<223> OTHER INFORMATION: Primer

<400> SEQUENCE: 874
agggtttgtg acaggagcac gtta                                         24

<210> SEQ ID NO 875
<211> LENGTH: 20
<212> TYPE: DNA
<213> ORGANISM: Artificial Sequence
<220> FEATURE:
<223> OTHER INFORMATION: Primer
```

```
<400> SEQUENCE: 875
ctctcaaacc gtggttgacc                                              20

<210> SEQ ID NO 876
<211> LENGTH: 21
<212> TYPE: DNA
<213> ORGANISM: Artificial Sequence
<220> FEATURE:
<223> OTHER INFORMATION: Primer

<400> SEQUENCE: 876
agacccactc ccacaaggta a                                            21

<210> SEQ ID NO 877
<211> LENGTH: 24
<212> TYPE: DNA
<213> ORGANISM: Artificial Sequence
<220> FEATURE:
<223> OTHER INFORMATION: Primer

<400> SEQUENCE: 877
cttcttcacc aacccgattg actt                                         24

<210> SEQ ID NO 878
<211> LENGTH: 22
<212> TYPE: DNA
<213> ORGANISM: Artificial Sequence
<220> FEATURE:
<223> OTHER INFORMATION: Primer

<400> SEQUENCE: 878
aaggatgtcc agtttgcagt gg                                           22

<210> SEQ ID NO 879
<211> LENGTH: 22
<212> TYPE: DNA
<213> ORGANISM: Artificial Sequence
<220> FEATURE:
<223> OTHER INFORMATION: Primer

<400> SEQUENCE: 879
acaggcatct atgggatgtg ga                                           22

<210> SEQ ID NO 880
<211> LENGTH: 21
<212> TYPE: DNA
<213> ORGANISM: Artificial Sequence
<220> FEATURE:
<223> OTHER INFORMATION: Primer

<400> SEQUENCE: 880
tcggtactcc aaggttctgg a                                            21

<210> SEQ ID NO 881
<211> LENGTH: 22
<212> TYPE: DNA
<213> ORGANISM: Artificial Sequence
<220> FEATURE:
<223> OTHER INFORMATION: Primer

<400> SEQUENCE: 881
acccgagaga actggattgc gt                                           22

<210> SEQ ID NO 882
<211> LENGTH: 23
<212> TYPE: DNA
```

```
<213> ORGANISM: Artificial Sequence
<220> FEATURE:
<223> OTHER INFORMATION: Primer

<400> SEQUENCE: 882
ccaccaaagg aagtaaggta cac                                        23

<210> SEQ ID NO 883
<211> LENGTH: 22
<212> TYPE: DNA
<213> ORGANISM: Artificial Sequence
<220> FEATURE:
<223> OTHER INFORMATION: Primer

<400> SEQUENCE: 883
gagggccgaa attggtgttt ga                                         22

<210> SEQ ID NO 884
<211> LENGTH: 22
<212> TYPE: DNA
<213> ORGANISM: Artificial Sequence
<220> FEATURE:
<223> OTHER INFORMATION: Primer

<400> SEQUENCE: 884
agtgtacgcc actttgccct aa                                         22

<210> SEQ ID NO 885
<211> LENGTH: 22
<212> TYPE: DNA
<213> ORGANISM: Artificial Sequence
<220> FEATURE:
<223> OTHER INFORMATION: Primer

<400> SEQUENCE: 885
aagatgcctg tagtgacacc ga                                         22

<210> SEQ ID NO 886
<211> LENGTH: 22
<212> TYPE: DNA
<213> ORGANISM: Artificial Sequence
<220> FEATURE:
<223> OTHER INFORMATION: Primer

<400> SEQUENCE: 886
taccaccgaa gtaaaggacg gt                                         22

<210> SEQ ID NO 887
<211> LENGTH: 22
<212> TYPE: DNA
<213> ORGANISM: Artificial Sequence
<220> FEATURE:
<223> OTHER INFORMATION: Primer

<400> SEQUENCE: 887
ttctggtcag gttaccgcta ga                                         22

<210> SEQ ID NO 888
<211> LENGTH: 22
<212> TYPE: DNA
<213> ORGANISM: Artificial Sequence
<220> FEATURE:
<223> OTHER INFORMATION: Primer

<400> SEQUENCE: 888
gcgggtcatt ggaaaccttt gt                                         22
```

```
<210> SEQ ID NO 889
<211> LENGTH: 22
<212> TYPE: DNA
<213> ORGANISM: Artificial Sequence
<220> FEATURE:
<223> OTHER INFORMATION: Primer

<400> SEQUENCE: 889
aaaccgtcga ctcataacct cg                                              22

<210> SEQ ID NO 890
<211> LENGTH: 20
<212> TYPE: DNA
<213> ORGANISM: Artificial Sequence
<220> FEATURE:
<223> OTHER INFORMATION: Primer

<400> SEQUENCE: 890
ttaccgtgca ccgcgttgat                                                 20

<210> SEQ ID NO 891
<211> LENGTH: 22
<212> TYPE: DNA
<213> ORGANISM: Artificial Sequence
<220> FEATURE:
<223> OTHER INFORMATION: Primer

<400> SEQUENCE: 891
tcgtctcggt cacttggtgt ta                                              22

<210> SEQ ID NO 892
<211> LENGTH: 22
<212> TYPE: DNA
<213> ORGANISM: Artificial Sequence
<220> FEATURE:
<223> OTHER INFORMATION: Primer

<400> SEQUENCE: 892
acgatacgcc ttgttccgac ta                                              22

<210> SEQ ID NO 893
<211> LENGTH: 22
<212> TYPE: DNA
<213> ORGANISM: Artificial Sequence
<220> FEATURE:
<223> OTHER INFORMATION: Primer

<400> SEQUENCE: 893
cgaacctcgg tttcatagcc ta                                              22
```